US011939347B2

(12) United States Patent
Byun et al.

(10) Patent No.: US 11,939,347 B2
(45) Date of Patent: Mar. 26, 2024

(54) 1'-CYANO NUCLEOSIDE ANALOGS AND USES THEREOF

(71) Applicant: Gilead Sciences, Inc., Foster City, CA (US)

(72) Inventors: Daniel H. Byun, Foster City, CA (US); Byoung-Kwon Chun, Pleasanton, CA (US); Michael O. Clarke, Redwood City, CA (US); Petr Jansa, Foster City, CA (US); Rao V. Kalla, Cupertino, CA (US); Dmitry Koltun, Foster City, CA (US); Richard L. Mackman, Millbrae, CA (US); Thao D. Perry, San Jose, CA (US); Dustin S. Siegel, Half Moon Bay, CA (US); Scott P. Simonovich, San Francisco, CA (US)

(73) Assignee: Gilead Sciences, Inc., Foster City, CA (US)

( * ) Notice: Subject to any disclaimer, the term of this patent is extended or adjusted under 35 U.S.C. 154(b) by 283 days.

(21) Appl. No.: 17/355,813

(22) Filed: Jun. 23, 2021

(65) Prior Publication Data

US 2023/0040586 A1 Feb. 9, 2023

Related U.S. Application Data

(60) Provisional application No. 63/139,648, filed on Jan. 20, 2021, provisional application No. 63/043,349, filed on Jun. 24, 2020.

(51) Int. Cl.
| | |
|---|---|
| *A61K 31/675* | (2006.01) |
| *A61K 45/06* | (2006.01) |
| *A61P 31/12* | (2006.01) |
| *C07F 9/6561* | (2006.01) |

(52) U.S. Cl.
CPC ............ *C07F 9/6561* (2013.01); *A61K 45/06* (2013.01)

(58) Field of Classification Search
CPC .............................. A61K 31/675; A61P 31/12
USPC ......................................................... 514/80
See application file for complete search history.

(56) References Cited

U.S. PATENT DOCUMENTS

| | | | |
|---|---|---|---|
| 4,816,570 A | 3/1989 | Farquhar | |
| 4,968,788 A | 11/1990 | Farquhar | |
| 5,663,159 A | 9/1997 | Starrett, Jr. et al. | |
| 5,792,756 A | 8/1998 | Starrett, Jr. et al. | |
| 6,312,662 B1 | 11/2001 | Erion et al. | |
| 6,475,985 B1 | 11/2002 | Wagner et al. | |
| 6,476,030 B1 | 11/2002 | Carling et al. | |
| 6,656,915 B1 | 12/2003 | Bantia et al. | |
| 6,909,011 B2 | 6/2005 | Skranc et al. | |
| 7,078,403 B1 | 7/2006 | Wu et al. | |
| 7,105,493 B2 | 9/2006 | Sommadossi et al. | |
| 7,125,855 B2 | 10/2006 | Bhat et al. | |
| 7,166,604 B2 | 1/2007 | Watson et al. | |
| 7,176,203 B2 | 2/2007 | Chambers et al. | |
| 7,268,119 B2 | 9/2007 | Cook et al. | |
| 7,285,658 B2 | 10/2007 | Cook et al. | |
| 7,368,437 B1 | 5/2008 | Bojack et al. | |
| 7,390,791 B2 | 6/2008 | Becker et al. | |
| 7,429,571 B2 | 9/2008 | Chand et al. | |
| 7,514,410 B2 | 4/2009 | Babu et al. | |
| 7,560,434 B2 | 7/2009 | Babu et al. | |
| 7,598,230 B2 | 10/2009 | Cook et al. | |
| 7,608,597 B2 | 10/2009 | Sommadossi et al. | |
| 7,713,941 B2 | 5/2010 | Cook et al. | |
| 7,803,788 B2 | 9/2010 | Becker et al. | |
| 7,807,653 B2 | 10/2010 | Cook et al. | |
| 7,842,672 B2 | 11/2010 | Boojamra et al. | |
| 7,951,787 B2 | 5/2011 | McGuigan | |
| 7,973,013 B2 | 7/2011 | Cho et al. | |
| 7,994,139 B2 | 8/2011 | Babu et al. | |
| 8,008,264 B2 | 8/2011 | Butler et al. | |
| 8,012,941 B2 | 9/2011 | Cho et al. | |
| 8,012,942 B2 | 9/2011 | Butler et al. | |
| 8,071,568 B2 | 12/2011 | Narjes et al. | |
| 8,119,607 B2 | 2/2012 | Francom et al. | |
| 8,242,085 B2 | 8/2012 | Babu et al. | |
| 8,318,682 B2 | 11/2012 | Butler et al. | |
| 8,415,308 B2 | 4/2013 | Cho et al. | |
| 8,455,451 B2 | 6/2013 | Cho et al. | |
| 8,853,171 B2 | 10/2014 | Butler et al. | |
| 8,871,737 B2 | 10/2014 | Smith et al. | |
| 8,889,159 B2 | 11/2014 | Clearly et al. | |
| 8,980,865 B2 | 3/2015 | Wang | |
| 9,090,642 B2 | 7/2015 | Cho et al. | |
| 9,243,022 B2 | 1/2016 | Beigelman et al. | |

(Continued)

FOREIGN PATENT DOCUMENTS

| | | |
|---|---|---|
| CN | 110330540 | 10/2019 |
| CN | 110724174 | 1/2020 |

(Continued)

OTHER PUBLICATIONS

Anonymous [online], "University of Alabama & Multi-Center Collaboration Help Develop Remdesivir with Gilead Thanks to $37.5m from NIH," TrialSiteNews.com, retrieved on Mar. 13, 2023, URL <https://www.trialsitenews.com/a/university-of-alabama-multi-center-collaboration-help-develop-remdesivir-with-gilead-thanks-to-37-5m-from-nih>, Mar. 1, 2020, 5 pages.

Jonckers et al., "2'Deoxy-2'-spirocyclopropylcytidine Revisited: A New and Selective Inhibitor of the Hepatitis C Virus NS5B Polymerase," Journal of Medicinal Chemistry, Nov. 2010, 53(22)8150-60.

(Continued)

*Primary Examiner* — Raymond J Henley, III
(74) *Attorney, Agent, or Firm* — Fish & Richardson P.C.

(57) ABSTRACT

Compounds and methods of using said compounds, singly or in combination with additional agents, and pharmaceutical compositions of said compounds for the treatment of viral infections are disclosed.

45 Claims, No Drawings

(56) References Cited

U.S. PATENT DOCUMENTS

| | | |
|---|---|---|
| 9,249,174 B2 | 2/2016 | Beigelman et al. |
| 9,278,990 B2 | 3/2016 | Smith et al. |
| 9,388,208 B2 | 7/2016 | Clarke et al. |
| 9,393,256 B2 | 7/2016 | Ray et al. |
| 9,452,154 B2 | 9/2016 | Delaney et al. |
| 9,481,703 B2 | 11/2016 | Kalayanov et al. |
| 9,487,544 B2 | 11/2016 | Cho et al. |
| 9,504,701 B2 | 11/2016 | Casola et al. |
| 9,540,411 B2 | 1/2017 | Kalayanov et al. |
| 9,549,941 B2 | 1/2017 | Cleary et al. |
| 9,605,018 B2 | 3/2017 | Wang et al. |
| 9,616,076 B2 | 4/2017 | Casola et al. |
| 9,701,682 B2 | 7/2017 | Clarke et al. |
| 9,724,360 B2 | 8/2017 | Chun et al. |
| 9,828,408 B2 | 11/2017 | Kalayanov |
| RE46,762 E | 3/2018 | Butler et al. |
| 9,949,994 B2 | 4/2018 | Chun et al. |
| 10,023,600 B2 | 7/2018 | Butler et al. |
| 10,034,893 B2 | 7/2018 | Luly et al. |
| 10,059,716 B2 | 8/2018 | Clarke et al. |
| 10,065,958 B2 | 9/2018 | Mackman et al. |
| 10,251,898 B2 | 4/2019 | Chun et al. |
| 10,251,904 B2 | 4/2019 | Clarke et al. |
| 10,377,761 B2 | 8/2019 | Clarke et al. |
| RE47,589 E | 9/2019 | McGuigan |
| 10,675,296 B2 | 6/2020 | Larson |
| 10,682,368 B2 | 6/2020 | Perron et al. |
| 10,695,357 B2 | 6/2020 | Chun et al. |
| 10,695,361 B2 | 6/2020 | Clarke et al. |
| 10,696,679 B2 | 6/2020 | Mackman et al. |
| 10,836,787 B2 | 11/2020 | Brak et al. |
| 10,988,498 B2 | 4/2021 | Butler et al. |
| 11,007,208 B2 | 5/2021 | Clarke et al. |
| 11,225,508 B1 | 1/2022 | Baric et al. |
| 11,260,070 B2 | 3/2022 | Perron et al. |
| 11,266,666 B2 | 3/2022 | Chun et al. |
| 11,266,681 B2 | 3/2022 | Larson et al. |
| 11,344,565 B2 | 5/2022 | Axt et al. |
| 11,377,456 B2 | 7/2022 | Souza et al. |
| 11,382,926 B2 | 7/2022 | Clarke et al. |
| 11,491,169 B2 | 11/2022 | Cihlar |
| 11,492,353 B2 | 11/2022 | Mackman et al. |
| 11,541,071 B1 | 1/2023 | Liang et al. |
| 11,597,742 B2 | 3/2023 | Brak et al. |
| 11,613,553 B2 | 3/2023 | Badalov et al. |
| 11,660,307 B2 | 5/2023 | Cihlar et al. |
| 11,701,372 B2 | 7/2023 | Ellis et al. |
| 2003/0050229 A1 | 3/2003 | Sommadossi et al. |
| 2003/0092775 A1 | 5/2003 | Ernst et al. |
| 2004/0006002 A1 | 1/2004 | Sommadossi et al. |
| 2004/0023901 A1 | 2/2004 | Cook et al. |
| 2004/0063658 A1 | 4/2004 | Roberts et al. |
| 2004/0067901 A1 | 4/2004 | Bhat et al. |
| 2004/0138170 A1 | 7/2004 | Montgomery et al. |
| 2005/0187180 A1 | 8/2005 | Loeb et al. |
| 2005/0209166 A1 | 9/2005 | Eckhardt et al. |
| 2005/0215513 A1 | 9/2005 | Boojamra et al. |
| 2005/0250728 A1 | 11/2005 | Bantia et al. |
| 2006/0058303 A1 | 3/2006 | Chambers et al. |
| 2006/0142238 A1 | 6/2006 | McGuigan |
| 2006/0241064 A1 | 10/2006 | Roberts et al. |
| 2008/0107628 A1 | 5/2008 | Boojamra et al. |
| 2008/0161324 A1 | 7/2008 | Johansen et al. |
| 2008/0280842 A1 | 11/2008 | MacCoss et al. |
| 2009/0004138 A1 | 1/2009 | Francom et al. |
| 2009/0221524 A1 | 9/2009 | Kotra et al. |
| 2009/0233879 A1 | 9/2009 | Reddy et al. |
| 2009/0317361 A1 | 12/2009 | Cho et al. |
| 2010/0015094 A1 | 1/2010 | Babu et al. |
| 2010/0016251 A1 | 1/2010 | Sofia et al. |
| 2010/0021425 A1 | 1/2010 | Butler et al. |
| 2010/0035835 A1 | 2/2010 | Narjes et al. |
| 2010/0035836 A1 | 2/2010 | Francom et al. |
| 2010/0065512 A1 | 3/2010 | Bjorsvik |
| 2010/0203015 A1 | 8/2010 | Butler et al. |
| 2010/0234584 A1 | 9/2010 | Chang |
| 2010/0249068 A1 | 9/2010 | Beigelman et al. |
| 2010/0291031 A2 | 11/2010 | Francom et al. |
| 2010/0298257 A1 | 11/2010 | Ross et al. |
| 2010/0305202 A1 | 12/2010 | Hwang et al. |
| 2011/0070194 A1 | 3/2011 | Cho et al. |
| 2011/0084230 A1 | 4/2011 | Knochel et al. |
| 2011/0230654 A1 | 9/2011 | Butler et al. |
| 2011/0257122 A1 | 10/2011 | Sofia et al. |
| 2011/0293563 A1 | 12/2011 | Butler et al. |
| 2012/0009147 A1 | 1/2012 | Cho et al. |
| 2012/0020921 A1 | 1/2012 | Cho et al. |
| 2012/0027752 A1 | 2/2012 | Mackman et al. |
| 2012/0071434 A1 | 3/2012 | Smith et al. |
| 2012/0107274 A1 | 5/2012 | Clarke et al. |
| 2013/0034521 A1 | 2/2013 | Butler et al. |
| 2013/0143835 A1 | 6/2013 | Eneroth et al. |
| 2013/0281686 A1 | 10/2013 | Cho et al. |
| 2013/0315868 A1 | 11/2013 | Mayes |
| 2013/0344028 A2 | 12/2013 | Butler et al. |
| 2014/0219958 A1 | 8/2014 | Luly et al. |
| 2015/0031687 A1 | 1/2015 | Guo et al. |
| 2015/0111839 A1 | 4/2015 | Mackman et al. |
| 2015/0133395 A1 | 5/2015 | Clarke et al. |
| 2015/0152116 A1 | 6/2015 | Mackman et al. |
| 2015/0210682 A1 | 7/2015 | Han et al. |
| 2015/0252057 A1 | 9/2015 | Guo et al. |
| 2016/0058779 A1 | 3/2016 | Casola et al. |
| 2016/0122344 A1 | 5/2016 | Han et al. |
| 2016/0122356 A1 | 5/2016 | Axt et al. |
| 2016/0122374 A1 | 5/2016 | Chun |
| 2016/0176899 A1 | 6/2016 | Schwitter et al. |
| 2016/0220586 A1 | 8/2016 | Andre et al. |
| 2016/0237090 A1 | 8/2016 | Hu et al. |
| 2017/0071964 A1 | 3/2017 | Clark et al. |
| 2018/0346504 A1 | 12/2018 | Brak et al. |
| 2019/0023745 A1 | 1/2019 | Baric et al. |
| 2019/0083525 A1 | 3/2019 | Larson |
| 2020/0197422 A1 | 6/2020 | Axt et al. |
| 2020/0360420 A1 | 11/2020 | Larson |
| 2020/0376014 A1 | 12/2020 | Perron et al. |
| 2021/0052613 A1 | 2/2021 | Chun et al. |
| 2021/0061806 A1 | 3/2021 | Mackman et al. |
| 2021/0283150 A1 | 9/2021 | Cihlar et al. |
| 2021/0309689 A1 | 10/2021 | Badalov et al. |
| 2021/0330685 A1 | 10/2021 | Ellis et al. |
| 2021/0393653 A1 | 12/2021 | Cihlar et al. |
| 2021/0393659 A1 | 12/2021 | O'Neil et al. |
| 2021/0403497 A1 | 12/2021 | Butler et al. |
| 2022/0081462 A1 | 3/2022 | Chun et al. |
| 2022/0175805 A1 | 6/2022 | Cihlar |
| 2022/0280549 A1 | 9/2022 | Larson et al. |
| 2022/0354873 A1 | 11/2022 | Axt et al. |
| 2022/0356196 A1 | 11/2022 | Byun et al. |
| 2023/0027727 A1 | 1/2023 | Clarke et al. |
| 2023/0040586 A1 | 2/2023 | Byun et al. |
| 2023/0125751 A1 | 4/2023 | Mackman et al. |
| 2023/0151043 A1 | 5/2023 | Bunyan et al. |
| 2023/0233587 A1 | 7/2023 | Cihlar |

FOREIGN PATENT DOCUMENTS

| | | |
|---|---|---|
| CN | 110776512 | 2/2020 |
| CN | 111171078 | 5/2020 |
| CN | 111205294 | 5/2020 |
| CN | 111205327 | 5/2020 |
| CN | 111233869 | 6/2020 |
| CN | 111265532 | 6/2020 |
| CN | 111440176 | 7/2020 |
| CN | 111548384 | 8/2020 |
| CN | 111961057 | 11/2020 |
| CN | 202011613943.3 | 12/2020 |
| CN | 112778310 | 5/2021 |
| CN | 202110562244.9 | 5/2021 |
| CN | 113754665 | 6/2021 |
| CN | 113185519 | 7/2021 |
| CN | 113248508 | 8/2021 |
| CN | 113292565 | 8/2021 |
| CN | 113387954 | 9/2021 |

(56) References Cited

FOREIGN PATENT DOCUMENTS

| | | |
|---|---|---|
| CN | 113735862 | 9/2021 |
| CN | 113698405 | 11/2021 |
| CN | 114292272 | 12/2021 |
| CN | 114437159 | 5/2022 |
| CN | 114621229 | 6/2022 |
| CN | 114765979 | 7/2022 |
| IN | 202121023147 | 5/2021 |
| IN | 202134041493 | 9/2021 |
| IN | 202011021676 | 11/2021 |
| JP | 2005185235 | 7/2005 |
| JP | 2005187428 | 7/2005 |
| WO | WO1991019721 | 12/1991 |
| WO | WO1999045029 | 9/1999 |
| WO | WO2000056734 | 9/2000 |
| WO | WO2000075157 | 12/2000 |
| WO | WO2001032153 | 5/2001 |
| WO | WO2001060315 | 8/2001 |
| WO | WO2001090121 | 11/2001 |
| WO | WO2001091737 | 12/2001 |
| WO | WO2001092282 | 12/2001 |
| WO | WO2002008241 | 1/2002 |
| WO | WO2002018404 | 3/2002 |
| WO | WO2002032920 | 4/2002 |
| WO | WO2002057287 | 7/2002 |
| WO | WO2002057425 | 7/2002 |
| WO | WO2003093272 | 11/2003 |
| WO | WO2003093273 | 11/2003 |
| WO | WO2003100009 | 12/2003 |
| WO | WO2004046159 | 6/2004 |
| WO | WO2004046331 | 6/2004 |
| WO | WO2004112687 | 12/2004 |
| WO | WO2005009418 | 2/2005 |
| WO | WO2005092877 | 10/2005 |
| WO | WO2005123087 | 12/2005 |
| WO | WO2006031725 | 3/2006 |
| WO | WO2006050161 | 5/2006 |
| WO | WO2006064033 | 6/2006 |
| WO | WO2006065335 | 6/2006 |
| WO | WO2006121820 | 11/2006 |
| WO | WO2006135978 | 12/2006 |
| WO | WO2007027248 | 3/2007 |
| WO | WO2007056170 | 5/2007 |
| WO | WO2007062542 | 6/2007 |
| WO | WO2007064883 | 6/2007 |
| WO | WO2007064931 | 6/2007 |
| WO | WO2007065289 | 6/2007 |
| WO | WO2007065829 | 6/2007 |
| WO | WO2007095269 | 8/2007 |
| WO | WO2007097991 | 8/2007 |
| WO | WO2007113294 | 10/2007 |
| WO | WO2007135134 | 11/2007 |
| WO | WO2008005542 | 1/2008 |
| WO | WO2008011406 | 1/2008 |
| WO | WO2008055870 | 5/2008 |
| WO | WO2008079206 | 7/2008 |
| WO | WO2008082601 | 7/2008 |
| WO | WO2008085508 | 7/2008 |
| WO | WO2008089105 | 7/2008 |
| WO | WO2008116064 | 9/2008 |
| WO | WO2008121634 | 10/2008 |
| WO | WO2008141079 | 11/2008 |
| WO | WO2009009951 | 1/2009 |
| WO | WO2009018609 | 2/2009 |
| WO | WO2009131926 | 10/2009 |
| WO | WO2009132123 | 10/2009 |
| WO | WO2009132135 | 10/2009 |
| WO | WO2010002877 | 1/2010 |
| WO | WO2010036407 | 4/2010 |
| WO | WO2010039548 | 4/2010 |
| WO | WO2010093608 | 8/2010 |
| WO | WO2010099458 | 9/2010 |
| WO | WO2010108140 | 9/2010 |
| WO | WO2010135569 | 11/2010 |
| WO | WO2011011303 | 1/2011 |
| WO | WO2010111381 | 3/2011 |
| WO | WO2011035231 | 3/2011 |
| WO | WO2011035250 | 3/2011 |
| WO | WO2011080568 | 7/2011 |
| WO | WO2011100131 | 8/2011 |
| WO | WO2011123645 | 10/2011 |
| WO | WO2011123668 | 10/2011 |
| WO | WO2011123672 | 10/2011 |
| WO | WO2011150288 | 12/2011 |
| WO | WO2012012465 | 1/2012 |
| WO | WO2012012776 | 1/2012 |
| WO | WO2012039787 | 3/2012 |
| WO | WO2012039791 | 3/2012 |
| WO | WO2012051570 | 4/2012 |
| WO | WO2012040127 | 5/2012 |
| WO | WO2012121764 | 9/2012 |
| WO | WO2012142523 | 10/2012 |
| WO | WO2012158643 | 11/2012 |
| WO | WO2013084165 | 6/2013 |
| WO | WO2014033617 | 3/2014 |
| WO | WO2014042433 | 3/2014 |
| WO | WO2014078463 | 5/2014 |
| WO | WO2014078778 | 5/2014 |
| WO | WO2014116755 | 7/2014 |
| WO | WO2014169280 | 10/2014 |
| WO | WO2014209979 | 12/2014 |
| WO | WO2016107833 | 12/2014 |
| WO | WO2015054465 | 4/2015 |
| WO | WO2015069939 | 5/2015 |
| WO | WO2015173164 | 11/2015 |
| WO | WO2015200205 | 12/2015 |
| WO | WO2015200219 | 12/2015 |
| WO | WO2016012470 | 1/2016 |
| WO | WO2016023877 | 2/2016 |
| WO | WO2016069825 | 5/2016 |
| WO | WO2016069826 | 5/2016 |
| WO | WO2016069827 | 5/2016 |
| WO | WO2016102438 | 6/2016 |
| WO | WO2016107832 | 7/2016 |
| WO | WO2016120186 | 8/2016 |
| WO | WO2016128335 | 8/2016 |
| WO | WO2017049060 | 3/2017 |
| WO | WO2017165489 | 9/2017 |
| WO | WO2017184668 | 10/2017 |
| WO | WO2018085307 | 5/2018 |
| WO | WO2018121678 | 7/2018 |
| WO | WO2018145148 | 8/2018 |
| WO | WO2018204198 | 11/2018 |
| WO | WO2018217906 | 11/2018 |
| WO | WO2019014247 | 1/2019 |
| WO | WO2019053696 | 3/2019 |
| WO | WO2019079594 | 4/2019 |
| WO | WO2022098371 | 11/2020 |
| WO | WO2021021717 | 2/2021 |
| WO | WO2021040356 | 3/2021 |
| WO | WO2021050961 | 3/2021 |
| WO | WO2021102363 | 5/2021 |
| WO | WO2021147236 | 7/2021 |
| WO | WO2021154530 | 8/2021 |
| WO | WO2021175296 | 9/2021 |
| WO | WO2021188915 | 9/2021 |
| WO | WO2021195661 | 9/2021 |
| WO | WO2022142477 | 9/2021 |
| WO | WO2021202907 | 10/2021 |
| WO | WO2021207049 | 10/2021 |
| WO | WO2021213288 | 10/2021 |
| WO | WO2021222807 | 11/2021 |
| WO | WO2022143473 | 12/2021 |
| WO | WO2022008642 | 1/2022 |
| WO | WO2022029704 | 2/2022 |
| WO | WO2022047065 | 3/2022 |
| WO | WO2022047441 | 3/2022 |
| WO | WO2022081870 | 4/2022 |
| WO | WO2022093895 | 5/2022 |
| WO | WO2022165386 | 8/2022 |
| WO | WO2022174194 | 8/2022 |
| WO | WO2022197950 | 9/2022 |
| WO | WO2022217153 | 10/2022 |
| WO | WO2022217154 | 10/2022 |
| WO | WO2022217155 | 10/2022 |

(56) References Cited

FOREIGN PATENT DOCUMENTS

| WO | WO2022218274 | 10/2022 |
|---|---|---|
| WO | WO2022222994 | 10/2022 |
| WO | WO2022251663 | 12/2022 |
| WO | WO2022265964 | 12/2022 |

OTHER PUBLICATIONS

Jones et al., "Di- and Triester Prodrugs of the Varicella-Zoster Antiviral Agent 6-Methoxypurine Arabinoside," Journal of Medicinal Chemistry, Jan. 1992, 35(1):56-63.
Joseph [online], "As the coronavirus spreads, a drug that once raised the world's hopes is given a second shot," StatNews.com, retrieved on Mar. 13, 2023, URL <https://www.statnews.com/2020/03/16/remdesivir-surges-ahead-against-coronavirus>, Mar. 16, 2020, 11 pages.
Kim et al., "Synthesis and Evaluation of 2-Amino-6-fluoro-9-(4-hydroxy-3-hydroxymethylbut-1-yl) purine Mono—and Diesters as Potential Prodrugs of Penciclovir," Bioorganic & Medicinal Chemistry, Mar. 1999, 7(3):565-70.
Kim et al., "Synthesis and Evaluation of 2-Amino-9-(1,3-dihydroxy-2-propoxymethyl)-6-fluoropurine Mono—and Diesters as Potential Prodrugs of Ganciclovir," Journal of Medicinal Chemistry, Jan. 1999, 42(2):324-28.
Klumpp et al., "Chapter 20: Discovery and Clinical Evaluation of the Nucleoside Analog Balapiravir (R1626) for the Treatment of HCV Infection," Antiviral Drugs: From Basic Discovery through Clinical Trials, Jun. 20, 2011, pp. 287-304.
Koplon [online], "$37.5 million grant will address research of high-priority infections," UAB News, retrieved on Mar. 13, 2023, URL <https://www.uab.edu/news/health/item/10307-37-5-million-grant-will-address-research-of-high-priority-infections>, Mar. 20, 2019, 1 page.
Moorman et al., "5'-ester prodrugs of the varicella-zoster antiviral agent, 6-methoxypurine arabinoside," Antiviral Chemistry & Chemotherapy, Jun. 1992, 3(3):141-46.
Nilsson et al., "Discovery of 4'-azido-2'-deoxy-2'-C-methyl cytidine and prodrugs thereof: A potent inhibitor of Hepatitis C virus replication," Bioorganic & Medicinal Chemistry Letters, May 2012, 22(9):3265-68.
Remington's Pharmaceutical Science, 17th ed., Gennaro (ed)., 1985, Chapter 68, 58 pages.
Xu et al., "Off-Target In Vitro Profiling Demonstrates that Remdesivir Is a Highly Selective Antiviral Agent," Antimicrobial Agents and Chemotherapy, Jan. 20, 2021, 65(2), 14 pages.
Yan et al., "Advantages of the Parent Nucleoside GS-441524 over Remdesivir for Covid-19 Treatment," ACS Medicinal Chemistry Letters, Jun. 30, 2020, 11(7):1361-1366.
Yan et al., "Gilead should ditch remdesivir and focus on its simpler and safer ancestor," STAT Health Care News, May 14, 2020, 6 pages.
Yan et al., "Pharmacokinetics of 1 Orally Administered GS-441524 in Dogs," bioRxiv Preprint, May 31, 2021, 18 pages.
U.S. Appl. No. 17/458,023, filed Aug. 26, 2021, Byoung-Kwon Chun.
U.S. Appl. No. 18/098,950, filed Jan. 19, 2023, Byoung-Kwon Chun.
fda.gov [online], "Remdesivir by Gilead Sciences: FDA Warns of Newly Discovered Potential Drug Interaction That May Reduce Effectiveness of Treatment," Jun. 15, 2020, retrieved on Sep. 2, 2022, retrieved from URL <https://www.fda.gov/safety/medical-product-safety-information/remdesivir-gilead-sciences-fda-warns-newly-discovered-potential-drug-interaction-may-reduce>, 2 pages.
Khan et al., "Coronaviruses disease 2019 (COVID-19): Causative agent, mental health concerns, and potential management options," Journal of Infection and Public Health, Dec. 2020, 13(12):1840-1844.
Kulli, "K Banhatti Polynomials of Remdesivir, Chloroquine, Hydroxychloroquine: Research Advances for the Prevention and Treatment of COVID-19," SSRG International Journal of Applied Chemistry, May-Aug. 2020, 7(2):48-55.
Liu et al., "Hydroxychloroquine, a less toxic derivative of chloroquine, is effective in inhibiting SARS-CoV-2 infection in vitro," Cell Discovery, Mar. 18, 2020, 6:16, 4 pages.
Owusu et al., "A Comparison Analysis on Remdesivir, Favipiravir, Hydroxychloroquine, Chloroquine and Azithromycin in the Treatment of Corona Virus Disease 2019 (COVID-19)—A Review," World Journal of Pharmacy and Pharmaceutical Sciences, May 2020, 9(5):121-133.
Pizzorno et al., "In vitro evaluation of antiviral activity of single and combined repurposable drugs against SARS-CoV-2," Antiviral Research, Sep. 2020, 181:104878.
Rebeaud et al., "SARS-CoV-2 and the Use of Chloroquine as an Antiviral Treatment," Frontiers in Medicine, Apr. 24, 2020, 7:184, 6 pages.
Wang et al., "Remdesivir in adults with severe COVID-19: a randomised, double-blind, placebo-controlled, multicentre trial," Lancet, Apr. 29, 2020, 395:1569-1578.
Taiwanese Office Action in TW Appln. No. 110122894, dated Aug. 11, 2022, 14 pages (with English search report).
Adlington et al., "Synthesis of novel C-nucleosides with potential applications in combination and parallel synthesis," Tetrahedron Letters, 2000, 41:575-578.
Agostini et al., "Coronavirus Susceptibility to the Antiviral Remdesivir (GS5734) Is Mediated by the Viral Polymerase and the Proofreading Exoribonuclease", MBIO, Mar. 6, 2018, 9(2):1-15.
Alessandrini, et al., Synthesis of Differently Protected 1-C-methyl-ribofuranoses Intermediates for the Preparation of Biologically Active 1'-C-methyl-ribonucleosides, Journal of Carbohydrate Chemistry, 2008, pp. 332-344, vol. 27, No. 5.
Ali, et al., Quantitative structure-activity relationships (QSAR) of two series of O-aryl or N-acyl O-ethyl phosphoramidate and phosphorodiamidate fungicides incorporating amino acid ethyl esters, Bulletin of Environmental Contamination and Toxicology, 2000, pp. 415-420, vol. 65, No. 4.
Anonymous, "Gillings research on broad-spectrum antiviral could aid public health response to coronavirus outbreaks",—UNC Gillings School of Global Public Health, Jan. 10, 2020, retrieved on May 13, 2021, retrieved from URL <"https://sph.unc.edu/sph-news/gillings-research-on-broad-spectrum-antiviral-could-aid-public-health-response-to-coronavirus-outbreaks/">, 5 pages.
Arimilli, et al., Synthesis, In Vitro Biological Evaluation and Oral Bioavailability of 9-[2-(phosphonomethoxy)propyl]adenine (PMPA) Prodrugs, Antiviral Chemistry & Chemotherapy, 1997, pp. 557-564, vol. 8, No. 6.
Asbun, et al., Synthesis of 5-substituted Pyrimidines. II, Journal of Organic Chemistry, 1968, pp. 140-142, vol. 31.
Ballini, et al., Enantioselective Synthesis of the Lactone Moiety of the Mevinic Acids using D-Xylose as a Chiral Precursor, Journal of the Chemical Society, Perkin Transactions 1, 1991, pp. 490-491.
Balzarini, et al., Inhibition of Feline (FIPV) and Human (SARS) Coronavirus by Semisynthetic Derivatives of Glycopeptide Antibiotics, Antiviral Research, 2006, pp. 20-33, vol. 72.
Bandini, et al., Indium tribromide: a highly effective catalyst for the addition of trimethylsilyl cyanide to α-hetero-substituted ketone, Tetrahedron Letters, 2001, pp. 3041-3043. vol. 42.
Barker, et al., 2,3,5-Tri-O-benzyl-D-ribosyl and -L-arabinosyl Bromides, Journal of Organic Chemistry, 1961, pp. 4605-4609, vol. 26, No. 11.
Barl, et al., The halogen/magnesium-exchange using iPrMgCl•LiCl and related exchange reagents, Heterocycles, Jan. 2014, pp. 827-844, vol. 88, No. 2.
Beer et al., "Characteristics of Filoviridae: Marburg and Ebola Viruses," Naturwissenschaften, 1999, 86:8-17.
Behzadi et al., "Overview of Current Therapeutics and Novel Candidates Against Influenza Respiratory Syncytial Virus, and Middle East Respiratory Syndrome Coronavirus Infections," Frontiers in Microbiology, Jun. 2019, 10:1327, pp. 1-16.
Belokon et al., "Optimized catalysts for the asymmetric addition of trimethylsilyl cyanide to aldehydes and ketones," Tetrahedron, 2001, 57: 771-779.

(56) References Cited

OTHER PUBLICATIONS

Benksim et al., "A Novel Stereospecific Synthesis of Glycosyl Cyanides from 1,2-O-sulfinyl Derivatives," Organic Letters, 2004, 6(22): 3913-3915.
Benzaria et al., "Synthesis, In Vitro Antiviral Evaluation, and Stability Studies of Bis(S-acyl-2-thioethyl) Ester Derivatives of 9-[2-(phosphonomethoxy)ethyl]adenine (PMEA) as Potential PMEA prodrugs with Improved Oral Bioavailability," J. Med. Chem., 1996, 39(25): 4958-4965.
Bio et al., "Practical Synthesis of a Potent Hepatitis C Virus RNA Replication Inhibitor," J. Org. Chem., 2004, 69(19): 6257-6266.
Bobeck et al., "Advances in Nucleoside Monophosphate Prodrugs as Anti-HCV Agents," Antiviral Therapy, 2010, 15: 935-950.
Bobrowski et al., "Synergistic and Antagonistic Drug Combinations against SARS-CoV-2", Molecular Therapy, Feb. 2021, 29(2):873-885.
Bojack, et al., Design and Synthesis of Inhibitors of Adenosine and AMP Deaminases, Organic Letters, 2001, pp. 839-842, vol. 3, No. 6.
Bowie et al., "RIG-I: tri-ing to discriminate between self and non-self RNA," Trends in Immunology, Apr. 2007, 28(4): 147-150.
Boyer, et al., Pathogenesis, diagnosis and management of hepatitis C, Journal of Hepatology, 2000, pp. 98-112, vol. 32.
Bozza, Zika Outbreak, Brazil 2015, ISARIC, 2015, 28 pages.
Bradley et al., "The Management of Community-Acquired Pneumonia in Infants and Children Older Than 3 Months of Age: Clinical Practice Guidelines by the Pediatric Infectious Diseases Society and the Infectious Diseases Society of America", Pediatric Community Pneumonia Guidelines, Clinical Infectious Diseases, Oct. 2011, 53(7):e25-e76.
Brands et al., "Crystallization-Induced Diastereomer Transformations," Chem. Rev., 2006, 106(7): 2711-2733.
Brittain, Polymorphism in Pharmaceutical Solids, 2nd Edition, 2009, pp. 183-226, Informa Healthcare USA, Inc.
Brotschi et al., "Bipyridyl and biphenyl DNA: A recognition motif based on interstrand aromatic stacking," Chemistry—A European Journal, 2005, 11(6):1911-1923.
Brown et al., "Broad spectrum antiviral remdesivir inhibits human endemic and zoonotic deltacoronaviruses with a highly divergent RNA dependent RNA polymerase", Antiviral Research, Jun. 21, 2019, 169:1-31.
Brown, "Progress towards improving antiviral therapy for hepatitis C virus polymerase inhibitors", Part O: Nucleoside analogues, 2009, 18: 709-725.
Bullard-Feibelman et al., "The FDA-approved drug Sofosbuvir inhibits Zika Virus infection," Antiviral Res., Jan. 1, 2018, 137: 134-140.
Burns, "A Glimmer of Hope for Fatal Feline Disease," JAVMAnews, Dec. 15, 2017, 5 pages.
Butora et al., "Synthesis and HCV inhibitory properties of 9-deaza- and 7,9-dideaza-7-oxa-2'-C-methyladenosine," Bioorganic & Medicinal Chemistry, 2007, 15(15): 5219-5229.
Cabirol et al., Robust and Efficient, yet Uncatalyzed, Synthesis of Triarylsilyl-protected Cyanohydrins from Ketones, 2008, pp. 2446-2449, vol. 73.
Caira, "Crystalline Polymorphism of Organic Compounds," Topics in Current Chemistry, 1998, 198: 163-208.
Cales et al., "Treatment of liver fibrosis: clinical aspects," Gastroentérologie Clinique et Biologique, 2009, 33(10-11): 958-966.
Calisher et al., "Antigenic Relationships between Flaviviruses as Determined by Cross-neutralization Tests with Polyclonal Antisera," Journal of General Virology, 1989, 70: 37-43.
Camps, "Studies on Structurally Simple -αβ-butenolides-II," Tetrahedron, 1982, 38(15): 2395-2402.
Carey et al., "Addition, Condensation and Substitution Reactions of Carbonyl Compounds," Advanced Organic Chemistry: Part B: Reaction and Synthesis, Springer Science & Business Media, 2007, pp. 629-711.

Carroll, "Robust Antiviral Efficacy upon Administration of a Nucleoside Analog to Hepatitis C Virus-Infected Chimpanzees," Antimicrobial Agents and Chemotherapy, 2009, 53(3): 926-934.
Carryer et al., "The effect of cortisone on bronchial asthma and hay fever occurring in subjects sensitive to ragweed pollen", Journal of Allergy, Jul. 1950, 21(4): 282-287.
CAS No. 1476-52-4, "Desethyl Chloroquine", ChemSRc, retrieved on Jul. 29, 2021, retrieved from URL <"https://www.chemsrc.com/en/cas/1476-52-4_1032909.html">, 5 pages.
CAS No. 4298-15-1, "2-[4-[(7-chloroquinolin-4-yl)amino]pentylamino]ethanol", ChemSRc, retrieved on Jul. 29, 2021, retrieved from URL <"https://www.chemsrc.com/en/cas/4298-15-1_589766.html">, 4 pages.
CAS No. 54-05-7, "Chloroquine", ChemSRc, retrieved on Jul. 29, 2021, retrieved from URL <"https://www.chemsrc.com/en/cas/54-05-7_419322.html">, 16 pages.
CAS Registry No. 1809249-37-3, "L-Alanine, N-[(S)-hydroxyphenoxyphosphinyl]-, 2-ethylbutyl ester, 6-ester with 2-C-(4-aminopyrrolo[2,1-f][1,2,4]triazin-7-yl)-2,5-anhydro-D-altrononitrile", American Cemical Society, retrieved on Jul. 27, 2021, retrieved from URL <"https://commonchemistry.cas.org/detail?cas_rn=1809249-37-3">, 3 pages.
Chapman et al., "RSV604, a Novel Inhibitor of Respiratory Syncytial Virus Replication," Antimicrobial Agents and Chemotherapy, 2007, 51(9): 3346-3353.
Cho et al., "Discovery of the First C-Nucleoside HCV Polymerase Inhibitor (GS-6620) with Demonstrated Antiviral Response in HCV Infected Patients," J. Med. Chem., 2014, 57(5): 1812-1825.
Cho et al., "Synthesis and antiviral Activity of a Series of 1'-Substituted 4-aza-7,9-dideazaadenosine C-Nucleosides", Bioorganic & Medicinal Chemistry Letters, 2012, 22(8):2705-2707.
Cihlar et al., "Design and Profiling of GS-9148, a Novel Nucleotide Analog Active against Nucleoside-resistant Variants of Human Immunodeficiency Virus Type 1, and Its Orally Bioavailable Phosphonoamidate Prodrug, GS-9131," Antimicrobial Agents and Chemotherapy, 2008, 52(2): 655-665.
Clark et al., "Design, Synthesis, and Antiviral Activity of 2'-Deoxy-2'-fluoro-2'-C-methylcytidine, a Potent Inhibitor of Hepatitis C Virus Replication," Journal of Medicinal Chemistry, 2005, 48(17): 5504-5508.
Clarke et al., "Discovery of beta-D-2'-Deoxy-2'-alpha-Fluoro-4'-alpha-Cyano-5-aza-7,9-Dideaza Adenosine as a Potent Nucleoside Inhibitor of Respiratory Syncytial Virus with Excellent Selectivity Over Mitochondrial RNA and DNA Polymerases," Bioorganic & Medicinal Chemistry Letters, Apr. 29, 2015, 25: 2484-2487.
Colacino et al., "Synthesis and Biological Evaluation of Some 5-Nitro- and 5-Amino Derivatives of 2'-Deoxycytidine, 2',3'-Dideoxyuridine, and 2',3'-Dideoxycytidine," Nucleoside, Nucleotides & Nucleic Acids, 2003, 22(11): 2013-2026.
Cox et al., "Therapeutically administered ribonucleoside analogue MK-4482/EIDD-2801 blocks SARS-CoV-2 transmission in ferrets," Nature Microbiology, 2020, 6(1): 11-18.
Dai et al., "Synthesis of 2'-C-β-Fluoromethyluridine," Organic Letters, 2003, 5(6): 807-810.
Damont et al., "Synthesis of 1'-C-Fluoromethyladenosine," Nucleosides, Nucleotides, and Nucleic Acids, 2007, 26:1431-1434.
De Clercq, "Antiviral Drugs: Current State of the Art," J. Clin. Virol., 2001, 22(1):73-89.
De Clercq, "Molecular Targets for Antiviral Agents," The Journal of Pharmacology and Experimental Therapeutics, 2001, 297(1): 1-10.
De Francesco et al., "Approaching a New Era for Hepatitis C Virus Therapy: Inhibitors of the NS3-4A Serine Protease and the NS5B RNA-Dependent RNA Polymerase," Antiviral Research, 2003, 58(1): 1-16.
De Las Heras, "Synthesis of Ribosyl and Arabinosyl Cyanides by Reaction of 1-O-Acyl Sugars with Trimethylsilyl Cyanide," Journal of the Chemical Society, Perkin Transactions 1, 1982, pp. 903-907.
De Lombaert et al., "N-Phosphonomethyl Dipeptides and Their Phosphonate Prodrugs, a New Generation of Neutral Endopeptidase (NEP, EC 3.4.24.11) Inhibitors," J. Med. Chem., 1994, 37(4): 498-511.
Di Bisceglie et al., "The Unmet Challenges of Hepatitis C," Scientific American, Oct. 1999, pp. 80-85.

(56) References Cited

OTHER PUBLICATIONS

Dinnon et al., "A mouse-adapted model of SARS-CoV-2 to test COVID-19 countermeasures," Nature, Aug. 2020, 586: 560-566.
Dolzhenko et al., "Pyrazolo[1,5-a][1,3,5]Triazines(5-Aza-9-Deazapurines): Synthesis and Biological Activity," Heterocycles, 2008, 75(7): 1575-1622.
Domingo et al., "The quasispecies (extremely heterogeneous) nature of viral RNA genome populations: biological relevance—a review," Gene, 1985, 40: 1-8.
Dondoni et al., "Thiazole-Based Synthesis of Formyl C-Glycosides," Journal of Organic Chemistry, 1994, 59: 6404-6414.
Dudfield et al., "Synthesis of C-ribosyl imidazo[2,1-f][1,2,4]triazines as inhibitors of adenosine and AMP deaminases," J. Chem. Soc, Perkin Trans I, 1999, pp. 2929-2936.
Dudfield et al., "Synthesis of C-ribosyl 1,2,4-triazolo[3,4-f][1,2,4]triazines as Inhibitors of Adenosine and AMP Deaminasses," J. Chem. Soc., Perkin Trans. 1, 1999, pp. 2937-2942.
Durcan et al., "Hydroxychloroquine Blood Levels in Systemic Lupus Erythematosus: Clarifying Dosing Controversies and Improving Adherence", Journal of Rheumatology, 2015, 42(11):2092-2097.
Dymock et al., "Novel approaches to the treatment of hepatitis C virus infection," Antiviral Chemistry & Chemotherapy, 2000, 11(2): 79-96.
El Safadi et al., "5-Modified-2'-dU and 2'-dC as Mutagenic Anti HIV-1 Proliferation Agents: Synthesis and Activity," Journal of Medicinal Chemistry, 2010, 53(4): 1534-1545.
Farquhar et al., "Biologically Reversible Phosphate-Protective Groups," Journal of Pharmaceutical Sciences, 1983, 72(3): 324-325.
Fauquet et al., "Abbreviations for vertebrate virus species names", Archives of Virology, Dec. 31, 1999, pp. 1865-1880.
Flint et al., "Functional analysis of cell surface-expressed hepatitis C virus E2 glycoprotein," J. Virol., Aug. 1999, 73(8): 6782-6790.
Foster et al., "Deuterium isotope effects in studies of drug metabolism," Trends in Pharmacological Sciences, Jan. 1984, 5:524-527.
Franchetti et al., "Antitumor Activity of C-Methyl-β-D-ribofuranosyladenine Nuceoside Ribonuceotide Reductase Inhibitors," J. Med. Chem. 2005, 48: 4983-4989.
Freeman et al., "3 Prodrug Design for Phosphates and Phosphonates," Progress in Medicinal Chemistry, 1997, 34: 111-147.
Fukumoto et al., "Viral Dynamics of Hepatitis C Early After Orthotopic Liver Transplantation: Evidence for Rapid Turnover of Serum Virions," Hepatology, 1996, 24: 1351-1354.
Garcia et al., "Synthesis of (2,3,4,6-tetra-O-acetyl-alpha-D-glycopyranosyl)thiophene derivatives as new C-nucleoside analogues," J. Carbohydrate Chemistry, 2001, 20(7/8): 681-687.
Gardelli et al., "Phosphoramidate Prodrugs of 2'-C-Methylcytidine for Therapy of Hepatitis C Virus Infection," Journal of Medicinal Chemistry, 2009, 52(17): 5394-5407.
George et al., "Preparation of silyl- and germylmetallic compounds," Journal of the American Chemical Society, Jan. 1960, 82(2):403-6.
Gleeson et al., "Prediction of the Potency of Inhibitors of Adenosine Deaminase by QM/MM Calculations," Chem. Commun., 2003, pp. 2180-2181.
Gordon et al., "Remdesivir is a direct-acting antiviral that inhibits RNA-dependent RNA polymerase from severe acute respiratory syndrome coronavirus 2 with high potency," J. Biol. Chem., 2020, 295(20):6785-6797.
Gordon et al., "The antiviral compound remdesivir potently inhibits RNA-dependent RNA polymerase from Middle East respiratory syndrome coronavirus," Journal of Biol. Chemistry, 2020, 295(15):4773-4779.
Gordon et al., Control of Hepatitis C: A Medicinal Chemistry Perspective, J. Med. Chem., 2005, pp. 1-20, vol. 48, No. 1.
Greene et al., "Protective Groups in Organic Synthesis," John Wiley & Sons., 1991, pp. 118-142.
Greene et al., "Protective Groups in Organic Synthesis," published by John Wiley & Sons, v Inc., 1991, pp. 1-4, 10-14, 47-53 and 100-103.

Grein et al., "Compassionate Use of Remdesivir for Patients with Severe Covid-19", The New England Journal of Medicine, Apr. 2020, 382(24): 2327-2336.
Gudmundsson et al., "Synthesis of imidazo[1,2-a]pyridine C-Nucleosides with an Unexpected Site of Ribosylation," Journal of Organic Chemistry, 1997, 62: 3453-3459.
Gudmundsson et al., "The Condensation of 2,6-dichloroimidazo[1,2-a]pyridine C-nucleoside with an Unexpected Site of Ribosylation," Tetrahedron Letters, 1996, 7(14): 2365-2368.
Gunic et al., "Cyclic monophosphate prodrugs of base-modified 2'-C-methyl ribonucleosides as potent inhibitors of hepatitis C virus RNA replication," Bioorganic & Medicinal Chemistry Letters, 2007, 17: 2452-2455.
Hamann et al., "Synthesis and antiviral evaluation of 7,9-dideaza-8-thiapurine C-nucleoside derivatives," Collection Symposium Series, 2008, 10: 347-349.
Hamann et al., "Synthesis and antiviral evaluation of thieno[3,4-d]pyrimidine C-nucleoside analogues of 2',3'-dideoxy- and 2',3'-dideoxy-2',3'-didehydro-adenosine and -inosine," Bioorganic & Medicinal Chemistry, 2009, 17: 2321-2326.
Han et al., "Synthesis of 1-Chloroacetyl-1-dehydroxy-2, 3,5-tri-O-benzoyl-β-D-ribofuranose. A Potentially Versatile Intermediate for the Synthesis of C-Nucleosides," Synthetic Communications, 1992, 22(19): 2815-2822.
Haraguchi et al., "Stereoselective Synthesis of 1'-C-Branched Uracil Nucleosides From Uridine," Nucleosides & Nucleotides, 1995, 14(3-5): 417-420.
Harcourt et al., "Molecular Characterization of the Polymerase Gene and Genomic Termini of Nipah Virus," Virology, 2001, 287: 192-201.
Harki et al., "Synthesis and Antiviral Activity of 5-Substituted Cytidine Analogues: Identification of Potent Inhibitor of Viral RNA-Dependent RNA Polymerases," Journal of Medicinal Chemistry, 2006, 49(21): 6166-6169.
Hayashi et al., "C-Nucleosides, A Synthesis of 2-Substituted 7-(b-D-Ribofuranosyl)-Pyrrolo[2,1-f]-1,2,4-Triazines. A New Type of "Purine Like" C-Nucleoside," Heterocycles, 1992, 34(3): 569-574.
Hecker et al., "Liver Targeted Prodrugs of 2'-C-Methyladenosine for Therapy of Hepatitis C Virus Infection," J. Med. Chem., 2007, 50(16): 3891-3896.
Hoffmann et al., "When, in the context of drug design, can a fluorine atom successfully substitute a hydroxyl group?," International Journal of Quantum Chemistry, 2002, 89: 419-427.
Holshue et al., "First Case of 2019 Novel Coronavirus in the United States", The New England Journal of Medicine, Jan. 2020, 9 pages.
Huang et al., "Recent development of therapeutics for chronic HCV infection," Antiviral Research, Sep. 2006, 71(2-3): 351-362.
Itoh et al., "Divergent and Stereocontrolled Approach to the Synthesis of Uracil Nucleosides Branched at the Anomeric Position," J. Org. Chem, 1995, 60: 656-662.
Jasko et al., "5'-Phosphonates of Ribonucleosides and 2'-Deoxyribonucleosides: Synthesis and Antiviral Activity," Nucleosides & Nucleotides, 1993, 12(8): 879-893.
Kabat et al., "Nucleosides, CXLVIII, Synthesis of 6-(β-D-Ribofuranosyl)picolinamide: A Novel C-Nucleoside from D-Ribonolactone", Chemical & Pharmaceutical Bulletin, 1988, pp. 634-640, vol. 36, No. 2.
Kaewkhao et al., "High sensitivity methods to quantify chloroquine and its metabolite in human blood samples using LC-MS/MS", Bioanalysis, Mar. 2019, 11(5):333-347.
Kalil et al., "Baricitinib plus Remdesivir for hospitalized adults with Covid-19," New England Journal of Medicine, Dec. 11, 2020, 13 pages.
Khamnei et al., "Neighboring Group Catalysis in the Design of Nucleotide Prodrugs," J. Med. Chem., 1996, 39(20): 4109-4115.
Kim et al., "Reversal of the Progression of Fatal Coronavirus Infection in Cats by a Broad-Spectrum Coronavirus Protease Inhibitor," PLOS Pathogens, Mar. 30, 2016, 18 pages.
Klumpp et al., "The Novel Nucleoside Analog R1479 (4'-Azidocytidine) is a Potent Inhibitor of NS5B-dependent RNA Synthesis and Hepatitis C virus Replication in Cell Culture," Journal of Biological Chemistry, 2006, 281(7): 3793-3799.

(56) References Cited

OTHER PUBLICATIONS

Knaggs et al., A QSAR Study Investigating the Effect of L-Alanine Ester Variation on the Anti-HIV Activity of Some Phosphoramidate Derivatives of d4T, Bioorganic & Medicinal Chemistry Letters, 2000, 10: 2075-2078.
Knutsen et al., "Synthesis of Imidazo-fused Bridgehead-nitrogen C-Nucleosides : Coupling-Elimination Reactions of 2,5-Anhydro-3,4,6-tri-O-benzoyl-D-allonic Acid," J. Chem. Soc. Perkin Trans I, 1985, pp. 621-630.
Knutsen et al., "Synthesis of Imidazo-fused Bridgehead-nitrogen C-Nucleosides via Dehydrative Coupling Reactions of 2,5-Anhydro-3,4,6-tri-O-benzoyl-D-allonic Acid," J. Chem. Soc. Perkin Trans I, 1984, pp. 229-238.
Kobe et al., "Use of Distance Geometry Approach for the In Vitro Antiviral Activity Evaluation of N-bridgehead C-nucleosides," European J. Med. Chem., 1992, 27(3): 259-266.
Kushner et al., "Pharmacological uses and perspectives of heavy water and deuterated compounds," Canadian Journal of Physiology and Pharmacology, Feb. 1999, 77(2):79-88.
Kuzik et al., "Nebulized Hypertonic Saline in the Treatment of Viral Bronchiolitis in Infants", The Journal of Pediatrics, Sep. 2007, 151(3):266-270.e1.
Lefebvre et al., "Mononucleoside Phosphotriester Derivatives with S-Acyl-2-thioethyl Bioreversible Phosphate-Protecting Groups: Intracellular Delivery of 3'-Azido-2',3'-dideoxythymidine 5'-Monophosphate," Journal of Medicinal Chemistry, 1995, 38(20): 3941-3950.
Lefebvre et al., "Synthesis, Decomposition Pathways and 'In Vitro' Evaluation of Bioreversible Phosphotriesters of Azt, Nucleosides," Nucleotides & Nucleic Acids, 1995, 14(3-5): 763-766.
Leyssen et al., "Molecular strategies to inhibit the replication of RNA Viruses," Antiviral Research, 2008, 78:9-25.
Lindell et al., "Synthesis and Biochemical Testing of 3-(Carboxyphenylethyl)imidazo[2,1-f][1,2,4]triazines as Inhibitors of AMP Deaminase," ACS Medicinal Chemistry Letters, 2010, 1(6): 286-289.
Lo et al., "GS-5734 and its parent nucleoside analog inhibit Filo-, Pneumo-, and Paramyxoviruses," Scientific Reports, 2017, 7(43395):1-7.
Lovelette, "1,2,4-Triazines. Synthesis of selected members of the s-triazolo[3,4-f][1,2,4]triazine and tetrazolo[1,5-f][1,2,4]triazine ring systems," Journal of Heterocyclic Chemistry, 1979, 16: 555-560.
Lu, Chengping, Veterinary Microbiology 5th edition, Jan. 31, 2013, p. 431, China Agriculure Press (No English Translation available).
Martell et al., "Hepatitis C Virus (HCV) Circulates as a Population of Different but Closely Related Genomes: Quasispecies Nature of HCV Genome Distribution," Journal of Virology, 1992, 6695: 3225-3229.
Martin et al., "Hint2, A Mitochondrial Apoptotic Sensitizer Down-Regulated in Hepatocellular Carcinoma," Gastroenterology, Jun. 2006, 130(7):2179-2188.
Mason et al., "Polyadenylation-dependent screening assay for respiratory syncytial virus RNA transcriptase activity and identification of an inhibitor," Nucleic Acids Research, 2004, 32(16): 4758-4767.
Matulic-Adamic et al., "Synthesis of 3-(β-D-Ribofuranosyl)-2-Fluoropyridine and 3-(β-D-Ribofuranosyl)-Pyridin-2-one," Tetrahedron Letters, 1997, 38(2): 203-206.
Matulic-Adamic et al., "Synthesis of 5-(β-D-Ribofuranosyl)-Pyridin-2-one: a 'Deletion-Modified' Analogue of Uridine," Tetrahedron Letters, 1997, 38(10): 1669-1672.
McGuigan et al. "Application of Phosphoramidate ProTide Technology Significantly Improves Antiviral Potency of Carbocyclic Adenosine Derivatives," J. Med. Chem., 2006, 49: 7215-7226.
McGuigan et al., "Aryl Phosphoramidate Derivatives of d4T Have Improved Anti-HIV Efficacy in Tissue Culture and May Act by the Generation of a Novel Intracellular Metabolite," J. Med. Chem., 1996, 39: 1748-1753.
McGuigan et al., "Design, synthesis and biological evaluation of phosphorodiamidate prodrugs of antiviral and anticancer nucleosides," European Journal of Medical Chemistry, 2013, 70:326-340.
McGuigan et al., "Intracellular Delivery of Bioactive AZT Nucleotides by Aryl Phosphate Derivatives of AZT," J. Med. Chem., 1993, 36(8): 1048-1052.
Mehellou et al., "Aryloxy Phosphoramidate Triesters: a Technology for Delivering Monophosphorylated Nucleosides and Sugars into Cells," ChemMedChem, 2009, 4:1779-1791.
Meppen et al., "Cyclic phosphoramidates as prodrugs of 2'-C-methylcytidine," European Journal of Medicinal Chemistry, 2009, 49(9): 3765-3770.
Meppen et al., "Medi-404—A Prodrug Approach for the Treatment of HCV Infection," Abstracts of papers, 236th ACS National Meeting, Philadelphia, PA, United States, Aug. 17-21, 2008, 1 page.
Metobo et al., "Practical synthesis of 1'-substituted Tubercidin C-nucleoside analogs," Tetrahedron Letters, Feb. 2012, 53(5): 484-486.
Migliaccio et al., "Characterization of Resistance to Non-obligate Chain-terminating Ribonucleoside Analogs That Inhibit Hepatitis C Virus Replication in vitro," The Journal of Biological Chemistry, 2003, 278(49): 49164-49170.
Mitchell et al., "Bioreversible Protection for the Phospho Group: Bioactivation of the Di(4-acyloxybenzyl) and Mono(4-acyloxybenzyl) Phosphoesters of Methylphosphonate and Phosphonoacetate," J. Chem. Soc., Perkin Trans. 1, 1992, pp. 2345-2353.
Mitchell et al., "Synthesis of C-Nucleoside Isosteres of 9-(2-Hydroxyethoxymethyl)guanine (Acyclovir)," J. Het. Chem., 1984, 21(3): 697-699.
Moennig et al., "The Pestiviruses", Advances in Virus Research, 1992, 41: 53-98.
Moradpour et al., "Replication of hepatitis C virus," Nature Reviews Microbiology, 2007, 5(6): 453-463.
Morris, "Mechanisms of action and therapeutic role of corticosteroids in asthma", J. Allergy Clin. Immunol., Jan. 1985, 75(1 Pt):1-13.
Moscow et al., "Reduced Folate Carrier Gene (RFC1) Expression and Anti-Folate Resistance in Transfected and Non-Selected Cell Lines," International Journal of Cancer, 1997, 72: 184-190.
Mossel et al., "Exogenous ACE2 expression allows refractory cell lines to support severe acute respiratory syndrome coronavirus replication," Journal of Virology, Mar. 15, 2005, 79(6):3846-50.
Munster et al., "Hydroxychloroquine concentration—response relationships in patients with rheumatoid arthritis", Arthritis Rheumatology, Jun. 2002, 46(6):1460-1469.
Murakami et al., "Mechanism of Activation of Beta-D-2'-Fluoro-2'-C-Methylcytidine and Inhibition of Hepatitis C Virus NS5B RNA Polymerase", Antimicrob Agents Chemother., Feb. 2007, 51(2):503-509.
Murakami et al., "Mechanism of Activation of PSI-7851 and Its Diastereoisomer PSI-7977", The Journal of Biological Chemistry, 2010, 285(45):34337-34347.
Murphy et al., "The Nucleoside Analog GS-441524 Strongly Inhibits Feline Infectious Peritonisitis (FIP) Virus in Tissue Culture and Experimental Cat Infection Studies", Veterinary Microbiology, 2018, 219:226-233.
Neumann et al., "Hepatitis C Viral Dynamics in Vivo and the Antiviral Efficacy of Interferon-α Therapy", Science, 1998, 282:103-107.
Nishimura et al., "Synthesis of pyrrolo[2,1-f][1,2,4]triazine C-nucleosides. Isosteres of sangivamycin, tubercidin, and toyocamycin," Carbohydrate Research, 2001, 331: 77-82.
Ogura et al., "Reaction of Ethynyl Compounds with Lactones," Journal of Organic Chemistry, 1972, 37(1): 72-75.
Olsen et al., "A 7-Deaza-Adenosine Analog Is a Potent and Selective Inhibitor of Hepatitis C Virus Replication with Excellent Pharmacokinetic Properties," Antimicrobial agents and Chemotherapy, 2004, 3944-3953.
Otter et al., "Conformational Properties of Purine-Like C-Nucleosides," Nucleosides & Nucleotides, 1996, 15(1-3): 793-807.
Pankiewicz et al., "C-Nucleoside Analogues of Nicotinamide Mononucleotide (NMN)," Nucleosides and Nucleotides, 1988, 7(5 &6): 589-593.
Pankiewicz et al., "Efficient Synthesis of 5-(β-D-Ribofuranosyl)nicotinamide and its α-Isomer," Journal of Organic Chemistry, 1988, 53: 3473-3479.

(56) References Cited

OTHER PUBLICATIONS

Patani et al., "Bioisosterism: a rational approach in drug design," Chem. Rev., 1996, 96:3147-3176.
Patil et al., "4-Aza-7,9-Dideazaadenosine, a New Cytotoxic Synthetic C-Nucleoside Analogue of Adenosine, " Tetrahedron Letters, 1994, 35(30): 5339-5342.
Patil et al., "C-Glycosylation of Substituted Heterocycles under Friedel—Crafts Conditions (II): Robosylation of Multi-Functionalized Thiophenes and Furans for the Synthesis of Purine-Like C-Nucleosides," Nucleosides & Nucleotides, 1990, 9(7): 937-956.
Patil et al., "Synthesis of Pyrrolo[2,1-f][1,2,4]triazine Congeners of Nucleic Acid Purines via the N-Amination of 2-Substituted Pyrroles," J. Het. Chem., 1994, 31: 781-786.
Patil et al., "Synthesis of some new thieno[3,4-d]pyrimidines and their C-nucleosides," Journal of Heterocyclic Chemistry, 1993, 30(2): 509-515.
Pelet et al., "High throughput screening assay for negative single stranded RNA virus polymerase inhibitors," J. Virol. Methods, Sep. 2005, 128(1-2): 29-36.
Perrone et al., "Application of the Phosphoramidate ProTide Approach to 4'-Azidouridine Confers Sub-micromolar Potency versus Hepatitis C Virus on an Inactive Nucleoside", Journal of Medicinal Chemistry, 2007, 50(8):1840-1849.
Perrone et al., "First Example of Phosphoramidate Approach Applied to a 4'-Substituted Purine Nucleoside (4'-Azidoadenosine): Conversion of an Inactive Nucleoside to a Submicromolar Compound versus Hepatitis C Virus," Journal of Medicinal Chemistry, Oct. 2007, 50(22): 5463-5470.
Peterson et al., "Prodrug approaches to improving the oral absorption of antiviral nucleotide analogues," Expert Opinion, Drug Deliv., 2009, 6(4): 405-420.
Piccirilli et al., "A Direct Route to 3-(D-Ribofuranosyl)pyridine Nucleosides," Helvetica Chimica Acta, 1991, 74: 397-406.
Pierra et al., "Synthesis and Pharmacokinetics of Valopicitabine (NM283), and Efficient Prodrug of the Potent Anti-HCV Agent 2'-C-Methylcytidine," Journal of Medicinal Chemistry, 2006, 49(22): 6614-6620.
Poduch et al., "Design of Inhibitors of Orotidine Monophosphate Decarboxylase Using Bioisosteric Replacement and Determination of Inhibition Kinetics," Journal of Medicinal Chemistry, 2006, 49(16): 4937-4945.
Porter et al., "Zika virus, drug discovery, and student projects," ScienceBlogs, Mar. 9, 2016, 7 pages.
Pruijssers et al., "Remdesivir Inhibits SARS-CoV-2 in Human Lung Cells and Chimeric SARS-CoV Expressing the SARS-CoV-2 RNA Polymerase in Mice," Cell Reports, 2020, 32(107940):1-16.
Puech et al., "Intracellular Delivery of Nucleoside Monophosphates through a Reductase-mediated Activation Process," Antiviral Research, 1993, 22(4): 155-174.
Ramasamy et al., "Synthesis and Antitumor Activity of Certain 3-B-D-Ribofuranosyl-1,2,4-triazolo[3,4-f]-1,2,4-triazines Related to Formycin Prepared via Ring Closure of a 1,2,4-Triazine Precursor," J. Med. Chem., 1986, 29(11): 2231-2235.
Rao et al., "C-Glycosylation of Substituted Heterocycles under Friedel-Crafts Conditions (I): A Two-Step Synthesis of the Thieno[3,4-d]Pyrimidine C-Nucleoside Analog of Inosine," Tetrahedron Letters, 1988, 29(29): 3537-3540.
Reddy et al., "Stereoselective Synthesis of Nucleoside Monophosphate HepDirectTM Prodrugs," Tet. Lett., 2005, 46: 4321-4324.
Ross et al., "Synthesis of Diastereomerically Pure Nucleotide and Phosphoramidates," J. Org. Chem., 2011, 76: 8311-8319.
Sacramento et al., "The clinically approved antiviral drug Sofosbuvir inhibits Zika Virus replication," Nature, Jan. 18, 2017, 7: 40920, 12 pages.
Sahakijpijarn et al., "Development of Remdesivir as a Dry Powder for Inhalation by Thin Film Freezing," Pharmaceutics, Oct. 2020, 12(11):1002, 27 pages.
Schnirring, "China releases genetic data on new coronavirus, now deadly," CIDRAP News, Jan. 2020, retrieved on Mar. 15, 2022, retrieved from URL <https://www.cidrap.umn.edu/news-perspective/2020/01/china-releases-genetic-data-new-coronavirus-now-deadly>, 3 pages.
Schul et al., "A Dengue Fever Viremia Model in Mice Shows Reduction in Viral Replication and Suppression of the Inflammatory Response after Treatment with Antiviral Drugs," Journal of Infectious Diseases, 2007, 195: 665-674.
Schultz, "Prodrugs of Biologically Active Phosphate Esters," Bioorganic & Medicinal Chemistry, 2003, 11: 885-898.
Scott et al., "Interferon-a-2b Plus Ribavirin: A Review of its Use in the Management of Chronic Hepatitis C," Drugs, 2002, 62(3): 507-556.
Sheahan et al., "Broad-spectrum antiviral GS-5734 inhibits both epidemic and zoonotic coronaviruses", Science Translational Medicine, Jun. 2017, 9(396):eaal3653, 11 pages.
Sheahan et al., "Comparative therapeutic efficacy of remdesivir and combination lopinavir, ritonavir, and interferon beta against MER-CoV," Nature Communications, 2020, 11(222):1-14.
Sheahan, "Preparing for future pandemics, today with broad-spectrum antivirals", Nature Portfolio Microbiology Community, Jan. 10, 2020, retrieved on May 13, 2021, retrieved from URL <"https://naturemicrobiologycommunity.nature.com/posts/58125-preparing-for-future-pandemics-today-with-broad-spectrum-antivirals", 13 pages.
Shekunov et al., "Crystallization processes in pharmaceutical technology and drug delivery design," Journal of Crystal Growth, 2000, 211: 122-136.
Shi et al., "Synthesis and anti-viral activity of a series of d- and 1-2'-deoxy-2'-fluororibonucleosides in the subgenomic HCV replicon system," Bioorganic & Medicinal Chemistry, Mar. 2005, 13(5):1641-1652.
Siegel et al., "Discovery and Synthesis of a Phosphoramidate Prodrug of a Pyrrolo[2,1-f][triazin-4-amino] Adenine C-Nucleoside (GS-5734) for the Treatment of Ebola and Emerging Viruses," J. Med. Chem., 2017, 60, 5, 1648-1661 Supplementary Material.
Siegel et al., "Discovery and Synthesis of a Phosphoramidate Prodrug of a Pyrrolo[2,1-f][triazin-4-amino] Adenine C-Nucleoside(GS-5734) for the Treatment of Ebola and Emerging Viruses", Journal of Medicinal Chemistry, 2017, 60(5): 1648-1661.
Silverman et al., "The Organic Chemistry of Drug Design and Drug Action," Elsevier Science, 1992, pp. 19-23.
Silverman, "The Organic Chemistry of Drug Design and Drug Action," Elsevier Science, 2nd Ed., 2004, pp. 29-34.
Sofia et al., "Discovery of a β-d-2'-Deoxy-2'-α-fluoro-2'-β-C-methyluridine Nucleotide Prodrug (PSI-7977) for the Treatment of Hepatitis C Virus," Journal of Medicinal Chemistry, Sep. 2010, 53(19):7202-7218.
Srivastav et al., "Antiviral Activity of Various 1-(2'-Deoxy-β-D-lyxofuranosyl), 1-(2'-Fluoro-β-D-xylofuranosyl), 1-(3'-Fluor-β-D-arabinofuranosyl), and 2'-Fluoro-2',3'-didehydro-2',3'-dideoxyribose Pyrimidine Nucleoside Analogues against Duck Hepatitis B Virus (DHBV) and Human Hepatitis B Virus (HBV) Replication," Journal of Medicinal Chemistry, 2010, 53(19): 7156-7166.
Stein et al., "Phosphorylation of Nucleoside Analog Antiretrovirals: A Review for Clinicians," Pharmacotherapy, Jan. 2001, 21(1):11-34.
Stella et al., "Cyclodextrins," Toxicologic Pathology, 2008, 36(1):30-42.
Streetman, "Drug Interaction Concerns for COVID-19 Treatments", Wolters Kluwer, Apr. 15, 2020, retrieved on Sep. 7, 2021, retrieved from URL <"https://www.wolterskluwer.com/en/expert-insights/drug-interaction-concerns-for-covid-19-treatments">, 10 pages.
Sun, "Remdesivir for Treatment of COVID-19: Combination of Pulmonary and IV Administration May Offer Additional Benefit", The AAPS Journal, 2020, 22(77):1-6.
Szente et al., "Sulfobutylether-beta-cyclodextrin-enabled antiviral remdesivir: Characterization of electrospun- and lyophilized formulations," Carbohydrate Polymers, 2021, 264:118011, 8 pages.
Tapia et al., "Combination of a Mutagenic Agent with a Reverse Transcriptase Inhibitor Results n Systematic Inhibition of HIV-1 Infection," Virology, 2005, 338: 1-8.
Totura et al., "Broad-spectrum coronavirus antiviral drug discovery", Expert Opinion on Drug Discovery, Mar. 2019, 17 pages.

(56) References Cited

OTHER PUBLICATIONS

Towner et al., "Newly Discovered Ebola Virus Associated with Hemorrhagic Fever Outbreak in Uganda," PLoS Pathogens, 2008, 4(11): e1000212, 6 pages.
Tschesnokov et al., "Template-dependent inhibition of coronavirus RNA-dependent RNA polymerase by remdesivir reveals a second mechanism of action," J. Biol. Chem., 2020, 295(47):16156-16165.
Uchiyama et al., "O-selective Phosphorylation of Nucleosides without N-protection," J. Org. Chem., Jan. 1, 1993, 58(2): 373-379.
Vaghefi et al., "Synthesis and Antiviral Activity of Certain Nucleoside 5'-Phosphonoformate Derivatives," Journal of Medicinal Chemistry, 1986, 29(8): 1389-1393.
Venkatachalam et al., "Effect of change in nucleoside structure on the activation and antiviral activity of phosphoramidate derivatives," Bioorganic & Medicinal Chemistry, 2005, 13: 5408-5423.
Vermillion et al., "Inhaled remdesivir reduces viral burden in a nonhuman primate model of SARS-CoV-2 infection," Science Translational Medicine, Dec. 2021, 20 pages.
Walker et al., "Plasma chloroquine and desethylchloroquine concentrations in children during and after chloroquine treatment for malaria.", British Journal Clinical Pharmacology, Dec. 1983, 16(6):701-705.
Wang et al., "Annovar: functional annotation of genetic variants from high-throughput sequencing data," Nucleic Acids Research, 2010, 38(16): e164, 7 pages.
Wang et al., "Remdesivir and chloroquine effectively inhibit the recently emerged novel coronavirus (2019-nCoV) in vitro", Cell Research, 2020, 30:269-271.
Warren et al., "Protection against filovirus diseases by a novel broad-spectrum nucleoside analogue BCX4430", Nature, Apr. 2014, 508(7496):402-405.
Warren et al., "Therapeutic efficacy of the small molecules GS-5734 against Ebola virus in rhesus monkeys", Nature, Mar. 17, 2016, 531(7594): 381-385.
Wolfel et al., "Virological assessment of hospitalized patients with COVID-2019," Nature, Apr. 2020, 581: 465-470.
Wu et al., "Synthetic Methodologies for C-Nucleosides," Synthesis, 2004, 10: 1533-1553.
Xie et al., "A nanoluciferase SARS-CoV-2 for rapid neutralization testing and screening of anti-infective drugs for COVID-19," Nature Communications, Oct. 15, 2020, 11(1):1-11.
Xie et al., "Weinreb Amide Approach to the Practical Synthesis of a Key Remdesivir Intermediate," The Journal of Organic Chemistry, 2021, 86:5065-5072.
Yamanaka et al., "Metabolic Studies on BMS-200475, a New Antiviral Compound Active against Hepatitis B Virus," Antimicrobial Agents and Chemotherapy, 1999, p. 43(1): 190.
Yang et al., "Lewis acid catalyzed direct cyanation of indoles and pyrroles with N-cyano-N-phenyl-p-toluenesulfonamide (NCTS)," Organic Letters, 2011, 13(20): 5608-5611.
Yates et al., "The evolution of antiviral nucleoside analogues: A review for chemists and non-chemists. Part II: Complex modifications to the nucleoside scaffold", Antiviral Research, Dec. 8, 2018, 162:5-21.
Yoon et al., "High-throughput screening-based identification of paramyxovirus inhibitors," J. Biomol. Screen., Aug. 2008, 13(7): 591-608.
Yoshimura et al., "Synthesis and Biological Evaluation of 1'-C-Cyano-Pyrimidine Nucleosides," Nucleosides & Nucleotides, 1996, 15(1-3): 305-324.
Zhang et al., "A Practical Synthesis of (2R)-3,5-di-O-benzoyl-2-fluoro-2-C-methyl-D-ribono-y-lactone", Tetrahedron: Asymmetry, 2009, 20:305-312.
Zhu et al., "A novel coronavirus from patients with pneumonia in China, 2019," New England Journal of Medicine, Jan. 24, 2020, 14 pages.
PCT International Search Report and Written Opinion in International Application No. PCT/US2021/038645, dated Jan. 18, 2022, 27 pages.
Vieira et al., "Development of a Large-Scale Cyanation Process Using Continuous Flow Chemistry En Route to the Synthesis of Remdesivir," Organic Process Research & Development, May 2020, 24(10):2113-2121.
"Molecular Nuclear Medicine," First Edition, Wang (ed.), May 31, 2001, pp. 388-391, 11 pages (with English translation).
"Veterinary Microbiology," 4th Edition, Lu (ed.), 2007, p. 304: paragraph 2, p. 408: paragraph 1, p. 419: paragraphs 1-2, 7 pages (with English translation).
Al-Aly et al., "High-dimensional characterization of post-acute sequelae of COVID-19," Nature, Jun. 2021, 594(7862): 259-64.
Aleissa et al., "New Perspectives on Antimicrobial Agents: Remdesivir Treatment for COVID-19," Antimicrobial Agents and Chemotherapy, Dec. 2020, 65(1): 18 pages.
Anderson et al., "The use of convalescent plasma therapy and remdesivir in the successful management of a critically ill obstetric patient with novel coronavirus 2019 infection: A case report," Case Reports in Women's Health, May 2020, 27: 3 pages.
Assiri et al., "Epidemiological, Demographic, and Clinical Characteristics of 47 Cases of Middle East Respiratory Syndrome Coronavirus Disease From Saudi Arabia: A Descriptive Study," The Lancet Infectious Diseases, Sep. 2013, 13(9):752-61.
Austin, "An Introduction to Propensity Score Methods for Reducing the Effects of Confounding in Observational Studies," Multivariate behavioral research, May 2011, 46(3): 399-424.
Baker et al., "Prodrugs of 9-Beta-D-Arabinofuranosyladenine. 1. Synthesis and Evaluation of some 5'-(O-Acyl) Derivatives," Journal of Medicinal Chemistry, Dec. 1978, 21(12): 1218-1221.
Beigel et al., "Remdesivir for the Treatment of Covid-19—Final Report," New England Journal of Medicine, Nov. 5, 2020, 383(19): 1813-1826.
Bhimraj et al., "Infectious Diseases Society of America guidelines on the treatment and management of patients with COVID-19," Clinical Infectious Diseases, Apr. 27, 2020, 20 pages.
Bonilauri et al., "Animal Coronaviruses and SARS-COV-2 in Animals, What Do We Actually Know?" Life, Feb. 2021, 11(2): 1-17.
Bornholdt et al., "A Two-Antibody Pan-Ebolavirus Cocktail Confers Broad Therapeutic Protection in Ferrets and Nonhuman Primates," Cell Host Microbe, Jan. 2019, 25(1): 49-58, e1-e5.
Brannan et al., "Post-exposure immunotherapy for two ebolaviruses and Marburg virus in nonhuman primates," Nature Communications, Jan. 2019, 10: 105, 10 pages.
Center for Disease Control and Prevention (CDC) [online], "Animals & COVID-19," COVID-19, last updated Apr. 7, 2023, retrieved on Aug. 29, 2023, retrieved from URL: <https://www.cdc.gov/coronavirus/2019-ncov/daily-life-coping/animals.html>, 4 pages.
Center for Disease Control and Prevention (CDC) [online], "Classifications & Definitions," COVID-19, last updated Mar. 20, 2023, retrieved on Aug. 29, 2023, retrieved from URL: <https://www.cdc.gov/coronavirus/2019-ncov/variants/variant-classifications.html>, 6 pages.
Center for Disease Control and Prevention (CDC) [online], "COVID Data Tracker," last updated Aug. 24, 2023, retrieved on Aug. 25, 2023, retrieved from URL <https://covid.cdc.gov/covid-data-tracker/#datatracker-home>, 5 pages.
Center for Disease Control and Prevention (CDC) [online], "SARS-CoV-2 variant classifications and definitions," last updated Mar. 20, 2023, retrieved on Aug. 25, 2023, retrieved from URL <https://www.cdc.gov/coronavirus/2019-ncov/variants/variant-classifications.html>, 6 pages.
Charytan et al., "Decreasing Incidence of Acute Kidney Injury in Patients with COVID-19 Critical Illness in New York City," Kidney International Reports, Apr. 2021, 6(4):916-27.
Chinen et al., "Critical respiratory failure in pregnancy complicated with COVID-19: A case report." Case Reports in Women's Health, Apr. 2021, 30: 4 pages.
Choi et al., "Clinical Presentation and Outcomes of Middle East Respiratory Syndrome in the Republic of Korea," Infection & Chemotherapy, Jun. 2016, 48(2): 118-26.
Coffin et al., "Persistent Marburg Virus Infection in the Testes of Nonhuman Primate Survivors," Cell Host & Microbe, Sep. 2018, 24(1): 405-416.

(56) References Cited

OTHER PUBLICATIONS

Complexity Science Hub Vienna [online], "SARS-ANI VIS: A Global Open Access Dataset of Reported SARS-CoV-2 Events in Animals," last updated Jul. 12, 2023, retrieved on Aug. 29, 2023, retrieved from URL: <https://vis.csh.ac.at/sars-ani/#variants>, 2 pages.
Coppock et al., "COVID-19 treatment combinations and associations with mortality in a large multi-site healthcare system," PloS one, Jun. 11, 2021, 16(6): 13 pages.
Cross et al., Combination therapy protects macaques against advanced Marburg virus disease. Nature Communications, Mar. 2021, 12(1): 1891, 10 pages.
Dande et al., "Remdesivir in a pregnant patient with COVID-19 pneumonia," Journal of Community Hospital Internal Medicine Perspectives, Jan. 2021, 11(1): 103-6.
De Wit et al., "Prophylactic and Therapeutic Remdesivir (GS-5734) Treatment in the Rhesus Macaque Model of MERS-CoV Infection," Proceedings of the National Academy of Sciences of the United States of America, Mar. 2020, 117(12): 6771-6776.
De Wit et al., "SARS and MERS: Recent Insights Into Emerging Coronaviruses," Nature Review, Jun. 2016; 14: 523-34.
Douafer et al., "Scope and limitations on aerosol drug delivery for the treatment of infectious respiratory diseases," Journal of Controlled Release, Sep. 2020, 325: 276-292.
Easterlin et al.. "Extremely Preterm Infant Born to a Mother With Severe COVID-19 Pneumonia." Journal of Investigative Medicine High Impact Case Reports, Jul. 2020, 8: 1-5.
Eastman et al., "Remdesivir: A Review of Its Discovery and Development Leading to Emergency Use Authorization for Treatment of COVID-19," ACS Central Science, May 4, 2020; 6(5): 672-83.
ERA-EDTA Council et al., "Chronic kidney disease is a key risk factor for severe COVID-19: a call to action by the ERA-EDTA," Nephrology Dialysis Transplantation, Jan. 2021, 36(1): 87-94.
European Centre for Disease Prevention and Control (ECDC) [online], "SARS-CoV-2 variants of concern as of Aug. 24, 2023," last updated Aug. 24, 2023, retrieved on Aug. 29, 2023, retrieved from URL: <https://www.ecdc.europa.eu/en/covid-19/variants-concern>, 18 pages.
European Medicines Agency, "New vaccine for prevention of Ebola virus disease recommended for approval in the European Union," Press Release, May 29, 2020, 3 pages.
Feldmann et al., "Ebola," New England Journal of Medicine, May 2020, 382: 1832-42.
Flythe et al., "Characteristics and Outcomes of Individuals With Pre-existing Kidney Disease and COVID-19 Admitted to Intensive Care Units in the United States," American Journal of Kidney Diseases, Feb. 2021, 77(2): 190-203.
Geisbert et al., "Considerations in the Use of Nonhuman Primate Models of Ebola Virus and Marburg Virus Infection," The Journal of Infectious Diseases, Oct. 2015, 212(Suppl. 2), S91-97.
Geisbert et al., "Single-injection vaccine protects nonhuman primates against infection with marburg virus and three species of ebola virus," Journal of Virology, Jul. 2009, 83(14): 7296-7304.
Gil et al., "COVID-19: Drug Targets and Potential Treatments," Journal of Medicinal Chemistry, Jun. 2020, 63(21): 12359-12386.
Gilead Sciences, Inc., "Veklury 100 mg powder for concentrate for solution for infusion," Package Leaflet, last revised Jun. 2023, 12 pages.
Gilead Sciences, Inc., "Veklury® (remdesivir) Full Prescribing Information" last revised Jul. 2023, 44 pages.
Goldman et al., "COVID-19 in immunocompromised populations: implications for prognosis and repurposing of immunotherapies," Journal for Immunotherapy of Cancer, Jun. 11, 2021, 9(6): 1-13.
Goldman et al., "Remdesivir for 5 or 10 Days in Patients with Severe Covid-19," New England Journal of Medicine, May 2020, 383(19), 1827-37.
Gupta et al., "Factors Associated With Death in Critically Ill Patients With Coronavirus Disease 2019 in the US," JAMA Internal Medicine, Nov. 2020, 180(11): 1436-47.

Hadi et al., "Outcomes of COVID-19 in Solid Organ Transplant Recipients: A Propensity-matched Analysis of a Large Research Network," Transplantation, Jun. 1, 2021; 105(6): 1365-71.
Han et al., "Genetic, antigenic and pathogenic characterization of avian coronaviruses isolated from pheasants (*Phasianus colchicus*) in China," Veterinary Microbiology, Nov. 2019, 240: 1-14.
Harvey et al., "Association of SARS-CoV-2 Seropositive Antibody Test With Risk of Future Infection," JAMA Internal Medicine, Feb. 24, 2021; 181(5): 672-679.
He et al., Species Differences in Size Discrimination in the Paracellular Pathway Reflected by Oral Bioavailability of Poly(ethylene glycol) and D-peptides, Journal of Pharmaceutical Sciences, May 1998, 87(5): 626-633.
Henry et al., "Chronic kidney disease is associated with severe coronavirus disease 2019 (COVID-19) infection," International urology and nephrology, Jun. 2020, 52(6): 1193-4.
Herbert et al., "Development of an antibody cocktail for treatment of Sudan virus infection," Proceedings of the National Academy of Sciences, Feb. 2020, 117: 3768-78.
Higgs et al., "Prevail IV: A Randomized, Double-Blind, 2-Phase, Phase 2 Trial of Remdesivir vs Placebo for Reduction of Ebola Virus RNA in the Semen of Male Survivors," Clinical Infectious Diseases, Nov. 2021, 73(10): 1849-1856.
Hoste et al., "Assessment of renal function in recently admitted critically ill patients with normal serum creatinine," Nephrology Dialysis Transplantation, Apr. 2005, 20(4): 747-53.
Hsu et al., COVID-19 Among US Dialysis Patients: Risk Factors and Outcomes From a National Dialysis Provider, American Journal of Kidney Disease, May 2021, 77(5):748-56.
Humeniuk et al., "Pharmacokinetic, Pharmacodynamic, and Drug-Interaction Profile of Remdesivir, a SARS-CoV-2 Replication Inhibitor," Clinical pharmacokinetics, May 2021, 60(2021): 569-583.
Igbinosa et al., "Use of remdesivir for pregnant patients with severe novel coronavirus disease 2019," American Journal of Obstetrics & Gynecology, Aug. 2020, 223(5): 768-770.
Jacobson et al., "Use of dexamethasone, remdesivir, convalescent plasma and prone positioning in the treatment of severe COVID-19 infection in pregnancy: A case report," Case Reports in Women's Health, Jan. 2021, 29: 3 pages.
Khbou et al., "Coronaviruses in farm animals: Epidemiology and public health implications," Veterinary Medicine and Science, Sep. 2020, 7(2): 322-347.
Kim et al., "Detection of bovine coronavirus in nasal swab of non-captive wild water deer, Korea," Transboundary and Emerging Diseases, Mar. 2018, 65(3): 627-631.
Ksiazek et al., "A Novel Coronavirus Associated with Severe Acute Respiratory Syndrome," New England Journal of Medicine, May 2003, 348(20): 1953-66.
Languon et al., "Filovirus Disease Outbreaks: A Chronological Overview," Virology: Research and Treatment, Jun. 2019, 10: 1-12.
Lat et al., "Therapeutic options in the treatment of severe acute respiratory syndrome coronavirus 2 in pregnant patient," American Journal of Obstetrics & Gynecology MFM, Nov. 2020, 2(4): 100224.
Mackman et al., "Prodrugs of a 1'-CN-4-Aza-7,9-dideazaadenosine C-Nucleoside Leading to the Discovery of Remdesivir (GS-5734) as a Potent Inhibitor of Respiratory Syncytial Virus with Efficacy in the African Green Monkey Model of RSV," Journal of Medicinal Chemistry, Apr. 2021, 64(8): 5001-5017.
Maldarelli et al., "Remdesivir Treatment for Severe COVID-19 in Third-Trimester Pregnancy: Case Report and Management Discussion," Open Forum Infectious Diseases, Sep. 2020, 7(9): 4 pages.
Markham, "REGN-EB3: First Approval," Drugs, Jan. 2021, 81: 175-178.
Martin et al., "Genetic Conservation of SARS-CoV-2 RNA Replication Complex in Globally Circulating Isolates and Recently Emerged Variants from Humans and Minks Suggests Minimal Pre-Existing Resistance to Remdesivir," Antiviral Research, Apr. 2021, 188: 7 pages.
McCoy et al., "Compassionate use of remdesivir for treatment of severe coronavirus disease 2019 in pregnant women at a United States academic center," American Journal of Obstetrics & Gynecology MFM, Aug. 2020, 2(Suppl 3): 4 pages.

(56) References Cited

OTHER PUBLICATIONS

Mulangu et al., "A Randomized, Controlled Trial of Ebola Virus Disease Therapeutics," New England Journal of Medicine, Dec. 2019; 381(24): 2293-303.
Naqvi et al., "Tocilizumab and Remdesivir in a Pregnant Patient With Coronavirus Disease 2019 (COVID-19)," Obstetrics & Gynecology, Nov. 2020, 136(5): 1025-9.
Nasrallah et al., "Pharmacological treatment in pregnant women with moderate symptoms of coronavirus disease 2019 (COVID-19) pneumonia," The Journal of Maternal-Fetal & Neonatal Medicine Mar. 2021, 35(25): 5970-5977.
National Institute of Diabetes and Digestive and Kidney Diseases (NIDDK), "2009 CKD-EPI Creatinine Calculator," Chronic Kidney Disease Epidemiology Collaboration (CKD-EPI) equation, last reviewed Dec. 2022, retrieved from URL <https://www.niddk.nih.gov/health-information/professionals/clinical-tools-patient-management/kidney-disease/laboratory-evaluation/glomerular-filtration-rate-calculators/historical>, 2 pages.
Nguyen et al., "Favipiravir pharmacokinetics in Ebola-Infected patients of the JIKI trial reveals concentrations lower than targeted," PLoS Neglected Tropical Diseases, Feb. 2017, 11(2), 18 pages.
O'Toole et al., "Tracking the international spread of SARS-CoV-2 lineages B.1.1.7 and B.1.351/501Y-V2," Wellcome Open Research, May 2021, 18 pages.
Ozturk et al., "Mortality analysis of COVID-19 infection in chronic kidney disease, haemodialysis and renal transplant patients compared with patients without kidney disease: a nationwide analysis from Turkey," Nephrology Dialysis Transplantation, Dec. 2020, 35(12): 2083-95.
Patel et al., "Analysis of MarketScan Data for Immunosuppressive Conditions and Hospitalizations for Acute Respiratory Illness, United States," Emerging Infectious Diseases, Apr. 29, 2020; 26(8): 1720-30.
Pierce-Williams et al., "Clinical course of severe and critical coronavirus disease 2019 in hospitalized pregnancies: a United States cohort study," American Journal of Obstetrics & Gynecology MFM, Aug. 2020, 2(3): 12 pages.
Pilcer et al., "Formulation strategy and use of excipients in pulmonary drug delivery," International Journal of Pharmaceutics, Jun. 2010, 392(1-2): 1-19.
Porter et al., "Remdesivir (GS-5734) Is Efficacious in Cynomolgus Macaques Infected With Marburg Virus," The Journal of Infectious Diseases, Jun. 2020, 222(11): 1894-1901.
Prasad et al., "Resistance of Cynomolgus Monkeys to Nipah and Hendra Virus Disease Is Associated With Cell-Mediated and Humoral Immunity," The Journal of Infectious Diseases, May 2020, 221(Suppl. 4): S436-447.
Rahim et al., "Postexposure Protective Efficacy of T-705 (Favipiravir) Against Sudan Virus Infection in Guinea Pigs," The Journal of Infectious Diseases, Jul. 2018, 218(Suppl. 5): S649-S657.
Ronco et al., "Kidney Involvement in COVID-19 and Rationale for Extracorporeal Therapies," Nature Reviews Nephrology, Apr. 2020, 16: 308-310.
Saroyo et al., "Remdesivir Treatment for COVID 19 in Pregnant Patients with Moderate to Severe Symptoms: Serial Case Report," Infectious Disease Reports, May 2021, 13(2): 437-443.
Schindell et al., "Persistence and Sexual Transmission of Filoviruses," Viruses, Dec. 2018, 10(12), 22 pages.
Schnettler et al., "Severe acute respiratory distress syndrome in coronavirus disease 2019-infected pregnancy: obstetric and intensive care considerations," American Journal of Obstetrics & Gynecology MFM, Aug. 2020, 2(Suppl 3): 10 pages.
Shetty et al., "COVID-19-Associated Glomerular Disease," Journal of the American Society of Nephrology, Jan. 2021, 32(1): 33-40.
Singh et al., "Treatment With Remdesivir in Two Pregnant Patients With COVID-19 Pneumonia," Cureus, May 2021, 13(5): 6 pages.
Spinner et al., "Effect of Remdesivir vs Standard Care on Clinical Status at 11 Days in Patients With Moderate COVID-19: A Randomized Clinical Trial," Jama, Sep. 2020, 324(11): 1048-1057.
Taylor et al., "Neutralizing Monoclonal Antibodies for Treatment of COVID-19," Nature Reviews Immunology, Apr. 2021, 21(6): 382-393.
Taylor, "Aulton's Pharmaceutics: The Design and Manufacture of Medicines; Chapter 37: Pulmonary Drug Delivery," 5th ed., Aulton et al (ed), 2018: 653-670.
The Recovery Collaborative Group, "Dexamethasone in Hospitalized Patients with Covid-19," New England Journal of Medicine, Feb. 2020, 384(8): 693-704.
Thi et al., "Rescue of non-human primates from advanced Sudan ebolavirus infection with lipid encapsulated siRNA," Nature Microbiology, Aug. 2016, 1: 16142, 21 pages.
Third Party Opposition in Colombian Appln. No. NC2022/0018715, dated May 31, 2023, 22 pages (with English translation).
U.S. Department of Agriculture (USDA) [online], "Confirmed Cases of SARS-CoV-2 in Animals in the United States," last updated Aug. 29, 2023, retrieved on Aug. 29, 2023, retrieved from URL: <https://www.aphis.usda.gov/aphis/dashboards/tableau/sars-dashboard>, 1 page.
U.S. Department of Health and Human Services (HHS) [online], "Most common forms based on Pango lineage designations," last updated Aug. 25, 2023, retrieved on Aug. 29, 2023, retrieved from URL: <https://cov.lanl.gov/components/sequence/COV/pangocommonforms.comp>, 264 pages.
U.S. Food and Drug Administration (FDA), "First FDA-approved vaccine for the prevention of Ebola virus disease, marking a critical milestone in public health preparedness and response," Press Release, Dec. 19, 2019, 3 pages.
Vandesompele et al., "Accurate normalization of real-time quantitative RT-PCR data by geometric averaging of multiple internal control genes," Genome Biology, Jun. 2002, 3(7): 1-12.
V'kovski et al., "Coronavirus Biology and Replication: Implications for SARS-CoV-2," Nature Reviews Microbiology, Oct. 2021, 19(3): 155-170.
Warfield et al., "Homologous and heterologous protection of non-human primates by Ebola and Sudan virus-like particles," PLoS ONE, Mar. 2015, 10(3): 16 pages.
Wec et al., "Development of a Human Antibody Cocktail that Deploys Multiple Functions to Confer Pan-Ebolavirus Protection," Cell Host Microbe, Jan. 2019, 25(1): 39-48, e1-e5.
Williamson et al., "Factors associated with COVID-19-related death using OpenSAFELY," Nature, Aug. 2020, 584(7821): 430-6.
World Health Organization (WHO) [online], "Tracking SARS-CoV-2 variants," last updated Aug. 17, 2023, retrieved on Aug. 25, 2023, retrieved from URL <https://www.who.int/en/activities/tracking-SARS-CoV-2-variants>, 11 pages.
World Health Organization (WHO), "Ebola hemorrhagic fever in Zaire, 1976: Report of an International Commission," Bulletin of the World Health Organization, 1978, 56(2): 271-293.
Wu et al., "AKI and Collapsing Glomerulopathy Associated with COVID-19 and APOLI High-Risk Genotype," Journal of the American Society of Nephrology, Aug. 2020, 31(8):1688-95.
Xie et al., "Engineering SARS-CoV-2 using a reverse genetic system," Nature protocols, Jan. 29, 2021. 16(3): 1761-1784.
Zeng et al., "Identification and pathological characterization of persistent asymptomatic Ebola virus infection in rhesus monkeys," Nature Microbiology, Jul. 2017, 2(1), 11 pages.
Zhang et al., "A bacterial artificial chromosome (BAC)-vectored noninfectious replicon of SARS-CoV-2", Antiviral Research, Jan. 2021, 185(1), 9 pages.
U.S. Appl. No. 13/189,373, filed Jul. 22, 2011, Richard L. Mackman.
U.S. Appl. No. 14/613,719, filed Feb. 4, 2015, Richard L. Mackman.
U.S. Appl. No. 14/579,348, filed Dec. 22, 2014, Richard L. Mackman.
U.S. Appl. No. 16/042,085, filed Jul. 23, 2018, Richard L. Mackman.
U.S. Appl. No. 16/879,491, filed May 20, 2020, Richard L. Mackman.
U.S. Appl. No. 17/854,818, filed Jun. 30, 2022, Richard L. Mackman.
U.S. Appl. No. 17/333,389, filed May 28, 2021, Tomas Cihlar.
U.S. Appl. No. 17/676,920, filed Feb. 22, 2022, Tomas Cihlar.

(56) References Cited

OTHER PUBLICATIONS

U.S. Appl. No. 18/128,850, filed Mar. 30, 2023, Tomas Cihlar.
U.S. Appl. No. 17/222,125, filed Apr. 5, 2021, Scott Ellis.
U.S. Appl. No. 18/202,751, filed May 26, 2023, Scott Ellis.
U.S. Appl. No. 17/158,391, filed Jan. 26, 2021, Tomas Cihlar.
U.S. Appl. No. 18/131,106, filed Apr. 5, 2023, Tomas Cihlar.
U.S. Appl. No. 17/198,829, filed Mar. 11, 2021, Pavel R. Badalov.
U.S. Appl. No. 18/108,480, filed Feb. 10, 2023, Pavel R. Badalov.
U.S. Appl. No. 16/031,620, filed Jul. 10, 2018, Nate Larson.
U.S. Appl. No. 16/865,209, filed May 1, 2020, Nate Larson.
U.S. Appl. No. 17/585,651, filed Jan. 27, 2022, Nate Larson.
U.S. Appl. No. 18/241,303, filed Sep. 1, 2023, Nate Larson.
U.S. Appl. No. 15/919,750, filed Mar. 13, 2018, Michel Joseph Perron.
U.S. Appl. No. 16/852,102, filed Apr. 17, 2020, Michel Joseph Perron.
U.S. Appl. No. 17/578,682, filed Jan. 19, 2022, Michel Joseph Perron.
U.S. Appl. No. 17/895,123, filed Aug. 25, 2022, Michel Joseph Perron.
U.S. Appl. No. 18/133,612, filed Apr. 12, 2023, Michel Joseph Perron.
U.S. Appl. No. 15/964,597, filed Apr. 27, 2018, Katrien Brak.
U.S. Appl. No. 17/069,248, filed Oct. 13, 2020, Katrien Brak.
U.S. Appl. No. 18/099,477, filed Jan. 20, 2023, Katrien Brak.
U.S. Appl. No. 15/267,433, filed Sep. 16, 2016, Michael O'Neil Hanrahan Clarke.
U.S. Appl. No. 16/265,016, filed Feb. 1, 2019, Michael O'Neil Hanrahan Clarke.
U.S. Appl. No. 16/863,566, filed Apr. 30, 2020, Michael O'Neil Hanrahan Clarke.
U.S. Appl. No. 17/222,066, filed Apr. 5, 2021, Michael O'Neil Hanrahan Clarke.
U.S. Appl. No. 17/748,400, filed May 19, 2022, Michael O'Neil Hanrahan Clarke.
U.S. Appl. No. 14/926,063, filed Oct. 29, 2015, Steven Donald Axt.
U.S. Appl. No. 16/692,966, filed Nov. 22, 2019, Steven Axt.
U.S. Appl. No. 17/665,724, filed Feb. 7, 2022, Steven Donald Axt.
U.S. Appl. No. 14/926,062, filed Oct. 29, 2015, Byoung Chun.
U.S. Appl. No. 15/246,240, filed Aug. 24, 2016, Byoung Chun.
U.S. Appl. No. 15/902,690, filed Feb. 22, 2018, Byoung Chun.
U.S. Appl. No. 16/274,049, filed Feb. 12, 2019, Byoung Chun.
U.S. Appl. No. 16/881,419, filed May 22, 2020, Byoung-Kwon Chun.
U.S. Appl. No. 17/579,650, filed Jan. 20, 2022, Byoung Kwon Chun.
U.S. Appl. No. 17/897,380, filed Aug. 29, 2022, Byoung Kwon Chun.
U.S. Appl. No. 18/134,792, filed Apr. 14, 2023, Byoung Kwon Chun.
U.S. Appl. No. 14/746,430, filed Jun. 22, 2015, Aesop Cho.
U.S. Appl. No. 13/813,886, filed Jun. 25, 2013, Aesop Cho.
U.S. Appl. No. 12/886,248, filed Sep. 20, 2010, Thomas Butler.
U.S. Appl. No. 16/011,055, filed Jun. 18, 2018, Thomas Butler.
U.S. Appl. No. 16/988,250, filed Aug. 7, 2020, Thomas Butler.
U.S. Appl. No. 17/209,639, filed Mar. 23, 2021, Thomas Butler.
U.S. Appl. No. 12/428,176, filed Apr. 22, 2009, Thomas Butler.
U.S. Appl. No. 13/196,117, filed Aug. 2, 2011, Thomas Butler.
U.S. Appl. No. 13/649,511, filed Oct. 11, 2012, Thomas Butler.
U.S. Appl. No. 17/458,023, filed Aug. 26, 2021, Elaine Bunyan.
U.S. Appl. No. 18/098,950, filed Jan. 19, 2023, Elaine Bunyan.
U.S. Appl. No. 18/115,895, filed Mar. 1, 2023, Rao V. Kalla.
U.S. Appl. No. 18/115,955, filed Mar. 1, 2023, Mark J. Bartlett.
U.S. Appl. No. 18/117,858, filed Mar. 6, 2023, Mark J. Bartlett.
U.S. Appl. No. 18/117,878, filed Mar. 6, 2023, Mark J. Bartlett.
U.S. Appl. No. 18/117,913, filed Mar. 6, 2023, Mark J. Bartlett.
U.S. Appl. No. 18/237,152, filed Aug. 25, 2023, Mark J. Bartlett.
U.S. Appl. No. 18/205,745, filed Jun. 5, 2023, Roy Maxim Bannister.
U.S. Appl. No. 18/215,881, filed Jun. 29, 2023, Kassibla E. Dempah.
U.S. Appl. No. 18/215,217, filed Jun. 28, 2023, Kassibla E. Dempah.
Australian Office Action in AU Appln. No. 2021296841, dated Jan. 10, 2024, 5 pages.

1'-CYANO NUCLEOSIDE ANALOGS AND USES THEREOF

CROSS-REFERENCES TO RELATED APPLICATIONS

This application claims priority to the U.S. Provisional Patent Application No. 63/043,349, filed Jun. 24, 2020 and U.S. Provisional Patent Application No. 63/139,648, filed Jan. 20, 2021, each of which application is incorporated herein in its entirety for all purposes.

BACKGROUND

There is a need for compositions and methods for treating viral infections, for example Paramyxoviridae, Pneumoviridae, Picornaviridae, Flaviviridae, Filoviridae, Arenaviridae, Orthomyxovirus, and Coronaviridae infections. The present disclosure addresses these and other needs.

SUMMARY

Provided herein are compounds of Formula I:

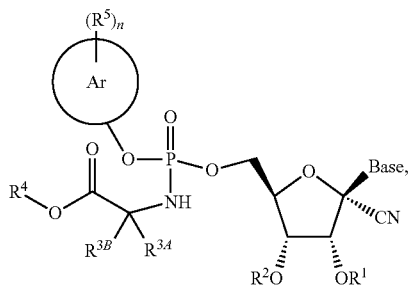

Formula I or a pharmaceutically acceptable salt thereof, wherein
each $R^1$ and $R^2$ is independently H, —(CO)$C_1$-$C_6$ alkyl or —(CO)O$C_1$-$C_6$ alkyl, wherein the —(C(O)$C_1$-$C_6$ alkyl or —(CO)O$C_1$-$C_6$ alkyl is optionally substituted with a $NH_2$ group; or
$R^1$ and $R^2$ are combined to form —CO—, —CO—CO—, or —C(O)—C($R^{1A}$)($R^{1B}$)—C(O)—; wherein each $R^{1A}$ and $R^{1B}$ is independently H or $C_1$-$C_6$ alkyl;
$R^{3A}$ is H or $C_1$-$C_6$ alkyl; wherein the $C_1$-$C_6$ alkyl is optionally substituted with a —OH or phenyl;
$R^{3B}$ is H or $C_1$-$C_3$ alkyl; and
$R^4$ is (i) $C_1$-$C_8$ alkyl, (ii) —(C$R^8R^9$C$R^{10}R^{11}$O)$_m R^{12}$, (iii) $C_3$-$C_{10}$ cycloalkyl, (iv) 4 to 6 membered heterocyclyl having 1 to 3 heteroatoms independently selected from N, O and S, or (v) 5 to 6 membered heteroaryl having 1 to 3 heteroatoms independently selected from N, O and S; wherein the $C_1$-$C_8$ alkyl, $C_3$-$C_{10}$ cycloalkyl, 4 to 6 membered heterocyclyl, or 5 to 6 membered heteroaryl is optionally substituted with one or two $R^{4A}$ groups; wherein
each $R^{4A}$ is independently $C_1$-$C_3$ alkyl, $C_1$-$C_3$ alkoxy, $C_1$-$C_3$ haloalkyl, $C_3$-$C_{10}$ cycloalkyl, $C_6$-$C_{10}$ aryl, or 4 to 6 membered heterocyclyl having 1 to 3 heteroatoms independently selected from N, O and S; wherein the $C_3$-$C_{10}$ cycloalkyl, $C_6$-$C_{10}$ aryl, or 4 to 6 membered heterocyclyl is optionally substituted with one or two substituents independently selected from the group consisting of $C_1$-$C_6$ alkyl, halo, $C_1$-$C_6$ haloalkyl, and $C_1$-$C_6$ alkoxy;

Base is

wherein
$R^6$ is —N(H)$R^{6A}$; and
each $R^{6A}$, $R^{7A}$ and $R^{7B}$ is independently H or —$CH_2$OP(O)(OH)$_2$;
Ar is $C_6$-$C_{10}$ aryl or 5 to 10 membered heteroaryl containing one, two, or three heteroatoms selected from the group consisting of O, N, and S;
n is 0, 1, 2, or 3;
each $R^5$ is independently halo, cyano, $C_1$-$C_6$ alkyl, $C_1$-$C_6$ haloalkyl, $C_3$-$C_6$ cycloalkyl, $C_1$-$C_6$ alkoxy, $C_3$-$C_6$ cycloalkoxy, —COO$R^{5A}$, —$SO_2R^{5A}$, 4 to 6 membered heterocycloalkyl containing one, two or three heteroatoms selected from N, O, and S, or 5 to 6 membered heteroaryl containing one, two or three heteroatoms selected from N, O, and S; wherein the $C_1$-$C_6$ alkyl, $C_1$-$C_6$ haloalkyl, $C_3$-$C_6$ cycloalkyl, $C_3$-$C_6$ cycloalkoxy, $C_1$-$C_6$ alkoxy, 4 to 6 membered heterocycloalkyl and 5 to 6 membered heteroaryl is optionally substituted with one or two $R^{5B}$ groups; or
two $R^5$ groups on adjacent carbon atoms are joined to form a $C_5$-$C_6$ cycloalkyl;
$R^{5A}$ is $C_1$-$C_6$ alkyl;
each $R^{5B}$ is independently —OH, —$OR^{5C}$, —COO$R^{5C}$ and —NHCOO$R^{5D}$; wherein $R^{5C}$ is $C_1$-$C_6$ alkyl and $R^{5D}$ is $C_{13}$ alkyl optionally substituted with a phenyl group;
each $R^8$, $R^9$, $R^{10}$, $R^{11}$ and $R^{12}$ is independently H or $C_1$-$C_3$ alkyl;
m is 1, 2, 3, 4, or 5;
provided that when $R^1$ and $R^2$ are both H then:
(i) n is 1, 2, or 3; or
(ii) $R^4$ is $C_1$-$C_8$ alkyl substituted with one or two groups independently selected from $C_1$-$C_3$ alkoxy, $C_1$-$C_3$ haloalkyl, $C_3$-$C_{10}$ cycloalkyl, $C_6$-$C_{10}$ aryl, or 4 to 6 membered heterocyclyl having 1 to 3 heteroatoms independently selected from N, O and S;
wherein the $C_3$-$C_{10}$ cycloalkyl, $C_6$-$C_{10}$ aryl, or 4 to 6 membered heterocyclyl is optionally substituted with one or two substituents independently selected from the group consisting of $C_1$-$C_6$ alkyl, halo, $C_1$-$C_6$ haloalkyl, and $C_1$-$C_6$ alkoxy; or
(iii) $R^4$ is (a) —(C$R^8R^9$C$R^{10}R^{11}$O)$_m R^{12}$, (b) monocyclic $C_3$-$C_{10}$ cycloalkyl substituted with substituted with one or two $R^{4A}$ groups, (c) bicyclic $C_3$-$C_{10}$ cycloalkyl, (d) 4 to 6 membered heterocyclyl having 1 to 3 heteroatoms independently selected from N, O and S, or (e) 5 to 6 membered heteroaryl having 1 to 3 heteroatoms independently selected from N, O and S;

wherein the bicyclic $C_3$-$C_{10}$ cycloalkyl, 4 to 6 membered heterocyclyl, or 5 to 6 membered heteroaryl is optionally substituted with one or two $R^{4A}$ groups; or (iv) Base is

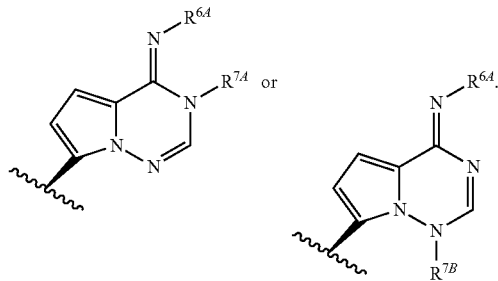

In some embodiments, the disclosure provides pharmaceutical compositions comprising a compound disclosed herein, or a pharmaceutically acceptable salt thereof.

In some embodiments, the disclosure provides methods of treating or preventing a viral infection in a human in need thereof, wherein the method comprises administering to the human a compound of the disclosure, or a pharmaceutically acceptable salt thereof.

In some embodiments, the disclosure provides methods for manufacturing a medicament for treating or preventing a viral infection in a human in need thereof, characterized in that a compound of the disclosure, or a pharmaceutically acceptable salt thereof, is used.

In some embodiments, the disclosure provides use of a compound of the disclosure, or a pharmaceutically acceptable salt thereof, for the manufacture of a medicament for the treatment or prevention of a viral infection in a human in need thereof.

DETAILED DESCRIPTION OF THE INVENTION

I. General

The invention relates generally to methods and compounds for treating or preventing viral infections, for example paramyxoviridae, pneumoviridae, picornaviridae, flaviviridae, filoviridae, arenaviridae, orthomyxovirus, and coronaviridae (including but not limited to MERS, SARS, and SARS-CoV-2) infections.

II. Definitions

Unless stated otherwise, the following terms and phrases as used herein are intended to have the following meanings:

As used herein, "a compound of the disclosure" or "a compound of Formula I" means a compound of Formula I, or a pharmaceutically acceptable salt, thereof. Similarly, with respect to isolatable intermediates, the phrase "a compound of Formula (number)" means a compound of that formula and pharmaceutically acceptable salts thereof.

"Alkyl" refers to an unbranched or branched saturated hydrocarbon chain. For example, an alkyl group can have 1 to 20 carbon atoms (i.e, $C_1$-$C_{20}$ alkyl), 1 to 8 carbon atoms (i.e., $C_1$-$C_8$ alkyl), 1 to 6 carbon atoms (i.e., $C_1$-$C_6$ alkyl), or 1 to 3 carbon atoms (i.e., $C_1$-$C_3$ alkyl). Examples of suitable alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), and 3,3-dimethyl-2-butyl (—$CH(CH_3)C(CH_3)_3$.

"Alkoxy" means a group having the formula —O-alkyl, in which an alkyl group, as defined above, is attached to the parent molecule via an oxygen atom. The alkyl portion of an alkoxy group can have 1 to 20 carbon atoms (i.e., $C_1$-$C_{20}$ alkoxy), 1 to 12 carbon atoms (i.e., $C_1$-$C_{12}$ alkoxy), 1 to 8 carbon atoms (i.e., $C_1$-$C_8$ alkoxy), 1 to 6 carbon atoms (i.e., $C_1$-$C_6$ alkoxy) or 1 to 3 carbon atoms (i.e., $C_1$-$C_3$ alkoxy). Examples of suitable alkoxy groups include, but are not limited to, methoxy (—O—$CH_3$ or —OMe), ethoxy (—$OCH_2CH_3$ or —OEt), t-butoxy (—O—$C(CH_3)_3$ or —OtBu) and the like.

"Haloalkyl" is an alkyl group, as defined above, in which one or more hydrogen atoms of the alkyl group is replaced with a halogen atom. The alkyl portion of a haloalkyl group can have 1 to 20 carbon atoms (i.e., $C_1$-$C_{20}$ haloalkyl), 1 to 12 carbon atoms (i.e., $C_1$-$C_{12}$ haloalkyl), 1 to 8 carbon atoms (i.e., $C_1$-$C_8$ haloalkyl), 1 to 6 carbon atoms (i.e., $C_1$-$C_6$ haloalkyl) or 1 to 3 carbon atoms (i.e., $C_1$-$C_3$ haloalkyl). Examples of suitable haloalkyl groups include, but are not limited to, —$CF_3$, —$CHF_2$, —$CFH_2$, —$CH_2CF_3$, and the like.

"Aryl" means an aromatic hydrocarbon radical derived by the removal of one hydrogen atom from a single carbon atom of a parent aromatic ring system. For example, an aryl group can have 6 to 20 carbon atoms, 6 to 14 carbon atoms, or 6 to 10 carbon atoms. Typical aryl groups include, but are not limited to, radicals derived from benzene (e.g., phenyl), substituted benzene, naphthalene, anthracene, biphenyl, and the like.

"Cycloalkyl" refers to a saturated or partially saturated cyclic alkyl group having a single ring or multiple rings including fused, bridged, and spiro ring systems. As used herein, cycloalkyl has from 3 to 20 ring carbon atoms (i.e., $C_{3-20}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). Examples of cycloalkyl groups include cyclopropyl, cyclobutyl, cyclopentyl, cyclohexyl, cycloheptyl, and cyclooctyl.

"Heterocycle" or "heterocyclyl" refer to a saturated or unsaturated cyclic alkyl group, with one or more ring heteroatoms independently selected from nitrogen, oxygen and sulfur. A heterocycloalkyl may be a single ring or multiple rings wherein the multiple rings may be fused, bridged, or spiro. As used herein, heterocyclyl has 3 to 20 ring atoms (i.e., 3 to 20 membered heterocyclyl), 3 to 12 ring atoms (i.e., 3 to 12 membered heterocyclyl), 3 to 10 ring atoms (i.e., 3 to 10 membered heterocyclyl), 3 to 8 ring atoms (i.e., 3 to 8 membered heterocyclyl), 4 to 12 ring carbon atoms (i.e., 4 to 12 membered heterocyclyl), 4 to 8 ring atoms (i.e., 4 to 8 membered heterocyclyl), or 4 to 6 ring atoms (i.e., 4 to 6 membered heterocyclyl). Examples of heterocyclyl groups include pyrrolidinyl, piperidinyl, piperazinyl, oxetanyl, dioxolanyl, azetidinyl, and morpholinyl.

The term "optionally substituted" in reference to a particular moiety of the compound of Formula I (e.g., an optionally substituted aryl group) refers to a moiety wherein all substituents are hydrogen or wherein one or more of the hydrogens of the moiety may be replaced by the listed substituents.

Unless otherwise specified, the carbon atoms of the compounds of Formula I are intended to have a valence of four. If in some chemical structure representations, carbon atoms do not have a sufficient number of variables attached to produce a valence of four, the remaining carbon substituents needed to provide a valence of four should be assumed to be hydrogen.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, refers to the act of treating, as "treating" is defined immediately above.

The term "therapeutically effective amount", as used herein, is the amount of compound of Formula I present in a composition described herein that is needed to provide a desired level of drug in the secretions and tissues of the airways and lungs, or alternatively, in the bloodstream of a subject to be treated to give an anticipated physiological response or desired biological effect when such a composition is administered by the chosen route of administration.

The precise amount will depend upon numerous factors, for example the particular compound of Formula I, the specific activity of the composition, the delivery device employed, the physical characteristics of the composition, its intended use, as well as patient considerations such as severity of the disease state, patient cooperation, etc., and can readily be determined by one skilled in the art based upon the information provided herein.

The term "adjacent carbons" as used herein refers to consecutive carbons atoms that are directly attached to each other. For example, in

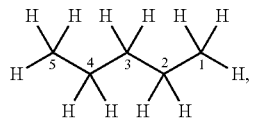

$C_1$ and $C_2$ are adjacent carbons, $C_2$ and $C_3$ are adjacent carbons, $C_3$ and $C_4$ are adjacent carbons, and $C_4$ and $C_5$ are adjacent carbons. Similarly, in

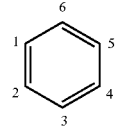

$C_1$ and $C_2$ are adjacent carbons, $C_2$ and $C_3$ are adjacent carbons, $C_3$ and $C_4$ are adjacent carbons, and $C_4$ and $C_5$ are adjacent carbons, $C_5$ and $C_6$ are adjacent carbons and $C_6$ and $C_1$ are adjacent carbons.

Compound structures using a "P*" notation refers to the isolated (R)- or (S)-isomer where the specific stereochemistry at that position is unassigned.

III. Compounds

Provided herein are compounds of Formula I:

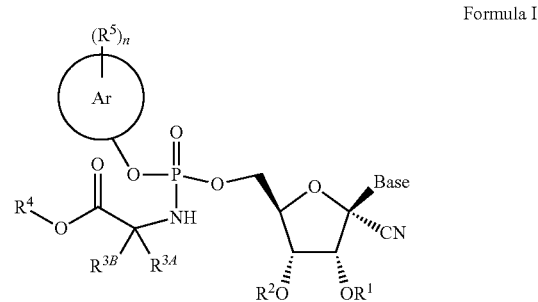

Formula I or a pharmaceutically acceptable salt thereof, wherein
each $R^1$ and $R^2$ is independently H, —(CO)$C_1$-$C_6$ alkyl or —(CO)O$C_1$-$C_6$ alkyl, wherein the —(C(O)$C_1$-$C_6$ alkyl or —(CO)O$C_1$-$C_6$ alkyl is optionally substituted with a NH$_2$ group; or $R^1$ and $R^2$ are combined to form —CO—, —CO—CO—, or —C(O)—C(R$^{1A}$)(R$^{1B}$)—C(O)—; wherein each $R^{1A}$ and $R^{1B}$ is independently H or $C_1$-$C_6$ alkyl;

$R^{3A}$ is H or $C_1$-$C_6$ alkyl; wherein the $C_1$-$C_6$ alkyl is optionally substituted with a —OH or phenyl;

$R^{3B}$ is H or $C_1$-$C_3$ alkyl; and $R^4$ is (i) $C_1$-$C_8$ alkyl, (ii) —(CR$^8$R$^9$CR$^{10}$R$^{11}$O)$_m$R$^{12}$, (iii) $C_3$-$C_{10}$ cycloalkyl, (iv) 4 to 6 membered heterocyclyl having 1 to 3 heteroatoms independently selected from N, O and S, or (v) 5 to 6 membered heteroaryl having 1 to 3 heteroatoms independently selected from N, O and S; wherein the $C_1$-$C_8$ alkyl, $C_3$-$C_{10}$ cycloalkyl, 4 to 6 membered heterocyclyl, or 5 to 6 membered heteroaryl is optionally substituted with one or two $R^{4A}$ groups; wherein each $R^{4A}$ is independently $C_1$-$C_3$ alkyl, $C_1$-$C_3$ alkoxy, $C_1$-$C_3$ haloalkyl, $C_3$-$C_{10}$ cycloalkyl, $C_6$-$C_{10}$ aryl, or 4 to 6 membered heterocyclyl having 1 to 3 heteroatoms independently selected from N, O and S; wherein the $C_3$-$C_{10}$ cycloalkyl, $C_6$-$C_{10}$ aryl, or 4 to 6 membered heterocyclyl is optionally substituted with one or two substituents independently selected from the group consisting of $C_1$-$C_6$ alkyl, halo, $C_1$-$C_6$ haloalkyl, and $C_1$-$C_6$ alkoxy;

Base is

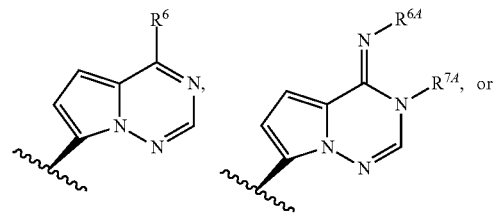

-continued

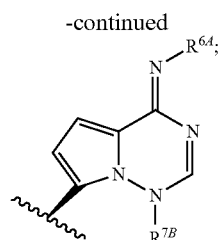

wherein
R⁶ is —N(H)R⁶ᴬ; and
each R⁶ᴬ, R⁷ᴬ and R⁷ᴮ is independently H or —CH₂OP(O)(OH)₂;
Ar is C₆-C₁₀ aryl or 5 to 10 membered heteroaryl containing one, two, or three heteroatoms selected from the group consisting of O, N, and S;
n is 0, 1, 2, or 3;
each R⁵ is independently halo, cyano, C₁-C₆ alkyl, C₁-C₆ haloalkyl, C₃-C₆ cycloalkyl, C₁-C₆ alkoxy, C₃-C₆ cycloalkoxy, —COOR⁵ᴬ, —SO₂R⁵ᴬ, 4 to 6 membered heterocycloalkyl containing one, two or three heteroatoms selected from N, O, and S, or 5 to 6 membered heteroaryl containing one, two or three heteroatoms selected from N, O, and S; wherein the C₁-C₆ alkyl, C₁-C₆ haloalkyl, C₃-C₆ cycloalkyl, C₃-C₆ cycloalkoxy, C₁-C₆ alkoxy, 4 to 6 membered heterocycloalkyl and 5 to 6 membered heteroaryl is optionally substituted with one or two R⁵ᴮ groups; or two R⁵ groups on adjacent carbon atoms are joined to form a C₅-C₆ cycloalkyl;
R⁵ᴬ is C₁-C₆ alkyl;
each R⁵ᴮ is independently —OH, —OR⁵ᶜ, —COOR⁵ᶜ and —NHCOOR⁵ᴰ; wherein R⁵ᶜ is C₁-C₆ alkyl and R⁵ᴰ is C₁₃ alkyl optionally substituted with a phenyl group;
each R⁸, R⁹, R¹⁰, R¹¹ and R¹² is independently H or C₁-C₃ alkyl;
m is 1, 2, 3, 4, or 5;
provided that when R¹ and R² are both H then:
(i) n is 1, 2, or 3; or
(ii) R⁴ is C₁-C₈ alkyl substituted with one or two groups independently selected from C₁-C₃ alkoxy, C₁-C₃ haloalkyl, C₃-C₁₀ cycloalkyl, C₆-C₁₀ aryl, or 4 to 6 membered heterocyclyl having 1 to 3 heteroatoms independently selected from N, O and S;
wherein the C₃-C₁₀ cycloalkyl, C₆-C₁₀ aryl, or 4 to 6 membered heterocyclyl is optionally substituted with one or two substituents independently selected from the group consisting of C₁-C₆ alkyl, halo, C₁-C₆ haloalkyl, and C₁-C₆ alkoxy; or
(iii) R⁴ is (a) —(CR⁸R⁹CR¹⁰R¹¹O)ₘR¹², (b) monocyclic C₃-C₁₀ cycloalkyl substituted with substituted with one or two R⁴ᴬ groups, (c) bicyclic C₃-C₁₀ cycloalkyl, (d) 4 to 6 membered heterocyclyl having 1 to 3 heteroatoms independently selected from N, O and S, or (e) 5 to 6 membered heteroaryl having 1 to 3 heteroatoms independently selected from N, O and S;
wherein the bicyclic C₃-C₁₀ cycloalkyl, 4 to 6 membered heterocyclyl, or 5 to 6 membered heteroaryl is optionally substituted with one or two R⁴ᴬ groups; or (iv) Base is

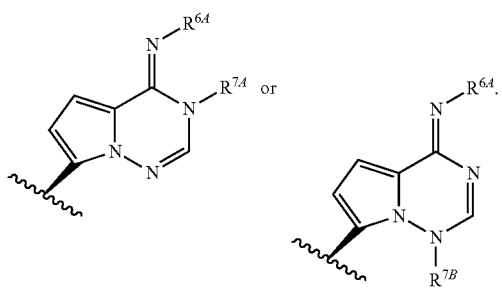

In some embodiments, the compound of Formula I is a compound of Formula Ia:

Formula Ia

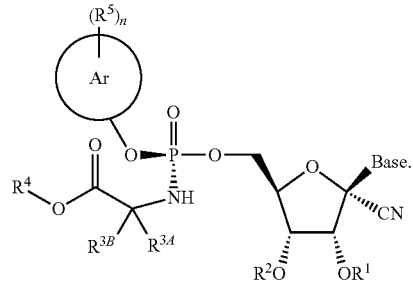

In some embodiments, the compound of Formula I is a compound of Formula Ib:

Formula Ib

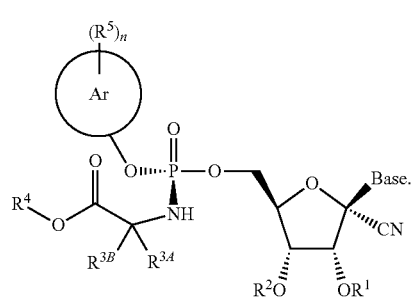

In some embodiments of the compounds of Formula I, Ia, and Ib, the Base is

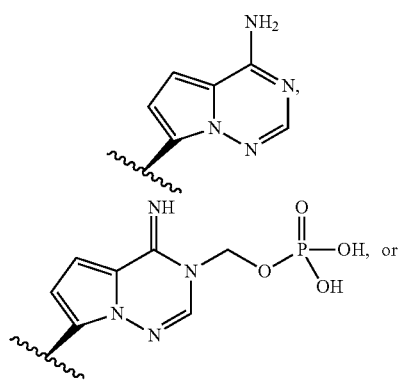

-continued

In some embodiments, the Base

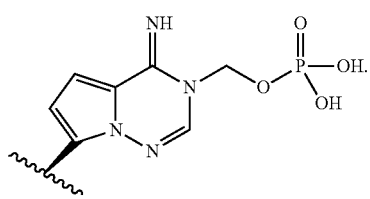

In some embodiments, the Base is

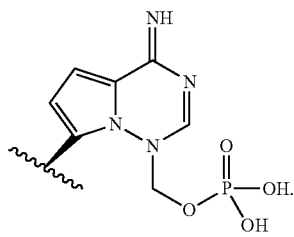

In some embodiments, the Base is

In some embodiments, the compound of Formula I has a Formula II:

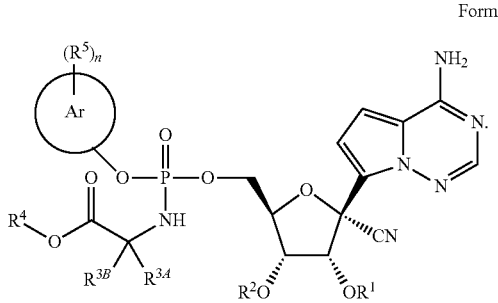

Formula II

In some embodiments, the compound of Formula I, Ia or II has a Formula IIa:

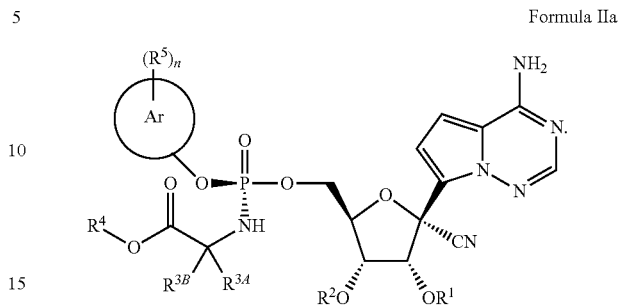

Formula IIa

In some embodiments, the compound of Formula I, Ib or II has a Formula IIb:

Formula IIb

In some embodiments of the compounds of Formula I, Ia, Ib, II, IIa, or IIb, $R^{3A}$ is $C_1$-$C_6$ alkyl optionally substituted with —OH or phenyl. In some embodiments, $R^{3A}$ is $C_1$-$C_6$ alkyl optionally substituted with —OH. In some embodiments of the, $R^{3A}$ is $C_1$-$C_6$ alkyl optionally substituted with a phenyl.

In some embodiments of the compounds of Formula I, Ia, Ib, II, IIa, or IIb, $R^{3A}$ is $C_1$-$C_3$ alkyl optionally substituted with —OH or phenyl. In some embodiments, $R^{3A}$ is $C_1$-$C_3$ alkyl optionally substituted with —OH. In some embodiments of the, $R^{3A}$ is $C_1$-$C_3$ alkyl optionally substituted with a phenyl.

In some embodiments of the compounds of Formula I, Ia, Ib, II, IIa, or IIb, $R^{3A}$ is H or $C_1$-$C_6$ alkyl. In some embodiments, $R^{3A}$ is H or $C_1$-$C_3$ alkyl. In some embodiments, $R^{3A}$ is H. In some embodiments, $R^{3A}$ is $C_1$-$C_6$ alkyl. In some embodiments, $R^{3A}$ is $C_1$-$C_3$ alkyl. In some embodiments, $R^{3A}$ is methyl.

In some embodiments of the compounds of Formula I, Ia, Ib, II, IIa, or IIb, $R^{3B}$ is H. In some embodiments, $R^{3B}$ is $C_1$-$C_3$ alkyl. In some embodiments, $R^{3B}$ is methyl.

In some embodiments of the compounds of Formula I, Ia, Ib, II, IIa, or IIb, both $R^{3A}$ and $R^{3B}$ are H. In some embodiments, $R^{3A}$ is $C_1$-$C_6$ alkyl and $R^{3B}$ is H. In some embodiments, $R^{3A}$ is $C_1$-$C_3$ alkyl and $R^{3B}$ is H. In some embodiments, $R^{3A}$ is methyl and $R^{3B}$ is H. In some embodiments, both $R^{3A}$ and $R^{3B}$ are $C_1$-$C_3$ alkyl. In some embodiments both $R^{3A}$ and $R^{3B}$ are methyl.

In some embodiments of the compounds of Formula I, Ia, Ib, II, IIa, or IIb, $R^{3A}$ is a $C_1$-$C_6$ alkyl optionally substituted with —OH or phenyl, and $R^{3B}$ is a H. In some embodiments, $R^{3A}$ is a $C_1$-$C_3$ alkyl optionally substituted with —OH or phenyl, and $R^{3B}$ is a H. In some embodiments, $R^{3A}$ is methyl optionally substituted with —OH or phenyl and $R^{3B}$ is H.

In some embodiments, the compound of Formula I, Ia, Ib, II, IIa, or IIb is a compound of Formula III:

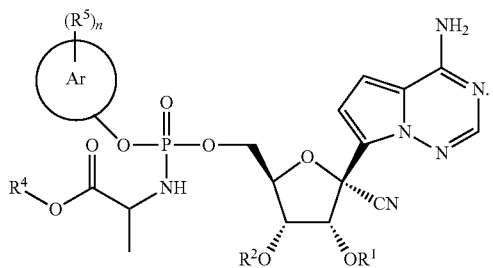

Formula III

In some embodiments, the compound of Formula I, Ia, II, or IIa is a compound of Formula IIIa:

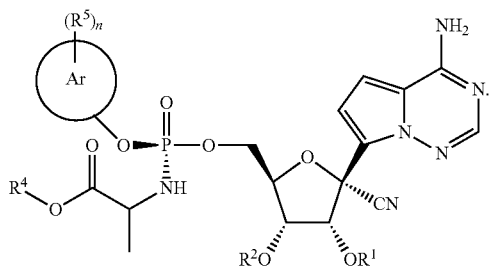

Formula IIIa

In some embodiments, the compound of Formula I, Ib, II, or IIb, has a Formula IIIb:

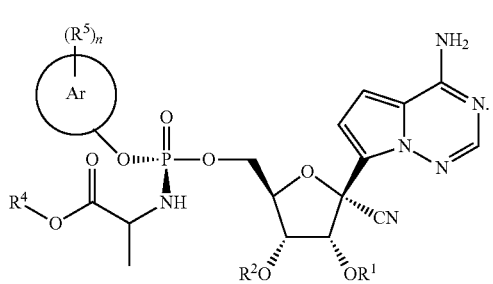

Formula IIIb

In some embodiments, the compound of Formula I, Ia, II, IIa, III, or IIIa has a Formula IIIc:

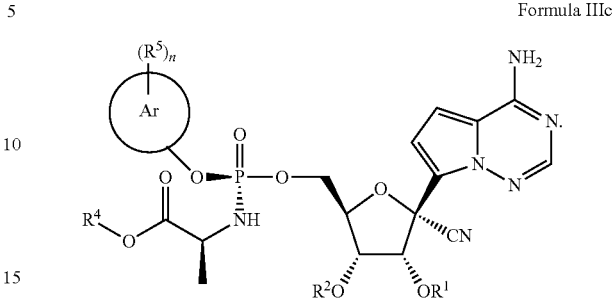

Formula IIIc

In some embodiments of the compounds of Formula I, Ia, Ib, II, IIa, IIb, III, IIIa, IIIb and IIIc, or a pharmaceutically acceptable salt thereof, one of $R^1$ and $R^2$ is H and the other is —(CO)$C_1$-$C_6$ alkyl or —(CO)O$C_1$-$C_6$ alkyl. In some embodiments, $R^1$ is H and $R^2$ is —(CO)$C_1$-$C_6$ alkyl or —(CO)O$C_1$-$C_6$ alkyl. In some embodiments, $R^1$ is H and $R^2$ is —(CO)$C_1$-$C_3$ alkyl or —(CO)O$C_1$-$C_3$ alkyl. In some embodiments, $R^1$ is —(CO)$C_1$-$C_6$ alkyl or —(CO)O$C_1$-$C_6$ alkyl and $R^2$ is H. In some embodiments, $R^1$ is —(CO)$C_1$-$C_3$ alkyl or —(CO)O$C_1$-$C_3$ alkyl and $R^2$ is H.

In some embodiments of the compounds of Formula I, Ia, Ib, II, IIa, IIb, III, IIIa, IIIb, and IIIc, or a pharmaceutically acceptable salt thereof, one of $R^1$ and $R^2$ is H and the other is a —(CO)$C_1$-$C_6$ alkyl. In some embodiments, $R^1$ is H and $R^2$ is —(CO)$C_1$-$C_6$ alkyl. In some embodiments, $R^1$ is H and $R^2$ is —(CO)$C_1$-$C_3$ alkyl. In some embodiments, $R^1$ is H and $R^2$ is —(CO)methyl, —(CO)ethyl, —(CO)n-propyl, or —(CO)iso-propyl. In some embodiments, $R^1$ is H and $R^2$ is —(CO)methyl. In some embodiments, $R^1$ is H and $R^2$ is —(CO)ethyl. In some embodiments, $R^1$ is H and $R^2$ is —(CO)n-propyl. In some embodiments, $R^1$ is H and $R^2$ is —(CO)iso-propyl.

In some embodiments of the compounds of Formula I, Ia, Ib, II, IIa, IIb, III, IIIa, IIIb, and IIIc, or a pharmaceutically acceptable salt thereof, $R^1$ is —(CO)$C_1$-$C_6$ alkyl and $R^2$ is H. In some embodiments, $R^1$ is —(CO)$C_1$-$C_3$ alkyl and $R^2$ is H. In some embodiments, $R^1$ is —(CO)methyl, —(CO)ethyl, —(CO)n-propyl, or —(CO)iso-propyl and $R^2$ is H. In some embodiments, $R^1$ is —(CO)methyl and $R^2$ is H. In some embodiments, $R^1$ is —(CO)ethyl and $R^2$ is H. In some embodiments, $R^1$ is —(CO)n-propyl and $R^2$ is H. In some embodiments, $R^1$ is —(CO)iso-propyl and $R^2$ is H.

In some embodiments of the compounds of Formula I, Ia, Ib, II, IIa, IIb, III, IIIa, IIIb, and IIIc, or a pharmaceutically acceptable salt thereof, $R^1$ is —COCH(CH$_3$)$_2$, —COCH$_3$, —COCH$_2$CH$_3$, —COCH$_2$CH(CH$_3$)$_2$ or —COCH(NH$_2$)CH(CH$_3$)$_2$.

In some embodiments of the compounds of Formula I, Ia, Ib, II, IIa, IIb, III, IIIa, IIIb, and IIIc, or a pharmaceutically acceptable salt thereof, $R^2$ is —COCH(CH$_3$)$_2$, —COCH$_3$, —COCH$_2$CH$_3$, —COCH$_2$CH(CH$_3$)$_2$ or —COCH(NH$_2$)CH(CH$_3$)$_2$.

In some embodiments of the compounds of Formula I, Ia, Ib, II, IIa, IIb, III, IIIa, IIIb, and IIIc, or a pharmaceutically acceptable salt thereof, both $R^1$ and $R^2$ are independently selected from the group consisting of —COCH(CH$_3$)$_2$, —COCH$_3$, —COCH$_2$CH$_3$, —COCH$_2$CH(CH$_3$)$_2$ or —COCH(NH$_2$)CH(CH$_3$)$_2$.

In some embodiments of the compounds of Formula I, Ia, Ib, II, IIa, IIb, III, IIIa, IIIb, and IIIc, or a pharmaceutically acceptable salt thereof, $R^1$ is a —(CO)$C_1$-$C_6$ alkyl and $R^2$ is a —(CO)$C_1$-$C_6$ alkyl. In some embodiments, $R^1$ is a —(CO)$C_1$-$C_3$ alkyl and $R^2$ is a —(CO)$C_1$-$C_3$ alkyl.

In some embodiments, $R^1$ is —(CO)methyl, —(CO)ethyl, —(CO)n-propyl, or —(CO)iso-propyl and $R^2$ is —(CO)methyl, —(CO)ethyl, —(CO)n-propyl, or —(CO)iso-propyl. In some embodiments, $R^1$ is —(CO)methyl and $R^2$ is —(CO)methyl, —(CO)ethyl, —(CO)n-propyl, or —(CO)iso-propyl. In some embodiments, $R^1$ is —(CO)ethyl and $R^2$ is —(CO)methyl, —(CO)ethyl, —(CO)n-propyl, or —(CO)iso-propyl. In some embodiments, $R^1$ is —(CO)n-propyl and $R^2$ is —(CO)methyl, —(CO)ethyl, —(CO)n-propyl, or —(CO)iso-propyl. In some embodiments, $R^1$ is —(CO)iso-propyl and $R^2$ is —(CO)methyl, —(CO)ethyl, —(CO)n-propyl, or —(CO)iso-propyl.

In some embodiments, $R^1$ is —(CO)methyl, —(CO)ethyl, —(CO)n-propyl, or —(CO)iso-propyl and $R^2$ is —(CO)methyl. In some embodiments, $R^1$ is —(CO)methyl, —(CO)ethyl, —(CO)n-propyl, or —(CO)iso-propyl and $R^2$ is —(CO)ethyl. In some embodiments, $R^1$ is —(CO)methyl, —(CO)ethyl, —(CO)n-propyl, or —(CO)iso-propyl and $R^2$ is —(CO)n-propyl. In some embodiments, $R^1$ is —(CO)methyl, —(CO)ethyl, —(CO)n-propyl, or —(CO)iso-propyl and $R^2$ is —(CO)iso-propyl.

In some embodiments, both $R^1$ and $R^2$ are —(CO)methyl. In some embodiments, both $R^1$ and $R^2$ are —(CO)ethyl. In some embodiments, both $R^1$ and $R^2$ are —(CO)n-propyl. In some embodiments, both $R^1$ and $R^2$ are —(CO)iso-propyl.

In some embodiments of the compounds of Formula I, Ia, Ib, II, IIa, IIb, III, IIIa, IIIb, and IIIc, $R^1$ and $R^2$ are combined to form —C(O)—, —C(O)—C($R^{1A}$)($R^{1B}$)—C(O)— or —C(O)—C(O)—, wherein each $R^{1A}$ and $R^{1B}$ is independently H or $C_1$-$C_6$ alkyl. In some embodiments, $R^1$ and $R^2$ are combined to form —C(O)— or —C(O)—C($R^{1A}$)($R^{1B}$)—C(O)— wherein each $R^{1A}$ and $R^{1B}$ is independently H or $C_1$-$C_6$ alkyl. In some embodiments, $R^1$ and $R^2$ are combined to form —C(O)—C($R^{1A}$)($R^{1B}$)—C(O)—, wherein each $R^{1A}$ and $R^{1B}$ is independently H or $C_1$-$C_6$ alkyl. In some embodiments, $R^1$ and $R^2$ are combined to form —C(O)—C($R^{1A}$)($R^{1B}$)—C(O)—, wherein each $R^{1A}$ and $R^{1B}$ is independently H, methyl, or ethyl. In some embodiments, $R^1$ and $R^2$ are combined to form —C(O)—C($R^{1A}$)($R^{1B}$)—C(O)—, wherein $R^{1A}$ is H and $R^{1B}$ is H, methyl, or ethyl. In some embodiments, $R^1$ and $R^2$ are combined to form —C(O)—C($R^{1A}$)($R^{1B}$)—C(O)—, wherein $R^{1A}$ is H and $R^{1B}$ is methyl, or ethyl.

In some embodiments of the compounds of Formula I, Ia, Ib, II, IIa, IIb, III, IIIa, IIIb, and IIIc, $R^1$ and $R^2$ are combined to form —C(O)—C(O)—.

In some embodiments of the compounds of Formula I, Ia, Ib, II, IIa, IIb, III, IIIa, IIIb, and IIIc, $R^1$ and $R^2$ are combined to form —C(O)—.

In some embodiments of the compounds of Formula I, Ia, Ib, II, IIa, IIb, III, IIIa, IIIb, or IIIc, $R^1$ and $R^2$ are both H; and
(i) n is 1, 2, or 3; or
(ii) $R^4$ is $C_1$-$C_8$ alkyl substituted with one or two groups independently selected from $C_1$-$C_3$ alkoxy, $C_1$-$C_3$ haloalkyl, $C_3$-$C_{10}$ cycloalkyl, $C_6$-$C_{10}$ aryl, or 4 to 6 membered heterocyclyl having 1 to 3 heteroatoms independently selected from N, O and S;
wherein the $C_3$-$C_{10}$ cycloalkyl, $C_6$-$C_{10}$ aryl, or 4 to 6 membered heterocyclyl is optionally substituted with one or two substituents independently selected from the group consisting of $C_1$-$C_6$ alkyl, halo, $C_1$-$C_6$ haloalkyl, and $C_1$-$C_6$ alkoxy; or (iii) $R^4$ is (a) —(CR$^8$R$^9$CR$^{10}$R$^{11}$O)$_m$R$^{12}$, (b) monocyclic $C_3$-$C_{10}$ cycloalkyl substituted with one or two $R^{4A}$ groups, (c) bicyclic $C_3$-$C_{10}$ cycloalkyl, (d) 4 to 6 membered heterocyclyl having 1 to 3 heteroatoms independently selected from N, O and S, or (e) 5 to 6 membered heteroaryl having 1 to 3 heteroatoms independently selected from N, O and S;
wherein the bicyclic $C_3$-$C_{10}$ cycloalkyl, 4 to 6 membered heterocyclyl, or 5 to 6 membered heteroaryl is optionally substituted with one or two $R^{4A}$ groups; or
(iv) Base is

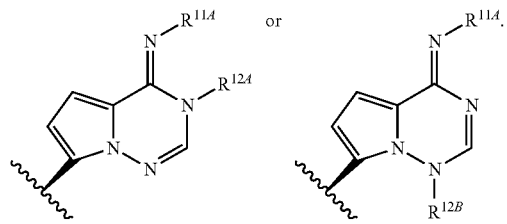

In some embodiments of the compounds of Formula I, Ia, Ib, II, IIa, IIb, III, IIIa, IIIb, or IIIc, $R^1$ and $R^2$ are both H and $R^4$ is (a) —(CR$^8$R$^9$CR$^{10}$R$^{11}$O)$_m$R$^{12}$, (b) monocyclic $C_3$-$C_{10}$ cycloalkyl substituted with one or two $R^{4A}$ groups, (c) bicyclic $C_3$-$C_{10}$ cycloalkyl, (d) 4 to 6 membered heterocyclyl having 1 to 3 heteroatoms independently selected from N, O and S, or (e) 5 to 6 membered heteroaryl having 1 to 3 heteroatoms independently selected from N, O and S; wherein the bicyclic $C_3$-$C_{10}$ cycloalkyl, 4 to 6 membered heterocyclyl, or 5 to 6 membered heteroaryl is optionally substituted with one or two $R^{4A}$ groups.

In some embodiments of the compounds of Formula I, Ia, Ib, II, IIa, IIb, III, IIIa, IIIb, or IIIc, $R^1$ and $R^2$ are both H and $R^4$ is a monocyclic $C_3$-$C_{10}$ cycloalkyl substituted with one or two $R^{4A}$ groups. In some embodiments, $R^1$ and $R^2$ are both H and $R^4$ is a bicyclic $C_3$-$C_{10}$ cycloalkyl optionally substituted with one or two $R^{4A}$ groups. In some embodiments, $R^1$ and $R^2$ are both H and $R^4$ is a 4 to 6 membered heterocyclyl having 1 to 3 heteroatoms independently selected from N, O and S, and optionally substituted with one or two $R^{4A}$ groups. In some embodiments, $R^1$ and $R^2$ are both H and $R^4$ is a 5 to 6 membered heteroaryl having 1 to 3 heteroatoms independently selected from N, O and S, and optionally substituted with one or two $R^{4A}$ groups.

In some embodiments of the compounds of Formula I, Ia, Ib, II, IIa, IIb, III, IIIa, IIIb, or IIIc, $R^1$ and $R^2$ are both H, and $R^4$ is $C_1$-$C_8$ alkyl substituted with one or two groups independently selected from $C_1$-$C_3$ alkoxy, $C_1$-$C_3$ haloalkyl, $C_3$-$C_{10}$ cycloalkyl, $C_6$-$C_{10}$ aryl, or 4 to 6 membered heterocyclyl having 1 to 3 heteroatoms independently selected from N, O and S; wherein the $C_3$-$C_{10}$ cycloalkyl, $C_6$-$C_{10}$ aryl, or 4 to 6 membered heterocyclyl is optionally substituted with one or two substituents independently selected from the group consisting of $C_1$-$C_6$ alkyl, halo, $C_1$-$C_6$ haloalkyl, and $C_1$-$C_6$ alkoxy. In some embodiments, both $R^1$ and $R^2$ are both H, and $R^4$ is $C_1$-$C_8$ alkyl substituted with one or two groups independently selected from $C_1$-$C_3$ alkoxy, $C_1$-$C_3$ haloalkyl, $C_3$-$C_{10}$ cycloalkyl, $C_6$-$C_{10}$ aryl, or 4 to 6 membered heterocyclyl having 1 to 3 heteroatoms independently selected from N, O and S.

In some embodiments of the compounds of Formula I, Ia, Ib, II, IIa, IIb, III, IIIa, IIIb, or IIIc, $R^1$ and $R^2$ are both H. In some embodiments, $R^1$ and $R^2$ are both H and n is 1, 2, or 3. In some embodiments, $R^1$ and $R^2$ are both H and $R^4$ is $-(CR^8R^9CR^{10}R^{11}O)_mR^{12}$. In some embodiments, $R^1$ and $R^2$ are both H and Base is

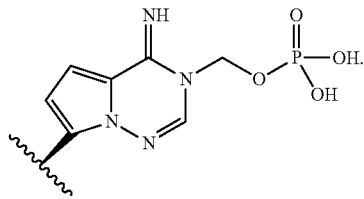

In some embodiments, for the compounds of Formula I, Ia, Ib, II, IIa, IIb, III, IIIa, and IIIc, $R^4$ is (i) $C_1$-$C_8$ alkyl, (ii) $-(CR^8R^9CR^{10}R^{11}O)_mR^{12}$, (iii) $C_3$-$C_{10}$ cycloalkyl, (iv) 4 to 6 membered heterocyclyl having 1 to 3 heteroatoms independently selected from N, O and S, or (v) 5 to 6 membered heteroaryl having 1 to 3 heteroatoms independently selected from N, O and S; wherein the $C_1$-$C_8$ alkyl, $C_3$-$C_{10}$ cycloalkyl, 4 to 6 membered heterocyclyl, and 5 to 6 membered heteroaryl is optionally substituted with one or two $R^{4A}$. In some embodiments, $R^4$ is (i) $C_1$-$C_8$ alkyl, (ii) $-(CR^8R^9CR^{10}R^{11}O)_mR^{12}$, (iii) $C_3$-$C_{10}$ cycloalkyl, or (iv) 4 to 6 membered heterocyclyl having 1 to 3 heteroatoms independently selected from N, O and S; wherein the $C_1$-$C_8$ alkyl, $C_3$-$C_{10}$ cycloalkyl, or 4 to 6 membered heterocyclyl is optionally substituted with one or two $R^{4A}$. In some embodiments, $R^4$ is (i) $C_1$-$C_8$ alkyl, (ii) $-(CR^8R^9CR^{10}R^{11}O)_mR^{12}$, or (iii) $C_3$-$C_{10}$ cycloalkyl; wherein the $C_1$-$C_8$ alkyl or $C_3$-$C_{10}$ cycloalkyl is optionally substituted with one or two $R^{4A}$.

In some embodiments, for the compounds of Formula I, Ia, Ib, II, IIa, IIb, III, IIIa, IIIb, and IIIc, $R^4$ is (i) $C_1$-$C_8$ alkyl, (ii) $-(CR^8R^9CR^{10}R^{11}O)_mR^{12}$, or (iii) 4 to 6 membered heterocyclyl having 1 to 3 heteroatoms independently selected from N, O and S; wherein the $C_1$-$C_8$ alkyl or 4 to 6 membered heterocyclyl is optionally substituted with one or two $R^{4A}$. In some embodiments, $R^4$ is (i) $C_3$-$C_{10}$ cycloalkyl, (ii) $-(CR^8R^9CR^{10}R^{11}O)_mR^{12}$, or (iii) 4 to 6 membered heterocyclyl having 1 to 3 heteroatoms independently selected from N, O and S; wherein the $C_3$-$C_{10}$ cycloalkyl or 4 to 6 membered heterocyclyl is optionally substituted with one or two $R^{4A}$. In some embodiments, $R^4$ is $C_1$-$C_8$ alkyl optionally substituted with one or two $R^{4A}$. In some embodiments, $R^4$ is $C_3$-$C_{10}$ cycloalkyl optionally substituted with one or two $R^{4A}$. In some embodiments, $R^4$ is 4 to 6 membered heterocyclyl having 1 to 3 heteroatoms independently selected from N, O and S, and optionally substituted with one or two $R^{4A}$. In some embodiments, $R^4$ is 5 to 6 membered heteroaryl having 1 to 3 heteroatoms independently selected from N, O and S, and optionally substituted with one or two $R^{4A}$.

In some embodiments, for the compounds of Formula I, Ia, Ib, II, IIa, IIb, III, IIIa, IIIb, and IIIc, $R^4$ is (i) $C_1$-$C_8$ alkyl, (ii) $-(CR^8R^9CR^{10}R^{11}O)_mR^{12}$, (iii) $C_3$-$C_{10}$ cycloalkyl, or (iv) 4 to 6 membered heterocyclyl having 1 to 3 heteroatoms independently selected from N, O and S. In some embodiments, $R^4$ is (i) $C_1$-$C_8$ alkyl, (ii) $-(CR^8R^9CR^{10}R^{11}O)_mR^{12}$, or (iii) $C_3$-$C_{10}$ cycloalkyl. In some embodiments, $R^4$ is (i) $C_1$-$C_8$ alkyl, (ii) $-(CR^8R^9CR^{10}R^{11}O)_mR^{12}$, or (iii) 4 to 6 membered heterocyclyl having 1 to 3 heteroatoms independently selected from N, O and S. In some embodiments, $R^4$ is (i) $C_3$-$C_{10}$ cycloalkyl or (ii) 4 to 6 membered heterocyclyl having 1 to 3 heteroatoms independently selected from N, O and S. In some embodiments, $R^4$ is $C_1$-$C_8$ alkyl.

In some embodiments, $R^4$ is $C_3$-$C_{10}$ cycloalkyl. In some embodiments, $R^4$ is 4 to 6 membered heterocyclyl having 1 to 3 heteroatoms independently selected from N, O and S. In some embodiments, $R^4$ is 5 to 6 membered heteroaryl having 1 to 3 heteroatoms independently selected from N, O and S.

In some embodiments, $R^4$ is $C_1$-$C_8$ alkyl optionally substituted with one $R^{4A}$. In some embodiments, $R^4$ is a $C_{1-6}$ alkyl optionally substituted with one $R^{4A}$. In some embodiments, $R^4$ is $C_1$-$C_4$ alkyl optionally substituted with one $R^{4A}$. In some embodiments, $R^4$ is methyl, ethyl, propyl, or butyl optionally substituted with one $R^{4A}$. In some embodiments, $R^4$ is methyl optionally substituted with one $R^{4A}$. In some embodiments, $R^4$ is ethyl optionally substituted with one $R^{4A}$. In some embodiments, $R^4$ is propyl optionally substituted with one $R^{4A}$. In some embodiments, $R^4$ is butyl optionally substituted with one $R^{4A}$.

In some embodiments, $R^4$ is $C_1$-$C_8$ alkyl. In some embodiments, $R^4$ is a $C_{1-6}$ alkyl. In some embodiments, $R^4$ is a $C_{1-4}$ alkyl. In some embodiments, $R^4$ is methyl, ethyl, propyl, or butyl. In some embodiments, $R^4$ is methyl. In some embodiments, $R^4$ is ethyl. In some embodiments, $R^4$ is propyl. In some embodiments, $R^4$ is butyl.

In some embodiments, $R^4$ is $C_3$-$C_{10}$ cycloalkyl optionally substituted with one $R^{4A}$. For example, $R^4$ is cyclopropyl, cyclobutyl, cyclopentyl, cyclohexyl, cycloheptyl, or cyclooctyl optionally substituted with one $R^{4A}$. In some example, $R^4$ is cyclobutyl, cyclohexyl, or cyclooctyl optionally substituted with one $R^{4A}$. In some embodiments, $R^4$ is cyclopropyl optionally substituted with one $R^{4A}$. In some embodiments, $R^4$ is cyclobutyl optionally substituted with one $R^{4A}$. In some embodiments, $R^4$ is cyclopentyl optionally substituted with one $R^{4A}$. In some embodiments, $R^4$ is cyclohexyl optionally substituted with one $R^{4A}$. In some embodiments, $R^4$ is cycloheptyl optionally substituted with one $R^{4A}$. In some embodiments, $R^4$ is cyclooctyl optionally substituted with one $R^{4A}$.

In some embodiments, $R^4$ is $C_3$-$C_{10}$ cycloalkyl. For example, $R^4$ is cyclopropyl, cyclobutyl, cyclopentyl, cyclohexyl, cycloheptyl, or cyclooctyl. In some embodiments, $R^4$ is cyclobutyl, cyclohexyl, or cyclooctyl. In some embodiments, $R^4$ is cyclopropyl. In some embodiments, $R^4$ is cyclobutyl. In some embodiments, $R^4$ is cyclopentyl. In some embodiments, $R^4$ is cyclohexyl. In some embodiments, $R^4$ is cycloheptyl. In some embodiments, $R^4$ is cyclooctyl.

In some embodiments, $R^4$ is a 4 to 6 membered heterocyclyl having 1 to 3 heteroatoms independently selected from N, O and S, wherein the 4 to 6 membered heterocyclyl is optionally substituted with one $R^{4A}$. In some embodiments, $R^4$ is a 4 to 6 membered heterocyclyl having 1 or 2 heteroatoms independently selected from N, O and S, wherein the 4 to 6 membered heterocyclyl is optionally substituted with one $R^{4A}$. In some embodiments, $R^4$ is a 4 to 6 membered heterocyclyl having 1 heteroatom selected from N, O and S, wherein the 4 to 6 membered heterocyclyl is optionally substituted with one $R^{4A}$. In some embodiments, $R^4$ is a 4 to 6 membered heterocyclyl having one O atom, wherein the 4 to 6 membered heterocyclyl is optionally substituted with one $R^{4A}$. In some embodiments, $R^4$ is a oxetanyl, tetrahydrofuryl, or tetrahydropyranyl, each of which is optionally substituted with one $R^{4A}$. In some embodiments, $R^4$ is a oxetanyl or tetrahydropyranyl, each of which is optionally substituted with one $R^{4A}$. In some embodiments, $R^4$ is a oxetanyl optionally substituted with one $R^{4A}$. In some embodiments, $R^4$ is a tetrahydropyranyl optionally substituted with one $R^{4A}$.

In some embodiments, $R^4$ is a 4 to 6 membered heterocyclyl having 1 to 3 heteroatoms independently selected from N, O and S. In some embodiments, $R^4$ is a 4 to 6 membered heterocyclyl having 1 or 2 heteroatoms independently selected from N, O and S. In some embodiments, $R^4$ is a 4 to 6 membered heterocyclyl having 1 heteroatom selected from N, O and S. In some embodiments, $R^4$ is a 4 to 6 membered heterocyclyl having one O atom. In some embodiments, $R^4$ is a oxetanyl, tetrahydrofuryl, or tetrahydropyranyl. In some embodiments, $R^4$ is a oxetanyl or tetrahydropyranyl. In some embodiments, $R^4$ is a oxetanyl. In some embodiments, $R^4$ is a tetrahydropyranyl.

In some embodiment, $R^4$ is $C_1$-$C_8$ alkyl, $C_3$-$C_{10}$ cycloalkyl, or 4-6 membered heterocyclyl containing one heteroatom selected from N, O, and S, wherein the $C_1$-$C_8$ alkyl, $C_3$-$C_{10}$ cycloalkyl, or 4-6 membered heterocyclyl is optionally substituted with one $R^{4A}$. In some embodiment, $R^4$ is $C_1$-$C_8$ alkyl, $C_3$-$C_{10}$ cycloalkyl, or 4-6 membered heterocyclyl containing one O atom, wherein the $C_1$-$C_8$ alkyl, $C_3$-$C_{10}$ cycloalkyl, or 4-6 membered heterocyclyl is optionally substituted with one $R^{4A}$. For example, $R^4$ is a $C_{1-6}$ alkyl, $C_3$-$C_8$ cycloalkyl, or 4-6 membered heterocyclyl containing one heteroatom selected from N, O, and S, wherein the $C_{1-6}$ alkyl, $C_3$-$C_8$ cycloalkyl, or 4-6 membered heterocyclyl is optionally substituted with one $R^{4A}$. In some embodiments, $R^4$ is a $C_{1-4}$ alkyl, $C_3$-$C_8$ cycloalkyl, or 4-6 membered heterocyclyl containing one heteroatom selected from N, O, and S, wherein the $C_{1-4}$ alkyl, $C_3$-$C_8$ cycloalkyl, or 4-6 membered heterocyclyl is optionally substituted with one $R^{4A}$. In some embodiments $R^4$ is methyl, ethyl, propyl, butyl, cyclobutyl, cyclohexyl, cyclooctyl, oxetanyl, tetrahydrofuryl, or tetrahydropyranyl, each of which is optionally substituted with one $R^{4A}$.

In some embodiment, $R^4$ is $C_1$-$C_8$ alkyl, $C_3$-$C_{10}$ cycloalkyl, or 4-6 membered heterocyclyl containing one heteroatom selected from N, O, and S. For example, $R^4$ is a $C_1$-$C_6$ alkyl, $C_3$-$C_8$ cycloalkyl, or 4-6 membered heterocyclyl containing one heteroatom selected from N, O, and S. In some embodiments $R^4$ is methyl, ethyl, propyl, butyl, pentyl, hexyl, cyclobutyl, cyclohexyl, cyclooctyl, oxetanyl, tetrahydrofuryl, or tetrahydropyranyl.

In some embodiments of the compounds of Formula I, Ia, Ib, II, IIa, IIb, III, IIIa, IIIb, and IIIc $R^4$ is —(CR$^8$R$^9$CR$^{10}$R$^{11}$O)$_m$R$^{12}$, wherein m is 1, 2, 3, 4, or 5; each R$^8$, R$^9$, R$^{10}$, and R$^{11}$ is independently H or methyl; and R$^{12}$ is $C_1$-$C_3$ alkyl. In some embodiments, m is 1, 2, 3, 4, or 5; each R$^8$, R$^9$, R$^{10}$, and R$^{11}$ is H; and R$^{12}$ is $C_1$-$C_3$ alkyl.

In some embodiments of the compounds of Formula I, Ia, Ib, II, IIa, IIb, III, IIa, IIIb, or IIIc, $R^4$ is methyl, ethyl, n-propyl, isopropyl, cyclobutyl, cyclohexyl, cyclooctyl,

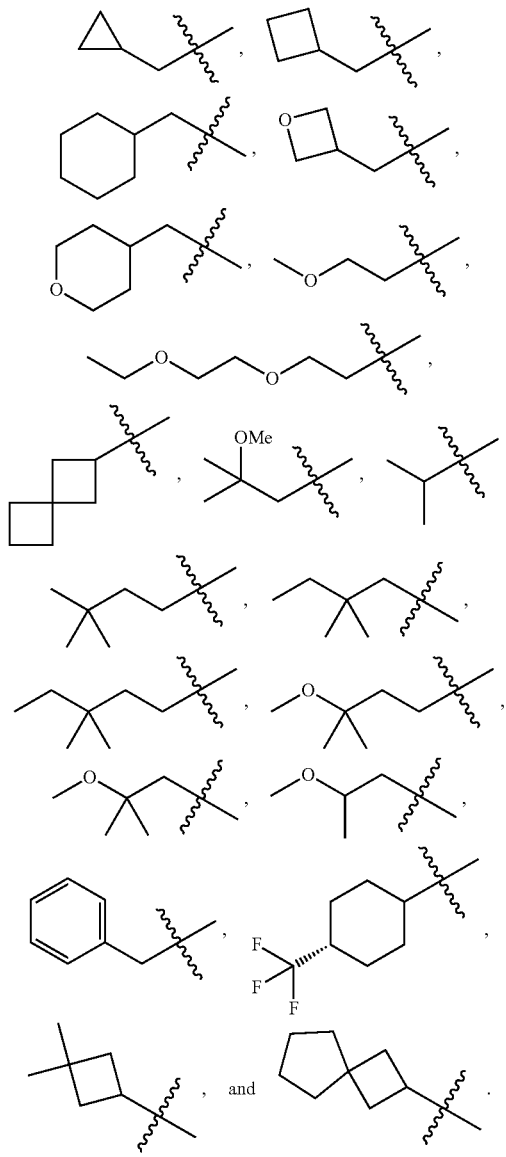

In some embodiments of the compounds of Formula I, Ia, Ib, II, IIa, IIb, III, IIa, IIIb, and IIIc, $R^4$ is methyl, ethyl,

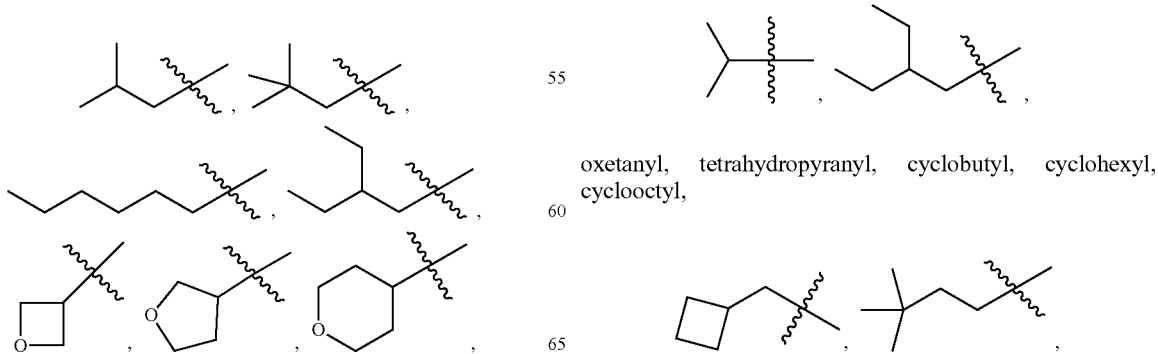

oxetanyl, tetrahydropyranyl, cyclobutyl, cyclohexyl, cyclooctyl, $C_1$ alkyl substituted with a tetrahydropyranyl,

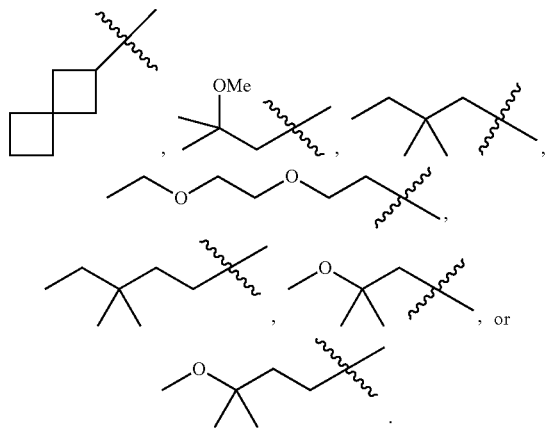

In some embodiments of the compounds of Formula I, Ia, Ib, II, IIa, IIb, III, IIIa, IIIb, and IIIc, $R^1$ is a —(CO)$C_1$-$C_3$ alkyl, $R^2$ is a —(CO)$C_1$-$C_3$ alkyl, and $R^4$ is $C_1$-$C_8$ alkyl, —(CR$^8$R$^9$CR$^{10}$R$^{11}$O)$_m$R$^{12}$, $C_3$-$C_{10}$ cycloalkyl, or 4-6 membered heterocyclyl containing one heteroatom selected from N, O, and S, wherein the $C_1$-$C_8$ alkyl, $C_3$-$C_{10}$ cycloalkyl, or 4-6 membered heterocyclyl is optionally substituted with one $R^{4A}$. For example, $R^1$ is a —(CO)$C_1$-$C_3$ alkyl, $R^2$ is a —(CO)$C_1$-$C_3$ alkyl, and $R^4$ is $C_1$-$C_6$ alkyl, —(CR$^8$R$^9$CR$^{10}$R$^{11}$O)$_m$R$^{12}$, $C_3$-$C_{10}$ cycloalkyl, or 4-6 membered heterocyclyl containing one O atom, wherein the $C_1$-$C_6$ alkyl, $C_3$-$C_{10}$ cycloalkyl, or 4-6 membered heterocyclyl is optionally substituted with one $R^{4A}$. In some embodiments $R^1$ is —(CO)methyl, —(CO)ethyl, —(CO)n-propyl, or —(CO)i-propyl, $R^2$—(CO)methyl, —(CO)ethyl, —(CO)n-propyl, or —(CO)i-propyl, and $R^4$ is methyl, ethyl, propyl, butyl, cyclobutyl, cyclohexyl, cyclooctyl, oxetanyl, tetrahydrofuryl, or tetrahydropyranyl, each of which is optionally substituted with one $R^{4A}$.

In some embodiments of the compounds of Formula I, Ia, Ib, II, IIa, IIb, III, IIIa, IIIb, and IIIc described herein, $R^{4A}$ is $C_1$-$C_3$ alkyl, $C_1$-$C_3$ alkoxy, $C_1$-$C_3$ haloalkyl, $C_3$-$C_{10}$ cycloalkyl, $C_6$-$C_{10}$ aryl, or 4 to 6 membered heterocyclyl having 1 to 3 heteroatoms independently selected from N, O and S; wherein the $C_3$-$C_{10}$ cycloalkyl, $C_6$-$C_{10}$ aryl, or 4 to 6 membered heterocyclyl is optionally substituted with one or two substituents independently selected from the group consisting of $C_1$-$C_6$ alkyl, halo, $C_1$-$C_6$ haloalkyl, and $C_1$-$C_6$ alkoxy. In some embodiments, $R^{4A}$ is $C_1$-$C_3$ alkyl, $C_1$-$C_3$ alkoxy, $C_1$-$C_3$ haloalkyl, $C_3$-$C_{10}$ cycloalkyl, $C_6$-$C_{10}$ aryl, or 4 to 6 membered heterocyclyl having 1 to 3 heteroatoms independently selected from N, O and S. In some embodiments, $R^{4A}$ is $C_1$-$C_3$ alkyl, $C_1$-$C_3$ alkoxy, $C_1$-$C_3$ haloalkyl, $C_3$-$C_{10}$ cycloalkyl, $C_6$-$C_{10}$ aryl, or 4 to 6 membered heterocyclyl having 1 or 2 heteroatoms independently selected from N, O and S. In some embodiments, $R^{4A}$ is $C_1$-$C_3$ alkyl, $C_1$-$C_3$ alkoxy, $C_1$-$C_3$ haloalkyl, $C_3$-$C_{10}$ cycloalkyl, $C_6$-$C_{10}$ aryl, or 4 to 6 membered heterocyclyl having one heteroatom selected from N, O and S. In some embodiments, $R^{4A}$ is $C_1$-$C_3$ alkyl, $C_1$-$C_3$ alkoxy, $C_1$-$C_3$ haloalkyl, $C_3$-$C_{10}$ cycloalkyl, or 4 to 6 membered heterocyclyl having one heteroatom selected from N, O and S. For example, $R^{4A}$ is methyl, ethyl, propyl, halo methyl, methoxy, halo ethyl, halo propyl, cyclopropyl, cyclobutyl, cyclopropyl, cyclohexyl, oxetanyl, tetrahydrofuryl, or tetrahydropyranyl. In some embodiments, $R^{4A}$ is methyl, ethyl, propyl, methoxy, cyclopropyl, cyclobutyl, cyclopropyl, cyclohexyl, oxetanyl, tetrahydrofuryl, or tetrahydropyranyl. In some embodiments, $R^{4A}$ is methyl, ethyl, methoxy, cyclobutyl, cyclohexyl, oxetanyl, or tetrahydropyranyl. In some embodiments, $R^{4A}$ is methoxy, cyclobutyl, cyclohexyl, oxetanyl, or tetrahydropyranyl.

In some embodiments of the compounds of Formula I, Ia, Ib, II, IIa, IIb, III, IIIa, IIIb, and IIIc described herein, n is 0, 1, 2, or 3. For example n is 0, 1, or 2, or n is 0 or 1. In some embodiments n is 0. In some embodiments n is 1. In some embodiments, n is 2. In some embodiments, n is 3.

In some embodiments of the compounds of Formula I, Ia, Ib, II, IIa, IIb, III, IIIa, IIIb, and IIIc described herein, each $R^5$ is independently halo, cyano, $C_1$-$C_6$ alkyl, $C_1$-$C_6$ haloalkyl, $C_3$-$C_6$ cycloalkyl, $C_1$-$C_6$ alkoxy, $C_3$-$C_6$ cycloalkoxy, —COOR$^{5A}$, —SO$_2$R$^{5A}$, 4 to 6 membered heterocycloalkyl containing one, two or three heteroatoms selected from N, O, and S, or 5 to 6 membered heteroaryl containing one, two or three heteroatoms selected from N, O, and S; wherein the $C_1$-$C_6$ alkyl, $C_1$-$C_6$ haloalkyl, $C_3$-$C_6$ cycloalkyl, $C_3$-$C_6$ cycloalkoxy, $C_1$-$C_6$ alkoxy, 4 to 6 membered heterocycloalkyl and 5 to 6 membered heteroaryl is optionally substituted with one or two $R^{5B}$ groups; or two $R^5$ groups on adjacent carbon atoms are joined to form a $C_5$-$C_6$ cycloalkyl.

In some embodiments of the compounds of Formula I, Ia, Ib, II, IIa, IIb, III, IIIa, IIIb, and IIIc described herein, each $R^5$ is independently halo, cyano, $C_1$-$C_6$ alkyl, $C_1$-$C_6$ haloalkyl, $C_3$-$C_6$ cycloalkyl, $C_3$-$C_6$ cycloalkoxy, $C_1$-$C_6$ alkoxy, —COOR$^{5A}$, or —SO$_2$R$^{5A}$; wherein the $C_1$-$C_6$ alkyl, $C_1$-$C_6$ haloalkyl, $C_3$-$C_6$ cycloalkyl, $C_3$-$C_6$ cycloalkoxy and $C_1$-$C_6$ alkoxy is optionally substituted with one or two $R^{5B}$ groups.

In some embodiments of the compounds of Formula I, Ia, Ib, II, IIa, IIb, III, IIIa, IIIb, and IIIc described herein, $R^5$ is independently halo, cyano, $C_1$-$C_6$ alkyl, $C_3$-$C_6$ cycloalkyl, $C_1$-$C_6$ alkoxy, or —SO$_2$R$^{5A}$; wherein the $C_1$-$C_6$ alkyl, $C_3$-$C_6$ cycloalkyl and $C_1$-$C_6$ alkoxy is optionally substituted with one or two $R^{5B}$ groups; or two $R^5$ groups on adjacent carbon atoms are joined to form a $C_5$-$C_6$ cycloalkyl. In some embodiments, each $R^5$ is independently halo, cyano, $C_1$-$C_6$ alkyl, $C_3$-$C_6$ cycloalkyl, $C_1$-$C_6$ alkoxy, or —SO$_2$R$^{5A}$; wherein the $C_1$-$C_6$ alkyl is optionally substituted with one or two $R^{5B}$ groups. In some embodiments, each $R^{5A}$ is independently $C_1$-$C_6$ alkyl and each $R^{5B}$ is independently —COOR$^{5C}$ and —NHCOOR$^{5D}$; wherein $R^{5C}$ is $C_1$-$C_6$ alkyl and $R^{5D}$ is $C_1$-$C_3$ alkyl optionally substituted with a phenyl group.

In some embodiments, two $R^5$ groups on adjacent carbon atoms are joined to form a $C_5$-$C_6$ cycloalkyl. In some embodiments, each $R^5$ is independently halo, cyano, $C_1$-$C_6$ alkyl, or $C_3$-$C_6$ cycloalkyl. In some embodiments, each $R^5$ is independently $C_1$-$C_6$ alkyl or $C_3$-$C_6$ cycloalkyl. In some embodiments, each $R^5$ is independently methyl, tert butyl, or cyclopropyl.

In some embodiments, n is 1, 2, or 3, and each $R^5$ is independently $C_1$-$C_6$ alkyl or $C_3$-$C_6$ cycloalkyl. In some embodiments, n is 1 or 2, and each $R^5$ is independently $C_1$-$C_6$ alkyl or $C_3$-$C_6$ cycloalkyl. In some embodiments, n is 1, 2, or 3, and each $R^5$ is independently methyl, tert butyl, or cyclopropyl.

In some embodiments of the compounds of Formula I, Ia, Ib, II, IIa, IIb, III, IIIa, IIIb, and IIIc described herein, $R^5$ is $C_1$-$C_4$ alkyl. In some embodiments, in some embodiments, $R^5$ is methyl, ethyl, propyl, or butyl. In some embodiments $R^5$ is methyl or tert-butyl.

In some embodiments of the compounds of Formula I, Ia, Ib, II, IIa, IIb, III, IIIa, IIIb, or IIIc,

is or 5 to 10 membered heteroaryl containing one, two, or three heteroatoms selected from the group consisting of O, N, and S.

In some embodiments of the compounds of Formula I, Ia, Ib, II, IIa, IIb, III, IIIa, IIIb, or IIIc,

is a $C_6$-$C_{10}$ aryl; n is 0, 1, 2, or 3; and each $R^5$ is independently halo, cyano, $C_1$-$C_6$ alkyl, $C_3$-$C_6$ cycloalkyl, $C_1$-$C_6$ alkoxy, or —$SO_2R^{5A}$; or two $R^5$ groups on adjacent carbon atoms are joined to form a $C_5$-$C_6$ cycloalkyl.

In some embodiments of the compounds of Formula I, Ia, Ib, II, IIa, IIb, III, IIIa, IIIb, or IIIc,

is a $C_6$-$C_{10}$ aryl; n is 0, 1, or 2; and each $R^5$ is independently halo, cyano, $C_1$-$C_6$ alkyl, $C_3$-$C_6$ cycloalkyl, $C_1$-$C_6$ alkoxy, or —$SO_2R^{5A}$; or two $R^5$ groups on adjacent carbon atoms are joined to form a $C_5$-$C_6$ cycloalkyl. In some embodiments,

is a $C_6$-$C_{10}$ aryl, n is 0, 1, 2, or 3, and each $R^5$ is independently $C_1$-$C_6$ alkyl or $C_3$-$C_6$ cycloalkyl; or two $R^5$ groups on adjacent carbon atoms are joined to form a $C_5$-$C_6$ cycloalkyl. In some embodiments,

is a $C_6$-$C_{10}$ aryl, n is 0, 1, or 2, and each $R^5$ is independently $C_1$-$C_6$ alkyl or $C_3$-$C_6$ cycloalkyl; or wherein two $R^5$ groups on adjacent carbon atoms are joined to form a $C_5$-$C_6$ cycloalkyl. In some embodiments,

is a phenyl or napthyl; n is 0, 1, 2, or 3, and each $R^5$ is independently $C_1$-$C_6$ alkyl or $C_3$-$C_6$ cycloalkyl; or two $R^5$ groups on adjacent carbon atoms are joined to form a $C_5$-$C_6$ cycloalkyl. In some embodiments,

is a phenyl or napthyl; n is 0, 1, or 2, and each $R^5$ is independently $C_1$-$C_6$ alkyl or $C_3$-$C_6$ cycloalkyl; or two $R^5$ groups on adjacent carbon atoms are joined to form a $C_5$-$C_6$ cycloalkyl. In some embodiments,

is a phenyl, n is 0, 1, 2, or 3, and each $R^5$ is independently $C_1$-$C_6$ alkyl or $C_3$-$C_6$ cycloalkyl; or two $R^5$ groups on adjacent carbon atoms are joined to form a $C_5$-$C_6$ cycloalkyl. In some embodiments,

is a phenyl, n is 0, 1, or 2, and each $R^5$ is independently $C_1$-$C_6$ alkyl or $C_3$-$C_6$ cycloalkyl; or two $R^5$ groups on adjacent carbon atoms are joined to form a $C_5$-$C_6$ cycloalkyl. In some embodiments,

is a napthyl, n is 0, 1, 2, or 3, and each $R^5$ is independently $C_1$-$C_6$ alkyl or $C_3$-$C_6$ cycloalkyl; or two $R^5$ groups on adjacent carbon atoms are joined to form a $C_5$-$C_6$ cycloalkyl. In some embodiments,

is a napthyl; n is 0, 1, or 2; and each $R^5$ is independently $C_1$-$C_6$ alkyl or $C_3$-$C_6$ cycloalkyl; or two $R^5$ groups on adjacent carbon atoms are joined to form a $C_5$-$C_6$ cycloalkyl. In some embodiments,

is a phenyl or napthyl; n is 0, 1, 2, or 3; and each $R^5$ is independently $C_1$-$C_6$ alkyl or $C_3$-$C_6$ cycloalkyl. In some embodiments,

is a phenyl or napthyl; n is 0, 1, or 2; and each $R^5$ is independently $C_1$-$C_6$ alkyl or $C_3$-$C_6$ cycloalkyl. In some embodiments,

is a phenyl; n is 0, 1, 2, or 3; and each $R^5$ is independently $C_1$-$C_6$ alkyl or $C_3$-$C_6$ cycloalkyl. In some embodiments,

is a phenyl; n is 0, 1, or 2; and each $R^5$ is independently $C_1$-$C_6$ alkyl or $C_3$-$C_6$ cycloalkyl. In some embodiments,

is a napthyl; n is 0, 1, 2, or 3; and each $R^5$ is independently $C_1$-$C_6$ alkyl or $C_3$-$C_6$ cycloalkyl. In some embodiments,

is a napthyl; n is 0, 1, or 2; and each $R^5$ is independently $C_1$-$C_6$ alkyl or $C_3$-$C_6$ cycloalkyl. In some embodiments,

is a phenyl and n is 0. In some embodiments, Ar is a napthyl and n is 0.

In some embodiments of the compounds of Formula I, Ia, Ib, II, IIa, IIb, III, IIIa, IIIb, or IIIc, is a $C_6$-$C_{10}$ aryl optionally substituted with one or two $R^5$ groups; wherein each $R^5$ is independently halo, cyano, $C_1$-$C_6$ alkyl, $C_3$-$C_6$ cycloalkyl, $C_1$-$C_6$ alkoxy, or —$SO_2R^{5A}$; or two $R^5$ groups on adjacent carbon atoms are joined to form a $C_5$-$C_6$ cycloalkyl. In some embodiments,

is a $C_6$-$C_{10}$ aryl optionally substituted with one or two $R^5$ groups; wherein each $R^5$ is independently $C_1$-$C_6$ alkyl or $C_3$-$C_6$ cycloalkyl; or two $R^5$ groups on adjacent carbons atoms are joined to form a $C_5$-$C_6$ cycloalkyl. In some embodiments,

is a $C_6$-$C_{10}$ aryl optionally substituted with one or two $R^5$ groups; wherein each $R^5$ is independently $C_1$-$C_6$ alkyl or $C_3$-$C_6$ cycloalkyl. In some embodiments,

is a phenyl or napthyl; wherein the phenyl or naphthyl is optionally substituted with one or two $R^5$ groups; wherein each $R^5$ is independently $C_1$-$C_6$ alkyl or $C_3$-$C_6$ cycloalkyl; or two $R^5$ groups on adjacent carbon atoms are joined to form a $C_5$-$C_6$ cycloalkyl. In some embodiments,

is a phenyl or napthyl; wherein the phenyl or naphthyl is optionally substituted with one or two $R^5$ groups; wherein each $R^5$ is independently $C_1$-$C_6$ alkyl or $C_3$-$C_6$ cycloalkyl. In some embodiments,

is a phenyl optionally substituted with one or two $R^5$ groups; wherein each $R^5$ is independently $C_1$-$C_6$ alkyl or $C_3$-$C_6$ cycloalkyl; or two $R^5$ groups on adjacent carbon atoms are joined to form a $C_5$-$C_6$ cycloalkyl. In some embodiments,

is a phenyl optionally substituted with one or two R⁵ groups; wherein each R⁵ is independently $C_1$-$C_6$ alkyl or $C_3$-$C_6$ cycloalkyl. In some embodiments,

is a phenyl.

In some embodiments of the compounds of Formula I, Ia, Ib, II, IIa, IIb, III, IIIa, IIIb, or IIIc,

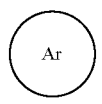

is a napthyl optionally substituted with one or two R⁵ groups; wherein each R⁵ is independently $C_1$-$C_6$ alkyl or $C_3$-$C_6$ cycloalkyl; or two R⁵ groups on adjacent carbon atoms are joined to form a $C_5$-$C_6$ cycloalkyl. In some embodiments,

is a napthyl optionally substituted with one or two R⁵ groups; wherein each R⁵ is independently $C_1$-$C_6$ alkyl or $C_3$-$C_6$ cycloalkyl. In some embodiments,

is 1-napthyl or 2-napthyl.

In some embodiments of the compounds of Formula I, Ia, Ib, II, IIa, IIb, III, IIIa, IIIb, or IIIc,

is selected from the group consisting of:

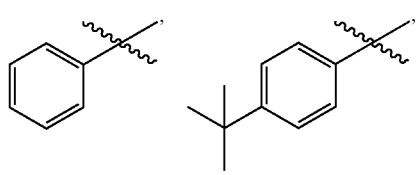

-continued

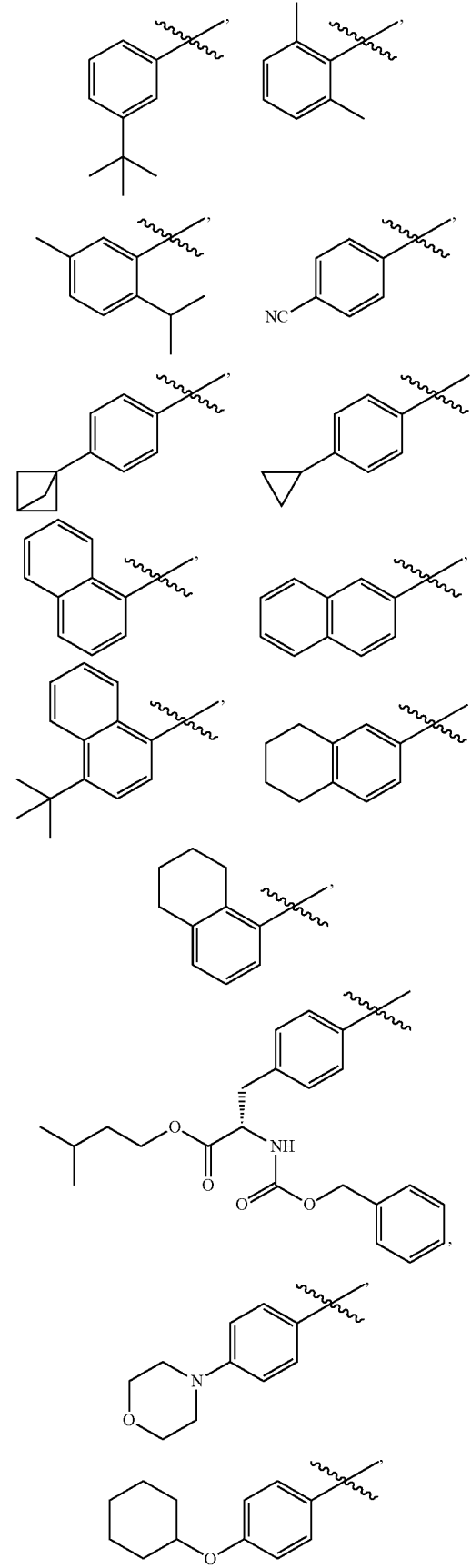

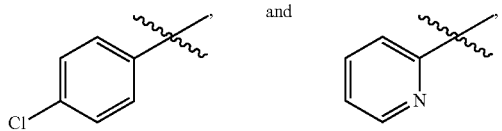

In some embodiments of the compounds of Formula I, Ia, Ib, II, IIa, IIb, III, IIIa, IIIb, or IIIc:
$R^1$ is a —(CO)$C_1$-$C_3$ alkyl;
$R^2$ is a —(CO)$C_1$-$C_3$ alkyl;
$R^4$ is $C_1$-$C_8$ alkyl, —(CR$^8$R$^9$CR$^{10}$R$^{11}$O)$_m$R$^{12}$, $C_3$-$C_{10}$ cycloalkyl, or 4-6 membered heterocyclyl containing one heteroatom selected from N, O, and S, wherein the $C_1$-$C_8$ alkyl, $C_3$-$C_{10}$ cycloalkyl, or 4-6 membered heterocyclyl is optionally substituted with one or two $R^{4.4}$;
each $R^8$, $R^9$, $R^{10}$, $R^{11}$ and $R^{12}$ is independently H or $C_1$-$C_3$ alkyl; $R^{4.4}$ is $C_1$-$C_3$ alkyl, $C_1$-$C_3$ alkoxy, $C_1$-$C_3$ haloalkyl, $C_3$-$C_{10}$ cycloalkyl, or 4 to 6 membered heterocyclyl having one heteroatom selected from N, O and S;

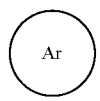

is napthyl or phenyl;
n is 0, 1, or 2; and
$R^5$ is $C_1$-$C_6$ alkyl or $C_3$-$C_6$ cycloalkyl.

In some embodiments of the compounds of Formula I, Ia, Ib, II, IIa, IIb, III, IIIa, IIIb, or IIIc:
$R^1$ is a —(CO)$C_1$-$C_3$ alkyl;
$R^2$ is a —(CO)$C_1$-$C_3$ alkyl;
$R^4$ is $C_1$-$C_8$ alkyl, —(CR$^8$R$^9$CR$^{10}$R$^{11}$O)$_m$R$^{12}$, $C_3$-$C_{10}$ cycloalkyl, or 4-6 membered heterocyclyl containing one O atom, wherein the $C_1$-$C_8$ alkyl, $C_3$-$C_{10}$ cycloalkyl, or 4-6 membered heterocyclyl is optionally substituted with one or two $R^{4.4}$;
each $R^8$, $R^9$, $R^{10}$, $R^{11}$ and $R^{12}$ is independently H or $C_1$-$C_3$ alkyl;
$R^{4.4}$ is methyl, ethyl, propyl, halo methoxy, halo ethyl, halo propyl, cyclopropyl, cyclobutyl, cyclopropyl, cyclohexyl, oxetanyl, tetrahydrofuryl, or tetrahydropyranyl;

is napthyl or phenyl;
n is 0, 1, or 2; and
$R^5$ is $C_1$-$C_6$ alkyl or $C_3$-$C_6$ cycloalkyl.

In some embodiments of the compounds of Formula I, Ia, Ib, II, IIa, IIb, III, IIIa, IIIb, or IIIc:
$R^1$ is a —(CO)$C_1$-$C_3$ alkyl;
$R^2$ is a —(CO)$C_1$-$C_3$ alkyl;
$R^4$ is $C_1$-$C_8$ alkyl, $C_3$-$C_{10}$ cycloalkyl, or 4-6 membered heterocyclyl containing one 0 atom, wherein the $C_1$-$C_8$ alkyl, $C_3$-$C_{10}$ cycloalkyl, or 4-6 membered heterocyclyl is optionally substituted with one or two $R^{4.4}$;
$R^{4.4}$ is methyl, methoxy, ethyl, propyl, cyclopropyl, cyclobutyl, cyclopropyl, cyclohexyl, oxetanyl, tetrahydrofuryl, or tetrahydropyranyl;

is napthyl or phenyl;
n is 0 or 1; and
$R^5$ is $C_1$-$C_6$ alkyl or $C_3$-$C_6$ cycloalkyl.

In some embodiments of the compounds of Formula I, Ia, Ib, II, IIa, IIb, III, IIIa, IIIb, or IIIc:
$R^1$ is a —(CO)$C_1$-$C_3$ alkyl;
$R^2$ is a —(CO)$C_1$-$C_3$ alkyl;
$R^4$ is $C_1$-$C_8$ alkyl, —(CR$^8$R$^9$CR$^{10}$R$^{11}$O)$_m$R$^{12}$, $C_3$-$C_{10}$ cycloalkyl, or 4-6 membered heterocyclyl containing one O atom, wherein the $C_1$-$C_8$ alkyl, $C_3$-$C_{10}$ cycloalkyl, or 4-6 membered heterocyclyl is optionally substituted with one or two $R^{4.4}$;
each $R^8$, $R^9$, $R^{10}$, $R^{11}$ and $R^{12}$ is independently H or methyl;
$R^{4.4}$ is methyl, methoxy, ethyl, cyclobutyl, cyclohexyl, oxetanyl, or tetrahydropyranyl;

is napthyl or phenyl;
n is 0, 1, or 2; and
$R^5$ is $C_1$-$C_6$ alkyl or cyclopropyl.

In some embodiments of the compounds of Formula I, Ia, Ib, II, IIa, IIb, III, IIa, IIIb, or IIIc:
$R^1$ is a —(CO)$C_1$-$C_3$ alkyl;
$R^2$ is a —(CO)$C_1$-$C_3$ alkyl;
$R^4$ is $C_1$-$C_8$ alkyl, —(CR$^8$R$^9$CR$^{10}$R$^{11}$O)$_m$R$^{12}$, $C_3$-$C_{10}$ cycloalkyl, or 4-6 membered heterocyclyl containing one O atom, wherein the $C_1$-$C_8$ alkyl, $C_3$-$C_{10}$ cycloalkyl, or 4-6 membered heterocyclyl is optionally substituted with one or two $R^{4.4}$;
each $R^8$, $R^9$, $R^{10}$, $R^{11}$ and $R^{12}$ is independently H or methyl;
$R^{4.4}$ is cyclobutyl, cyclohexyl, methoxy, oxetanyl, or tetrahydropyranyl;
n is 0, 1 or 2; and
$R^5$ is $C_1$-$C_6$ alkyl or cyclopropyl.

In some embodiments, the compound of Formula I, Ia, Ib, II, IIa, IIb, III, IIIa, IIIb, or IIIc, is selected from the group consisting of:

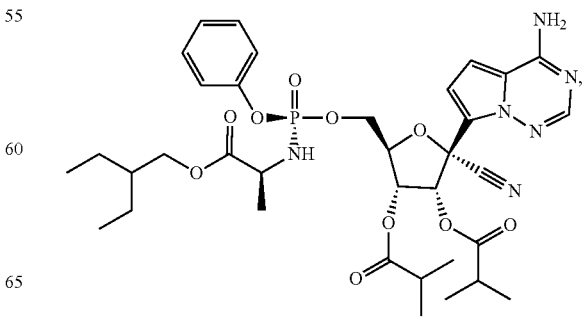

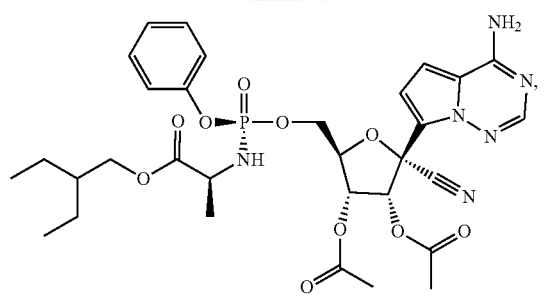
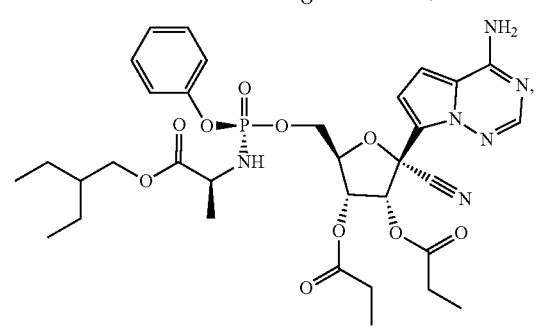
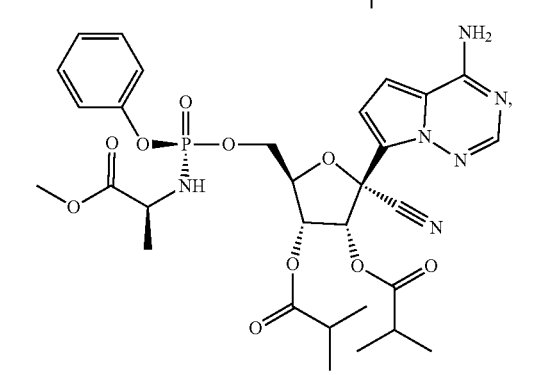
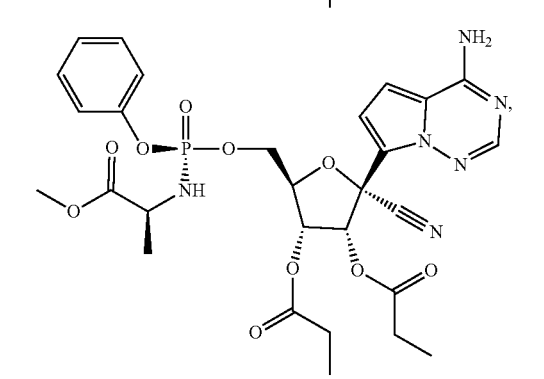
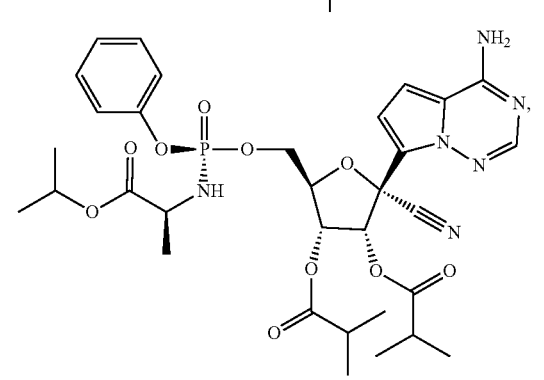
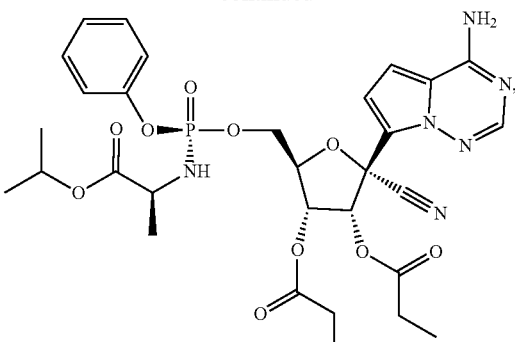
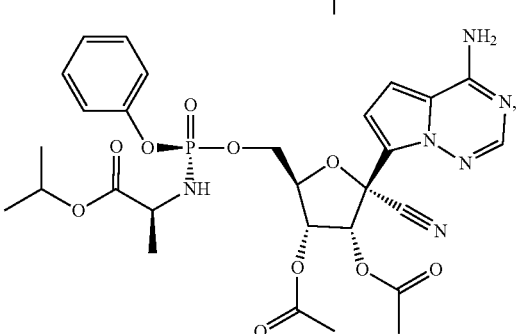
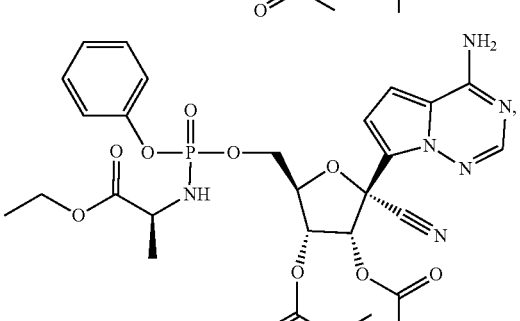
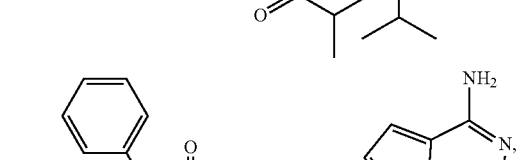
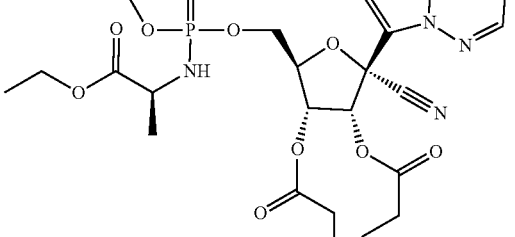
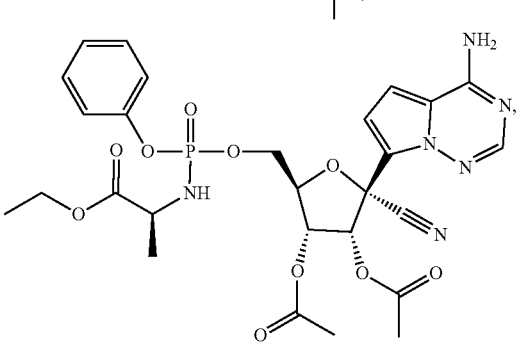

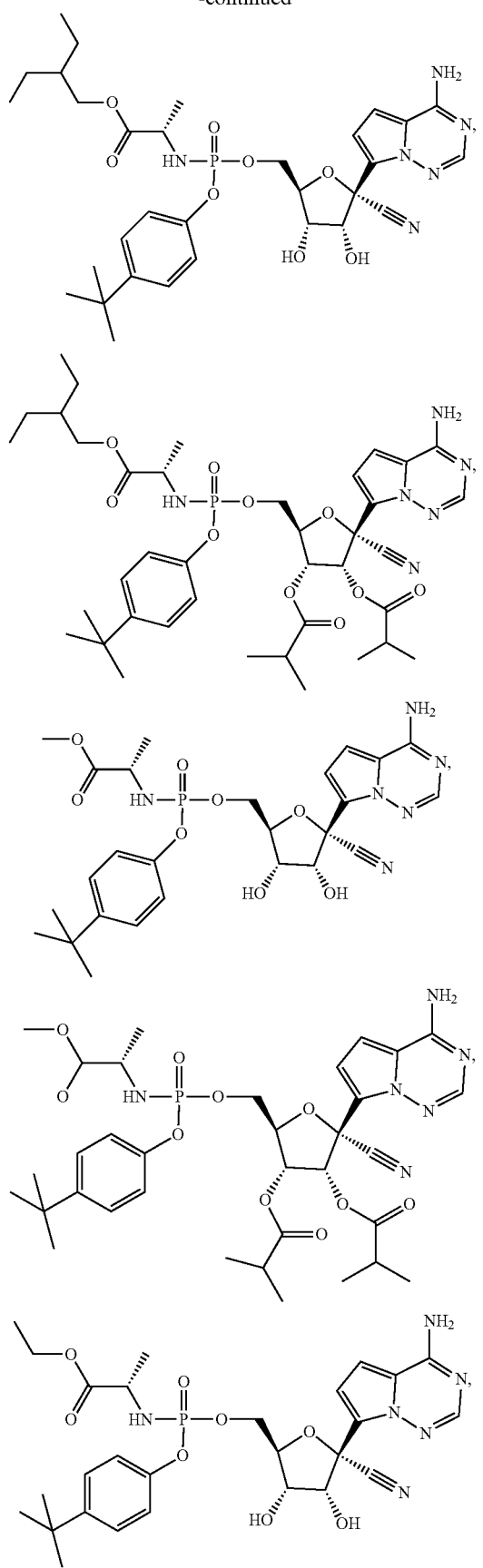
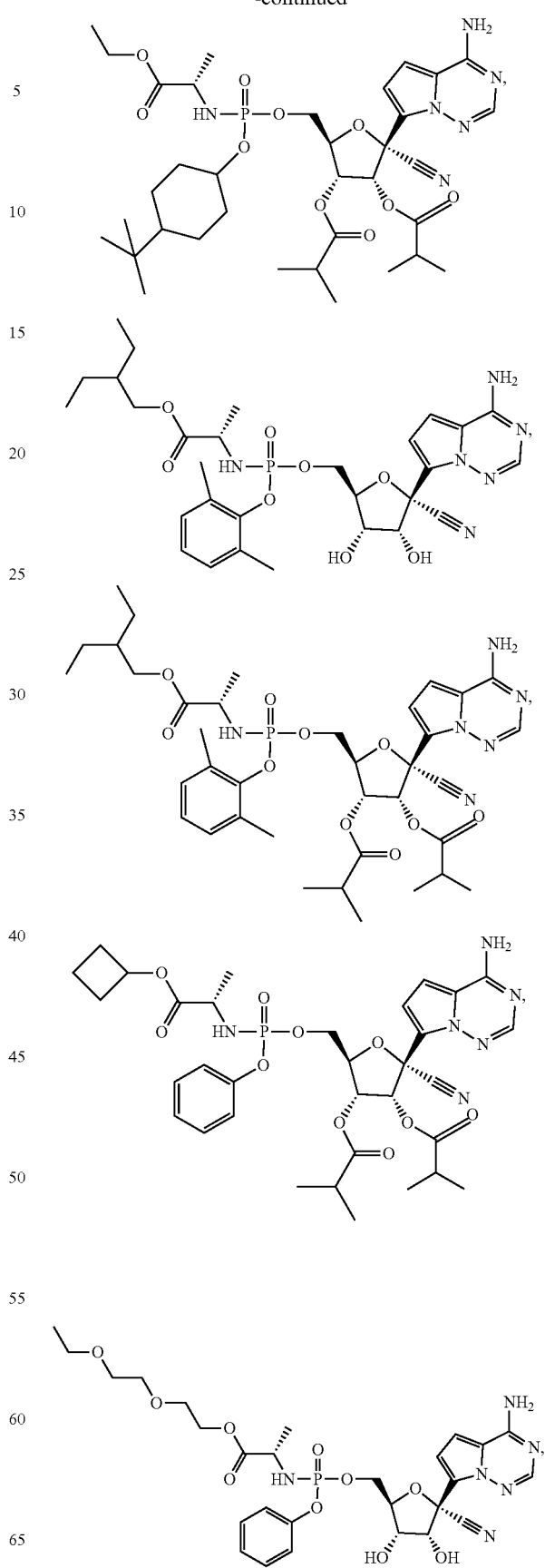

33
-continued
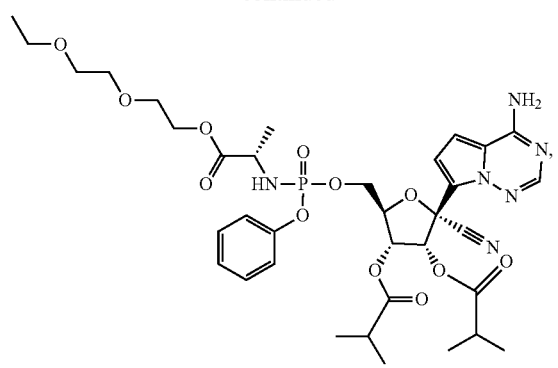
34
-continued
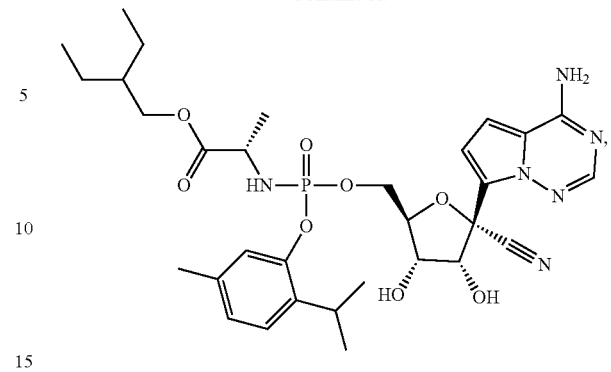
In some embodiments, the compound of Formula I, Ia, Ib, II, IIa, IIb, III, IIIa, IIIB, or IIIc, is selected from the group consisting of:
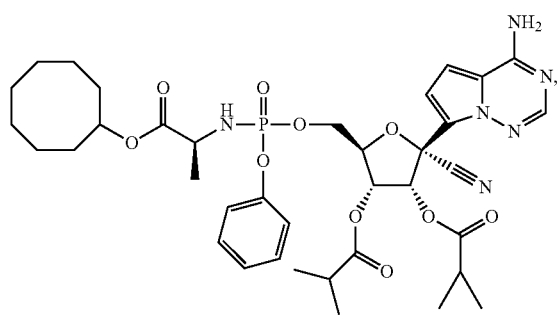

-continued
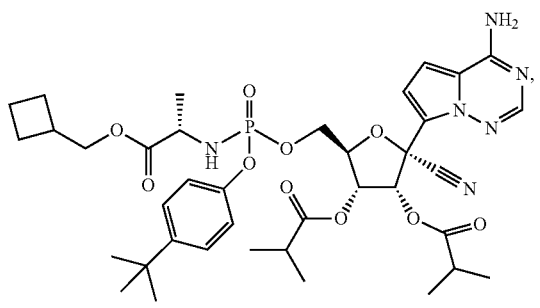
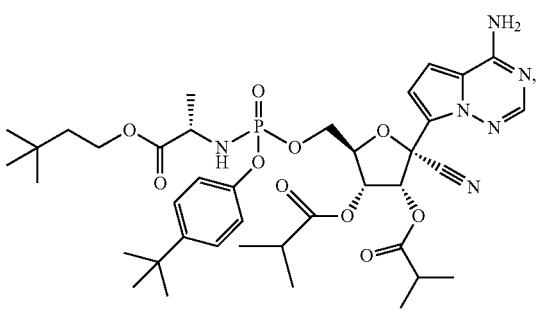
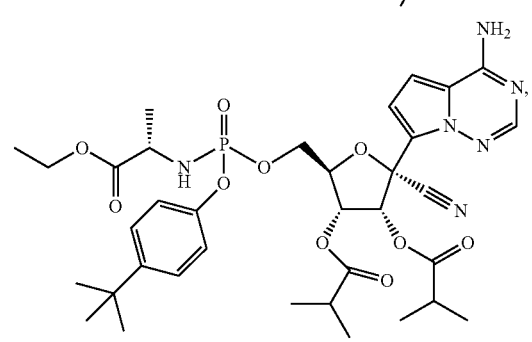
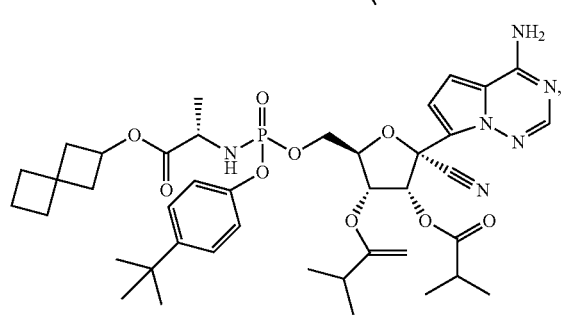
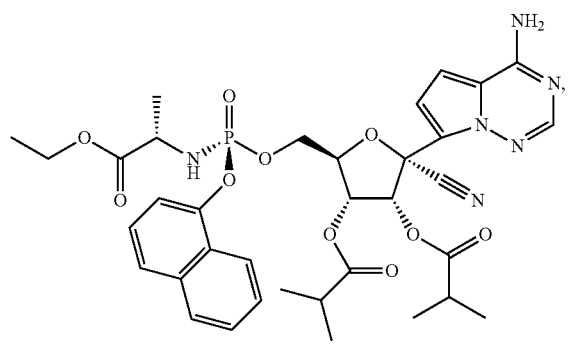

-continued
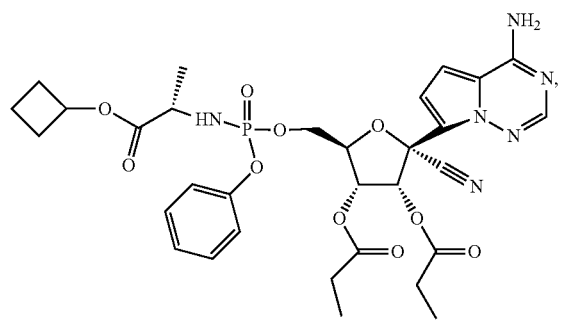
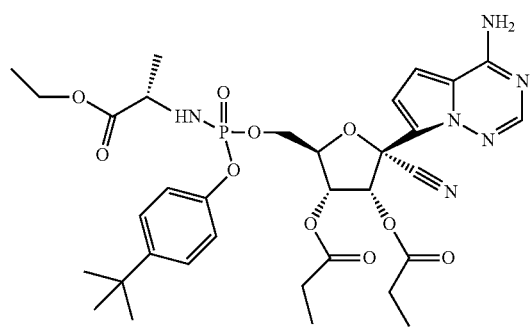
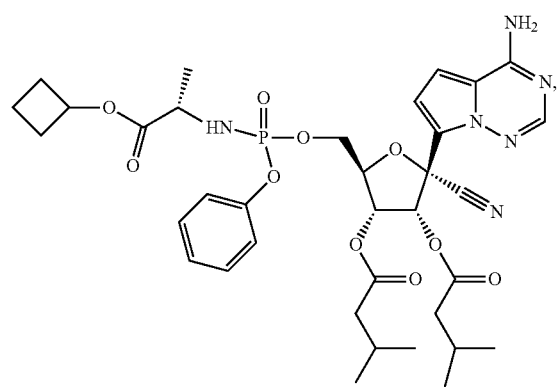
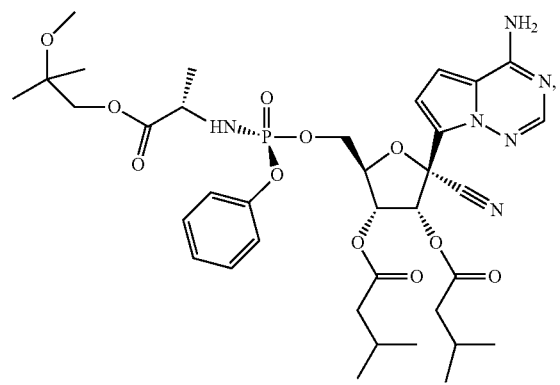

-continued
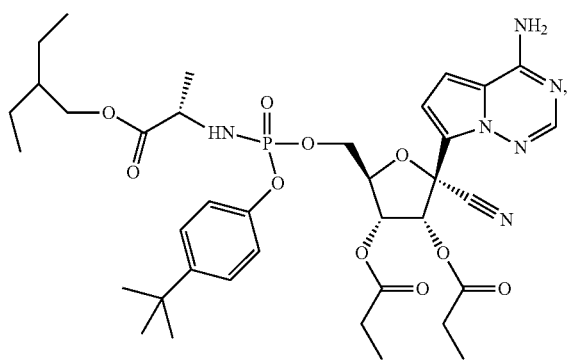
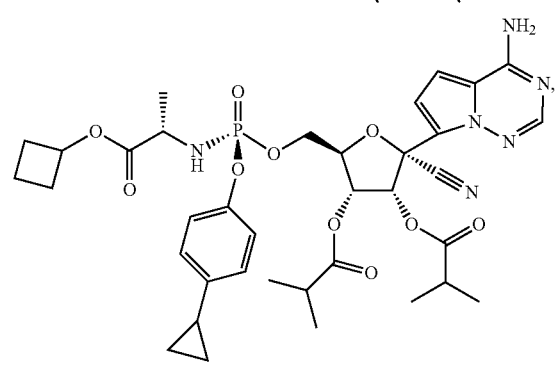
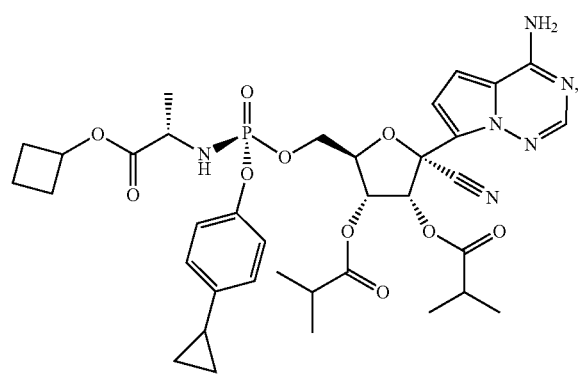
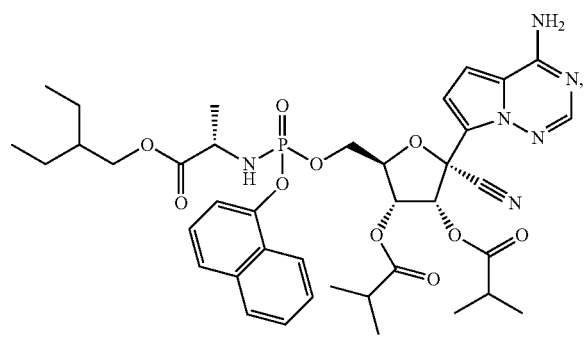

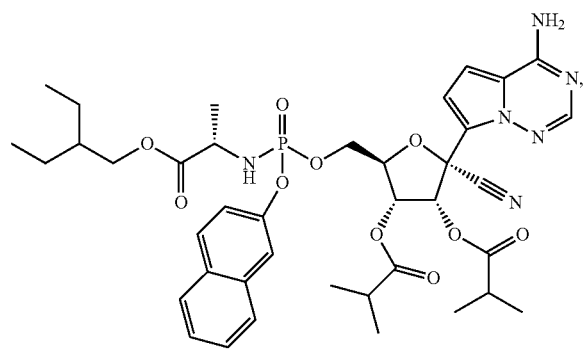
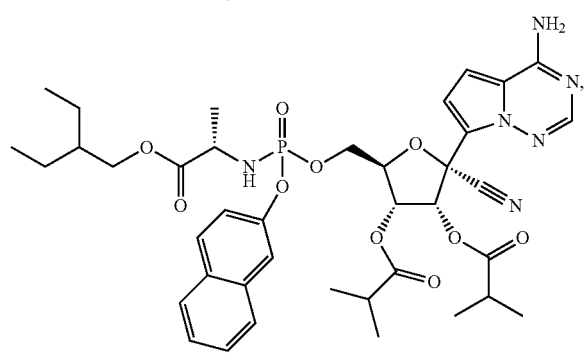
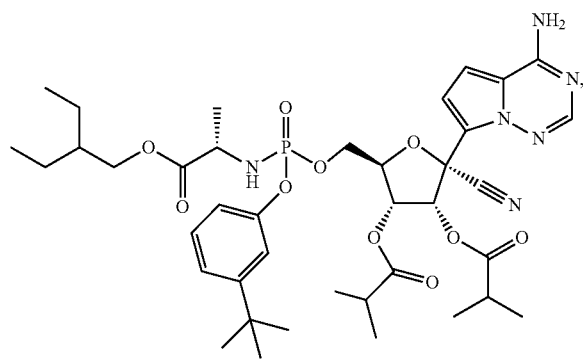
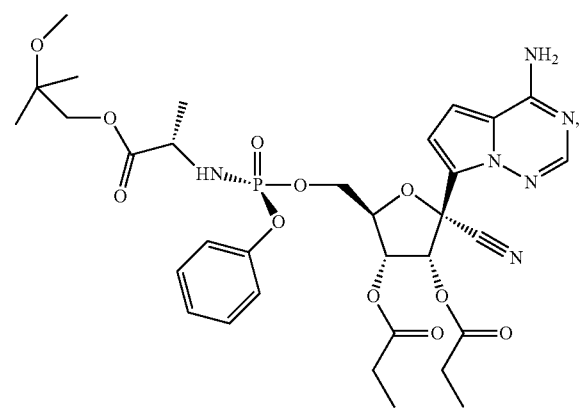

-continued
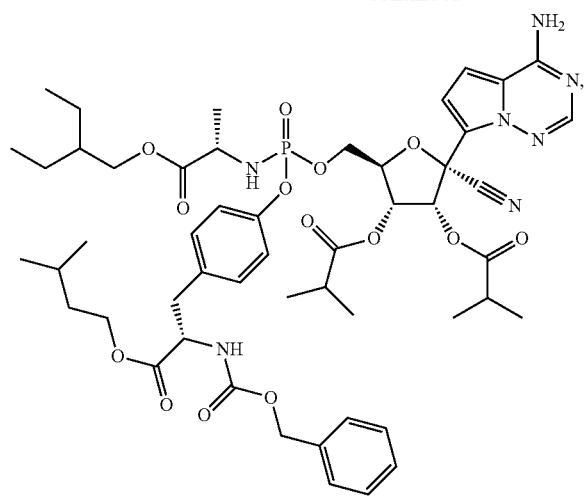
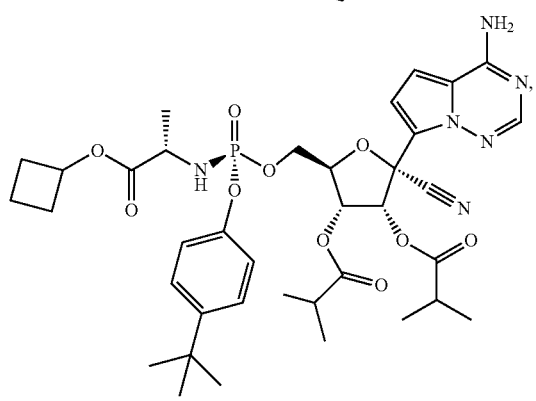
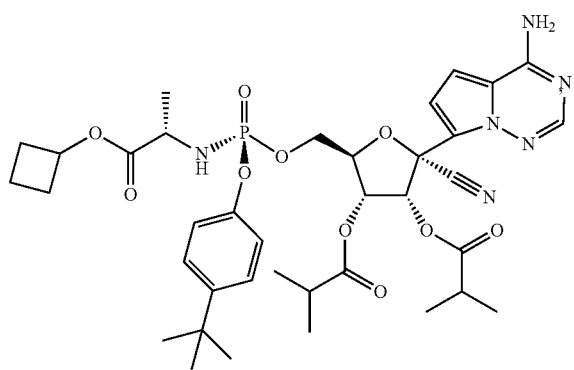
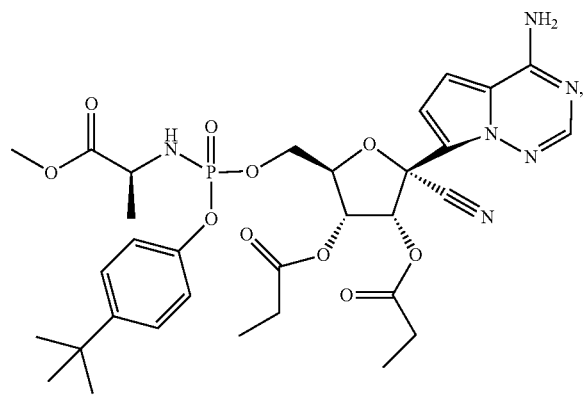

-continued
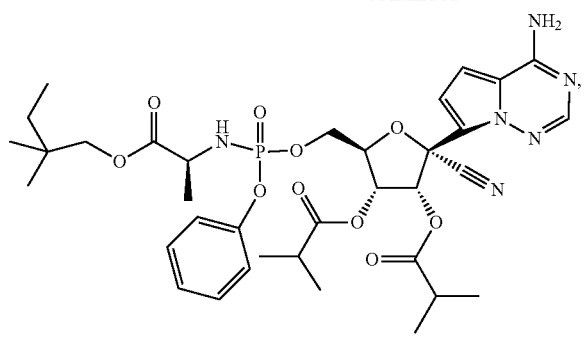
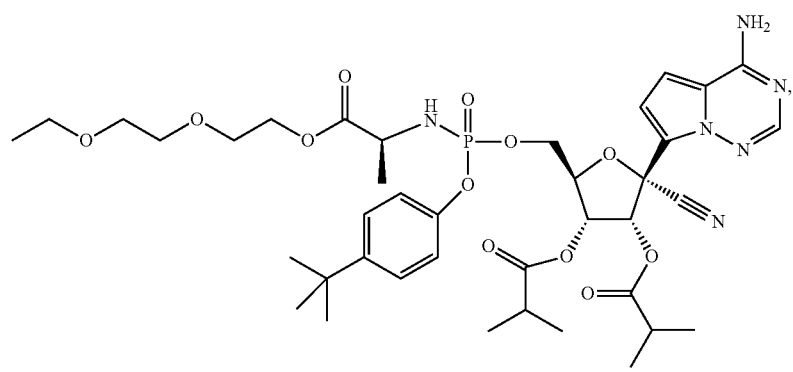
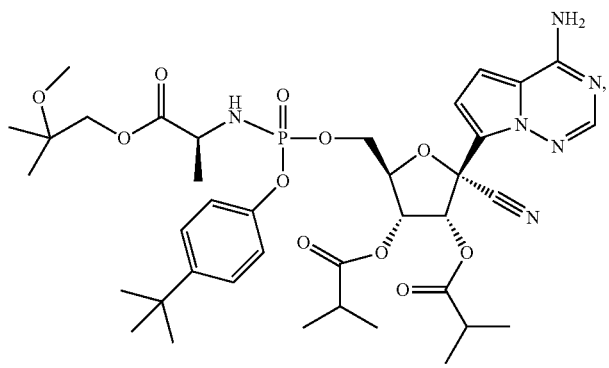
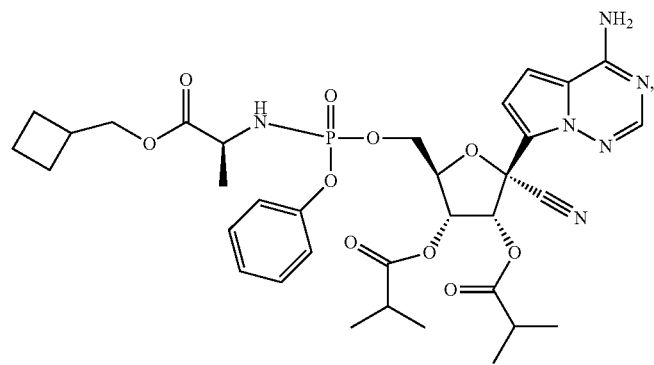

-continued
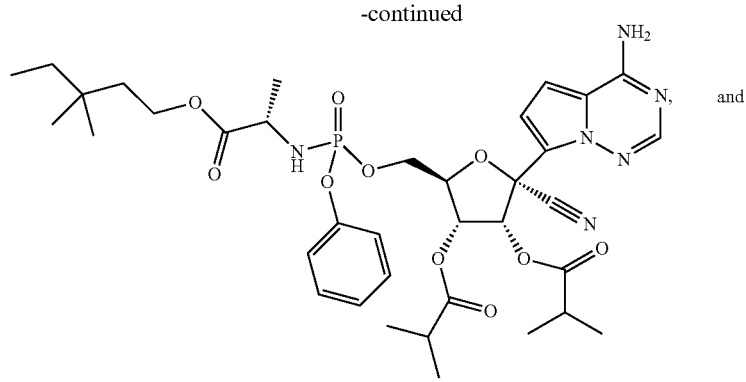
and
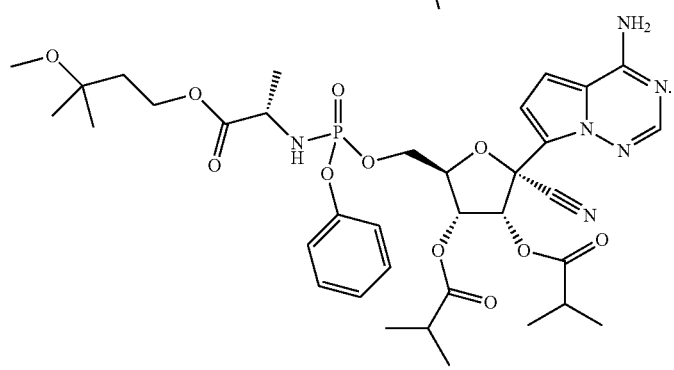
30
In some embodiments, the compound of Formula I, Ia, Ib, II, IIa, IIb, III, IIIa, IIIb, or IIIc, is selected from the group consisting of:
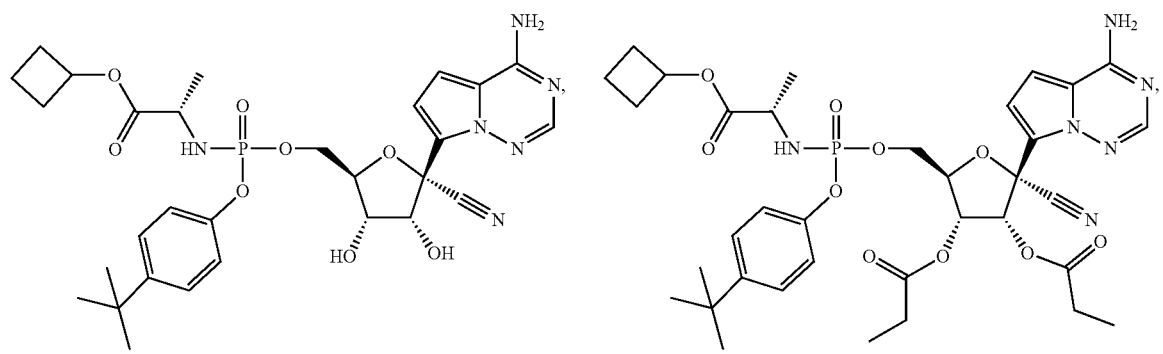
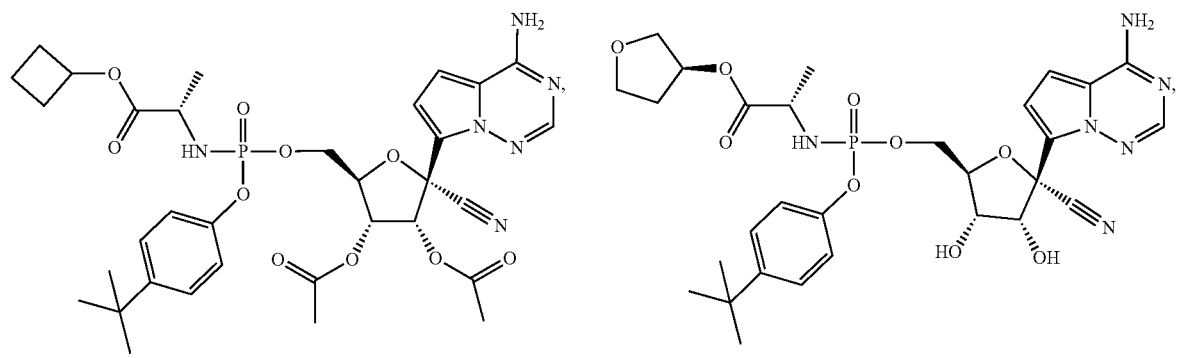

49 50
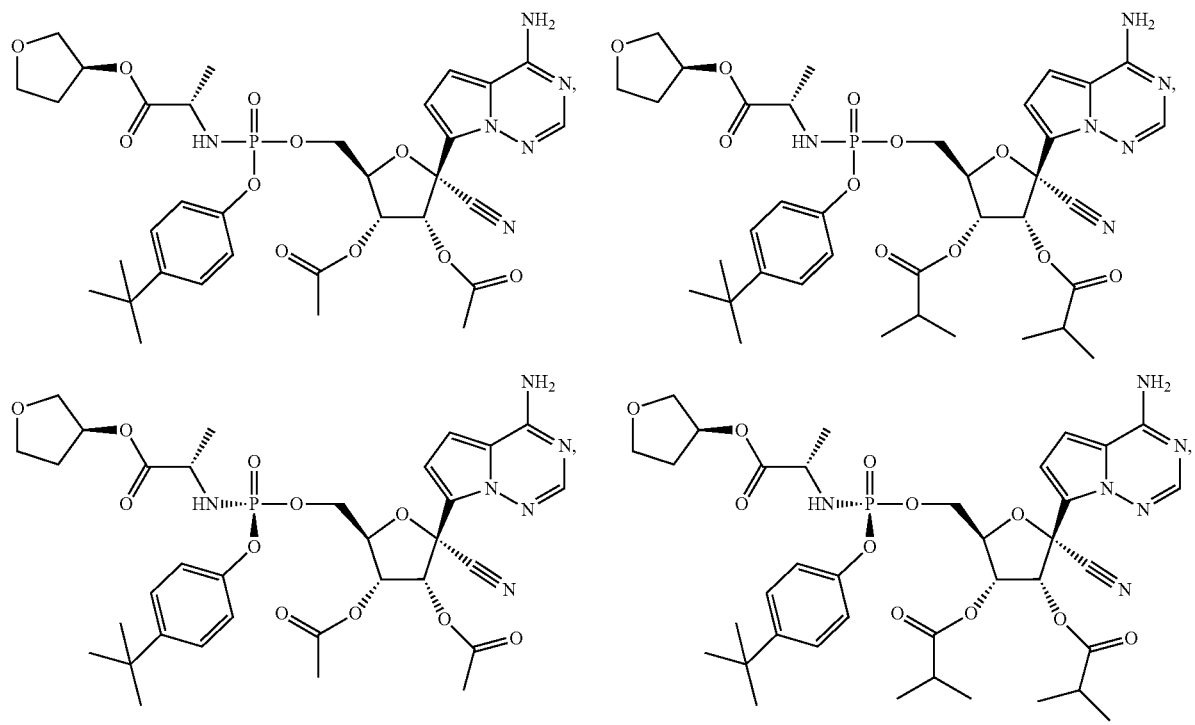
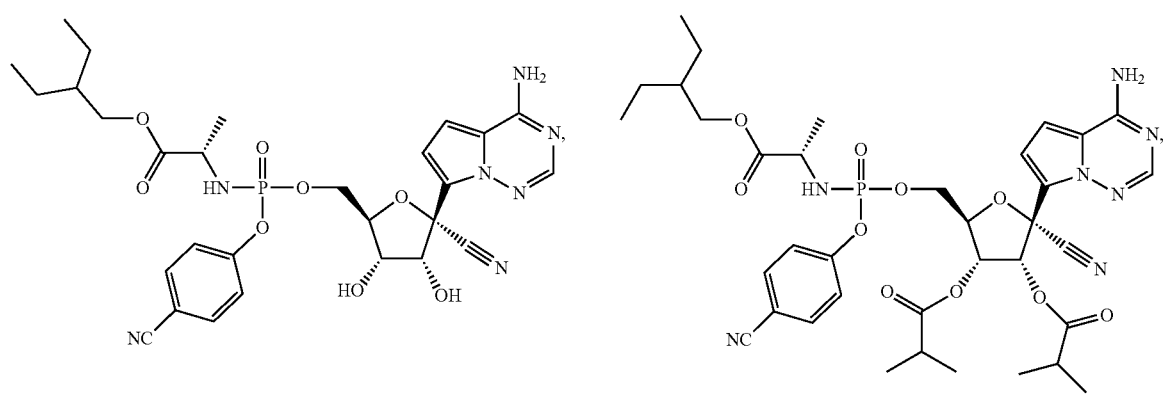
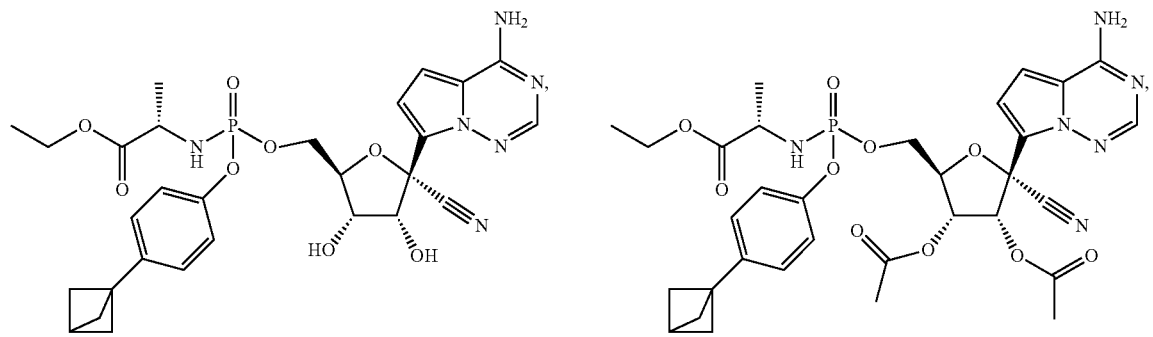

-continued
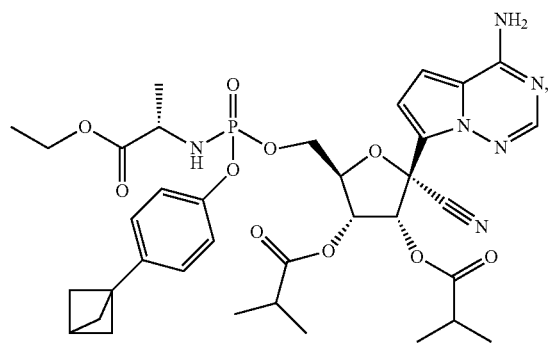
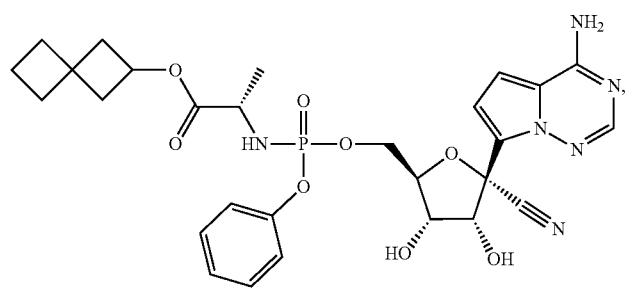
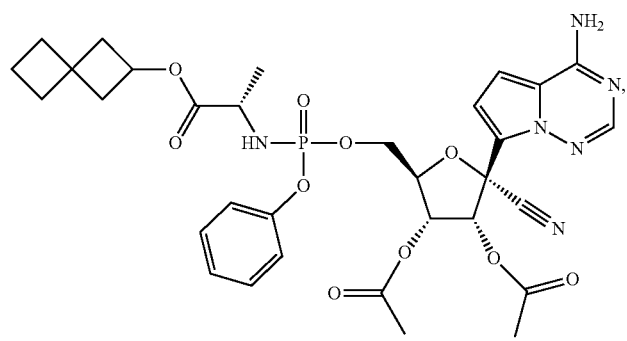
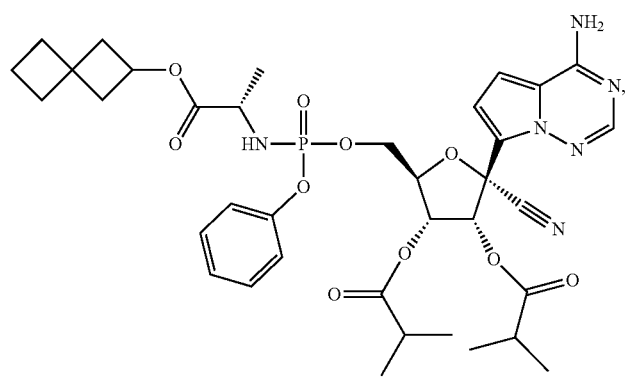
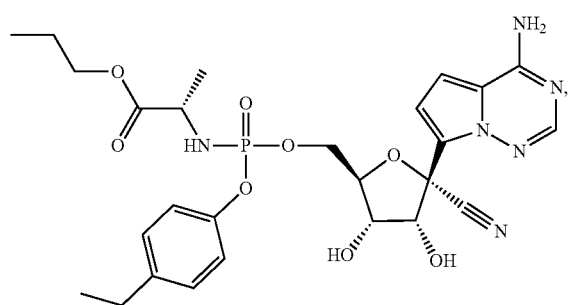
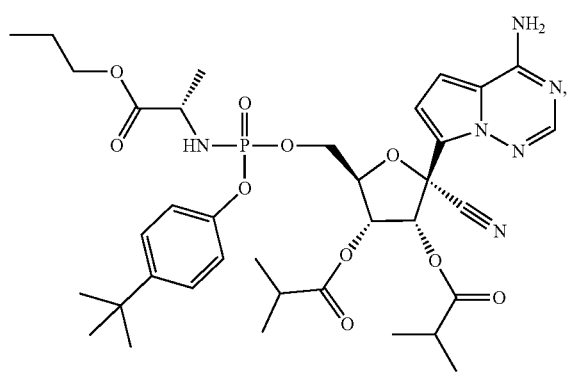

53
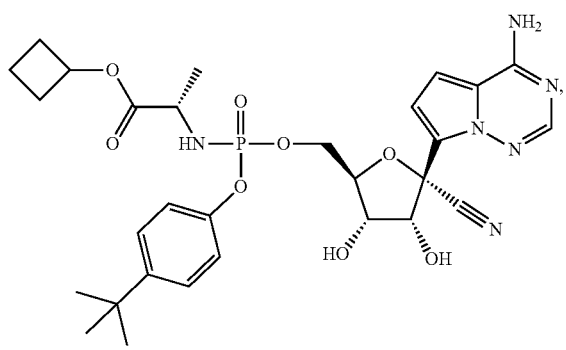
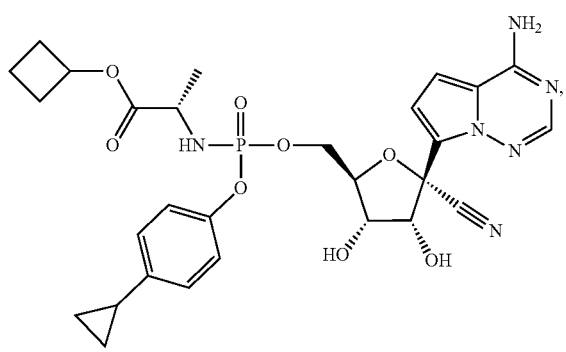
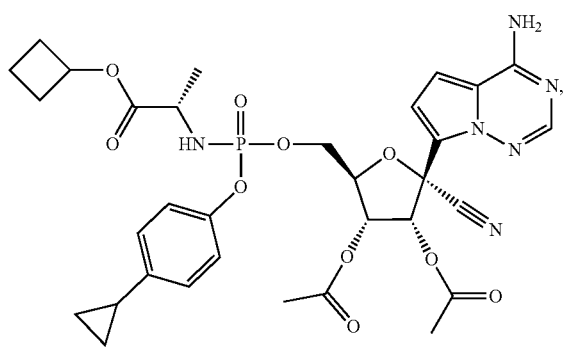
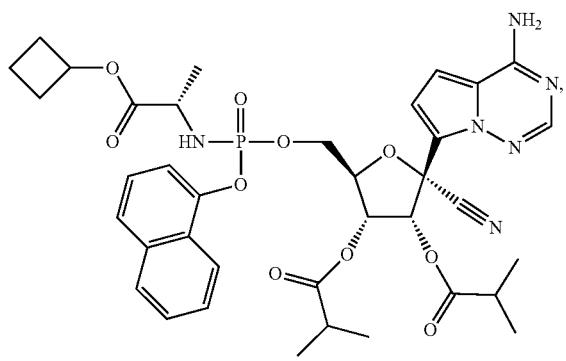
54
-continued
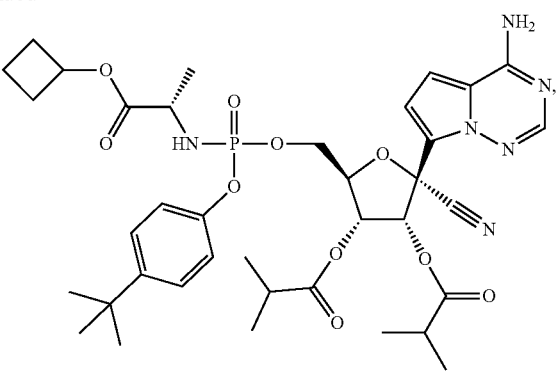
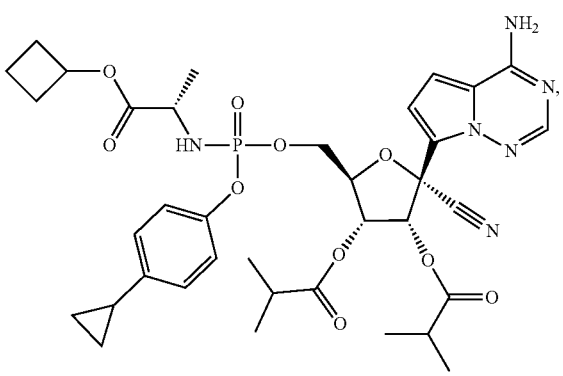
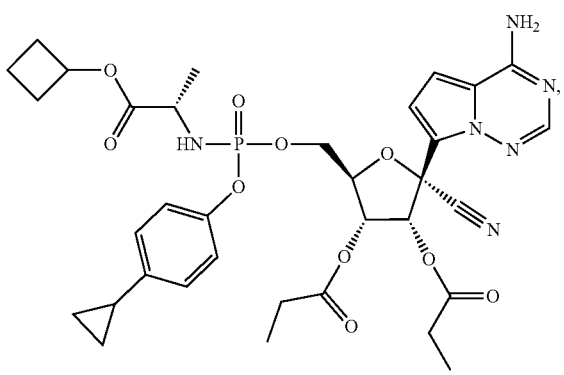

-continued
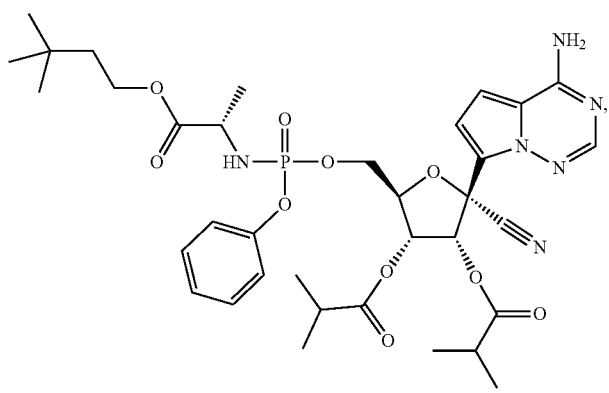
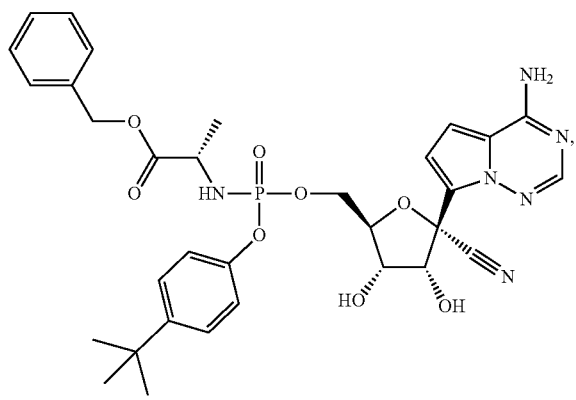
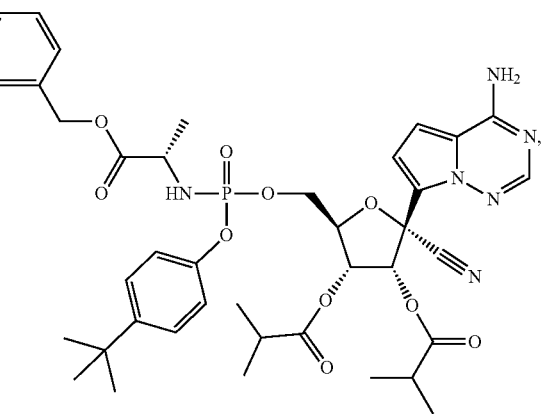
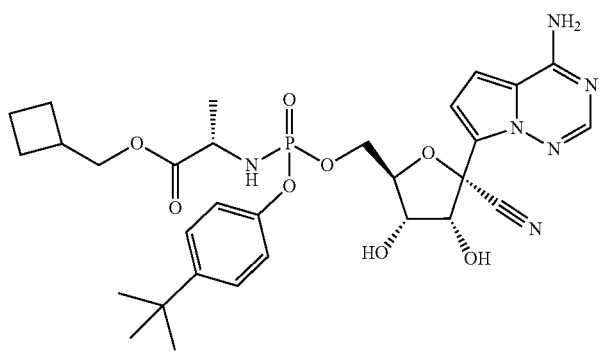
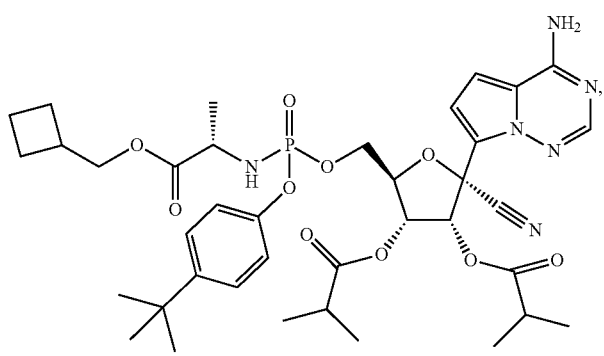

-continued
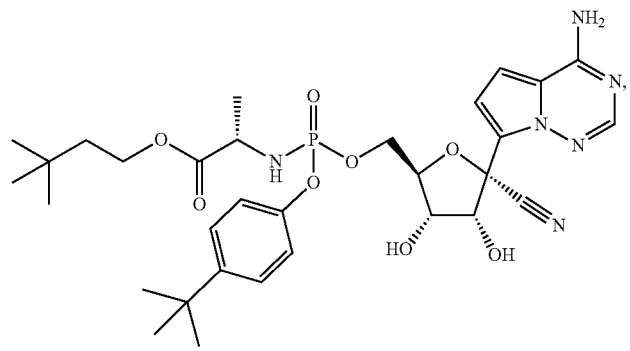
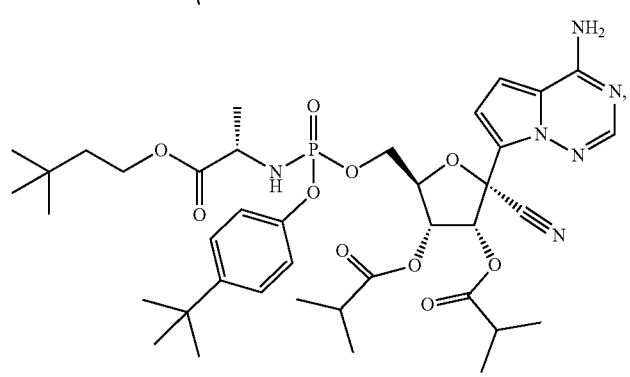
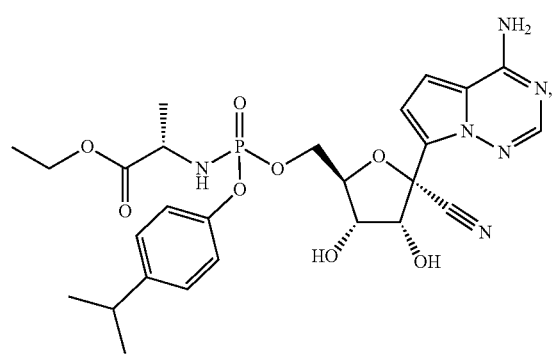
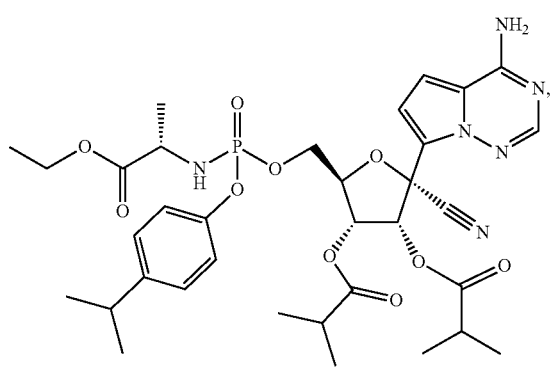
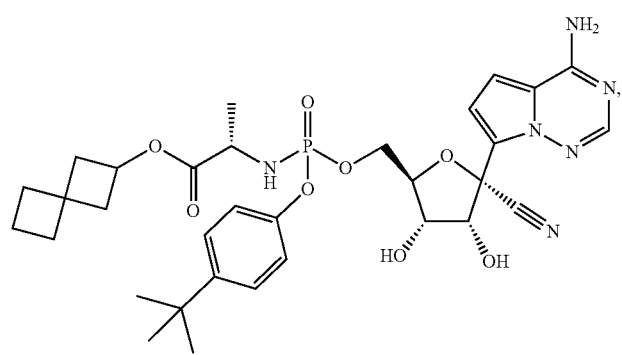

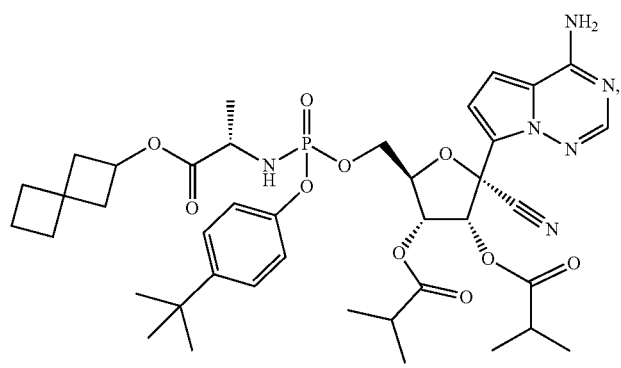
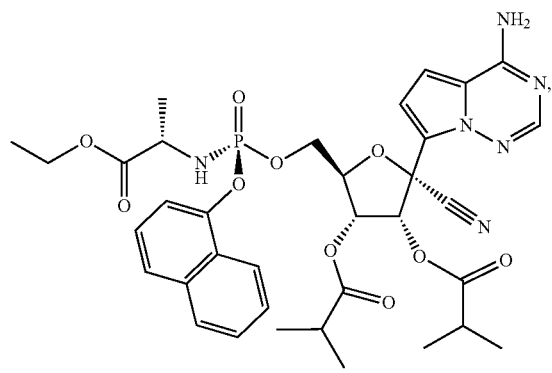
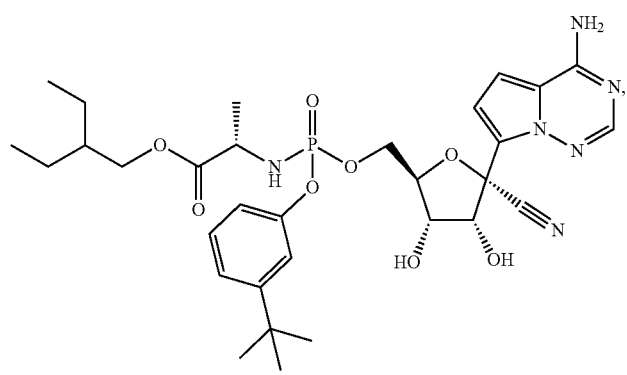
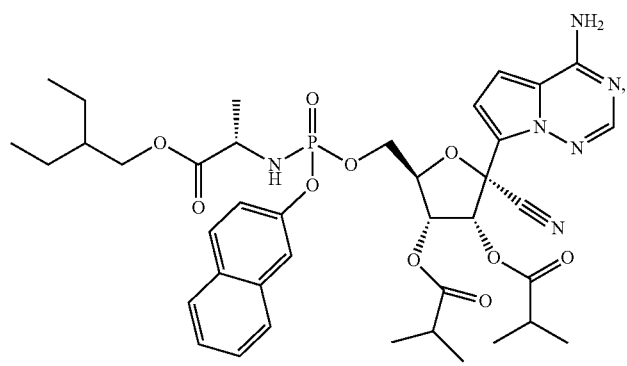

-continued
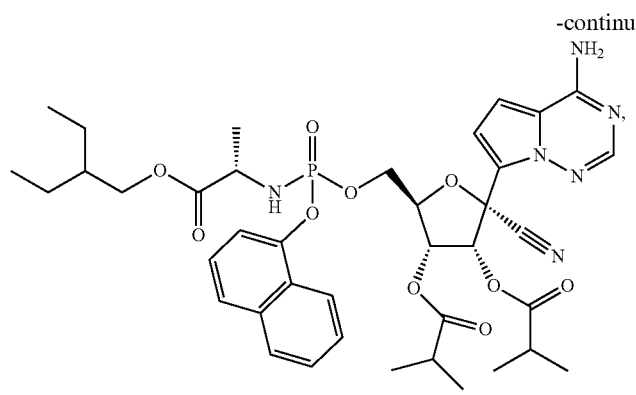
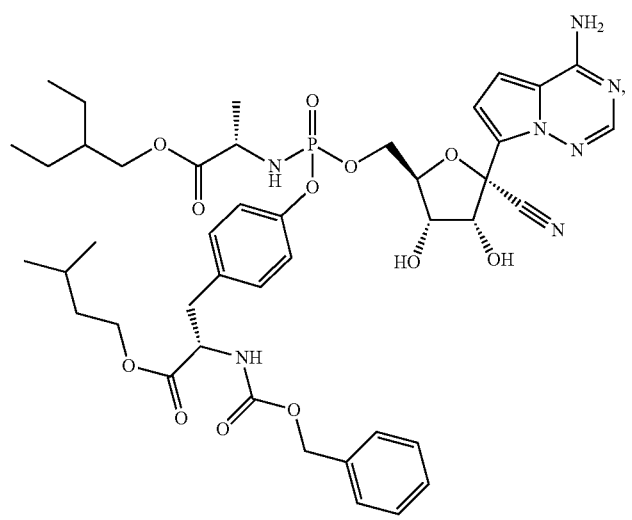
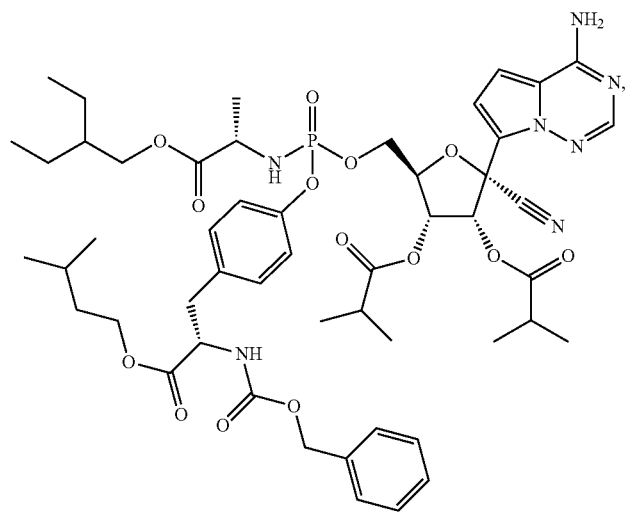

-continued
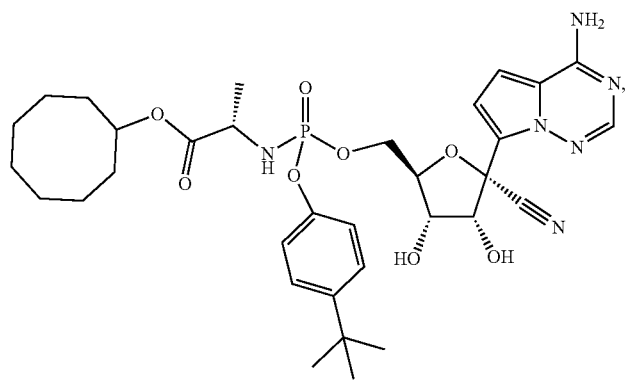
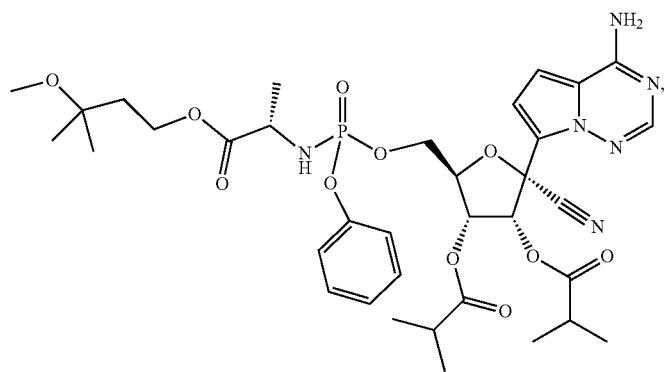
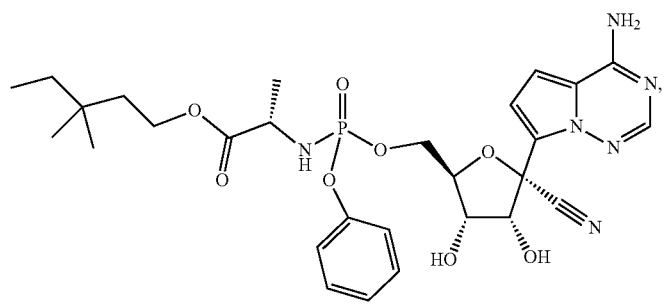
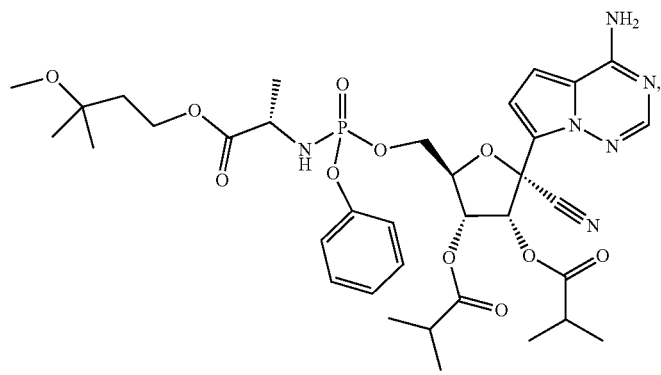

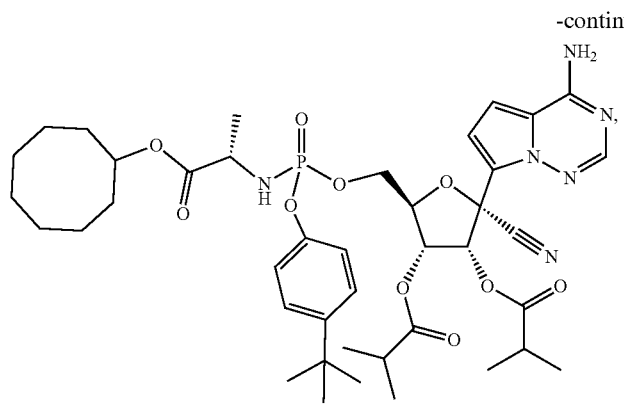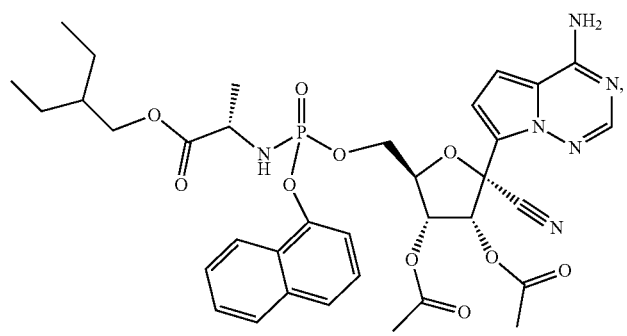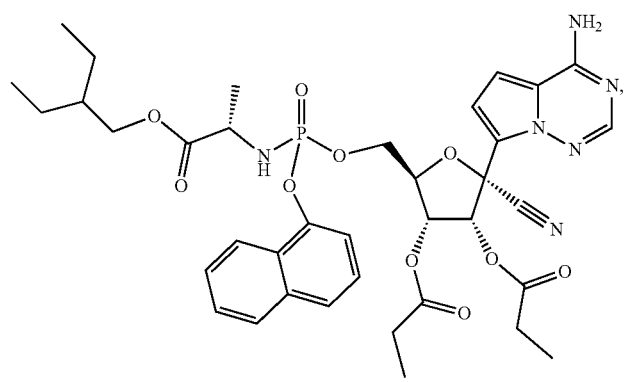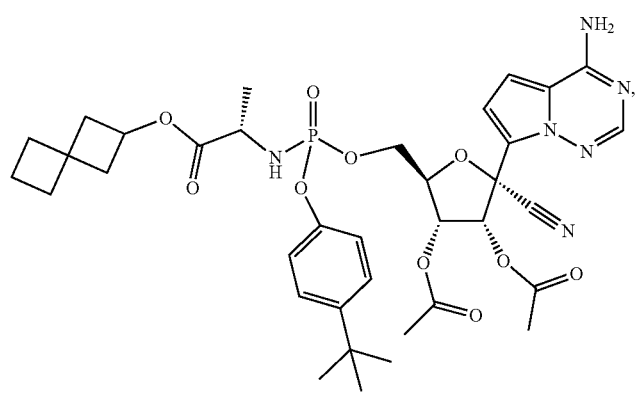

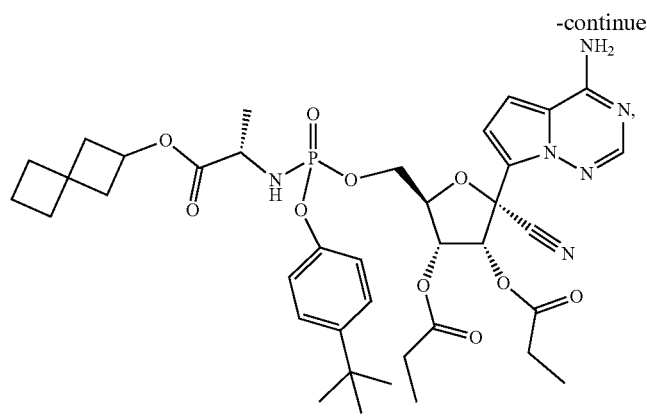
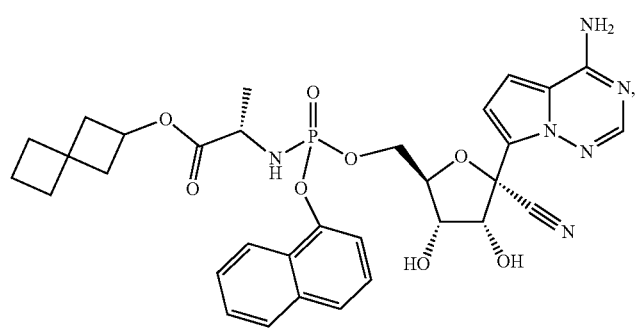
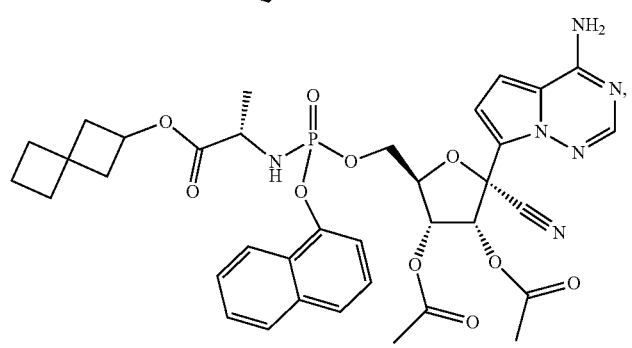
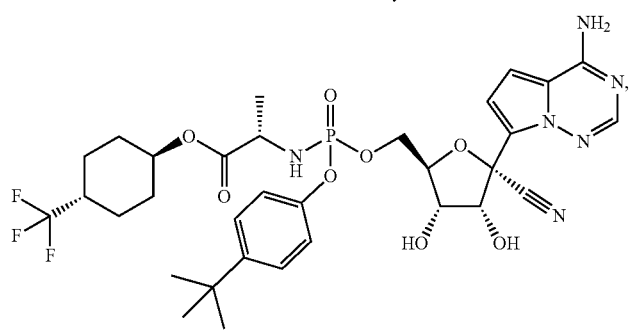
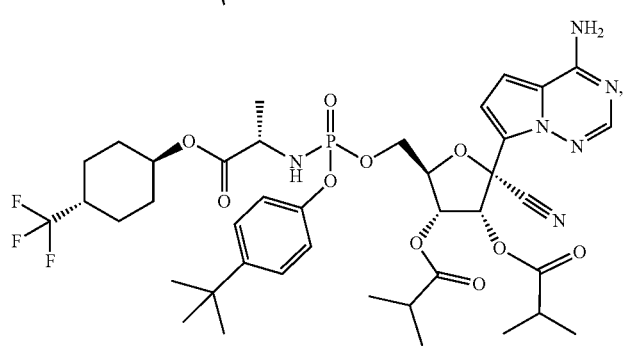

-continued
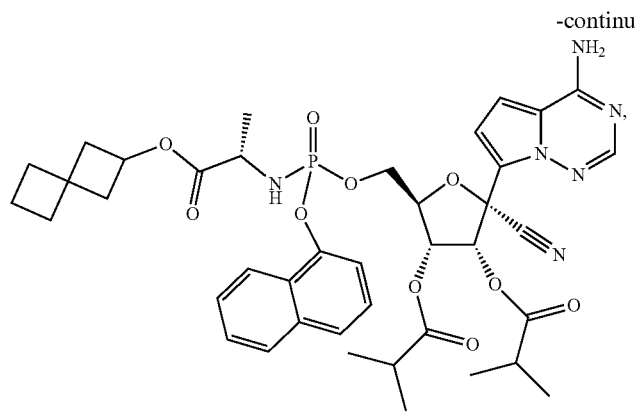
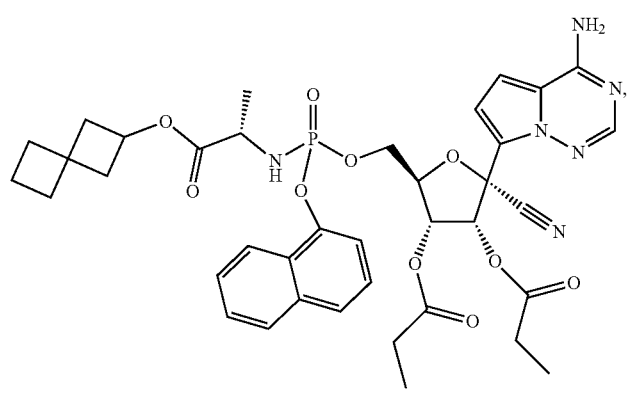
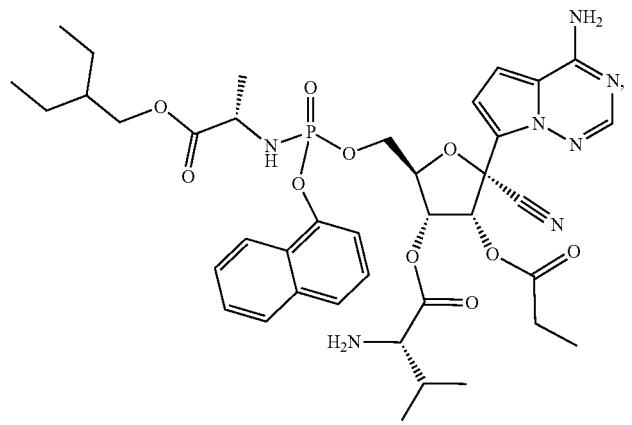
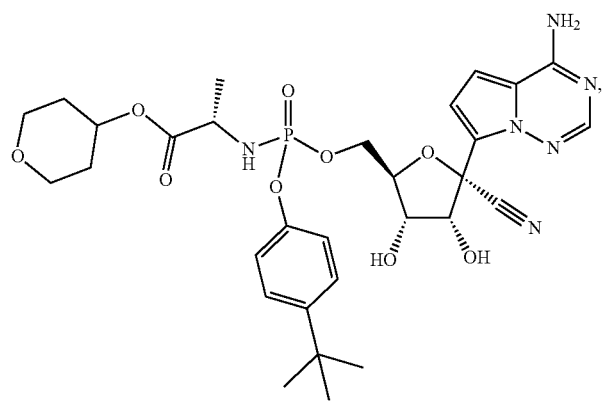

71
-continued
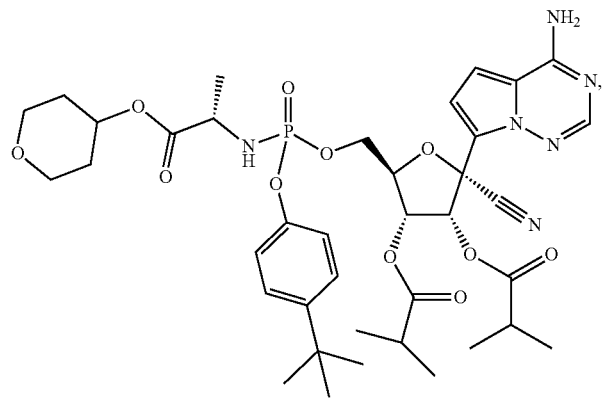
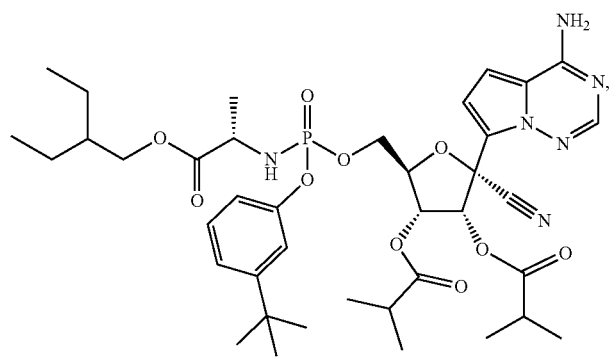
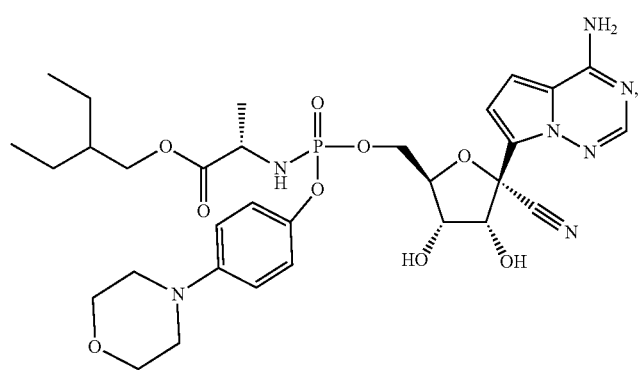
72
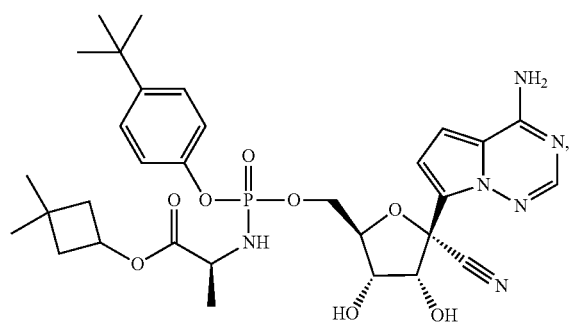
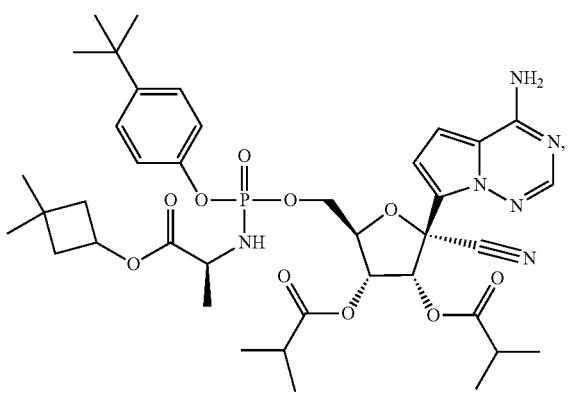

-continued
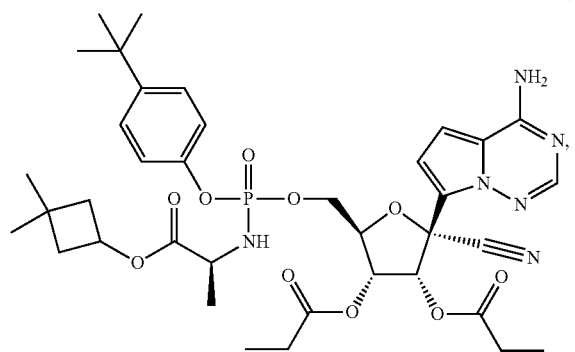
73
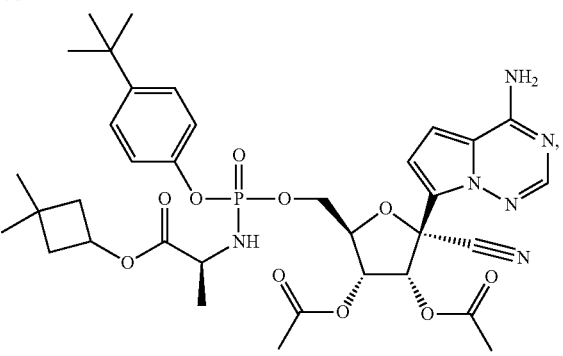
74
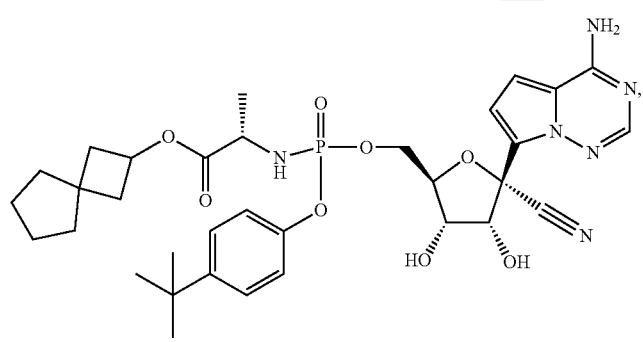
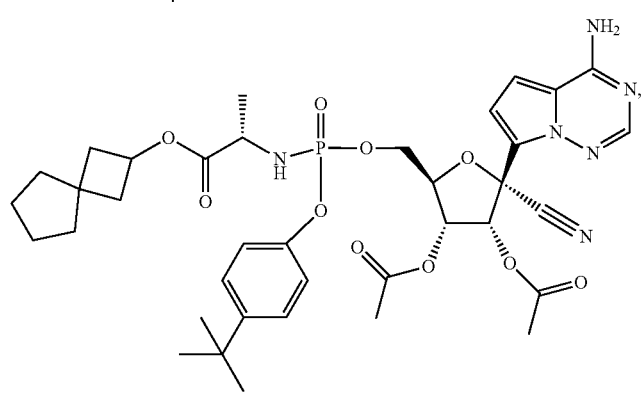
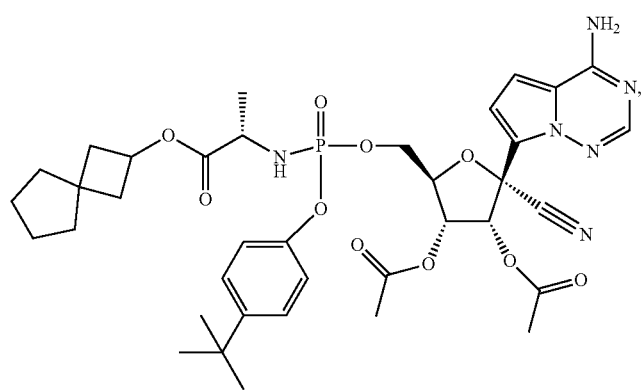

-continued
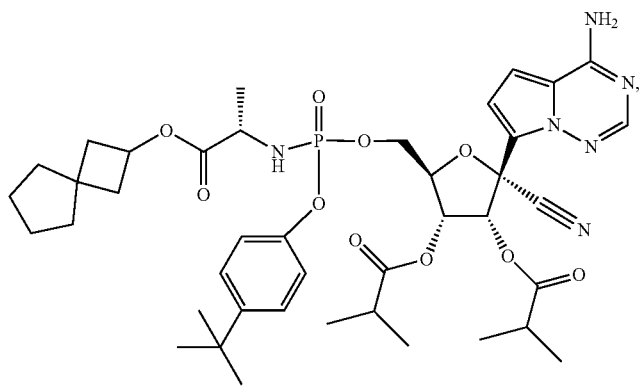
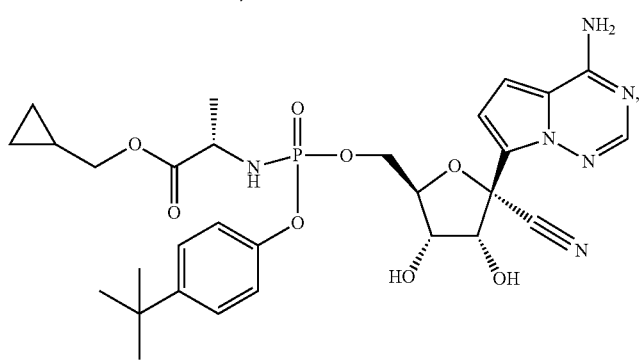
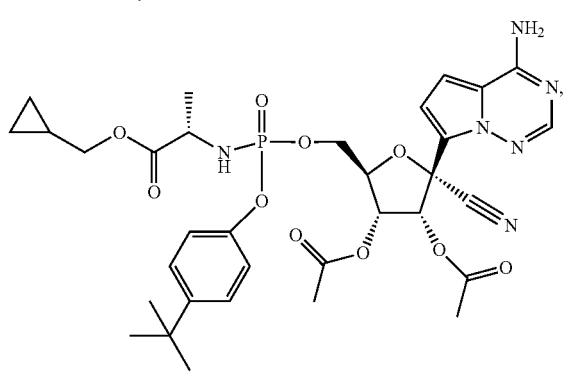
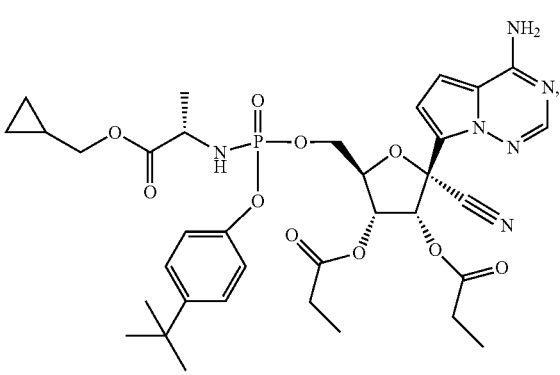
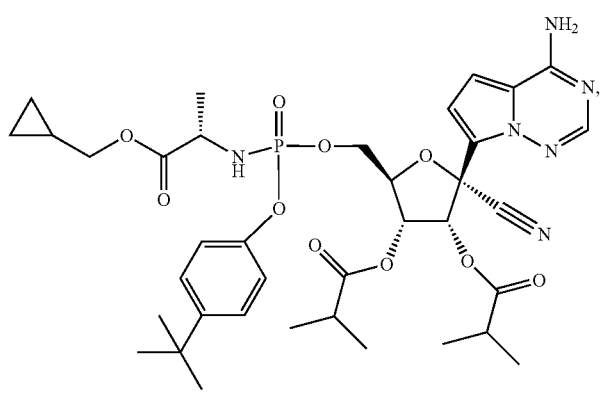

-continued
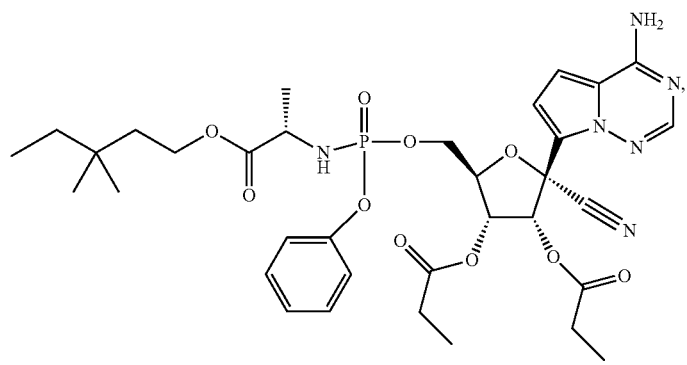
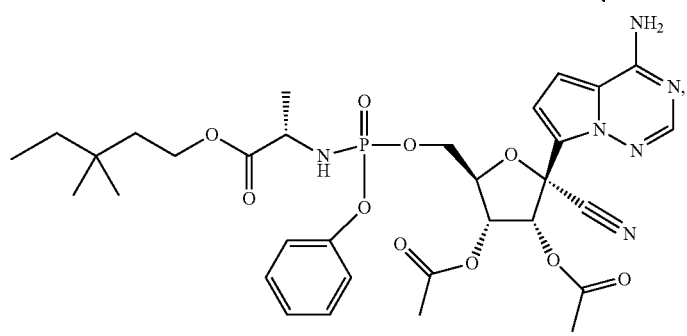
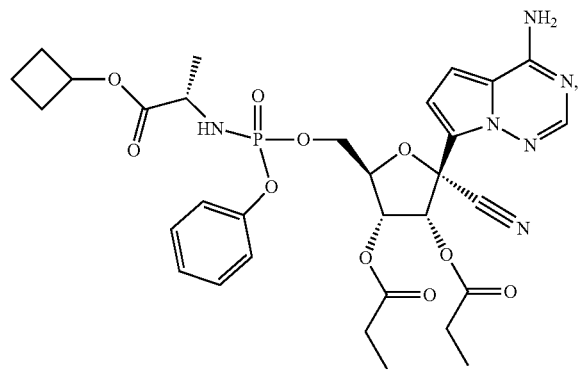
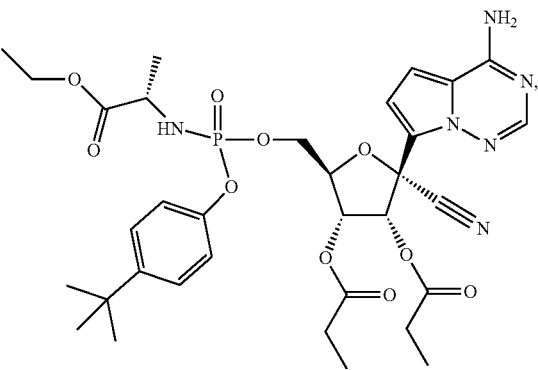
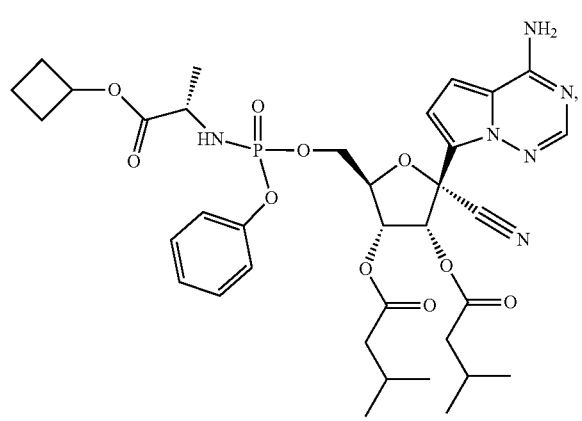
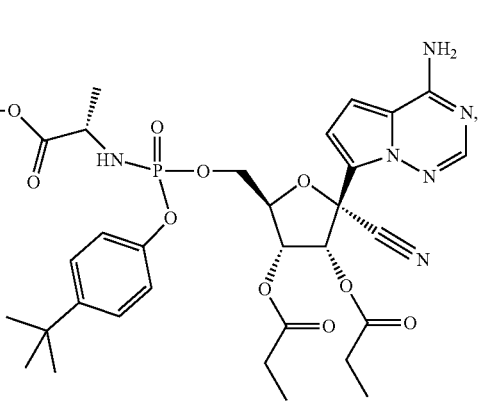

-continued
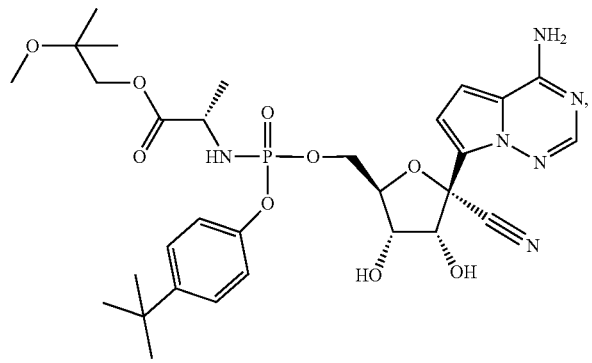
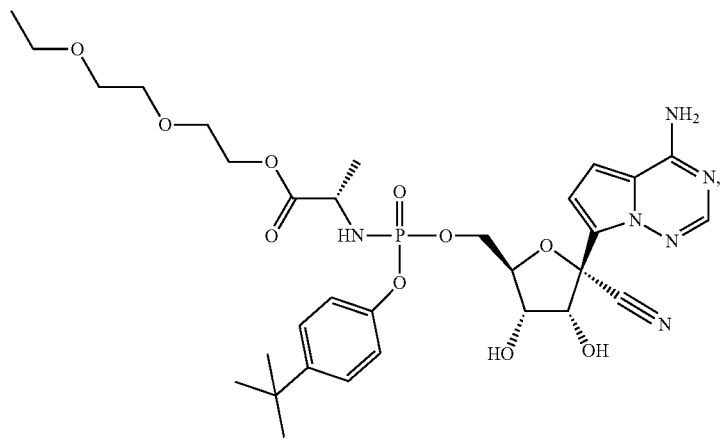
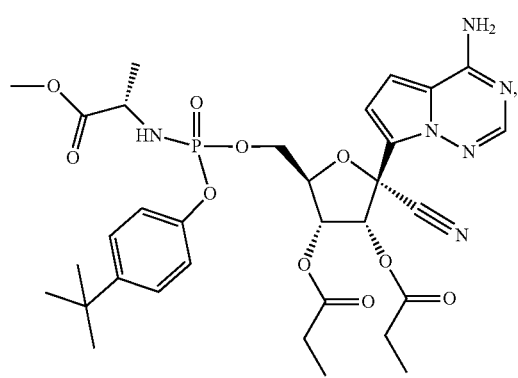
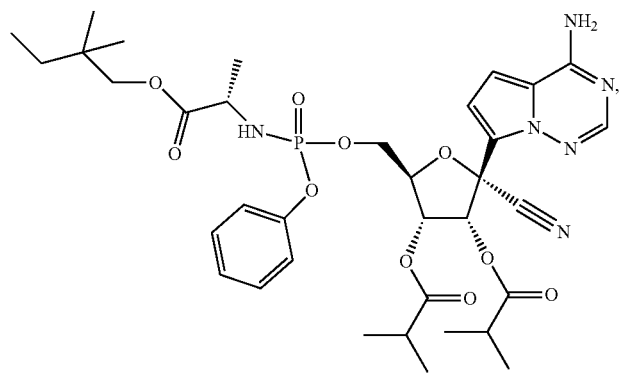

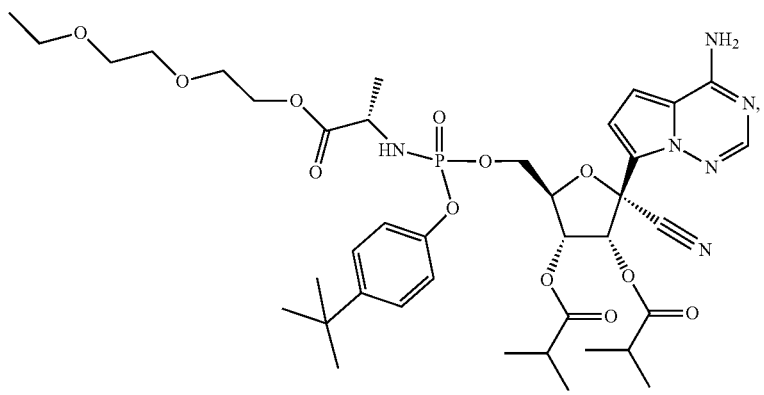
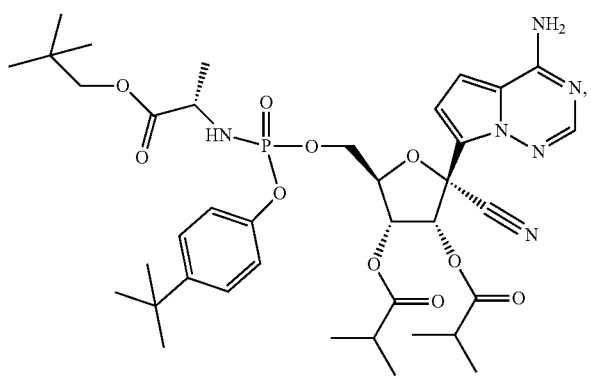
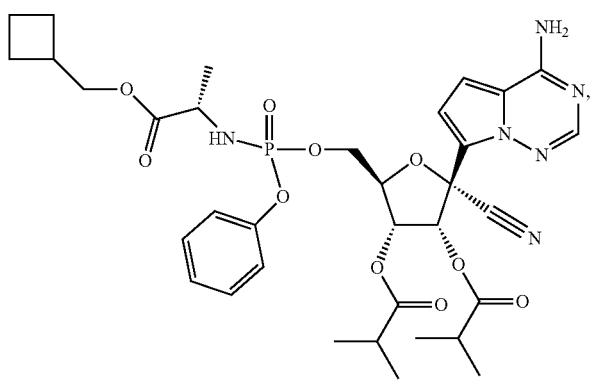
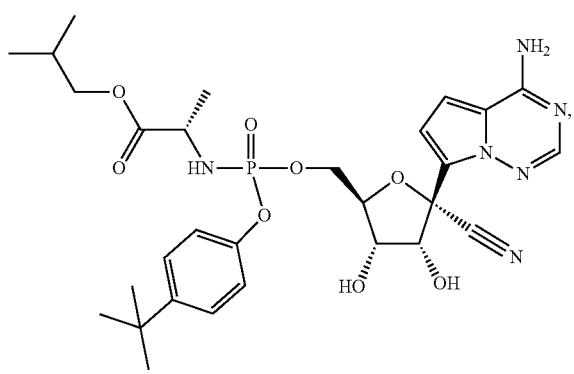

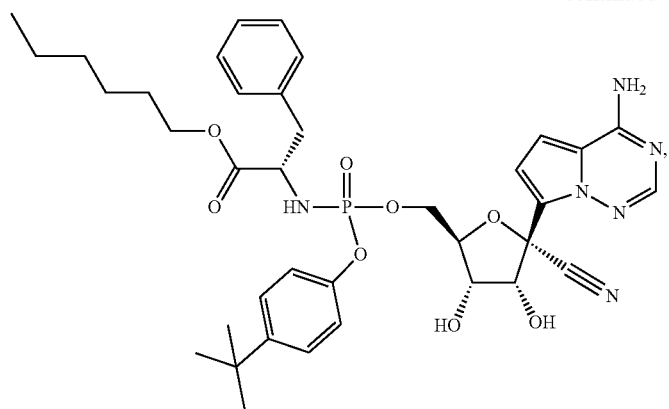
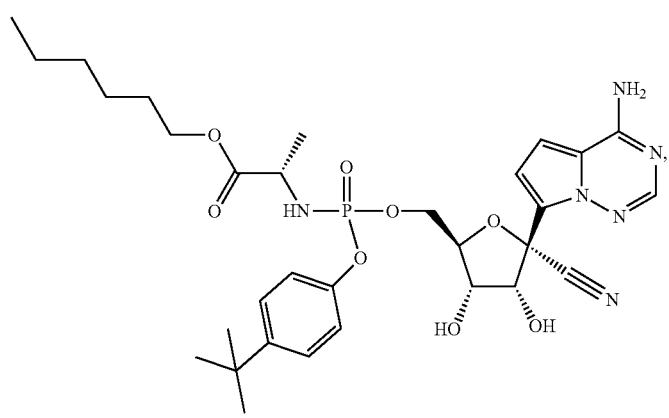
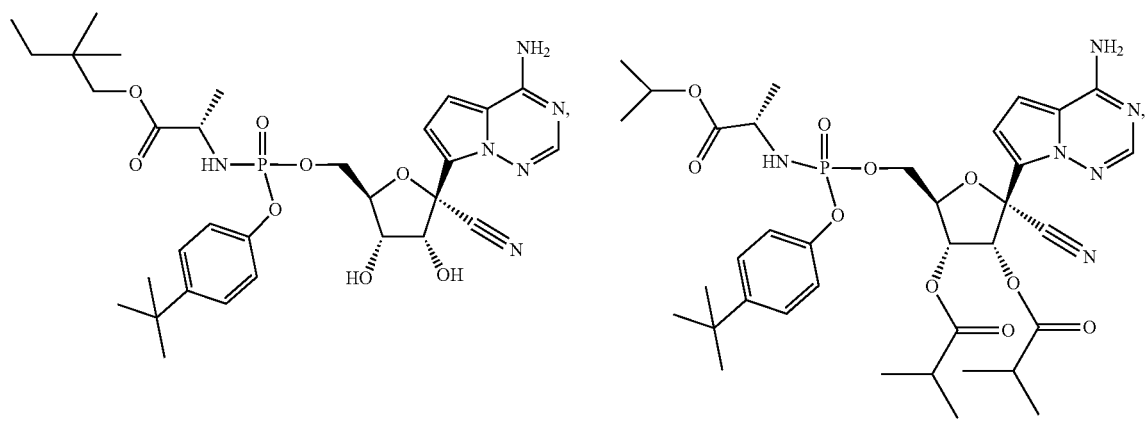
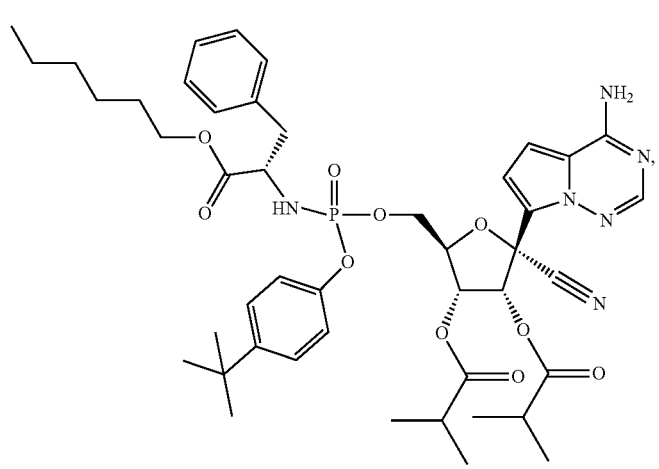

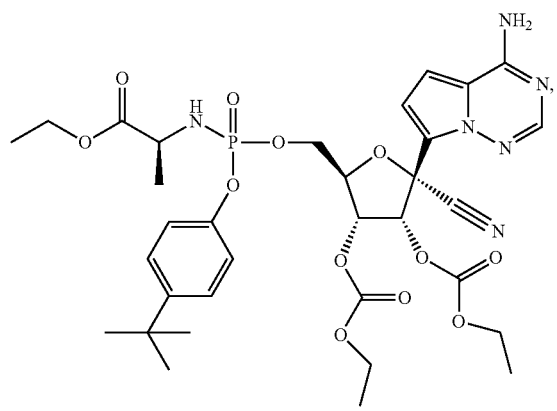
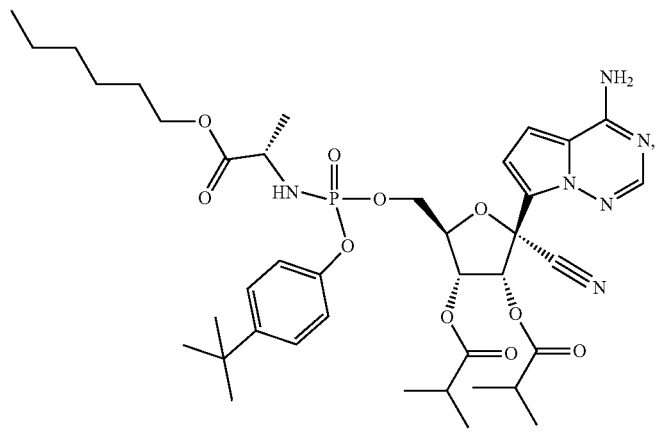
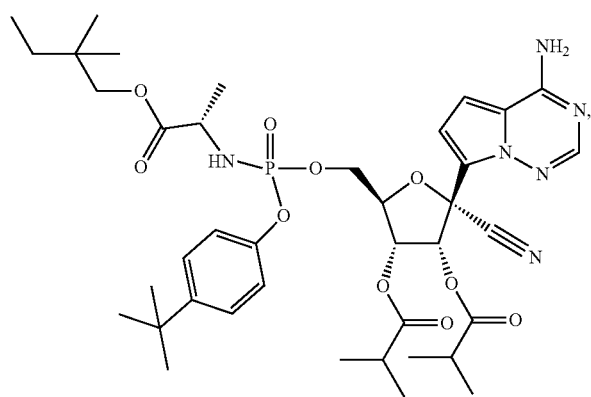
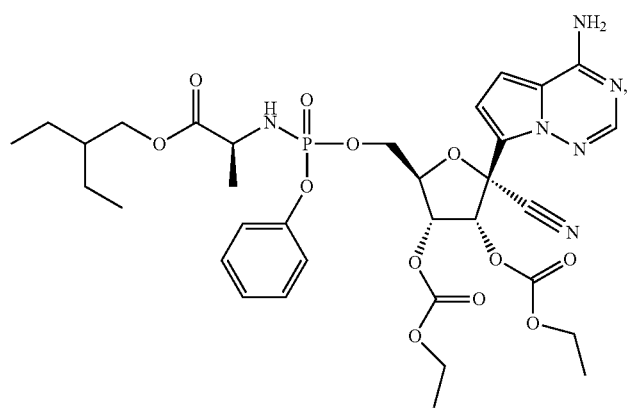

87
88
-continued
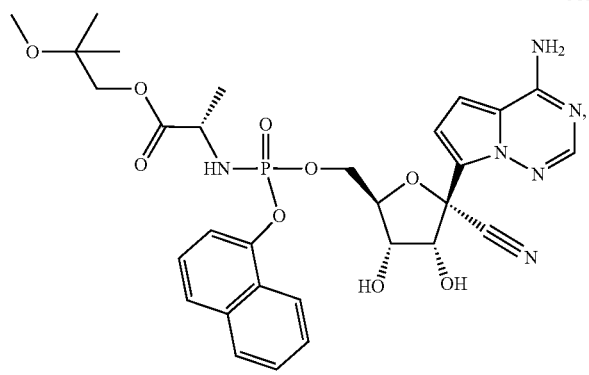
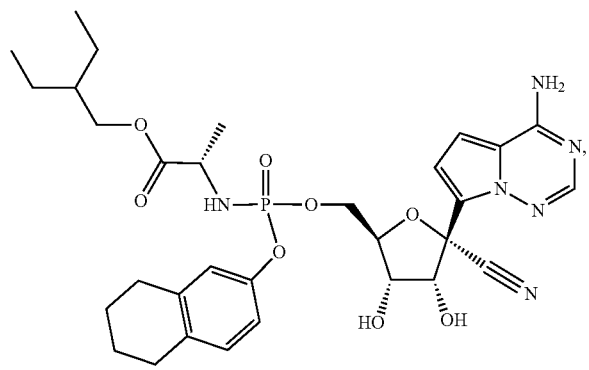
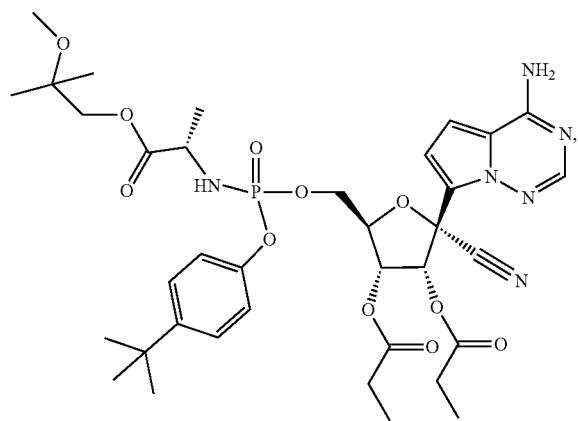
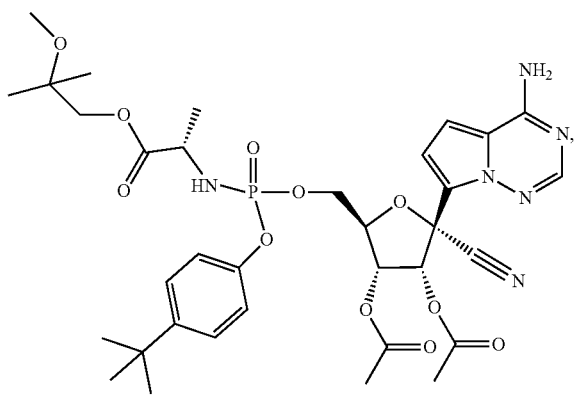
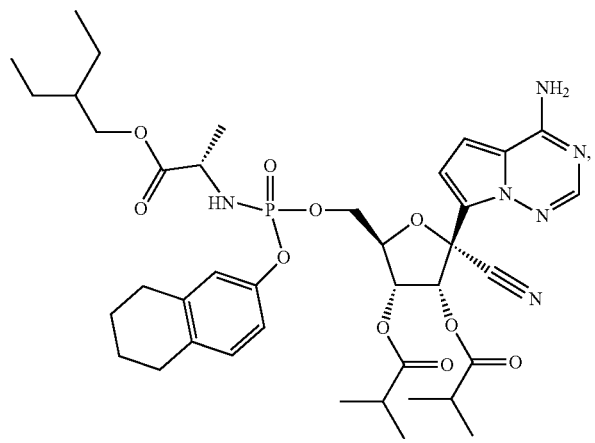
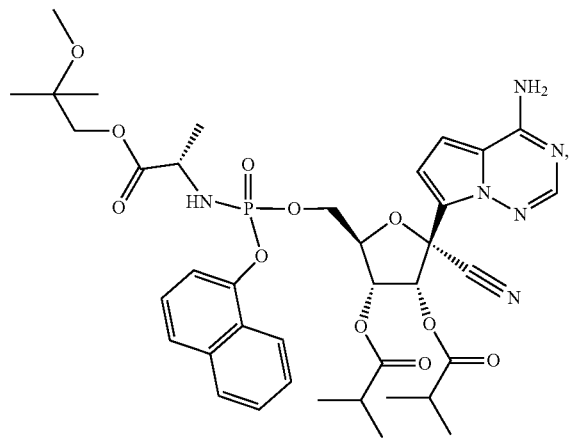

89
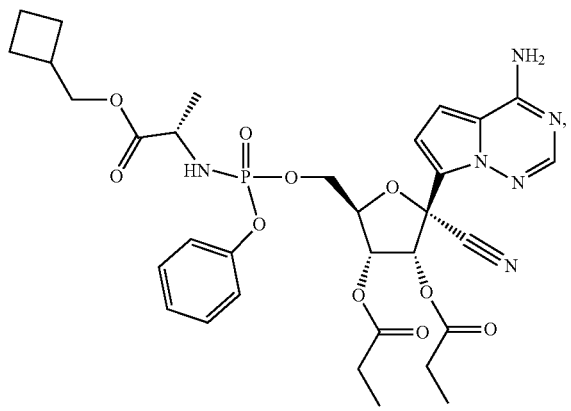
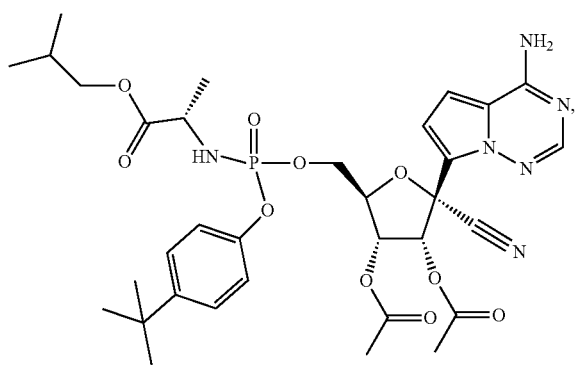
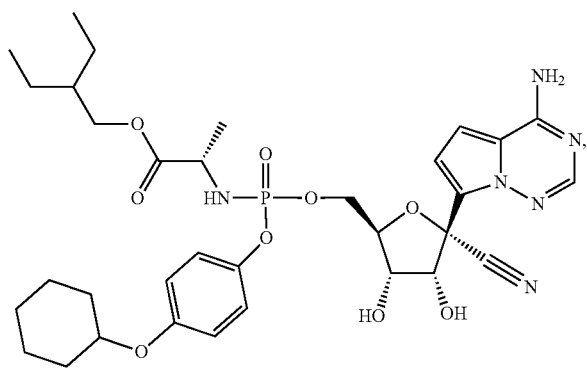
90
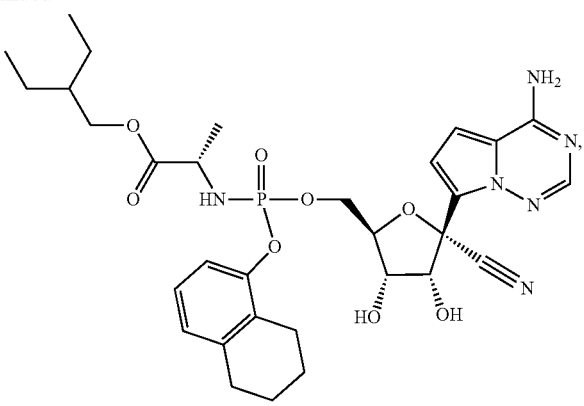
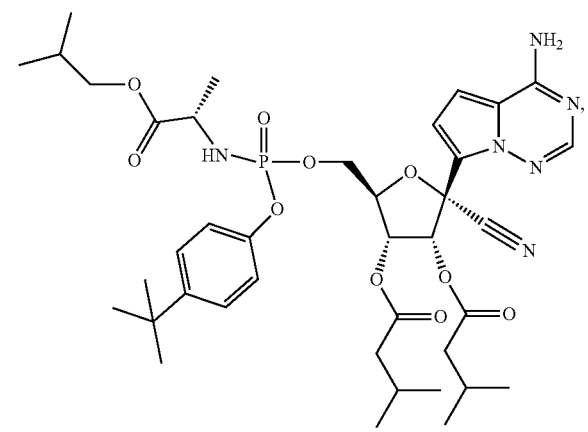

-continued
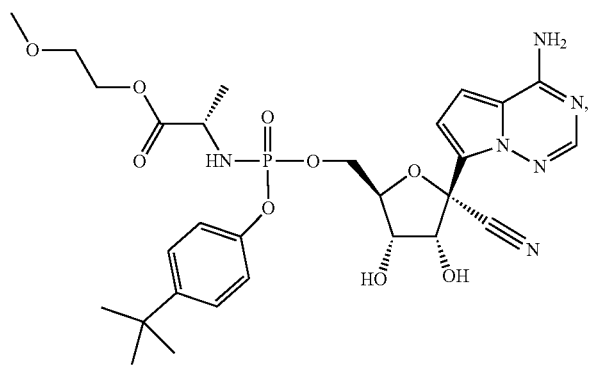
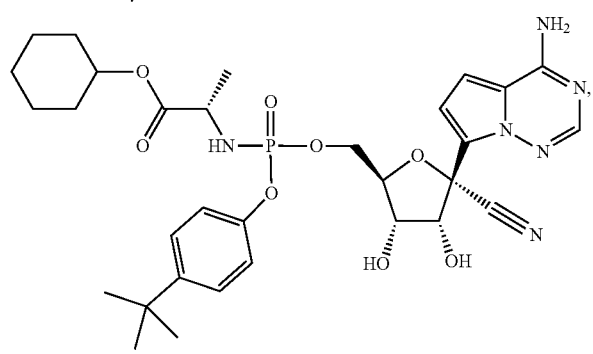
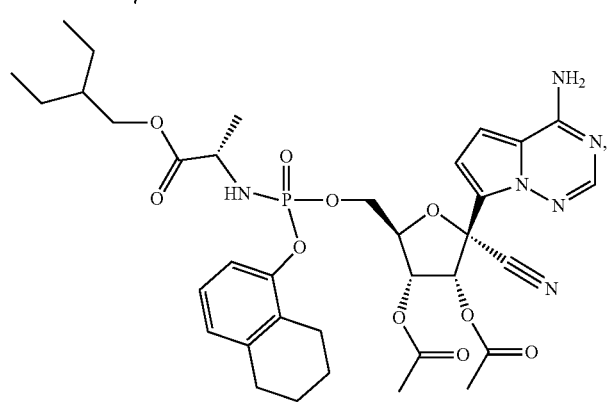
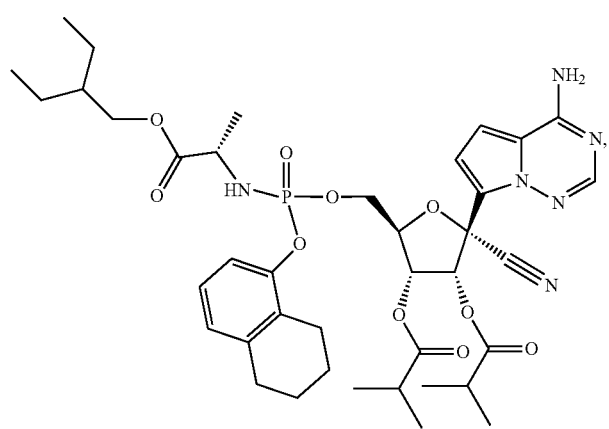

-continued
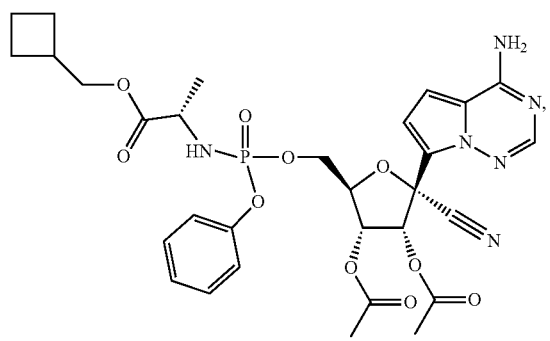
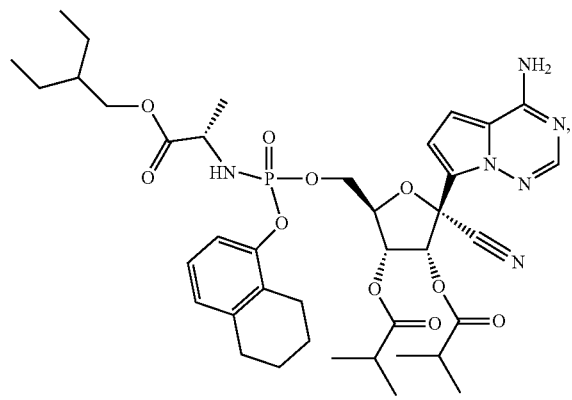
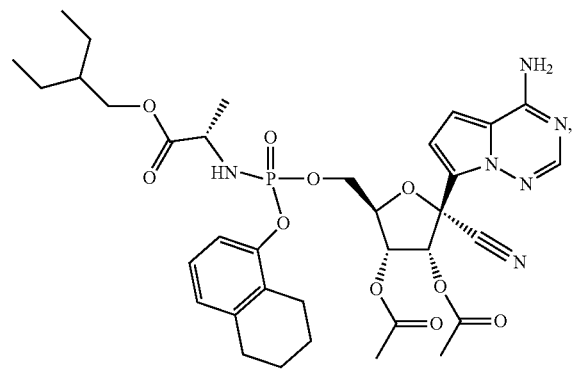
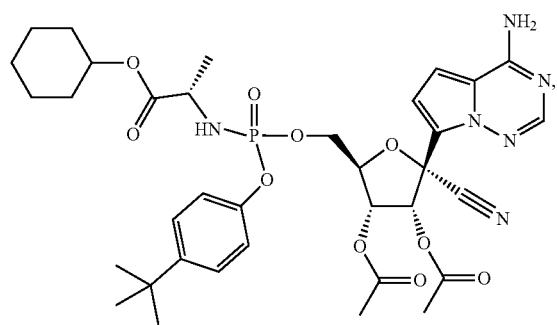
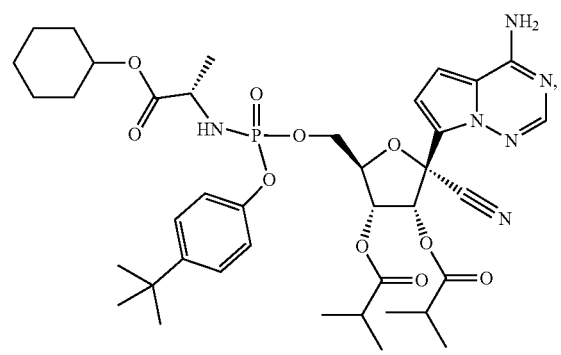
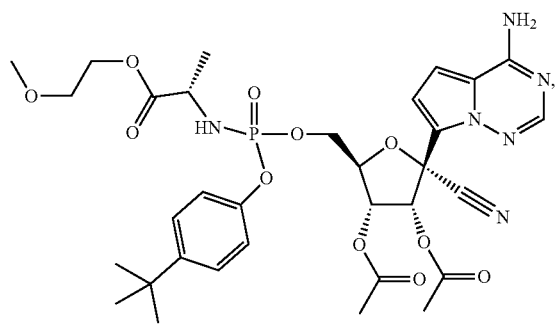
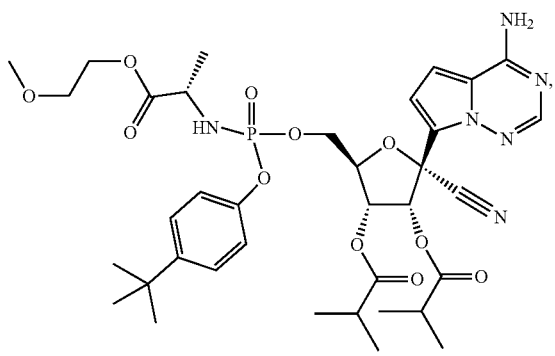

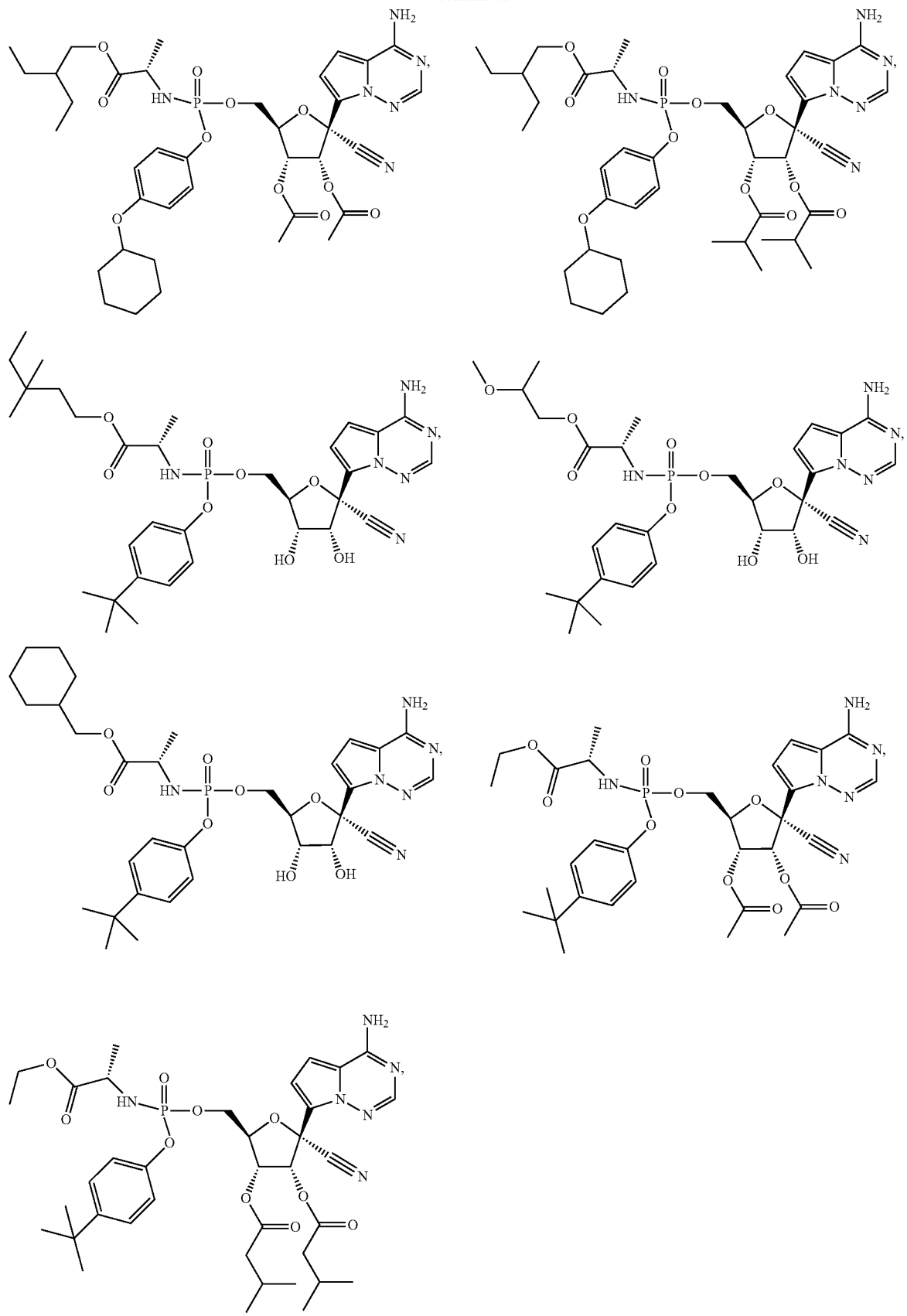

-continued
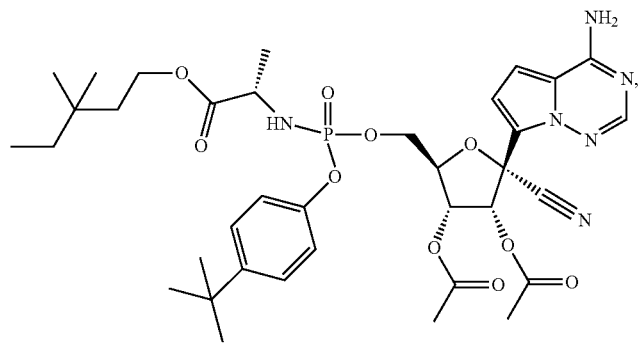
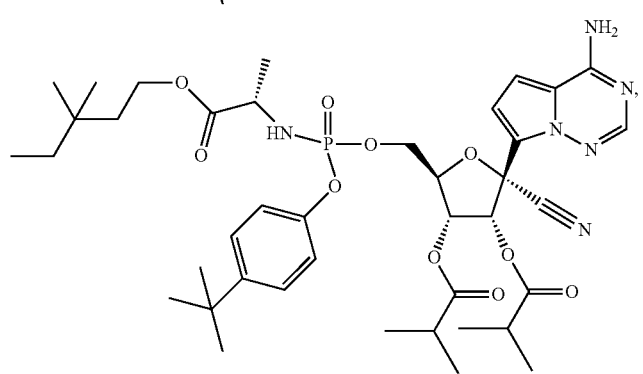
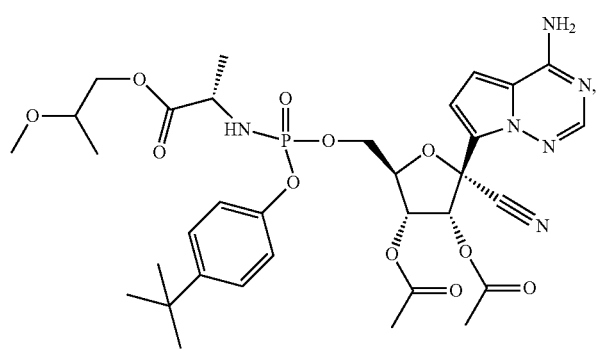
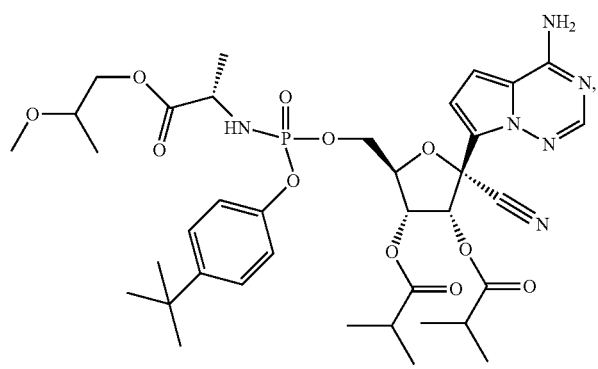

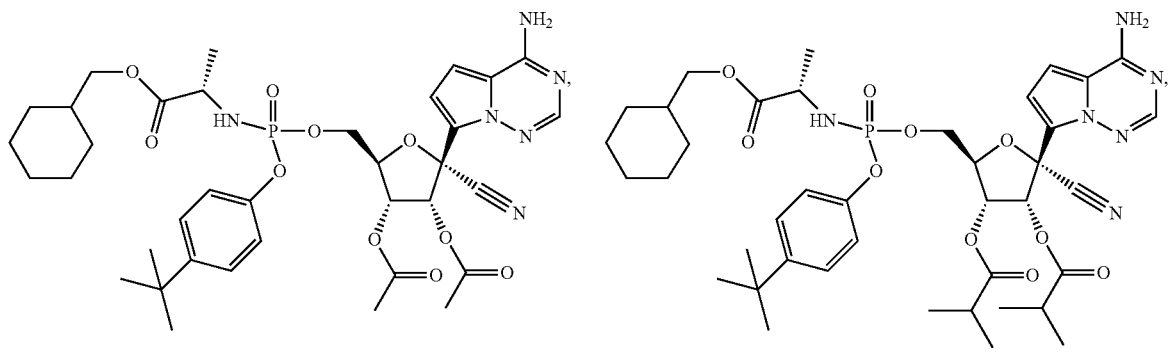
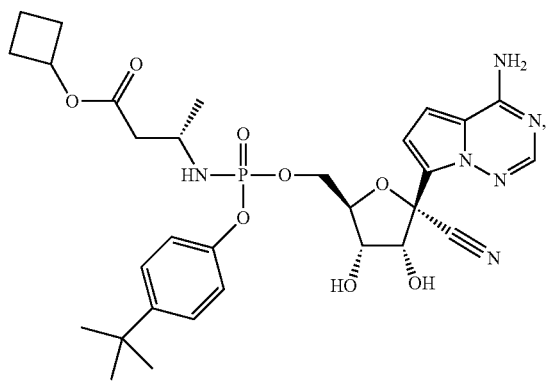
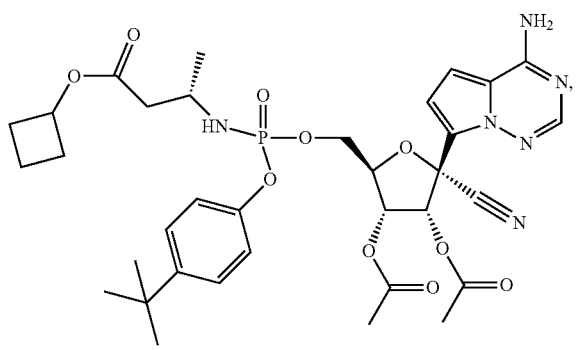
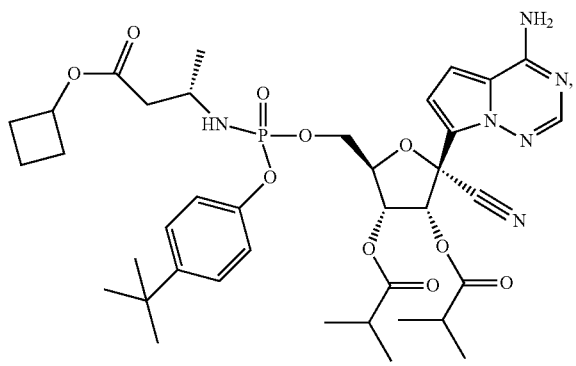

-continued
101
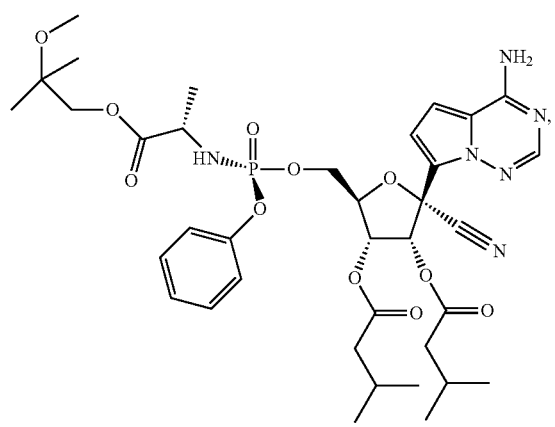
102
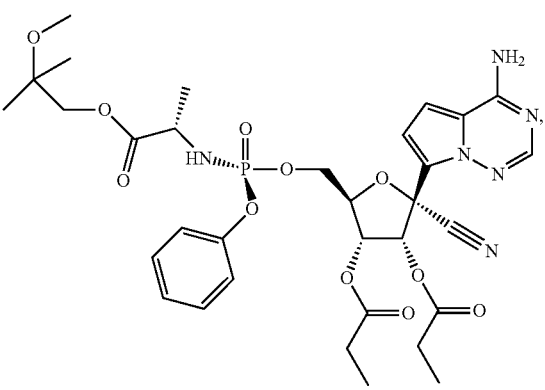
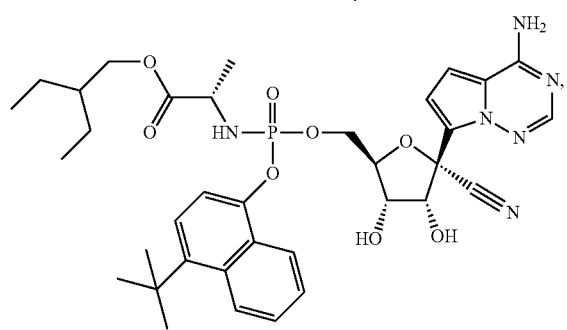
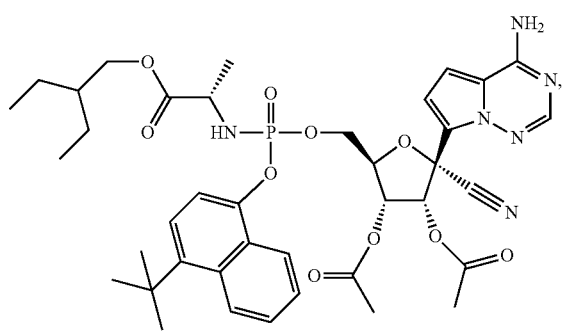
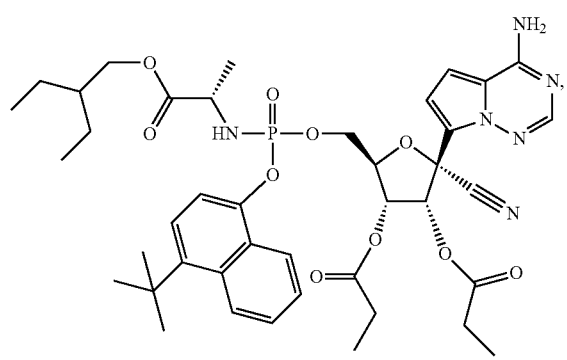
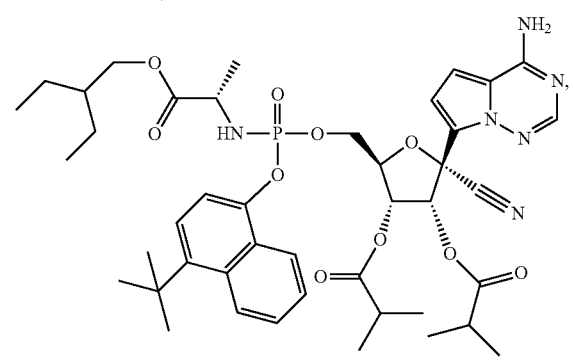
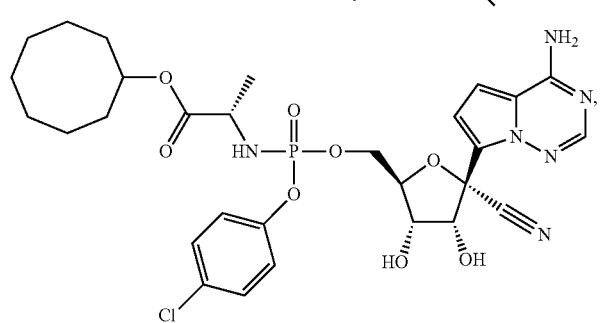
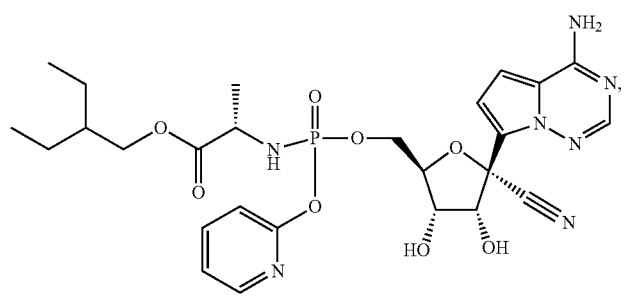

-continued
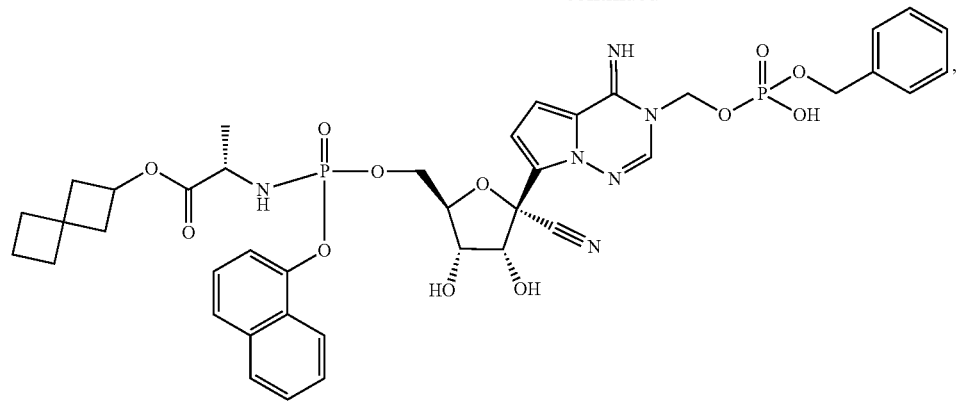
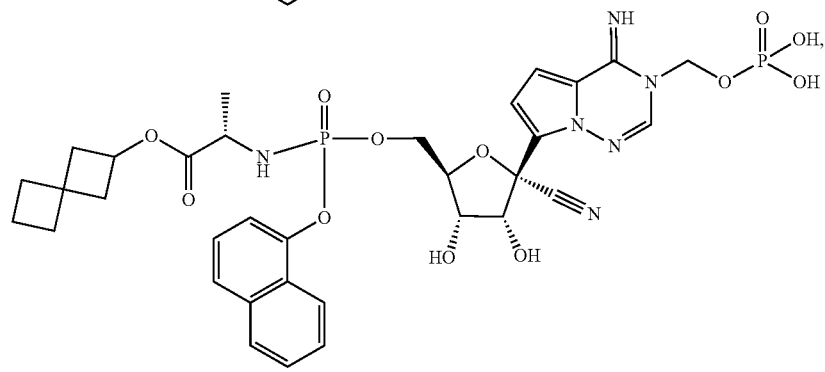
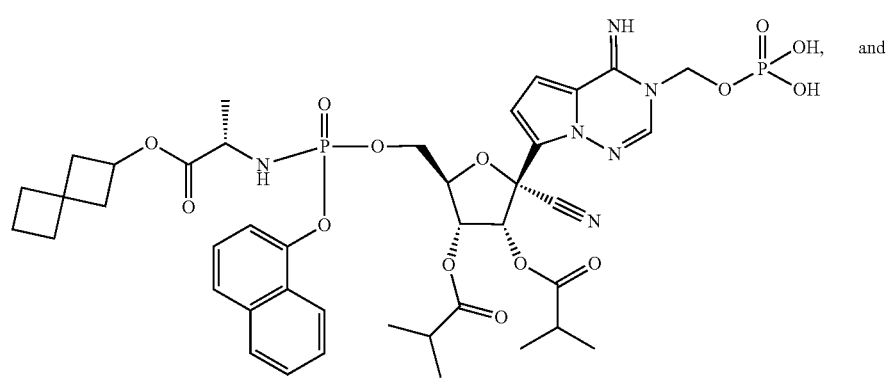
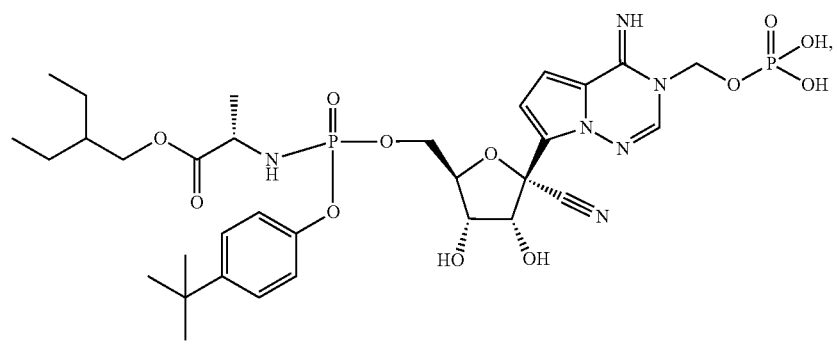
or a pharmaceutically acceptable salt thereof.

In some embodiments, the compound of Formula I, Ia, Ib, II, IIa, IIb, III, IIIa, IIIb, or IIIc, is selected from the group consisting of:

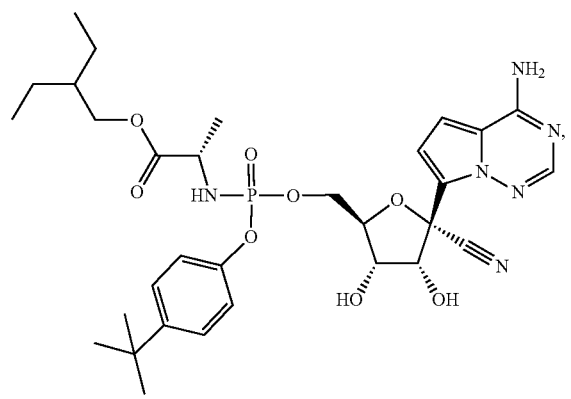

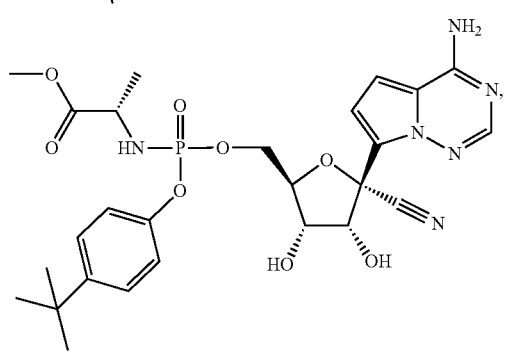

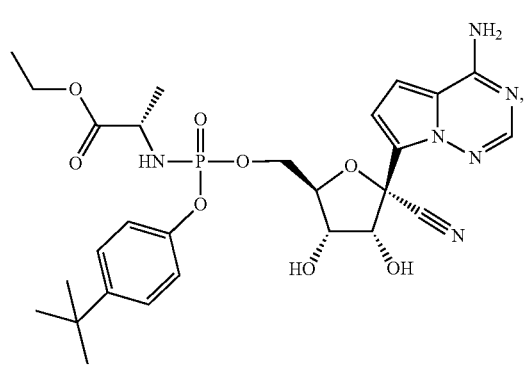

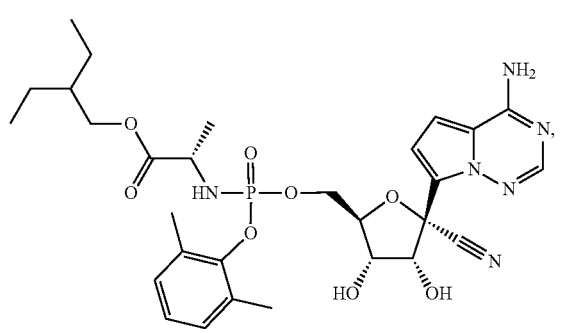

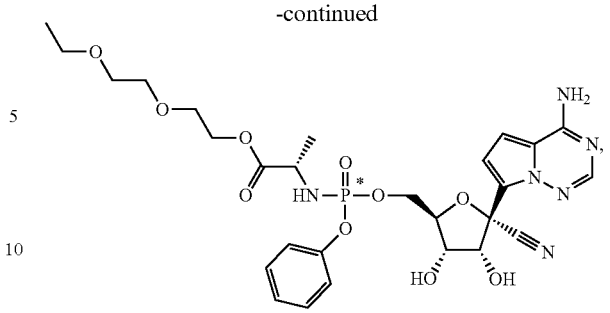

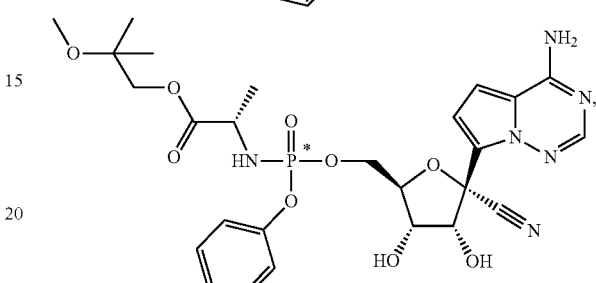

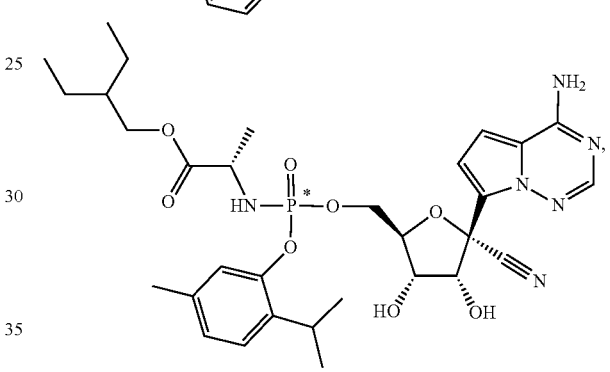

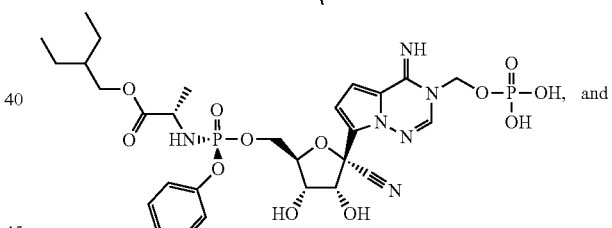

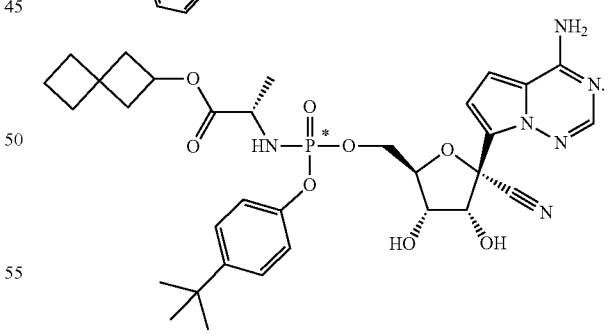

Any reference to the compounds of the invention described herein also includes a reference to a pharmaceutically acceptable salt thereof. Examples of pharmaceutically acceptable salts of the compounds of the invention include salts derived from an appropriate base, such as an alkali metal or an alkaline earth (for example, Na$^+$, Li$^+$, K$^+$, Ca$^{+2}$ and Mg$^{+2}$), ammonium and NR$_4^+$ (wherein R is defined herein). Pharmaceutically acceptable salts of a nitrogen atom or an amino group include (a) acid addition salts formed with inorganic acids, for example, hydrochloric acid, hydrobromic acid, sulfuric acid, sulfamic acids, phosphoric acid, nitric acid and the like; (b) salts formed with organic acids such as, for example, acetic acid, oxalic acid, tartaric acid, succinic acid, maleic acid, fumaric acid, gluconic acid, citric acid, malic acid, ascorbic acid, benzoic acid, isethionic acid, lactobionic acid, tannic acid, palmitic acid, alginic acid, polyglutamic acid, naphthalenesulfonic acid, methanesulfonic acid, p-toluenesulfonic acid, benzenesulfonic acid, naphthalenedisulfonic acid, polygalacturonic acid, malonic acid, sulfosalicylic acid, glycolic acid, 2-hydroxy-3-naphthoate, pamoate, salicylic acid, stearic acid, phthalic acid, mandelic acid, lactic acid, ethanesulfonic acid, lysine, arginine, glutamic acid, glycine, serine, threonine, alanine, isoleucine, leucine and the like; and (c) salts formed from elemental anions for example, chlorine, bromine, and iodine. Pharmaceutically acceptable salts of a compound of a hydroxy group include the anion of said compound in combination with a suitable cation such as $Na^+$ and $NR_4^+$.

The compounds disclosed herein (e.g. compounds of Formula I, Ia, Ib, II, IIa, IIb, III, IIIa, IIIb, or IIIc) and its pharmaceutically acceptable salts may exist as different polymorphs or pseudopolymorphs. As used herein, crystalline polymorphism means the ability of a crystalline compound to exist in different crystal structures. The crystalline polymorphism may result from differences in crystal packing (packing polymorphism) or differences in packing between different conformers of the same molecule (conformational polymorphism). As used herein, crystalline pseudopolymorphism means the ability of a hydrate or solvate of a compound to exist in different crystal structures. The pseudopolymorphs of the instant invention may exist due to differences in crystal packing (packing pseudopolymorphism) or due to differences in packing between different conformers of the same molecule (conformational pseudopolymorphism). The instant invention comprises all polymorphs and pseudopolymorphs of the compounds of Formula I, Ia, Ib, II, IIa, IIb, III, IIIa, IIIb, or IIIc, and their pharmaceutically acceptable salts.

The compounds disclosed herein (e.g. compounds of Formula I, Ia, Tb, II, IIa, IIb, III, IIIa, IIIb, or IIIc) and its pharmaceutically acceptable salts may also exist as an amorphous solid. As used herein, an amorphous solid is a solid in which there is no long-range order of the positions of the atoms in the solid. This definition applies as well when the crystal size is two nanometers or less. Additives, including solvents, may be used to create the amorphous forms of the instant invention. The instant invention comprises all amorphous forms of the compounds of Formula I, Ta, Tb, II, IIa, IIb, III, IIIa, IIIb, or IIIc, and their pharmaceutically acceptable salts.

For therapeutic use, salts of active ingredients of the compounds of the invention will be pharmaceutically acceptable, i.e. they will be salts derived from a pharmaceutically acceptable acid or base. However, salts of acids or bases which are not pharmaceutically acceptable may also find use, for example, in the preparation or purification of a pharmaceutically acceptable compound. All salts, whether or not derived form a pharmaceutically acceptable acid or base, are within the scope of the present invention.

Finally, it is to be understood that the compositions herein comprise compounds of the invention in their un-ionized, as well as zwitterionic form, and combinations with stoichiometric amounts of water as in hydrates.

It is to be noted that all enantiomers, diastereomers, and racemic mixtures, tautomers, polymorphs, pseudopolymorphs of compounds within the scope of Formula I and pharmaceutically acceptable salts thereof are embraced by the present invention. All mixtures of such enantiomers and diastereomers are within the scope of the present invention.

The compounds of the invention, exemplified by Formula I may have chiral centers, e.g. chiral carbon or phosphorus atoms. The compounds of the invention thus include racemic mixtures of all stereoisomers, including enantiomers, diastereomers, and atropisomers. In addition, the compounds of the invention include enriched or resolved optical isomers at any or all asymmetric, chiral atoms. In other words, the chiral centers apparent from the depictions are provided as the chiral isomers or racemic mixtures. Both racemic and diastereomeric mixtures, as well as the individual optical isomers isolated or synthesized, substantially free of their enantiomeric or diastereomeric partners, are all within the scope of the invention. The racemic mixtures are separated into their individual, substantially optically pure isomers through appropriate techniques such as, for example, the separation of diastereomeric salts formed with optically active adjuncts, e.g., acids or bases followed by conversion back to the optically active substances. In most instances, the desired optical isomer is synthesized by means of stereospecific reactions, beginning with the appropriate stereoisomer of the desired starting material.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l, D and L, or (+) and (−) are employed to designate the sign of rotation of plane-polarized light by the compound, with S, (−), or l meaning that the compound is levorotatory while a compound prefixed with R, (+), or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The compounds of the invention may also exist as tautomeric isomers in certain cases. Although only one delocalized resonance structure may be depicted, all such forms are contemplated within the scope of the invention. For example, ene-amine tautomers can exist for purine, pyrimidine, imidazole, guanidine, amidine, and tetrazole systems and all their possible tautomeric forms are within the scope of the invention.

Any formula or structure given herein, including Formula I compounds, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2H$ (deuterium, D), $^3H$ (tritium), $^{11}$C, $^{13}$C, $^{14}$C, $^{15}$N, $^{18}$F, $^{31}$P, $^{32}$P, $^{35}$S, $^{36}$Cl and $^{125}$I. Various isotopically labeled compounds of the present disclosure, for example those into which radioactive isotopes such as $^{3}$H, $^{13}$C and $^{14}$C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also includes compounds of Formula I in which from 1 to n hydrogens attached to a carbon atom is/are replaced by deuterium, in which n is the number of hydrogens in the molecule. Such compounds exhibit increased resistance to metabolism and are thus useful for increasing the half-life of any compound of Formula I when administered to a mammal, particularly a human. See, for example, Foster, "Deuterium Isotope Effects in Studies of Drug Metabolism", Trends Pharmacol. Sci. 5(12):524-527 (1984). In view of the present disclosure, such compounds are synthesized by means known in the art, for example by employing starting materials in which one or more hydrogens have been replaced by deuterium.

Deuterium labeled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compound of Formula I.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

Whenever a compound described herein is substituted with more than one of the same designated group, e.g., "R" or "R", then it will be understood that the groups may be the same or different, i.e., each group is independently selected.

Wavy lines, ⌇⌇⌇⌇, indicate the site of covalent bond attachments to the adjoining substructures, groups, moieties, or atoms.

IV. Pharmaceutical Formulations

The compounds disclosed herein (e.g. compounds of Formula I, Ia, Tb, II, IIa, IIb, III, IIIa, IIIb, or IIIc) may be formulated with conventional carriers and excipients. For example, tablets will contain excipients, glidants, fillers, binders and the like. Aqueous formulations are prepared in sterile form, and when intended for delivery by other than oral administration generally will be isotonic. All formulations may optionally contain excipients such as those set forth in the "Handbook of Pharmaceutical Excipients" (1986). Excipients include ascorbic acid and other antioxidants, chelating agents such as EDTA, carbohydrates such as dextran, hydroxyalkylcellulose, hydroxyalkylmethylcellulose, stearic acid and the like. The pH of the formulations ranges from about 3 to about 11, but is ordinarily about 7 to 10. In some embodiments, the pH of the formulations ranges from about 2 to about 5, but is ordinarily about 3 to 4.

While it is possible for the compounds of the disclosure ("the active ingredients") to be administered alone it may be preferable to present them as pharmaceutical formulations. The formulations, both for veterinary and for human use, of the invention comprise at least one active ingredient, as above defined, together with one or more acceptable carriers therefor and optionally other therapeutic ingredients, particularly those additional therapeutic ingredients as discussed herein. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any appropriate method known in the art of pharmacy. Techniques and formulations generally are found in Remington's Pharmaceutical Sciences (Mack Publishing Co., Easton, PA). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

For infections of the eye or other external tissues e.g. mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate. Further emulgents and emulsion stabilizers suitable for use in the formulation of the invention include Tween® 80.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention comprise a compound according to the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared.

Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcellulose, sodium alginate, polyvinylpyrrolidone, gum tragacanth and gum acacia, and dispersing or wetting agents such as a naturally-occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin. Further non-limiting examples of suspending agents include Cyclodextrin and Captisol (Sulfobutyl ether beta-cyclodextrin; SEB-beta-CD).

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or *arachis* oil, a mineral oil, such as liquid paraffin, or a mixture of these. Suitable emulsifying agents include naturally-occurring gums, such as gum acacia and gum tragacanth, naturally-occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables. Among the acceptable vehicles and solvents that may be employed are water, Ringer's solution isotonic sodium chloride solution, and hypertonic sodium chloride solution.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10%, and particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

In some embodiments, the compounds disclosed herein are administered by inhalation. In some embodiments, formulations suitable for intrapulmonary or nasal administration have a particle size for example in the range of 0.1 to 500 microns, such as 0.5, 1, 30, 35 etc., which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents. In some embodiments, the compounds used herein are formulated and dosed as dry powder. In some embodiments, the compounds used herein are formulated and dosed as a nebulized formulation. In some embodiments, the compounds used herein are formulated for delivery by a face mask. In some embodiments, the compounds used herein are formulated for delivery by a face tent.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention are used to provide controlled release pharmaceutical formulations containing as active ingredient one or more compounds of the invention ("controlled release formulations") in which the release of the active ingredient are controlled and regulated to allow less frequency dosing or to improve the pharmacokinetic or toxicity profile of a given active ingredient.

V. Kits

Also provided is a kit that includes a compound disclosed herein (e.g. compounds of Formula I, Ia, Ib, II, IIa, IIb, III, IIIa, IIIb, or IIIc), a pharmaceutically acceptable salt, stereoisomer, mixture of stereoisomers or tautomer thereof. In some embodiments the kits described herein may comprise a label and/or instructions for use of the compound in the treatment of a disease or condition in a subject (e.g., human) in need thereof. In some embodiments, the disease or condition is viral infection.

In some embodiments, the kit may also comprise one or more additional therapeutic agents and/or instructions for use of additional therapeutic agents in combination with the compound of Formula I in the treatment of the disease or condition in a subject (e.g., human) in need thereof.

In some embodiments, the kits provided herein comprises individual dose units of a compound as described herein, or a pharmaceutically acceptable salt, racemate, enantiomer, diastereomer, tautomer, polymorph, pseudopolymorph, amorphous form, hydrate or solvate thereof. Examples of individual dosage units may include pills, tablets, capsules, prefilled syringes or syringe cartridges, IV bags, inhalers, nebulizers etc., each comprising a therapeutically effective amount of the compound in question, or a pharmaceutically acceptable salt, racemate, enantiomer, diastereomer, tautomer, polymorph, pseudopolymorph, amorphous form, hydrate or solvate thereof. In some embodiments, the kit may contain a single dosage unit and in others multiple dosage units are present, such as the number of dosage units required for a specified regimen or period.

Also provided are articles of manufacture that include a compound of Formula I, or a pharmaceutically acceptable salt, stereoisomer, mixture of stereoisomers or tautomer thereof; and a container. In some embodiments, the container of the article of manufacture is a vial, jar, ampoule, preloaded syringe, blister package, tin, can, bottle, box, an intravenous bag, an inhaler, or a nebulizer.

VI. Administration

One or more compounds of the invention are administered by any route appropriate to the condition to be treated. Suitable routes include oral, rectal, inhalation, pulmonary, topical (including buccal and sublingual), vaginal and parenteral (including subcutaneous, intramuscular, intravenous, intradermal, intrathecal and epidural), and the like. In some embodiments, the compounds disclosed herein are administered by inhalation or intravenously. It will be appreciated that the preferred route may vary with for example the condition of the recipient.

In the methods of the present invention for the treatment of a viral infection, the compounds of the present invention can be administered at any time to a human who may come into contact with the virus or is already suffering from the viral infection. In some embodiments, the compounds of the present invention can be administered prophylactically to humans coming into contact with humans suffering from the viral infection or at risk of coming into contact with humans suffering from the viral infection, e.g. healthcare providers. In some embodiments, administration of the compounds of the present invention can be to humans testing positive for the viral infection but not yet showing symptoms of the viral infection. In some embodiments, administration of the compounds of the present invention can be to humans upon commencement of symptoms of the viral infection.

In some embodiments, the methods disclosed herein comprise event driven administration of the compound of Formula I, or a pharmaceutically acceptable salt thereof, to the subject.

As used herein, the terms "event driven" or "event driven administration" refer to administration of the compound of Formula I, or a pharmaceutically acceptable salt thereof, (1) prior to an event (e.g., 2 hours, 1 day, 2 days, 5 day, or 7 or more days prior to the event) that would expose the individual to the virus (or that would otherwise increase the individual's risk of acquiring the viral infection); and/or (2) during an event (or more than one recurring event) that would expose the individual to the virus (or that would otherwise increase the individual's risk of acquiring the viral infection); and/or (3) after an event (or after the final event in a series of recurring events) that would expose the individual to the virus (or that would otherwise increase the individual's risk of acquiring the viral infection). In some embodiments, the event driven administration is performed pre-exposure of the subject to the virus. In some embodiments, the event driven administration is performed post-exposure of the subject to the virus. In some embodiments, the event driven administration is performed pre-exposure of the subject to the virus and post-exposure of the subject to the virus.

In certain embodiments, the methods disclosed herein involve administration prior to and/or after an event that would expose the individual to the virus or that would otherwise increase the individual's risk of acquiring the viral infection, e.g., as pre-exposure prophylaxis (PrEP) and/or as post-exposure prophylaxis (PEP). In some embodiments, the methods disclosed herein comprise pre-exposure prophylaxis (PrEP). In some embodiments, methods disclosed herein comprise post-exposure prophylaxis (PEP).

In some embodiments, the compound of Formula I, or a pharmaceutically acceptable salt thereof, is administered before exposure of the subject to the virus.

In some embodiments, the compound of Formula I, or a pharmaceutically acceptable salt thereof, is administered before and after exposure of the subject to the virus.

In some embodiments, the compound of Formula I, or a pharmaceutically acceptable salt thereof, is administered after exposure of the subject to the virus.

An example of event driven dosing regimen includes administration of the compound of Formula I, or a pharmaceutically acceptable salt thereof, within 24 to 2 hours prior to the virus, followed by administration of the compound of Formula I, or a pharmaceutically acceptable salt, every 24 hours during the period of exposure, followed by a further administration of the compound of Formula I, or a pharmaceutically acceptable salt thereof, after the last exposure, and one last administration of the compound of Formula I, or a pharmaceutically acceptable salt thereof, 24 hours later.

A further example of an event driven dosing regimen includes administration of the compound of Formula I, or a pharmaceutically acceptable salt thereof, within 24 hours before the viral exposure, then daily administration during the period of exposure, followed by a last administration approximately 24 hours later after the last exposure (which may be an increased dose, such as a double dose).

Effective dose of active ingredient depends at least on the nature of the condition being treated, toxicity, whether the compound is being used prophylactically or against an active viral infection, the method of delivery, and the pharmaceutical formulation, and will be determined by the clinician using conventional dose escalation studies. It can be expected to be from about 0.0001 to about 100 mg/kg body weight per day; typically, from about 0.01 to about 10 mg/kg body weight per day; more typically, from about 0.01 to about 5 mg/kg body weight per day; most typically, from about 0.05 to about 0.5 mg/kg body weight per day. For example, the daily candidate dose for an adult human of approximately 70 kg body weight will range from 1 mg to 1000 mg, preferably between 5 mg and 500 mg, and may take the form of single or multiple doses.

Any suitable period of time for administration of the compounds of the present invention is contemplated. For example, administration can be for from 1 day to 100 days, including 2, 3, 4, 5, 6, 7, 8, 9, 10, 15, 20, 25, 30, 40, 50, 60, 70, 80, or 90 days. The administration can also be for from 1 week to 15 weeks, including 2, 3, 4, 5, 6, 7, 8, 9, 10, 11, 12, 13, or 14 weeks. Longer periods of administration are also contemplated.

In some embodiments, the compounds disclosed herein are administered once daily. In some embodiments, the compounds disclosed herein are administered once every alternate day. In some embodiments, the compounds disclosed herein are administered once a week. In some embodiments, the compounds disclosed herein are administered twice a week.

In some embodiments, one or more compounds disclosed herein are administered once daily. The once daily dose may be administered for as long as required, for example for up to 5 days, up to 7 days, up to 10 days, up to 15 days, up to 20 days, up to 25 days, up to a month or longer. In some embodiments, the once daily dose is administered for up to 20 days, up to 15 days, up to 14 days, up to 13 days, up to 12 days, up to 10 days, up to 8 days, up to 6 days, up to 4 days, up to 3 days, up to 2 days or for one day.

In some embodiments, the one or more compounds disclosed herein are dosed once daily, for about 6 to 12 days, for example for about 8-10 days. In some embodiments, the one or more compounds are administered once daily for about 9 days. In some embodiments, the one or more compounds are administered once daily for about 10 days. In some embodiments about 50-150 mg of one or more compounds disclosed herein is administered once daily for about 5 to 12 days, for e.g. for about 10 days. In some embodiments about 100 mg of one or more compounds disclosed herein is administered once daily for about 5 to 12 days, for e.g. for about 10 days.

VII. Methods of Use

The present disclosure also provides a method of treating or preventing a viral infection in a subject (e.g. human) in need thereof, the method comprising administering to the subject a compound described herein.

In some embodiments, the present disclosure provides a method of treating a viral infection in a subject (e.g. human) in need thereof, the method comprising administering to a subject in need thereof a compound described herein.

In some embodiments, the present disclosure provides for methods of treating or preventing a viral infection in a subject (e.g. human) in need thereof, the method comprising administering to the subject a compound disclosed herein and at least one additional active therapeutic agent.

In some embodiments, the present disclosure provides for methods of treating a viral infection in a subject (e.g. human) in need thereof, the method comprising administering to the subject a compound disclosed herein, and at least one additional active therapeutic agent.

In one embodiment, the present disclosure provides for methods of inhibiting a viral polymerase in a cell, the methods comprising contacting the cell infected a virus with a compound disclosed herein, whereby the viral polymerase is inhibited.

In one embodiment, the present disclosure provides for methods of inhibiting a viral polymerase in a cell, the methods comprising contacting the cell infected a virus with a compound disclosed herein, and at least one additional active therapeutic agent, whereby the viral polymerase is inhibited.

Also provided here are the uses of the compounds disclosed herein for use in treating or preventing a viral infection in a subject in need thereof. For example, provided herein are uses of the compounds disclosed herein for use in treating a viral infection in a subject in need thereof.

In some embodiments, the viral infection is a paramyxoviridae virus infection. As such, in some embodiments, the present disclosure provides methods for treating a paramyxoviridae infection in a subject (e.g. a human) in need thereof, the method comprising administering to the subject a compound disclosed herein. Paramyxoviridae viruses include, but are not limited to Nipah virus, Hendra virus, measles, mumps, and parainfluenze virus.

In some embodiments, the viral infection is a pneumoviridae virus infection. As such, in some embodiments, the present disclosure provides a method of treating a pneumoviridae virus infection in a human in need thereof, the method comprising administering to the human a compound provided herein. Pneumoviridae viruses include, but are not limited to, respiratory snycytial virus and human metapneumovirus. In some embodiments, the pneumoviridae virus infection is a respiratory syncytial virus infection. In some embodiments, the pneumoviridae virus infection is human metapneumovirus infection.

In some embodiments, the present disclosure provides a compound disclosed herein, for use in the treatment of a pneumoviridae virus infection in a human in need thereof. In some embodiments, the pneumoviridae virus infection is a respiratory syncytial virus infection. In some embodiments, the pneumoviridae virus infection is human metapneumovirus infection.

In some embodiments, the present disclosure provides methods for treating a RSV infection in a human in need thereof, the method comprising administering to the human a compound provided herein. In some embodiments, the human is suffering from a chronic respiratory syncytial viral infection. In some embodiments, the human is acutely infected with RSV.

In some embodiments, a method of inhibiting RSV replication is provided, wherein the method comprises administering to a human in need thereof, a compound disclosed herein, wherein the administration is by inhalation.

In some embodiments, the present disclosure provides a method for reducing the viral load associated with RSV infection, wherein the method comprises administering to a human infected with RSV a compound disclosed herein.

In some embodiments, the viral infection is a picornaviridae virus infection. As such, in some embodiments, the present disclosure provides a method of treating a picornaviridae virus infection in a human in need thereof, the method comprising administering to the human a compound of the present disclosure. Picornaviridae viruses are enet-eroviruses causing a heterogeneous group of infections including herpangina, aseptic meningitis, a common-cold-like syndrome (human rhinovirus infection), a non-paralytic poliomyelitis-like syndrome, epidemic pleurodynia (an acute, febrile, infectious disease generally occurring in epidemics), hand-foot-mouth syndrome, pediatric and adult pancreatitis and serious myocarditis. In some embodiments, the Picornaviridae virus infection is human rhinovirus infection.

In some embodiments, the present disclosure provides a compound, for use in the treatment of a picornaviridae virus infection in a human in need thereof. In some embodiments, the picornaviridae virus infection is human rhinovirus infection.

In some embodiments, the viral infection is a flaviviridae virus infection. As such, in some embodiments, the present disclosure provides a method of treating a flaviviridae virus infection in a human in need thereof, the method comprising administering to the human a compound described herein. Representative flaviviridae viruses include, but are not limited to, dengue, Yellow fever, West Nile, Zika, Japanese encephalitis virus, and Hepatitis C (HCV). In some embodiments, the flaviviridae virus infection is a dengue virus infection. In some embodiments, the flaviviridae virus infection is a yellow fever virus infection. In some embodiments, the flaviviridae virus infection is a West Nile virus infection. In some embodiments, the flaviviridae virus infection is a zika virus infection. In some embodiments, the flaviviridae virus infection is a Japanese ensephalitis virus infection. In some embodiments, the flaviviridae virus infection is a hepatitis C virus infection.

In some embodiments, the present disclosure provides use of a compound disclosed herein for treatment of a flaviviridae virus infection in a human in need thereof. In some embodiments, the flaviviridae virus infection is a dengue virus infection. In some embodiments, the flaviviridae virus infection is a yellow fever virus infection. In some embodiments, the flaviviridae virus infection is a West Nile virus infection. In some embodiments, the flaviviridae virus infection is a zika virus infection. In some embodiments, the flaviviridae virus infection is a hepatitis C virus infection.

In some embodiments, the viral infection is a filoviridae virus infection. As such, in some embodiments, provided herein is a method of treating a filoviridae virus infection in a human in need thereof, the method comprising administering to the human a compound disclosed herein. Representative filoviridae viruses include, but are not limited to, ebola (variants Zaire, Bundibugio, Sudan, Tai forest, or Reston) and marburg. In some embodiments, the filoviridae virus infection is an ebola virus infection. In some embodiments, the filoviridae virus infection is a marburg virus infection.

In some embodiments, the present disclosure provides a compound for use in the treatment of a filoviridae virus infection in a human in need thereof. In some embodiments, the filoviridae virus infection is an ebola virus infection. In some embodiments, the filoviridae virus infection is a marburg virus infection.

In some embodiments, the viral infection is a coronavirus infection. As such, in some embodiments, provided herein is a method of treating a coronavirus infection in a human in need thereof, wherein the method comprises administering to the human a compound provided herein.

In some embodiments, the coronavirus infection is a Severe Acute Respiratory Syndrome (SARS) infection, Middle Eastern Respiratory Syndrome (MERS) infection, SARS-CoV-2 infection, other human coronavirus (229E, NL63, OC43, HKU1, or WIV1) infections, zoonotic coronavirus (PEDV or HKU CoV isolates such as HKU3, HKU5, or HKU9) infections. In some embodiments, the viral infection is a Severe Acute Respiratory Syndrome (SARS) infection. In some embodiments, the viral infection is a Middle Eastern Respiratory Syndrome (MERS) infection. In some embodiments, the viral infection is SARS-CoV-2 infection.

In some embodiments, the present disclosure provides a compound for use in the treatment of a coronavirus virus infection in a human in need thereof. In some embodiments, the coronavirus infection is a Severe Acute Respiratory Syndrome (SARS) infection, Middle Eastern Respiratory Syndrome (MERS) infection, SARS-CoV-2 infection, other human coronavirus (229E, NL63, OC43, HKU1, or WIV1) infections, zoonotic coronavirus (PEDV or HKU CoV isolates such as HKU3, HKU5, or HKU9) infections. In some embodiments, the viral infection is a Severe Acute Respiratory Syndrome (SARS) infection. In some embodiments, the viral infection is a Middle Eastern Respiratory Syndrome (MERS) infection. In some embodiments, the viral infection is SARS-CoV-2 infection (COVID19).

In some embodiments, the viral infection is an arenaviridae virus infection. As such, in some embodiments, the disclosure provides a method of treating an arenaviridae virus infection in a human in need thereof, the method comprising administering to the human a compound disclosed herein. In some embodiments, the arenaviridae virus infection is a Lassa infection or a Junin infection.

In some embodiments, the present disclosure provides a compound for use in the treatment of a arenaviridae virus infection in a human in need thereof. In some embodiments, the arenaviridae virus infection is a Lassa infection or a Junin infection.

In some embodiments, the viral infection is an orthomyxovirus infection, for example, an influenza virus infection. In some embodiments, the viral infection is an influenza virus A, influenza virus B, or influenza virus C infection.

As described more fully herein, the compounds described herein can be administered with one or more additional therapeutic agent(s) to an individual (e.g. a human) infected with a viral infection. The additional therapeutic agent(s) can be administered to the infected individual at the same time as the compound of the present disclosure or before or after administration of the compound of the present disclosure.

VIII. Combination Therapy

The compounds described herein can also be used in combination with one or more additional therapeutic agents. As such, also provided herein are methods of treatment of the a viral infection in a subject in need thereof, wherein the methods comprise administering to the subject a compound disclosed therein and a therapeutically effective amount of one or more additional therapeutic agents.

In some embodiments, the additional therapeutic agent is an antiviral agent. Any suitable antiviral agent can be used in the methods described herein. In some embodiments, the antiviral agent is selected from the group consisting of 5-substituted 2'-deoxyuridine analogues, nucleoside analogues, pyrophosphate analogues, nucleoside reverse transcriptase inhibitors, non-nucleoside reverse transcriptase inhibitors, protease inhibitors, integrase inhibitors, entry inhibitors, acyclic guanosine analogues, acyclic nucleoside phosphonate analogues, HCV NS5A/NS5B inhibitors, influenza virus inhibitors, interferons, immunostimulators, oligonucleotides, antimitotic inhibitors, and combinations thereof.

In some embodiments, the additional therapeutic agent is a 5-substituted 2'-deoxyuridine analogue. For example, in some embodiments, the additional therapeutic agent is selected from the group consisting of idoxuridine, trifluridine, brivudine [BVDU], and combinations thereof.

In some embodiments, the additional therapeutic agent is a nucleoside analogue. For example, in some embodiments, the additional therapeutic agent is selected from the group consisting of vidarabine, entecavir (ETV), telbivudine, lamivudine, adefovir dipivoxil, tenofovir disoproxil fumarate (TDF) and combinations thereof. In some embodiments, the additional therapeutic agent is favipiravir, ribavirin, galidesivir, β-D-N4-hydroxycytidine or a combination thereof.

In some embodiments, the additional therapeutic agent is a pyrophosphate analogue. For example, in some embodiments, the additional therapeutic agent is foscarnet or phosphonoacetic acid. In some embodiments, the additional therapeutic agent is foscarnet.

In some embodiments, the additional therapeutic agent is nucleoside reverse transcriptase inhibitor. In some embodiments, the antiviral agent is zidovudine, didanosine, zalcitabine, stavudine, lamivudine, abacavir, emtricitabine, and combinations thereof.

In some embodiments, the additional therapeutic agent is a non-nucleoside reverse transcriptase inhibitor. In some embodiments, the antiviral agent is selected from the group consisting of nevirapine, delavirdine, efavirenz, etravirine, rilpivirine, and combinations thereof.

In some embodiments, the additional therapeutic agent is a protease inhibitor. In some embodiments, the protease inhibitor is a HIV protease inhibitor. For example, in some embodiments, the antiviral agent is selected from the group consisting of saquinavir, ritonavir, indinavir, nelfinavir, amprenavir, lopinavir, atazanavir, fosamprenavir, darunavir, tipranavir, cobicistat, and combinations thereof. In some embodiments, the antiviral agent is selected from the group consisting of saquinavir, ritonavir, indinavir, nelfinavir, amprenavir, lopinavir, atazanavir, fosamprenavir, darunavir, tipranavir, and combinations thereof. In some embodiments, the protease inhibitor is a HCV NS3/4A protease inhibitor. For example, in some embodiments, the additional therapeutic agent is selected from the group consisting of voxilaprevir, asunaprevir, boceprevir, paritaprevir, simeprevir, telaprevir, vaniprevir, grazoprevir, ribavirin, danoprevir, faldaprevir, vedroprevir, sovaprevir, deldeprevir, narlaprevir and combinations thereof. In some embodiments, the additional therapeutic agent is selected from the group consisting of voxilaprevir, asunaprevir, boceprevir, paritaprevir, simeprevir, telaprevir, vaniprevir, grazoprevir, and combinations thereof.

In some embodiments, the additional therapeutic agent is an integrase inhibitor. For example, in some embodiments, the additional therapeutic agent is selected from the group consisting of raltegravir, dolutegravir, elvitegravir, abacavir, lamivudine, and combinations thereof. In some embodiments, the additional therapeutic agent is selected from the group consisting of bictegravir, raltegravir, dolutegravir, cabotegravir, elvitegravir, and combinations thereof. In some embodiments, the additional therapeutic agent is selected from the group consisting of bictegravir, dolutegravir, and cabotegravir, and combinations thereof. In some embodiments, the additional therapeutic agent is bictegravir.

In some embodiments, the additional therapeutic agent is an entry inhibitor. For example, in some embodiments, the additional therapeutic agent is selected from the group consisting of docosanol, enfuvirtide, maraviroc, ibalizumab, fostemsavir, leronlimab, ibalizumab, fostemsavir, leronlimab, palivizumab, respiratory syncytial virus immune globulin, intravenous [RSV-IGIV], varicella-zoster immunoglobulin [VariZIG], varicella-zoster immune globulin [VZIG]), and combinations thereof.

In some embodiments, the additional therapeutic agent is an acyclic guanosine analogue. For example, in some embodiments, the additional therapeutic agent is selected from the group consisting of acyclovir, ganciclovir, valacyclovir (also known as valaciclovir), valganciclovir, penciclovir, famciclovir, and combinations thereof.

In some embodiments, the additional therapeutic agent is an acyclic nucleoside phosphonate analogues. For example, in some embodiments, the additional therapeutic agent is selected from a group consisting of cidofovir, adefovir, adefovir dipivoxil, tenofovir, TDF, emtricitabine, efavirenz, rilpivirine, elvitegravir, and combinations thereof. In some embodiment, the additional therapeutic agent is selected from the group consisting of cidofovir, adefovir, adefovir dipivoxil, tenofovir, TDF, and combinations thereof. In some embodiment, the additional therapeutic agent is selected from the group consisting of cidofovir, adefovir dipivoxil, TDF, and combinations thereof.

In some embodiments, the additional therapeutic agent is a HCV NS5A/NS5B inhibitor. In some embodiments, the additional therapeutic agent is a NS3/4A protease inhibitor. In some embodiments, the additional therapeutic agent is a NS5A protein inhibitor. In some embodiments, the additional therapeutic agent is a NS5B polymerase inhibitor of the nucleoside/nucleotide type. In some embodiments, the additional therapeutic agent is a NS5B polymerase inhibitor of the nonnucleoside type. In some embodiments, the additional therapeutic agent is selected from the group consisting of daclatasvir, ledipasvir, velpatasvir, ombitasvir, elbasvir, sofosbuvir, dasabuvir, ribavirin, asunaprevir, simeprevir, paritaprevir, ritonavir, elbasvir, grazoprevir, and combinations thereof. In some embodiments, the additional therapeutic agent is selected from the group consisting of daclatasvir, ledipasvir, velpatasvir, ombitasvir, elbasvir, sofosbuvir, dasabuvir, and combinations thereof.

In some embodiments, the additional therapeutic agent is an influenza virus inhibitor. In some embodiments, the additional therapeutic agents is a matrix 2 inhibitor. For example, in some embodiments, the additional therapeutic agent is selected from the group consisting of amantadine, rimantadine, and combinations thereof. In some embodiments, the additional therapeutic agent is a neuraminidase inhibitor. For example, in some embodiments, the additional therapeutic agent is selected from the group consisting of zanamivir, oseltamivir, peramivir, laninamivir octanoate, and combinations thereof. In some embodiments, the additional therapeutic agent is a polymerase inhibitor. For example, in some embodiments, the additional therapeutic agent is selected from the group consisting of ribavirin, favipiravir, and combinations thereof. In some embodiments, the additional therapeutic agent is selected from the group consisting of amantadine, rimantadine, arbidol (umifenovir), baloxavir marboxil, oseltamivir, peramivir, ingavirin, laninamivir octanoate, zanamivir, favipiravir, ribavirin, and combinations thereof. In some embodiments, the additional therapeutic agent is selected from the group consisting of amantadine, rimantadine, zanamivir, oseltamivir, peramivir, laninamivir octanoate, ribavirin, favipiravir, and combinations thereof.

In some embodiments, the additional therapeutic agent is an interferon. In some embodiments, the additional therapeutic agent is selected from the group consisting of interferon alfacon 1, interferon alfa 1b, interferon alfa 2a, interferon alfa 2b, pegylated interferon alfacon 1, pegylated interferon alfa 1b, pegylated interferon alfa 2a (PegIFNα-2a), and PegIFNα-2b. e embodiments, the additional therapeutic agent is selected from the group consisting of interferon alfacon 1, interferon alfa 1b, interferon alfa 2a, interferon alfa 2b, pegylated interferon alfa 2a (PegIFNα-2a), and PegIFNα-2b. In some embodiments, the additional therapeutic agent is selected from the group consisting of interferon alfacon 1, pegylated interferon alfa 2a (PegIFNα-2a), PegIFNα-2b, and ribavirin. In some embodiments, the additional therapeutic agent is pegylated interferon alfa-2a, pegylated interferon alfa-2b, or a combination thereof.

In some embodiments, the additional therapeutic agent is an immunostimulatory agent. In some embodiments, the additional therapeutic agent is an oligonucleotide. In some embodiments, the additional therapeutic agent is an antimitotic inhibitor. For example, in some embodiments, the additional therapeutic agent is selected from the group consisting of fomivirsen, podofilox, imiquimod, sinecatechins, and combinations thereof.

In some embodiments, the additional therapeutic agent is selected from the group consisting of besifovir, nitazoxanide, REGN2222, doravirine, sofosbuvir, velpatasvir, daclatasvir, asunaprevir, beclabuvir, FV100, and letermovir, and combinations thereof.

In some embodiments, the additional therapeutic agent is an agent for treatment of RSV. For example, in some embodiments, the antiviral agent is ribavirin, ALS-8112 or presatovir. For example, in some embodiments, the antiviral agent is ALS-8112 or presatovir.

In some embodiments, the additional therapeutic agent is an agent for treatment of picornavirus. In some embodiments, the additional therapeutic agent is selected from the group consisting of hydantoin, guanidine hydrochloride, L-buthionine sulfoximine, Py-11, and combinations thereof. In some embodiments, the additional therapeutic agent is a picornavirus polymerase inhibitor. In some embodiments, the additional therapeutic agent is rupintrivir.

In some embodiments, the additional therapeutic agent is an agent for treatment of malaria. In some embodiments, the additional therapeutic agent is chloroquine.

In some embodiments, the additional therapeutic agent is selected from the group consisting of hydroxychloroquine, chloroquine, artemether, lumefantrine, atovaquone, proguanil, tafenoquine, pyronaridine, artesunate, artenimol, piperaquine, artesunate, amodiaquine, pyronaridine, artesunate, halofantrine, quinine sulfate, mefloquine, solithromycin, pyrimethamine, MMV-390048, ferroquine, artefenomel mesylate, ganaplacide, DSM-265, cipargamin, artemisone, and combinations thereof.

In some embodiments, the additional therapeutic agent is an agent for treatment of coronavirus. In some embodiments, the additional therapeutic agent is selected from a group consisting of IFX-1, FM-201, CYNK-001, DPP4-Fc, ranpirnase, nafamostat, LB-2, AM-1, anti-viroporins, and combinations thereof.

In some embodiments, the additional therapeutic agent is an agent for treatment of ebola virus. For example, in some embodiments, the additional therapeutic agent is selected from the group consisting of ribavirin, palivizumab, motavizumab, RSV-IGIV (RespiGam©), MEDI-557, A-60444, MDT-637, BMS-433771, amiodarone, dronedarone, verapamil, Ebola Convalescent Plasma (ECP), TKM-100201, BCX4430 ((2S,3S,4R,5R)-2-(4-amino-5H-pyrrolo[3,2-d]pyrimidin-7-yl)-5-(hydroxymethyl)pyrrolidine-3,4-diol), favipiravir (also known as T-705 or Avigan), T-705 monophosphate, T-705 diphosphate, T-705 triphosphate, FGI-106 (1-N,7-N-bis[3-(dimethylamino)propyl]-3,9-dimethylquinolino[8,7-h]quinolone-1,7-diamine), JK-05, TKM-Ebola, ZMapp, rNAPc2, VRC-EBOADC076-00-VP, OS-2966, MVA-BN filo, brincidofovir, Vaxart adenovirus vector 5-based ebola vaccine, Ad26-ZEBOV, FiloVax vaccine, GOVX-E301, GOVX-E302, ebola virus entry inhibitors (NPC1 inhibitors), rVSV-EBOV, and combinations thereof. In some embodiments, the additional therapeutic agent is ZMapp, mAB114, REGEN-EB3, and combinations thereof.

In some embodiments, the additional therapeutic agent is an agent for treatment of HCV. In some embodiments, the additional therapeutic agent is a HCV polymerase inhibitor. For example, in some embodiments, the additional therapeutic agent is selected from the group consisting of sofosbuvir, GS-6620, PSI-938, ribavirin, tegobuvir, radalbuvir, MK-0608, and combinations thereof. In some embodiments, the additional therapeutic agent is a HCV protease inhibitor. For example, in some embodiments, the additional therapeutic agent is selected from the group consisting of such as GS-9256, vedroprevir, voxilaprevir, and combinations thereof.

In some embodiments, the additional therapeutic agent is a NS5A inhibitor. For example, in some embodiments, the additional therapeutic agent is selected from the group consisting of ledipasvir, velpatasvir, and combinations thereof.

In some embodiments, the additional therapeutic agent is an anti HBV agent. For example, in some embodiments, the additional therapeutic agent is tenofovir disoproxil fumarate and emtricitabine, or a combination thereof. Examples of additional anti HBV agents include but are not limited to alpha-hydroxytropolones, amdoxovir, antroquinonol, beta-hydroxycytosine nucleosides, ARB-199, CCC-0975, ccc-R08, elvucitabine, ezetimibe, cyclosporin A, gentiopicrin (gentiopicroside), HH-003, hepalatide, JNJ-56136379, nitazoxanide, birinapant, NJK14047, NOV-205 (molixan, BAM-205), oligotide, mivotilate, feron, GST-HG-131, levamisole, Ka Shu Ning, alloferon, WS-007, Y-101 (Ti Fen Tai), rSIFN-co, PEG-IIFNm, KW-3, BP-Inter-014, oleanolic acid, HepB-nRNA, cTP-5 (rTP-5), HSK-II-2, HEISCO-106-1, HEISCO-106, Hepbarna, IBPB-0061A, Hepuyinfen, DasKloster 0014-01, ISA-204, Jiangantai (Ganxikang), MIV-210, OB-AI-004, PF-06, picroside, DasKloster-0039, hepulantai, IMB-2613, TCM-800B, reduced glutathione, RO-6864018, RG-7834, QL-007sofosbuvir, ledipasvir, UB-551, and ZH-2N, and the compounds disclosed in US20150210682, (Roche), US 2016/0122344 (Roche), WO2015173164, WO2016023877, US2015252057A (Roche), WO16128335A1 (Roche), WO16120186A1 (Roche), US2016237090A (Roche), WO16107833A1 (Roche), WO16107832A1 (Roche), US2016176899A (Roche), WO16102438A1 (Roche), WO16012470A1 (Roche), US2016220586A (Roche), and US2015031687A (Roche). In some embodiments, the additional therapeutic agent is a HBV polymerase inhibitor. Examples of HBV DNA polymerase inhibitors include, but are not limited to, adefovir (HEPSERA®), emtricitabine (EMTRIVA®), tenofovir disoproxil fumarate (VIREAD®), tenofovir alafenamide, tenofovir, tenofovir disoproxil, tenofovir alafenamide fumarate, tenofovir alafenamide hemifumarate, tenofovir dipivoxil, tenofovir dipivoxil fumarate, tenofovir octadecyloxyethyl ester, CMX-157, tenofovir exalidex, besifovir, entecavir (BARACLUDE®), entecavir maleate, telbivudine (TYZEKA®), filocilovir, pradefovir, clevudine, ribavirin, lamivudine (EPIVIR-HBV®), phosphazide, famciclovir, fusolin, metacavir, SNC-019754, FMCA, AGX-1009, AR-II-04-26, HIP-1302, tenofovir disoproxil aspartate, tenofovir disoproxil orotate, and HS-10234. In some embodiments, the additional therapeutic agent is a HBV capsid inhibitor.

In some embodiments, the additional therapeutic agent is an agent for treatment of HIV. In some embodiments, the additional therapeutic agent is selected from the group consisting of HIV protease inhibitors, HIV integrase inhibitors, entry inhibitors, HIV nucleoside reverse transcriptase inhibitors, HIV nonnucleoside reverse transcriptase inhibitors, acyclic nucleoside phosphonate analogues, and combinations thereof.

In some embodiments, the additional therapeutic agent is selected from the group consisting of HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, immunomodulators, immunotherapeutic agents, antibody-drug conjugates, gene modifiers, gene editors (such as CRISPR/Cas9, zinc finger nucleases, homing nucleases, synthetic nucleases, TALENs), and cell therapies (such as chimeric antigen receptor T-cell, CAR-T, and engineered T cell receptors, TCR-T, autologous T cell therapies).

In some embodiments, the additional therapeutic agent is selected from the group consisting of combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, and bispecific antibodies, and "antibody-like" therapeutic proteins, and combinations thereof.

In some embodiments, the additional therapeutic agent is a HIV combination drug.

Examples of the HIV combination drugs include, but are not limited to ATRIPLA® (efavirenz, tenofovir disoproxil fumarate, and emtricitabine); BIKTARVY® (bictegravir, emtricitabine, and tenofovir alafenamide); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); SYMTUZA® (darunavir, tenofovir alafenamide hemifumarate, emtricitabine, and cobicistat); SYMFI™ (efavirenz, lamivudine, and tenofovir disoproxil fumarate); CIMDU™ (lamivudine and tenofovir disoproxil fumarate); tenofovir and lamivudine; tenofovir alafenamide and emtricitabine-; tenofovir alafenamide hemifumarate and emtricitabine; tenofovir alafenamide hemifumarate, emtricitabine, and rilpivirine; tenofovir alafenamide hemifumarate, emtricitabine, cobicistat, and elvitegravir; COMBIVIR® (zidovudine and lamivudine; AZT+3TC); EPZICOM® (LIVEXA®; abacavir sulfate and lamivudine; ABC+3TC); KALETRA® (ALUVIA®; lopinavir and ritonavir); TRIUMEQ® (dolutegravir, abacavir, and lamivudine); TRIZIVIR® (abacavir sulfate, zidovudine, and lamivudine; ABC+AZT+3TC); atazanavir and cobicistat; atazanavir sulfate and cobicistat; atazanavir sulfate and ritonavir; darunavir and cobicistat; dolutegravir and rilpivirine; dolutegravir and rilpivirine hydrochloride; dolutegravir, abacavir sulfate, and lamivudine; lamivudine, nevirapine, and zidovudine; raltegravir and lamivudine; doravirine, lamivudine, and tenofovir disoproxil fumarate; doravirine, lamivudine, and tenofovir disoproxil; dapivirine+levonorgestrel, dolutegravir+lamivudine, dolutegravir+emtricitabine+tenofovir alafenamide, elsulfavirine+emtricitabine+tenofovir disoproxil, lamivudine+abacavir+zidovudine, lamivudine+abacavir, lamivudine+tenofovir disoproxil fumarate, lamivudine+zidovudine+nevirapine, lopinavir+ritonavir, lopinavir+ritonavir+abacavir+lamivudine, lopinavir+ritonavir+zidovudine+lamivudine, tenofovir+lamivudine, and tenofovir disoproxil fumarate+emtricitabine+rilpivirine hydrochloride, lopinavir, ritonavir, zidovudine and lamivudine.

In some embodiments, the additional therapeutic agent is a HIV protease inhibitor. For example, in some embodiments the additional therapeutic agent is selected from the group consisting of saquinavir, ritonavir, indinavir, nelfinavir, amprenavir, lopinavir, atazanavir, fosamprenavir, darunavir, tipranavir, cobicistat, ASC-09, AEBL-2, MK-8718, GS-9500, GS-1156, and combinations thereof. For example, in some embodiments the additional therapeutic agent is selected from the group consisting of saquinavir, ritonavir, indinavir, nelfinavir, amprenavir, lopinavir, atazanavir, fosamprenavir, darunavir, tipranavir, cobicistat. In some embodiments, the additional therapeutic agent is selected from the group consisting of amprenavir, atazanavir, brecanavir, darunavir, fosamprenavir, fosamprenavir calcium, indinavir, indinavir sulfate, lopinavir, nelfinavir, nelfinavir mesylate, ritonavir, saquinavir, saquinavir mesylate, tipranavir, DG-17, TMB-657 (PPL-100), T-169, BL-008, MK-8122, TMB-607, TMC-310911, and combinations thereof.

In some embodiments, the additional therapeutic agent is a HIV integrase inhibitor. For example, in some embodiment, the additional therapeutic agent is selected from the group consisting of raltegravir, elvitegravir, dolutegravir, abacavir, lamivudine, bictegravir and combinations thereof. In some embodiment, the additional therapeutic agent is bictegravir. In some embodiments, the additional therapeutic agent is selected from a group consisting of bictegravir, elvitegravir, curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, raltegravir, dolutegravir, JTK-351, bictegravir, AVX-15567, BMS-986197, cabotegravir (long-acting injectable), diketo quinolin-4-1 derivatives, integrase-LEDGF inhibitor, ledgins, M-522, M-532, NSC-310217, NSC-371056, NSC-48240, NSC-642710, NSC-699171, NSC-699172, NSC-699173, NSC-699174, stilbenedisulfonic acid, T-169, VM-3500, cabotegravir, and combinations thereof.

In some embodiments, the additional therapeutic agent is a HIV entry inhibitor. For example, in some embodiments, the additional therapeutic agent is selected from the group consisting of enfuvirtide, maraviroc, and combinations thereof. Further examples of HIV entry inhibitors include, but are not limited to, cenicriviroc, CCR5 inhibitors, gp41 inhibitors, CD4 attachment inhibitors, DS-003 (BMS-599793), gp120 inhibitors, and CXCR4 inhibitors. Examples of CCR5 inhibitors include aplaviroc, vicriviroc, maraviroc, cenicriviroc, leronlimab (PRO-140), adaptavir (RAP-101), nifeviroc (TD-0232), anti-GP120/CD4 or CCR5 bispecific antibodies, B-07, MB-66, polypeptide C25P, TD-0680, and vMIP (Haimipu). Examples of CXCR4 inhibitors include plerixafor, ALT-1188, N15 peptide, and vMIP (Haimipu).

In some embodiments, the additional therapeutic agent is a HIV nucleoside reverse transcriptase inhibitors. In some embodiments, the additional therapeutic agent is a HIV nonnucleoside reverse transcriptase inhibitors. In some embodiments, the additional therapeutic agent is an acyclic nucleoside phosphonate analogue. In some embodiments, the additional therapeutic agent is a HIV capsid inhibitor.

In some embodiments, the additional therapeutic agent is a HIV nucleoside or nucleotide inhibitor of reverse transcriptase. For example, the additional therapeutic agent is selected from the group consisting of adefovir, adefovir dipivoxil, azvudine, emtricitabine, tenofovir, tenofovir alafenamide, tenofovir alafenamide fumarate, tenofovir alafenamide hemifumarate, tenofovir disoproxil, tenofovir disoproxil fumarate, tenofovir disoproxil hemifumarate, VIDEX® and VIDEX EC® (didanosine, ddI), abacavir, abacavir sulfate, alovudine, apricitabine, censavudine, didanosine, elvucitabine, festinavir, fosalvudine tidoxil, CMX-157, dapivirine, doravirine, etravirine, OCR-5753, tenofovir disoproxil orotate, fozivudine tidoxil, islatravir, lamivudine, phosphazid, stavudine, zalcitabine, zidovudine, rovafovir etalafenamide (GS-9131), GS-9148, MK-8504, MK-8591, MK-858, VM-2500, KP-1461, and combinations thereof.

In some embodiments, the additional therapeutic agent is a HIV non-nucleoside or non-nucleotide inhibitor of reverse transcriptase. For example, the additional agent is selected from the group consisting of dapivirine, delavirdine, delavirdine mesylate, doravirine, efavirenz, etravirine, lentinan, MK-8583, nevirapine, rilpivirine, TMC-278LA, ACC-007, AIC-292, KM-023, PC-1005, elsulfavirine rilp (VM-1500), combinations thereof.

In some embodiments, the additional therapeutic agents are selected from ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); adefovir; adefovir dipivoxil; cobicistat; emtricitabine; tenofovir; tenofovir disoproxil; tenofovir disoproxil fumarate; tenofovir alafenamide; tenofovir alafenamide hemifumarate; TRIUMEQ® (dolutegravir, abacavir, and lamivudine); dolutegravir, abacavir sulfate, and lamivudine; raltegravir; raltegravir and lamivudine; maraviroc; enfuvirtide; ALUVIA® (KALETRA®; lopinavir and ritonavir); COMBIVIR® (zidovudine and lamivudine; AZT+3TC); EPZICOM® (LIVEXA®; abacavir sulfate and lamivudine; ABC+3TC); TRIZIVIR® (abacavir sulfate, zidovudine, and lamivudine; ABC+AZT+3TC); rilpivirine; rilpivirine hydrochloride; atazanavir sulfate and cobicistat; atazanavir and cobicistat; darunavir and cobicistat; atazanavir; atazanavir sulfate; dolutegravir; elvitegravir; ritonavir; atazanavir sulfate and ritonavir; darunavir; lamivudine; prolastin; fosamprenavir; fosamprenavir calcium efavirenz; etravirine; nelfinavir; nelfinavir mesylate; interferon; didanosine; stavudine; indinavir; indinavir sulfate; tenofovir and lamivudine; zidovudine; nevirapine; saquinavir; saquinavir mesylate; aldesleukin; zalcitabine; tipranavir; amprenavir; delavirdine; delavirdine mesylate; Radha-108 (receptol); lamivudine and tenofovir disoproxil fumarate; efavirenz, lamivudine, and tenofovir disoproxil fumarate; phosphazid; lamivudine, nevirapine, and zidovudine; abacavir; and abacavir sulfate.

In some embodiments, the additional therapeutic agent is selected from the group consisting of colistin, valrubicin, icatibant, bepotastine, epirubicin, epoprosetnol, vapreotide, aprepitant, caspofungin, perphenazine, atazanavir, efavirenz, ritonavir, acyclovir, ganciclovir, penciclovir, prulifloxacin, bictegravir, nelfinavir, tegobuvi, nelfinavir, praziquantel, pitavastatin, perampanel, eszopiclone, and zopiclone.

In some embodiments, the additional therapeutic agent is an inhibitor of Bruton tyrosine kinase (BTK, AGMX1, AT, ATK, BPK, IGHD3, IMD1, PSCTK1, XLA; NCBI Gene ID: 695). For example, in some embodiments, the additional therapeutic agent is selected from the group consisting of (S)-6-amino-9-(1-(but-2-ynoyl)pyrrolidin-3-yl)-7-(4-phenoxyphenyl)-7H-purin-8(9H)-one, acalabrutinib (ACP-196), BGB-3111, CB988, HM71224, ibrutinib (Imbruvica), M-2951 (evobrutinib), M7583, tirabrutinib (ONO-4059), PRN-1008, spebrutinib (CC-292), TAK-020, vecabrutinib, ARQ-531, SHR-1459, DTRMWXHS-12, TAS-5315, AZD6738, calquence, danvatirsen, and combinations thereof. In some embodiments, the additional therapeutic agent is selected from a group consisting of tirabrutinib, ibrutinib, acalabrutinib, and combinations thereof. In some embodiments, the additional therapeutic agent is selected from a group consisting of tirabrutinib, ibrutinib, and combinations thereof. In some embodiments, the additional therapeutic agent is tyrphostin A9 (A9).

In some embodiments, the additional therapeutic agent is a KRAS inhibitor. For example, in some embodiments, the additional therapeutic agent is selected from the group consisting of AMG-510, COTI-219, MRTX-1257, ARS-3248, ARS-853, WDB-178, BI-3406, BI-1701963, ARS-1620 (G12C), SML-8-73-1 (G12C), Compound 3144 (G12D), Kobe0065/2602 (Ras GTP), RT11, MRTX-849 (G12C) and K-Ras(G12D)-selective inhibitory peptides, including KRpep-2 (Ac-RRCPLYISYDPVCRR-NH2), KRpep-2d (Ac-RRRRCPLYISYDPVCRRRR-NH2), and combinations thereof.

In some embodiments, the additional therapeutic agent is a proteasome inhibitor. For example, in some embodiments, the additional therapeutic agent is selected from a group consisting of ixazomib, carfilzomib, marizomib, bortezomib, and combinations thereof. in some embodiments, the additional therapeutic agent is carfilzomib.

In some embodiments, the additional therapeutic agent is a vaccine. For example, in some embodiments, the additional therapeutic agent is a DNA vaccine, RNA vaccine, live-attenuated vaccine, therapeutic vaccine, prophylactic vaccine, protein based vaccine, or a combination thereof. In some embodiments, the additional therapeutic agent is mRNA-1273. In some embodiments, the additional therapeutic agent is INO-4800 or INO-4700. In some embodiments, the additional therapeutic agent is live-attenuated RSV vaccine MEDI-559, human monoclonal antibody REGN2222 against RSV, palivizumab, respiratory syncytial virus immune globulin, intravenous [RSV-IGIV], and combinations thereof. In some embodiments, the additional therapeutic agent is a HBV vaccine, for example pediarix, engerix-B, and recombivax HB. In some embodiments, the additional therapeutic agent is a VZV vaccine, for example zostavax and varivax. In some embodiments, the additional therapeutic agent is a HPV vaccine, for example cervarix, gardasil 9, and gardasil. In some embodiments, the additional therapeutic agent is an influenza virus vaccine. For example, a (i) monovalent vaccine for influenza A (e.g. influenza A [H5N1] virus monovalent vaccine and influenza A [H1N1] 2009 virus monovalent vaccines), (ii) trivalent vaccine for influenza A and B viruses (e.g. Afluria, Agriflu, Fluad, Fluarix, Flublok, Flucelvax, FluLaval, Fluvirin, and Fluzone), and (iii) quadrivalent vaccine for influenza A and B viruses (FluMist, Fluarix, Fluzone, and FluLaval). In some embodiments, the additional therapeutic agent is a human adenovirus vaccine (e.g. Adenovirus Type 4 and Type 7 Vaccine, Live, Oral). In some embodiments, the additional therapeutic agent is a rotavirus vaccine (e.g. Rotarix for rotavirus serotype G1, G3, G4, or G9 and RotaTeq for rotavirus serotype G1, G2, G3, or G4). In some embodiments, the additional therapeutic agent is a hepatitis A virus vaccine (e.g. Havrix and Vagta). In some embodiments, the additional therapeutic agent is poliovirus vaccines (e.g. Kinrix, Quadracel, and Ipol). In some embodiments, the additional therapeutic agent is a yellow fever virus vaccine (e.g. YF-Vax). In some embodiments, the additional therapeutic agent is a Japanese encephalitis virus vaccines (e.g. Ixiaro and JE-Vax). In some embodiments, the additional therapeutic agent is a measles vaccine (e.g. M-M-R II and ProQuad). In some embodiments, the additional therapeutic agent is a mumps vaccine (e.g. M-M-R II and ProQuad). In some embodiments, the additional therapeutic agent is a rubella vaccine (e.g. M-M-R II and ProQuad). In some embodiments, the additional therapeutic agent is a varicella vaccine (e.g. ProQuad). In some embodiments, the additional therapeutic agent is a rabies vaccine (e.g. Imovax and RabAvert). In some embodiments, the additional therapeutic agent is a variola virus (smallpox) vaccine (ACAM2000). In some embodiments, the additional therapeutic agent is a and hepatitis E virus (HEV) vaccine (e.g. HEV239). In some embodiments, the additional therapeutic agent is a 2019-nCov vaccine.

In some embodiments, the additional therapeutic agent is an antibody, for example a monoclonal antibody. For example, the additional therapeutic agent is an antibody against 2019-nCov selected from the group consisting of the Regeneron antibodies, the Wuxi Antibodies, the Vir Biotechnology Antibodies, antibodies that target the SARS-CoV-2 spike protein, antibodies that can neutralize SARS-CoV-2 (SARS-CoV-2 neutralizing antibodies), and combinations thereof. In some embodiments, the additional therapeutic agent is anti-SARS CoV antibody CR-3022. In some embodiments, the additional therapeutic agent is aPD-1 antibody.

In some embodiments, the additional therapeutic agent is recombinant cytokine gene-derived protein injection.

In some embodiments, the additional therapeutic agent is a polymerase inhibitor. In some embodiments, the additional therapeutic agent is a DNA polymerase inhibitor. For example, in some embodiments, the additional therapeutic agent is cidofovir. In some embodiments, the additional therapeutic agent is a RNA polymerase inhibitor. For example, in some embodiments, the additional therapeutic agent is selected from the group consisting of ribavirin, favipiravir, lamivudine, pimodivir and combination thereof.

In some embodiments, the additional therapeutic agent is selected from the group consisting of lopinavir, ritonavir, interferon-alpha-2b, ritonavir, arbidol, hydroxychloroquine, darunavir and cobicistat, abidol hydrochloride, oseltamivir, litonavir, emtricitabine, tenofovir alafenamide fumarate, baloxavir marboxil, ruxolitinib, and combinations thereof.

In some embodiments, the additional therapeutic agent is selected from the group consisting of 6'-fluorinated aristeromycin analogues, acyclovir fleximer analogues, disulfiram, thiopurine analogues, ASC09F, GC376, GC813, phenylisoserine derivatives, neuroiminidase inhibitor analogues, pyrithiobac derivatives, bananins and 5-hydroxychromone derivatives, SSYA10-001, griffithsin, HR2P-M1, HR2P-M2, P21S10, Dihydrotanshinone E-64-C and E-64-D, OC43-HR2P, MERS-5HB, 229E-HR1P, 229E-HR2P, resveratrol, 1-thia-4-azaspiro[4.5]decan-3-one derivatives, gemcitabine hydrochloride, loperamide, recombinant interferons, cyclosporine A, alisporivir, imatinib mesylate, dasatinib, selumetinib, trametinib, rapamycin, saracatinib, chlorpromazine, triflupromazine, fluphenazine, thiethylperazine, promethazine, cyclophilin inhibitors, K11777, camostat, k22, teicoplanin derivatives, benzo-heterocyclic amine derivatives N30, mycophenolic acid, silvestrol, and combinations thereof.

In some embodiments, the additional therapeutic agent is an antibody. In some embodiments, the additional therapeutic agent is an antibody that binds to a coronavirus, for example an antibody that binds to SARS or MERS. In some embodiments, the additional therapeutic agent is a of 2019-nCoV virus antibody.

Compositions of the invention are also used in combination with other active ingredients. For the treatment of 2019-nCoV virus infections, preferably, the other active therapeutic agent is active against coronavirus infections, for example 2019-nCoV virus infections. The compounds and compositions of the present invention are also intended for use with general care provided patients with 2019-nCoV viral infections, including parenteral fluids (including dextrose saline and Ringer's lactate) and nutrition, antibiotic (including metronidazole and cephalosporin antibiotics, such as ceftriaxone and cefuroxime) and/or antifungal prophylaxis, fever and pain medication, antiemetic (such as metoclopramide) and/or antidiarrheal agents, vitamin and mineral supplements (including Vitamin K and zinc sulfate), anti-inflammatory agents (such as ibuprofen or steroids), corticosteroids such as methylprednisolone, immonumodulatory medications (e.g. interferon), other small molecule or biologics antiviral agents targeting 2019-nCoV (such as but not limited to lopinavir/ritonavir, EIDD-1931, favipiravir, ribavirine, neutralizing antibodies, etc.), vaccines, pain medications, and medications for other common diseases in the patient population, such anti-malarial agents (including artemether and artesunate-lumefantrine combination therapy), typhoid (including quinolone antibiotics, such as ciprofloxacin, macrolide antibiotics, such as azithromycin, cephalosporin antibiotics, such as ceftriaxone, or aminopenicillins, such as ampicillin), or shigellosis. In some embodiments, the additional therapeutic agent is dihydroartemisinin/piperaquine.

In some embodiments, the additional therapeutic agent is an immunomodulator. Examples of immune-based therapies include toll-like receptors modulators such as tlr1, tlr2, tlr3, tlr4, tlr5, tlr6, tlr7, tlr8, tlr9, tlr10, tlr11, tlr12, and tlr13; programmed cell death protein 1 (Pd-1) modulators; programmed death-ligand 1 (Pd-L1) modulators; IL-15 modulators; DermaVir; interleukin-7; plaquenil (hydroxychloroquine); proleukin (aldesleukin, IL-2); interferon alfa; interferon alfa-2b; interferon alfa-n3; pegylated interferon alfa; interferon gamma; hydroxyurea; mycophenolate mofetil (MPA) and its ester derivative mycophenolate mofetil (MMF); ribavirin; polymer polyethyleneimine (PEI); gepon; IL-12; WF-10; VGV-1; MOR-22; BMS-936559; CYT-107, interleukin-15/Fc fusion protein, AM-0015, ALT-803, NIZ-985, NKTR-255, NKTR-262, NKTR-214, normferon, peginterferon alfa-2a, peginterferon alfa-2b, recombinant interleukin-15, Xmab-24306, RPI-MN, STING modulators, RIG-I modulators, NOD2 modulators, SB-9200, and IR-103. In some embodiments, the additional therapeutic agent is fingolimod, leflunomide, or a combination thereof. In some embodiments, the additional therapeutic agent is thalidomide.

In some embodiments, the additional therapeutic agent is an IL-6 inhibitor, for example tocilizumab, sarilumab, or a combination thereof.

In some embodiments, the additional therapeutic agent is an anti-TNF inhibitor. For example, the additional therapeutic agent is adalimumab, etanercept, golimurmab, infliximab, or a combination thereof.

In some embodiments, the additional therapeutic agent is a JAK inhibitor, for example the additional therapeutic agent is baricitinib, filgotinib, olumiant, or a combination thereof.

In some embodiments, the additional therapeutic agent is an inflammation inhibitor, for example pirfenidone.

In some embodiments, the additional therapeutic agent is an antibiotic for secondary bacterial pneumonia. For example, the additional therapeutic agent is macrolide antibiotics (e.g. azithromycin, clarithromycin, and *Mycoplasma pneumoniae*), fluoroquinolones (e.g. ciprofloxacin and levofloxacin), tetracyclines (e.g. doxycycline and tetracycline), or a combination thereof.

In some embodiments, the compounds disclosed herein are used in combination with pneumonia standard of care (see e.g. Pediatric Community Pneumonia Guidelines, CID 2011:53 (1 October)). Treatment for pneumonia generally involves curing the infection and preventing complications. Specific treatment will depend on several factors, including the type and severity of pneumonia, age and overall health of the individuals. The options include: (i) antibiotics, (ii) cough medicine, and (iii) fever reducers/pain relievers (for e.g. aspirin, ibuprofen (Advil, Motrin IB, others) and acetaminophen (Tylenol, others)). In some embodiments, the additional therapeutic agent is bromhexine anti-cough.

In some embodiments, the compounds disclosed herein are used in combination with immunoglobulin from cured COVID-19 patients. In some embodiments, the compounds disclosed herein are used in combination with plasma transfusion. In some embodiments, the compounds disclosed herein are used in combination with stem cells.

In some embodiments, the additional therapeutic agent is an TLR agonist. Examples of TLR agonists include, but are not limited to, vesatolimod (GS-9620), GS-986, IR-103, lefitolimod, tilsotolimod, rintatolimod, DSP-0509, AL-034, G-100, cobitolimod, AST-008, motolimod, GSK-1795091, GSK-2245035, VTX-1463, GS-9688, LHC-165, BDB-001, RG-7854, telratolimod.RO-7020531.

In some embodiments, the additional therapeutic agent is selected from the group consisting of bortezomid, flurazepam, ponatinib, sorafenib, paramethasone, clocortolone, flucloxacillin, sertindole, clevidipine, atorvastatin, cinolazepam, clofazimine, fosaprepitant, and combinations thereof.

In some embodiments, the additional therapeutic agent is carrimycin, suramin, triazavirin, dipyridamole, bevacizumab, meplazumab, GD31 (rhizobium), NLRP inflammasome inhibitor, or α-ketoamine. In some embodiments, the additional therapeutic agent is recombinant human angiotensin-converting enzyme 2 (rhACE2). In some embodiments, the additional therapeutic agent is viral macrophage inflammatory protein (vMIP).

In some embodiments, the additional therapeutic agent is an anti-viroporin therapeutic. For example, the additional therapeutic agent is BIT-314 or BIT-225. In some embodiments, the additional therapeutic agent is coronavirus E protein inhibitor. For example, the additional therapeutic agent is BIT-009. Further examples of additional therapeutic agents include those described in WO-2004112687, WO-2006135978, WO-2018145148, and WO-2009018609.

It is also possible to combine any compound of the invention with one or more additional active therapeutic agents in a unitary dosage form for simultaneous or sequential administration to a patient. The combination therapy may be administered as a simultaneous or sequential regimen. When administered sequentially, the combination may be administered in two or more administrations.

Co-administration of a compound of the invention with one or more other active therapeutic agents generally refers to simultaneous or sequential administration of a compound of the invention and one or more other active therapeutic agents, such that therapeutically effective amounts of the compound of the invention and one or more other active therapeutic agents are both present in the body of the patient.

Co-administration includes administration of unit dosages of the compounds of the invention before or after administration of unit dosages of one or more other active therapeutic agents, for example, administration of the compounds of the invention within seconds, minutes, or hours of the administration of one or more other active therapeutic agents. For example, a unit dose of a compound of the invention can be administered first, followed within seconds or minutes by administration of a unit dose of one or more other active therapeutic agents.

Alternatively, a unit dose of one or more other therapeutic agents can be administered first, followed by administration of a unit dose of a compound of the invention within seconds or minutes. In some cases, it may be desirable to administer a unit dose of a compound of the invention first, followed, after a period of hours (e.g., 1-12 hours), by administration of a unit dose of one or more other active therapeutic agents. In other cases, it may be desirable to administer a unit dose of one or more other active therapeutic agents first, followed, after a period of hours (e.g., 1-12 hours), by administration of a unit dose of a compound of the invention.

The combination therapy may provide "synergy" and "synergistic", i.e. the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g. in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together. A synergistic anti-viral effect denotes an antiviral effect which is greater than the predicted purely additive effects of the individual compounds of the combination.

1. Combination Therapy for the Treatment of Pneumoviridae

The compounds provided herein are also used in combination with other active therapeutic agents. For the treatment of Pneumoviridae virus infections, preferably, the other active therapeutic agent is active against Pneumoviridae virus infections, particularly respiratory syncytial virus infections and/or metapneumovirus infections. Non-limiting examples of these other active therapeutic agents active against RSV are ribavirin, palivizumab, motavizumab, RSV-IGIV (RespiGam®), MEDI-557, A-60444 (also known as RSV604), MDT-637, BMS-433771, ALN-RSV0, ALX-0171 and mixtures thereof. Other non-limiting examples of other active therapeutic agents active against respiratory syncytial virus infections include respiratory syncytial virus protein F inhibitors, such as AK-0529; RV-521, ALX-0171, JNJ-53718678, BTA-585, and presatovir; RNA polymerase inhibitors, such as lumicitabine and ALS-8112; anti-RSV G protein antibodies, such as anti-G-protein mAb; viral replication inhibitors, such as nitazoxanide.

In some embodiments, the other active therapeutic agent may be a vaccine for the treatment or prevention of RSV, including but not limited to MVA-BN RSV, RSV-F, MEDI-8897, JNJ-64400141, DPX-RSV, SynGEM, GSK-3389245A, GSK-300389-1A, RSV-MEDI deltaM2-2 vaccine, VRC-RSVRGP084-00VP, Ad35-RSV-FA2, Ad26-RSV-FA2, and RSV fusion glycoprotein subunit vaccine.

Non-limiting examples of other active therapeutic agents active against metapneumovirus infections include sialidase modulators such as DAS-181; RNA polymerase inhibitors, such as ALS-8112; and antibodies for the treatment of Metapneumovirus infections, such as EV-046113.

In some embodiments, the other active therapeutic agent may be a vaccine for the treatment or prevention of metapneumovirus infections, including but not limited to mRNA-1653 and rHMPV-Pa vaccine.

2. Combination Therapy for the Treatment of Picornaviridae

The compounds provided herein are also used in combination with other active therapeutic agents. For the treatment of Picornaviridae virus infections, preferably, the other active therapeutic agent is active against Picornaviridae virus infections, particularly Enterovirus infections. Non-limiting examples of these other active therapeutic agents are capsid binding inhibitors such as pleconaril, BTA-798 (vapendavir) and other compounds disclosed by Wu, et al. (U.S. Pat. No. 7,078,403) and Watson (U.S. Pat. No. 7,166,604); fusion sialidase protein such as DAS-181; a capsid protein VP1 inhibitor such as VVX-003 and AZN-001; a viral protease inhibitor such as CW-33; a phosphatidylinositol 4 kinase beta inhibitor such as GSK-480 and GSK-533; anti-EV71 antibody.

In some embodiments, the other active therapeutic agent may be a vaccine for the treatment or prevention of Picornaviridae virus infections, including but not limited to EV71 vaccines, TAK-021, and EV-D68 adenovector-based vaccine.

3. Combination Therapy for Respiratory Infections

Many of the infections of the Pneumoviridae and Picornaviridae viruses are respiratory infections. Therefore, additional active therapeutics used to treat respiratory symptoms and sequelae of infection may be used in combination with the compounds provided herein. The additional agents are preferably administered orally or by direct inhalation. For example, other preferred additional therapeutic agents in combination with the compounds provided herein for the treatment of viral respiratory infections include, but are not limited to, bronchodilators and corticosteroids.

Glucocorticoids

Glucocorticoids, which were first introduced as an asthma therapy in 1950 (Carryer, Journal of Allergy, 21, 282-287, 1950), remain the most potent and consistently effective therapy for this disease, although their mechanism of action is not yet fully understood (Morris, J. Allergy Clin. Immunol., 75 (1 Pt) 1-13, 1985). Unfortunately, oral glucocorticoid therapies are associated with profound undesirable side effects such as truncal obesity, hypertension, glaucoma, glucose intolerance, acceleration of cataract formation, bone mineral loss, and psychological effects, all of which limit their use as long-term therapeutic agents (Goodman and Gilman, 10th edition, 2001). A solution to systemic side effects is to deliver steroid drugs directly to the site of inflammation. Inhaled corticosteroids (ICS) have been developed to mitigate the severe adverse effects of oral steroids. Non-limiting examples of corticosteroids that may be used in combinations with the compounds provided herein are dexamethasone, dexamethasone sodium phosphate, fluorometholone, fluorometholone acetate, loteprednol, loteprednol etabonate, hydrocortisone, prednisolone, fludrocortisones, triamcinolone, triamcinolone acetonide, betamethasone, beclomethasone diproprionate, methylprednisolone, fluocinolone, fluocinolone acetonide, flunisolide, fluocortin-21-butylate, flumethasone, flumetasone pivalate, budesonide, halobetasol propionate, mometasone furoate, fluticasone, AZD-7594, ciclesonide; or a pharmaceutically acceptable salts thereof.

Anti-Inflammatory Agents

Other anti-inflammatory agents working through anti-inflammatory cascade mechanisms are also useful as additional therapeutic agents in combination with the compounds provided herein for the treatment of viral respiratory infections. Applying "anti-inflammatory signal transduction modulators" (referred to in this text as AISTM), like phosphodiesterase inhibitors (e.g. PDE-4, PDE-5, or PDE-7 specific), transcription factor inhibitors (e.g. blocking NFκB through IKK inhibition), or kinase inhibitors (e.g. blocking P38 MAP, JNK, PI3K, EGFR or Syk) is a logical approach to switching off inflammation as these small molecules target a limited number of common intracellular pathways—those signal transduction pathways that are critical points for the anti-inflammatory therapeutic intervention (see review by P. J. Barnes, 2006). These non-limiting additional therapeutic agents include: 5-(2,4-Difluoro-phenoxy)-1-isobutyl-1H-indazole-6-carboxylic acid (2-dimethylamino-ethyl)-amide (P38 Map kinase inhibitor ARRY-797); 3-Cyclopropylmethoxy-N-(3,5-dichloro-pyridin-4-yl)-4-difluorormethoxy-benzamide (PDE-4 inhibitor Roflumilast); 4-[2-(3-cyclopentyloxy-4-methoxyphenyl)-2-phenyl-ethyl]-pyridine (PDE-4 inhibitor CDP-840); N-(3,5-dichloro-4-pyridinyl)-4-(difluoromethoxy)-8-[(methylsulfonyl)amino]-1-dibenzofurancarboxamide (PDE-4 inhibitor Oglemilast); N-(3,5-Dichloro-pyridin-4-yl)-2-[1-(4-fluorobenzyl)-5-hydroxy-1H-indol-3-yl]-2-oxo-acetamide (PDE-4 inhibitor AWD 12-281); 8-Methoxy-2-trifluoromethyl-quinoline-5-carboxylic acid (3,5-dichloro-1-oxy-pyridin-4-yl)-amide (PDE-4 inhibitor Sch 351591); 4-[5-(4-Fluorophenyl)-2-(4-methanesulfinyl-phenyl)-1H-imidazol-4-yl]-pyridine (P38 inhibitor SB-203850); 4-[4-(4-Fluoro-phenyl)-1-(3-phenyl-propyl)-5-pyridin-4-yl-1H-imidazol-2-yl]-but-3-yn-1-ol (P38 inhibitor RWJ-67657); 4-Cyano-4-(3-cyclopentyloxy-4-methoxy-phenyl)-cyclohexanecarboxylic acid 2-diethylamino-ethyl ester (2-diethyl-ethyl ester prodrug of Cilomilast, PDE-4 inhibitor); (3-Chloro-4-fluorophenyl)-[7-methoxy-6-(3-morpholin-4-yl-propoxy)-quinazolin-4-yl]-amine (Gefitinib, EGFR inhibitor); and 4-(4-Methyl-piperazin-1-ylmethyl)-N-[4-methyl-3-(4-pyridin-3-yl-pyrimidin-2-ylamino)-phenyl]-benzamide (Imatinib, EGFR inhibitor).

β2-Adrenoreceptor Agonist Bronchodilators

Combinations comprising inhaled 02-adrenoreceptor agonist bronchodilators such as formoterol, albuterol or salmeterol with the compounds provided herein are also suitable, but non-limiting, combinations useful for the treatment of respiratory viral infections.

Combinations of inhaled 02-adrenoreceptor agonist bronchodilators such as formoterol or salmeterol with ICS's are also used to treat both the bronchoconstriction and the inflammation (Symbicort® and Advair®, respectively). The combinations comprising these ICS and 02-adrenoreceptor agonist combinations along with the compounds provided herein are also suitable, but non-limiting, combinations useful for the treatment of respiratory viral infections.

Other examples of Beta 2 adrenoceptor agonists are bedoradrine, vilanterol, indacaterol, olodaterol, tulobuterol, formoterol, abediterol, salbutamol, arformoterol, levalbuterol, fenoterol, and TD-5471.

Anticholinergics

For the treatment or prophylaxis of pulmonary bronchoconstriction, anticholinergics are of potential use and, therefore, useful as an additional therapeutic agent in combination with the compounds provided herein for the treatment of viral respiratory infections. These anticholinergics include, but are not limited to, antagonists of the muscarinic receptor (particularly of the M3 subtype) which have shown therapeutic efficacy in man for the control of cholinergic tone in COPD (Witek, 1999); 1-{4-Hydroxy-1-[3,3,3-tris-(4-fluoro-phenyl)-propionyl]-pyrrolidine-2-carbonyl}-pyrrolidine-2-carboxylic acid (1-methyl-piperidin-4-ylmethyl)-amide; 3-[3-(2-Diethylamino-acetoxy)-2-phenyl-propionyloxy]-8-isopropyl-8-methyl-8-azonia-bicyclo [3.2.1]octane (Ipratropium-N,N-diethylglycinate); 1-Cyclohexyl-3,4-dihydro-1H-isoquinoline-2-carboxylic acid 1-aza-bicyclo[2.2.2]oct-3-yl ester (Solifenacin); 2-Hydroxymethyl-4-methanesulfinyl-2-phenyl-butyric acid 1-aza-bicyclo[2.2.2]oct-3-yl ester (Revatropate); 2-{1-[2-(2, 3-Dihydro-benzofuran-5-yl)-ethyl]-pyrrolidin-3-yl}-2,2-diphenyl-acetamide (Darifenacin); 4-Azepan-1-yl-2,2-diphenyl-butyramide (Buzepide); 7-[3-(2-Diethylamino-acetoxy)-2-phenyl-propionyloxy]-9-ethyl-9-methyl-3-oxa-9-azonia-tricyclo[3.3.1.02,4]nonane (Oxitropium-N,N-diethylglycinate); 7-[2-(2-Diethylamino-acetoxy)-2,2-dithiophen-2-yl-acetoxy]-9,9-dimethyl-3-oxa-9-azonia-tricyclo[3.3.1.02,4]nonane (Tiotropium-N,N-diethylglycinate); Dimethylamino-acetic acid 2-(3-diisopropylamino-1-phenyl-propyl)-4-methyl-phenyl ester (Tolterodine-N,N-dimethylglycinate); 3-[4,4-Bis-(4-fluoro-phenyl)-2-oxo-imidazolidin-1-yl]-1-methyl-1-(2-oxo-2-pyridin-2-yl-ethyl)-pyrrolidinium; 1-[1-(3-Fluoro-benzyl)-piperidin-4-yl]-4,4-bis-(4-fluoro-phenyl)-imidazolidin-2-one; 1-Cyclooctyl-3-(3-methoxy-1-aza-bicyclo[2.2.2]oct-3-yl)-1-phenyl-prop-2-yn-1-ol; 3-[2-(2-Diethylamino-acetoxy)-2,2-di-thiophen-2-yl-acetoxy]-1-(3-phenoxy-propyl)-1-azonia-bicyclo[2.2.2]octane (Aclidinium-N,N-diethylglycinate); or (2-Diethylamino-acetoxy)-di-thiophen-2-yl-acetic acid 1-methyl-1-(2-phenoxy-ethyl)-piperidin-4-yl ester; revefenacin, glycopyrronium bromide, umeclidinium bromide, tiotropium bromide, aclidinium bromide, bencycloquidium bromide.

Mucolytic Agents

The compounds provided herein may also be combined with mucolytic agents to treat both the infection and symptoms of respiratory infections. A non-limiting example of a mucolytic agent is ambroxol. Similarly, the compounds may be combined with expectorants to treat both the infection and symptoms of respiratory infections. A non-limiting example of an expectorant is guaifenesin.

Nebulized hypertonic saline is used to improve immediate and long-term clearance of small airways in patients with lung diseases (Kuzik, *J. Pediatrics* 2007, 266). Thus, the compounds provided herein may also be combined with nebulized hypertonic saline particularly when the virus infection is complicated with bronchiolitis. The combination of the compound provided herein with hypertonic saline may also comprise any of the additional agents discussed above. In one embodiment, nebulized about 3% hypertonic saline is used.

4. Combination Therapy for the Treatment of Flaviviridae Virus Infections

The compounds and compositions provided herein are also used in combination with other active therapeutic agents. For the treatment of Flaviviridae virus infections, preferably, the other active therapeutic agent is active against Flaviviridae virus infections.

For treatment of the dengue virus infection, non-limiting examples of the other active therapeutic agents are host cell factor modulators, such as GBV-006; fenretinide ABX-220, BRM-211; alpha-glucosidase 1 inhibitors, such as celgosivir; platelet activating factor receptor (PAFR) antagonists, such as modipafant; cadherin-5/Factor Ia modulators, such as FX-06; NS4B inhibitors, such as JNJ-8359; viral RNA splicing modulators, such as ABX-202; a NS5 polymerase inhibitor; a NS3 protease inhibitor; and a TLR modulator.

In some embodiments, the other active therapeutic agent may be a vaccine for the treatment or prevention of dengue, including but not limited to TetraVax-DV, Dengvaxia®, DPIV-001, TAK-003, live attenuated dengue vaccine, tetravalent dengue fever vaccine, tetravalent DNA vaccine, rDEN2delta30-7169; and DENV-1 PIV.

5. Combination Therapy for the Treatment of Filoviridae Virus Infections

The compounds provided herein are also used in combination with other active therapeutic agents. For the treatment of Filoviridae virus infections, preferably, the other active therapeutic agent is active against Filoviridae virus infections, particularly Marburg virus, Ebola virus and Cueva virus infections. Non-limiting examples of these other active therapeutic agents are: ribavirin, palivizumab, motavizumab, RSV-IGIV (RespiGam®), MEDI-557, A-60444, MDT-637, BMS-433771, amiodarone, dronedarone, verapamil, Ebola Convalescent Plasma (ECP), TKM-100201, BCX4430 ((2S,3S,4R,5R)-2-(4-amino-5H-pyrrolo[3,2-d] pyrimidin-7-yl)-5-(hydroxymethyl)pyrrolidine-3,4-diol), TKM-Ebola, T-705 monophosphate, T-705 diphosphate, T-705 triphosphate, FGI-106 (1-N,7-N-bis[3-(dimethylamino)propyl]-3,9-dimethylquinolino[8,7-h]quinolone-1,7-diamine), rNAPc2, OS-2966, brincidofovir, remdesivir; RNA polymerase inhibitors, such as galidesivir, favipiravir (also known as T-705 or Avigan), JK-05; host cell factor modulators, such as GMV-006; cadherin-5/factor Ia modulators, such as FX-06; and antibodies for the treatment of Ebola, such as REGN-3470-3471-3479 and ZMapp.

Other non-limiting active therapeutic agents active against Ebola include an alpha-glucosidase 1 inhibitor, a cathepsin B inhibitor, a CD29 antagonist, a dendritic ICAM-3 grabbing nonintegrin 1 inhibitor, an estrogen receptor antagonist, a factor VII antagonist HLA class II antigen modulator, a host cell factor modulator, a Interferon alpha ligand, a neutral alpha glucosidase AB inhibitor, a niemann-Pick C1 protein inhibitor, a nucleoprotein inhibitor, a polymerase cofactor VP35 inhibitor, a Serine protease inhibitor, a tissue factor inhibitor, a TLR-3 agonist, a viral envelope glycoprotein inhibitor, and an Ebola virus entry inhibitors (NPC1 inhibitors).

In some embodiments, the other active therapeutic agent may be a vaccine for the treatment or prevention of Ebola, including but not limited to VRC-EBOADC076-00-VP, adenovirus-based Ebola vaccine, rVSV-EBOV, rVSVN4CT1-EBOVGP, MVA-BN Filo+Ad26-ZEBOV regimen, INO-4212, VRC-EBODNA023-00-VP, VRC-EBOADC069-00-VP, GamEvac-combi vaccine, SRC VB Vector, HPIV3/EboGP vaccine, MVA-EBOZ, Ebola recombinant glycoprotein vaccine, Vaxart adenovirus vector 5-based Ebola vaccine, FiloVax vaccine, GOVX-E301, and GOVX-E302.

The compounds provided herein may also be used in combination with phosphoramidate morpholino oligomers (PMOs), which are synthetic antisense oligonucleotide analogs designed to interfere with translational processes by forming base-pair duplexes with specific RNA sequences. Examples of PMOs include but are not limited to AVI-7287, AVI-7288, AVI-7537, AVI-7539, AVI-6002, and AVI-6003.

The compounds provided herein are also intended for use with general care provided to patients with Filoviridae viral infections, including parenteral fluids (including dextrose saline and Ringer's lactate) and nutrition, antibiotic (including metronidazole and cephalosporin antibiotics, such as ceftriaxone and cefuroxime) and/or antifungal prophylaxis, fever and pain medication, antiemetic (such as metoclopramide) and/or antidiarrheal agents, vitamin and mineral supplements (including Vitamin K and zinc sulfate), anti-inflammatory agents (such as ibuprofen), pain medications, and medications for other common diseases in the patient population, such anti-malarial agents (including artemether and artesunate-lumefantrine combination therapy), typhoid (including quinolone antibiotics, such as ciprofloxacin, macrolide antibiotics, such as azithromycin, cephalosporin antibiotics, such as ceftriaxone, or aminopenicillins, such as ampicillin), or shigellosis.

IX. Compound Preparation

In some embodiments, the present disclosure provides processes and intermediates useful for preparing the compounds provided herein or pharmaceutically acceptable salts thereof.

Compounds described herein can be purified by any of the means known in the art, including chromatographic means, such as high performance liquid chromatography (HPLC), preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography.

During any of the processes for preparation of the compounds provided herein, it may be necessary and/or desirable to protect sensitive or reactive groups on any of the molecules concerned. This may be achieved by means of conventional protecting groups as described in standard works, such as T. W. Greene and P. G. M. Wuts, "Protective Groups in Organic Synthesis," 4$^{th}$ ed., Wiley, New York 2006. The protecting groups may be removed at a convenient subsequent stage using methods known from the art.

Exemplary chemical entities useful in methods of the embodiments will now be described by reference to illustrative synthetic schemes for their general preparation herein and the specific examples that follow. Skilled artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent.

Furthermore, one of skill in the art will recognize that the transformations shown in the schemes below may be performed in any order that is compatible with the functionality of the particular pendant groups.

The methods of the present disclosure generally provide a specific enantiomer or diastereomer as the desired product, although the stereochemistry of the enantiomer or diastereomer was not determined in all cases. When the stereochemistry of the specific stereocenter in the enantiomer or diastereomer is not determined, the compound is drawn without showing any stereochemistry at that specific stereocenter even though the compound can be substantially enantiomerically or disatereomerically pure.

Representative syntheses of compounds of the present disclosure are described in the schemes below, and the particular examples that follow.

General Synthetic Schemes

General Reaction Schemes I, II, and III are provided as further embodiments of the present disclosure and illustrate general methods which were used to prepare certain compounds of the present disclosure and which can be used to prepare additional compounds of the present disclosure. Each of the variables (e.g. $R^1$, $R^2$, $R^{3A}$, $R^{3B}$, $R^4$, and $R^5$) of formulas (i)-(xiv) are as defined herein.

The compounds of the present disclosure may be prepared using the methods disclosed herein and routine modifications thereof, which will be apparent to a skilled artisan given the disclosure herein and methods well known in the art. Conventional and well-known synthetic methods may be used in addition to the teachings herein. The synthesis of typical compounds described herein may be accomplished as described in the following examples. If available, reagents may be purchased commercially, e.g., from Sigma Aldrich or other chemical suppliers.

In general, compounds described herein are typically stable and isolatable at room temperature and pressure. The compounds prepared herein can be purified using the methods known to the person of ordinary skill in the art, including those described herein. A skilled artisan will appreciate that when acids (e.g. TFA) are present in purification solvents, then the final product may be isolated as a salt (for e.g. TFA salt).

Typical embodiments of compounds disclosed herein may be synthesized using the general reaction schemes described below. It will be apparent to a skilled artisan given the description herein that the general schemes may be altered by substitution of the starting materials with other materials having similar structures to result in products that are correspondingly different. Descriptions of syntheses follow to provide numerous examples of how the starting materials may vary to provide corresponding products. Given a desired product for which the substituent groups are defined, the necessary starting materials generally may be determined by inspection. Starting materials are typically obtained from commercial sources or synthesized using published methods. For synthesizing compounds which are embodiments disclosed in the present disclosure, inspection of the structure of the compound to be synthesized will provide the identity of each substituent group. The identity of the final product will generally render apparent the identity of the necessary starting materials by a simple process of inspection, given the examples herein.

The terms "solvent", "inert organic solvent", or "inert solvent" refer to a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, and the like). Unless specified to the contrary, the solvents used in the reactions of the present disclosure are inert organic solvents, and the reactions are carried out under an inert gas, preferably nitrogen or argon.

Reaction Scheme I:

Exemplary compounds of Formula I, Formula Ia, and Formula Ib may be prepared using the methods similar to the Reaction Scheme I shown below.

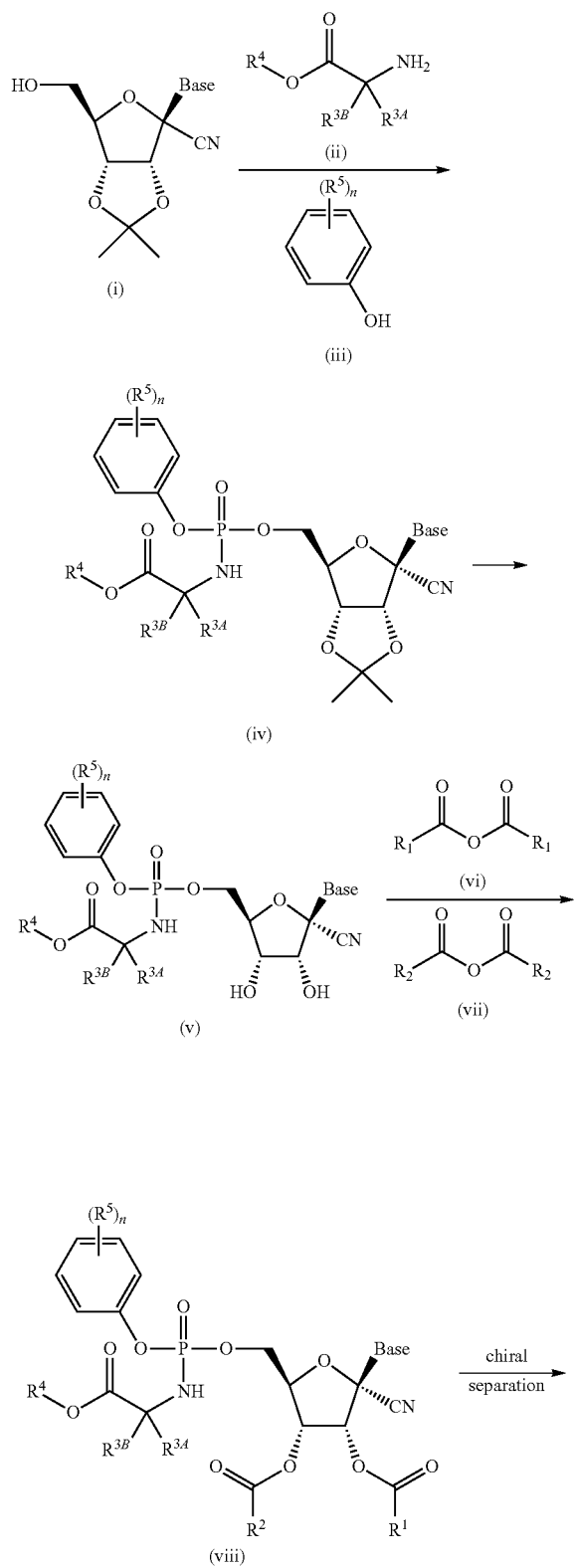

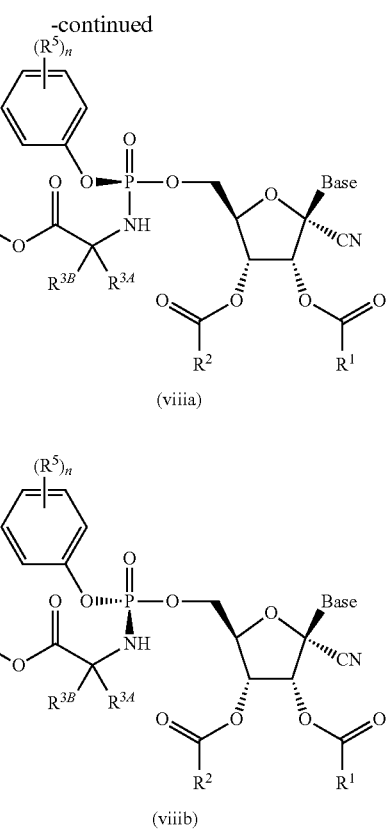

Phenol (iii) and phosphorus(V)oxychloride are mixed in presence of a base (e.g. N, N-diisopropylethylamine) in a suitable solvent (for e.g. dichloromethane) at a suitable temperature (e.g. at −78° C. to room temperature). Once reacted, natural or unnatural amino acid ester (ii) is added along with a suitable base at a suitable temperature (e.g. at −78° C.). After reaction, pentafluorophenol and a suitable base is added to generate the phosphoramidate reagent. Alternatively, the natural or unnatural amino acid ester (ii) is reacted with phenyl dichlorophosphate in the presence of a suitable base (e.g. triethylamine) at a suitable temperature (e.g. −78° C. to room temp). Once reacted, pentfluorophenol along with a suitable base are added to form the phosphoramidate reagent. The phosphoramidate reagents can be purified using any suitable method, e.g. chromatography (e.g. HPLC).

The nucleoside (i) is converted to (iv) by adding the phosphoramidate reagent as described above to (i) in a suitable solvent (e.g. acetonitrile), then adding magnesium chloride and a base (e.g. N,N-disisopropylamine). This reaction is conducted at any suitable temperature (for example at 0° C. to room temperature). Intermediate (iv) is then treated with an acid e.g. (HCl) to provide the phosphoramidate nucleoside (v). Separation of the isomers at phosphorus can be performed using HPLC, chiral HPLC methods, or other suitable methods.

Intermediate (v) in a suitable solvent (e.g. tetrahydrofuran), is treated with an anhydride (e.g. isobutyric anhydride, acetic anhydride or propionic anhydride and the like), in the presence of a suitable base (e.g. 4-dimethylaminopyridine), to form the compound (viii). Suitable methods, e.g. Chiral chromatography, or other chromatography methods e.g. HPLC can then be used to isolate compounds (viiia) and (viiib).

Reaction Scheme II:

Exemplary compounds of Formula III, Formula IIIa, and Formula IIIb may be prepared using the methods similar to the Reaction Scheme II shown below.

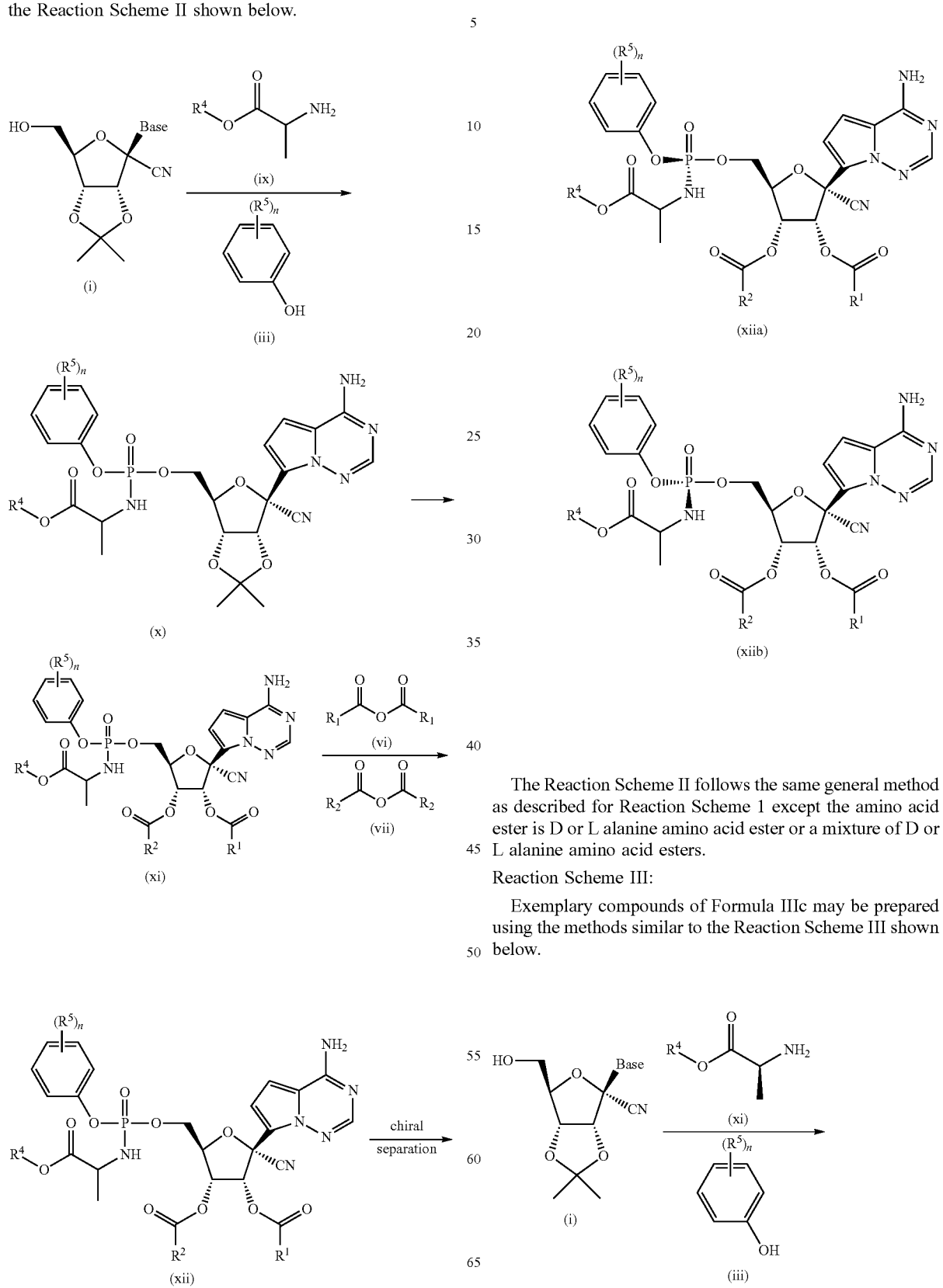

The Reaction Scheme II follows the same general method as described for Reaction Scheme 1 except the amino acid ester is D or L alanine amino acid ester or a mixture of D or L alanine amino acid esters.

Reaction Scheme III:

Exemplary compounds of Formula IIIc may be prepared using the methods similar to the Reaction Scheme III shown below.

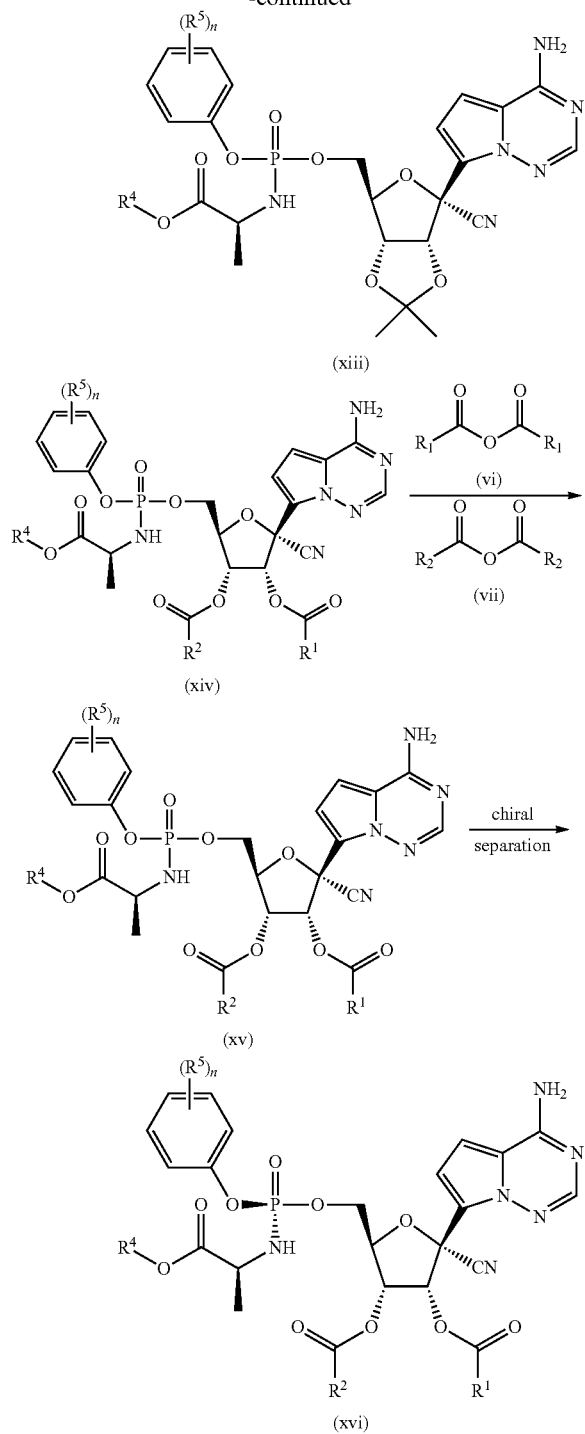

(xiii)

(xiv)

(xv)

(xvi)

The scheme follows the same general method as described for Reaction Scheme I except the amino acid ester is L alanine amino acid ester.

X. EXAMPLES

Exemplary chemical entities of the present disclosure are provided in the specific examples that follow. Those skilled in the art will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the particular pendant groups.

The Examples provided herein describe the synthesis of compounds disclosed herein as well as intermediates used to prepare the compounds. It is to be understood that individual steps described herein may be combined. It is also to be understood that separate batches of a compound may be combined and then carried forth in the next synthetic step.

In the following description of the Examples, specific embodiments are described. These embodiments are described in sufficient detail to enable those skilled in the art to practice certain embodiments of the present disclosure. Other embodiments may be utilized and logical and other changes may be made without departing from the scope of the disclosure. The following description is, therefore, not intended to limit the scope of the present disclosure.

Intermediates

Intermediate A1: 2-Ethylbutyl (2S)-2-[[(4-tert-butylphenoxy)-(2,3,4,5,6-pentafluorophenoxy)phosphoryl]amino]propanoate

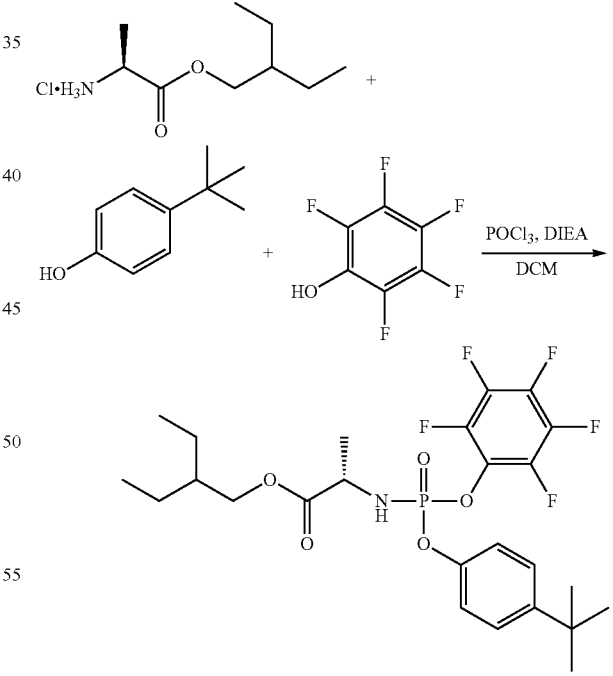

A1

To a solution of phosphorus(V) oxychloride (5.00 g, 32.6 mmol) in dichloromethane (80 mL) under an atmosphere of argon was added 4-tert-butylphenol (4.90 g, 32.6 mmol) at −78° C. N,N-diisopropylethylamine (5.68 mL, 32.6 mmol) was added over 5 minutes. After 15 minutes, the reaction was allowed to warm to 0° C. After 15 minutes, the reaction was cooled to −78° C. 2-Ethylbutyl (2S)-2-aminopropanoate hydrochloride (6.84 g, 32.6 mmol) was added. N,N-diisopropylethylamine (11.4 mL, 65.2 mmol) was added over 5 minutes. After 30 minutes, 2,3,4,5,6-pentafluorophenol (6.0 g, 32.6 mmol) was added. N,N-diisopropylethylamine (5.68 mL, 32.6 mmol) was added over 5 minutes. After 15 minutes, the reaction was allowed to warm to room temperature. After 30 minutes, the reaction was acidified with acetic acid (5 mL). The reaction was washed with water (50 mL). The organics were dried over sodium sulfate, filtered and concentrated. The product was purified by silica gel chromatography (0-20% ethyl acetate in hexanes) to afford intermediate A1. LCMS: MS m/z=551.8 [M+1], $t_R$=1.39 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 µL/min. $^1$H NMR (400 MHz, DMSO-$d_6$) δ (1:1 mixture of diastereomers) 7.44-7.39 (m, 2H), 7.22-7.11 (m, 2H), 6.96-6.81 (m, 1H), 4.09-3.91 (m, 3H), 1.54-1.40 (m, 1H), 1.36-1.22 (m, 16H), 0.90-0.77 (m, 6H). $^{31}$P NMR (162 MHz, DMSO-$d_6$) δ 0.82-0.49 (m). $^{19}$F NMR (376 MHz, DMSO-$d_6$) δ −153.93−−154.64 (m, 2F), −160.57−−161.18 (m, 1F), −163.37−−163.90 (m, 2F).

Intermediate B1. Methyl (2S)-2-[[(4-tert-butylphenoxy)-(2,3,4,5,6-pentafluorophenoxy)phosphoryl]amino]propanoate

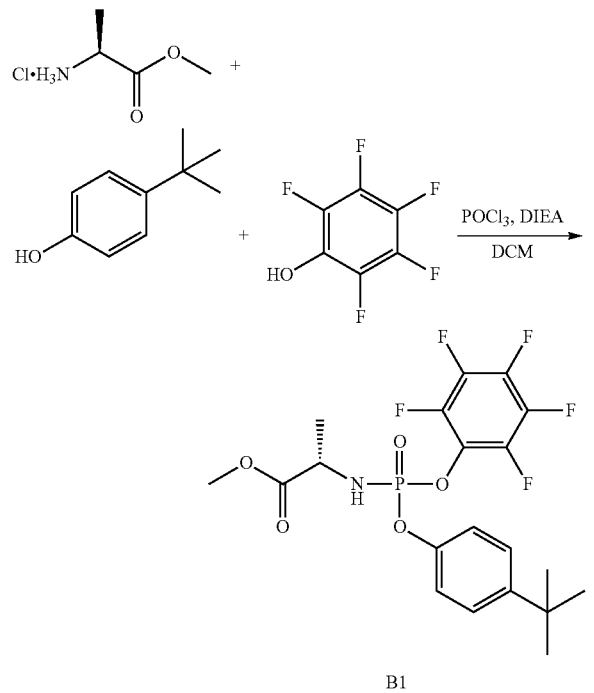

B1

Intermediate B1 was made in a similar manner as intermediate A1 except that methyl (2S)-2-aminopropanoate hydrochloride was used instead of 2-ethylbutyl (2S)-2-aminopropanoate hydrochloride. LCMS: MS m/z=481.8 and 481.8 [M+1], $t_R$=1.23 and 1.29 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 µL/min. $^1$H NMR (400 MHz, DMSO-$d_6$) δ (1:1 mixture of diastereomers) 7.45-7.40 (m, 2H), 7.23-7.11 (m, 2H), 6.96-6.84 (m, 1H), 4.08-3.94 (m, 1H), 3.61-3.58 (m, 3H) 1.34-1.23 (m, 12H). $^{31}$P NMR (162 MHz, DMSO-$d_6$) δ 5.67−−3.80 (m). $^{19}$F NMR (376 MHz, DMSO-$d_6$) δ −154.04−−154.40 (m, 2F), −160.57−−160.99 (m, 1F), −163.41−−163.87 (m, 2F).

Intermediate C1. Ethyl (2S)-2-[[(4-tert-butylphenoxy)-(2,3,4,5,6-pentafluorophenoxy)phosphoryl]amino]propanoate

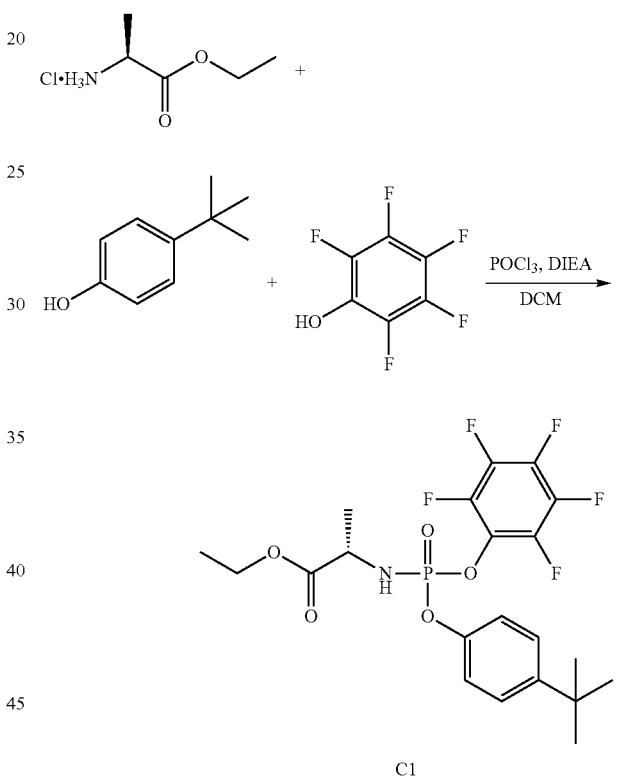

C1

Intermediate C1 was made in a similar manner as intermediate A1 except that ethyl (2S)-2-aminopropanoate hydrochloride was used instead of 2-ethylbutyl (2S)-2-aminopropanoate hydrochloride. LCMS: MS m/z=495.8 and 495.8 [M+1], $t_R$=1.23 and 1.20 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 µL/min. $^1$H NMR (400 MHz, DMSO-$d_6$) δ (1:1 mixture of diastereomers) 7.47-7.38 (m, 2H), 7.21-7.11 (m, 2H), 6.93-6.81 (m, 1H), 4.10-4.02 (m, 2H), 4.00-3.90 (m, 1H), 1.32-1.24 (m, 12H), 1.19-1.11 (m, 3H). $^{31}$P NMR (162 MHz, DMSO-$d_6$) δ 0.98-0.49 (m). $^{19}$F NMR (376 MHz, DMSO-$d_6$) δ −153.96−−154.41 (m, 2F), −160.63−−160.98 (m, 1F), −163.35−−163.82 (m, 2F).

Intermediate D1. 2-Ethylbutyl (2S)-2-[[(2,6-dimethylphenoxy)-(2,3,4,5,6-pentafluorophenoxy)phosphoryl]amino]propanoate

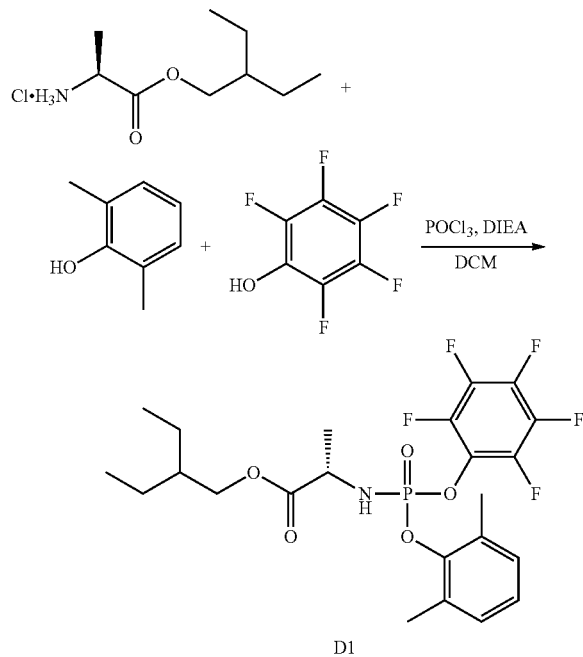

D1

Intermediate D1 was made in a similar manner as intermediate A1 except that 2,6-dimethyl phenol was used instead of 4-tert-butyl phenol (43% yield). LCMS: MS m/z=523.8 [M+1], $t_R$=1.29 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min. $^1$H NMR (400 MHz, DMSO-d6) δ (1:1 mixture of diastereomers) 6.97-6.89 (m, 2H), 6.86-6.76 (m, 1H), 4.15-4.07 (m, 1H), 4.05-3.91 (m, 2H), 1.55-1.44 (m, 1H), 1.38-1.20 (m, 7H), 0.91-0.80 (m, 6H). $^{31}$P NMR (162 MHz, DMSO-d6) δ −4.16-−4.87 (m). $^{19}$F NMR (376 MHz, DMSO-d6) δ −163.11-−163.56 (m, 2F), −166.91-−167.32 (m, 2F), −175.35-−176.22 (m 1F).

Intermediate E1. Spiro[3.3]heptan-2-yl L-alaninate hydrochloride

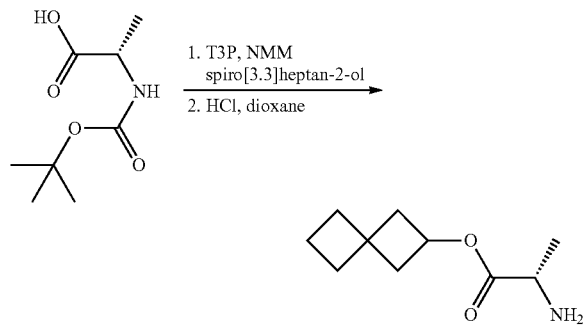

To a stirred solution of (tert-butoxycarbonyl)-L-alanine (2.5 g, 13.2 mmol) and spiro[3.3]heptan-2-ol (1.48 g, 13.2 mmol) in dry dichloromethane (35 mL) were added N-methylmorpholine (2.9 mL, 26.4 mmol), 4-(dimethylamino)pyridine (0.016 g, 0.13 mmol) and tri-propylphosphonic acid cyclic anhydride (T3P, 10.3 g, 16.1 mmol, 50% in ethyl acetate) at 0° C. under an atmosphere of argon. The reaction mixture was then stirred at room temperature for 2 hours. The reaction mixture was washed with water (50 mL), twice with 10% solution of citric acid (2×40 mL), twice with saturated aqueous sodium bicarbonate solution (2×40 mL) and once with brine (50 mL), dried over sodium sulfate, filtered through a 3 cm layer of silica gel which was washed with additional dichloromethane. The combined organics were concentrated down under reduced pressure, co-distilled with dichloromethane and dried under high vacuum overnight to afford the title compound. The residue was used without further purification.

The residue was then dissolved in 10 mL of 4 M HCl in 1,4-dioxane and the reaction mixture was stirred at room temperature for 2 hours, concentrated under reduced pressure and co-distilled with toluene to give the product which was dried under high vacuum for 1 hour. The residue was used without further purification. LCMS: MS m/z=184.1 [M+1]

Intermediate E2. Spiro[3.3]heptan-2-yl (2S)-2-[[(4-tert-butylphenoxy)-(2,3,4,5,6-pentafluorophenoxy)phosphoryl]amino]propanoate

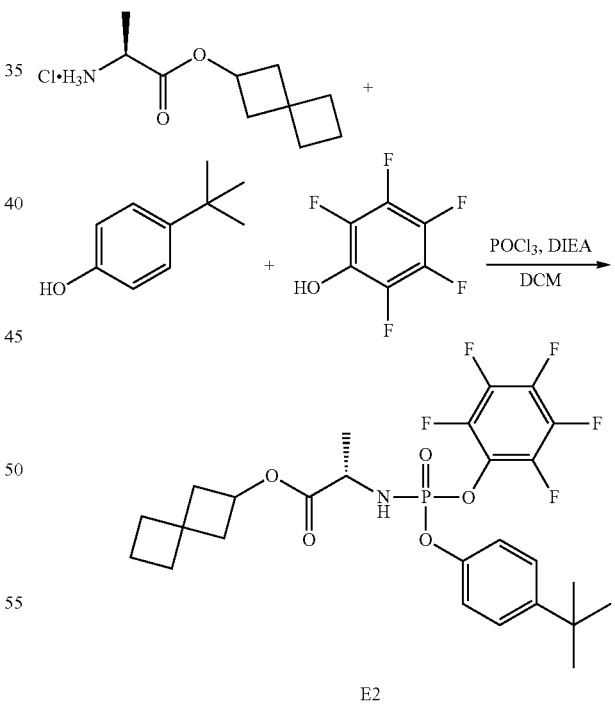

E2

To a solution of phosphorus(V) oxychloride (0.33 g, 2.16 mmol) in dichloromethane (8 mL) under an atmosphere of argon was added 4-tert-butylphenol (0.325 g, 2.16 mmol) at −78° C. N,N-diisopropylethylamine (0.38 mL, 2.16 mmol) over 5 minutes. After 15 minutes, the reaction was allowed to warm to 0° C. After 15 minutes, the reaction was cooled to −78° C. Spiro[3.3]heptan-2-yl (2S)-2-aminopropanoate hydrochloride (0.475 g, 2.16 mmol) was added. N,N-diisopropylethylamine (0.75 mL, 4.32 mmol) was added over 5 minutes. After 30 minutes, 2,3,4,5,6-pentafluorophenol (0.40 g, 2.16 mmol) was added. N,N-diisopropylethylamine (0.38 mL, 2.16 mmol) was added over 5 minutes. After 15 minutes, the reaction was allowed to warm to room temperature. After 30 minutes, the reaction was acidified with acetic acid (3 mL). The reaction was washed with water (50 mL). The organics were dried over sodium sulfate, filtered and concentrated. The product was purified by silica gel chromatography (0-20% ethyl acetate in hexanes) to afford spiro[3.3]heptan-2-yl (2S)-2-[[(4-tert-butylphenoxy)-(2,3,4,5,6-pentafluorophenoxy)phosphoryl]amino]propanoate.
LCMS: MS m/z=562.5 [M+1]; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid.

Intermediate G1. 2-(2-Ethoxyethoxy)ethyl (tert-butoxycarbonyl)-L-alaninate

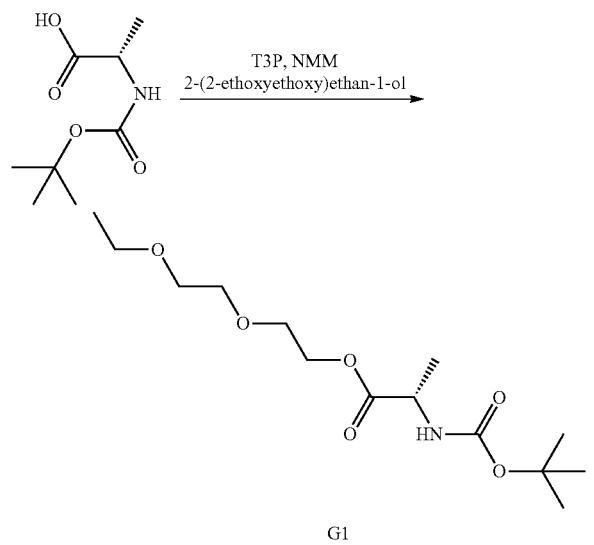

G1

To a stirred solution of (tert-butoxycarbonyl)-L-alanine (12.41 g, 66 mmol) and 2-(2-ethoxyethoxy)ethan-1-ol (8.00 g, 60 mmol) in dry dichloromethane (100 mL) were added N-methylmorpholine (19.67 mL, 179 mmol), 4-(dimethylamino)pyridine (0.15 g, 1.2 mmol) and tri-propylphosphonic acid cyclic anhydride (T3P, 42.6 mL, 72 mmol, 50% in ethyl acetate) at 0° C. under an atmosphere of argon. The reaction mixture was then stirred at room temperature for 2 hours. The reaction mixture was washed with water (50 mL), twice with 10% solution of citric acid (2×40 mL), twice with saturated aqueous sodium bicarbonate solution (2×40 mL) and once with brine (50 mL), dried over sodium sulfate, filtered through a 3 cm layer of silica gel which was washed with additional dichloromethane. The combined organics were concentrated down under reduced pressure, co-distilled with dichloromethane and dried under high vacuum overnight to afford the title compound. $^1$H NMR (400 MHz, DMSO-$d_6$) δ 7.27 (d, J=7.4 Hz, 1H), 4.23-4.14 (m, 1H), 4.14-4.06 (m, 1H), 4.05-3.94 (m, 1H), 3.64-3.56 (m, 2H), 3.55-3.49 (m, 2H), 3.49-3.39 (m, 4H), 1.38 (s, 9H), 1.23 (d, J=7.4 Hz, 3H), 1.09 (t, J=7.0 Hz, 3H).

Intermediate G2. 2-(2-Ethoxyethoxy)ethyl ((perfluorophenoxy)(phenoxy)phosphoryl)-L-alaninate

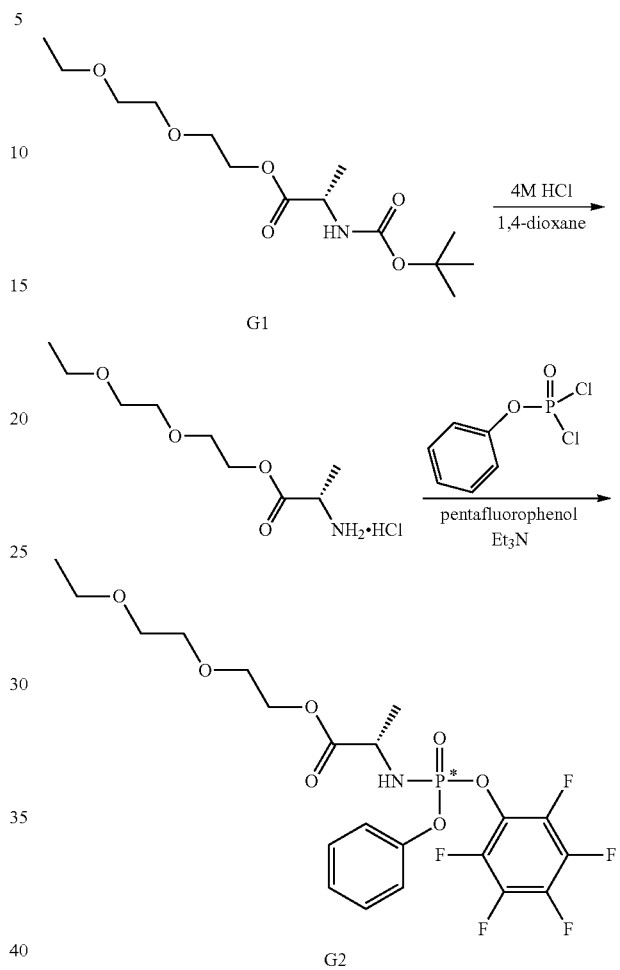

The intermediate G1 (18.3 g, 59.93 mmol) was dissolved in 50 mL of 4 M HCl in 1,4-dioxane and the reaction mixture was stirred at room temperature for 2 hours, concentrated under reduced pressure and co-distilled with toluene to give the cure solid which was dried under high vacuum for 1 hour. The solids were suspended in dichloromethane (100 mL) and phenyl dichlorophosphate (9.81 mL, 65.92 mmol) and triethylamine (18.28 mL, 131.84 mmol) were sequentially added at −78° C. and the resulting mixture was stirred at room temperature for 2 hours. The reaction mixture was cooled down to 0° C. and pentafluorophenol (11.03 g, 59.93 mmol) and triethylamine (10.80 mL, 78.05 mmol) were then sequentially added and the resulting mixture was then allowed to warm to room temperature. After 3 hours, the reaction mixture was cooled down to 0° C. and solids were filtered off, the filtrate was washed with saturated ammonium chloride water solution (100 mL), water (100 mL) and brine (50 mL). The organics were dried over sodium sulfate and filtered through a 3 cm layer of silica gel which was washed with 1:1 ethyl acetate and dichloromethane mixture (100 mL). Combined organics were concentrated down under reduced pressure to afford the crude product. The solids were dissolved in minimum amount of boiling diisopropyl ether and the mixture was vigorously stirred at room temperature overnight. The product was filtered off and washed with cold diisopropyl ether (2×20 mL) and hexane (3×40 mL) to afford the title compound. $^1$H NMR (400 MHz, DMSO-$d_6$) δ 7.47-7.36 (m, 2H), 7.30-7.20 (m, 3H), 6.92 (dd, J=14.2, 9.9 Hz, 1H), 4.21-4.08 (m, 2H), 4.07-3.92 (m, 1H), 3.62-3.56 (m, 2H), 3.53-3.47 (m, 2H), 3.45-3.36 (m, 4H), 1.29 (d, J=7.1 Hz, 3H), 1.07 (t, J=7.0 Hz, 3H). $^{19}$F NMR (376 MHz, DMSO-$d_6$) δ −154.24 (d, J=21.5 Hz, 2F), −160.86 (t, J=23.1 Hz, 1F), −163.68 (t, J=21.7 Hz, 2F). $^{31}$P NMR (162 MHz, DMSO-$d_6$) δ 0.40. LCMS: MS m/z=528.06 [M+1], $t_R$=1.64 min; LC system: Thermo Accela 1250 UHPLC; MS system: Thermo LCQ Fleet; Column: Kinetex 2.6μ XB-C18 100A, 50×4.6 mm; Solvents: acetonitrile with 0.1% acetic acid, water with 0.1% acetic acid; Gradient: 0 min-0.2 min 2% acetonitrile, 0.2 min-1.5 min 2-100% acetonitrile, 1.5 min-2.2 min 100% acetonitrile, 2.2 min-2.4 min 100%-2% acetonitrile, 2.4 min-2.5 min 2% acetonitrile at 2 μl/min.

Intermediate H1. 2-Methoxy-2-methylpropyl (tert-butoxycarbonyl)-L-alaninate

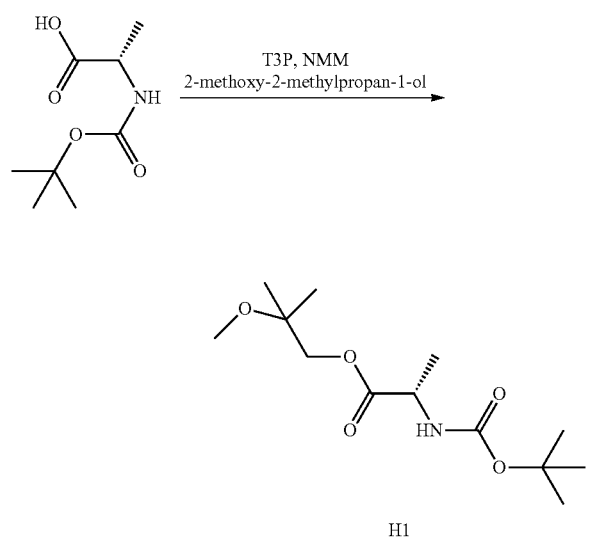

H1

To a stirred solution of (tert-butoxycarbonyl)-L-alanine (4.00 g, 21 mmol) and 2-methoxy-2-methylpropan-1-ol (2.00 g, 19 mmol) in dry dichloromethane (50 mL) were added N-methylmorpholine (6.33 mL, 58 mmol), 4-(dimethylamino)pyridine (0.05 g, 0.4 mmol) and tri-propylphosphonic acid cyclic anhydride (T3P, 13.72 mL, 23 mmol, 50% in ethyl acetate) at 0° C. under an atmosphere of argon. The reaction mixture was then stirred at room temperature for 2 hours. The reaction mixture was washed with water (30 mL), twice with 10% solution of citric acid (2×20 mL), twice with saturated aqueous sodium bicarbonate solution (2×20 mL) and once with brine (20 mL), dried over sodium sulfate, filtered through a 3 cm layer of silica gel which was washed with 3:1 mixture of dichloromethane and ethyl acetate. The combined organics were concentrated down under reduced pressure, co-distilled with dichloromethane and dried under high vacuum overnight to afford the title compound. $^1$H NMR (400 MHz, DMSO-$d_6$) δ 7.30 (d, J=7.4 Hz, 1H), 4.10-3.77 (m, 3H), 3.11 (s, 3H), 1.37 (s, 9H), 1.24 (d, J=7.4 Hz, 3H), 1.10 (s, 6H).

Intermediate H2. 2-Methoxy-2-methylpropyl (perfluorophenoxy)(phenoxy)phosphoryl)-L-alaninate

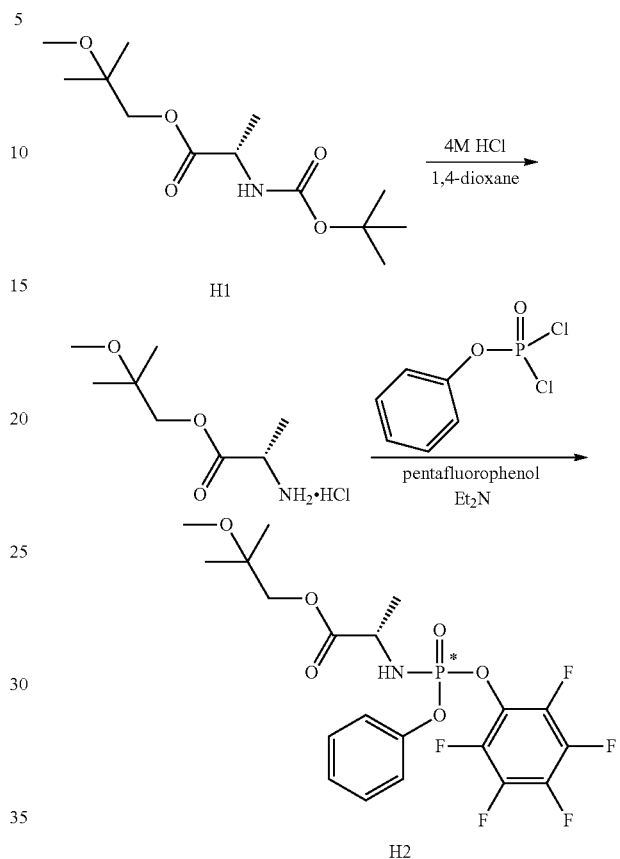

The intermediate H1 (5.1 g, 18.52 mmol) was dissolved in 15 mL of 4M HCl in 1,4-dioxane and the reaction mixture was stirred at room temperature for 2 hours, concentrated under reduced pressure and co-distilled with toluene to give the cure solid which was dried under high vacuum for 1 hour. The solids were suspended in dichloromethane (100 mL) and phenyl dichlorophosphate (3.03 mL, 20.37 mmol) and triethylamine (5.65 mL, 40.75 mmol) were sequentially added at −78° C. and the resulting mixture was stirred at room temperature for 2 hours. The reaction mixture was cooled down to 0° C. and pentafluorophenol (3.41 g, 18.52 mmol) and triethylamine (3.59 mL, 25.93 mmol) were then sequentially added and the resulting mixture was then allowed to warm to room temperature. After 3 hours, the reaction mixture was cooled down to 0° C. and solids were filtered off, the filtrate was washed with saturated ammonium chloride water solution (100 mL), water (100 mL) and brine (50 mL). The organics were dried over sodium sulfate and filtered through a 3 cm layer of silica gel which was washed with 1:3 ethyl acetate and dichloromethane mixture (100 mL). Combined organics were concentrated down under reduced pressure to afford the crude product (as a mixture of both isomers on phosphorus based on the NMR). The solids were dissolved in boiling diisopropyl ether (50 mL) and the mixture was vigorously stirred at room temperature overnight. The solid product was filtered off and washed with cold diisopropyl ether (2×10 mL) and hexane (3×20 mL) to afford the title compound (a single isomer on phosphorus based on the NMR). $^1$H NMR (400 MHz, DMSO-$d_6$) δ 7.46-7.36 (m, 2H), 7.29-7.16 (m, 3H), 6.92 (dd, J=14.2, 9.9 Hz, 1H), 4.12-3.86 (m, 3H), 3.09 (s, 3H), 1.31 (d, J=7.1 Hz, 3H), 1.09 (s, 6H). $^{19}$F NMR (376 MHz, DMSO-$d_6$) δ -154.22 (d, J=21.4 Hz, 2F), -160.89 (td, J=23.4, 3.2 Hz, 1F), -163.69 (td, J=23.4, 4.0 Hz, 2F). $^{31}$P NMR (162 MHz, DMSO-$d_6$) δ 0.43. LCMS: MS m/z=497.9 [M+1], $t_R$=1.65 min; LC system: Thermo Accela 1250 UHPLC; MS system: Thermo LCQ Fleet; Column: Kinetex 2.6p XB-C18 100A, 50×4.6 mm; Solvents: acetonitrile with 0.1% acetic acid, water with 0.1% acetic acid; Gradient: 0 min-0.2 min 2% acetonitrile, 0.2 min-1.5 min 2-100% acetonitrile, 1.5 min-2.2 min 100% acetonitrile, 2.2 min-2.4 min 100%-2% acetonitrile, 2.4 min-2.5 min 2% acetonitrile at 2 μl/min.

Intermediate M1. 2-Ethylbutyl ((S)-(((2R,3S,4R,5R)-5-(3-((((benzyloxy)(hydroxy)phosphoryl)oxy)methyl)-4-imino-3,4-dihydropyrrolo[2,1-f][1,2,4]triazin-7-yl)-5-cyano-3,4-dihydroxytetrahydrofuran-2-yl)methoxy)(phenoxy)phosphoryl)-L-alaninate To a solution of 2-ethylbutyl ((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)-L-alaninate (prepared according to WO2016069825, 300 mg, 0.498 mmol) and sodium iodide (224 mg, 1.49 mmol) in HMPA (5.50 mL) was added dibenzylchloromethyl phosphate (0.244 g, 0.747 mmol) at 0° C. The reaction was allowed to warm to RT and stirred for 2 h. The reaction was diluted with ethyl acetate, washed with sodium bicarbonate, water then brine. The organics were dried over sodium sulfate, filtered and concentrated. The product was purified by HPLC chromatography (using gradient from 0-100% acetonitrile in water) to afford intermediate M1. LCMS: MS m/z=803.2 [M+1], $t_R$=0.85 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min. $^1$H NMR (400 MHz, DMSO-d6) δ

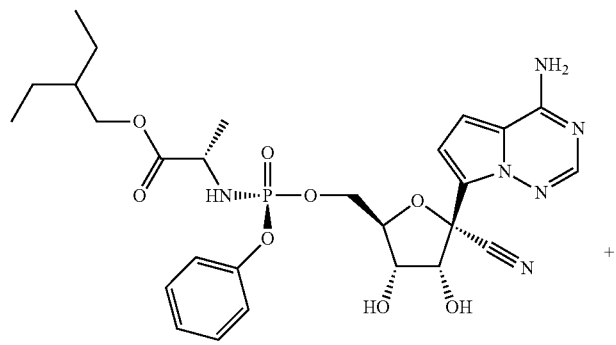

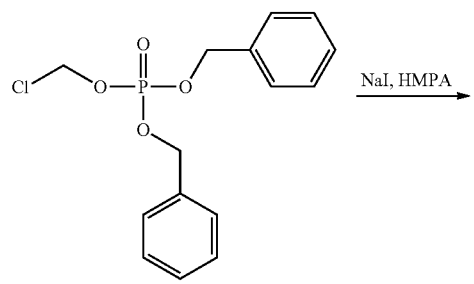

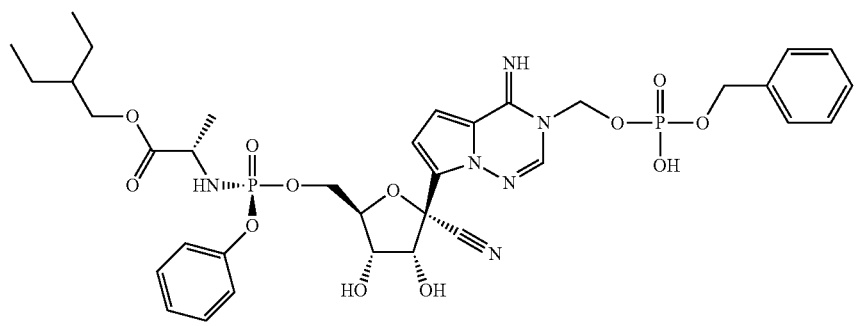

M1

8.54 (s, 1H), 7.48-7.15 (m, 11H), 7.01 (d, J=4.7 Hz, 1H), 6.65-6.60 (m, 1H), 6.15-6.06 (m, 1H), 5.72-5.64 (m, 2H), 5.52 (s, 1H), 4.79 (d, J=7.0 Hz, 2H), 4.54-4.48 (m, 1H), 4.32-4.22 (m, 2H), 4.16-4.07 (m, 1H), 4.03-3.78 (m, 5H), 1.48-1.39 (m, 1H), 1.32-1.20 (m, 7H), 0.85-0.77 (m, 6H). $^{31}$P NMR (162 MHz, DMSO-d6) δ 4.17-3.77 (m), 0.33--0.08 (m).

Intermediate L1. 2-Ethylbutyl ((2-isopropyl-5-methylphenoxy)(perfluorophenoxy)phosphoryl)-L-alaninate

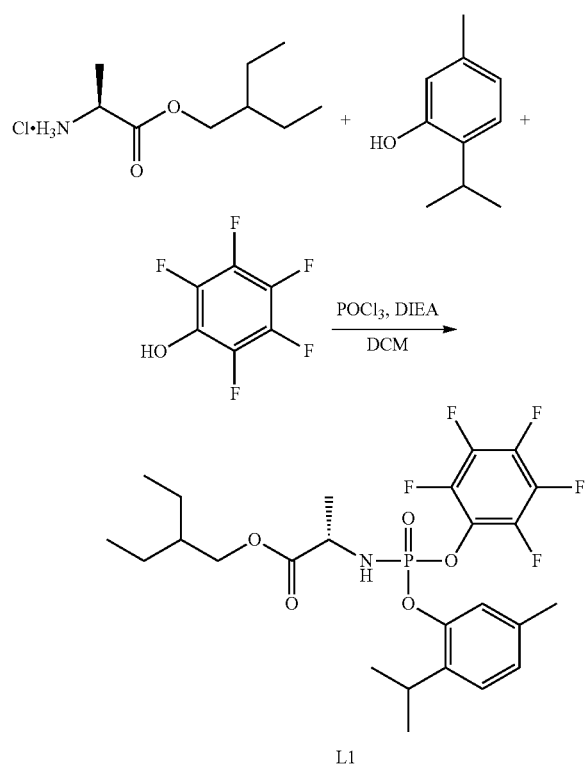

L1

To a solution of phosphorus(V) oxychloride (5.30 g, 34.6 mmol) in dry dichloromethane (75 mL) under an atmosphere of argon was added 2-isopropyl-5-methylphenol (5.19 g, 34.6 mmol) at −78° C. N,N-diisopropylethylamine (6.02 mL, 34.6 mmol) was added slowly over 5 minutes. After 15 minutes, the reaction was allowed to warm to 0° C. After 15 minutes, the reaction was cooled to −78° C. 2-ethylbutyl (2S)-2-aminopropanoate hydrochloride (7.25 g, 34.6 mmol) was added. N,N-diisopropylethylamine (12.04 mL, 69.2 mmol) was added slowly over 5 minutes. After 30 minutes, 2,3,4,5,6-pentafluorophenol (6.36 g, 34.6 mmol) was added. N,N-diisopropylethylamine (6.02 mL, 34.6 mmol) was added slowly over 5 minutes. After 15 minutes, the reaction was allowed to warm to room temperature. After 30 minutes, the reaction was acidified with acetic acid (5 mL). The reaction was washed with water (50 mL). The organics were dried over sodium sulfate, filtered and concentrated. The product was purified by silica gel chromatography (0-20% ethyl acetate in hexanes) to afford intermediate L1. LCMS: MS m/z=551.7 [M+1], $t_R$=1.34 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 µL/min. $^1$H NMR (400 MHz, DMSO-d$_6$) δ 7.27-7.13 (m, 2H), 7.03-6.99 (m, 1H), 6.98-6.88 (m, 1H), 4.13-3.80 (m, 3H), 3.23-2.98 (m, 1H), 2.25 (s, 3H), 1.51-1.37 (m, 1H), 1.37-1.19 (m, 7H), 1.18-1.05 (m, 6H), 0.85-0.74 (m, 6H). $^{19}$F NMR (376 MHz, DMSO-d$_6$) δ −153.87--154.49 (m, 2F), −160.25--161.26 (m, 1F), −163.46--164.19 (m, 2F). $^{31}$P NMR (162 MHz, DMSO-d$_6$) δ (1:1 mixture of diastereomers) 0.40-0.15 (m, 1P), 0.09--0.35 (m, 1P).

EXAMPLES

Example 1: (2R,3R,4R,5R)-2-(4-aminopyrrolo[2,1-f][1,2,4]triazin-7-yl)-2-cyano-5-((((S)-(((S)-1-(2-ethylbutoxy)-1-oxopropan-2-yl)amino)(phenoxy)phosphoryl)oxy)methyl)tetrahydrofuran-3,4-diyl bis(2-methylpropanoate)

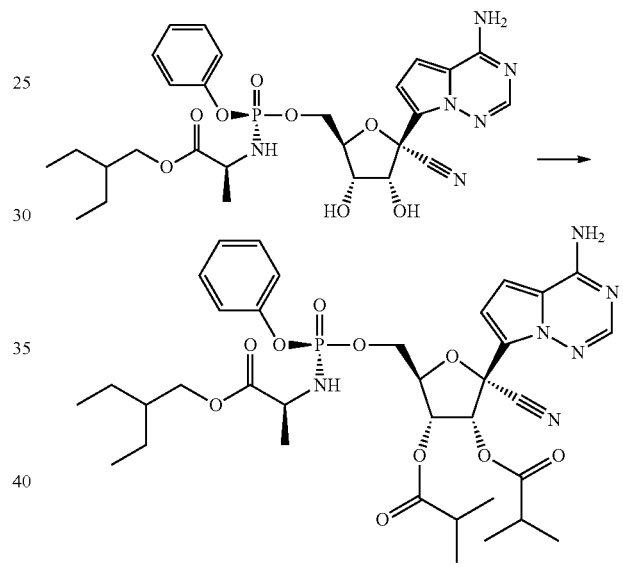

To a mixture of 2-ethylbutyl ((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)-L-alaninate (prepared according to WO2016/069826 or WO2016069825, 500 mg, 0.83 mmol) and 4-(dimethylamino)pyridine (15.2 mg, 0.124 mmol) in tetrahydrofuran (8 mL) was added isobutyric anhydride (275 µL, 1.66 mmol) at RT. After 30 min, the reaction mixture was diluted with ethyl acetate (50 mL) and the resulting mixture was washed with saturated sodium bicarbonate solution (50 mL). The organic phase was dried over anhydrous sodium sulfate and concentrated under reduced pressure. The crude residue was purified by silica gel chromatography eluting with ethyl acetate in hexanes (0-100%) to afford the product. $^1$H NMR (400 MHz, methanol-d$_4$) δ 7.87 (s, 1H), 7.32-7.24 (m, 2H), 7.21-7.12 (m, 3H), 6.88-6.81 (m, 2H), 6.20 (d, J=5.9 Hz, 1H), 5.57 (dd, J=5.8, 3.7 Hz, 1H), 4.64-4.59 (m, 1H), 4.47-4.34 (m, 2H), 4.07 (dd, J=10.9, 5.8 Hz, 1H), 3.98 (dd, J=10.9, 5.7 Hz, 1H), 3.95-3.86 (m, 1H), 2.75-2.58 (m, 2H), 1.55-1.45 (m, 1H), 1.41-1.22 (m, 13H), 1.20 (d, J=7.0 Hz, 6H), 0.89 (t, J=7.5 Hz, 6H). $^{31}$P NMR (162 MHz, methanol-d$_4$) δ 3.51. MS m/z=743.20 [M+1].

Example 2: (2R,3R,4R,5R)-2-(4-aminopyrrolo[2,1-f][1,2,4]triazin-7-yl)-2-cyano-5-((((S)-(((S)-1-(2-ethylbutoxy)-1-oxopropan-2-yl)amino)(phenoxy)phosphoryl)oxy)methyl)tetrahydrofuran-3,4-diyl diacetate Example 3: (2R,3R,4R,5R)-2-(4-aminopyrrolo[2,1-f][1,2,4]triazin-7-yl)-2-cyano-5-((((S)-(((S)-1-(2-ethylbutoxy)-1-oxopropan-2-yl)amino)(phenoxy)phosphoryl)oxy)methyl)tetrahydrofuran-3,4-diyl dipropionate

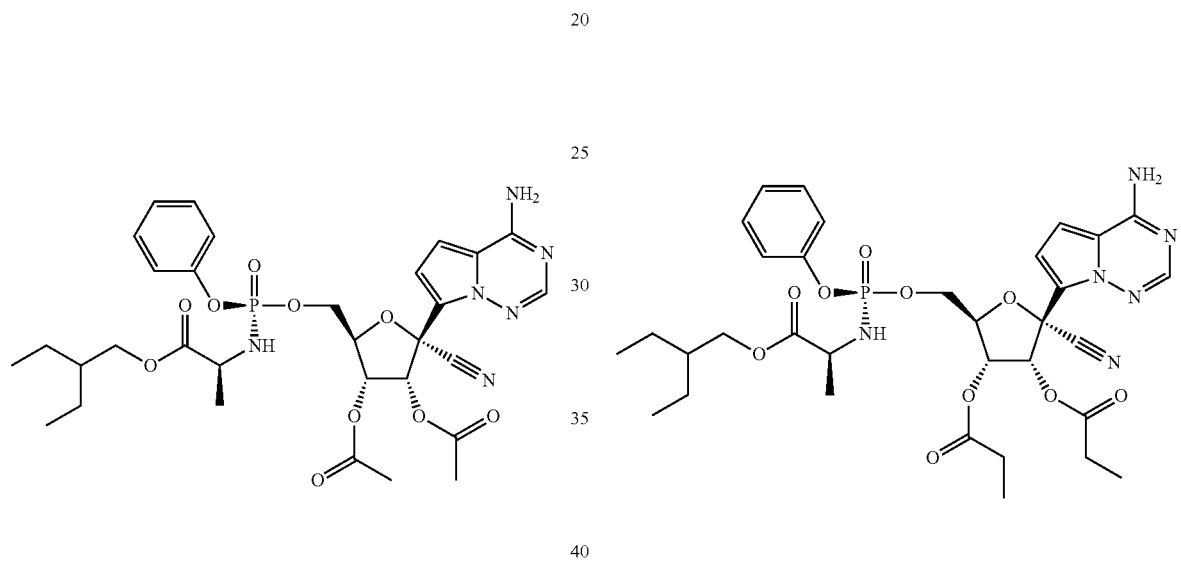

To a mixture of 2-ethylbutyl ((S)-((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)-L-alaninate (prepared according to WO2016/069826, WO2016/069825, or WO2016069825, 500 mg, 0.83 mmol) and 4-(dimethylamino)pyridine (15.2 mg, 0.124 mmol) in tetrahydrofuran (8 mL) was added acetic anhydride (157 µL, 1.66 mmol) at RT. After 30 min, the reaction mixture was diluted with ethyl acetate (50 mL) and the resulting mixture was washed with saturated sodium bicarbonate solution (50 mL). The organic phase was dried over anhydrous sodium sulfate and concentrated under reduced pressure. The crude residue was purified by silica gel chromatography eluting with ethyl acetate in hexanes (0-100%) to afford the product. $^1$H NMR (400 MHz, Methanol-d$_4$) δ 7.87 (s, 1H), 7.33-7.24 (m, 2H), 7.20-7.11 (m, 3H), 6.89-6.81 (m, 2H), 6.21 (d, J=5.9 Hz, 1H), 5.55 (dd, J=5.9, 4.3 Hz, 1H), 4.65-4.59 (m, 1H), 4.46-4.33 (m, 2H), 4.06 (dd, J=11.0, 5.8 Hz, 1H), 3.97 (dd, J=10.9, 5.6 Hz, 1H), 3.94-3.86 (m, 1H), 2.17 (s, 3H), 2.14 (s, 3H), 1.54-1.43 (m, 1H), 1.41-1.28 (m, 7H), 0.89 (t, J=7.5 Hz, 6H). $^{31}$P NMR (162 MHz, methanol-d$_4$) δ 3.53. MS m/z=687.20 [M+1].

To a mixture of 2-ethylbutyl ((S)-((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)-L-alaninate (prepared according to WO2016/069826, WO2016/069825, or WO2016069825, 500 mg, 0.83 mmol) and 4-(dimethylamino)pyridine (15.2 mg, 0.124 mmol) in tetrahydrofuran (8 mL) was added propionic anhydride (214 µL, 1.66 mmol) at RT. After 30 min, the reaction mixture was diluted with ethyl acetate (50 mL) and the resulting mixture was washed with saturated sodium bicarbonate solution (50 mL). The organic phase was dried over anhydrous sodium sulfate and concentrated under reduced pressure. The crude residue was purified by silica gel chromatography eluting with ethyl acetate in hexanes (0-100%) to afford the product. $^1$H NMR (400 MHz, Methanol-d$_4$) δ 7.87 (s, 1H), 7.32-7.25 (m, 2H), 7.20-7.12 (m, 3H), 6.88-6.82 (m, 2H), 6.22 (d, J=5.9 Hz, 1H), 5.58 (dd, J=5.9, 4.1 Hz, 1H), 4.65-4.59 (m, 1H), 4.47-4.33 (m, 2H), 4.06 (dd, J=10.9, 5.8 Hz, 1H), 3.97 (dd, J=10.9, 5.7 Hz, 1H), 3.95-3.85 (m, 1H), 2.52-2.37 (m, 4H), 1.55-1.44 (m, 1H), 1.41-1.28 (m, 8H), 1.20 (t, J=7.6 Hz, 3H), 1.16 (t, J=7.6 Hz, 3H), 0.89 (t, J=7.4 Hz, 6H). $^{31}$P NMR (162 MHz, methanol-d$_4$) δ 3.53. MS m/z=715.20 [M+1].

159

Example 4: (2R,3R,4R,5R)-2-(4-aminopyrrolo[2,1-f][1,2,4]triazin-7-yl)-2-cyano-5-((((S)-(((S)-1-methoxy-1-oxopropan-2-yl)amino)(phenoxy)phosphoryl)oxy)methyl)tetrahydrofuran-3,4-diyl bis(2-methylpropanoate)

160

Example 5: (2R,3R,4R,5R)-2-(4-aminopyrrolo[2,1-f][1,2,4]triazin-7-yl)-2-cyano-5-((((S)-(((S)-1-methoxy-1-oxopropan-2-yl)amino)(phenoxy)phosphoryl)oxy)methyl)tetrahydrofuran-3,4-diyl dipropionate

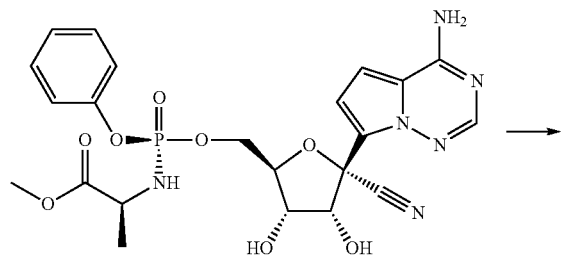

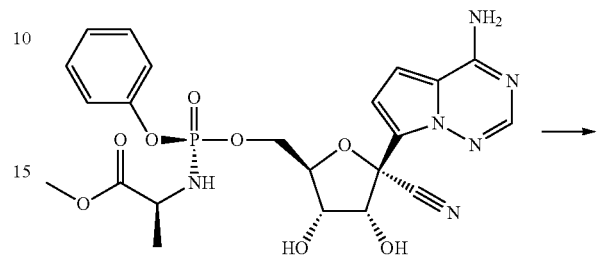

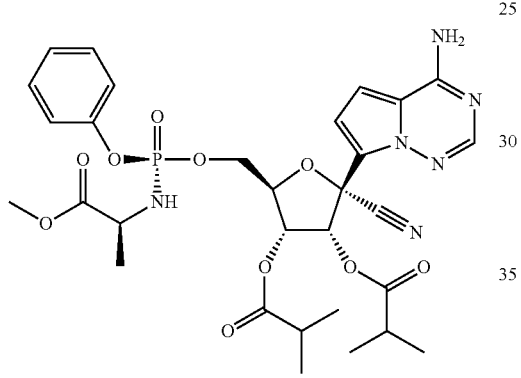

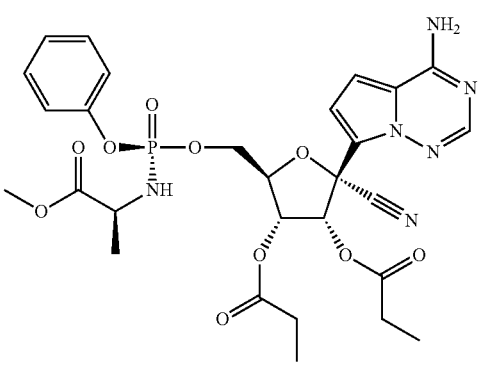

To a mixture of methyl ((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)-L-alaninate (prepared according to WO2017049060, 100 mg, 0.18 mmol) and 4-(dimethylamino)pyridine (3.4 mg, 0.028 mmol) in tetrahydrofuran (2 mL) was added isobutyric anhydride (62 µL, 0.376 mmol) at RT. After 30 min, the reaction mixture was diluted with ethyl acetate (50 mL) and the resulting mixture was washed with saturated sodium bicarbonate solution (50 mL). The organic phase was dried over anhydrous sodium sulfate and concentrated under reduced pressure. The crude residue was purified by preparatory HPLC (Gemini Sum NX-C18 110A LC column 100×30 mm, 95% to 0% water acetonitrile gradient) to afford the product. $^1$H NMR (400 MHz, methanol-$d_4$) δ 7.87 (s, 1H), 7.31-7.25 (m, 2H), 7.21-7.13 (m, 3H), 6.86 (d, J=4.7 Hz, 1H), 6.83 (d, J=4.7 Hz, 1H), 6.21 (d, J=5.9 Hz, 1H), 5.60-5.57 (m, 1H), 4.66-4.60 (m, 1H), 4.45-4.34 (m, 2H), 3.93-3.83 (m, 1H), 3.66 (s, 3H), 2.77-2.57 (m, 2H), 1.30-1.16 (m, 15H). $^{31}$P NMR (162 MHz, methanol-$d_4$) δ 3.54. MS m/z=673.20 [M+1].

To a mixture of methyl ((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)-L-alaninate (prepared according to WO2017049060, 100 mg, 0.188 mmol) and 4-(dimethylamino)pyridine (3.4 mg, 0.028 mmol) in tetrahydrofuran (8 mL) was added propionic anhydride (48 µL, 0.376 mmol) at RT. After 30 min, the reaction mixture was diluted with ethyl acetate (50 mL) and the resulting mixture was washed with saturated sodium bicarbonate solution (50 mL). The organic phase was dried over anhydrous sodium sulfate and concentrated under reduced pressure. The crude residue was purified by preparatory HPLC (Gemini Sum NX-C18 110A LC column 100×30 mm, 95% to 0% water acetonitrile gradient) to afford the product. $^1$H NMR (400 MHz, Methanol-$d_4$) δ 7.87 (s, 1H), 7.36-7.25 (m, 3H), 7.22-7.12 (m, 3H), 6.88-6.83 (m, 2H), 6.22 (d, J=5.8 Hz, 1H), 5.62-5.56 (m, 1H), 4.68-4.61 (m, 1H), 4.49-4.33 (m, 2H), 3.93-3.82 (m, 1H), 3.66 (s, 3H), 2.54-2.35 (m, 4H), 1.29 (dd, J=7.1, 1.0 Hz, 3H), 1.24-1.12 (m, 6H). $^{31}$P NMR (162 MHz, methanol-$d_4$) δ 3.53. MS m/z=645.10 [M+1].

Example 6: (2R,3R,4R,5R)-2-(4-aminopyrrolo[2,1-f][1,2,4]triazin-7-yl)-2-cyano-5-((((S)-(((S)-1-methoxy-1-oxopropan-2-yl)amino)(phenoxy)phosphoryl)oxy)methyl)tetrahydrofuran-3,4-diyl diacetate Example 7: (2R,3R,4R,5R)-2-(4-aminopyrrolo[2,1-f][1,2,4]triazin-7-yl)-2-cyano-5-((((S)-(((S)-1-isopropoxy-1-oxopropan-2-yl)amino)(phenoxy)phosphoryl)oxy)methyl)tetrahydrofuran-3,4-diyl bis(2-methylpropanoate)

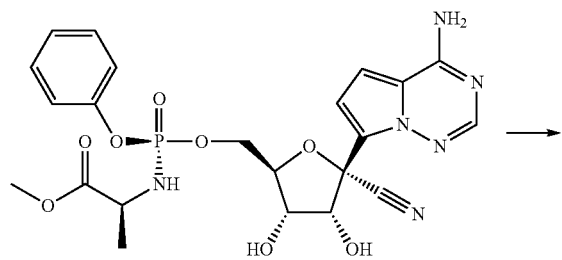

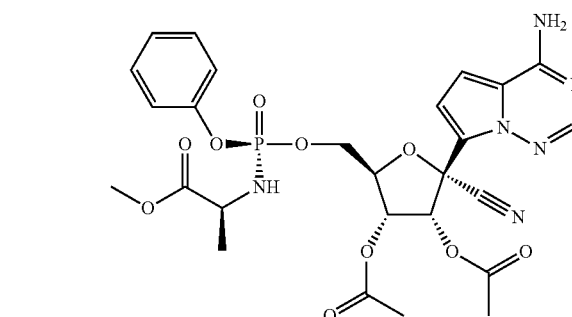

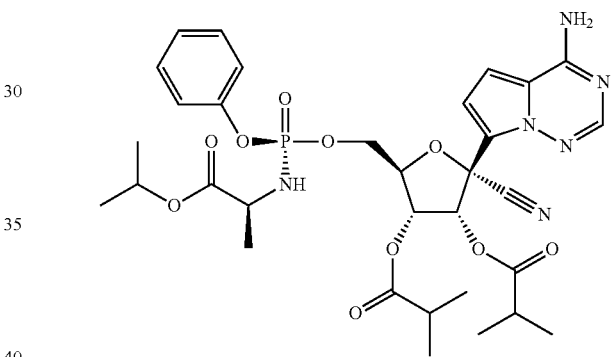

To a mixture of methyl ((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)-L-alaninate (prepared according to WO2017049060, 100 mg, 0.188 mmol) and 4-(dimethylamino)pyridine (3.4 mg, 0.028 mmol) in tetrahydrofuran (8 mL) was added acetic anhydride (35 µL, 0.376 mmol) at RT. After 30 min, the reaction mixture was diluted with ethyl acetate (50 mL) and the resulting mixture was washed with saturated sodium bicarbonate solution (50 mL). The organic phase was dried over anhydrous sodium sulfate and concentrated under reduced pressure. The crude residue was purified by preparatory HPLC (Gemini 5 um NX-C18 110A LC column 100×30 mm, 95% to 0% water acetonitrile gradient) to afford the product. $^1$H NMR (400 MHz, Methanol-$d_4$) δ $^1$H NMR (400 MHz, Methanol-$d_4$) δ 7.87 (s, 1H), 7.36-7.25 (m, 2H), 7.21-7.13 (m, 3H), 6.88-6.84 (m, 2H), 6.21 (d, J=5.9 Hz, 1H), 5.56 (dd, J=5.9, 4.2 Hz, 1H), 4.68-4.60 (m, 1H), 4.48-4.33 (m, 2H), 3.93-3.82 (m, 1H), 3.66 (s, 3H), 2.18 (s, 3H), 2.14 (s, 3H), 1.28 (d, J=7.1 Hz, 3H). $^{31}$P NMR (162 MHz, methanol-$d_4$) δ 3.54. MS m/z=617.20 [M+1].

To a mixture of isopropyl ((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)-L-alaninate (prepared according to WO2017049060, 100 mg, 0.18 mmol) and 4-(dimethylamino)pyridine (3.3 mg, 0.027 mmol) in tetrahydrofuran (2 mL) was added isobutyric anhydride (59.2 µL, 0.36 mmol) at RT. After 30 min, the reaction mixture was diluted with ethyl acetate (50 mL) and the resulting mixture was washed with saturated sodium bicarbonate solution (50 mL). The organic phase was dried over anhydrous sodium sulfate and concentrated under reduced pressure. The crude residue was purified by preparatory HPLC (Gemini 5 um NX-C18 110A LC column 100×30 mm, 95% to 0% water acetonitrile gradient) to afford the product. $^1$H NMR (400 MHz, methanol-$d_4$) δ 7.87 (s, 1H), 7.33-7.25 (m, 2H), 7.21-7.11 (m, 3H), 6.86 (d, J=4.6 Hz, 1H), 6.83 (d, J=4.6 Hz, 1H), 6.22 (d, J=5.9 Hz, 1H), 5.58 (dd, J=5.8, 3.7 Hz, 1H), 5.00-4.90 (m, 1H), 4.68-4.59 (m, 1H), 4.50-4.32 (m, 2H), 3.91-3.77 (m, 1H), 2.78-2.55 (m, 2H), 1.35-1.14 (m, 21H). $^{31}$P NMR (162 MHz, methanol-$d_4$) δ 3.64. MS m/z=700.80 [M+1].

Example 8: (2R,3R,4R,5R)-2-(4-aminopyrrolo[2,1-f][1,2,4]triazin-7-yl)-2-cyano-5-((((S)-(((S)-1-isopropoxy-1-oxopropan-2-yl)amino)(phenoxy)phosphoryl)oxy)methyl)tetrahydrofuran-3,4-diyl dipropionate Example 9: (2R,3R,4R,5R)-2-(4-aminopyrrolo[2,1-f][1,2,4]triazin-7-yl)-2-cyano-5-((((S)-(((S)-1-isopropoxy-1-oxopropan-2-yl)amino)(phenoxy)phosphoryl)oxy)methyl)tetrahydrofuran-3,4-diyl diacetate

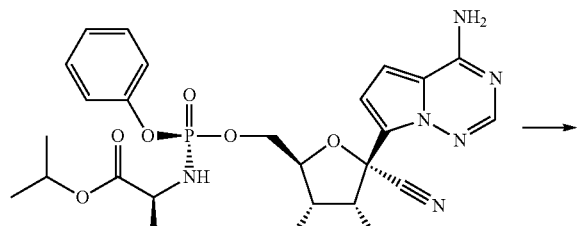

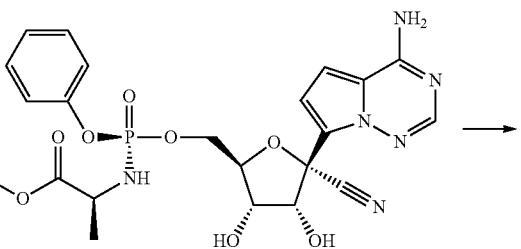

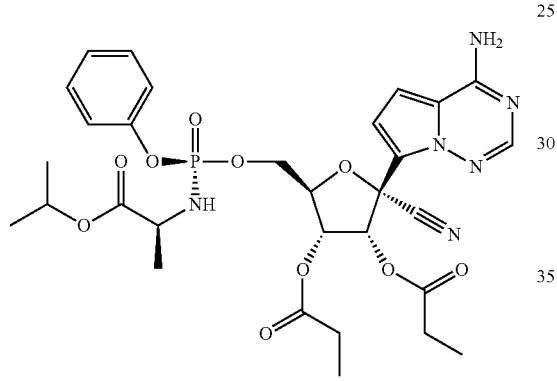

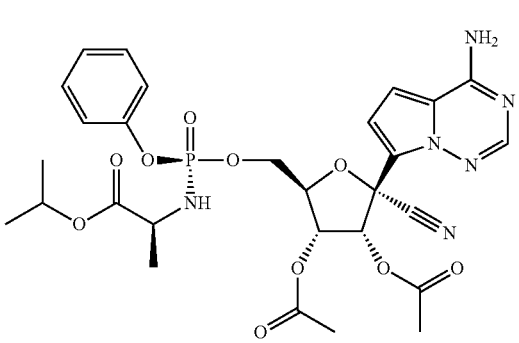

To a mixture of isopropyl ((S)-((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)-L-alaninate (Prepared according to WO2017049060, 100 mg, 0.18 mmol) and 4-(dimethylamino)pyridine (3.3 mg, 0.027 mmol) in tetrahydrofuran (2 mL) was added propionic anhydride (46 µL, 0.36 mmol) at RT. After 30 min, the reaction mixture was diluted with ethyl acetate (50 mL) and the resulting mixture was washed with saturated sodium bicarbonate solution (50 mL). The organic phase was dried over anhydrous sodium sulfate and concentrated under reduced pressure. The crude residue was purified by preparatory HPLC (Gemini 5 um NX-C18 110A LC column 100×30 mm, 95% to 0% water acetonitrile gradient) to afford the product. $^1$H NMR (400 MHz, methanol-$d_4$) δ 7.87 (s, 1H), 7.33-7.25 (m, 2H), 7.21-7.13 (m, 3H), 6.88-6.82 (m, 2H), 6.23 (d, J=5.9 Hz, 1H), 5.62-5.55 (m, 1H), 5.00-4.90 (m, 1H), 4.66-4.59 (m, 1H), 4.48-4.33 (m, 2H), 3.90-3.77 (m, 1H), 2.53-2.37 (m, 4H), 1.28 (dd, J=7.1, 1.1 Hz, 3H), 1.23-1.13 (m, 12H). $^{31}$P NMR (162 MHz, methanol-$d_4$) δ 3.60. MS m/z=672.80 [M+1].

To a mixture of isopropyl ((S)-((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)-L-alaninate (prepared according to WO2017049060, 100 mg, 0.18 mmol) and 4-(dimethylamino)pyridine (3.3 mg, 0.027 mmol) in tetrahydrofuran (2 mL) was added acetic anhydride (36 µL, 0.36 mmol) at RT. After 30 min, the reaction mixture was diluted with ethyl acetate (50 mL) and the resulting mixture was washed with saturated sodium bicarbonate solution (50 mL). The organic phase was dried over anhydrous sodium sulfate and concentrated under reduced pressure. The crude residue was purified by preparatory HPLC (Gemini 5 um NX-C18 110A LC column 100×30 mm, 95% to 0% water acetonitrile gradient) to afford the product. $^1$H NMR (400 MHz, methanol-$d_4$) δ 7.87 (s, 1H), 7.32-7.24 (m, 2H), 7.21-7.12 (m, 3H), 6.89-6.81 (m, 2H), 6.22 (d, J=5.9 Hz, 1H), 5.56 (dd, J=5.9, 4.2 Hz, 1H), 5.01-4.90 (m, 1H), 4.66-4.60 (m, 1H), 4.48-4.31 (m, 2H), 3.88-3.78 (m, 1H), 2.17 (s, 3H), 2.14 (s, 3H), 1.28 (dd, J=7.1, 1.1 Hz, 3H), 1.21 (dd, J=6.3, 1.4 Hz, 6H). $^{31}$P NMR (162 MHz, methanol-$d_4$) δ 3.64. MS m/z=644.80 [M+1].

Example 10: (2R,3R,4R,5R)-2-(4-aminopyrrolo[2,1-f][1,2,4]triazin-7-yl)-2-cyano-5-((((((S)-1-ethoxy-1-oxopropan-2-yl)amino)(phenoxy)phosphoryl)oxy)methyl)tetrahydrofuran-3,4-diyl bis(2-methylpropanoate)

Example 11: (2R,3R,4R,5R)-2-(4-aminopyrrolo[2,1-f][1,2,4]triazin-7-yl)-2-cyano-5-((((((S)-1-ethoxy-1-oxopropan-2-yl)amino)(phenoxy)phosphoryl)oxy)methyl)tetrahydrofuran-3,4-diyl dipropionate

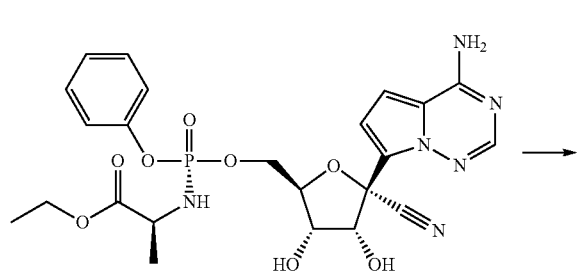

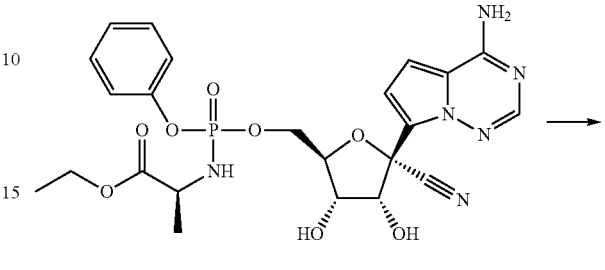

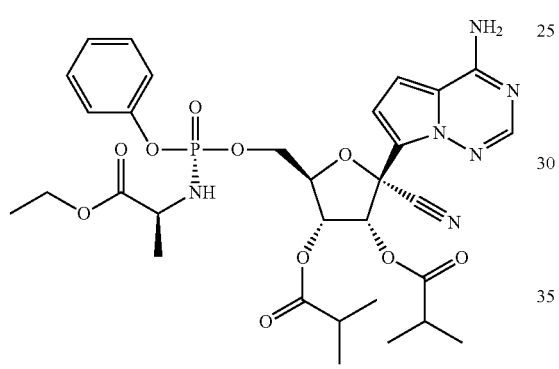

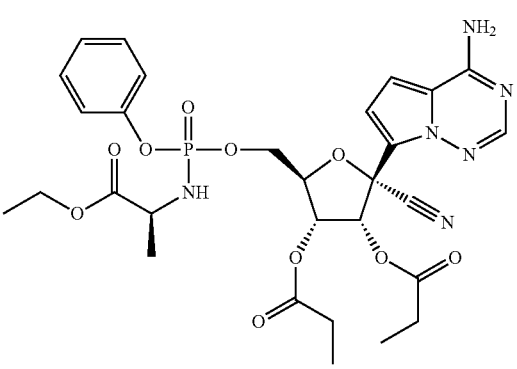

To a mixture of ethyl (((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)-L-alaninate (prepared according to WO2017049060, 200 mg, 0.37 mmol) and 4-(dimethylamino)pyridine (6.7 mg, 0.055 mmol) in tetrahydrofuran (2 mL) was added isobutyric anhydride (121 μL, 0.73 mmol) at RT. After 30 min, the reaction mixture was diluted with ethyl acetate (50 mL) and the resulting mixture was washed with saturated sodium bicarbonate solution (50 mL). The organic phase was dried over anhydrous sodium sulfate and concentrated under reduced pressure. The crude residue was purified by preparatory HPLC (Gemini 5 um NX-C18 110A LC column 100×30 mm, 95% to 0% water acetonitrile gradient) to afford the product. $^1$H NMR (400 MHz, Methanol-$d_4$) δ 7.87 (s, 1H), 7.37-7.25 (m, 2H), 7.23-7.12 (m, 3H), 6.94-6.81 (m, 2H), 6.30 (d, J=5.9 Hz, 0.5H), 6.21 (d, J=5.9 Hz, 0.5H), 5.62-5.55 (m, 1H), 4.69-4.59 (m, 1H), 4.54-4.33 (m, 2H), 4.19-4.03 (m, 2H), 3.92-3.70 (m, 1H), 2.77-2.55 (m, 2H), 1.36-1.10 (m, 18H). $^{31}$P NMR (162 MHz, methanol-$d_4$) δ 3.60. MS m/z=686.80 [M+1].

To a mixture of ethyl (((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)-L-alaninate (prepared according to WO2017049060, 200 mg, 0.37 mmol) and 4-(dimethylamino)pyridine (6.7 mg, 0.055 mmol) in tetrahydrofuran (2 mL) was added propionic anhydride (94 μL, 0.73 mmol) at RT. After 30 min, the reaction mixture was diluted with ethyl acetate (50 mL) and the resulting mixture was washed with saturated sodium bicarbonate solution (50 mL). The organic phase was dried over anhydrous sodium sulfate and concentrated under reduced pressure. The crude residue was purified by preparatory HPLC (Gemini 5 um NX-C18 110A LC column 100×30 mm, 95% to 0% water acetonitrile gradient) to afford the product. $^1$H NMR (400 MHz, Methanol-$d_4$) δ 7.89-7.84 (m, 1H), 7.37-7.25 (m, 2H), 7.22-7.12 (m, 3H), 6.94-6.82 (m, 2H), 6.32 (d, J=5.9 Hz, 0H), 6.23 (d, J=5.8 Hz, 1H), 5.64-5.54 (m, 1H), 4.68-4.61 (m, 1H), 4.54-4.31 (m, 2H), 4.20-4.02 (m, 2H), 3.94-3.70 (m, 1H), 2.55-2.37 (m, 4H), 1.33-1.10 (m, 12H). $^{31}$P NMR (162 MHz, methanol-$d_4$) δ 3.60. MS m/z=658.80 [M+1].

Example 12: (2R,3R,4R,5R)-2-(4-aminopyrrolo[2,1-f][1,2,4]triazin-7-yl)-2-cyano-5-((((((S)-1-ethoxy-1-oxopropan-2-yl)amino)(phenoxy)phosphoryl)oxy)methyl)tetrahydrofuran-3,4-diyl diacetate

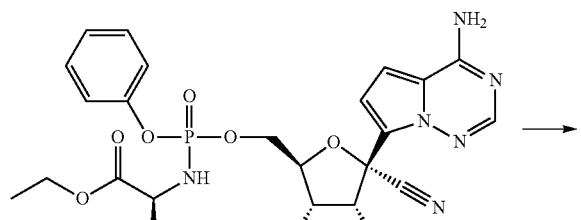

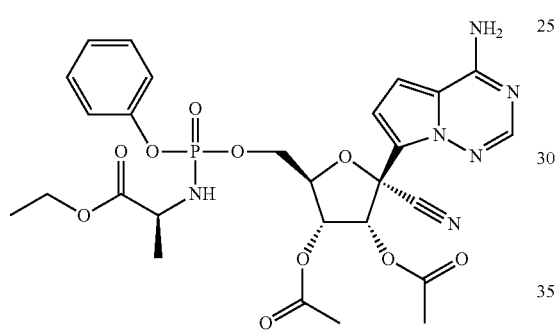

To a mixture of ethyl (((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)-L-alaninate (prepared according to WO2017049060, 200 mg, 0.37 mmol) and 4-(dimethylamino)pyridine (6.7 mg, 0.055 mmol) in tetrahydrofuran (2 mL) was added acetic anhydride (69 µL, 0.73 mmol) at RT. After 30 min, the reaction mixture was diluted with ethyl acetate (50 mL) and the resulting mixture was washed with saturated sodium bicarbonate solution (50 mL). The organic phase was dried over anhydrous sodium sulfate and concentrated under reduced pressure. The crude residue was purified by preparatory HPLC (Gemini 5 um NX-C18 110A LC column 100×30 mm, 95% to 0% water acetonitrile gradient) to afford the product. $^1$H NMR (400 MHz, Methanol-$d_4$) δ 7.87 (s, 0.5H), 7.86 (s, 0.5H), 7.36-7.25 (m, 2H), 7.22-7.13 (m, 3H), 6.93-6.90 (m, 1H), 6.88-6.84 (m, 1H), 6.30 (d, J=5.9 Hz, 0.5H), 6.21 (d, J=5.9 Hz, 0.5H), 5.62-5.52 (m, 1H), 4.69-4.59 (m, 1H), 4.53-4.29 (m, 2H), 4.18-4.01 (m, 2H), 3.91-3.70 (m, 1H), 2.19-2.12 (m, 6H), 1.31-1.15 (m, 6H). $^{31}$P NMR (162 MHz, methanol-$d_4$) δ 3.60. MS m/z=630.80 [M+1].

Example 13: 2-ethylbutyl (2S)-2-[[[(2R,5R)-5-(4-aminopyrrolo[2,1-f][1,2,4]triazin-7-yl)-5-cyano-3,4-dihydroxy-tetrahydrofuran-2-yl]methoxy-(4-tert-butylphenoxy)phosphoryl]amino]propanoate

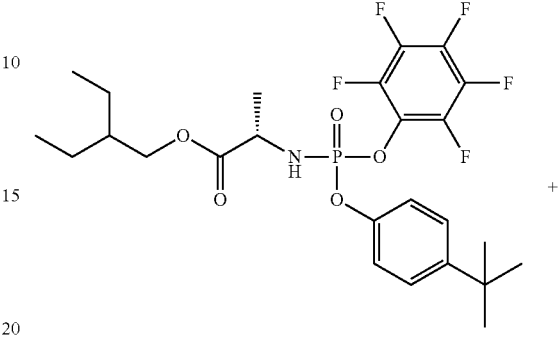

A1

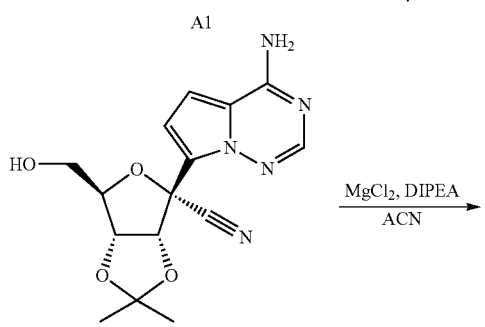

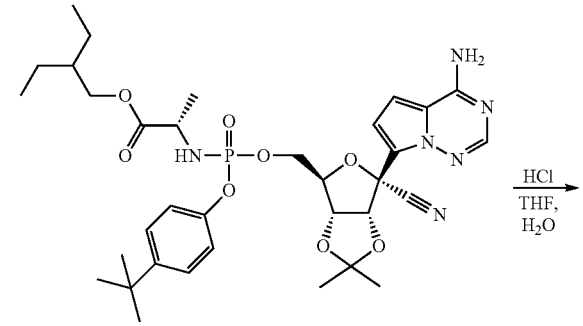

A2

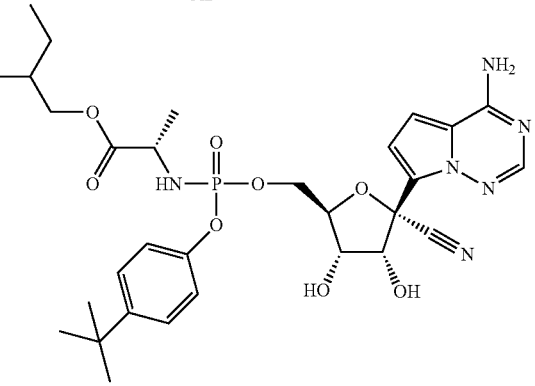

13

To a suspension of 2-ethylbutyl (2S)-2-[[(4-tert-butylphenoxy)-(2,3,4,5,6-pentafluorophenoxy)phosphoryl]amino]propanoate (Intermediate A1, 0.366 g, 0.664 mmol), (3aR, 4R,6R,6aR)-4-(4-aminopyrrolo[2,1-f][1,2,4]triazin-7-yl)-6-(hydroxymethyl)-2,2-dimethyltetrahydrofuro[3,4-d][1,3]

dioxole-4-carbonitrile (prepared according to WO2017049060, 0.200 g, 0.604 mmol) and magnesium chloride (0.058 g, 0.604 mmol) in acetonitrile (6 mL) under an atmosphere of argon was added N,N-diisopropylethylamine (0.263 mL, 1.51 mmol) at 0° C. After 10 min, the reaction was heated to 50° C. After 2 h, the reaction was cooled to room temperature, diluted with ethyl acetate and the organics were washed with water, dried over sodium sulfate, filtered and concentrated to afford Intermediate A2 (LCMS: MS m/z=698.8 and 698.8 [M+1], $t_R$=1.13 and 1.16 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min).

Intermediate A2 was taken up in tetrahydrofuran (2 mL) and concentrated hydrochloric acid (11.7 M, 0.400 mL, 4.66 mmol) was added. After 2 h, the reaction was diluted with ethyl acetate and neutralized with a saturated aqueous solution of sodium bicarbonate. The layers were separated, and the organics were washed with water, saturated aqueous sodium chloride, dried over sodium sulfate, filtered and concentrated. The product was purified by HPLC chromatography (0-100% acetonitrile in water) to afford the title compound (13). LCMS: MS m/z=658.9 and 658.9 [M+1], $t_R$=1.00 and 1.01 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min. $^1$H NMR (400 MHz, Methanol-$d_4$) δ (3:2 mixture of diastereomers) 7.89 (s, 0.6H), 7.87 (s, 0.4H), 7.36-7.28 (m, 2H), 7.14-7.09 (m, 1H), 7.09-7.04 (m, 1H), 6.98-6.91 (m, 2H), 4.82-4.79 (m, 1H), 4.48-4.26 (m, 3H), 4.20-4.16 (m, 1H), 4.10-3.83 (m, 3H), 1.55-1.44 (m, 1H), 1.40-1.25 (m, 16H), 0.95-0.85 (m, 6H). $^{31}$P NMR (162 MHz, Methanol-$d_4$) δ 3.99-3.73 (m). HPLC: $t_R$=3.10 min; HPLC system: Agilent 1100 series; Column: Gemini 5p C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min.

Individual isomers of Compound 13 were separated by preparatory HPLC (Gemini Sum NX-C18 110A LC column 100×30 mm, 95% to 0% water acetonitrile gradient).

Peak 1 Example 13a: LCMS: MS m/z=659.3 [M+1], $^1$H NMR (400 MHz, Methanol-d4) δ 7.87 (s, 1H), 7.32-7.26 (m, 2H), 7.09-7.02 (m, 2H), 6.93 (d, J=1.2 Hz, 2H), 4.80 (d, J=5.5 Hz, 1H), 4.48-4.36 (m, 2H), 4.32 (ddd, J=11.0, 5.7, 3.8 Hz, 1H), 4.17 (t, J=5.5 Hz, 1H), 4.08-3.95 (m, 2H), 3.88 (dq, J=9.2, 7.1 Hz, 1H), 1.50 (dt, J=12.4, 6.2 Hz, 1H), 1.35 (pd, J=7.4, 1.2 Hz, 4H), 1.30-1.25 (m, 12H), 0.89 (t, J=7.5 Hz, 6H); $^{31}$P NMR (162 MHz, Methanol-d4) δ 3.85.

Peak 2 Example 13b: LCMS: MS m/z=659.3 [M+1], $^1$H NMR (400 MHz, Methanol-d4) δ 7.88 (s, 1H), 7.36-7.29 (m, 2H), 7.14-7.08 (m, 2H), 6.98-6.88 (m, 2H), 4.81 (d, J=5.4 Hz, 1H), 4.47-4.33 (m, 2H), 4.33-4.24 (m, 1H), 4.18 (t, J=5.6 Hz, 1H), 4.04 (dd, J=10.9, 5.8 Hz, 1H), 3.93 (ddd, J=19.5, 10.3, 6.4 Hz, 2H), 1.48 (dt, J=12.4, 6.1 Hz, 1H), 1.41-1.20 (m, 16H), 0.87 (t, J=7.5 Hz, 6H); $^{31}$P NMR (162 MHz, Methanol-d4) δ 3.81.

Example 14: (2R,3R,4R,5R)-2-(4-aminopyrrolo[2,1-f][1,2,4]triazin-7-yl)-5-((((4-(tert-butyl)phenoxy) (((S)-1-(2-ethylbutoxy)-1-oxopropan-2-yl)amino) phosphoryl)oxy)methyl)-2-cyanotetrahydrofuran-3, 4-diyl bis(2-methylpropanoate

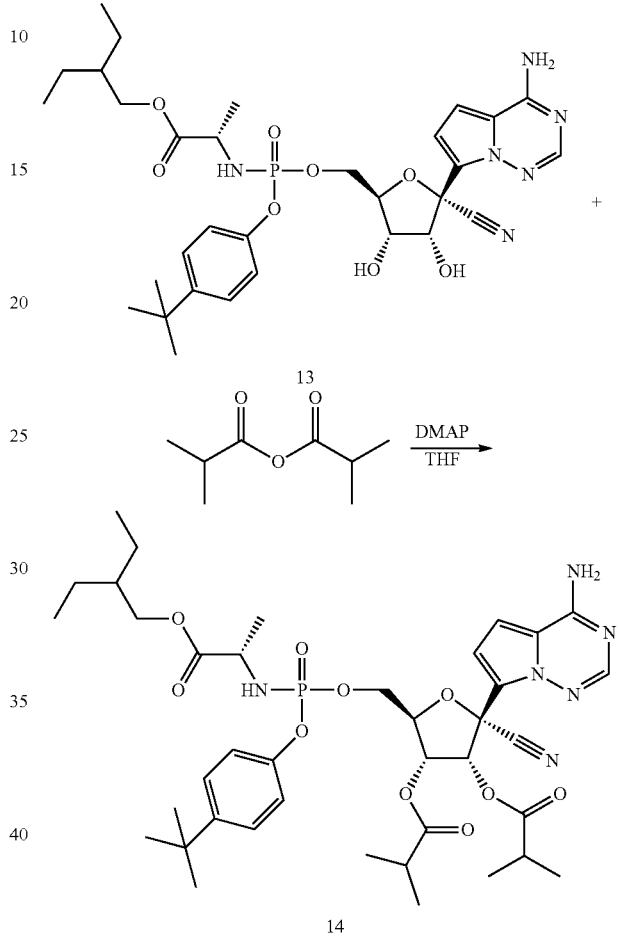

To a solution of 2-ethylbutyl (2S)-2-[[[(2R,5R)-5-(4-aminopyrrolo[2,1-f][1,2,4]triazin-7-yl)-5-cyano-3,4-dihydroxytetrahydrofuran-2-yl]methoxy-(4-tert-butylphenoxy)phosphoryl]amino]propanoate (Example 13, 50 mg, 0.0759 mmol) and 2-methylpropanoyl 2-methylpropanoate (26.4 mg, 0.167 mmol) in tetrahydrofuran (1 mL) was added 4-(dimethylamino)pyridine (1.4 mg, 0.011 mmol). After 1 h, the reaction was purified by HPLC chromatography (25-100% acetonitrile in water) to afford the title compound 14. LCMS: MS m/z=798.8 and 798.8 [M+1], $t_R$=1.23 and 1.29 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min. $^1$H NMR (400 MHz, Methanol-$d_4$) δ (1:1 mixture of diastereomers) 7.89-7.87 (m, 1H), 7.41-7.24 (m, 2H), 7.13-7.05 (m, 2H), 6.96-6.82 (m, 2H), 6.28 (d, J=5.9 Hz, 0.5H), 6.15 (d, J=5.9 Hz, 0.5H), 5.66-5.51 (m, 1H), 4.68-4.57 (m, 1H), 4.49-4.33 (m, 2H), 4.12-3.79 (m, 3H), 2.79-2.56 (m, 2H), 1.60-1.46 (m, 1H), 1.43-1.11 (m, 28H), 0.93-0.84 (m, 6H). $^{31}$P NMR (162

MHz, Methanol-$d_4$) δ 3.85-3.55 (m). HPLC: $t_R$=3.71 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min.

Example 15: Methyl (((((2R,3S,4R,5R)-5-(4-aminopyrrolo[2,1-f][1,2,4]triazin-7-yl)-5-cyano-3,4-dihydroxytetrahydrofuran-2-yl)methoxy)(4-(tert-butyl)phenoxy)phosphoryl)-L-alaninate Intermediate B2 was made in a similar manner as intermediate A2 except that intermediate B1 was used instead of intermediate A1. LCMS: MS m/z=628.9 and 628.9 [M+1], $t_R$=0.94 and 0.97 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min.

Compound 15 was made in a similar manner as compound 13 except that intermediate B2 was used instead of intermediate A2. LCMS: MS m/z=588.8 and 588.8 [M+1], $t_R$=0.80 and 0.82 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min. $^1$H NMR (400 MHz, Methanol-$d_4$) δ (1:1 mixture of diastereomers) 7.89 (s, 0.5H), 7.87 (s, 0.5H), 7.34-7.29 (m, 2H), 7.13-7.08 (m, 1H), 7.07-7.02 (m, 1H), 6.98-6.90 (m, 2H), 4.83-4.80 (m, 1H), 4.46-4.37 (m, 2H), 4.36-4.27 (m, 1H), 4.23-4.16 (m, 1H), 3.95-3.79 (m, 1H), 3.68-3.63 (m, 3H), 1.38-1.23 (m, 12H). $^{31}$P NMR (162 MHz, Methanol-$d_4$) δ 3.84. HPLC: $t_R$=2.62 and 2.65 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min.

Example 16: (2R,3R,4R,5R)-2-(4-aminopyrrolo[2,1-f][1,2,4]triazin-7-yl)-5-((((4-(tert-butyl)phenoxy)(((S)-1-methoxy-1-oxopropan-2-yl)amino)phosphoryl)oxy)methyl)-2-cyanotetrahydrofuran-3,4-diyl bis(2-methylpropanoate)

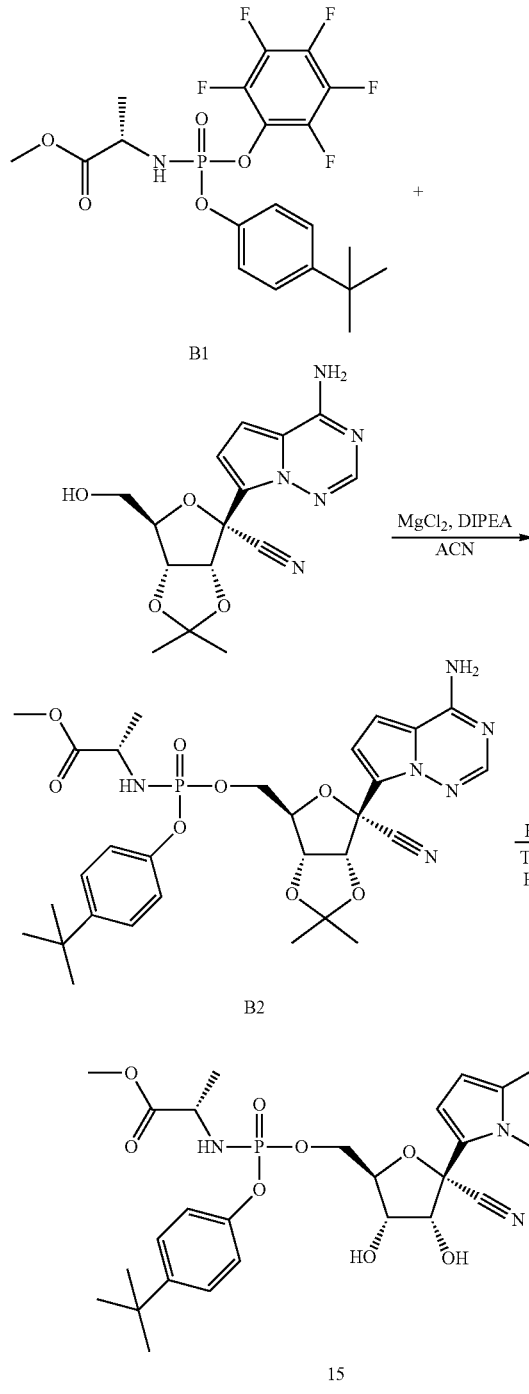

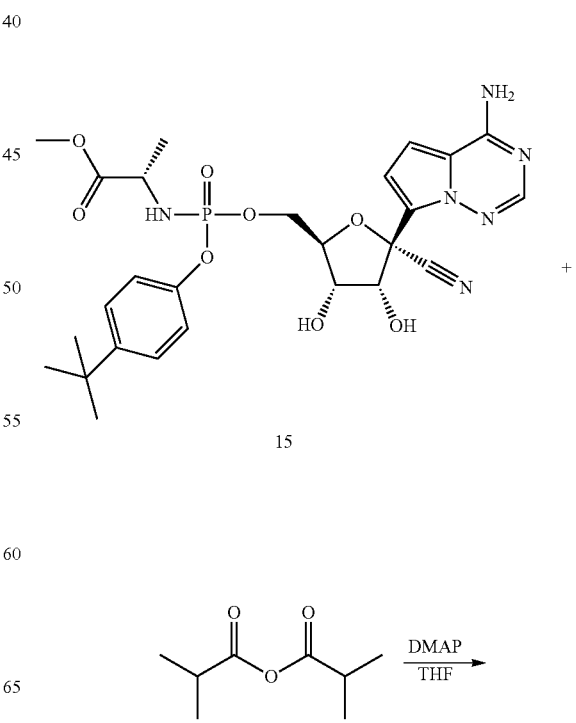

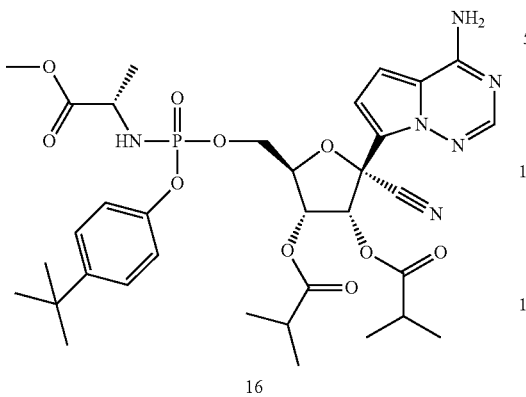

16

Compound 16 was made in a similar manner as compound 14 except that compound 15 was used instead of compound 13. LCMS: MS m/z=728.8 [M+1], $t_R$=1.09 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 µL/min. $^1$H NMR (400 MHz, Methanol-$d_4$) δ (1:1 mixture of diastereomers) 7.88 (s, 0.5H), 7.87 (s, 0.5H), 7.37-7.32 (m, 1H), 7.31-7.26 (m, 1H), 7.17-7.01 (m, 2H), 6.98-6.84 (m, 2H), 6.29 (d, J=5.9 Hz, 0.5H), 6.16 (d, J=5.9 Hz, 0.5H), 5.62-5.54 (m, 1H), 4.71-4.61 (m, 1H), 4.51-4.32 (m, 2H), 3.93-3.83 (m, 0.5H), 3.82-3.72 (m, 0.5H), 3.69-3.62 (m, 3H), 2.82-2.57 (m, 2H), 1.39-1.15 (m, 24H). $^{31}$P NMR (162 MHz, Methanol-$d_4$) δ 3.84-3.56 (m). HPLC: $t_R$=3.29 min; HPLC system: Agilent 1100 series; Column: Gemini 5µ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min.

Example 17: Ethyl ((((2R,3S,4R,5R)-5-(4-aminopyrrolo[2,1-f][1,2,4]triazin-7-yl)-5-cyano-3,4-dihydroxytetrahydrofuran-2-yl)methoxy)(4-(tert-butyl)phenoxy)phosphoryl)-L-alaninate

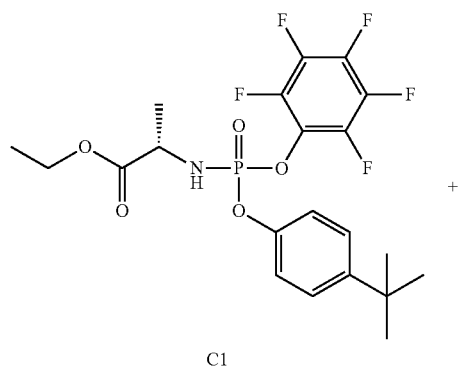

C1

+

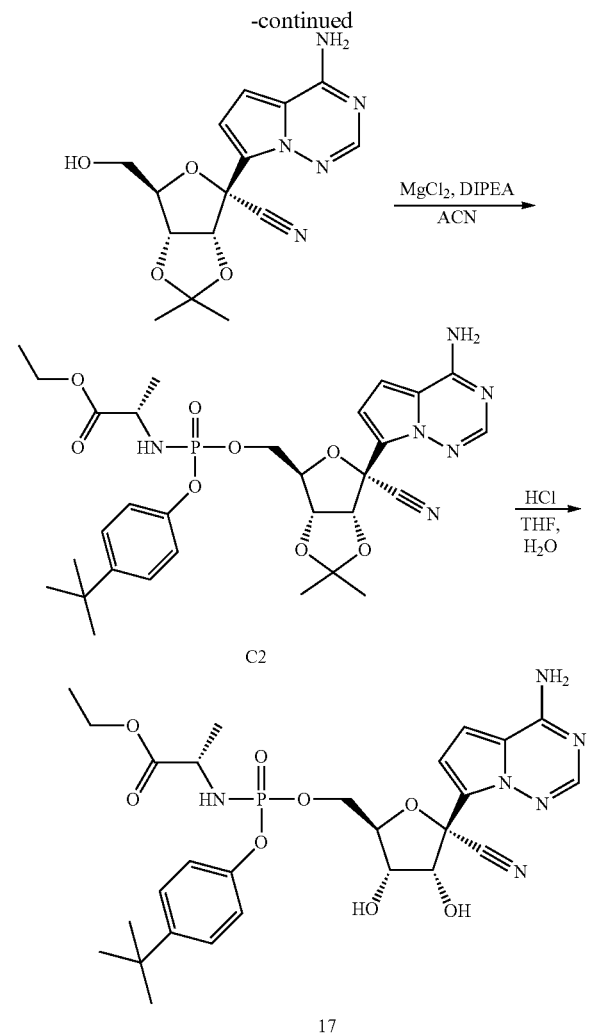

Intermediate C2 was made in a similar manner as intermediate A2 except that intermediate C1 was used instead of intermediate A1. LCMS: MS m/z=642.8 and 642.8 [M+1], $t_R$=0.98 and 1.00 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 µL/min.

Compound 17 was made in a similar manner as compound 13 except that intermediate C2 was used instead of intermediate A2. LCMS: MS m/z=602.8 and 602.8 [M+1], $t_R$=0.84 and 0.86 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 µL/min. $^1$H NMR (400 MHz, Methanol-$d_4$) δ (1:1 mixture of diastereomers) 7.89 (s, 0.5H), 7.87 (s, 0.5H), 7.36-7.28 (m, 2H), 7.13-7.08 (m, 1H), 7.08-7.04 (m, 1H), 6.98-6.90 (m, 2H), 4.84-4.79 (m, 1H), 4.48-4.36 (m, 2H), 4.35-4.25 (m, 1H), 4.21-4.17 (m, 1H), 4.15-4.05 (m, 2H), 3.92-3.78 (m, 1H), 1.36-1.14 (m, 15H). $^{31}$P NMR (162 MHz, Methanol-$d_4$) δ 4.04-3.76 (m). HPLC: $t_R$=2.78 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min.

Example 18: (2R,3R,4R,5R)-2-(4-aminopyrrolo[2,1-f][1,2,4]triazin-7-yl)-5-(((((4-(tert-butyl)phenoxy) (((S)-1-ethoxy-1-oxopropan-2-yl)amino)phosphoryl) oxy)methyl)-2-cyanotetrahydrofuran-3,4-diyl bis(2-methylpropanoate)

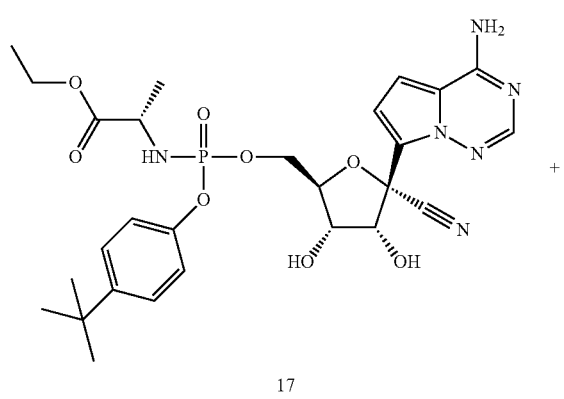

17

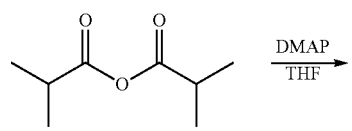

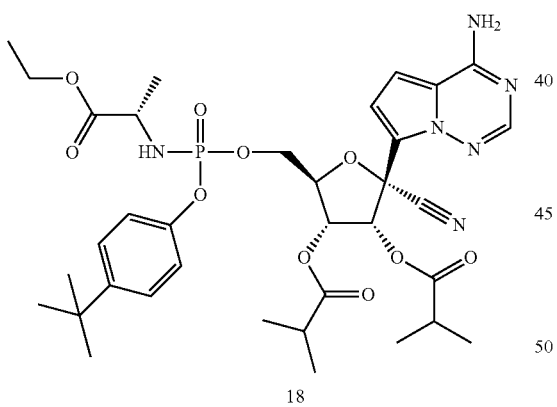

18

Compound 18 was made in a similar manner as compound 14 except that compound 17 was used instead of compound 13. LCMS: MS m/z=742.8 and 742.8 [M+1], $t_R$=1.12 and 1.13 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min. $^1$H NMR (400 MHz, Methanol-$d_4$) δ (1:1 mixture of diastereomers) 7.89-7.87 (m, 1H), 7.37-7.32 (m, 1H), 7.31-7.27 (m, 1H), 7.12-7.05 (m, 2H), 6.94-6.85 (m, 2H), 6.28 (d, J=5.9 Hz, 0.5H), 6.17 (d, J=5.9 Hz, 0.5H), 5.60-5.54 (m, 1H), 4.68-4.60 (m, 1H), 4.48-4.34 (m, 2H), 4.18-4.05 (m, 2H), 3.93-3.83 (m, 0.5H), 3.81-3.71 (m, 0.5H), 2.74-2.57 (m, 2H), 1.34-1.16 (m, 27H). $^{31}$P NMR (162 MHz, Methanol-$d_4$) δ 3.84-3.59 (m). HPLC: $t_R$=3.37 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min.

Individual isomers of Compound 18 were separated by preparatory HPLC (Gemini 5 um NX-C18 110A LC column 100×30 mm, 95% to 0% water acetonitrile gradient).

Peak 1: Example 18a: LCMS: MS m/z=743.3 [M+1], $^1$H NMR (400 MHz, Methanol-d4) δ 7.87 (s, 1H), 7.37-7.31 (m, 2H), 7.14-7.06 (m, 2H), 6.96-6.85 (m, 2H), 6.28 (d, J=5.9 Hz, 1H), 5.56 (dd, J=5.9, 3.9 Hz, 1H), 4.64 (dt, J=5.8, 2.8 Hz, 1H), 4.42 (qdd, J=11.6, 5.6, 3.5 Hz, 2H), 4.10 (qd, J=7.2, 2.5 Hz, 2H), 3.77 (dq, J=9.2, 7.1 Hz, 1H), 3.62 (q, J=7.0 Hz, 1H), 2.66 (dp, J=20.9, 7.0 Hz, 2H), 1.31 (s, 9H), 1.29-1.22 (m, 8H), 1.19 (dt, J=6.9, 2.0 Hz, 13H); $^{31}$P NMR (162 MHz, Methanol-d4) δ 3.69.

Peak 2: Example 18b: LCMS: MS m/z=743.3 [M+1], $^1$H NMR (400 MHz, Methanol-d4) δ 7.88 (s, 1H), 7.32-7.26 (m, 2H), 7.12-7.04 (m, 2H), 6.93-6.84 (m, 2H), 6.17 (d, J=5.9 Hz, 1H), 5.57 (dd, J=5.9, 3.8 Hz, 1H), 4.62 (qd, J=3.8, 1.8 Hz, 1H), 4.48-4.32 (m, 2H), 4.12 (qd, J=7.1, 3.1 Hz, 2H), 3.88 (dq, J=9.8, 7.1 Hz, 1H), 3.62 (q, J=7.0 Hz, 1H), 3.37 (s, 1H), 2.66 (dp, J=23.6, 7.0 Hz, 2H), 1.33-1.27 (m, 14H), 1.26 (s, 3H), 1.25-1.22 (m, 4H), 1.22-1.17 (m, 8H); $^{31}$P NMR (162 MHz, Methanol-d4) δ 3.81-3.56 (m).

Example 19: 2-Ethylbutyl (((((2R,3S,4R,5R)-5-(4-aminopyrrolo[2,1-f][1,2,4]triazin-7-yl)-5-cyano-3,4-dihydroxytetrahydrofuran-2-yl)methoxy)(2,6-dimethylphenoxy)phosphoryl)-L-alaninate

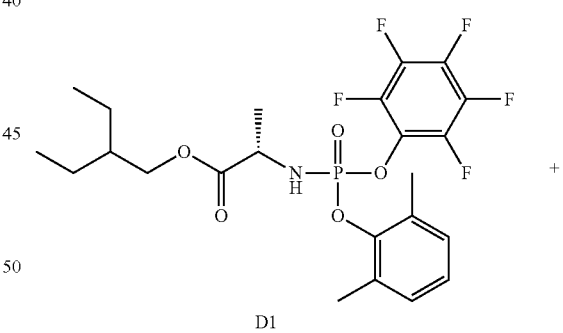

D1

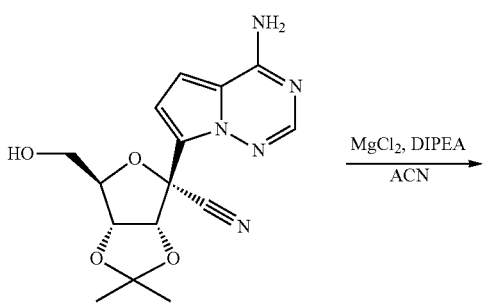

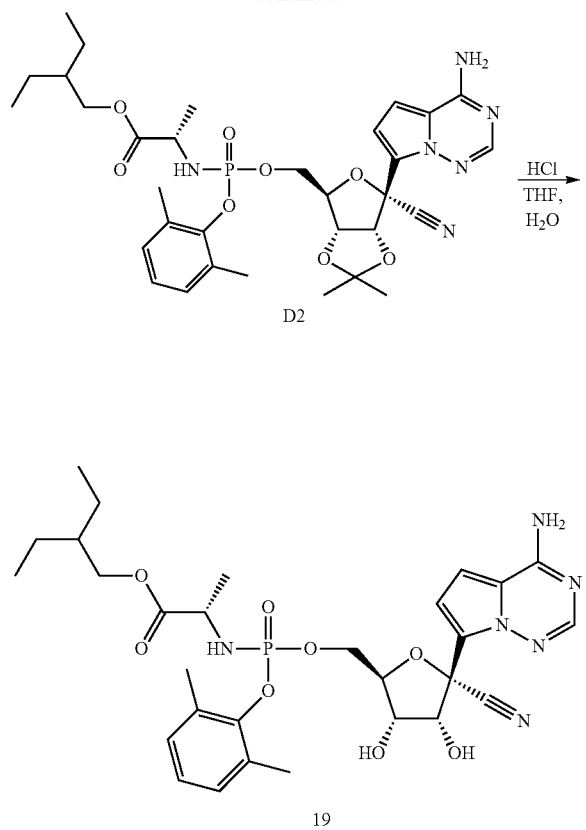

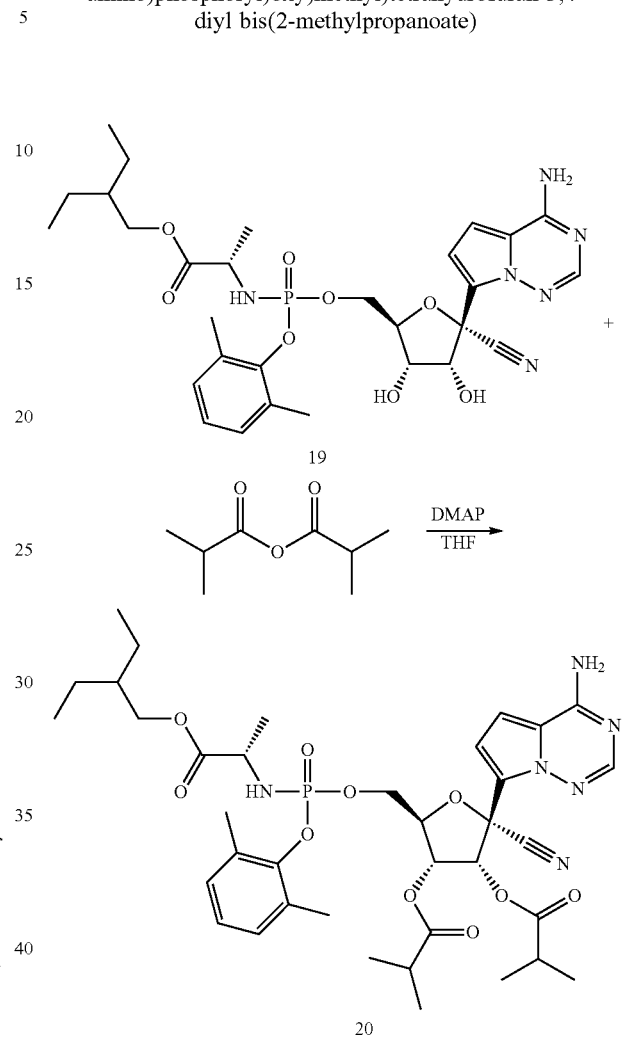

Example 20: (2R,3R,4R,5R)-2-(4-aminopyrrolo[2,1-f][1,2,4]triazin-7-yl)-2-cyano-5-((((2,6-dimethylphenoxy)(((S)-1-(2-ethylbutoxy)-1-oxopropan-2-yl)amino)phosphoryl)oxy)methyl)tetrahydrofuran-3,4-diyl bis(2-methylpropanoate)

Intermediate D2 was made in a similar manner as intermediate A2 except that intermediate D1 was used instead of intermediate A1. LCMS: MS m/z=670.8 and 670.8 [M+1], $t_R$=1.08 and 1.11 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min.

Compound 19 was made in a similar manner as compound 13 except that intermediate D2 was used instead of intermediate A2. LCMS: MS m/z=630.8 and 630.8 [M+1], $t_R$=0.92 and 0.94 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min. $^1$H NMR (400 MHz, Methanol-$d_4$) δ (5:2 mixture of diastereomers) 7.89 (s, 0.7H), 7.88 (s, 0.3H), 7.01-6.88 (m, 5H), 4.70 (d, J=5.6 Hz, 0.3H), 4.67 (d, J=5.4 Hz, 0.7H), 4.40-4.19 (m, 3H), 4.15-4.11 (m, 1H), 4.09-3.89 (m, 3H), 2.33-2.27 (m, 6H), 1.53-1.45 (m, 1H), 1.41-1.26 (m, 7H), 0.91-0.84 (m, 6H). $^{31}$P NMR (162 MHz, Methanol-$d_4$) δ (5:2 mixture of diastereomers) 4.29-4.08 (m, 0.3P), 3.92-3.64 (m, 0.7P). HPLC: $t_R$=2.91 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min.

Compound 20 was made in a similar manner as compound 14 except that compound 19 was used instead of compound 13. LCMS: MS m/z=770.8 and 770.8 [M+1], $t_R$=1.19 and 1.21 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min. $^1$H NMR (400 MHz, Methanol-d4) δ (1:1 mixture of diastereomers) 7.88 (s, 1H), 7.03-6.92 (m, 3H), 6.89-6.87 (m, 1H), 6.83-6.79 (m, 1H), 6.12 (s, 0.5H), 6.11 (s, 0.5H), 5.53-5.49 (m, 1H), 4.56-4.51 (m, 1H), 4.37-4.33 (m, 2H), 4.10-4.04 (m, 1H), 4.01-3.91 (m, 2H), 2.73-2.57 (m, 2H), 2.36-2.22 (m, 6H), 1.56-1.45 (m, 1H), 1.41-1.31 (m, 7H), 1.29-1.22 (m, 6H), 1.20-1.16 (m, 6H), 0.92-0.87 (m, 6H). $^{31}$P NMR (162 MHz, Methanol-$d_4$) δ 3.80-3.55 (m). HPLC: $t_R$=3.57 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min.

Example 21: (2R,3R,4R,5R)-2-(4-Aminopyrrolo[2,1-f][1,2,4]triazin-7-yl)-2-cyano-5-((((((S)-1-cyclobutoxy-1-oxopropan-2-yl)amino)(phenoxy)phosphoryl)oxy)methyl)tetrahydrofuran-3,4-diyl bis(2-methylpropanoate)

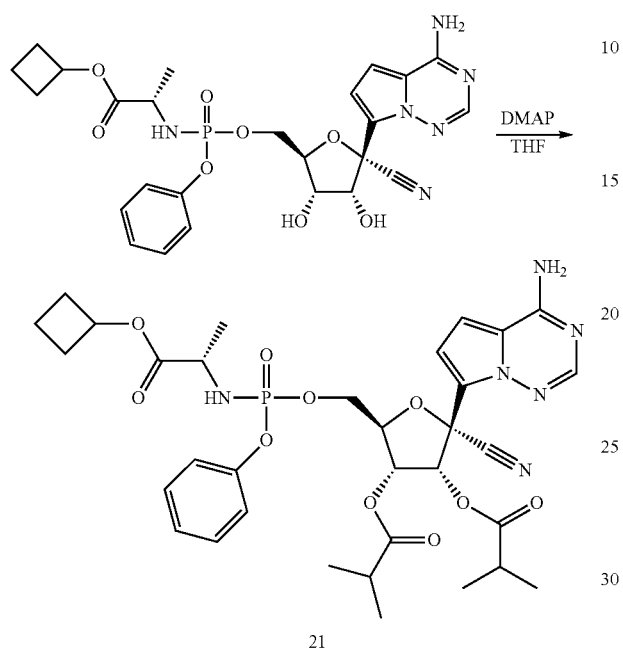

Compound 21 was made in a similar manner as compound 14 except that cyclobutyl ((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)-L-alaninate (prepared according to US 2015 14926062) was used instead of compound 13. LCMS: MS m/z=712.8 and 712.8 [M+1], $t_R$=1.05 and 1.06 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min. $^1$H NMR (400 MHz, Methanol-d$_4$) δ (1:1 mixture of diastereomers) 7.89-7.85 (m, 1H), 7.36-7.26 (m, 2H), 7.22-7.15 (m, 3H), 6.93-6.89 (m, 1H), 6.88-6.81 (m, 1H), 6.30 (d, J=5.9 Hz, 0.5H), 6.22 (d, J=5.9 Hz, 0.5H), 5.61-5.54 (m, 1H), 4.92-4.89 (m, 1H), 4.67-4.59 (m, 1H), 4.50-4.32 (m, 2H), 3.92-3.73 (m, 1H), 2.76-2.58 (m, 2H), 2.37-2.25 (m, 2H), 2.11-1.98 (m, 2H), 1.85-1.72 (m, 1H), 1.71-1.60 (m, 1H), 1.34-1.15 (m, 15H). $^{31}$P NMR (162 MHz, Methanol-d$_4$) δ 3.60. HPLC: $t_R$=3.17 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min.

Individual isomers of Compound 21 were separated by preparatory HPLC (Gemini Sum NX-C18 110A LC column 100×30 mm, 95% to 0% water acetonitrile gradient).

Peak 1: Example 21a LCMS: MS m/z=713.3 [M+1], $^1$H NMR (400 MHz, Methanol-d4) δ 7.87 (s, 1H), 7.32-7.25 (m, 2H), 7.22-7.12 (m, 3H), 6.89-6.81 (m, 2H), 6.22 (d, J=5.9 Hz, 1H), 5.58 (dd, J=5.9, 3.8 Hz, 1H), 4.98-4.89 (m, 1H), 4.61 (qd, J=3.9, 1.7 Hz, 1H), 4.40 (qdd, J=11.5, 6.2, 3.9 Hz, 2H), 3.85 (dq, J=9.8, 7.1 Hz, 1H), 2.66 (dp, J=24.1, 7.0 Hz, 2H), 2.37-2.23 (m, 1H), 2.12-1.95 (m, 1H), 1.85-1.72 (m, 1H), 1.71-1.58 (m, 1H), 1.34-1.22 (m, 9H), 1.19 (d, J=7.0 Hz, 6H), 1.11 (d, J=6.9 Hz, 1H); $^{31}$P NMR (162 MHz, Methanol-d4) δ 3.55.

Peak 2: Example 21b: LCMS: MS m/z=713.3 [M+1], $^1$H NMR (400 MHz, Methanol-d4) δ 7.87 (s, 1H), 7.32 (dd, J=8.8, 7.1 Hz, 2H), 7.19 (dd, J=8.0, 1.3 Hz, 3H), 6.91 (s, 2H), 6.30 (d, J=5.9 Hz, 1H), 5.58 (dd, J=5.9, 3.8 Hz, 1H), 4.92 (q, J=7.5 Hz, 1H), 4.65 (qd, J=3.7, 1.9 Hz, 1H), 4.53-4.34 (m, 2H), 3.78 (dq, J=9.3, 7.1 Hz, 1H), 2.66 (dp, J=22.4, 7.0 Hz, 2H), 2.36-2.23 (m, 2H), 2.11-1.94 (m, 2H), 1.85-1.73 (m, 1H), 1.70-1.58 (m, 1H), 1.25 (dd, J=9.1, 7.0 Hz, 7H), 1.19 (ddd, J=7.1, 3.7, 1.2 Hz, 10H), 1.15 (d, J=7.0 Hz, 1H). $^{31}$P NMR (162 MHz, Methanol-d$_4$) δ 3.61.

Example 22: 2-(2-Ethoxyethoxy)ethyl ((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)-L-alaninate

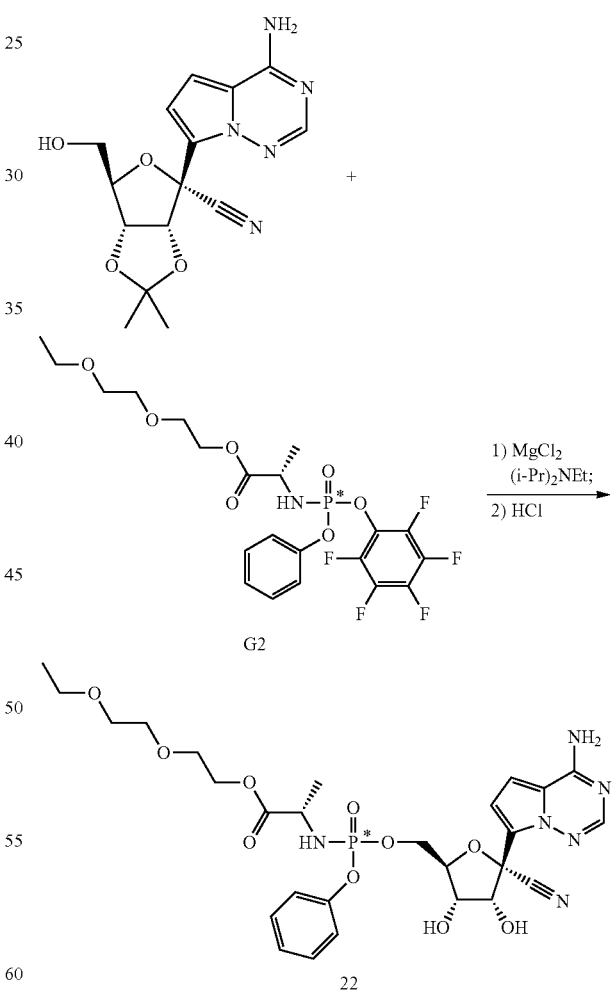

Tetrahydrofuran (14 mL) was added to a mixture of (3aR,4R,6R,6aR)-4-(4-aminopyrrolo[2,1-f][1,2,4]triazin-7-yl)-6-(hydroxymethyl)-2,2-dimethyltetrahydrofuro[3,4-d][1,3]dioxole-4-carbonitrile (prepared according to WO2016069825, 2.00 g, 6.04 mmol), intermediate G2 (4.14 g, 7.85 mmol), and magnesium chloride (862 mg, 9.05 mmol) at room temperature. The mixture was heated to 40° C. for 10 min, and N,N-diisopropylethylamine (2.63 mL, 15.1 mmol) was added. After stirring for 2 hours at 40° C., the reaction mixture was allowed to cool to room temperature and was concentrated down under reduced pressure. The crude residue was dissolved in ethyl acetate (100 mL) and the resulting mixture was washed with water (100 mL) and brine (100 mL). The organic layer was separated, dried over anhydrous sodium sulfate and concentrated under reduced pressure. The crude residue was dissolved in acetonitrile (100 mL) and concentrated aqueous hydrochloric acid (5.03 mL) was added dropwise at 0° C. After 4 hours at 0° C., the reaction mixture was diluted with ethyl acetate (100 mL) and water (100 mL) at 0° C. and the resulting mixture was washed with saturated aqueous sodium bicarbonate solution (100 mL) and brine (50 mL). The organic layer was dried over anhydrous sodium sulfate and concentrated under reduced pressure. The crude residue was purified by silica gel column chromatography using gradient from 0-10% methanol in dichloromethane to afford the title compound. LCMS: MS m/z=634.8 [M+1], $t_R$=0.71 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min. $^1$H NMR (400 MHz, DMSO-$d_6$) δ 8.03-7.83 (m, 3H), 7.40-7.29 (m, 2H), 7.22-7.09 (m, 3H), 6.88 (d, J=4.5 Hz, 1H), 6.82 (d, J=4.5 Hz, 1H), 6.35 (d, J=6.1 Hz, 1H), 6.17-5.98 (m, 1H), 5.39 (d, J=5.7 Hz, 1H), 4.70-4.54 (m, 1H), 4.29-4.19 (m, 2H), 4.18-4.02 (m, 3H), 4.00-3.91 (m, 1H), 3.88-3.73 (m, 1H), 3.60-3.51 (m, 2H), 3.50-3.44 (m, 2H), 3.45-3.36 (m, 4H), 1.20 (d, J=7.1 Hz, 3H), 1.07 (t, J=7.0 Hz, 3H). $^{31}$P NMR (162 MHz, DMSO-$d_6$) δ 3.81. HPLC: $t_R$=2.36 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min.

Example 23: (2R,3R,4R,5R)-2-(4-Aminopyrrolo[2,1-f][1,2,4]triazin-7-yl)-2-cyano-5-(((((S)-1-(2-(2-ethoxyethoxy)ethoxy)-1-oxopropan-2-yl)amino)(phenoxy)phosphoryl)oxy)methyl)tetrahydrofuran-3,4-diyl bis(2-methylpropanoate)

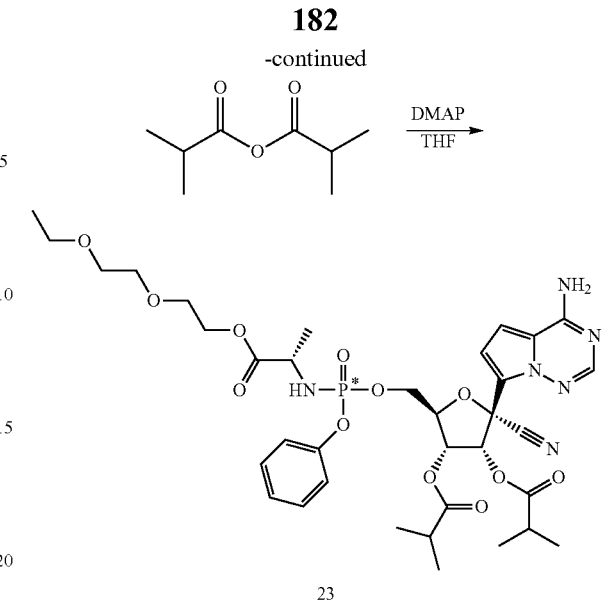

Compound 23 was made in a similar manner as compound 14 except that compound 22 was used instead of compound 13. LCMS: MS m/z=774.8 [M+1], $t_R$=1.00 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min. $^1$H NMR (400 MHz, Methanol-$d_4$) δ 7.88 (s, 1H), 7.33-7.26 (m, 2H), 7.21-7.13 (m, 3H), 6.86 (d, J=4.6 Hz, 1H), 6.83 (d, J=4.6 Hz, 1H), 6.20 (d, J=5.8 Hz, 1H), 5.59 (dd, J=5.8, 3.6 Hz, 1H), 4.67-4.61 (m, 1H), 4.47-4.36 (m, 2H), 4.27-4.16 (m, 2H), 3.95-3.84 (m, 1H), 3.69-3.65 (m, 2H), 3.62-3.59 (m, 2H), 3.58-3.48 (m, 4H), 2.76-2.57 (m, 2H), 1.34-1.24 (m, 9H), 1.21-1.15 (m, 9H). $^{31}$P NMR (162 MHz, Methanol-$d_4$) δ 3.62-3.33 (m). HPLC: $t_R$=3.02 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min.

Example 24: 2-Methoxy-2-methylpropyl ((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)-L-alaninate

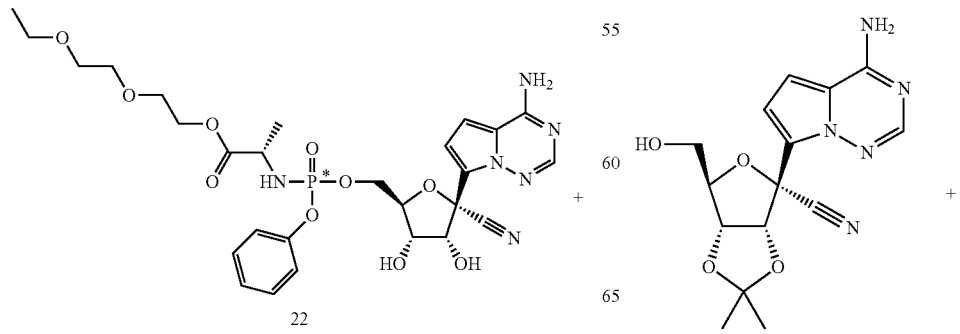

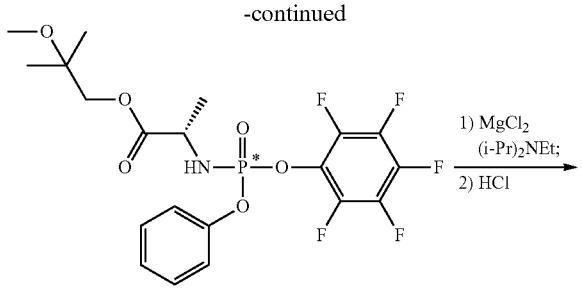

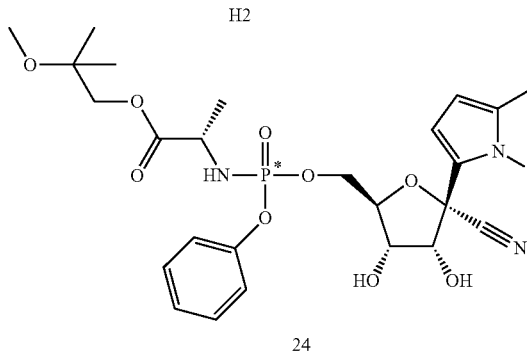

Tetrahydrofuran (11 mL) was added to a mixture of (3aR,4R,6R,6aR)-4-(4-aminopyrrolo[2,1-f][1,2,4]triazin-7-yl)-6-(hydroxymethyl)-2,2-dimethyltetrahydrofuro[3,4-d][1,3]dioxole-4-carbonitrile (prepared according to WO2016069825, 1500 mg, 4.53 mmol), intermediate H2 (2480 mg, 4.98 mmol), and magnesium chloride (647 mg, 6.79 mmol) at room temperature. The mixture was heated to 40° C. for 10 min, and N,N-diisopropylethylamine (1.97 mL, 11.3 mmol) was added. After stirring for 2 hours at 40° C., the reaction mixture was allowed to cool to room temperature and was concentrated down under reduced pressure. The crude residue was dissolved in ethyl acetate (100 mL) and the resulting mixture was washed with water (100 mL) and brine (100 mL). The organic layer was separated, dried over anhydrous sodium sulfate and concentrated under reduced pressure. The crude residue was dissolved in acetonitrile (75 mL) and concentrated aqueous hydrochloric acid (3.77 mL) was added dropwise at 0° C. After 4 hours at 0° C., the reaction mixture was diluted with ethyl acetate (100 mL) and water (100 mL) at 0° C. and the resulting mixture was washed with saturated aqueous sodium bicarbonate solution (100 mL) and brine (50 mL). The organic layer was dried over anhydrous sodium sulfate and concentrated under reduced pressure. The crude residue was purified by silica gel column chromatography using gradient from 0-10% methanol in dichloromethane to afford the title compound. LCMS: MS m/z=604.8 [M+1], $t_R$=0.72 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min. $^1$H NMR (400 MHz, DMSO-$d_6$) δ 8.17-7.81 (m, 3H), 7.41-7.27 (m, 2H), 7.27-7.06 (m, 3H), 6.89 (d, J=4.5 Hz, 1H), 6.82 (d, J=4.5 Hz, 1H), 6.36 (d, J=6.1 Hz, 1H), 6.21-5.97 (m, 1H), 5.39 (d, J=5.8 Hz, 1H), 4.71-4.51 (m, 1H), 4.35-4.18 (m, 2H), 4.14-4.03 (m, 1H), 4.01-3.89 (m, 2H), 3.90-3.74 (m, 2H), 3.06 (s, 3H), 1.22 (d, J=7.1 Hz, 3H), 1.06 (s, 6H). $^{31}$P NMR (162 MHz, DMSO-$d_6$) δ 3.83. HPLC: $t_R$=2.36 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min.

Example 25: (2R,3R,4R,5R)-2-(4-aminopyrrolo[2,1-f][1,2,4]triazin-7-yl)-2-cyano-5-((((((S)-1-(2-methoxy-2-methylpropoxy)-1-oxopropan-2-yl)amino)(phenoxy)phosphoryl)oxy)methyl)tetrahydrofuran-3,4-diyl bis(2-methylpropanoate)

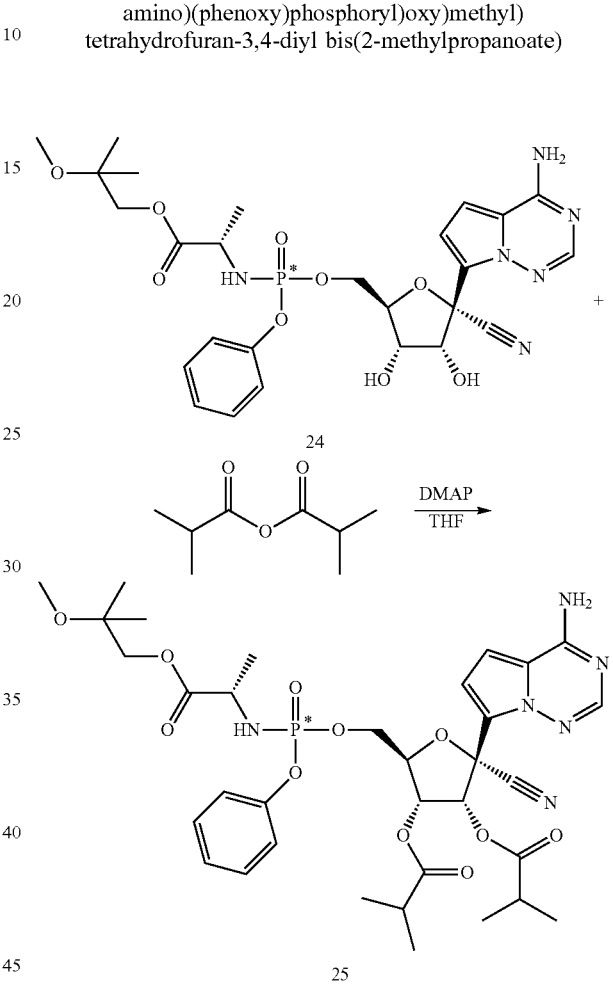

Compound 25 was made in a similar manner as compound 14 except that compound 24 was used instead of compound 13. LCMS: MS m/z=744.8 [M+1], $t_R$=1.01 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min. $^1$H NMR (400 MHz, Methanol-$d_4$) δ 7.88 (s, 1H), 7.31-7.26 (m, 2H), 7.21-7.13 (m, 3H), 6.86 (d, J=4.7 Hz, 1H), 6.82 (d, J=4.7 Hz, 1H), 6.19 (d, J=5.9 Hz, 1H), 5.57 (dd, J=5.9, 3.7 Hz, 1H), 4.70-4.58 (m, 1H), 4.52-4.34 (m, 2H), 4.07 (d, J=11.5 Hz, 1H), 4.00-3.90 (m, 2H), 3.21 (s, 3H), 2.75-2.57 (m, 2H), 1.36-1.31 (m, 3H), 1.29-1.23 (m, 6H), 1.21-1.16 (m, 12H). $^{31}$P NMR (162 MHz, Methanol-$d_4$) δ 3.63-3.28 (m). HPLC: $t_R$=3.04 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min.

Example 26. 2-Ethylbutyl ((((2R,3S,4R,5R)-5-(4-aminopyrrolo[2,1-f][1,2,4]triazin-7-yl)-5-cyano-3,4-dihydroxytetrahydrofuran-2-yl)methoxy)(2-isopropyl-5-methylphenoxy)phosphoryl)-L-alaninate

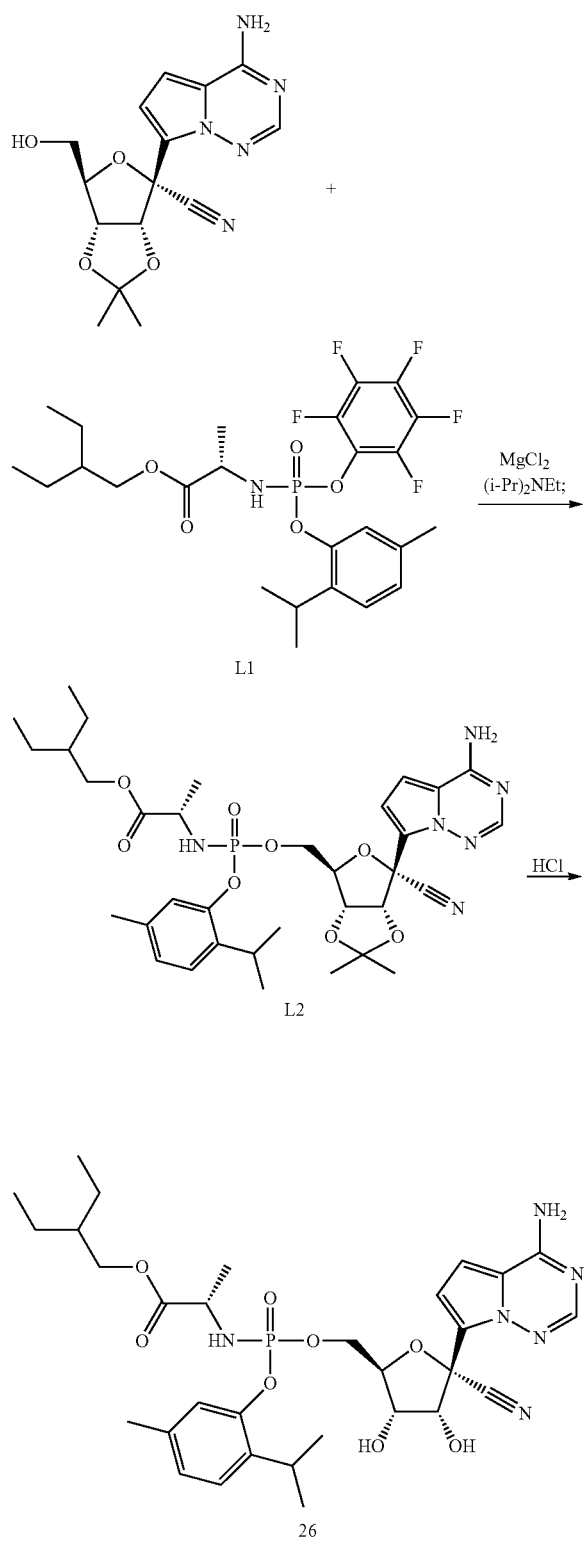

Tetrahydrofuran (11 mL) was added to a mixture of (3aR,4R,6R,6aR)-4-(4-aminopyrrolo[2,1-f][1,2,4]triazin-7-yl)-6-(hydroxymethyl)-2,2-dimethyltetrahydrofuro[3,4-d][1,3]dioxole-4-carbonitrile (prepared according to WO2016069825, 1000 mg, 3.02 mmol), intermediate L1 (2160 mg, 3.92 mmol), and magnesium chloride (431 mg, 4.53 mmol) at room temperature. The mixture was heated to 40° C. for 10 min, and N,N-diisopropylethylamine (1.3 mL, 7.55 mmol) was added. After stirring for 2 hours at 40° C., the reaction mixture was allowed to cool to room temperature and was concentrated down under reduced pressure. The crude residue was dissolved in ethyl acetate (30 mL) and the resulting mixture was washed with water (20 mL) and brine (20 mL). The organic layer was separated, dried over anhydrous sodium sulfate and concentrated under reduced pressure to afford crude intermediate L2. LCMS: MS m/z=698.8 and 698.8 [M+1], $t_R$=1.15 and 1.17 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min.

The crude residue was dissolved in acetonitrile (50 mL) and concentrated aqueous hydrochloric acid (2.52 mL) was added dropwise at 0° C. After 4 hours at 0° C., the reaction mixture was diluted with ethyl acetate (100 mL) and water (30 mL) at 0° C. and the resulting mixture was washed with saturated aqueous sodium bicarbonate solution (30 mL) and brine (20 mL). The organic layer was dried over anhydrous sodium sulfate and concentrated under reduced pressure. The crude residue was purified by silica gel column chromatography using gradient from 0-10% methanol in dichloromethane to afford the title compound 26. Single isomers of 26 were separated by preparatory HPLC (Gemini Sum NX-C18 110A LC column 100×30 mm, 95% to 0% water acetonitrile gradient).

Peak 1 (26a) (faster eluting isomer) data: LCMS: MS m/z=658.9 [M+1], $t_R$=0.99 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min. $^1$H NMR (400 MHz, DMSO-d$_6$) δ 8.07-7.83 (m, 3H), 7.14 (d, J=7.9 Hz, 1H), 7.06 (s, 1H), 6.91 (d, J=7.7 Hz, 1H), 6.87 (d, J=4.5 Hz, 1H), 6.80 (d, J=4.5 Hz, 1H), 6.34 (d, J=6.2 Hz, 1H), 6.13-6.01 (m, 1H), 5.41 (d, J=5.7 Hz, 1H), 4.67-4.53 (m, 1H), 4.29-4.21 (m, 2H), 4.16-4.04 (m, 1H), 4.02-3.85 (m, 3H), 3.82-3.64 (m, 1H), 3.23-3.10 (m, 1H), 2.15 (s, 3H), 1.51-1.36 (m, 1H), 1.31-1.22 (m, 4H), 1.19 (d, J=7.0 Hz, 3H), 1.13-1.06 (m, 6H), 0.85-0.74 (m, 6H). $^{31}$P NMR (162 MHz, DMSO-d$_6$) δ 3.69. HPLC: $t_R$=3.03 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min.

Peak 2 (26b) (slower eluting isomer) data: LCMS: MS m/z=658.9 [M+1], $t_R$=1.01 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min. $^1$H NMR (400 MHz, DMSO-$d_6$) δ 8.01-7.81 (m, 3H), 7.16 (d, J=7.9 Hz, 1H), 7.11 (s, 1H), 6.93 (d, J=7.2 Hz, 1H), 6.87 (d, J=4.5 Hz, 1H), 6.79 (d, J=4.5 Hz, 1H), 6.36 (d, J=6.1 Hz, 1H), 6.17-5.87 (m, 1H), 5.38 (d, J=5.8 Hz, 1H), 4.71-4.54 (m, 1H), 4.29-4.16 (m, 2H), 4.12-4.01 (m, 1H), 4.00-3.72 (m, 4H), 3.27-3.11 (m, 1H), 2.19 (s, 3H), 1.54-1.31 (m, 1H), 1.32-1.18 (m, 7H), 1.12 (d, J=6.9 Hz, 6H), 0.79 (t, J=7.4 Hz, 6H). $^{31}$P NMR (162 MHz, DMSO-$d_6$) δ 3.74. HPLC: $t_R$=3.04 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min.

Example 27: (2R,3R,4R,5R)-2-(4-Aminopyrrolo[2,1-f][1,2,4]triazin-7-yl)-2-cyano-5-((((((S)-1-(2-ethylbutoxy)-1-oxopropan-2-yl)amino)(2-isopropyl-5-methylphenoxy)phosphoryl)oxy)methyl)tetrahydrofuran-3,4-diyl bis(2-methylpropanoate)

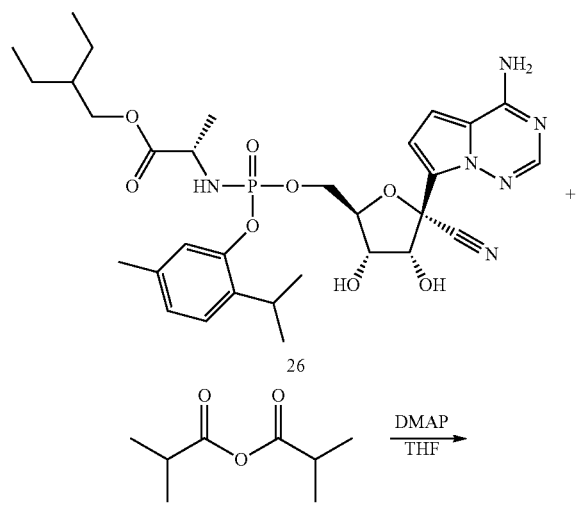

Compound 27 was made in a similar manner as compound 14 except that compound 26 was used instead of compound 13. LCMS: MS m/z=798.8 and 798.8 [M+1], $t_R$=1.24 and 1.26 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min. $^1$H NMR (400 MHz, Methanol-$d_4$) δ (1:1 mixture of diastereomers) 7.86 (s, 0.5H), 7.85 (s, 0.5H), 7.19-7.10 (m, 2H), 6.97-6.92 (m, 1H), 6.91-6.87 (m, 1H), 6.86-6.80 (m, 1H), 6.29 (d, J=6.0 Hz, 0.5H), 6.20 (d, J=5.9 Hz, 0.5H), 5.65-5.59 (m, 0.5H), 5.59-5.52 (m, 0.5H), 4.70-4.64 (m, 0.5H), 4.64-4.59 (m, 0.5H), 4.51-4.35 (m, 2H), 4.10-3.79 (m, 3H), 3.30-3.22 (m, 1H), 2.73-2.58 (m, 2H), 2.26-2.18 (m, 3H), 1.55-1.45 (m, 1H), 1.39-1.29 (m, 5H), 1.29-1.12 (m, 20H), 0.93-0.85 (m, 6H). $^{31}$P NMR (162 MHz, Methanol-$d_4$) δ (1:1 mixture of diastereomers) 3.69-3.47 (m, 0.5P), 3.44-3.27 (m, 0.5P). HPLC: $t_R$=3.71 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min.

Example 28. 2-Ethylbutyl ((S)-(((2R,3S,4R,5R)-5-cyano-3,4-dihydroxy-5-(4-imino-3-((phosphonooxy)methyl)-3,4-dihydropyrrolo[2,1-f][1,2,4]triazin-7-yl)tetrahydrofuran-2-yl)methoxy)(phenoxy)phosphoryl)-L-alaninate

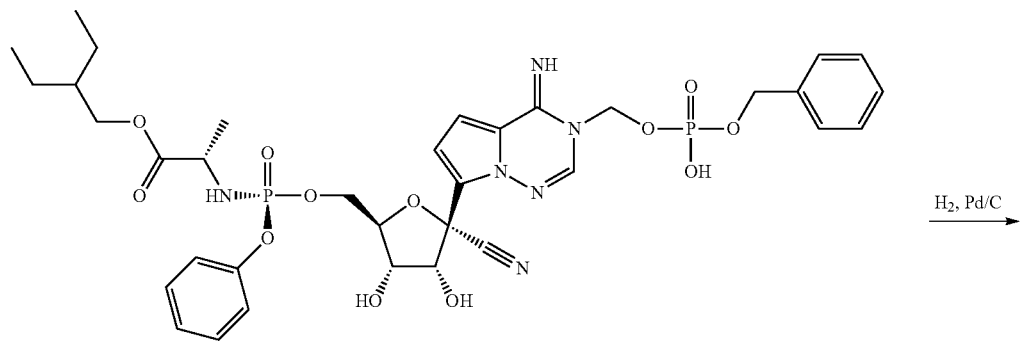

M1

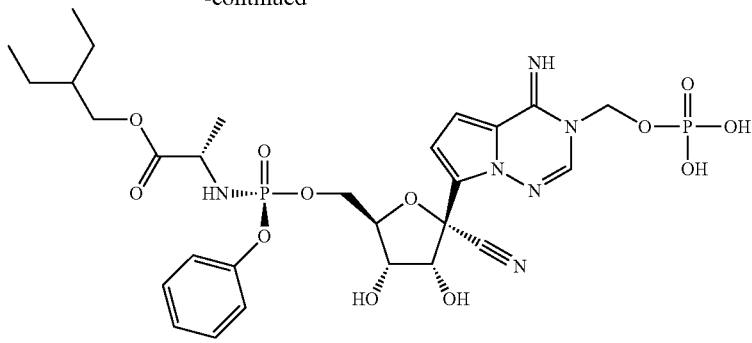

28

A solution of intermediate M1 (0.130 g, 0.162 mmol) in ethanol was evacuated under reduced pressure and filled with argon 3 times. Palladium (10.0% on carbon, 17.2 mg, 0.0162 mmol) was added. The reaction vessel was evacuated under reduced pressure and filled with hydrogen gas 5 times. The reaction was allowed to stir under an atmosphere of hydrogen gas. After 4 h, the reaction was evacuated and filled with argon gas 2 times. The reaction was filtered through a pad of celite and concentrated. The product was purified by HPLC chromatography (using gradient from 0-100% acetonitrile in water) to afford compound 28. LCMS: MS m/z=713.1 [M+1], $t_R$=0.78 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 µL/min. $^1$H NMR (400 MHz, DMSO-$d_6$) δ 10.37 (s, 1H), 8.54 (s, 1H), 7.44 (d, J=4.7 Hz, 1H), 7.39-7.33 (m, 2H), 7.22-7.15 (m, 3H), 6.99 (d, J=4.7 Hz, 1H), 6.61-6.56 (m, 1H), 6.17-6.02 (m, 1H), 5.69-5.59 (m, 2H), 5.54-5.45 (m, 1H), 4.55-4.46 (m, 1H), 4.31-4.21 (m, 2H), 4.14-4.04 (m, 1H), 4.02-3.79 (m, 4H), 1.51-1.38 (m, 1H), 1.34-1.20 (m, 7H), 0.87-0.78 (m, 6H). $^{31}$P NMR (162 MHz, DMSO-d6) δ 4.18-3.79 (m), 0.59-0.35 (m). HPLC: $t_R$=2.78 min; HPLC system: Agilent 1100 series; Column: Gemini 5µ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min.

Example 29. Spiro[3.3]heptan-2-yl (2S)-2-[[[(2R,3S,4R,5R)-5-(4-aminopyrrolo[2,1-f][1,2,4]triazin-7-yl)-5-cyano-3,4-dihydroxy-tetrahydrofuran-2-yl]methoxy-(4-tert-butylphenoxy)phosphoryl]amino]propanoate

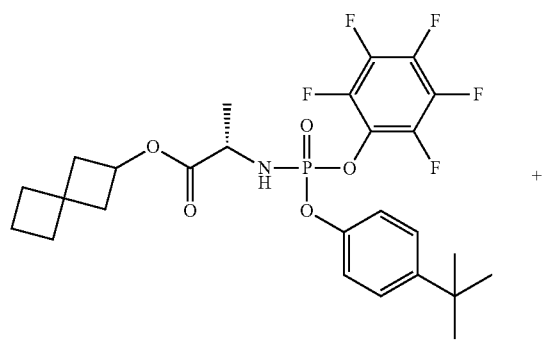

+

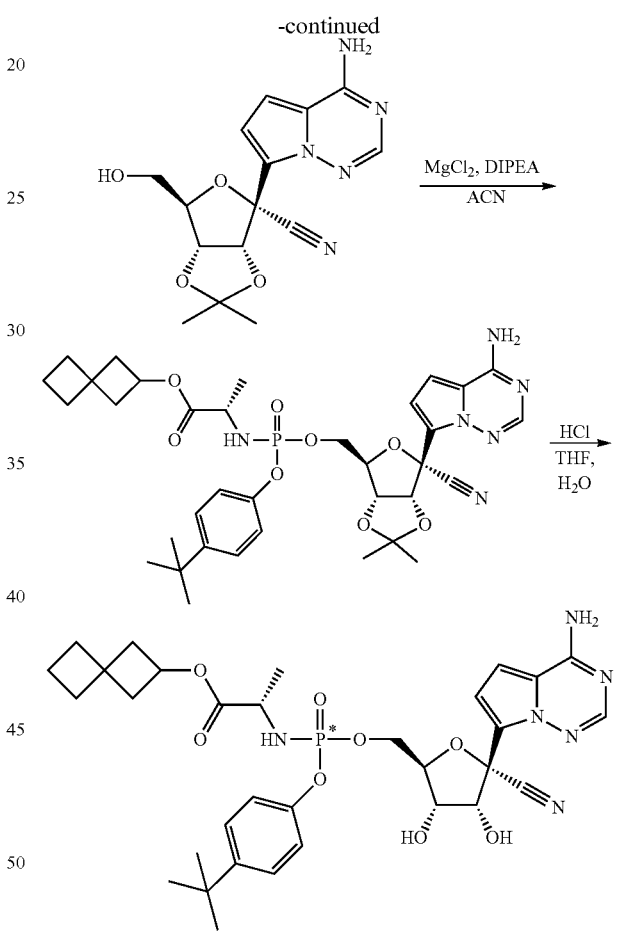

29

To a suspension of spiro[3.3]heptan-2-yl (2S)-2-[[(4-tert-butylphenoxy)-(2,3,4,5,6-pentafluorophenoxy)phosphoryl]amino]propanoate (intermediate E2, 0.110 g, 0.020 mmol), (3aR,4R,6R,6aR)-4-(4-aminopyrrolo[2,1-f][1,2,4]triazin-7-yl)-6-(hydroxymethyl)-2,2-dimethyltetrahydrofuro[3,4-d][1,3]dioxole-4-carbonitrile (prepared according to WO2017049060, 0.065 g, 0.20 mmol) and magnesium chloride (0.019 g, 0.0.20 mmol) in acetonitrile (2 mL) under an atmosphere of argon was added N,N-diisopropylethylamine (0.07 mL, 0.39 mmol) at 0° C. After 10 min, the reaction was heated to 50° C. After 30 min, the reaction was cooled to room temperature, diluted with ethyl acetate and the organics were washed with water, dried over sodium sulfate, filtered and concentrated to afford spiro[3.3]heptan-2-yl (2S)-2-[[[(3aR,4R,6R,6aR)-4-(4-aminopyrrolo[2,1-f][1,2,4]triazin-7-yl)-4-cyano-2,2-dimethyl-6,6a-dihydro-3aH-furo[3,4-d][1,3]dioxol-6-yl]methoxy-(4-tert-butylphenoxy)phosphoryl]amino]propanoate (LCMS: MS m/z=709.7 and 709.7 [M+1], $t_R$=1.13 and 1.16 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min).

Spiro[3.3]heptan-2-yl (2S)-2-[[[(3aR,4R,6R,6aR)-4-(4-aminopyrrolo[2,1-f][1,2,4]triazin-7-yl)-4-cyano-2,2-dimethyl-6,6a-dihydro-3aH-furo[3,4-d][1,3]dioxol-6-yl]methoxy-(4-tert-butylphenoxy)phosphoryl]amino]propanoate was taken up in tetrahydrofuran (2 mL) and concentrated hydrochloric acid (11.7 M, 0.400 mL, 4.66 mmol) was added. After 2 h, the reaction was diluted with ethyl acetate and neutralized with a saturated aqueous solution of sodium bicarbonate. The layers were separated, and the organics were washed with water, saturated aqueous sodium chloride, dried over sodium sulfate, filtered and concentrated. The product was purified by HPLC chromatography (0-100% acetonitrile in water) to afford the title compound. LCMS: MS m/z=669.7 [M+1], $t_R$=1.01 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min. $^1$H NMR (400 MHz, Methanol-$d_4$) δ 7.87 (s, 1H), 7.31 (d, J=8.7 Hz, 2H), 7.09 (dd, J=8.8, 1.3 Hz, 2H), 6.96-6.86 (m, 2H), 4.81-4.74 (m, 2H), 4.43-4.32 (m, 2H), 4.27 (ddd, J=10.3, 5.8, 4.1 Hz), 4.15 (t, J=5.6 Hz, 1H), 3.81 (dq, J=9.7, 7.1 Hz, 1H), 2.42-2.31 (m, 2H), 2.03-1.97 (m, 2H), 1.92 (qd, J=7.9, 7.1, 3.4 Hz, 4H); $^{31}$P NMR (162 MHz, Methanol-$d_4$) δ 3.83 (s).

Example 30. Spiro[3.3]heptan-2-yl (2S)-2-[[(4-tert-butylphenoxy)-[[(2R,3R,4R,5R)-3,4-diacetoxy-5-(4-aminopyrrolo[2,1-f][1,2,4]triazin-7-yl)-5-cyano-tetrahydrofuran-2-yl]methoxy]phosphoryl]amino]propanoate

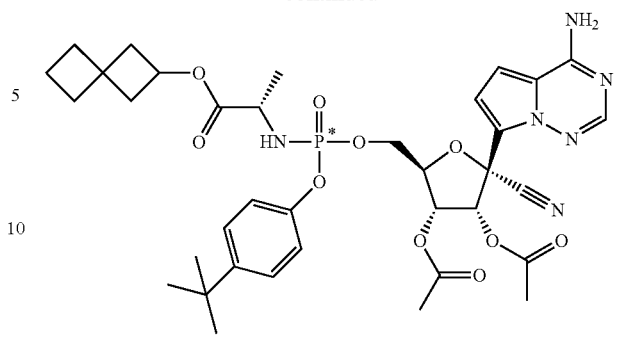

To a solution of spiro[3.3]heptan-2-yl (2S)-2-[[[(2R,3S,4R,5R)-5-(4-aminopyrrolo[2,1-f][1,2,4]triazin-7-yl)-5-cyano-3,4-dihydroxy-tetrahydrofuran-2-yl]methoxy-(4-tert-butylphenoxy)phosphoryl]amino]propanoate (29, 25 mg, 0.04 mmol) and acetic anhydride (0.12 mL, 0.12 mmol) in tetrahydrofuran (1 mL) was added 4-(dimethylamino)pyridine (1.4 mg, 0.011 mmol). After 30 min, the reaction was purified by HPLC chromatography (25-100% acetonitrile in water) to afford the title compound. LCMS: MS m/z=753.8 [M+1], $t_R$=1.11 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min. $^1$H NMR (400 MHz, Methanol-$d_4$) δ 7.84 (s, 1H), 7.32 (d, J=8.7 Hz, 2H), 7.10-7.04 (m, 2H), 6.90 (d, J=1.0 Hz, 2H), 6.26 (d, J=6.0 Hz, 1H), 5.53 (dd, J=6.0, 4.2 Hz, 1H), 4.75 (p, J=7.3 Hz, 2H), 4.63 (s, 1H), 4.44-4.34 (m, 2H), 3.74 (t, J=8.1 Hz, 1H), 2.37 (dd, J=11.7, 7.6 Hz, 2H), 2.14 (d, J=12.2 Hz, 6H), 1.96 (dd, J=15.9, 9.1 Hz, 5H), 1.83 (q, J=8.1 Hz, 2H), 1.33 (s, 2H), 1.29 (s, 9H), 1.17-1.14 (m, 1H). $^{31}$P NMR (162 MHz, Methanol-$d_4$) δ 3.70 (s).

Intermediate T1. Cyclobutyl ((4-(tert-butyl)phenoxy)(perfluorophenoxy)phosphoryl)-L-alaninate

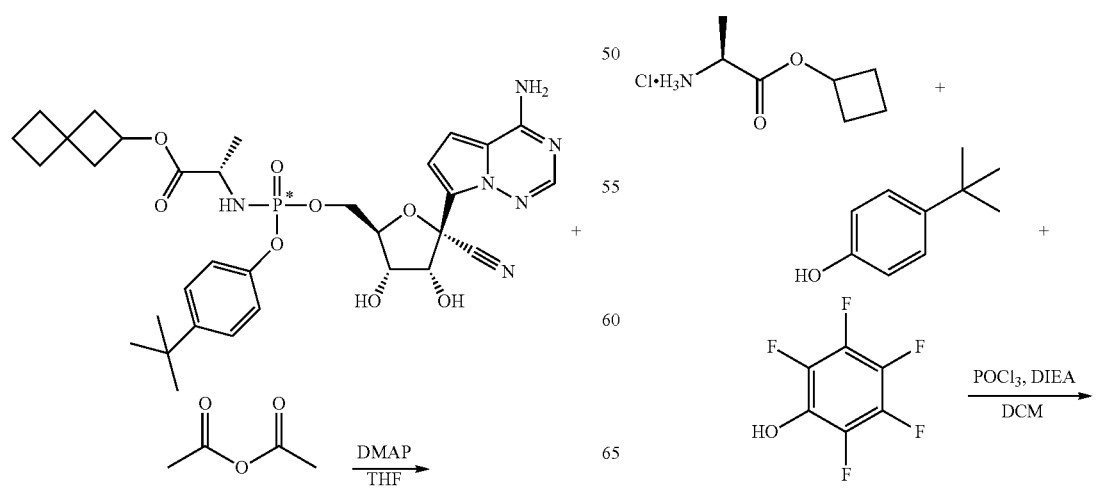

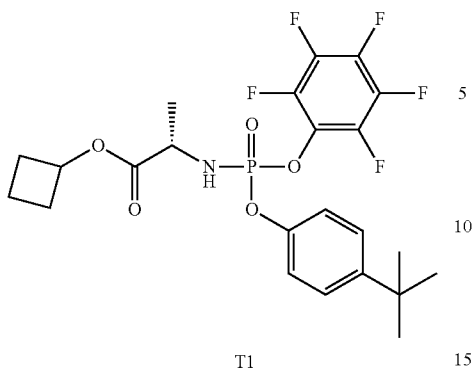

T1

Intermediate T1 (2.52 g, 42%) was made in a similar manner as intermediate E2 except that cyclobutyl L-alaninate hydrochloride (1.76 g, 9.78 mmol) was used instead of spiro[3.3]heptan-2-yl (2S)-2-aminopropanoate hydrochloride. LCMS: MS m/z=522.1 [M+1], $t_R$=1.25 min; $^1$H NMR (400 MHz, DMSO-d6) δ 7.42 (dd, J=8.7, 1.7 Hz, 2H), 7.16 (ddd, J=14.9, 8.7, 1.1 Hz, 2H), 6.86 (td, J=13.9, 9.9 Hz, 1H), 4.87 (q, J=7.8 Hz, 1H), 3.94 (ddd, J=10.4, 6.8, 3.6 Hz, 1H), 2.23 (dtq, J=10.2, 8.0, 2.3 Hz, 2H), 1.98-1.87 (m, 2H), 1.75-1.53 (m, 2H), 1.34-1.23 (m, 12H). $^{19}$F NMR (376 MHz, DMSO-d6) δ −154.23 (dd, J=26.2, 21.0 Hz, 2F), −160.49--161.47 (m, 1F), −163.73 (td, J=24.0, 19.7 Hz, 2F). $^{31}$P NMR (162 MHz, DMSO-d6) δ 0.70 (dd, J=27.6, 13.5 Hz).

Example 31: Cyclobutyl (((((2R,3S,4R,5R)-5-(4-aminopyrrolo[2,1-f][1,2,4]triazin-7-yl)-5-cyano-3,4-dihydroxytetrahydrofuran-2-yl)methoxy)(4-(tert-butyl)phenoxy)phosphoryl)-L-alaninate

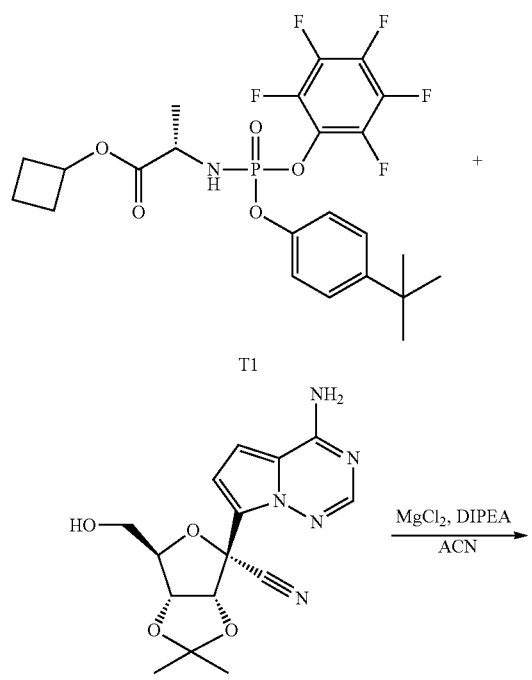

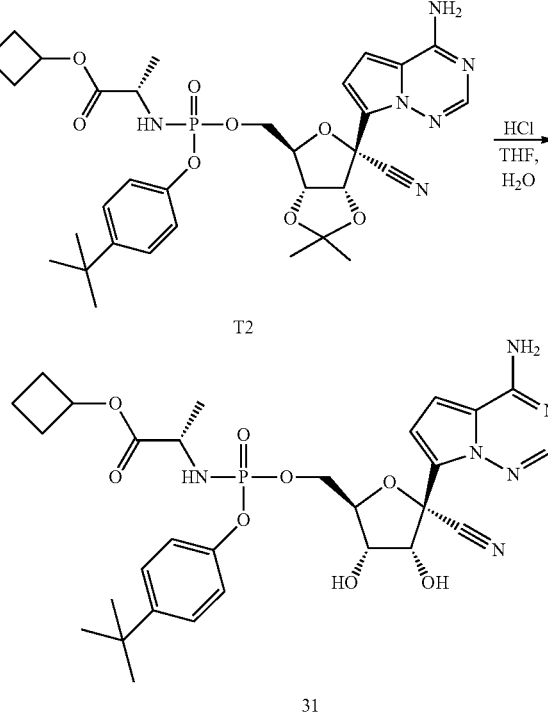

Intermediate T2 was made in a similar manner as intermediate A2 except that intermediate T1 (389 mg, 0.746 mmol) was used instead of intermediate A1. T2 was isolated after column chromatography eluting with ethyl acetate/hexane (0-100%). LCMS: MS m/z=669.2 and 669.2 [M+1], $t_R$=1.02 and 1.05 min.

Compound 31 was made in a similar manner as Compound 13 except that intermediate T2 (346 mg, 0.517 mmol) was used instead of intermediate A2. The 1:1 mixture of diastereomers was isolated by column chromatography using 10% methanol in dichloromethane as eluting solvent mixture. 50 mg of Compound 31 was further purified by preparatory HPLC (Gemini Sum NX-C18 110A LC column 100×30 mm, 95% to 0% water acetonitrile gradient). LCMS: MS m/z=629.2 and 629.2 [M+1], $t_R$=0.89 and 0.90 min; $^1$H NMR (400 MHz, DMSO-d6) δ 7.93 (d, J=3.0 Hz, 3H), 7.38-7.26 (m, 2H), 7.12-6.99 (m, 2H), 6.92 (d, J=4.5 Hz, 1H), 6.85 (dd, J=5.9, 4.5 Hz, 1H), 6.35 (dd, J=9.1, 6.1 Hz, 1H), 6.04-5.93 (m, 1H), 5.42 (dd, J=5.7, 3.8 Hz, 1H), 4.89-4.75 (m, 1H), 4.65 (td, J=5.5, 2.9 Hz, 1H), 4.31-4.18 (m, 2H), 4.18-4.02 (m, 1H), 3.96 (d, J=5.5 Hz, 1H), 3.82-3.62 (m, 1H), 2.27-2.11 (m, 2H), 1.92 (dtt, J=9.9, 4.8, 2.4 Hz, 2H), 1.56 (s, 2H), 1.25 (d, J=5.7 Hz, 9H), 1.21-1.08 (m, 3H). $^{31}$P NMR (162 MHz, DMSO-$d_6$) δ 4.16-3.73 (m).

Individual isomers of compound 31 were separated by preparatory HPLC (Gemini Sum NX-C18 110A LC column 100×30 mm, 95% to 0% water acetonitrile gradient).

Peak 1 (31a) (faster eluting isomer) data: LCMS: MS m/z=629.2 [M+1], $t_R$=0.89 min; $^1$H NMR (400 MHz, DMSO-d6) δ 7.93 (s, 3H), 7.35-7.22 (m, 2H), 7.09-6.99 (m, 2H), 6.92 (d, J=4.5 Hz, 1H), 6.84 (d, J=4.5 Hz, 1H), 6.33 (d, J=6.2 Hz, 1H), 6.00 (dd, J=13.1, 10.0 Hz, 1H), 5.41 (d, J=5.6 Hz, 1H), 4.87-4.74 (m, 1H), 4.65 (dd, J=6.2, 5.0 Hz, 1H), 4.27 (d, J=7.6 Hz, 2H), 4.16-4.06 (m, 1H), 3.99-3.90 (m, 1H), 3.76-3.61 (m, 1H), 2.26-2.13 (m, 2H), 1.92 (ddq, J=11.9, 7.3, 2.5, 2.0 Hz, 2H), 1.74-1.62 (m, 1H), 1.58-1.47 (m, 1H), 1.25 (s, 10H), 1.18-1.06 (m, 3H). $^{31}$P NMR (162 MHz, DMSO-$d_6$) δ 3.84.

Peak 2 (31b) (slower eluting isomer) data: LCMS: MS m/z=629.2 [M+1], $t_R$=0.90 min; $^1$H NMR (400 MHz, DMSO-d6) δ 8.05-7.83 (m, 3H), 7.38-7.26 (m, 2H), 7.14-7.03 (m, 2H), 6.92 (d, J=4.5 Hz, 1H), 6.86 (d, J=4.6 Hz, 1H), 6.35 (d, J=6.2 Hz, 1H), 6.00 (dd, J=13.1, 10.0 Hz, 1H), 5.41 (d, J=5.7 Hz, 1H), 4.83 (t, J=7.5 Hz, 1H), 4.69-4.61 (m, 1H), 4.24 (tt, J=5.7, 2.9 Hz, 2H), 4.14-4.02 (m, 1H), 3.96 (q, J=5.7 Hz, 1H), 3.81-3.67 (m, 1H), 2.20 (ddt, J=10.0, 7.5, 2.5 Hz, 2H), 1.91 (dddd, J=9.7, 7.1, 4.8, 2.2 Hz, 2H), 1.75-1.47 (m, 2H), 1.26 (s, 9H), 1.19 (d, J=7.1 Hz, 3H). $^{31}$P NMR (162 MHz, DMSO-d$_6$) δ 4.00.

Example 32: (2R,3R,4R,5R)-2-(4-aminopyrrolo[2,1-f][1,2,4]triazin-7-yl)-5-((((4-(tert-butyl)phenoxy)(((S)-1-cyclobutoxy-1-oxopropan-2-yl)amino)phosphoryl)oxy)methyl)-2-cyanotetrahydrofuran-3,4-diyl dipropionate

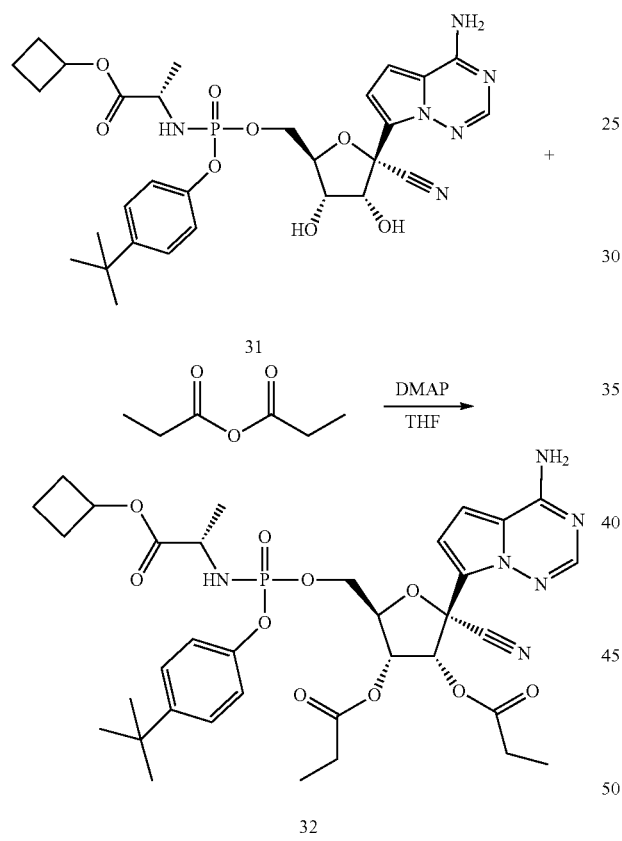

Compound 32 was made in a similar manner as Example 5 except that 31 (42.5 mg, 0.068 mmol) was used instead of methyl ((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)-L-alaninate.

Individual isomers of Compound 32 were separated by preparatory HPLC (Gemini 5 um NX-C18 110A LC column 100×30 mm, 95% to 0% water acetonitrile gradient).

Peak 1 (32a) (faster eluting isomer) data: LCMS: MS m/z=741.2 [M+1], $t_R$=1.09 min; $^1$H NMR (400 MHz, DMSO-d6) δ 7.93 (s, 3H), 7.38-7.24 (m, 2H), 7.10-6.99 (m, 2H), 6.95 (d, J=4.6 Hz, 1H), 6.78 (d, J=4.6 Hz, 1H), 6.05 (m, J=5.9 Hz, 1H), 5.97 (dd, J=13.3, 10.1 Hz, 1H), 5.45 (dd, J=5.9, 4.1 Hz, 1H), 4.86-4.76 (m, 1H), 4.64 (d, J=3.5 Hz, 1H), 4.27 (t, J=4.9 Hz, 2H), 2.47-2.31 (m, 4H), 2.29-2.13 (m, 2H), 1.99-1.83 (m, 2H), 1.69 (d, J=10.1 Hz, 1H), 1.61-1.49 (m, 1H), 1.25 (s, 7H), 1.15-1.02 (m, 7H). $^{31}$P NMR (162 MHz, DMSO-d$_6$) δ 3.65.

Peak 1 (32b) (slower eluting isomer) data: LCMS: MS m/z=741.2 [M+1], $t_R$=1.10 min; $^1$H NMR (400 MHz, DMSO-d6) δ 8.08-7.87 (m, 3H), 7.34-7.21 (m, 2H), 7.11-6.98 (m, 2H), 6.94 (d, J=4.5 Hz, 1H), 6.78 (d, J=4.6 Hz, 1H), 6.09-5.96 (m, 2H), 5.46 (dd, J=6.0, 4.1 Hz, 1H), 4.90-4.78 (m, 1H), 4.60 (d, J=4.3 Hz, 1H), 4.31-4.15 (m, 2H), 3.81-3.65 (m, 1H), 2.46-2.33 (m, 4H), 2.27-2.15 (m, 2H), 1.92 (q, J=9.6 Hz, 2H), 1.70 (d, J=10.3 Hz, 1H), 1.62-1.50 (m, 1H), 1.25 (s, 7H), 1.18 (d, J=7.1 Hz, 2H), 1.07 (dt, J=17.1, 7.5 Hz, 5H). $^{31}$P NMR (162 MHz, DMSO-d$_6$) δ 3.90.

Example 33: (2R,3R,4R,5R)-2-(4-aminopyrrolo[2,1-f][1,2,4]triazin-7-yl)-5-((((4-(tert-butyl)phenoxy)(((S)-1-cyclobutoxy-1-oxopropan-2-yl)amino)phosphoryl)oxy)methyl)-2-cyanotetrahydrofuran-3,4-diyl diacetate

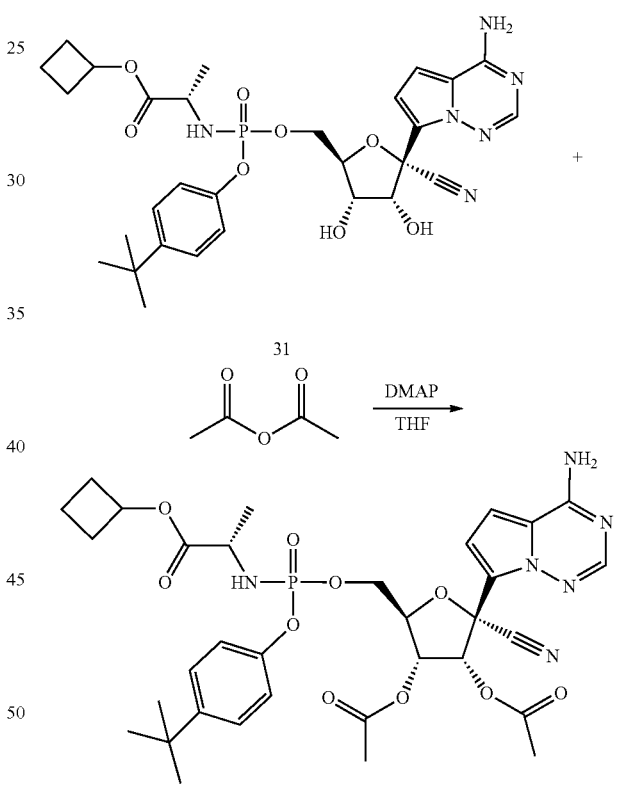

Compound 33 was made in a similar manner as Example 30 except that 31 (42.5 mg, 0.068 mmol) was used instead of 29.

Individual isomers of Compound 33 were separated by preparatory HPLC (Gemini 5um NX-C18 110A LC column 100×30 mm, 95% to 0% water acetonitrile gradient).

Peak 1 (33a) (faster eluting isomer) data: LCMS: MS m/z=713.2 [M+1], $t_R$=1.02 min; $^1$H NMR (400 MHz, DMSO-d6) δ 8.04 (d, J=31.4 Hz, 2H), 7.94 (s, 1H), 7.30 (d, J=8.6 Hz, 2H), 7.03 (d, J=8.4 Hz, 2H), 6.95 (d, J=4.6 Hz, 1H), 6.78 (d, J=4.6 Hz, 1H), 6.05-5.95 (m, 2H), 5.41 (dd, J=5.9, 4.2 Hz, 1H), 4.86-4.74 (m, 1H), 4.64 (d, J=4.0 Hz, 1H), 4.26 (t, J=4.9 Hz, 2H), 3.64 (d, J=7.1 Hz, 1H), 2.19 (dt, J=12.3, 4.2 Hz, 2H), 2.12 (s, 6H), 1.99-1.83 (m, 2H), 1.69 (d, J=10.0 Hz, 1H), 1.55 (dd, J=10.4, 8.1 Hz, 1H), 1.25 (s, 9H), 1.09 (d, J=7.0 Hz, 3H). $^{31}$P NMR (162 MHz, DMSO-d$_6$) δ 3.64.

Peak 2 (33b) (slower eluting isomer) data: LCMS: MS m/z=713.2 [M+1], t$_R$=1.03 min; $^1$H NMR (400 MHz, DMSO-d6) δ 8.13-7.89 (m, 3H), 7.33-7.21 (m, 2H), 7.03 (dt, J=9.6, 2.0 Hz, 2H), 6.94 (d, J=4.6 Hz, 1H), 6.78 (d, J=4.6 Hz, 1H), 6.12-5.94 (m, 2H), 5.42 (dd, J=6.0, 4.3 Hz, 1H), 4.88-4.76 (m, 1H), 4.60 (d, J=4.2 Hz, 1H), 4.23 (ddd, J=18.8, 6.4, 4.4 Hz, 2H), 3.72 (d, J=7.1 Hz, 1H), 2.21 (td, J=7.8, 2.8 Hz, 2H), 2.12 (d, J=3.7 Hz, 6H), 1.99-1.86 (m, 2H), 1.75-1.63 (m, 1H), 1.56 (dd, J=10.4, 8.1 Hz, 1H), 1.25 (s, 9H), 1.17 (d, J=7.1 Hz, 3H). $^{31}$P NMR (162 MHz, DMSO-d6) δ 3.90.

Intermediate T6: (S)-tetrahydrofuran-3-yl L-alaninate hydrochloride

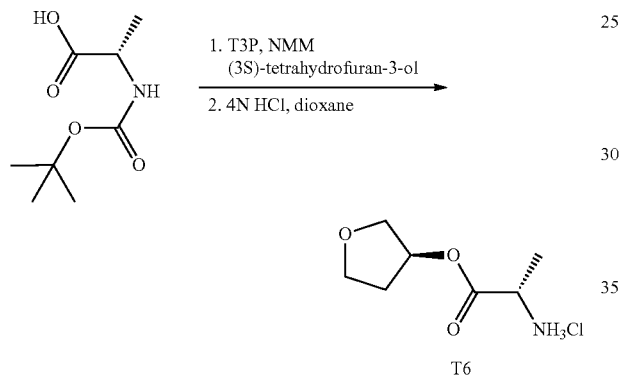

Intermediate T6 was made in a similar manner as intermediate E1 except that (3S)-tetrahydrofuran-3-ol (500 mg, 5.68 mmol) was used instead of spiro[3.3]heptan-2-ol. $^1$H NMR (400 MHz, Methanol-d4) δ 5.55-5.37 (m, 1H), 4.13 (q, J=7.2 Hz, 1H), 4.00-3.79 (m, 4H), 2.37-2.22 (m, 1H), 2.17-2.00 (m, 1H), 1.56 (d, J=7.3 Hz, 3H).

Intermediate T7: (S)-tetrahydrofuran-3-yl ((4-(tert-butyl)phenoxy)(perfluorophenoxy)phosphoryl)-L-alaninate Intermediate T7 was made in a similar manner as intermediate E2 except that T6 (467 mg, 3.26 mmol) was used instead of spiro[3.3]heptan-2-yl (2S)-2-aminopropanoate hydrochloride. LCMS: MS m/z=538.1 [M+1], t$_R$=1.15 min.

Example 34: (S)-tetrahydrofuran-3-yl ((((2R,3S,4R,5R)-5-(4-aminopyrrolo[2,1-f][1,2,4]triazin-7-yl)-5-cyano-3,4-dihydroxytetrahydrofuran-2-yl)methoxy)(4-(tert-butyl)phenoxy)phosphoryl)-L-alaninate

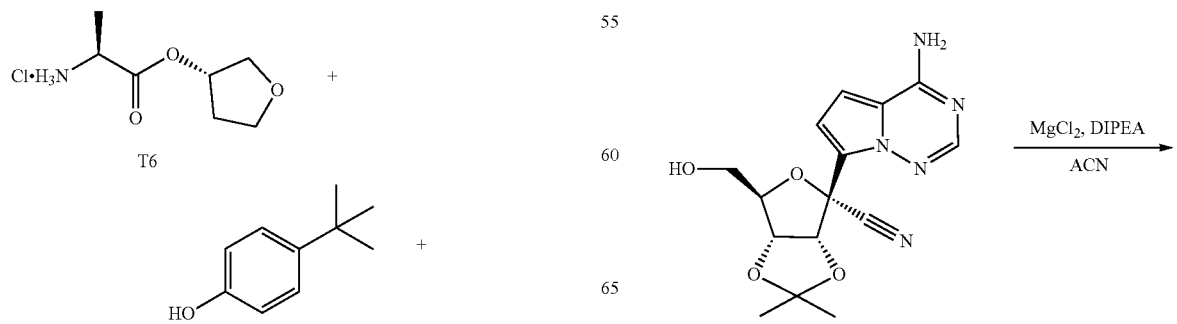

-continued

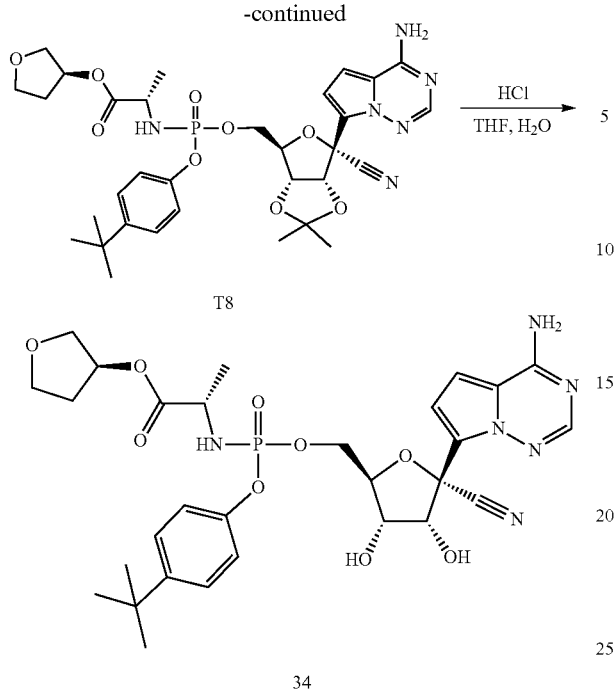

T8

34

Intermediate T8 was made in a similar manner as intermediate A2 except that intermediate T7 (520 mg, 0.968 mmol) was used instead of intermediate A1. LCMS: MS m/z=685.2 and 685.2 [M+1], $t_R$=0.939 and 0.963 min.

Compound 34 was made in a similar manner as Compound 13 except that intermediate T8 (516 mg, 0.754 mmol) was used instead of intermediate A2. The 1:1 mixture of diastereomers was isolated by column chromatography using 10% methanol in dichloromethane as eluting solvent mixture. Mixture of isomers: LCMS: MS m/z=645.2 [M+1], $t_R$=0.803 min and 0.814 min; $^1$H NMR (400 MHz, Methanol-d4) δ 7.88 (d, J=5.7 Hz, 1H), 7.32 (dd, J=10.5, 7.8 Hz, 2H), 7.16-7.03 (m, 2H), 6.99-6.90 (m, 2H), 5.25 (td, J=6.6, 4.6 Hz, 1H), 4.81 (dd, J=9.2, 5.4 Hz, 1H), 4.48-4.26 (m, 3H), 4.19 (td, J=5.6, 3.5 Hz, 1H), 3.91-3.70 (m, 5H), 2.14 (ddd, J=14.0, 9.1, 7.0 Hz, 1H), 1.96 (dd, J=13.3, 6.4 Hz, 1H), 1.35-1.22 (m, 12H); $^{31}$P NMR (162 MHz, Methanol-d4) δ 3.83.

Example 35: (2R,3R,4R,5R)-2-(4-aminopyrrolo[2,1-f][1,2,4]triazin-7-yl)-5-((((4-(tert-butyl)phenoxy)(((S)-1-oxo-1-(((S)-tetrahydrofuran-3-yl)oxy)propan-2-yl)amino)phosphoryl)oxy)methyl)-2-cyanotetrahydrofuran-3,4-diyl diacetate

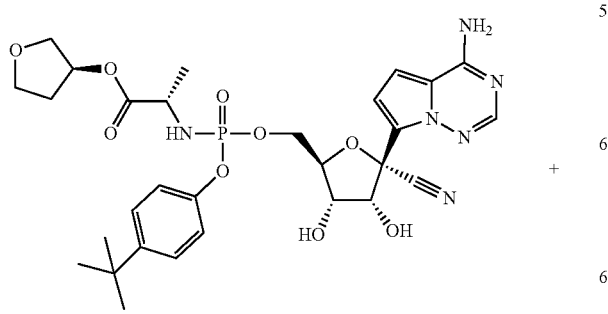

+

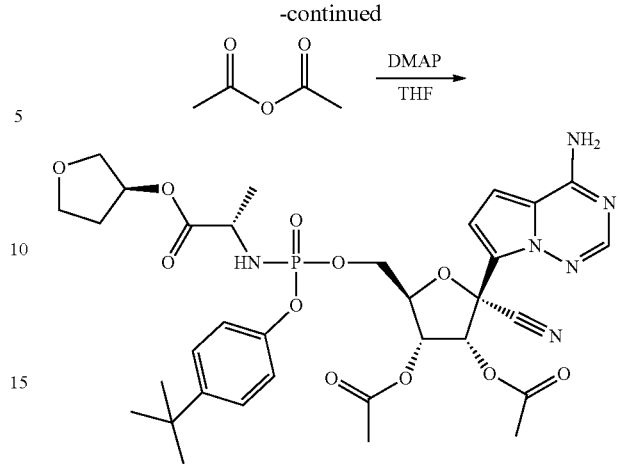

Compound 35 was made in a similar manner as Example 30 except that 34 (43.6 mg, 0.064 mmol) was used instead of 29. The desired analog was isolated using preparatory HPLC (Gemini 5um NX-C18 110A LC column 100×30 mm, 95% to 0% water acetonitrile gradient). Mixture of stereoisomers: LCMS: MS m/z=729.2 and 729.2[M+1], $t_R$=0.924 min and 0.934 min; $^1$H NMR (400 MHz, Methanol-d4) δ 7.88 (d, J=4.9 Hz, 1H), 7.39-7.23 (m, 2H), 7.12-7.04 (m, 2H), 6.96-6.86 (m, 2H), 6.23 (dd, J=36.9, 6.0 Hz, 1H), 5.55 (ddd, J=5.9, 4.2, 1.4 Hz, 1H), 5.30-5.19 (m, 1H), 4.70-4.59 (m, 1H), 4.41 (ttd, J=11.6, 5.7, 3.2 Hz, 2H), 3.95-3.68 (m, 5H), 2.23-2.09 (m, 7H), 2.03-1.91 (m, 1H), 1.38-1.23 (m, 12H); $^{31}$P NMR (162 MHz, Methanol-d4) δ 3.69.

Example 36: (2R,3R,4R,5R)-2-(4-aminopyrrolo[2,1-f][1,2,4]triazin-7-yl)-5-((((4-(tert-butyl)phenoxy)(((S)-1-oxo-1-(((S)-tetrahydrofuran-3-yl)oxy)propan-2-yl)amino)phosphoryl)oxy)methyl)-2-cyanotetrahydrofuran-3,4-diyl bis(2-methylpropanoate)

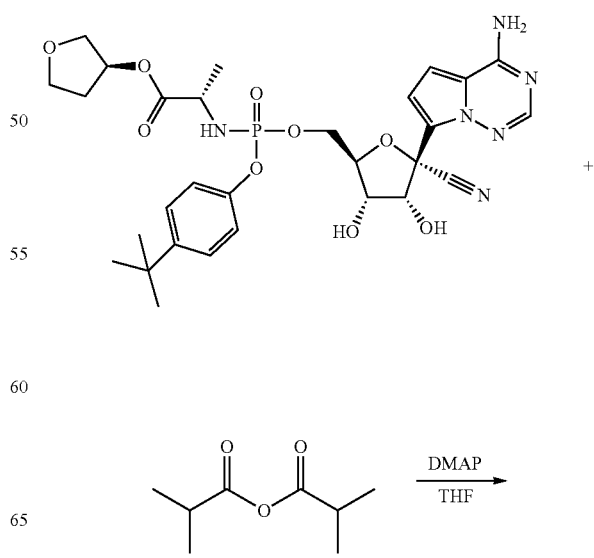

-continued

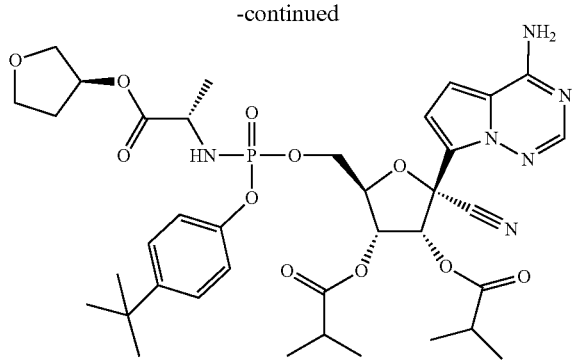

Compound 36 was made in a similar manner as Example 14 except that 34 (51.5 mg, 0.080 mmol) was used instead of A3. Mixture of stereoisomers: LCMS: MS m/z=785.2 [M+1], t$_R$=1.07 min; $^1$H NMR (400 MHz, Methanol-d4) δ 7.88 (d, J=0.9 Hz, 1H), 7.37-7.25 (m, 2H), 7.14-7.04 (m, 2H), 6.94-6.84 (m, 2H), 6.22 (dd, J=47.4, 5.9 Hz, 1H), 5.56 (dt, J=6.0, 3.6 Hz, 1H), 5.31-5.21 (m, 1H), 4.67-4.58 (m, 1H), 4.49-4.36 (m, 2H), 3.93-3.71 (m, 5H), 2.75-2.56 (m, 2H), 2.15 (ddd, J=13.9, 6.4, 1.4 Hz, 1H), 2.03-1.93 (m, 1H), 1.36-1.13 (m, 24H); $^{31}$P NMR (162 MHz, Methanol-d4) δ 3.67.

Example 37: (2R,3R,4R,5R)-2-(4-aminopyrrolo[2,1-f][1,2,4]triazin-7-yl)-5-((((4-(tert-butyl)phenoxy)(((S)-1-oxo-1-(((S)-tetrahydrofuran-3-yl)oxy)propan-2-yl)amino)phosphoryl)oxy)methyl)-2-cyanotetrahydrofuran-3,4-diyl diacetate

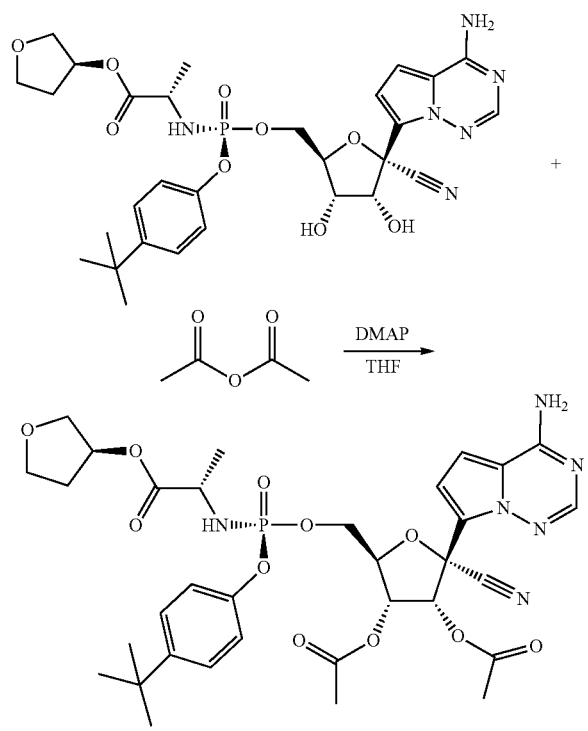

Compound 37 was made in a similar manner as Example 30 except that the individual isomer of compound 34 (52.5 mg, 0.081 mmol) was used instead of 29.

Individual isomer: LCMS: MS m/z=729.2 [M+1], t$_R$=0.925 min; $^1$H NMR (400 MHz, Methanol-d4) δ 7.87 (s, 1H), 7.35 (d, J=8.6 Hz, 2H), 7.10 (d, J=8.4 Hz, 2H), 6.97-6.87 (m, 2H), 6.27 (d, J=6.0 Hz, 1H), 5.56 (dd, J=5.9, 4.2 Hz, 1H), 5.28-5.19 (m, 1H), 4.70-4.62 (m, 1H), 4.42 (ddd, J=15.0, 5.6, 3.6 Hz, 2H), 3.90-3.70 (m, 5H), 2.16 (d, J=11.6 Hz, 7H), 2.01-1.92 (m, 1H), 1.31 (s, 9H), 1.18 (d, J=7.1 Hz, 3H); $^{31}$P NMR (162 MHz, Methanol-d4) δ 3.67.

Example 38: (2R,3R,4R,5R)-2-(4-aminopyrrolo[2,1-f][1,2,4]triazin-7-yl)-5-((((4-(tert-butyl)phenoxy)(((S)-1-oxo-1-(((S)-tetrahydrofuran-3-yl)oxy)propan-2-yl)amino)phosphoryl)oxy)methyl)-2-cyanotetrahydrofuran-3,4-diyl bis(2-methylpropanoate)

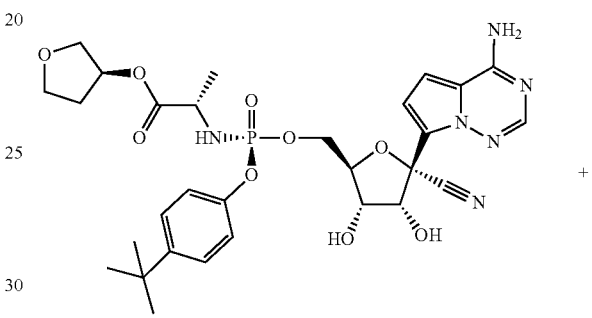

Compound 38 was made in a similar manner as Example 14 except that the individual isomer of 34 (52.5 mg, 0.081 mmol) was used instead of A3. Individual isomer: LCMS: MS m/z=785.2 [M+1], t$_R$=1.07 min; $^1$H NMR (400 MHz, Methanol-d4) δ 7.88 (s, 1H), 7.37-7.32 (m, 2H), 7.13-7.08 (m, 2H), 6.95-6.87 (m, 2H), 6.27 (d, J=5.9 Hz, 1H), 5.56 (dd, J=6.0, 3.7 Hz, 1H), 5.24 (ddd, J=6.2, 4.0, 1.8 Hz, 1H), 4.65 (dd, J=3.7, 2.4 Hz, 1H), 4.50-4.36 (m, 2H), 3.91-3.72 (m, 6H), 2.66 (dp, J=22.3, 7.0 Hz, 2H), 2.20-2.11 (m, 1H), 1.97 (dd, J=13.0, 6.5 Hz, 1H), 1.34-1.16 (m, 28H); $^{31}$P NMR (162 MHz, Methanol-d4) δ 3.66.

Intermediate T9: 2-ethylbutyl ((4-cyanophenoxy)(perfluorophenoxy)phosphoryl)-L-alaninate

Intermediate T9 (682 mg, 34%) was made in a similar manner as intermediate A1 except that 4-hydroxybenzonitrile (388 mg, 3.26 mmol) was used instead of 4-(tert-butyl)phenol. LCMS: MS m/z=521.1 [M+1], $t_R$=1.16 min.

Example 39: 2-ethylbutyl ((((2R,3S,4R,5R)-5-(4-aminopyrrolo[2,1-f][1,2,4]triazin-7-yl)-5-cyano-3,4-dihydroxytetrahydrofuran-2-yl)methoxy)(4-cyanophenoxy)phosphoryl)-L-alaninate

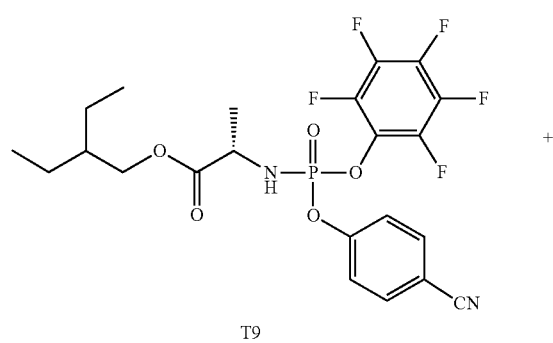

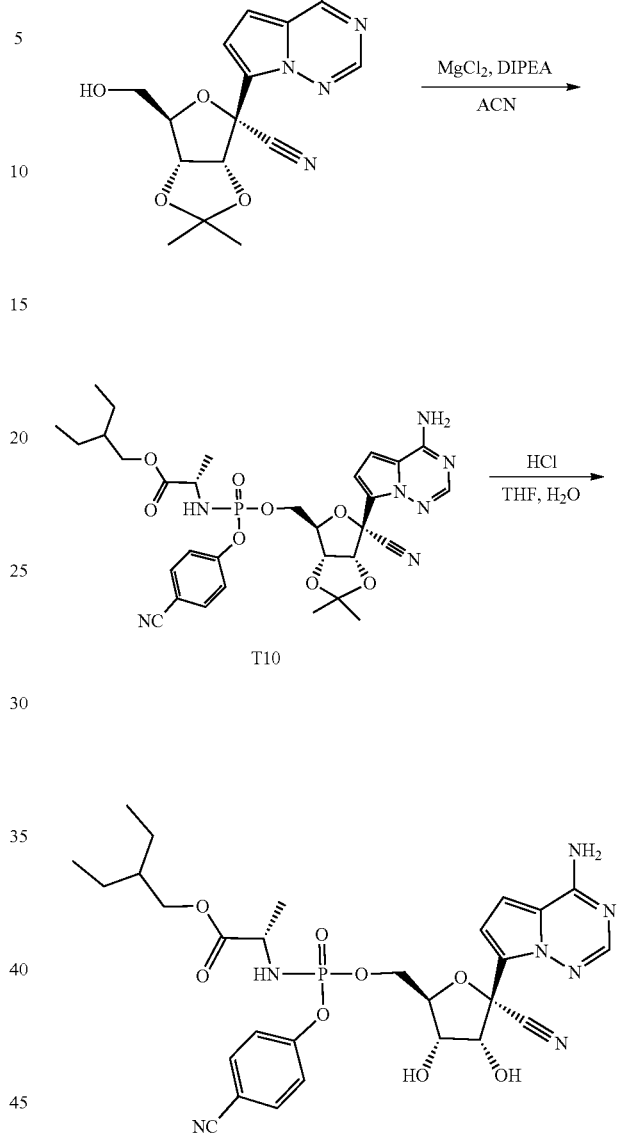

Intermediate T10 was made in a similar manner as intermediate A2 except that intermediate T9 (340 mg, 0.653 mmol) was used instead of intermediate A1. LCMS: MS m/z=668.2 [M+1], $t_R$=0.994 min.

Compound 39 was made in a similar manner as Compound 13 except that intermediate T10 (140 mg, 0.210 mmol) was used instead of intermediate A2. The 1:1 mixture of diastereomers was isolated by preparatory HPLC (Gemini 5 um NX-C18 110A LC column 100×30 mm, 95% to 0% water acetonitrile gradient). Mixture of isomers: LCMS: MS m/z=628.2 [M+1], $t_R$=0.856 min; $^1$H NMR (400 MHz, Methanol-d4) δ 7.86 (d, J=6.3 Hz, 1H), 7.68 (dd, J=10.3, 8.7 Hz, 2H), 7.35 (ddd, J=19.8, 8.9, 1.1 Hz, 2H), 6.98-6.84 (m, 2H), 4.84 (t, J=5.8 Hz, 1H), 4.51-4.31 (m, 3H), 4.22 (d, J=5.4 Hz, 1H), 4.07-3.88 (m, 3H), 1.48 (d, J=6.1 Hz, 1H), 1.33 (dddd, J=13.4, 8.6, 5.4, 1.5 Hz, 8H), 0.88 (td, J=7.4, 3.6 Hz, 6H); $^{31}$P NMR (162 MHz, Methanol-d4) δ 3.34.

Example 40: (2R,3R,4R,5R)-2-(4-aminopyrrolo[2,1-f][1,2,4]triazin-7-yl)-2-cyano-5-((((4-cyanophenoxy)(((S)-1-(2-ethylbutoxy)-1-oxopropan-2-yl)amino)phosphoryl)oxy)methyl)tetrahydrofuran-3,4-diyl bis(2-methylpropanoate)

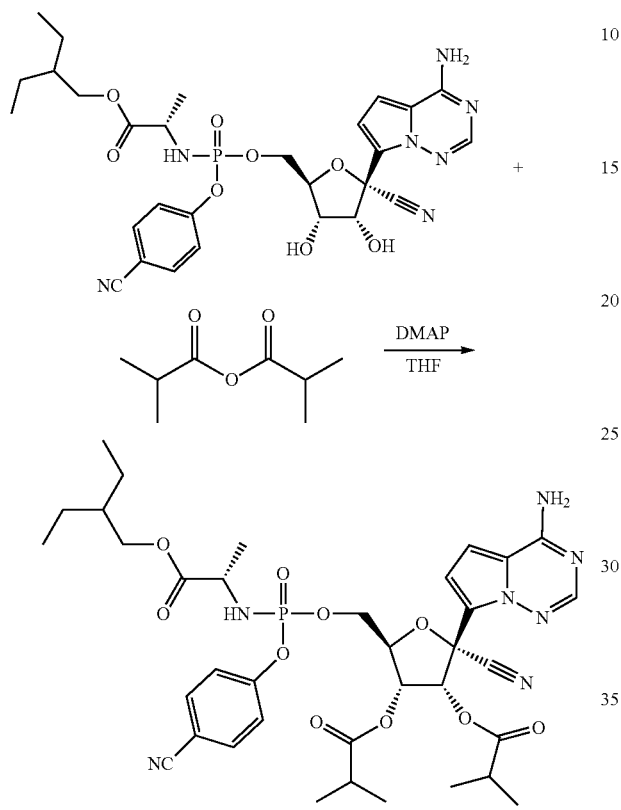

Compound 40 was made in a similar manner as Example 14 except that 39 (38 mg, 0.061 mmol) was used instead of A3. Mixture of stereoisomers: LCMS: MS m/z=768.4 and 768.4 [M+1], $t_R$=1.10 min and 1.11 min; $^1$H NMR (400 MHz, Methanol-d4) δ 7.86 (d, J=3.3 Hz, 1H), 7.71-7.59 (m, 2H), 7.33 (td, J=9.0, 1.1 Hz, 2H), 6.95-6.79 (m, 2H), 6.22 (dd, J=35.5, 5.9 Hz, 1H), 5.56 (ddd, J=6.8, 6.0, 3.7 Hz, 1H), 4.64 (ddd, J=12.8, 3.8, 2.0 Hz, 1H), 4.46 (ddd, J=18.7, 6.1, 3.8 Hz, 2H), 4.12-3.84 (m, 3H), 2.75-2.57 (m, 2H), 1.49 (dt, J=12.4, 6.2 Hz, 1H), 1.41-1.13 (m, 19H), 0.89 (td, J=7.5, 4.4 Hz, 6H); $^{31}$P NMR (162 MHz, Methanol-d$_4$) δ 3.22.

Intermediate T11: ethyl ((4-(bicyclo[1.1.1]pentan-1-yl)phenoxy)(perfluorophenoxy)phosphoryl)-L-alaninate

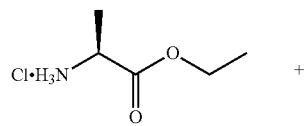

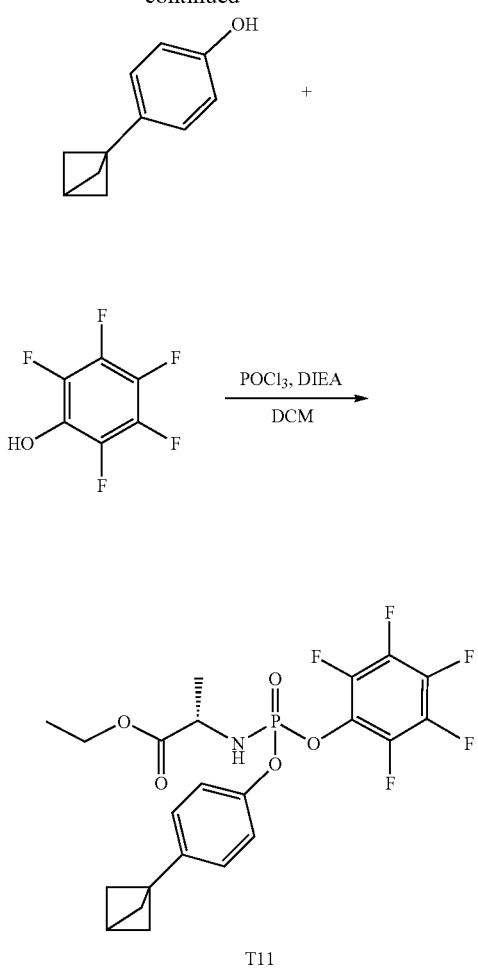

Intermediate T11 was made in a similar manner as intermediate C$_1$ except that 4-(bicyclo[1.1.1]pentan-1-yl)phenol (522 mg, 3.26 mmol) was used instead of 4-(tert-butyl)phenol. LCMS: MS m/z=506.1 [M+1], $t_R$=1.19 min.

Example 41: Ethyl ((((2R,3S,4R,5R)-5-(4-aminopyrrolo[2,1-f][1,2,4]triazin-7-yl)-5-cyano-3,4-dihydroxytetrahydrofuran-2-yl)methoxy)(4-(bicyclo[1.1.1]pentan-1-yl)phenoxy)phosphoryl)-L-alaninate

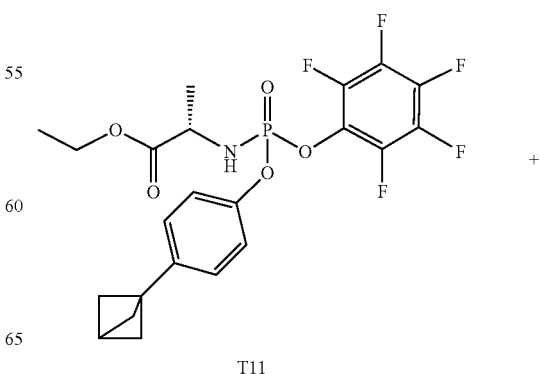

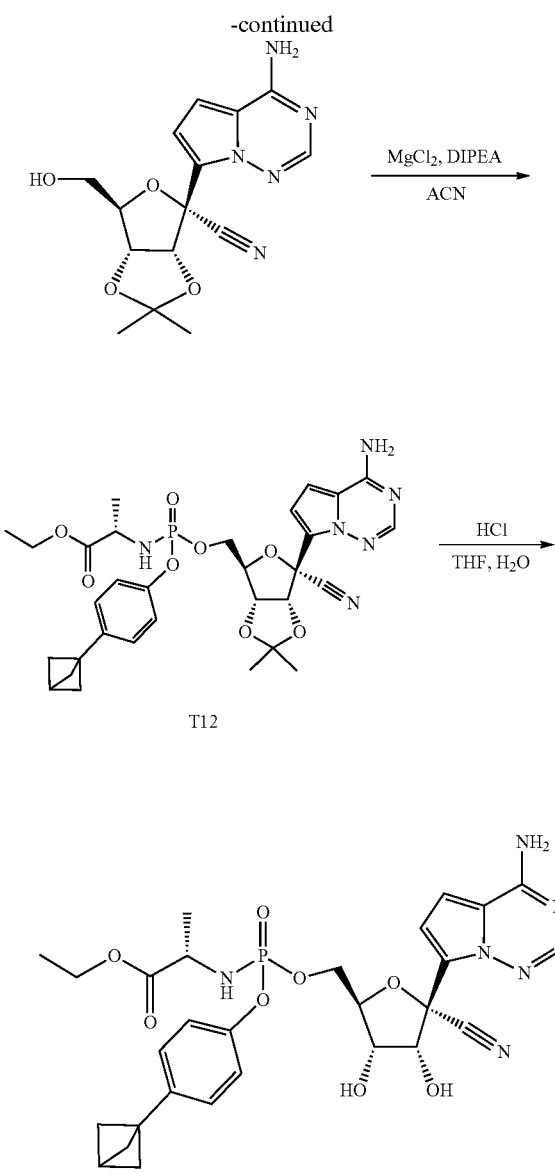

T12

Intermediate T12 was made in a similar manner as intermediate A2 except that intermediate T11 (377 mg, 0.746 mmol) was used instead of intermediate A1. LCMS: MS m/z=653.2 [M+1], Compound 41 was made in a similar manner as Compound 13 except that intermediate T12 (318 mg, 0.487 mmol) was used instead of intermediate A2. The 1:1 mixture of diastereomers was isolated by column chromatography using 10% methanol in dichloromethane as eluting solvent mixture. 50 mg of Compound 41 was further purified by preparatory HPLC (Gemini Sum NX-C18 110A LC column 100×30 mm, 95% to 0% water acetonitrile gradient). Mixture of stereoisomers: LCMS: MS m/z=613.2 and 613.2 [M+1], $t_R$=0.99 min and 1.02 min. $^1$H NMR (400 MHz, Methanol-d4) δ 7.88 (d, J=5.6 Hz, 1H), 7.15-7.02 (m, 4H), 6.99-6.88 (m, 2H), 4.81 (t, J=5.8 Hz, 1H), 4.46-4.36 (m, 2H), 4.31 (ddd, J=10.8, 5.9, 3.8 Hz, 1H), 4.20 (td, J=5.5, 1.8 Hz, 1H), 4.15-4.05 (m, 2H), 3.90-3.77 (m, 1H), 2.53 (d, J=1.5 Hz, 1H), 2.07 (d, J=3.1 Hz, 6H), 1.35-1.14 (m, 6H); $^{31}$P NMR (162 MHz, Methanol-d4) δ 3.78.

Example 42: (2R,3R,4R,5R)-2-(4-aminopyrrolo[2,1-f][1,2,4]triazin-7-yl)-5-((((4-(bicyclo[1.1.1]pentan-1-yl)phenoxy)(((S)-1-ethoxy-1-oxopropan-2-yl)amino) phosphoryl)oxy)methyl)-2-cyanotetrahydrofuran-3,4-diyl diacetate

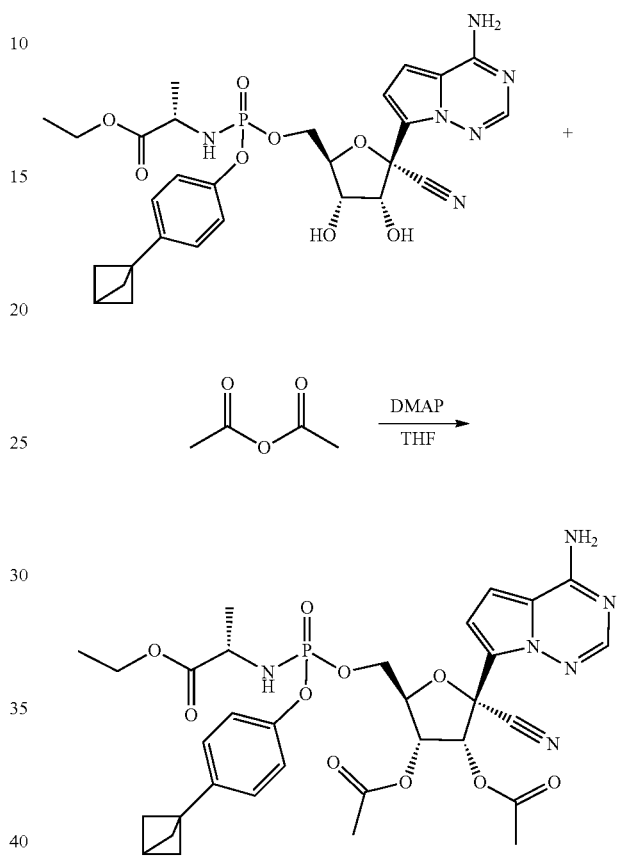

Compound 42 was made in a similar manner as Example 30 except that 41 (48 mg, 0.078 mmol) was used instead of 29.

Individual isomers of Compound 42 were separated by preparatory HPLC (Gemini Sum NX-C18 110A LC column 100×30 mm, 95% to 0% water acetonitrile gradient).

Peak 1 (42a) (faster eluting isomer): LCMS: MS m/z=697.2 [M+1], $t_R$=0.97 min; $^1$H NMR (400 MHz, Methanol-d4) δ 7.86 (s, 1H), 7.18-7.02 (m, 4H), 6.96-6.87 (m, 2H), 6.27 (d, J=6.0 Hz, 1H), 5.56 (dd, J=6.0, 4.3 Hz, 1H), 4.65 (dd, J=4.0, 2.3 Hz, 1H), 4.50-4.34 (m, 2H), 4.09 (qd, J=7.2, 3.2 Hz, 2H), 3.76 (dd, J=9.2, 7.1 Hz, 1H), 2.54 (s, 1H), 2.31-1.84 (m, 12H), 1.28-1.06 (m, 6H); $^{31}$P NMR (162 MHz, Methanol-d4) δ 3.64.

Peak 2 (42b) (slower eluting isomer): LCMS: MS m/z=697.2 [M+1], $t_R$=0.99 min; $^1$H NMR (400 MHz, Methanol-d4) δ 7.87 (d, J=3.9 Hz, 1H), 7.14-7.02 (m, 4H), 6.93-6.86 (m, 2H), 6.17 (d, J=6.0 Hz, 1H), 5.55 (dd, J=6.0, 4.3 Hz, 1H), 4.62 (dd, J=3.8, 1.9 Hz, 1H), 4.39 (ddd, J=12.2, 6.1, 3.7 Hz, 2H), 4.11 (qd, J=7.2, 3.6 Hz, 2H), 3.86 (dd, J=9.8, 7.1 Hz, 1H), 2.53 (s, 1H), 2.16 (d, J=12.7 Hz, 6H), 2.07 (d, J=5.7 Hz, 6H), 1.32-1.15 (m, 6H); $^{31}$P NMR (162 MHz, Methanol-d4) δ 3.66.

Example 43: (2R,3R,4R,5R)-2-(4-aminopyrrolo[2,1-f][1,2,4]triazin-7-yl)-5-(((((4-(bicyclo[1.1.1]pentan-1-yl)phenoxy)(((S)-1-ethoxy-1-oxopropan-2-yl)amino)phosphoryl)oxy)methyl)-2-cyanotetrahydrofuran-3,4-diyl bis(2-methylpropanoate)

Compound 43 was made in a similar manner as Example 14 except that 41 (48 mg, 0.078 mmol) was used instead of A3. Mixture of stereoisomers: LCMS: MS m/z=753.2 and 753.2 [M+1], $t_R$=1.11 min and 1.13 min; $^1$H NMR (400 MHz, Methanol-d4) δ 7.87 (s, 1H), 7.19-7.00 (m, 4H), 6.95-6.81 (m, 2H), 6.21 (dd, J=46.8, 5.9 Hz, 1H), 5.57 (ddd, J=5.8, 3.9, 1.4 Hz, 1H), 4.69-4.56 (m, 1H), 4.49-4.33 (m, 2H), 4.11 (dqd, J=9.4, 7.1, 2.6 Hz, 2H), 3.82 (ddd, J=40.8, 9.5, 7.1 Hz, 1H), 2.74-2.59 (m, 2H), 2.53 (d, J=3.0 Hz, 1H), 2.07 (d, J=6.4 Hz, 6H), 1.38-1.12 (m, 18H); $^{31}$P NMR (162 MHz, Methanol-d4) δ 3.62.

Intermediate T16: spiro[3.3]heptan-2-yl ((perfluorophenoxy)(phenoxy)phosphoryl)-L-alaninate

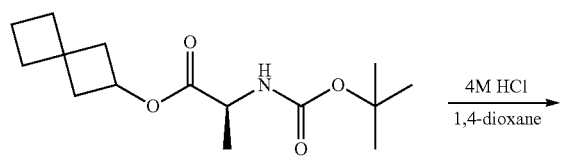

Intermediate T16 was made in a similar manner as intermediate H2 except that intermediate T15 (590 mg, 2.69 mmol) was used instead of 2-methoxy-2-methylpropyl L-alaninate hydrochloride and N-ethyl-N-isopropyl-propan-2-amine (1.4 mL, 8.06 mmol, 3 equiv) was used as base instead of triethylamine. LCMS: MS m/z=506.0 [M+1], $t_R$=1.19 min.

Example 44: spiro[3.3]heptan-2-yl ((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)-L-alaninate

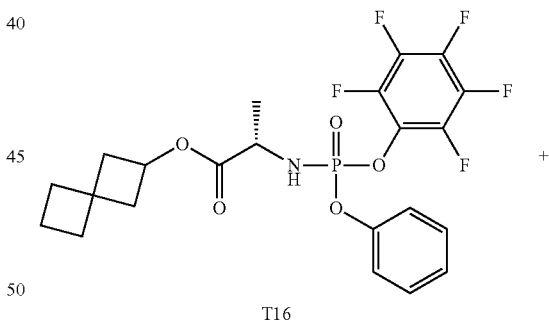

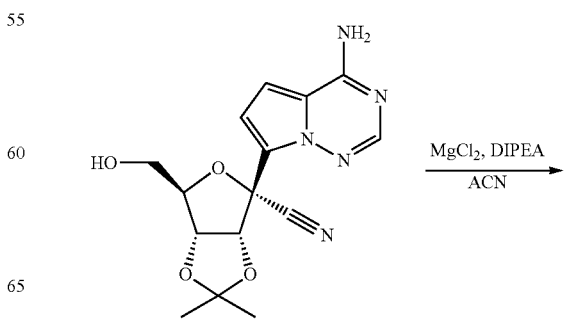

211
-continued

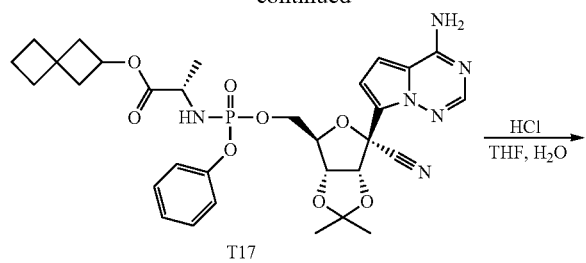

T17

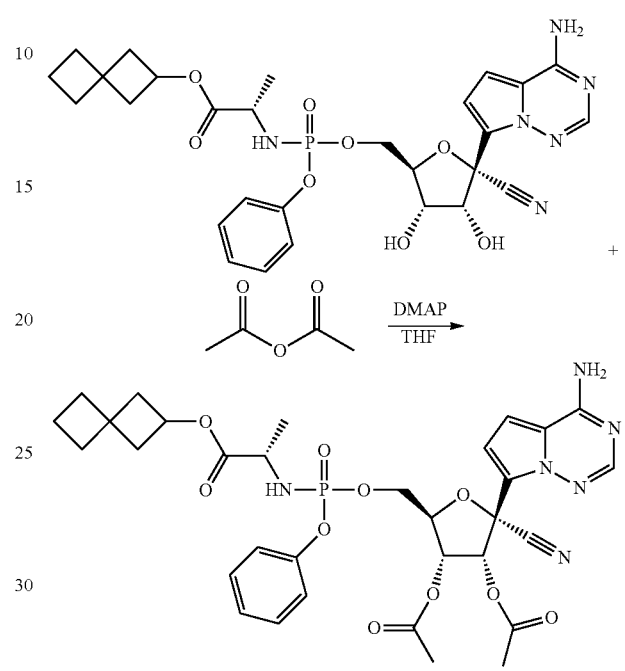

Intermediate T17 was made in a similar manner as intermediate A2 except that intermediate T16 (408 mg, 0.808 mmol) was used instead of intermediate A1. LCMS: MS m/z=653.2 and 6.53.2 [M+1], $t_R$=0.997 min and 1.01 min.

Compound 44 was made in a similar manner as Compound 13 except that intermediate T17 (431 mg, 0.662 mmol) was used instead of intermediate A2. The 1:1 mixture of diastereomers was isolated by column chromatography using 10% methanol in dichloromethane as eluting solvent mixture. Mixture of stereoisomers: LCMS: MS m/z=613.2 and 613.2 [M+1], $t_R$=0.859 min and 0.870 min; $^1$H NMR (400 MHz, Methanol-d4) δ 7.88 (d, J=7.0 Hz, 1H), 7.32 (dt, J=8.7, 7.0 Hz, 2H), 7.24-7.13 (m, 3H), 6.98-6.84 (m, 2H), 4.83-4.75 (m, 2H), 4.41 (ddd, J=11.5, 5.4, 2.3 Hz, 2H), 4.35-4.27 (m, 1H), 4.20 (dt, J=14.0, 5.5 Hz, 1H), 3.90-3.77 (m, 1H), 2.45-2.34 (m, 2H), 2.07-1.90 (m, 6H), 1.89-1.79 (m, 2H), 1.25 (ddd, J=17.4, 7.1, 1.1 Hz, 3H); $^{31}$P NMR (162 MHz, Methanol-d4) δ 3.67.

Compound 44 was further purified by preparatory HPLC (Gemini Sum NX-C18 110A LC column 100×30 mm, 95% to 0% water acetonitrile gradient) to separate the individual isomers.

Peak 1 (44a) (faster eluting isomer): LCMS: MS m/z=613.2 [M+1], $t_R$=0.86 min; $^1$H NMR (400 MHz, Methanol-d4) δ 7.87 (s, 1H), 7.31 (t, J=7.8 Hz, 2H), 7.20-7.12 (m, 3H), 6.98-6.88 (m, 2H), 4.83-4.75 (m, 2H), 4.46-4.37 (m, 2H), 4.32 (ddd, J=10.7, 5.7, 3.7 Hz, 1H), 4.22 (t, J=5.4 Hz, 1H), 3.88-3.75 (m, 1H), 2.40 (ddt, J=9.4, 7.2, 2.6 Hz, 2H), 2.09-1.78 (m, 9H), 1.23 (dd, J=7.1, 1.2 Hz, 3H); $^{31}$P NMR (162 MHz, Methanol-d4) δ 3.70.

Peak 2 (44b) (slower eluting isomer): LCMS: MS m/z=613.2 [M+1], $t_R$=0.87 min; $^1$H NMR (400 MHz, Methanol-d4) δ 7.89 (s, 1H), 7.38-7.29 (m, 2H), 7.21 (dd, J=7.6, 1.1 Hz, 3H), 6.96-6.86 (m, 2H), 4.84-4.75 (m, 2H), 4.45-4.35 (m, 2H), 4.34-4.25 (m, 1H), 4.19 (s, 1H), 3.84 (dq, J=9.8, 7.1 Hz, 1H), 2.42-2.32 (m, 2H), 2.04-1.81 (m, 8H), 1.28 (dd, J=7.1, 1.1 Hz, 3H); $^{31}$P NMR (162 MHz, Methanol-d4) δ 3.65.

Example 45: (2R,3R,4R,5R)-2-(4-aminopyrrolo[2,1-f][1,2,4]triazin-7-yl)-2-cyano-5-((((((S)-1-oxo-1-(spiro[3.3]heptan-2-yloxy)propan-2-yl)amino)(phenoxy)phosphoryl)oxy)methyl)tetrahydrofuran-3,4-diyl diacetate Compound 45 was made in a similar manner as Example 30 except that the compound 44 (50 mg, 0.082 mmol) was used instead of 29. Mixture of stereoisomers: LCMS: MS m/z=697.2 and 697.2 [M+1], $t_R$=0.975 min and 0.990 min; $^1$H NMR (400 MHz, Methanol-d4) δ 7.87 (d, J=4.4 Hz, 1H), 7.31 (ddd, J=15.5, 8.8, 7.3 Hz, 2H), 7.17 (q, J=7.5 Hz, 3H), 6.96-6.81 (m, 2H), 6.26 (dd, J=33.3, 5.9 Hz, 1H), 5.56 (ddd, J=7.9, 5.9, 4.2 Hz, 1H), 4.85-4.75 (m, 1H), 4.64 (ddt, J=9.6, 3.9, 1.9 Hz, 1H), 4.48-4.32 (m, 2H), 3.81 (ddd, J=26.1, 9.5, 7.1 Hz, 1H), 2.43-2.35 (m, 2H), 2.16 (dd, J=12.8, 2.0 Hz, 6H), 2.08-1.77 (m, 7H), 1.33-1.24 (m, 2H); $^{31}$P NMR (162 MHz, Methanol-d4) δ 3.54 (d, J=11.9 Hz).

Compound 45 was further purified by preparatory HPLC (Gemini Sum NX-C18 110A LC column 100×30 mm, 95% to 0% water acetonitrile gradient) to separate the individual isomers.

Peak 1 (45a) (faster eluting isomer): LCMS: MS m/z=697.2 [M+1], $t_R$=0.98 min; $^1$H NMR (400 MHz, Methanol-d4) δ 7.86 (s, 1H), 7.37-7.29 (m, 2H), 7.19 (dq, J=8.1, 1.1 Hz, 3H), 6.98-6.89 (m, 2H), 6.30 (d, J=6.0 Hz, 1H), 5.57 (dd, J=6.0, 4.2 Hz, 1H), 4.83-4.73 (m, 1H), 4.65 (dq, J=3.8, 1.7 Hz, 1H), 4.49-4.34 (m, 2H), 3.77 (dd, J=9.2, 7.1 Hz, 1H), 2.45-2.31 (m, 2H), 2.15 (d, J=12.5 Hz, 6H), 2.05-1.77 (m, 8H), 1.18 (dd, J=7.1, 1.2 Hz, 3H); $^{31}$P NMR (162 MHz, Methanol-d4) δ 3.63.

Peak 2 (45b) (slower eluting isomer): LCMS: MS m/z=697.2 [M+1], $t_R$=1.00 min; $^1$H NMR (400 MHz, Methanol-d4) δ 7.87 (s, 1H), 7.29 (dd, J=8.7, 7.1 Hz, 2H), 7.17 (dt, J=8.0, 1.1 Hz, 3H), 6.87 (s, 1H), 6.21 (d, J=5.9 Hz, 1H), 5.55 (dd, J=5.9, 4.3 Hz, 1H), 4.84-4.76 (m, 1H), 4.62 (dd, J=3.9, 1.7 Hz, 1H), 4.42-4.27 (m, 2H), 3.84 (dd, J=9.8, 7.1 Hz, 1H), 2.45-2.33 (m, 2H), 2.16 (d, J=13.2 Hz, 6H), 2.07-1.77 (m, 8H), 1.28 (dd, J=7.1, 1.1 Hz, 3H); ³¹P NMR (162 MHz, Methanol-d4) δ 3.54.

Example 46: (2R,3R,4R,5R)-2-(4-aminopyrrolo[2,1-f][1,2,4]triazin-7-yl)-2-cyano-5-((((((S)-1-oxo-1-(spiro[3.3]heptan-2-yloxy)propan-2-yl)amino)(phenoxy)phosphoryl)oxy)methyl)tetrahydrofuran-3,4-diyl bis(2-methylpropanoate)

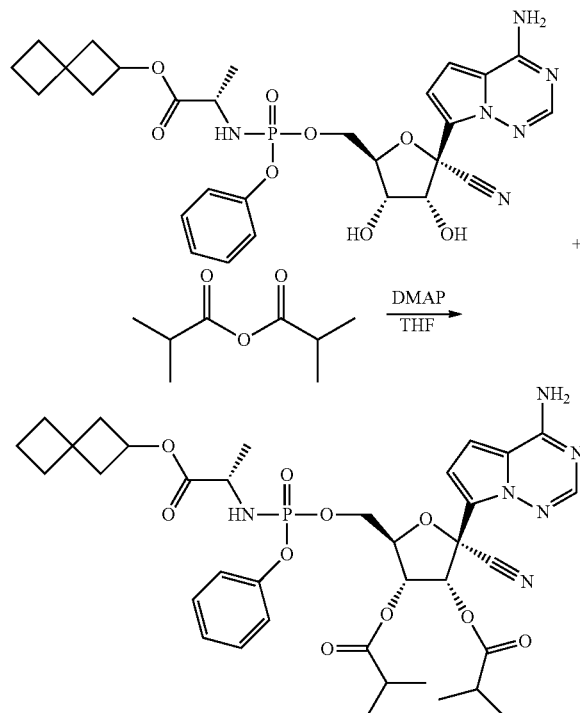

Compound 46 was made in a similar manner as Example 14 except that 44 (54 mg, 0.078 mmol) was used instead of A3. Mixture of stereoisomers: LCMS: MS m/z=753.4 and 753.4 [M+1], $t_R$=1.12 min and 1.13 min; ¹H NMR (400 MHz, Methanol-d4) δ 7.87 (d, J=1.4 Hz, 1H), 7.37-7.25 (m, 2H), 7.24-7.13 (m, 3H), 6.97-6.81 (m, 2H), 6.25 (dd, J=36.6, 5.9 Hz, 1H), 5.58 (td, J=5.6, 3.7 Hz, 1H), 4.80 (dt, J=18.8, 7.4 Hz, 1H), 4.68-4.58 (m, 1H), 4.49-4.34 (m, 2H), 3.81 (ddd, J=23.0, 9.5, 7.1 Hz, 1H), 2.73-2.59 (m, 2H), 2.44-2.34 (m, 2H), 2.07-1.77 (m, 8H), 1.32-1.16 (m, 15H); ³¹P NMR (162 MHz, Methanol-d4) δ 3.53.

Compound 46 was further purified by preparatory HPLC (Gemini 5 um NX-C18 110A LC column 100×30 mm, 95% to 0% water acetonitrile gradient) to separate the individual isomers.

Peak 1 (46a) (faster eluting isomer): LCMS: MS m/z=753.2 [M+1], $t_R$=1.14 min; ¹H NMR (400 MHz, Methanol-d4) δ 7.87 (s, 1H), 7.39-7.27 (m, 2H), 7.26-7.05 (m, 3H), 6.91 (s, 2H), 6.30 (d, J=5.9 Hz, 1H), 5.58 (dd, J=5.9, 3.8 Hz, 1H), 4.78 (p, J=7.4 Hz, 1H), 4.65 (dd, J=3.8, 2.0 Hz, 1H), 4.49-4.35 (m, 2H), 4.12 (dd, J=24.1, 5.3 Hz, 1H), 3.87-3.74 (m, 1H), 3.65-3.45 (m, 1H), 2.66 (dp, J=23.0, 7.0 Hz, 2H), 2.45-2.34 (m, 2H), 2.10-1.56 (m, 8H), 1.35-1.18 (m, 15H); ³¹P NMR (162 MHz, Methanol-d4) δ 3.63.

Peak 2 (46b) (slower eluting isomer): LCMS: MS m/z=753.2 [M+1], $t_R$=1.00 min; ¹H NMR (400 MHz, Methanol-d4) δ 7.87 (s, 1H), 7.29 (dd, J=8.7, 7.0 Hz, 2H), 7.17 (d, J=7.8 Hz, 3H), 6.91-6.80 (m, 2H), 6.21 (d, J=5.8 Hz, 1H), 5.57 (dd, J=5.9, 3.7 Hz, 1H), 4.61 (dd, J=4.1, 1.8 Hz, 2H), 4.40 (pd, J=11.1, 4.2 Hz, 2H), 4.19-4.03 (m, 1H), 3.90-3.79 (m, 1H), 3.62-3.45 (m, 1H), 2.67 (dp, J=24.1, 7.0 Hz, 2H), 2.39 (td, J=12.5, 12.0, 7.1 Hz, 2H), 2.09-1.77 (m, 8H), 1.36-1.19 (m, 15H); ³¹P NMR (162 MHz, Methanol-d4) δ 3.48.

Intermediate P1: 1-propyl L-alaninate hydrochloride

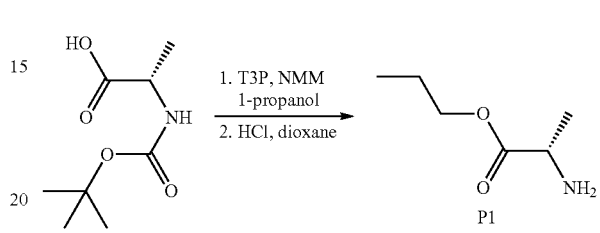

To a stirred solution of (tert-butoxycarbonyl)-L-alanine (7.5 g, 39.6 mmol) and 1-propanol (2.74 mL, 36.6 mmol) in dry dichloromethane (50 mL) were added N-methylmorpholine (12.1 mL, 110 mmol), 4-(dimethylamino)pyridine (90 mg, 0.73 mmol) and tri-propylphosphonic acid cyclic anhydride (T3P, 26.2 mL, 50% in ethyl acetate) at 0° C. under an atmosphere of argon. The reaction mixture was then stirred at room temperature for 2 hours. The reaction mixture was washed with water (2×50 mL), and once with brine (50 mL), dried over magnesium sulfate, filtered through a 3 cm layer of silica gel which was washed with additional dichloromethane. The combined organics were concentrated down under reduced pressure and dried under high vacuum.

The residue was then dissolved in 30 mL of 4 M HCl in 1,4-dioxane and the reaction mixture was stirred at room temperature for 2 hours, concentrated under reduced pressure and co-distilled with toluene to give the product which was dried under high vacuum for 1 hour. The residue was used without further purification. ¹H NMR (400 MHz, DMSO-d₆): □ 8.62 (broad s, 3H), 4.20-4.01 (m, 3H), 1.67-1.57 (m, 2H), 1.42 (d, J=7.2 Hz, 3H), 0.91 (t, J=7.2 Hz, 3H).

Intermediate P2: 1-propyl (2S)-2-[[(4-tert-butylphenoxy)-(2,3,4,5,6-pentafluorophenoxy)phosphoryl]amino]propanoate

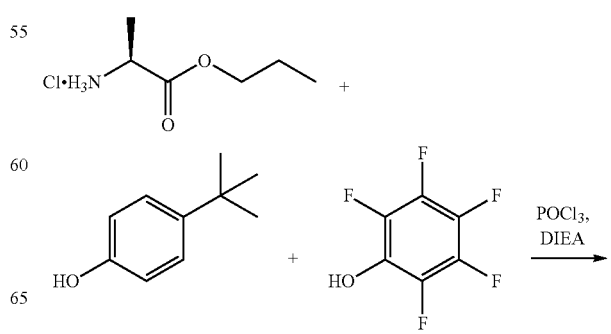

-continued

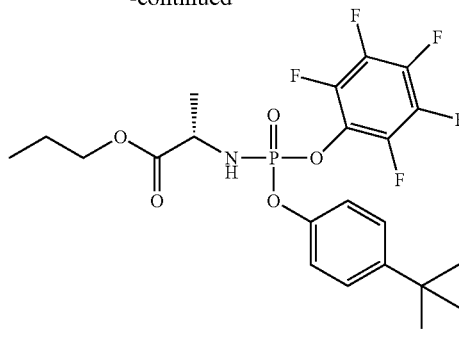

P2

To a solution of phosphorus (V) oxychloride (0.572 mL, 6.14 mmol) in dichloromethane (20 mL) under an atmosphere of argon was added 4-tert-butylphenol (0.922 g, 6.14 mmol) at −78° C. N,N-diisopropylethylamine (1.07 mL, 6.14 mmol) over 5 minutes. After 15 minutes, the reaction was allowed to warm to 0° C. 1-propyl L-alaninate hydrochloride (1.03 g, 6.14 mmol) was added. N,N-diisopropylethylamine (2.14 mL, 12.3 mmol) over 5 minutes. After 30 minutes, 2,3,4,5,6-pentafluorophenol (1.13 g, 6.14 mmol) was added. N,N-diisopropylethylamine (1.07 mL, 6.14 mmol) over 5 minutes. After 15 minutes, the reaction mixture was allowed to warm to room temperature. After 30 minutes, the reaction was acidified with acetic acid using pH paper. The reaction was washed with water (50 mL). The organics were dried over sodium sulfate, filtered and concentrated. The product was purified by silica gel chromatography (0-20% ethyl acetate in hexanes) to afford P2, 1-propyl (2S)-2-[[[(4-tert-butylphenoxy)-(2,3,4,5,6-pentafluorophenoxy)phosphoryl]amino]propanoate. LCMS: MS m/z=1041.1 [2M+Na$^+$].

Example 47: 1-propyl (2S)-2-[[[(2R,3S,4R,5R)-5-(4-aminopyrrolo[2,1-f][1,2,4]triazin-7-yl)-5-cyano-3,4-dihydroxy-tetrahydrofuran-2-yl]methoxy-(4-tert-butylphenoxy)phosphoryl]amino]propanoate

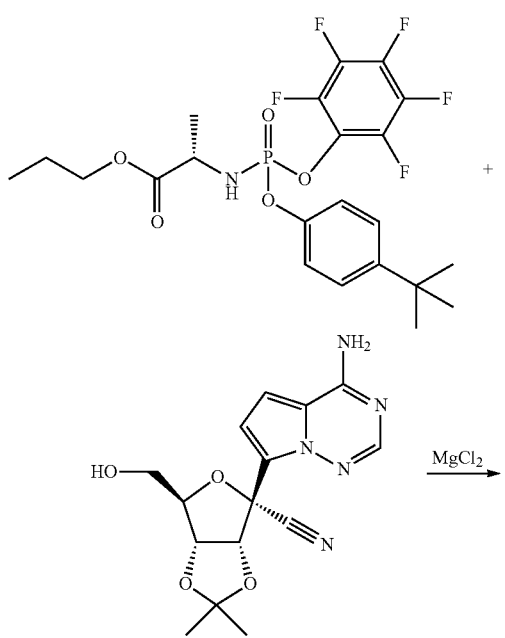

-continued

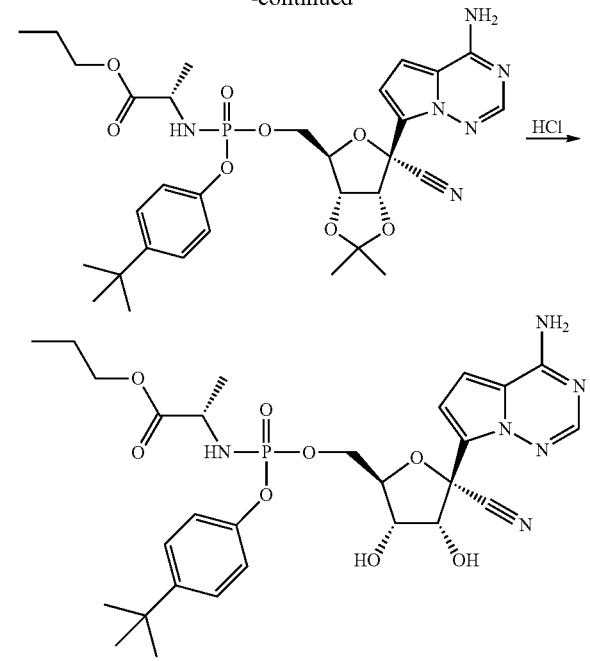

To a suspension of 1-propyl (2S)-2-[[[(4-tert-butylphenoxy)-(2,3,4,5,6-pentafluorophenoxy)phosphoryl]amino]propanoate (0.332 g, 0.554 mmol), (3aR,4R,6R,6aR)-4-(4-aminopyrrolo[2,1-f][1,2,4]triazin-7-yl)-6-(hydroxymethyl)-2,2-dimethyltetrahydrofuro[3,4-d][1,3]dioxole-4-carbonitrile (prepared according to WO2017049060, 0.184 g, 0.554 mmol) and magnesium chloride (0.057 g, 0.594 mmol) in acetonitrile (10 mL) under an atmosphere of argon was added N,N-diisopropylethylamine (0.10 mL, 0.594 mmol) at room temperature. After 10 min, the reaction was heated to 50° C. After 2 h, the reaction was cooled to room temperature, diluted with ethyl acetate and the organics were washed with water, dried over sodium sulfate, filtered and concentrated to afford 1-propyl (2S)-2-[[[(3aR,4R,6R,6aR)-4-(4-aminopyrrolo[2,1-f][1,2,4]triazin-7-yl)-4-cyano-2,2-dimethyl-6,6a-dihydro-3aH-furo[3,4-d][1,3]dioxol-6-yl]methoxy-(4-tert-butylphenoxy)phosphoryl]amino]propanoate. LCMS: MS m/z=657.2 [M+H$^+$].

1-Propyl (2S)-2-[[[(3aR,4R,6R,6aR)-4-(4-aminopyrrolo[2,1-f][1,2,4]triazin-7-yl)-4-cyano-2,2-dimethyl-6,6a-dihydro-3aH-furo[3,4-d][1,3]dioxol-6-yl]methoxy-(4-tert-butylphenoxy)phosphoryl]amino]propanoate was taken up in tetrahydrofuran (2 mL) and concentrated hydrochloric acid (11.7 M, 0.400 mL, 4.66 mmol) was added. After 2 h, the reaction was diluted with ethyl acetate and neutralized with a saturated aqueous solution of sodium bicarbonate. The layers were separated, and the organics were washed with water, saturated aqueous sodium chloride, dried over sodium sulfate, filtered and concentrated. The products were separated by HPLC chromatography (0-100% acetonitrile in water) to afford the title compound.

Peak 1: Compound 47a (First eluting isomer): LCMS: MS m/z=617.2 [M+H$^+$]. $^1$H NMR (400 MHz, Methanol-d4) δ 7.87 (s, 1H), 7.35-7.23 (m, 2H), 7.11-7.00 (m, 2H), 7.00-6.88 (m, 2H), 4.81 (d, J=5.5 Hz, 1H), 4.50-4.36 (m, 2H), 4.32 (ddd, J=11.0, 5.6, 3.7 Hz, 1H), 4.19 (t, J=5.5 Hz, 1H), 4.12-3.94 (m, 2H), 3.84 (dq, J=9.1, 7.1 Hz, 1H), 1.73-1.54 (m, 2H), 1.29 (s, 9H), 1.28-1.21 (m, 3H), 0.93 (t, J=7.4 Hz, 3H). $^{31}$P NMR (162 MHz, Methanol-d$_4$) δ 3.70 (s).

Peak 2: Compound 47b Second eluting isomer: LCMS: MS m/z=617.2 [M+H⁺]. ¹H NMR (400 MHz, Methanol-d4) δ 7.89 (s, 1H), 7.35-7.25 (m, 2H), 7.12-7.00 (m, 2H), 6.97-6.90 (m, 2H), 4.82 (d, J=5.4 Hz, 1H), 4.45-4.35 (m, 2H), 4.35-4.25 (m, 1H), 4.19 (t, J=5.6 Hz, 1H), 4.10-3.95 (m, 2H), 3.93-3.82 (m, 1H), 1.67-1.55 (m, 2H), 1.32-1.28 (m, 12H), 0.92 (t, J=7.4 Hz, 3H). ³¹P NMR (162 MHz, Methanol-d₄) δ 3.67 (s).

Example 48: (2R,3R,4R,5R)-2-(4-aminopyrrolo[2,1-f][1,2,4]triazin-7-yl)-5-((((4-(tert-butyl)phenoxy)(((S)-1-oxo-1-propoxypropan-2-yl)amino)phosphoryl)oxy)methyl)-2-cyanotetrahydrofuran-3,4-diyl bis(2-methylpropanoate)

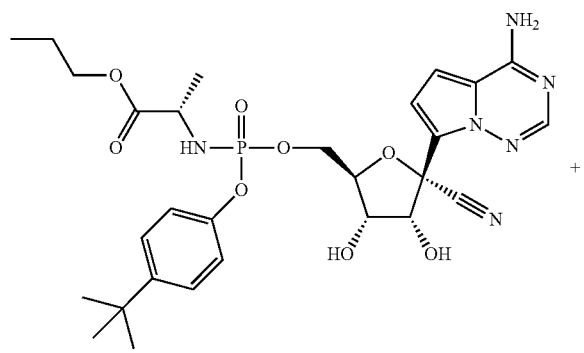

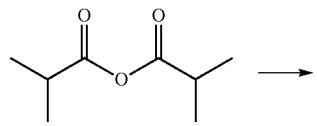

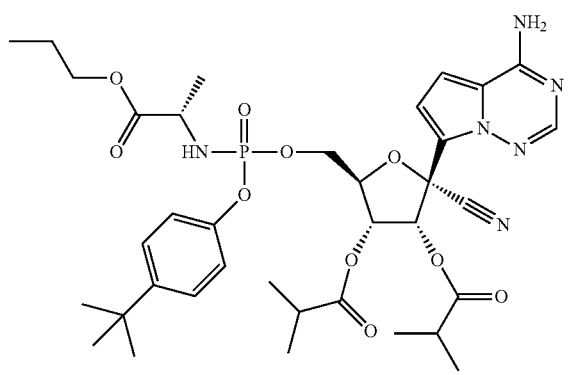

Compound 48 was made in a similar manner as compound 14 except that compound 48 was used instead of compound 13. Individual isomers of Compound 48 were separated by preparatory HPLC (Gemini Sum NX-C18 110A LC column 100×30 mm, 95% to 0% water acetonitrile gradient).

Peak 1: Compound 48a: First eluting isomer: LCMS: MS m/z=757.3 [M+H⁺]. ¹H NMR (400 MHz, Methanol-d4) δ 7.88 (d, J=2.9 Hz, 1H), 7.38-7.25 (m, 2H), 7.09 (ddd, J=10.3, 8.7, 1.3 Hz, 2H), 6.95-6.83 (m, 2H), 5.56 (ddd, J=6.0, 3.8, 2.7 Hz, 1H), 4.51-4.34 (m, 2H), 4.15-3.93 (m, 2H), 3.84 (ddd, J=38.2, 9.4, 7.1 Hz, 1H), 2.76-2.56 (m, 2H), 1.71-1.55 (m, 2H), 1.34-1.09 (m, 24H), 0.93 (q, J=7.4 Hz, 3H). ³¹P NMR (162 MHz, Methanol-d₄) δ 3.57 (s).

Peak 2: Compound 48b: Second eluting isomer: LCMS: MS m/z=757.3 [M+H⁺]. ¹H NMR (400 MHz, Methanol-d4) δ 7.88 (s, 1H), 7.32-7.26 (m, 2H), 7.10-7.04 (m, 2H), 6.92-6.84 (m, 2H), 6.16 (d, J=5.9 Hz, 1H), 5.57 (dd, J=5.9, 3.7 Hz, 1H), 4.70-4.56 (m, 1H), 4.48-4.32 (m, 2H), 4.11-3.97 (m, 2H), 3.89 (dq, J=9.9, 7.1 Hz, 1H), 2.67 (dp, J=24.1, 7.0 Hz, 2H), 1.64 (hept, J=6.9 Hz, 2H), 1.36-1.22 (m, 21H), 1.20 (d, J=7.0 Hz, 6H), 0.94 (t, J=7.4 Hz, 3H). ³¹P NMR (162 MHz, Methanol-d₄) δ 3.57-3.51 (m).

Intermediate P3: cyclobutyl L-alaninate hydrochloride

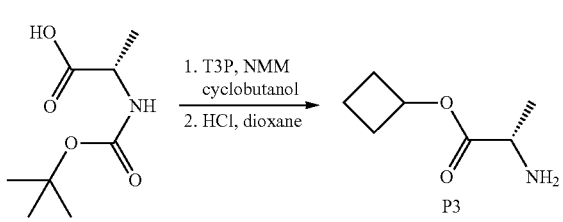

To a stirred solution of (tert-butoxycarbonyl)-L-alanine (4.91 g, 26.0 mmol) and cyclobutanol (1.70 g, 23.6 mmol) in dry dichloromethane (50 mL) were added N-methylmorpholine (7.78 mL, 70.7 mmol), 4-(dimethylamino)pyridine (57.6 mg, 0.47 mmol) and tri-propylphosphonic acid cyclic anhydride (T3P, 16.8 mL, 50% in ethyl acetate, 28.3 mmol) at 0° C. under an atmosphere of argon. The reaction mixture was then stirred at room temperature for 2 h. The reaction mixture was washed with water (2×50 mL), and once with brine (50 mL), dried over magnesium sulfate, filtered through a 3 cm layer of silica gel which was washed with additional dichloromethane. The combined organics were concentrated down under reduced pressure and dried under high vacuum overnight.

The residue was then dissolved in 30 mL of 4 M HCl in 1,4-dioxane and the reaction mixture was stirred at room temperature for 2 hours, concentrated under reduced pressure and co-distilled with toluene to give the product which was dried under high vacuum for 1 hour. The residue was used without further purification. ¹H NMR (400 MHz, DMSO-d₆) δ 8.38 (broad s, 3H), 5.01 (pd, J=7.5, 7.1, 0.9 Hz, 1H), 4.08 (q, J=7.2 Hz, 1H), 2.40-2.22 (m, 2H), 2.07 (dqd, J=12.6, 10.0, 7.9 Hz, 2H), 1.87-1.70 (m, 1H), 1.70-1.54 (m, 1H), 1.39 (d, J=7.2 Hz, 3H).

Intermediate P4: cyclobutyl (2S)-2-[[(4-tert-butylphenoxy)-(2,3,4,5,6-pentafluorophenoxy)phosphoryl]amino]propanoate

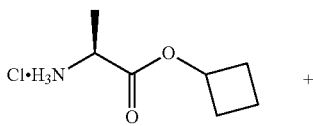

219 -continued

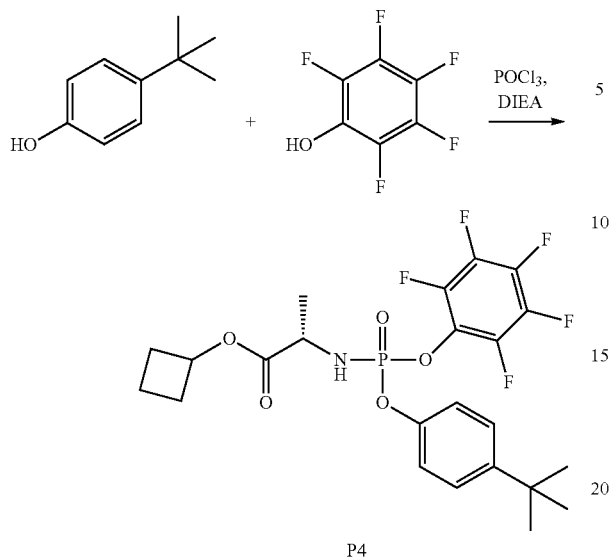

P4

To a solution of phosphorus (V) oxychloride (0.534 mL, 5.73 mmol) in dichloromethane (20 mL) under an atmosphere of argon was added 4-tert-butylphenol (0.769 g, 5.12 mmol) at −78° C. N,N-diisopropylethylamine (1.0 mL, 5.73 mmol) over 5 minutes. After 15 minutes, the reaction was allowed to warm to 0° C. Cyclopropyl L-alaninate hydrochloride (1.03 g, 6.14 mmol) was added. N,N-diisopropylethylamine (2.0 mL, 11.5 mmol) over 5 minutes. After 30 minutes, 2,3,4,5,6-pentafluorophenol (1.054 g, 5.73 mmol) was added. N,N-diisopropylethylamine (1.0 mL, 5.73 mmol) over 5 minutes. After 15 minutes, the reaction was allowed to warm to room temperature. After 30 minutes, the reaction was acidified with acetic acid using pH paper. The reaction was washed with water (50 mL). The organics were dried over sodium sulfate, filtered and concentrated. The product P4 was purified by silica gel chromatography (0-20% ethyl acetate in hexanes) to afford cyclobutyl (2S)-2-[[(4-tert-butylphenoxy)-(2,3,4,5,6-pentafluorophenoxy)phosphoryl]amino]propanoate. LCMS: MS m/z=521.8 [M+H$^+$].

Example 49: cyclobutyl (2S)-2-[[[(2R,3S,4R,5R)-5-(4-aminopyrrolo[2,1-f][1,2,4]triazin-7-yl)-5-cyano-3,4-dihydroxy-tetrahydrofuran-2-yl]methoxy-(4-tert-butylphenoxy)phosphoryl]amino]propanoate

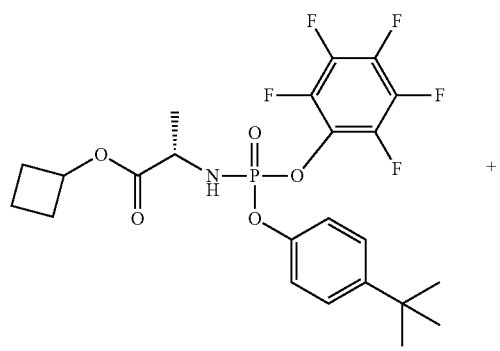

220 -continued

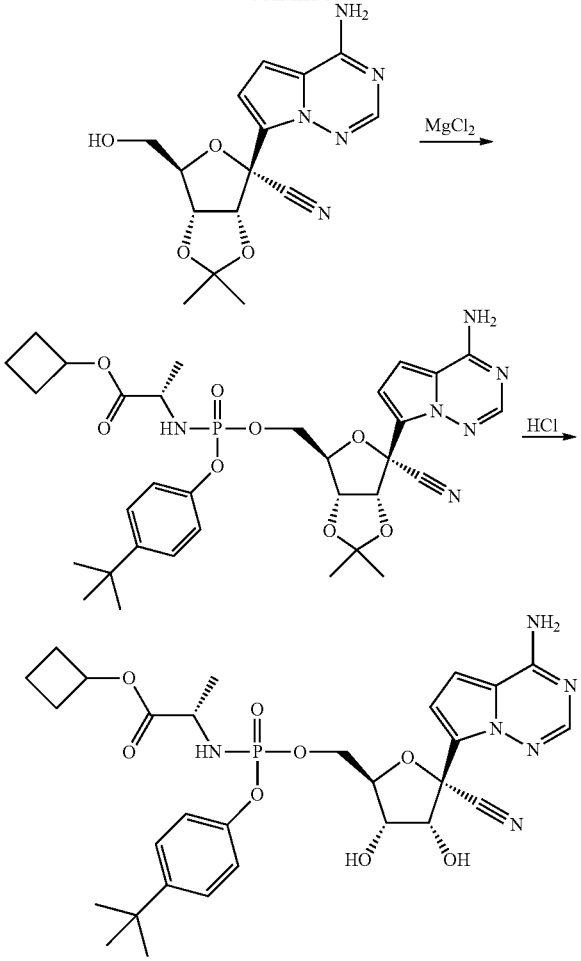

To a suspension of cyclobutyl (2S)-2-[[(4-tert-butylphenoxy)-(2,3,4,5,6-pentafluorophenoxy)phosphoryl]amino]propanoate (0.292 g, 0.477 mmol), (3aR,4R,6R,6aR)-4-(4-aminopyrrolo[2,1-f][1,2,4]triazin-7-yl)-6-(hydroxymethyl)-2,2-dimethyltetrahydrofuro[3,4-d][1,3]dioxole-4-carbonitrile (prepared according to WO2017049060, 0.158 g, 0.477 mmol) and magnesium chloride (0.049 g, 0.511 mmol) in acetonitrile (10 mL) under an atmosphere of argon was added N,N-diisopropylethylamine (89 uL, 0.511 mmol) at room temperature. After 10 min, the reaction was heated to 50° C. After 2 h, the reaction was cooled to room temperature, diluted with ethyl acetate and the organics were washed with water, dried over sodium sulfate, filtered and concentrated to afford cyclobutyl (2S)-2-[[[(3aR,4R,6R,6aR)-4-(4-aminopyrrolo[2,1-f][1,2,4]triazin-7-yl)-4-cyano-2,2-dimethyl-6,6a-dihydro-3aH-furo[3,4-d][1,3]dioxol-6-yl]methoxy-(4-tert-butylphenoxy)phosphoryl]amino]propanoate. LCMS: MS m/z=668.9 [M+H$^+$].

Cyclobutyl (2S)-2-[[[(3aR,4R,6R,6aR)-4-(4-aminopyrrolo[2,1-f][1,2,4]triazin-7-yl)-4-cyano-2,2-dimethyl-6,6a-dihydro-3aH-furo[3,4-d][1,3]dioxol-6-yl]methoxy-(4-tert-butylphenoxy)phosphoryl]amino]propanoate was taken up in tetrahydrofuran (2 mL) and concentrated hydrochloric acid (11.7 M, 0.400 mL, 4.66 mmol) was added. After 2 h, the reaction was diluted with ethyl acetate and neutralized with a saturated aqueous solution of sodium bicarbonate. The layers were separated, and the organics were washed with water, saturated aqueous sodium chloride, dried over sodium sulfate, filtered and concentrated. The product was purified by HPLC chromatography (0-100% acetonitrile in water) to afford the title compound as a mixture of stereoisomers. LCMS: MS m/z=628.8 [M+H⁺].

Example 50: (2R,3R,4R,5R)-2-(4-aminopyrrolo[2,1-f][1,2,4]triazin-7-yl)-5-((((4-(tert-butyl)phenoxy)(((S)-1-oxo-cyclobutoxypropan-2-yl)amino)phosphoryl)oxy)methyl)-2-cyanotetrahydrofuran-3,4-diyl bis(2-methylpropanoate)

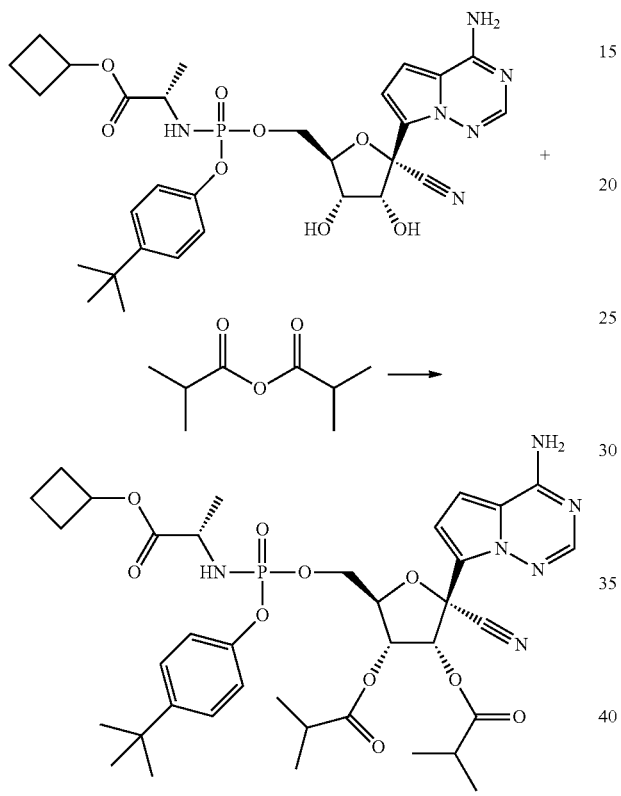

Compound 50 was made in a similar manner as compound 14 except that compound 49 was used instead of compound 13. Individual isomers of Compound 50 were separated by preparatory HPLC (Gemini 5 um NX-C18 110A LC column 100×30 mm, 95% to 0% water acetonitrile gradient).

Peak 1: First eluting isomer Compound 50a: LCMS: MS m/z=768.8 [M+H⁺]. ¹H NMR (400 MHz, Methanol-d4) δ 7.88 (d, J=2.7 Hz, 1H), 7.38-7.31 (m, 2H), 7.13-7.05 (m, 2H), 6.97-6.84 (m, 2H), 6.28 (d, J=5.9 Hz, 1H), 5.56 (dd, J=5.9, 3.8 Hz, 1H), 4.77-4.57 (m, 2H), 4.41 (s, 1H), 3.82-3.69 (m, 1H), 2.66 (dt, J=22.2, 7.0 Hz, 1H), 2.39-2.21 (m, 2H), 2.11-1.90 (m, 2H), 1.86-1.74 (m, 1H), 1.72-1.56 (m, 1H), 1.38-1.06 (m, 24H). ³¹P NMR (162 MHz, Methanol-d4) δ 3.53 (s).

Peak 2: Second eluting isomer Compound 50b: LCMS: MS m/z=768.8 [M+H⁺]. ¹H NMR (400 MHz, Methanol-d4) δ 7.88 (d, J=2.9 Hz, 1H), 7.38-7.25 (m, 2H), 7.09 (ddd, J=10.3, 8.7, 1.3 Hz, 2H), 6.95-6.83 (m, 2H), 5.56 (ddd, J=6.0, 3.8, 2.7 Hz, 1H), 4.51-4.34 (m, 2H), 4.15-3.93 (m, 2H), 3.84 (ddd, J=38.2, 9.4, 7.1 Hz, 1H), 2.76-2.56 (m, 2H), 1.71-1.55 (m, 2H), 1.34-1.09 (m, 24H), 0.93 (q, J=7.4 Hz, 3H). ³¹P NMR (162 MHz, Methanol-d₄) δ 3.57 (s).

Intermediate P5: cyclobutyl ((4-(cyclopropyl)phenoxy)(perfluorophenoxy)phosphoryl)-L-alaninate

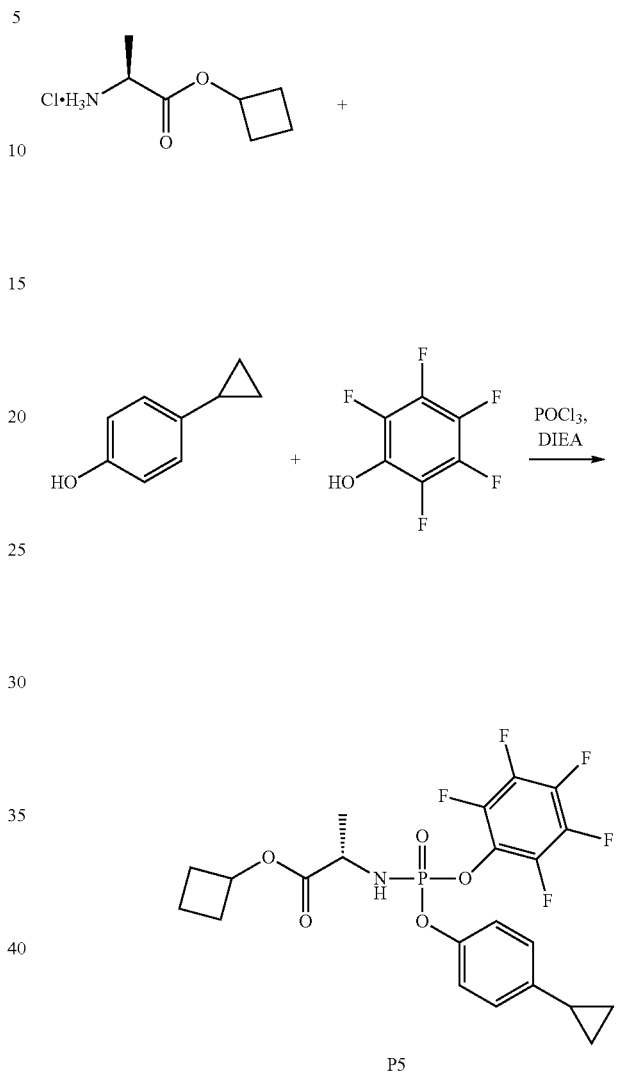

P5

To a solution of phosphorus (V) oxychloride (0.878 mL, 5.73 mmol) in dichloromethane (20 mL) under an atmosphere of argon was added cyclopropylphenol (0.769 g, 5.73 mmol) at −78° C. N,N-diisopropylethylamine (1.0 mL, 5.73 mmol) over 5 minutes. After 15 minutes, the reaction was allowed to warm to 0° C. Cyclopropyl L-alaninate hydrochloride (1.03 g, 6.14 mmol) was added. N,N-diisopropylethylamine (2.0 mL, 11.5 mmol) over 5 minutes. After 30 minutes, 2,3,4,5,6-pentafluorophenol (1.054 g, 5.73 mmol) was added. N,N-diisopropylethylamine (1.0 mL, 5.73 mmol) over 5 minutes. After 15 minutes, the reaction was allowed to warm to room temperature. After 30 minutes, the reaction was acidified with acetic acid using pH paper. The reaction was washed with water (50 mL). The organics were dried over sodium sulfate, filtered and concentrated. The product was purified by silica gel chromatography (0-20% ethyl acetate in hexanes) to afford cyclobutyl (2S)-2-[[(cyclopropylbutylphenoxy)-(2,3,4,5,6-pentafluorophenoxy)phosphoryl]amino]propanoate. LCMS: MS m/z=505.8 [M+H⁺].

Example 51: cyclobutyl (2S)-2-[[[(2R,3S,4R,5R)-5-(4-aminopyrrolo[2,1-f][1,2,4]triazin-7-yl)-5-cyano-3,4-dihydroxy-tetrahydrofuran-2-yl]methoxy-(cyclopropylphenoxy)phosphoryl]amino]propanoate

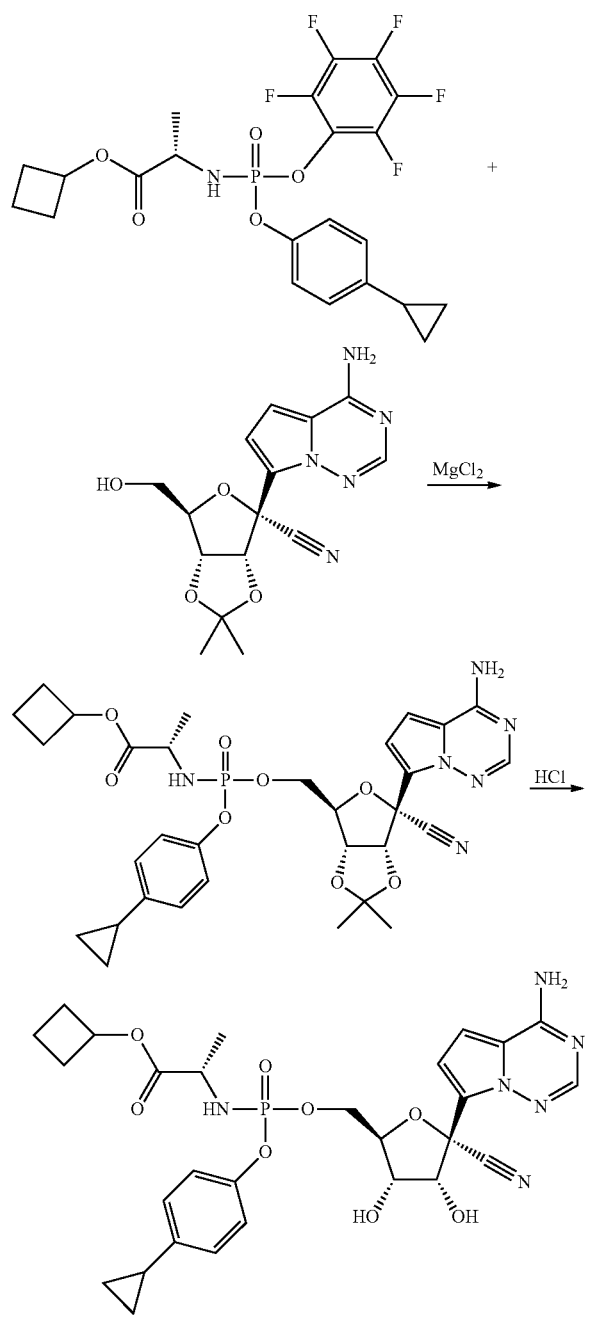

To a suspension of cyclobutyl (2S)-2-[[(cyclopropylphenoxy)-(2,3,4,5,6-pentafluorophenoxy)phosphoryl]amino]propanoate (0.314 g, 0.546 mmol), (3aR,4R,6R,6aR)-4-(4-aminopyrrolo[2,1-f][1,2,4]triazin-7-yl)-6-(hydroxymethyl)-2,2-dimethyltetrahydrofuro[3,4-d][1,3]dioxole-4-carbonitrile (prepared according to WO2017049060, 0.181 g, 0.546 mmol) and magnesium chloride (0.057 g, 0.601 mmol) in acetonitrile (10 mL) under an atmosphere of argon was added N,N-diisopropylethylamine (105 uL, 0.601 mmol) at room temperature. After 10 min, the reaction was heated to 50° C. After 2 h, the reaction was cooled to room temperature, diluted with ethyl acetate and the organics were washed with water, dried over sodium sulfate, filtered and concentrated to afford cyclobutyl (2S)-2-[[[(3aR,4R,6R,6aR)-4-(4-aminopyrrolo[2,1-f][1,2,4]triazin-7-yl)-4-cyano-2,2-dimethyl-6,6a-dihydro-3aH-furo[3,4-d][1,3]dioxol-6-yl]methoxy-(cyclopropylphenoxy)phosphoryl]amino]propanoate. LCMS: MS m/z=652.8 [M+H$^+$].

Cyclobutyl (2S)-2-[[[(3aR,4R,6R,6aR)-4-(4-aminopyrrolo[2,1-f][1,2,4]triazin-7-yl)-4-cyano-2,2-dimethyl-6,6a-dihydro-3aH-furo[3,4-d][1,3]dioxol-6-yl]methoxy-(cyclopropylphenoxy)phosphoryl]amino]propanoate was taken up in tetrahydrofuran (2 mL) and concentrated hydrochloric acid (11.7 M, 0.400 mL, 4.66 mmol) was added. After 2 h, the reaction was diluted with ethyl acetate and neutralized with a saturated aqueous solution of sodium bicarbonate. The layers were separated, and the organics were washed with water, saturated aqueous sodium chloride, dried over sodium sulfate, filtered and concentrated. The products were separated by HPLC chromatography (0-100% acetonitrile in water) to afford the title compound(s). Individual isomers of Compound 51 were separated by preparatory HPLC (Gemini Sum NX-C18 110A LC column 100×30 mm, 95% to 0% water acetonitrile gradient).

Peak 1: First eluting isomer Compound 51a: LCMS: MS m/z=612.8 [M+H$^+$]. $^1$H NMR (400 MHz, Methanol-d4) δ 7.87 (s, 1H), 7.04-6.96 (m, 4H), 6.93 (s, 2H), 4.90 (d, J=12.9 Hz, 1H), 4.78 (d, J=5.4 Hz, 1H), 4.46-4.35 (m, 2H), 4.31 (ddd, J=10.8, 5.6, 3.5 Hz, 1H), 4.20 (t, J=5.4 Hz, 1H), 3.85-3.73 (m, 1H), 2.30 (dddd, J=14.9, 9.9, 5.3, 2.6 Hz, 2H), 2.11-1.95 (m, 2H), 1.88 (tt, J=8.4, 5.1 Hz, 1H), 1.84-1.72 (m, 1H), 1.64 (qt, J=10.5, 8.1 Hz, 1H), 1.34-1.15 (m, 3H), 0.99-0.89 (m, 2H), 0.68-0.56 (m, 2H). $^{31}$P NMR (162 MHz, Methanol-d4) δ 3.69 (s).

Peak 2: Second eluting isomer Compound 51b: LCMS: MS m/z=612.8 [M+H$^+$]. $^1$H NMR (400 MHz, Methanol-d4) δ 7.89 (s, 1H), 7.10-7.00 (m, 2H), 7.04-6.87 (m, 4H), 4.98-4.83 (m, 2H), 4.80 (d, J=5.4 Hz, 1H), 4.45-4.34 (m, 2H), 4.33-4.23 (m, 1H), 4.19 (t, J=5.6 Hz, 1H), 3.83 (dq, J=9.8, 7.1 Hz, 1H), 2.35-2.21 (m, 1H), 2.09-1.93 (m, 1H), 1.88 (tt, J=8.4, 5.0 Hz, 1H), 1.84-1.70 (m, 1H), 1.71-1.54 (m, 1H), 1.30-1.22 (m, 1H), 1.28 (dd, J=7.1, 1.1 Hz, 3H), 1.02-0.89 (m, 2H), 0.70-0.56 (m, 2H). $^{31}$P NMR (162 MHz, Methanol-d$_4$) δ 3.70-3.65 (m).

Example 52: (2R,3R,4R,5R)-2-(4-aminopyrrolo[2,1-f][1,2,4]triazin-7-yl)-5-((((4-(cyclopropylphenoxy)(((S)-1-oxo-cyclobutoxypropan-2-yl)amino)phosphoryl)oxy)methyl)-2-cyanotetrahydrofuran-3,4-diyl bis(2-methylpropanoate)

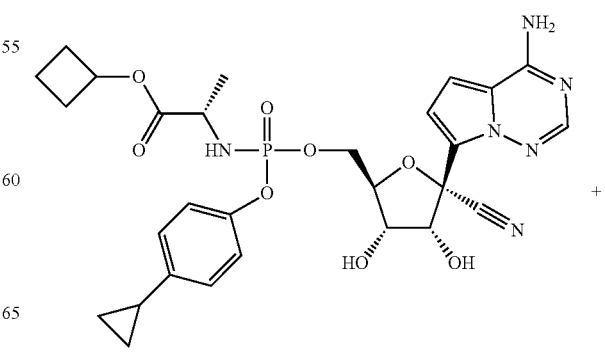

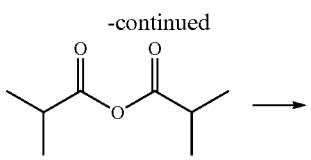

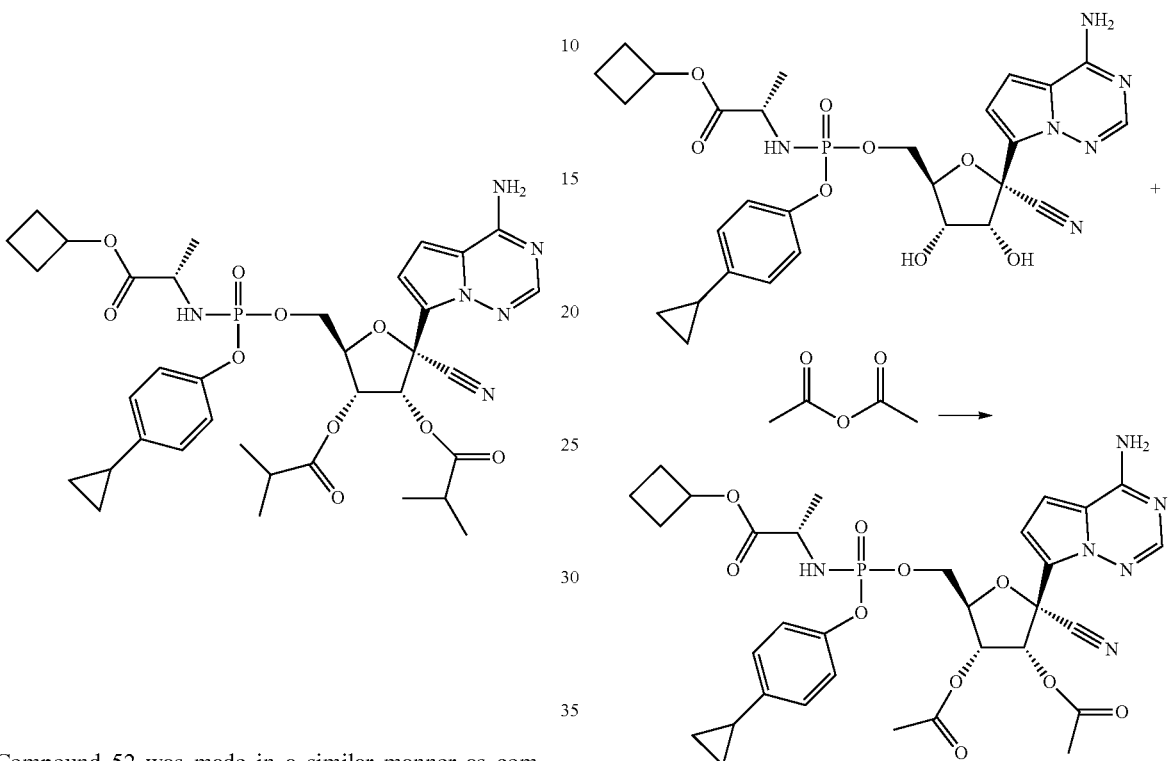

Compound 52 was made in a similar manner as compound 14 except that compound 51 was used instead of compound 13. Individual isomers of Compound 52 were separated by preparatory HPLC (Gemini Sum NX-C18 110A LC column 100×30 mm, 95% to 0% water acetonitrile gradient).

Peak 1: First eluting isomer Compound 52a: LCMS: MS m/z=753.4 [M+H⁺]. ¹H NMR (400 MHz, Methanol-d4) δ 7.87 (s, 1H), 7.10-6.97 (m, 4H), 6.99-6.85 (m, 2H), 6.27 (d, J=5.9 Hz, 1H), 5.56 (dd, J=5.9, 3.8 Hz, 1H), 4.98-4.84 (m, 1H), 4.64 (dt, J=5.7, 2.8 Hz, 1H), 4.41 (qdd, J=11.5, 5.7, 3.6 Hz, 2H), 3.75 (dq, J=9.2, 7.1 Hz, 1H), 2.66 (dhept, J=21.0, 7.0 Hz, 2H), 2.35-2.23 (m, 2H), 2.12-1.94 (m, 2H), 1.89 (tt, J=8.4, 5.0 Hz, 1H), 1.85-1.72 (m, 1H), 1.72-1.57 (m, 1H), 1.33-1.22 (m, 6H), 1.26-1.15 (m, 9H), 1.00-0.89 (m, 2H), 0.70-0.58 (m, 2H). ³¹P NMR (162 MHz, Methanol-d4) δ 3.55 (s).

Peak 2: Second eluting isomer Compound 52b: LCMS: MS m/z=753.4 [M+H⁺]. ¹H NMR (400 MHz, Methanol-d4) δ 7.88 (s, 1H), 7.07-7.00 (m, 2H), 7.00-6.93 (m, 2H), 6.88 (d, J=4.6 Hz, 1H), 6.82 (d, J=4.6 Hz, 1H), 6.15 (d, J=5.9 Hz, 1H), 5.56 (dd, J=5.9, 3.7 Hz, 1H), 4.98-4.84 (m, 1H), 4.61 (qd, J=3.8, 1.8 Hz, 1H), 4.39 (qdd, J=11.4, 8.1, 3.8 Hz, 2H), 3.91-3.77 (m, 1H), 2.67 (dp, J=22.7, 7.0 Hz, 2H), 2.38-2.23 (m, 2H), 2.12-1.94 (m, 2H), 1.87 (ddt, J=13.6, 10.3, 5.1 Hz, 1H), 1.82-1.71 (m, 1H), 1.71-1.53 (m, 1H), 1.34-1.22 (m, 9H), 1.20 (d, J=7.0 Hz, 6H), 0.94 (ddd, J=8.5, 4.3, 2.3 Hz, 2H), 0.69-0.53 (m, 2H). ³¹P NMR (162 MHz, Methanol-d₄) δ 3.54 (s).

Example 53: (2R,3R,4R,5R)-2-(4-aminopyrrolo[2,1-f][1,2,4]triazin-7-yl)-2-cyano-5-(((((S)-1-cyclobutoxy-1-oxopropan-2-yl)amino)(4-cyclopropylphenoxy)phosphoryl)oxy)methyl)tetrahydrofuran-3,4-diyl diacetate Compound 53 was made in a similar manner as compound 14 except that compound 51 was used instead of compound 13 and acetic anhydride was used in place of isobutyric anhydride. Individual isomers of Compound 53 were separated by preparatory HPLC (Gemini Sum NX-C18 110A LC column 100×30 mm, 95% to 0% water acetonitrile gradient).

Peak 1: First eluting isomer Compound 53a: LCMS: MS m/z=696.8 [M+H⁺]. ¹H NMR (400 MHz, Methanol-d4) δ 7.86 (s, 1H), 7.10-6.98 (m, 4H), 6.92 (d, J=1.0 Hz, 2H), 6.27 (d, J=6.0 Hz, 1H), 5.55 (dd, J=6.0, 4.2 Hz, 1H), 4.71-4.55 (m, 1H), 4.52-4.32 (m, 2H), 3.86-3.65 (m, 1H), 2.39-2.22 (m, 2H), 2.17 (s, 3H), 2.14 (s, 3H), 2.03 (dddd, J=14.5, 9.8, 7.3, 5.0 Hz, 2H), 1.97-1.86 (m, 1H), 1.86-1.73 (m, 1H), 1.72-1.53 (m, 1H), 1.18 (dd, J=7.2, 1.2 Hz, 3H), 1.01-0.88 (m, 2H), 0.70-0.57 (m, 2H). ³¹P NMR (162 MHz, Methanol-d₄) δ 3.58 (s).

Peak 2: Second eluting isomer Compound 53b: LCMS: MS m/z=696.8 [M+H⁺]. ¹H NMR (400 MHz, Methanol-d4) δ 7.87 (s, 1H), 7.03 (dd, J=8.8, 1.2 Hz, 2H), 6.96 (d, J=8.7 Hz, 2H), 6.90-6.82 (m, 2H), 6.17 (d, J=5.9 Hz, 1H), 5.54 (dd, J=6.0, 4.2 Hz, 1H), 4.96-4.90 (m, 1H), 4.66-4.55 (m, 1H), 4.37 (dddd, J=21.5, 11.5, 6.1, 3.8 Hz, 2H), 3.94-3.77 (m, 1H), 2.39-2.24 (m, 2H), 2.18 (s, 3H), 2.14 (s, 3H), 2.04 (s, 2H), 1.94-1.83 (m, 1H), 1.78 (q, J=10.2 Hz, 1H), 1.72-1.55 (m, 1H), 1.28 (dd, J=7.2, 1.1 Hz, 3H), 0.95 (dd, J=8.4, 2.0 Hz, 2H), 0.62 (dt, J=5.1, 1.4 Hz, 2H). ³¹P NMR (162 MHz, Methanol-d₄) δ 3.59 (s).

Example 54: (2R,3R,4R,5R)-2-(4-aminopyrrolo[2,1-f][1,2,4]triazin-7-yl)-2-cyano-5-((((((S)-1-cyclobutoxy-1-oxopropan-2-yl)amino)(4-cyclopropylphenoxy)phosphoryl)oxy)methyl)tetrahydrofuran-3,4-diyl dipropionate

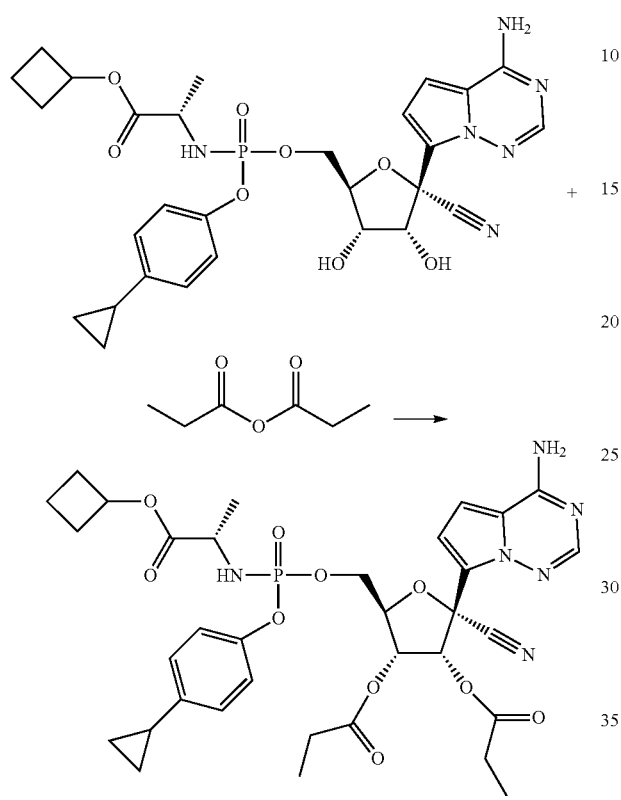

Compound 54 was made in a similar manner as compound 14 except that compound 51 was used instead of compound 13 and propionic anhydride was used in place of isobutyric anhydride. Individual isomers of Compound 54 were separated by preparatory HPLC (Gemini Sum NX-C18 110A LC column 100×30 mm, 95% to 0% water acetonitrile gradient).

Peak 1: First eluting isomer Compound 54a: LCMS: MS m/z=724.8 [M+H$^+$]. $^1$H NMR (400 MHz, Methanol-d4) δ 7.87 (s, 1H), 7.12-6.98 (m, 4H), 6.91 (d, J=3.6 Hz, 2H), 6.29 (d, J=5.9 Hz, 1H), 5.57 (dd, J=5.9, 4.1 Hz, 1H), 4.71-4.57 (m, 1H), 4.53-4.29 (m, 2H), 3.85-3.66 (m, 1H), 2.61-2.39 (m, 4H), 2.29 (dtt, J=12.4, 4.8, 2.6 Hz, 2H), 2.12-1.96 (m, 2H), 1.89 (ddd, J=13.4, 8.5, 5.0 Hz, 1H), 1.84-1.73 (m, 1H), 1.63 (qt, J=10.5, 8.0 Hz, 1H), 1.25-1.08 (m, 9H), 0.95 (dd, J=8.5, 2.1 Hz, 2H), 0.64 (d, J=6.6 Hz, 2H). $^{31}$P NMR (162 MHz, Methanol-d4) δ 3.59 (s).

Peak 2: Second eluting isomer Compound 54b: LCMS: MS m/z=724.8 [M+H$^+$]. $^1$H NMR (400 MHz, Methanol-d4) δ 7.87 (s, 1H), 7.03 (dd, J=8.8, 1.2 Hz, 2H), 6.96 (d, J=8.7 Hz, 2H), 6.89 (d, J=4.7 Hz, 1H), 6.85 (d, J=4.7 Hz, 1H), 6.18 (d, J=5.9 Hz, 1H), 5.57 (dd, J=5.9, 4.1 Hz, 1H), 4.71-4.55 (m, 1H), 4.38 (qdd, J=11.4, 6.0, 3.8 Hz, 2H), 3.94-3.69 (m, 1H), 2.57-2.36 (m, 4H), 2.36-2.19 (m, 2H), 2.04 (dtdd, J=13.4, 12.2, 6.7, 3.7 Hz, 2H), 1.94-1.72 (m, 2H), 1.72-1.52 (m, 1H), 1.29 (dd, J=7.1, 1.1 Hz, 3H), 1.18 (dt, J=17.6, 7.5 Hz, 6H), 1.00-0.86 (m, 2H), 0.71-0.54 (m, 2H). $^{31}$P NMR (162 MHz, Methanol-d4) δ 3.57 (s).

Intermediate P6: cyclobutyl ((naphthalen-1-yloxy)(perfluorophenoxy)phosphoryl)-L-alaninate

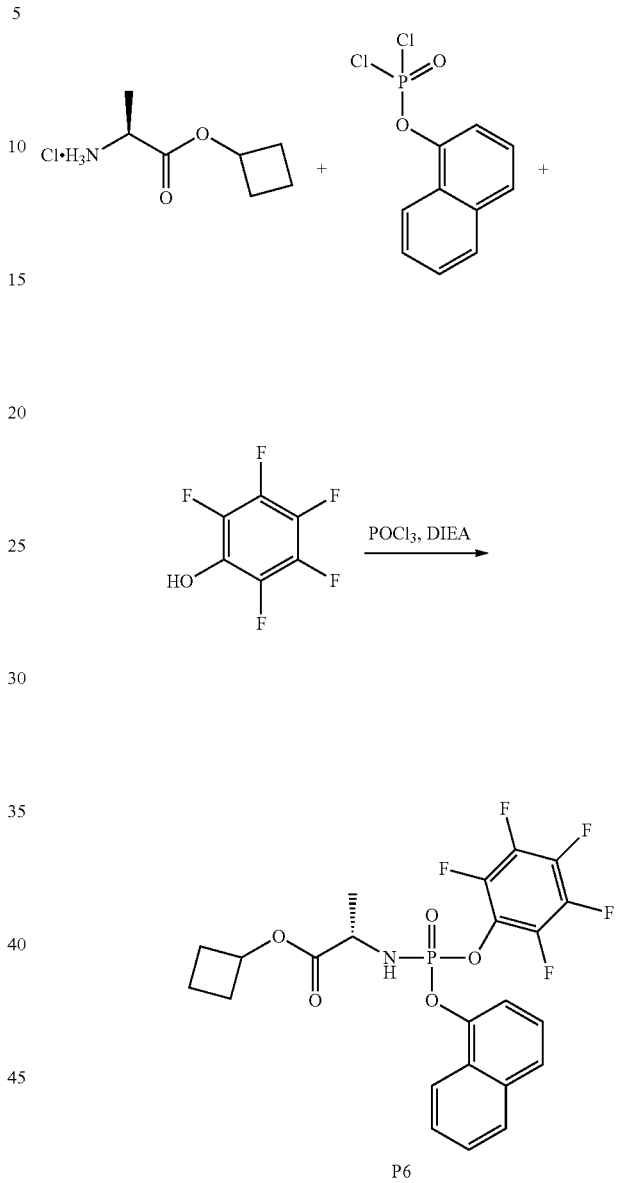

P6

To a solution of 1-dichlorophosphoryloxynaphthalene (0.925 g, 3.54 mmol) in dichloromethane (10 mL) under an atmosphere of argon was added cyclobutyl L-alaninate hydrochloride (0.451 g, 3.54 mmol). N,N-diisopropylethylamine (1.23 mL, 7.09 mmol) over 5 minutes. After 30 minutes, 2,3,4,5,6-pentafluorophenol (625 mg, 3.54 mmol) was added. N,N-diisopropylethylamine (0.62 mL, 3.54 mmol) over 5 minutes. After 15 minutes, the reaction was allowed to warm to room temperature. After 30 minutes, the reaction was acidified with acetic acid using pH paper. The reaction was washed with water (50 mL). The organics were dried over sodium sulfate, filtered and concentrated. The product P6 was purified by silica gel chromatography (0-20% ethyl acetate in hexanes) to afford cyclobutyl ((naphthalen-1-yloxy)(perfluorophenoxy)phosphoryl)-L-alaninate. LCMS: MS m/z=1052.3 [2M+Na$^+$].

Intermediate P6a: cyclobutyl ((((2R,3S,4R,5R)-5-(4-aminopyrrolo[2,1-f][1,2,4]triazin-7-yl)-5-cyano-3,4-dihydroxytetrahydrofuran-2-yl)methoxy)(naphthalen-1-yloxy)phosphoryl)-L-alaninate

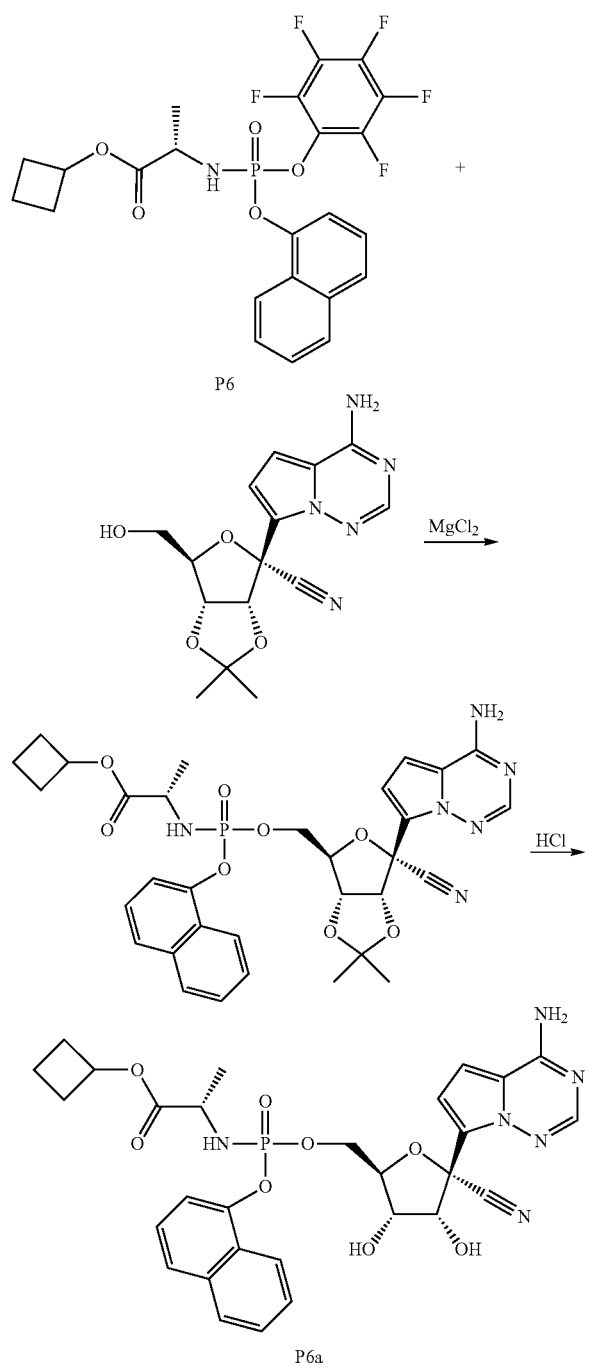

To a suspension of cyclobutyl ((naphthalen-1-yloxy)(perfluorophenoxy)phosphoryl)-L-alaninate (0.610 g, 1.07 mmol), (3aR,4R,6R,6aR)-4-(4-aminopyrrolo[2,1-f][1,2,4]triazin-7-yl)-6-(hydroxymethyl)-2,2-dimethyltetrahydrofuro[3,4-d][1,3]dioxole-4-carbonitrile (prepared according to WO2017049060, 0.353 g, 1.07 mmol) and magnesium chloride (0.101 g, 1.07 mmol) in acetonitrile (10 mL) under an atmosphere of argon was added N,N-diisopropylethylamine (204 uL, 1.17 mmol) at room temperature. After 10 min, the reaction was heated to 50° C. After 2 h, the reaction was cooled to room temperature, diluted with ethyl acetate and the organics were washed with water, dried over sodium sulfate, filtered and concentrated to afford cyclobutyl ((((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methoxy)(naphthalen-1-yloxy)phosphoryl)-L-alaninate. LCMS: MS m/z=662.8 [M+H$^+$].

Cyclobutyl ((((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methoxy)(naphthalen-1-yloxy)phosphoryl)-L-alaninate was taken up in acetonitrile (2 mL) and concentrated hydrochloric acid (11.7 M, 0.400 mL, 4.66 mmol) was added. After 2 h, the reaction was diluted with ethyl acetate and neutralized with a saturated aqueous solution of sodium bicarbonate. The layers were separated, and the organics were washed with water, saturated aqueous sodium chloride, dried over sodium sulfate, filtered and concentrated. The products were separated by HPLC chromatography (0-100% acetonitrile in water) to afford the title compound(s).

Individual isomers of Intermediate P6a were separated by preparatory HPLC (Gemini 5 um NX-C18 110A LC column 100×30 mm, 95% to 0% water acetonitrile gradient).

Peak 1: First eluting isomer Intermediate P6a-1: LCMS: MS m/z=622.8 [M+H$^+$]. $^1$H NMR (400 MHz, Methanol-d4) δ 8.09 (dt, J=8.4, 0.8 Hz, 1H), 7.93-7.85 (m, 1H), 7.82 (s, 1H), 7.70 (d, J=8.2 Hz, 1H), 7.59-7.30 (m, 3H), 6.88 (d, J=0.5 Hz, 2H), 4.89-4.79 (m, 3H), 4.70 (d, J=5.6 Hz, 1H), 4.41 (s, 3H), 4.21 (t, J=5.4 Hz, 1H), 3.94-3.77 (m, 1H), 2.34-2.13 (m, 2H), 2.04-1.86 (m, 2H), 1.81-1.68 (m, 1H), 1.67-1.49 (m, 1H), 1.21 (dd, J=7.1, 1.3 Hz, 2H). $^{31}$P NMR (162 MHz, Methanol-d4) δ 3.97 (s).

Peak 2: Second eluting isomer Intermediate P6a-2: LCMS: MS m/z=622.8 [M+H$^+$]. $^1$H NMR (400 MHz, Methanol-d4) δ 8.20-8.08 (m, 1H), 7.86 (s, 2H), 7.74-7.65 (m, 1H), 7.53 (s, 2H), 7.46 (dt, J=7.7, 1.3 Hz, 1H), 7.40-7.31 (m, 1H), 6.87 (d, J=4.5 Hz, 1H), 6.83 (d, J=4.6 Hz, 1H), 4.92-4.84 (m, 1H), 4.73 (d, J=5.4 Hz, 1H), 4.54-4.29 (m, 3H), 4.22 (s, 1H), 3.93 (dq, J=9.8, 7.0 Hz, 1H), 2.35-2.15 (m, 2H), 2.09-1.89 (m, 2H), 1.82-1.68 (m, 1H), 1.68-1.52 (m, 1H), 1.27 (dd, J=7.1, 1.1 Hz, 3H). $^{31}$P NMR (162 MHz, Methanol-d4) δ 3.97 (s).

Example 55: (2R,3R,4R,5R)-2-(4-aminopyrrolo[2,1-f][1,2,4]triazin-7-yl)-2-cyano-5-((((((S)-1-cyclobutoxy-1-oxopropan-2-yl)amino)(naphthalen-1-yloxy)phosphoryl)oxy)methyl)tetrahydrofuran-3,4-diyl bis(2-methylpropanoate)

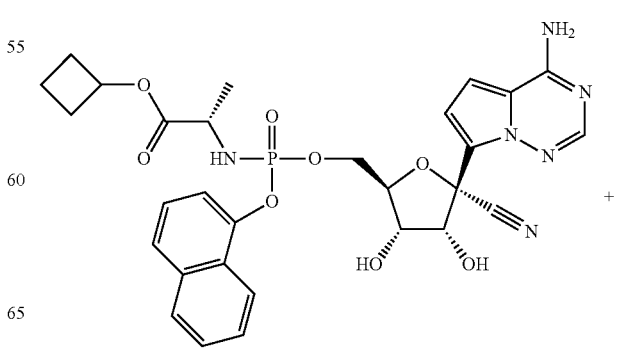

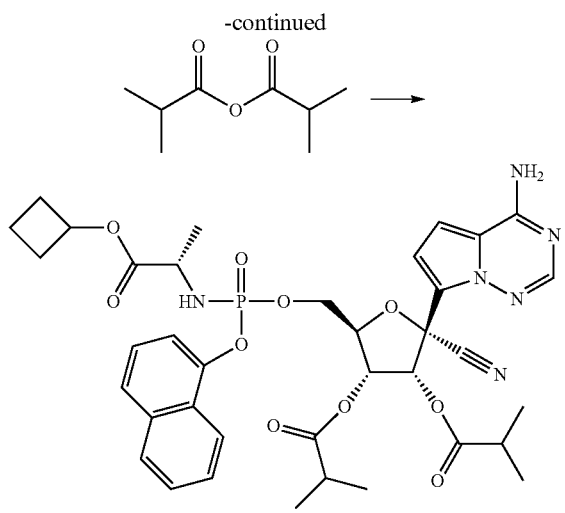

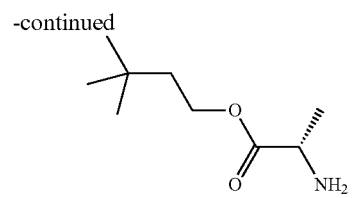

Compound 55 was made in a similar manner as compound 14 except that Intermediate P6a was used instead of compound 13. Individual isomers of Compound 55 were separated by preparatory HPLC (Gemini 5 um NX-C18 110A LC column 100×30 mm, 95% to 0% water acetonitrile gradient).

Peak 1: First eluting isomer Compound 55a: LCMS: MS m/z=762.8 [M+H$^+$]. $^1$H NMR (400 MHz, Methanol-d4) δ 8.17-8.11 (m, 1H), 7.90 (dd, J=7.0, 2.1 Hz, 1H), 7.80 (s, 1H), 7.73-7.68 (m, 1H), 7.54 (tt, J=7.0, 5.3 Hz, 2H), 7.47 (dt, J=7.6, 1.3 Hz, 1H), 7.39 (q, J=7.9, 7.2 Hz, 1H), 6.86 (d, J=0.9 Hz, 2H), 6.30 (d, J=6.0 Hz, 1H), 5.62 (dd, J=5.9, 3.7 Hz, 1H), 4.81 (dd, J=7.9, 7.0 Hz, 1H), 4.70-4.61 (m, 1H), 4.57-4.43 (m, 2H), 3.81 (dd, J=9.3, 7.1 Hz, 1H), 2.65 (dp, J=23.0, 7.0 Hz, 2H), 2.33-2.14 (m, 2H), 2.03-1.84 (m, 2H), 1.80-1.67 (m, 1H), 1.67-1.50 (m, 1H), 1.24 (dd, J=9.9, 6.8 Hz, 6H), 1.20-1.14 (m, 9H). $^{31}$P NMR (162 MHz, Methanol-d4) δ 3.76 (s).

Peak 2: Second eluting isomer Compound 55b: LCMS: MS m/z=762.8 [M+H$^+$]. $^1$H NMR (400 MHz, Methanol-d4) δ 8.13-8.07 (m, 1H), 7.88 (d, J=8.1 Hz, 1H), 7.82 (s, 1H), 7.69 (d, J=8.2 Hz, 1H), 7.58-7.39 (m, 4H), 7.33 (t, J=7.9 Hz, 1H), 6.77-6.70 (m, 2H), 6.20 (d, J=5.9 Hz, 1H), 5.61 (dd, J=5.9, 3.6 Hz, 1H), 4.65 (dt, J=5.7, 2.9 Hz, 1H), 4.55-4.37 (m, 2H), 3.93 (dq, J=9.9, 7.1 Hz, 1H), 2.66 (dp, J=19.6, 7.0 Hz, 2H), 2.35-2.19 (m, 2H), 2.10-1.88 (m, 2H), 1.84-1.69 (m, 1H), 1.69-1.55 (m, 1H), 1.29-1.22 (m, 9H), 1.20 (d, J=7.0 Hz, 6H). $^{31}$P NMR (162 MHz, Methanol-d$_4$) δ 3.81 (s).

Intermediate P7: 3,3-dimethylbutyl L-alaninate hydrochloride

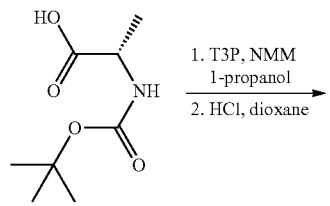

To a stirred solution of (tert-butoxycarbonyl)-L-alanine (4.56 g, 24.1 mmol) and 3,3-dimethylbutan-1-ol (2.2 g, 21.5 mmol) in dry dichloromethane (50 mL) were added N-methylmorpholine (7.1 mL, 64.6 mmol), 4-(dimethylamino)pyridine (52.6 mg, 0.258 mmol) and tri-propylphosphonic acid cyclic anhydride (T3P, 15.4 mL, 50% in ethyl acetate) at 0° C. under an atmosphere of argon. The reaction mixture was then stirred at room temperature for 2 hours. The reaction mixture was washed with water (2×50 mL), and once with brine (50 mL), dried over magnesium sulfate, filtered through a 3 cm layer of silica gel which was washed with additional dichloromethane. The combined organics were concentrated down under reduced pressure and dried under high vacuum overnight.

The residue was then dissolved in 30 mL of 4 M HCl in 1,4-dioxane and the reaction mixture was stirred at room temperature for 2 hours, concentrated under reduced pressure and co-distilled with toluene to give the product which was dried under high vacuum for 1 hour. The residue was used without further purification. $^1$H NMR (400 MHz, DMSO-d$_6$) δ 8.42 (s, 3H), 4.21 (qt, J=11.0, 7.3 Hz, 2H), 4.06 (d, J=7.2 Hz, 1H), 1.55 (t, J=7.3 Hz, 2H), 1.40 (d, J=7.1 Hz, 3H), 0.93 (s, 9H).

Intermediate P8: 3,3-dimethylbutyl ((perfluorophenoxy)(phenoxy)phosphoryl)-L-alaninate

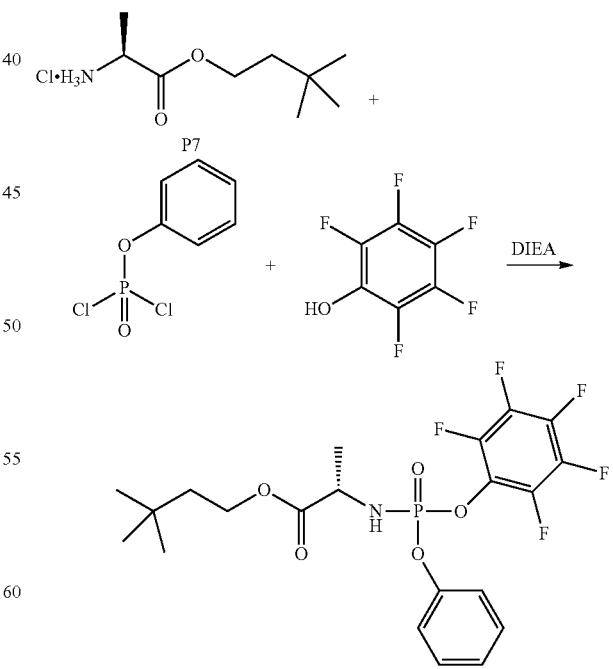

To a solution of dichlorophosphoryloxybenzene (0.544 mL, 3.64 mmol) in dichloromethane (20 mL) at 0° C. under an atmosphere of argon 3,3-dimethylbutyl L-alaninate hydrochloride (1.03 g, 6.14 mmol) was added. N,N-diisopropylethylamine (1.27 mL, 7.29 mmol) over 5 minutes. After 30 minutes, 2,3,4,5,6-pentafluorophenol (0.67 g, 7.29 mmol) was added. N,N-diisopropylethylamine (0.64 mL, 3.64 mmol) was added over 5 minutes. After 15 minutes, the reaction was allowed to warm to room temperature. After 30 minutes, the reaction was acidified with acetic acid using pH paper. The reaction was washed with water (50 mL). The organics were dried over sodium sulfate, filtered and concentrated. The product was purified by silica gel chromatography (0-20% ethyl acetate in hexanes) to afford 3,3-dimethylbutyl ((perfluorophenoxy)(phenoxy)phosphoryl)-L-alaninate. LCMS: MS m/z=496.2 [M+H$^+$].

Intermediate P8a: 3,3-dimethylbutyl (((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)-L-alaninate

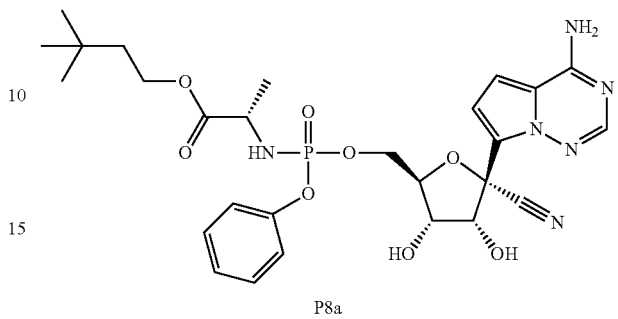

P8a

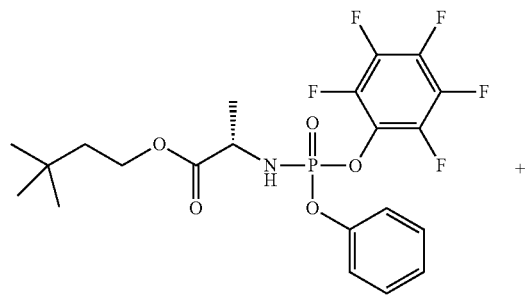

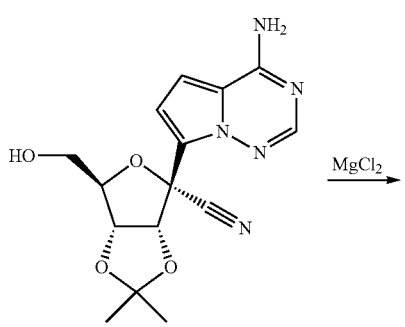

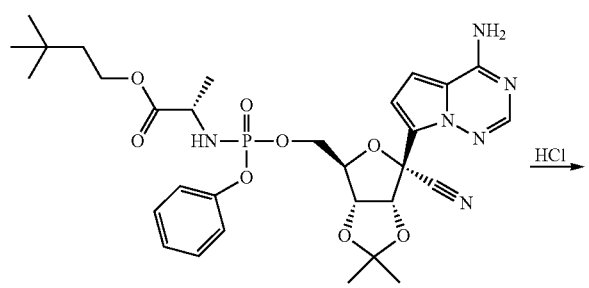

To a suspension of 3,3-dimethylbutyl ((perfluorophenoxy)(phenoxy)phosphoryl)-L-alaninate (0.333 g, 0.471 mmol), (3aR,4R,6R,6aR)-4-(4-aminopyrrolo[2,1-f][1,2,4]triazin-7-yl)-6-(hydroxymethyl)-2,2-dimethyltetrahydrofuro[3,4-d][1,3]dioxole-4-carbonitrile (prepared according to WO2017049060, 0.156 g, 0.471 mmol) and magnesium chloride (0.057 g, 0.601 mmol) in acetonitrile (10 mL) under an atmosphere of argon was added N,N-diisopropylethylamine (0.105 mL, 0.601 mmol) at room temperature. After 10 min, the reaction was heated to 50° C. After 2 h, the reaction was cooled to room temperature, diluted with ethyl acetate and the organics were washed with water, dried over sodium sulfate, filtered and concentrated to afford 3,3-dimethylbutyl (((((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methoxy)(phenoxy)phosphoryl)-L-alaninate. The product was purified using chromatography, ethyl acetate/hexanes, product eluted in pure ethyl acetate. LCMS: MS m/z=642.9 [M+H$^+$].

3,3-dimethylbutyl (((((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methoxy)(phenoxy)phosphoryl)-L-alaninate was taken up in tetrahydrofuran (2 mL) and concentrated hydrochloric acid (11.7 M, 0.400 mL, 4.66 mmol) was added. After 2 h, the reaction was diluted with ethyl acetate and neutralized with a saturated aqueous solution of sodium bicarbonate. The layers were separated, and the organics were washed with water, saturated aqueous sodium chloride, dried over sodium sulfate, filtered and concentrated. The product Intermediate P8a was purified by HPLC chromatography (0-100% acetonitrile in water) to afford the title compound as a mixture of isomers. LCMS: MS m/z=602.9 [M+H$^+$]. $^1$H NMR (400 MHz, Methanol-d4) δ 7.88 (d, J=7.2 Hz, 1H), 7.38-7.27 (m, 2H), 7.25-7.13 (m, 3H), 6.98-6.87 (m, 2H), 4.82 (d, J=5.3 Hz, 1H), 4.44 (dddd, J=17.1, 11.4, 5.7, 2.6 Hz, 2H), 4.33 (ddd, J=11.0, 5.6, 3.9 Hz, 1H), 4.27-4.14 (m, 1H), 4.17-4.01 (m, 2H), 3.83 (dq, J=9.1, 7.3 Hz, 1H), 1.56-1.44 (m, 2H), 1.34-1.13 (m, 3H), 0.92 (d, J=5.5 Hz, 9H). $^{31}$P NMR (162 MHz, Methanol-d4) δ 3.55 (s).

235

Example 56: (2R,3R,4R,5R)-2-(4-aminopyrrolo[2,1-f][1,2,4]triazin-7-yl)-2-cyano-5-(((((S)-1-(3,3-dimethylbutoxy)-1-oxopropan-2-yl)amino)(phenoxy)phosphoryl)oxy)methyl)tetrahydrofuran-3,4-diyl bis(2-methylpropanoate)

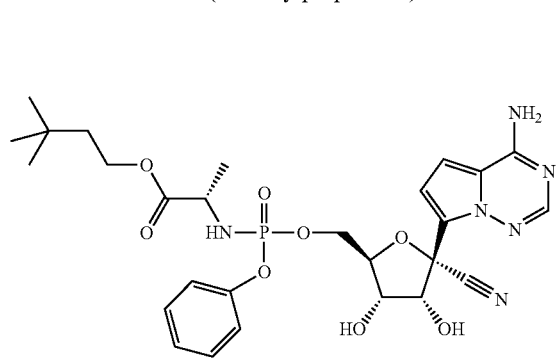

Compound 56 was made in a similar manner as compound 14 except that Intermediate P8a was used instead of compound 13. Individual isomers of Compound 56 were separated by preparatory HPLC (Gemini Sum NX-C18 110A LC column 100×30 mm, 95% to 0% water acetonitrile gradient).

Peak 1: First eluting isomer Compound 56a: LCMS: MS m/z=742.8 [M+H⁺]. ¹H NMR (400 MHz, Methanol-d4) δ 7.87 (s, 1H), 7.33 (dd, J=8.7, 7.1 Hz, 2H), 7.23-7.14 (m, 3H), 6.91 (s, 2H), 6.30 (d, J=5.8 Hz, 1H), 5.59 (dd, J=5.9, 3.8 Hz, 1H), 4.65 (dd, J=3.7, 2.2 Hz, 1H), 4.53-4.36 (m, 2H), 4.19-4.03 (m, 2H), 3.81 (dt, J=9.3, 7.2 Hz, 1H), 2.66 (dp, J=22.4, 7.0 Hz, 2H), 1.51 (t, J=7.4 Hz, 2H), 1.25 (dd, J=9.9, 7.0 Hz, 6H), 1.20 (ddd, J=7.0, 3.8, 1.4 Hz, 9H), 0.92 (s, 9H). $^{31}$P NMR (162 MHz, Methanol-d4) δ 3.51 (s).

Peak 2: Second eluting isomer Compound 56b: LCMS: MS m/z=742.8 [M+H⁺].

236

Intermediate P9: benzyl ((4-(tert-butyl)phenoxy)(perfluorophenoxy)phosphoryl)-L-alaninate

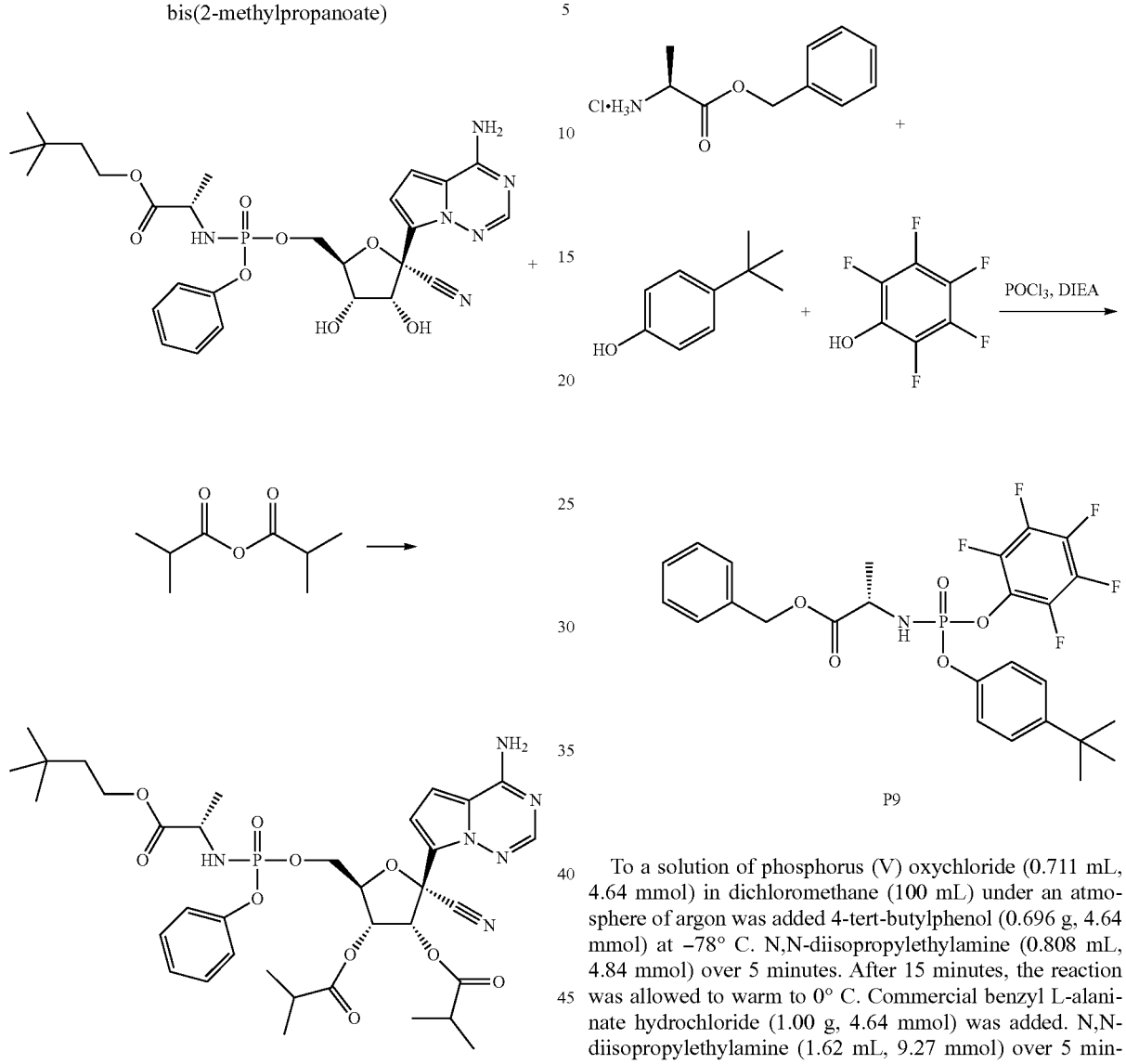

P9

To a solution of phosphorus (V) oxychloride (0.711 mL, 4.64 mmol) in dichloromethane (100 mL) under an atmosphere of argon was added 4-tert-butylphenol (0.696 g, 4.64 mmol) at −78° C. N,N-diisopropylethylamine (0.808 mL, 4.84 mmol) over 5 minutes. After 15 minutes, the reaction was allowed to warm to 0° C. Commercial benzyl L-alaninate hydrochloride (1.00 g, 4.64 mmol) was added. N,N-diisopropylethylamine (1.62 mL, 9.27 mmol) over 5 minutes. After 30 minutes, 2,3,4,5,6-pentafluorophenol (0.853 g, 9.27 mmol) was added. N,N-diisopropylethylamine (0.808 mL, 4.64 mmol) over 5 minutes. After 15 minutes, the reaction was allowed to warm to room temperature. After 30 minutes, the reaction was acidified with acetic acid using pH paper. The reaction was washed with water (50 mL). The organics were dried over sodium sulfate, filtered and concentrated. The product P9 was purified by silica gel chromatography (0-20% ethyl acetate in hexanes) to afford benzyl ((4-(tert-butyl)phenoxy)(perfluorophenoxy)phosphoryl)-L-alaninate. ¹H NMR (400 MHz, DMSO-d₆) δ 7.42-7.27 (m, 7H), 7.17-7.07 (m, 2H), 6.92 (ddd, J=13.5, 10.0, 3.1 Hz, 1H), 5.11 (d, J=3.6 Hz, 2H), 4.05 (dddd, J=15.6, 9.2, 7.2, 4.7 Hz, 1H), 3.33 (s, 1H), 1.33 (dd, J=7.1, 1.1 Hz, 3H), 1.26 (d, J=2.3 Hz, 9H). $^{31}$P NMR (162 MHz, Methanol-d4) δ 0.48 (s), 0.40 (s). $^{19}$F NMR (376 MHz, DMSO-d₆) δ −153.36—153.88 (m, 2F), −160.33 (tdd, J=24.1, 13.8, 3.3 Hz, 1F), −163.13 (tdd, J=23.6, 19.3, 4.0 Hz, 2F).

Example 57: Benzyl ((((2R,3S,4R,5R)-5-(4-aminopyrrolo[2,1-f][1,2,4]triazin-7-yl)-5-cyano-3,4-dihydroxytetrahydrofuran-2-yl)methoxy)(4-(tert-butyl)phenoxy)phosphoryl)-L-alaninate

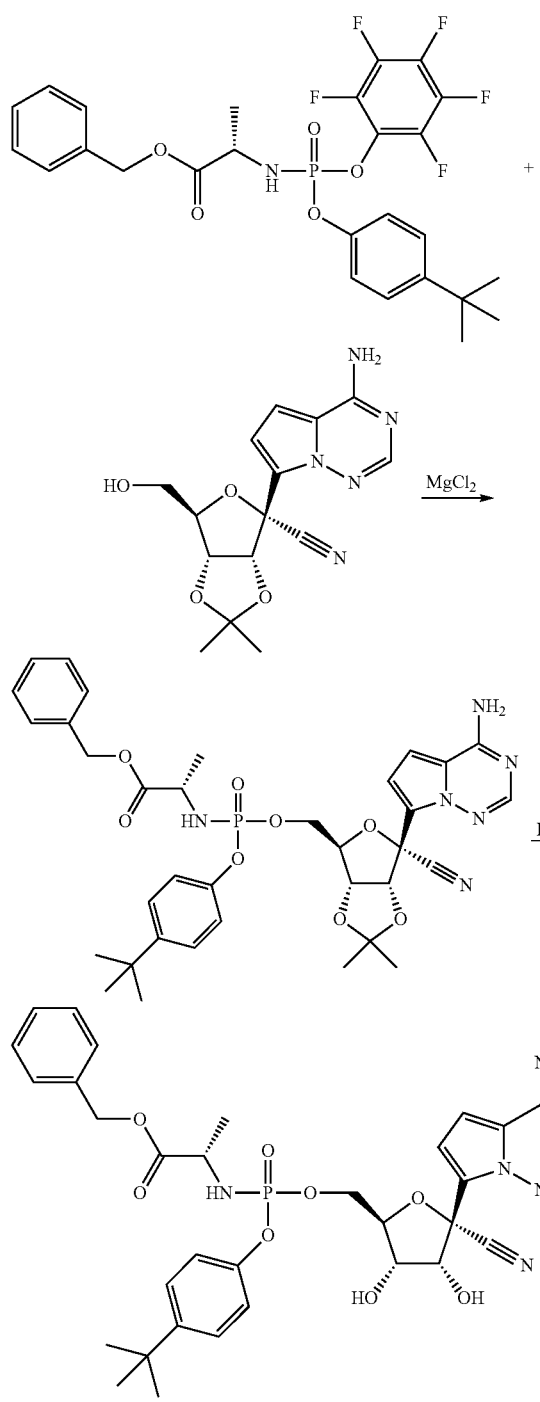

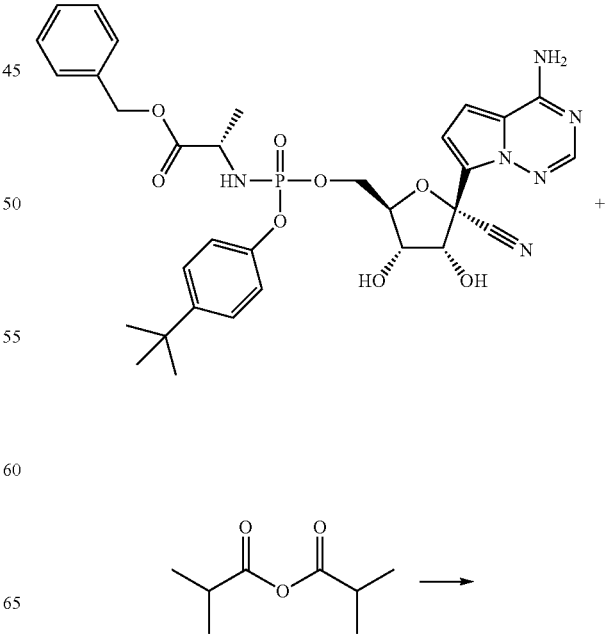

To a suspension of benzyl ((4-(tert-butyl)phenoxy)(perfluorophenoxy)phosphoryl)-L-alaninate (0.305 g, 0.546 mmol), (3aR,4R,6R,6aR)-4-(4-aminopyrrolo[2,1-f][1,2,4]triazin-7-yl)-6-(hydroxymethyl)-2,2-dimethyltetrahydrofuro[3,4-d][1,3]dioxole-4-carbonitrile (prepared according to WO2017049060, 0.181 g, 0.546 mmol) and magnesium chloride (0.057 g, 0.594 mmol) in acetonitrile (10 mL) under an atmosphere of argon was added N,N-diisopropylethylamine (0.105 mL, 0.601 mmol) at room temperature. After 10 min, the reaction was heated to 50° C. After 2 h, the reaction was cooled to room temperature, diluted with ethyl acetate and the organics were washed with water, dried over sodium sulfate, filtered and concentrated to afford benzyl (((((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methoxy)(4-(tert-butyl)phenoxy)phosphoryl)-L-alaninate. LCMS: MS m/z=705.2 [M+H$^+$].

Benzyl (((((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methoxy)(4-(tert-butyl)phenoxy)phosphoryl)-L-alaninate was taken up in tetrahydrofuran (2 mL) and concentrated hydrochloric acid (11.7 M, 0.400 mL, 4.66 mmol) was added. After 2 h, the reaction was diluted with ethyl acetate and neutralized with a saturated aqueous solution of sodium bicarbonate. The layers were separated, and the organics were washed with water, saturated aqueous sodium chloride, dried over sodium sulfate, filtered and concentrated. The product was purified by HPLC chromatography (0-100% acetonitrile in water) to afford the title Compound 57 as a mixture of stereoisomers. LCMS: MS m/z=665.2 [M+H$^+$]. $^1$H NMR (400 MHz, Methanol-d4) δ 7.87 (d, J=3.9 Hz, 1H), 7.39-7.22 (m, 7H), 7.13-6.98 (m, 2H), 6.98-6.88 (m, 2H), 5.17-5.02 (m, 2H), 4.79 (t, J=5.5 Hz, 1H), 4.43-4.33 (m, 2H), 4.32-4.20 (m, 1H), 4.17 (td, J=5.6, 2.7 Hz, 1H), 4.00-3.84 (m, 1H), 1.36-1.22 (m, 12H). $^{31}$P NMR (162 MHz, Methanol-d4) δ 3.70 (s).

Example 58: (2R,3R,4R,5R)-2-(4-aminopyrrolo[2,1-f][1,2,4]triazin-7-yl)-5-((((((S)-1-(benzyloxy)-1-oxopropan-2-yl)amino)(4-(tert-butyl)phenoxy)phosphoryl)oxy)methyl)-2-cyanotetrahydrofuran-3,4-diyl bis(2-methylpropanoate)

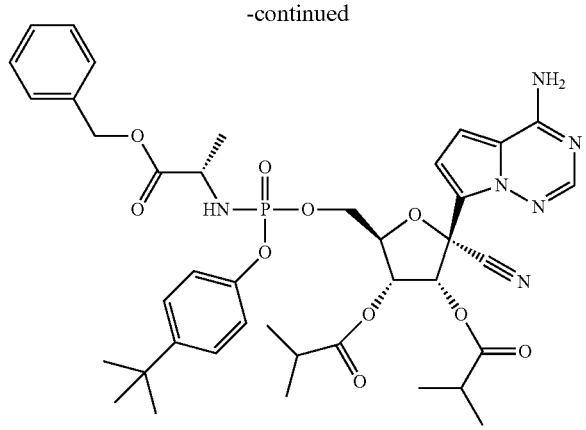

Compound 58 was made in a similar manner as compound 14 except that compound 57 was used instead of compound 13. The product Compound 58 was obtained as a mixture of stereoisomers. LCMS: MS m/z=805.3 [M+H$^+$]. $^1$H NMR (400 MHz, Methanol-d4) δ 7.87 (d, J=0.9 Hz, 1H), 7.33 (dddt, J=8.4, 6.6, 5.5, 1.7 Hz, 6H), 7.28-7.21 (m, 1H), 7.05 (ddt, J=7.6, 6.3, 1.3 Hz, 2H), 6.92-6.82 (m, 2H), 6.27 (d, J=6.0 Hz, 0.5H), 6.17 (d, J=5.9 Hz, 0.5H), 5.55 (td, J=5.7, 3.7 Hz, 1H), 5.17-5.05 (m, 2H), 4.58 (ddd, J=5.7, 3.8, 2.1 Hz, 1H), 4.44-4.25 (m, 2H), 3.90 (ddd, J=34.9, 9.6, 7.1 Hz, 1H), 2.76-2.56 (m, 2H), 1.40-1.11 (m, 24H). $^{31}$P NMR (162 MHz, Methanol-d4) δ 3.51 (s).

Example 59: cyclobutylmethyl (2S)-2-[[[(2R,3S,4R,5R)-5-(4-aminopyrrolo[2,1-f][1,2,4]triazin-7-yl)-5-cyano-3,4-dihydroxy-tetrahydrofuran-2-yl]methoxy-(4-tert-butylphenoxy)phosphoryl]amino]propanoate

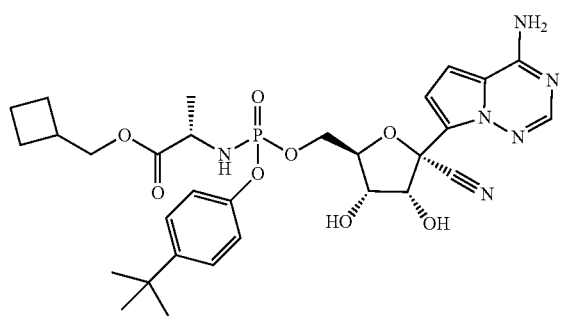 [SMILES: C[C@H](NP(=O)(OC[C@H]1O[C@@](C#N)(c2ccc3c(N)ncnn23)[C@H](O)[C@@H]1O)Oc1ccc(C(C)(C)C)cc1)C(=O)OCC1CCC1]

This compound was prepared from cyclobutylmethyl ((4-(tert-butyl)phenoxy)(perfluorophenoxy)phosphoryl)-L-alaninate (50 mg, 0.09 mmol) following the procedure for Example 13. Cyclobutylmethyl ((4-(tert-butyl)phenoxy)(perfluorophenoxy)phosphoryl)-L-alaninate was prepared from cyclobutylmethyl L-alaninate following the procedure for Intermediate H2. Cyclobutylmethyl L-alaninate was prepared from cyclobutylmethanol following the general procedure for Intermediate H1. LCMS: MS m/z=643.6 [M+1], t$_R$=0.94 min, 643.6 [M+1], 0.96 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min. Mixture of isomers: $^1$H NMR (400 MHz, Methanol-d4) δ 7.88 (d, J=7.0 Hz, 1H), 7.32 (t, J=8.5 Hz, 2H), 7.11 (dd, J=8.8, 1.3 Hz, 1H), 7.06 (dd, J=8.8, 1.3 Hz, 1H), 6.98-6.90 (m, 2H), 4.81 (t, J=5.3 Hz, 1H), 4.47-4.36 (m, 2H), 4.32 (ddd, J=10.9, 5.9, 3.9 Hz, 1H), 4.19 (t, J=5.5 Hz, 1H), 4.10-3.96 (m, 2H), 3.87 (ddd, J=12.3, 9.4, 7.0 Hz, 1H), 2.65-2.54 (m, 1H), 2.08-1.97 (m, 2H), 1.96-1.82 (m, 2H), 1.81-1.71 (m, 2H), 1.30 (d, J=4.3 Hz, 9H). $^{31}$P NMR (162 MHz, Methanol-d4) δ 3.82 (br s).

Example 60: [(2R,3R,4R,5R)-5-(4-aminopyrrolo[2,1-f][1,2,4]triazin-7-yl)-2-[[(4-tert-butylphenoxy)-[[(1S)-2-(cyclobutylmethoxy)-1-methyl-2-oxo-ethyl]amino]phosphoryl]oxymethyl]-5-cyano-4-(2-methylpropanoyloxy)tetrahydrofuran-3-yl]2-methylpropanoate

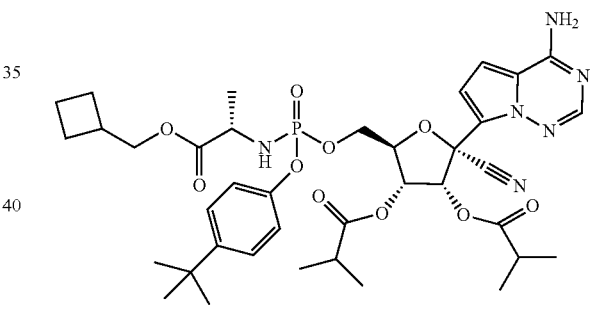

This compound was prepared from Example 59 (10 mg, 0.02 mmol) following the procedure for Example 14. LCMS: MS m/z=783.8 [M+1], t$_R$=1.19 min, 783.8 [M+1], t$_R$=1.21 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min. Mixture of isomers: $^1$H NMR (400 MHz, Methanol-d4) δ 7.88 (d, J=2.7 Hz, 1H), 7.34 (d, J=8.6 Hz, 1H), 7.29 (d, J=8.6 Hz, 1H), 7.09 (ddd, J=10.4, 8.7, 1.3 Hz, 2H), 6.94-6.85 (m, 2H), 6.28 (d, J=6.0 Hz, 0.5H), 6.17 (d, J=5.9 Hz, 0.5H), 5.56 (ddd, J=6.3, 3.8, 2.6 Hz, 1H), 4.67-4.59 (m, 1H), 4.48-4.35 (m, 2H), 4.04 (qdd, J=10.9, 8.2, 6.7 Hz, 2H), 3.86 (ddd, J=32.8, 9.5, 7.2 Hz, 1H), 2.75-2.54 (m, 3H), 2.10-1.96 (m, 2H), 1.97-1.83 (m, 2H), 1.83-1.71 (m, 2H), 1.31-1.19 (m, 24H). $^{31}$P NMR (162 MHz, Methanol-d4) δ 3.66 (s).

Example 61: 3,3-dimethylbutyl (2S)-2-[[[(2R,3S, 4R,5R)-5-(4-aminopyrrolo[2,1-f][1,2,4]triazin-7-yl)-5-cyano-3,4-dihydroxy-tetrahydrofuran-2-yl] methoxy-(4-tert-butylphenoxy)phosphoryl]amino] propanoate

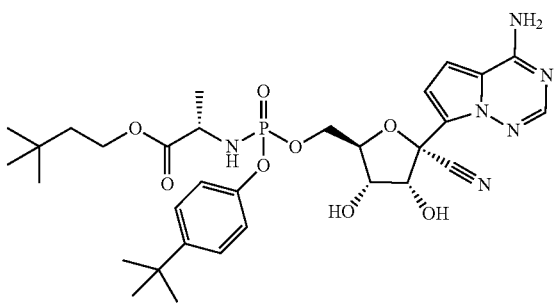 [SMILES: C[C@H](NP(=O)(OC[C@H]1O[C@@](C#N)(c2ccc3c(N)ncnn23)[C@H](O)[C@@H]1O)Oc1ccc(C(C)(C)C)cc1)C(=O)OCCC(C)(C)C]

This compound was prepared from 3,3-dimethylbutyl ((4-(tert-butyl)phenoxy) (perfluorophenoxy)phosphoryl)-L-alaninate (50 mg, 0.09 mmol) following the procedure for Example 13. 3,3-dimethylbutyl ((4-(tert-butyl)phenoxy) (perfluorophenoxy)phosphoryl)-L-alaninate was prepared from 3,3-dimethylbutyl L-alaninate following the procedure for Intermediate H2. 3,3-dimethylbutyl L-alaninate was prepared from 3,3-dimethylbutan-1-ol following the general procedure for Intermediate H1. LCMS: MS m/z=659.7 [M+1], $t_R$=1.01 min, 659.7 [M+1], $t_R$=1.02 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min. Mixture of isomers: $^1$H NMR (400 MHz, Methanol-d4) δ 7.88 (d, J=7.9 Hz, 1H), 7.32 (dd, J=10.5, 8.7 Hz, 2H), 7.14-7.03 (m, 2H), 6.98-6.90 (m, 2H), 4.81 (d, J=5.4 Hz, 1H), 4.43 (ddd, J=14.0, 10.7, 5.7 Hz, 2H), 4.32 (tt, J=10.9, 5.9 Hz, 1H), 4.20-4.06 (m, 3H), 3.85 (ddd, J=13.2, 9.4, 7.0 Hz, 1H), 1.52 (q, J=7.4 Hz, 2H), 1.35-1.23 (m, 13H), 0.92 (d, J=5.2 Hz, 8H). $^{31}$P NMR (162 MHz, Methanol-d4) δ 3.85 (s).

Example 62: [(2R,3R,4R,5R)-5-(4-aminopyrrolo[2,1-f][1,2,4]triazin-7-yl)-2-[[(4-tert-butylphenoxy)-[[(1S)-2-(3,3-dimethylbutoxy)-1-methyl-2-oxo-ethyl]amino]phosphoryl]oxymethyl]-5-cyano-4-(2-methylpropanoyloxy)tetrahydrofuran-3-yl]2-methylpropanoate

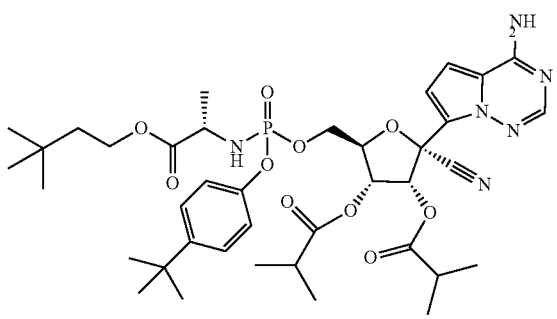 [SMILES: CC(C)C(=O)O[C@H]1[C@@H](OC(=O)C(C)C)[C@](C#N)(c2ccc3c(N)ncnn23)O[C@@H]1COP(=O)(N[C@@H](C)C(=O)OCCC(C)(C)C)Oc1ccc(C(C)(C)C)cc1]

This compound was prepared from Example 61 (10 mg, 0.02 mmol) following the procedure for Example 14. LCMS: MS m/z=799.9 [M+1], $t_R$=1.24 min, 799.9 [M+1], $t_R$=1.25 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min. Mixture of isomers: $^1$H NMR (400 MHz, Methanol-d$_4$) δ 7.87 (d, J=4.6 Hz, 1H), 7.38-7.32 (m, 1H), 7.32-7.25 (m, 1H), 7.13-7.03 (m, 2H), 6.94-6.84 (m, 2H), 6.28 (d, J=5.9 Hz, 0.5H), 6.15 (d, J=5.9 Hz, 0.5H), 5.57 (dd, J=5.9, 3.7 Hz, 1H), 4.68-4.58 (m, 1H), 4.41 (tdd, J=11.4, 5.9, 2.8 Hz, 2H), 4.21-4.07 (m, 2H), 3.83 (ddd, J=30.2, 9.4, 7.1 Hz, 1H), 2.66 (dtd, J=21.7, 7.0, 3.2 Hz, 2H), 1.54 (dt, J=13.2, 7.5 Hz, 2H), 1.33-1.15 (m, 24H), 0.93 (d, J=7.8 Hz, 9H). $^{31}$P NMR (162 MHz, Methanol-d$_4$) δ 3.68 (s).

Example 63: ethyl (2S)-2-[[[(3aR,4R,6R,6aR)-4-(4-aminopyrrolo[2,1-f][1,2,4]triazin-7-yl)-4-cyano-2,2-dimethyl-6,6a-dihydro-3aH-furo[3,4-d][1,3]dioxol-6-yl]methoxy-(4-isopropylphenoxy)phosphoryl] amino]propanoate

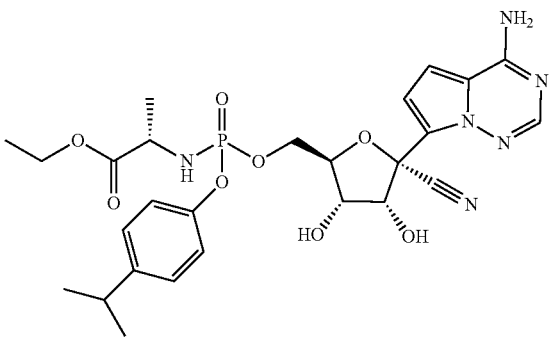 [SMILES: CCOC(=O)[C@H](C)NP(=O)(OC[C@H]1O[C@@](C#N)(c2ccc3c(N)ncnn23)[C@H](O)[C@@H]1O)Oc1ccc(C(C)C)cc1]

This compound was prepared from ethyl ((4-isopropylphenoxy)(perfluorophenoxy)phosphoryl)-L-alaninate (50 mg, 0.14 mmol) following the procedure for Example 13. Ethyl ((4-isopropylphenoxy)(perfluorophenoxy)phosphoryl)-L-alaninate was prepared from ethyl L-alaninate and 4-isopropylphenol following the procedure for Intermediate H2.

Individual isomers of compound 63 were separated by preparatory HPLC (Gemini Sum NX-C18 110A LC column 100×30 mm, 95% to 0% water acetonitrile gradient).

First eluting isomer Compound 63a: LCMS: MS m/z=589.5 [M+1], $t_R$=0.82 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min. $^1$H NMR (400 MHz, Methanol-d4) δ 7.87 (s, 1H), 7.14 (d, J=8.5 Hz, 2H), 7.09-7.01 (m, 2H), 6.93 (d, J=1.1 Hz, 2H), 4.80 (d, J=5.4 Hz, 1H), 4.67 (s, 1H), 4.48-4.38 (m, 2H), 4.32 (dd, J=10.3, 5.8 Hz, 1H), 4.20 (t, J=5.5 Hz, 1H), 4.11 (qd, J=7.1, 1.3 Hz, 2H), 3.86-3.77 (m, 1H), 2.88 (p, J=6.9 Hz, 1H), 1.29-1.13 (m, 11H). $^{31}$P NMR (162 MHz, Methanol-d4) δ 3.88 (s).

Second eluting isomer Compound 63b: LCMS: MS m/z=589.5 [M+1], $t_R$=0.84 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min. $^1$H NMR (400 MHz, Methanol-d4) δ 7.89 (s, 1H), 7.22-7.02 (m, 4H), 6.98-6.87 (m, 2H), 4.81 (d, J=5.4 Hz, 1H), 4.67 (s, 1H), 4.44-4.34 (m, 2H), 4.33-4.25 (m, 1H), 4.19 (t, J=5.5 Hz, 1H), 4.16-4.03 (m, 2H), 3.86 (dd, J=9.6, 7.1 Hz, 1H), 2.94-2.83 (m, 1H), 1.29 (dd, J=7.1, 1.0 Hz, 3H), 1.28-1.14 (m, 8H). $^{31}$P NMR (162 MHz, Methanol-d4) δ 3.88 (s).

Example 64: [(2R,3R,4R,5R)-5-(4-aminopyrrolo[2,1-f][1,2,4]triazin-7-yl)-5-cyano-2-[[[[(1S)-2-ethoxy-1-methyl-2-oxo-ethyl]amino]-(4-isopropylphenoxy)phosphoryl]-oxymethyl]-4-(2-methylpropanoyloxy)tetrahydrofuran-3-yl] 2-methylpropanoate

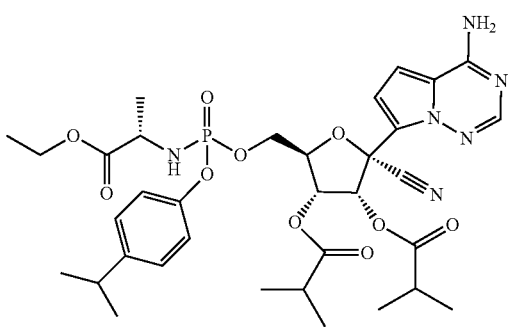 [SMILES: CCOC(=O)[C@H](C)NP(=O)(OC[C@H]1O[C@@](C#N)(c2ccc3c(N)ncnn23)[C@H](OC(=O)C(C)C)[C@@H]1OC(=O)C(C)C)Oc1ccc(C(C)C)cc1]

This compound was prepared from Example 63 (10 mg, 0.02 mmol) following the procedure for Example 14. LCMS: MS m/z=729.7 [M+1], $t_R$=1.09 min, 729.7 [M+1], $t_R$=1.10 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min. Mixture of isomers: $^1$H NMR (400 MHz, Methanol-d4) δ 7.88 (d, J=1.6 Hz, 1H), 7.21-7.04 (m, 4H), 6.95-6.81 (m, 2H), 6.28 (d, J=5.9 Hz, 0.5H), 6.17 (d, J=5.9 Hz, 0.5H), 5.57 (ddd, J=5.3, 3.8, 1.2 Hz, 1H), 4.91 (s, 2H), 4.68-4.58 (m, 1H), 4.41 (tdd, J=15.2, 7.7, 4.2 Hz, 2H), 4.11 (dqd, J=9.8, 7.1, 3.1 Hz, 2H), 3.86 (dd, J=9.7, 7.0 Hz, 0.5H), 3.76 (dd, J=9.0, 7.0 Hz, 0.5H), 2.94-2.82 (m, 1H), 2.74-2.59 (m, 2H), 1.32-1.14 (m, 22H). $^{31}$P NMR (162 MHz, Methanol-d4) δ 3.73 (s).

Example 65: spiro[3.3]heptan-2-yl (2S)-2-[[[(2R,3S,4R,5R)-5-(4-aminopyrrolo[2,1-f][1,2,4]triazin-7-yl)-5-cyano-3,4-dihydroxy-tetrahydrofuran-2-yl]methoxy-(4-tert-butylphenoxy)phosphoryl]amino]propanoate

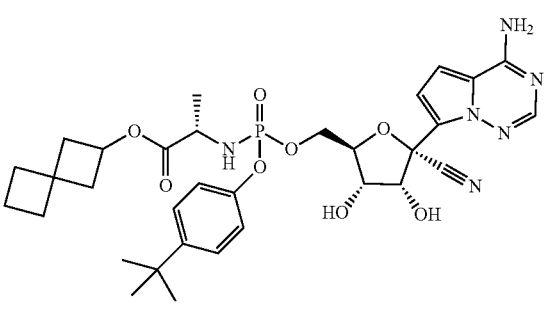 [SMILES: C[C@H](NP(=O)(OC[C@H]1O[C@@](C#N)(c2ccc3c(N)ncnn23)[C@H](O)[C@@H]1O)Oc1ccc(C(C)(C)C)cc1)C(=O)OC1CC2(CCC2)C1]

This compound was isolated from the same reaction mixture as in Example 29. LCMS: MS m/z=669.7 [M+1], $t_R$=1.00 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min. Individual isomer: $^1$H NMR (400 MHz, Methanol-d4) δ 7.87 (s, 1H), 7.34-7.27 (m, 2H), 7.09-7.01 (m, 2H), 6.94 (d, J=1.1 Hz, 2H), 4.83-4.75 (m, 2H), 4.46-4.36 (m, 2H), 4.32 (ddd, J=10.8, 5.6, 3.7 Hz, 1H), 4.18 (t, J=5.5 Hz, 1H), 3.79 (dt, J=9.3, 7.1 Hz, 1H), 2.40 (ddd, J=10.1, 7.2, 3.2 Hz, 2H), 2.07-1.93 (m, 6H), 1.90-1.80 (m, 2H), 1.29 (d, J=2.5 Hz, 9H), 1.24 (dd, J=7.2, 1.2 Hz, 3H). $^{31}$P NMR (162 MHz, Methanol-d$_4$) δ 3.85 (s).

Example 66: [(2R,3R,4R,5R)-5-(4-aminopyrrolo[2,1-f][1,2,4]triazin-7-yl)-2-[[(4-tert-butylphenoxy)-[[(1S)-1-methyl-2-oxo-2-spiro[3.3]heptan-2-yloxy-ethyl]amino]phosphoryl]oxymethyl]-5-cyano-4-(2-methylpropanoyloxy)tetrahydrofuran-3-yl] 2-methylpropanoate

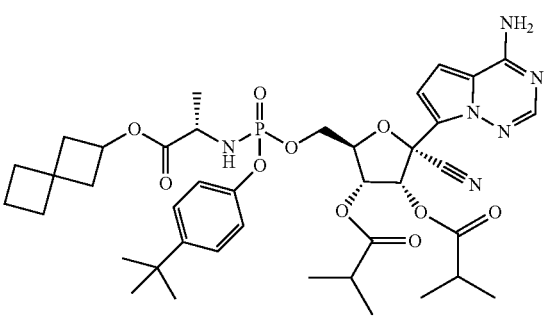 [SMILES: CC(C)C(=O)O[C@H]1[C@@H](OC(=O)C(C)C)[C@](C#N)(c2ccc3c(N)ncnn23)O[C@@H]1COP(=O)(N[C@@H](C)C(=O)OC1CC2(CCC2)C1)Oc1ccc(C(C)(C)C)cc1]

This compound was prepared from Example 65 (11 mg, 0.02 mmol) following the procedure for Example 14. LCMS: MS m/z=809.9 [M+1], $t_R$=1.24 min, 809.9 [M+1], $t_R$=1.26 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min. $^1$H NMR (400 MHz, Methanol-d4) δ 7.87 (d, J=3.3 Hz, 1H), 7.39-7.23 (m, 2H), 7.08 (td, J=9.0, 1.3 Hz, 2H), 6.89 (ddd, J=14.5, 9.6, 4.7 Hz, 2H), 6.28 (d, J=5.9 Hz, 0.5H), 6.16 (d, J=5.9 Hz, 0.5H), 5.56 (ddd, J=5.7, 3.8, 1.8 Hz, 1H), 4.80 (dt, J=23.5, 7.3 Hz, 3H), 4.67-4.59 (m, 1H), 4.41 (dtt, J=14.4, 7.1, 3.4 Hz, 2H), 3.80 (ddd, J=30.5, 9.4, 7.1 Hz, 1H), 2.75-2.58 (m, 2H), 2.40 (ddd, J=12.1, 9.6, 5.7 Hz, 2H), 2.08-1.90 (m, 6H), 1.90-1.80 (m, 2H), 1.35-1.12 (m, 22H). $^{31}$P NMR (162 MHz, Methanol-d4) δ 3.67 (s).

Intermediate S1: ethyl (2S)-2-[[[(2R,3S,4R,5R)-5-(4-aminopyrrolo[2,1-f][1,2,4]triazin-7-yl)-5-cyano-3,4-dihydroxy-tetrahydrofuran-2-yl]methoxy-(1-naphthyloxy)phosphoryl]amino]propanoate

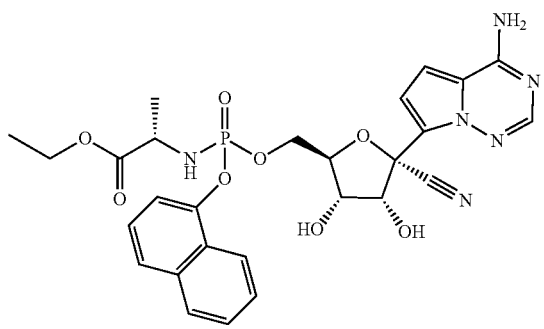 [SMILES: CCOC(=O)[C@H](C)NP(=O)(OC[C@H]1O[C@@](C#N)(c2ccc3c(N)ncnn23)[C@H](O)[C@@H]1O)Oc1cccc2ccccc12]

This intermediate S1 was prepared from ethyl ((naphthalen-1-yloxy)(perfluorophenoxy)phosphoryl)-L-alaninate (50 mg, 0.10 mmol) following the procedure for Example 13. Ethyl ((naphthalen-1-yloxy)(perfluorophenoxy)phosphoryl)-L-alaninate was prepared from ethyl L-alaninate and naphthalen-1-ol following the procedure for Intermediate H2. LCMS: MS m/z=597.5 [M+1], $t_R$=0.79 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min. Mixture of isomers: $^1$H NMR (400 MHz, Methanol-d4) δ 8.18-8.10 (m, 1H), 7.91-7.82 (m, 2H), 7.68 (d, J=8.2 Hz, 1H), 7.56-7.48 (m, 2H), 7.46 (dt, J=7.7, 1.3 Hz, 1H), 7.36 (t, J=7.9 Hz, 1H), 6.87 (d, J=4.6 Hz, 1H), 6.82 (d, J=4.6 Hz, 1H), 4.73 (d, J=5.4 Hz, 1H), 4.48 (ddd, J=11.0, 6.1, 2.7 Hz, 1H), 4.44-4.32 (m, 2H), 4.22 (t, J=5.5 Hz, 1H), 4.07 (qq, J=7.3, 3.6 Hz, 2H), 3.95 (dq, J=10.0, 7.2 Hz, 1H), 1.28 (dd, J=7.2, 1.1 Hz, 3H), 1.18 (t, J=7.1 Hz, 3H). $^{31}$P NMR (162 MHz, Methanol-d4) δ 4.10 (s).

Example 67: [(2R,3R,4R,5R)-5-(4-aminopyrrolo[2,1-f][1,2,4]triazin-7-yl)-5-cyano-2-[[[[(1S)-2-ethoxy-1-methyl-2-oxo-ethyl]amino]-(1-naphthyloxy)phosphoryl]oxymethyl]-4-(2-methylpropanoyloxy)tetrahydrofuran-3-yl] 2-methylpropanoate

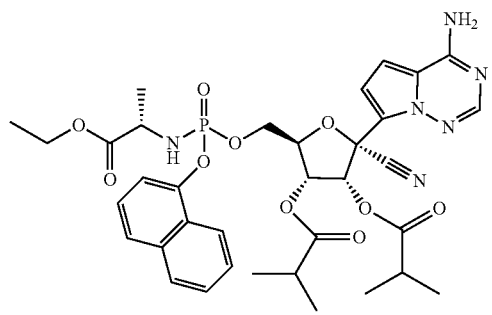 [SMILES: CCOC(=O)[C@H](C)NP(=O)(OC[C@H]1O[C@@](C#N)(c2ccc3c(N)ncnn23)[C@H](OC(=O)C(C)C)[C@@H]1OC(=O)C(C)C)Oc1cccc2ccccc12]

This compound was prepared from Intermediate S1 (10 mg, 0.02 mmol) following the procedure for Example 14. LCMS: MS m/z=737.7 [M+1], $t_R$=1.05 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min. Mixture of isomers: $^1$H NMR (400 MHz, Methanol-d4) δ 8.09 (d, J=8.3 Hz, 1H), 7.91-7.84 (m, 1H), 7.82 (s, 1H), 7.68 (d, J=8.1 Hz, 1H), 7.56-7.39 (m, 3H), 7.32 (t, J=7.9 Hz, 1H), 6.77-6.68 (m, 2H), 6.19 (d, J=5.9 Hz, 1H), 5.62 (dd, J=5.9, 3.6 Hz, 1H), 4.92-4.85 (m, 1H), 4.65 (dt, J=5.8, 2.8 Hz, 1H), 4.55-4.39 (m, 2H), 4.09 (q, J=7.1 Hz, 2H), 3.94 (dq, J=10.0, 7.1 Hz, 1H), 2.66 (dp, J=20.8, 7.0 Hz, 2H), 1.30-1.15 (m, 17H). $^{31}$P NMR (162 MHz, Methanol-d4) δ 3.95 (s).

Example 68: 2-ethylbutyl (2S)-2-[[[(3aR,4R,6R,6aR)-4-(4-aminopyrrolo[2,1-f][1,2,4]triazin-7-yl)-4-cyano-2,2-dimethyl-6,6a-dihydro-3aH-furo[3,4-d][1,3]dioxol-6-yl]methoxy-(3-tert-butylphenoxy)phosphoryl]amino]propanoate

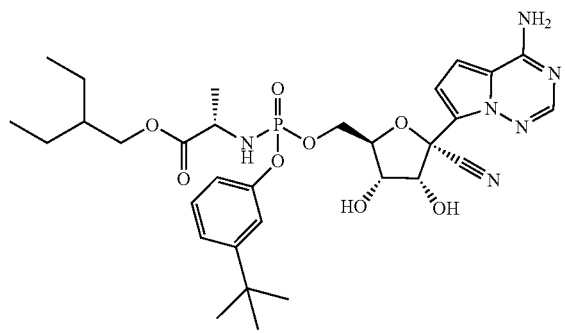 [SMILES: CCC(CC)COC(=O)[C@H](C)NP(=O)(OC[C@H]1O[C@@](C#N)(c2ccc3c(N)ncnn23)[C@H](O)[C@@H]1O)Oc1cccc(C(C)(C)C)c1]

This compound was prepared from 2-ethylbutyl ((3-(tert-butyl)phenoxy) (perfluorophenoxy)phosphoryl)-L-alaninate (50 mg, 0.09 mmol) following the procedure for Example 13. 2-ethylbutyl ((3-(tert-butyl)phenoxy) (perfluorophenoxy)phosphoryl)-L-alaninate was prepared from 2-ethylbutyl L-alaninate and 3-(tert-butyl)phenol following the procedure for Intermediate H2.

Individual isomers of compound 68 were separated by preparatory HPLC (Gemini 5 um NX-C18 110A LC column 100×30 mm, 95% to 0% water acetonitrile gradient).

First eluting isomer Compound 68a LCMS: MS m/z=659.7 [M+1], $t_R$=1.00 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 µL/min. $^1$H NMR (400 MHz, Methanol-d4) δ 7.87 (s, 1H), 7.25-7.19 (m, 3H), 6.99-6.90 (m, 3H), 4.80 (d, J=5.4 Hz, 1H), 4.47 (ddd, J=11.3, 5.6, 2.9 Hz, 1H), 4.40 (d, J=3.0 Hz, 1H), 4.32 (ddd, J=11.2, 5.4, 4.0 Hz, 1H), 4.21 (t, J=5.7 Hz, 1H), 4.03 (qd, J=10.9, 5.7 Hz, 2H), 3.89 (dd, J=9.1, 7.1 Hz, 1H), 1.55-1.46 (m, 1H), 1.40-1.25 (m, 16H), 0.92-0.85 (m, 6H). $^{31}$P NMR (162 MHz, Methanol-d4) δ 3.85 (s).

Second eluting isomer Compound 68b LCMS: MS m/z=659.7 [M+1], $t_R$=1.02 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 µL/min. $^1$H NMR (400 MHz, Methanol-d4) δ 7.88 (s, 1H), 7.29-7.19 (m, 3H), 7.03 (td, J=4.1, 2.3 Hz, 1H), 6.96-6.87 (m, 2H), 4.81 (d, J=5.3 Hz, 1H), 4.46-4.35 (m, 2H), 4.30 (dt, J=10.5, 5.1 Hz, 1H), 4.18 (t, J=5.7 Hz, 1H), 4.05 (dd, J=10.9, 5.8 Hz, 1H), 3.98-3.87 (m, 2H), 1.47 (dt, J=12.2, 6.0 Hz, 1H), 1.42-1.11 (m, 16H), 0.87 (t, J=7.5 Hz, 6H). $^{31}$P NMR (162 MHz, Methanol-d4) δ 3.66 (s).

Intermediate S2: 2-Ethylbutyl ((((2R,3S,4R,5R)-5-(4-aminopyrrolo[2,1-f][1,2,4]triazin-7-yl)-5-cyano-3,4-dihydroxytetrahydrofuran-2-yl)methoxy)(naphthalen-1-yloxy)phosphoryl)-L-alaninate

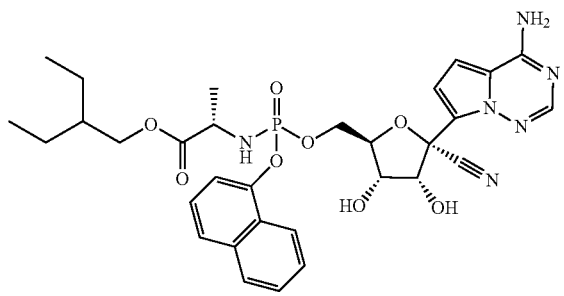 [SMILES: CCC(CC)COC(=O)[C@H](C)NP(=O)(OC[C@H]1O[C@@](C#N)(c2ccc3c(N)ncnn23)[C@H](O)[C@@H]1O)Oc1cccc2ccccc12]

This compound was prepared from 2-ethylbutyl ((naphthalen-1-yloxy)(perfluorophenoxy) phosphoryl)-L-alaninate (50 mg, 0.09 mmol) following the procedure for Example 13. 2-ethylbutyl ((naphthalen-1-yloxy)(perfluorophenoxy) phosphoryl)-L-alaninate was prepared from 2-ethylbutyl L-alaninate and naphthalen-1-ol following the procedure for Intermediate H2.

Mixture of isomers: Intermediate S2: LCMS: MS m/z=653.6 [M+1], $t_R$=0.90 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 µL/min. $^1$H NMR (400 MHz, Methanol-d$_4$) δ 8.09 (dd, J=8.4, 1.2 Hz, 1H), 7.91-7.86 (m, 1H), 7.82 (s, 1H), 7.70 (d, J=8.1 Hz, 1H), 7.56-7.42 (m, 3H), 7.37 (t, J=7.9 Hz, 1H), 6.90-6.84 (m, 2H), 4.69 (d, J=5.5 Hz, 1H), 4.50 (ddd, J=10.9, 5.7, 2.3 Hz, 1H), 4.45-4.35 (m, 2H), 4.20 (t, J=5.4 Hz, 1H), 4.02-3.87 (m, 3H), 1.43 (dt, J=12.5, 6.2 Hz, 1H), 1.37-1.21 (m, 7H), 0.84 (td, J=7.5, 1.8 Hz, 6H). $^{31}$P NMR (162 MHz, Methanol-d4) δ 4.10 (s).

Intermediate S3: 2-ethylbutyl ((((2R,3S,4R,5R)-5-(4-aminopyrrolo[2,1-f][1,2,4]triazin-7-yl)-5-cyano-3,4-dihydroxytetrahydrofuran-2-yl)methoxy)(naphthalen-2-yloxy)phosphoryl)-L-alaninate

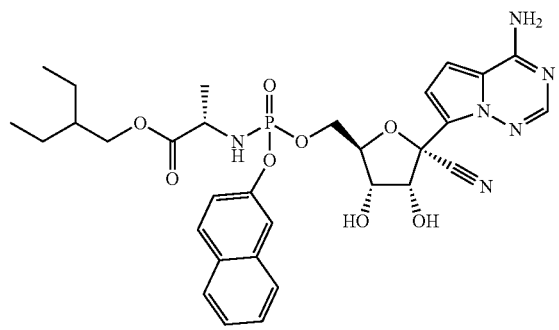 [SMILES: CCC(CC)COC(=O)[C@H](C)NP(=O)(OC[C@H]1O[C@@](C#N)(c2ccc3c(N)ncnn23)[C@H](O)[C@@H]1O)Oc1ccc2ccccc2c1]

This compound was prepared from 2-ethylbutyl ((naphthalen-2-yloxy)(perfluorophenoxy) phosphoryl)-L-alaninate (50 mg, 0.09 mmol) following the procedure for Example 13. 2-ethylbutyl ((naphthalen-2-yloxy)(perfluorophenoxy) phosphoryl)-L-alaninate was prepared from 2-ethylbutyl L-alaninate and naphthalen-2-ol following the procedure for Intermediate H2.

Individual isomers of intermediate S2 were separated by preparatory HPLC (Gemini 5um NX-C18 110A LC column 100×30 mm, 95% to 0% water acetonitrile gradient).

First eluting mixture of isomers Intermediate S3-a LCMS: MS m/z=653.6 [M+1], $t_R$=0.94 min, 653.6 [M+1], $t_R$=0.96 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 µL/min. $^1$H NMR (400 MHz, Methanol-d4) δ 7.89-7.78 (m, 3H), 7.77-7.59 (m, 2H), 7.47 (tdd, J=7.0, 5.9, 3.6 Hz, 2H), 7.33 (ddd, J=17.1, 8.9, 2.4 Hz, 1H), 6.95-6.82 (m, 2H), 4.79 (dd, J=5.4, 2.9 Hz, 1H), 4.54-4.32 (m, 3H), 4.23 (td, J=5.6, 4.2 Hz, 1H), 4.04-3.86 (m, 3H), 1.44 (dp, J=12.5, 6.3 Hz, 1H), 1.36-1.25 (m, 6H), 0.85 (dt, J=8.0, 6.5 Hz, 6H). $^{31}$P NMR (162 MHz, Methanol-d4) δ 3.87 (s).

Second eluting isomer Intermediate S3-b: LCMS: MS m/z=653.6 [M+1], $t_R$=0.94 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 µL/min. $^1$H NMR (400 MHz, Methanol-d4) δ 8.19-8.11 (m, 1H), 7.91-7.82 (m, 2H), 7.69 (d, J=8.0 Hz, 1H), 7.56-7.48 (m, 2H), 7.46 (dt, J=7.6, 1.3 Hz, 1H), 7.36 (t, J=7.9 Hz, 1H), 6.89-6.79 (m, 2H), 4.72 (d, J=5.4 Hz, 1H), 4.48 (ddd, J=10.9, 6.1, 2.7 Hz, 1H), 4.44-4.32 (m, 2H), 4.21 (t, J=5.5 Hz, 1H), 4.04-3.89 (m, 3H), 1.48-1.40 (m, 1H), 1.36-1.24 (m, 7H), 0.85 (t, J=7.4 Hz, 6H). $^{31}$P NMR (162 MHz, Methanol-d$_4$) δ 4.09 (s).

Example 69: [(2R,3R,4R,5R)-5-(4-aminopyrrolo[2,1-f][1,2,4]triazin-7-yl)-5-cyano-2-[[[[(1S)-2-(2-ethylbutoxy)-1-methyl-2-oxo-ethyl]amino]-(2-naphthyloxy)phosphoryl]oxymethyl]-4-(2-methylpropanoyloxy)tetrahydrofuran-3-yl] 2-methylpropanoate

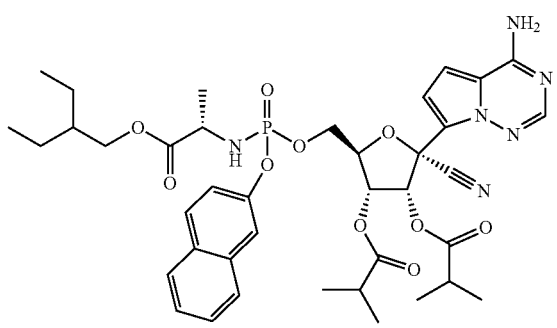 [SMILES: CCC(CC)COC(=O)[C@H](C)NP(=O)(OC[C@H]1O[C@@](C#N)(c2ccc3c(N)ncnn23)[C@H](OC(=O)C(C)C)[C@@H]1OC(=O)C(C)C)Oc1ccc2ccccc2c1]

This compound was prepared from Intermediate S3 (10 mg, 0.02 mmol) following the procedure for Example 14. Individual isomers of compound 69 were separated by preparatory HPLC (Gemini 5 um NX-C18 110A LC column 100×30 mm, 95% to 0% water acetonitrile gradient).

First eluent: Example 69a: LCMS: MS m/z=793.8 [M+1], t$_R$=1.11 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 µL/min. $^1$H NMR (400 MHz, Methanol-d4) δ 7.92-7.79 (m, 3H), 7.78-7.72 (m, 1H), 7.66 (d, J=2.2 Hz, 1H), 7.48 (tt, J=6.9, 5.2 Hz, 2H), 7.34 (dd, J=9.0, 2.4 Hz, 1H), 6.87 (q, J=4.7 Hz, 2H), 6.28 (d, J=5.9 Hz, 1H), 5.62 (dd, J=5.9, 3.8 Hz, 1H), 4.67 (dd, J=3.9, 2.3 Hz, 1H), 4.54-4.42 (m, 2H), 4.04-3.85 (m, 3H), 2.64 (tt, J=14.1, 7.0 Hz, 2H), 1.49-1.13 (m, 20H), 0.85 (td, J=7.5, 1.5 Hz, 6H). $^{31}$P NMR (162 MHz, Methanol-d$_4$) δ 3.76 (s).

Second eluent: Example 69b: LCMS: MS m/z=793.8 [M+1], t$_R$=1.20 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 µL/min. $^1$H NMR (400 MHz, Methanol-d4) δ 7.89-7.77 (m, 3H), 7.72-7.65 (m, 1H), 7.63 (d, J=2.0 Hz, 1H), 7.50-7.41 (m, 2H), 7.31 (ddd, J=8.9, 2.5, 0.9 Hz, 1H), 6.73-6.63 (m, 2H), 6.11 (d, J=5.9 Hz, 1H), 5.61 (dd, J=5.9, 3.5 Hz, 1H), 4.64 (qd, J=3.6, 2.1 Hz, 1H), 4.52-4.40 (m, 2H), 4.08-3.94 (m, 3H), 2.73-2.59 (m, 2H), 1.52-1.43 (m, 1H), 1.37-1.18 (m, 19H), 0.90-0.84 (m, 6H). $^{31}$P NMR (162 MHz, Methanol-d$_4$) δ 3.73 (s).

Example 70: [(2R,3R,4R,5R)-5-(4-aminopyrrolo[2,1-f][1,2,4]triazin-7-yl)-5-cyano-2-[[[[(1S)-2-(2-ethylbutoxy)-1-methyl-2-oxo-ethyl]amino]-(1-naphthyloxy)phosphoryl]oxymethyl]-4-(2-methylpropanoyloxy)tetrahydrofuran-3-yl] 2-methylpropanoate

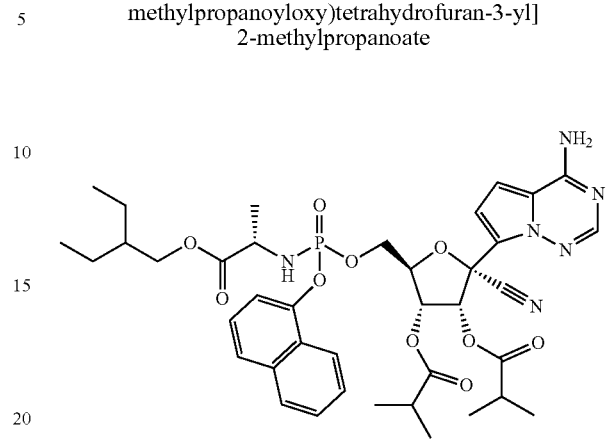

This compound was prepared from Intermediate S2 (25 mg, 0.04 mmol) following the procedure for Example 14. LCMS: MS m/z=793.8 [M+1], tR=1.19 min, 793.8 [M+1], tR=1.20 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 µL/min. Mixture of isomers: $^1$H NMR (400 MHz, Methanol-d4) δ 8.16-8.07 (m, 1H), 7.92-7.84 (m, 1H), 7.81 (d, J=5.5 Hz, 1H), 7.73-7.64 (m, 1H), 7.59-7.30 (m, 4H), 6.86 (s, 1H), 6.73 (q, J=4.7 Hz, 1H), 6.31 (d, J=5.9 Hz, 0.5H), 6.17 (d, J=5.9 Hz, 0.5H), 5.61 (ddd, J=5.9, 4.9, 3.7 Hz, 1H), 4.66 (ddd, J=7.7, 3.7, 2.2 Hz, 1H), 4.49 (ddt, J=16.1, 8.7, 3.3 Hz, 2H), 4.06-3.84 (m, 3H), 2.73-2.57 (m, 2H), 1.51-1.12 (m, 21H), 0.90-0.79 (m, 6H). 31P NMR (162 MHz, Methanol-d4) δ 3.95 (s).

Example 71: isopentyl (2S)-3-[4-[[[(2R,3S,4R,5R)-5-(4-aminopyrrolo[2,1-f][1,2,4]triazin-7-yl)-5-cyano-3,4-dihydroxy-tetrahydrofuran-2-yl]methoxy-[[(1S)-2-(2-ethylbutoxy)-1-methyl-2-oxo-ethyl]amino]phosphoryl]oxyphenyl]-2-(benzyloxycarbonylamino)propanoate

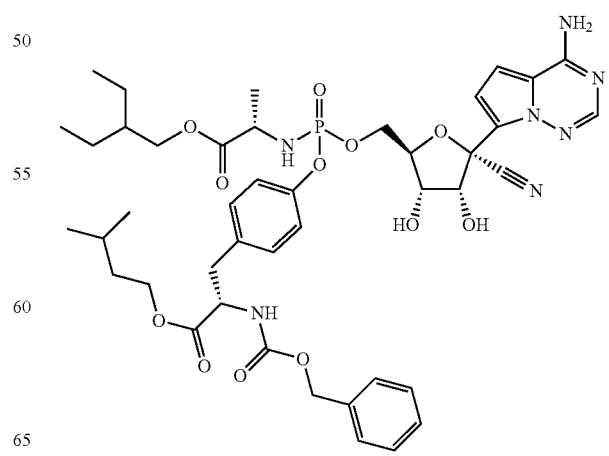

This compound was prepared from isopentyl (2S)-2-(((benzyloxy)carbonyl)amino)-3-(4-(((((S)-1-(2-ethylbutoxy)-1-oxopropan-2-yl)amino)(perfluorophenoxy)phosphoryl)oxy)phenyl) propanoate (200 mg, 0.25 mmol) following the procedure for Example 13. isopentyl (2S)-2-(((benzyloxy)carbonyl)amino)-3-(4-(((((S)-1-(2-ethylbutoxy)-1-oxopropan-2-yl)amino)(perfluorophenoxy)phosphoryl)oxy)phenyl)propanoate was prepared from 2-ethylbutyl L-alaninate and isopentyl ((benzyloxy)carbonyl)-L-tyrosinate following the procedure for Intermediate H2. Isopentyl ((benzyloxy)carbonyl)-L-tyrosinate was prepared from ((benzyloxy)carbonyl)-L-tyrosine and 3-methylbutan-1-ol following the general procedure for Intermediate H1. LCMS: MS m/z=894.9 [M+1], $t_R$=1.00 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min. Mixture of isomers: $^1$H NMR (400 MHz, Methanol-d4) δ 7.87 (d, J=7.7 Hz, 1H), 7.32 (dt, J=12.2, 6.2 Hz, 5H), 7.20-7.03 (m, 4H), 6.95-6.85 (m, 2H), 5.05 (d, J=1.6 Hz, 2H), 4.80 (dd, J=5.4, 2.7 Hz, 1H), 4.47-4.34 (m, 3H), 4.34-4.25 (m, 1H), 4.17 (dt, J=18.0, 6.2 Hz, 3H), 4.09-3.78 (m, 4H), 3.17-3.07 (m, 1H), 2.93 (t, J=11.2 Hz, 1H), 1.65 (dt, J=13.4, 6.8 Hz, 1H), 1.54-1.41 (m, 3H), 1.40-1.21 (m, 7H), 0.96-0.83 (m, 11H). $^{31}$P NMR (162 MHz, Methanol-d4) δ 3.78 (s).

Example 72: (2R,3R,4R,5R)-2-(4-aminopyrrolo[2,1-f][1,2,4]triazin-7-yl)-5-((((4-((S)-2-(((benzyloxy)carbonyl)amino)-3-(isopentyloxy)-3-oxopropyl)phenoxy)(((S)-1-(2-ethylbutoxy)-1-oxopropan-2-yl)amino)phosphoryl)oxy)methyl)-2-cyanotetrahydrofuran-3,4-diyl bis(2-methylpropanoate)

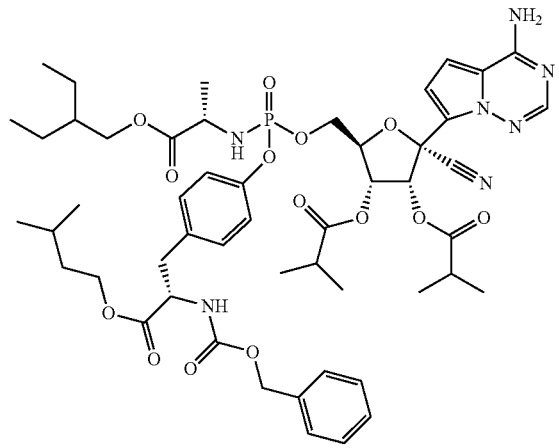 [SMILES: CCC(CC)COC(=O)[C@H](C)NP(=O)(OC[C@H]1O[C@@](C#N)(c2ccc3c(N)ncnn23)[C@H](OC(=O)C(C)C)[C@@H]1OC(=O)C(C)C)Oc1ccc(C[C@H](NC(=O)OCc2ccccc2)C(=O)OCCC(C)C)cc1]

This compound was prepared from Example 71 (30 mg, 0.03 mmol) following the procedure for Example 14. LCMS: MS m/z=1035.1 [M+1], $t_R$=1.26 min, 1035.1 [M+1], $t_R$ 1.28 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min. Mixture of isomers: $^1$H NMR (400 MHz, Methanol-d4) δ 7.86 (d, J=2.6 Hz, 1H), 7.41-7.23 (m, 5H), 7.21-7.03 (m, 4H), 6.93-6.86 (m, 1H), 6.82 (q, J=4.7 Hz, 1H), 6.28 (d, J=5.9 Hz, 0.5H), 6.19 (d, J=5.9 Hz, 0.5H), 5.56 (td, J=5.9, 3.7 Hz, 1H), 5.10-5.00 (m, 2H), 4.92-4.85 (m, 2H), 4.69-4.58 (m, 1H), 4.49-4.32 (m, 3H), 4.15 (td, J=6.7, 1.7 Hz, 2H), 4.06 (ddd, J=12.9, 10.9, 5.8 Hz, 1H), 3.98 (ddd, J=10.9, 5.7, 3.1 Hz, 1H), 3.86 (ddd, J=27.5, 9.4, 7.1 Hz, 1H), 3.18-3.06 (m, 1H), 2.93 (dt, J=14.0, 8.6 Hz, 1H), 2.74-2.57 (m, 2H), 1.65 (dt, J=12.8, 6.5 Hz, 1H), 1.50 (dq, J=7.7, 5.3, 4.6 Hz, 3H), 1.41-1.13 (m, 18H), 0.97-0.83 (m, 11H). $^{31}$P NMR (162 MHz, Methanol-d4) δ 3.64 (s).

Example 73: cyclooctyl (2S)-2-[[[(2R,3S,4R,5R)-5-(4-aminopyrrolo[2,1-f][1,2,4]triazin-7-yl)-5-cyano-3,4-dihydroxy-tetrahydrofuran-2-yl]methoxy-(4-tert-butylphenoxy)phosphoryl]amino]propanoate

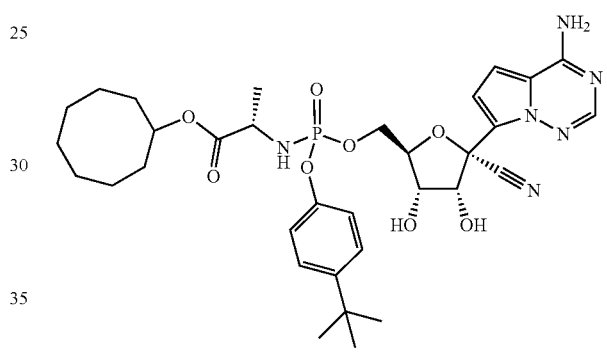

This compound was prepared from cyclooctyl ((4-(tert-butyl)phenoxy)(perfluorophenoxy) phosphoryl)-L-alaninate (150 mg, 0.26 mmol) following the procedure for Example 13. cyclooctyl ((4-(tert-butyl)phenoxy)(perfluorophenoxy) phosphoryl)-L-alaninate was prepared from cyclooctyl L-alaninate following the procedure for Intermediate H2. Cyclooctyl L-alaninate was prepared from cyclooctanol following the general procedure for Intermediate H1. LCMS: MS m/z=685.7 [M+1], $t_R$=1.04 min, 685.7 [M+1], $t_R$=1.06 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min. Mixture of isomers: $^1$H NMR (400 MHz, Methanol-d4) δ 7.93 (d, J=7.8 Hz, 1H), 7.33 (ddd, J=8.5, 6.8, 2.9 Hz, 2H), 7.15-6.97 (m, 3H), 5.52 (s, 1H), 4.79 (dd, J=5.4, 4.4 Hz, 1H), 4.48-4.25 (m, 2H), 4.17 (td, J=5.7, 4.4 Hz, 1H), 3.85 (tdd, J=14.5, 7.1, 2.0 Hz, 1H), 1.82-1.44 (m, 15H), 1.34-1.23 (m, 13H). $^{31}$P NMR (162 MHz, Methanol-d4) δ 3.90 (s), 2.50 (s).

Intermediate S4: 3,3-dimethylpentyl (2S)-2-[[[(2R,3S,4R,5R)-5-(4-aminopyrrolo[2,1-f][1,2,4]triazin-7-yl)-5-cyano-3,4-dihydroxy-tetrahydrofuran-2-yl]methoxy-phenoxy-phosphoryl]amino]propanoate

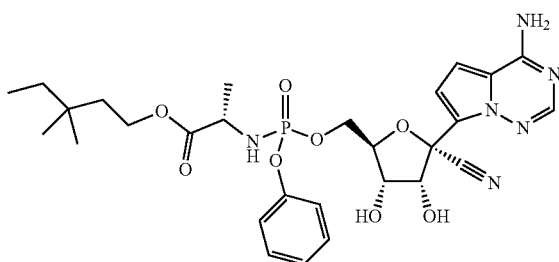 [SMILES: CCC(C)(C)CCOC(=O)[C@H](C)NP(=O)(OC[C@H]1O[C@@](C#N)(c2ccc3c(N)ncnn23)[C@H](O)[C@@H]1O)Oc1ccccc1]

This intermediate was prepared from 3,3-dimethylpentyl ((perfluorophenoxy)(phenoxy) phosphoryl)-L-alaninate (150 mg, 0.29 mmol) following the procedure for Example 13. 3,3-dimethylpentyl ((perfluorophenoxy)(phenoxy)phosphoryl)-L-alaninate was prepared from 3,3-dimethylpentyl L-alaninate following the procedure for Intermediate H2. 3,3-dimethylpentyl L-alaninate was prepared from 3,3-dimethylpentan-1-ol following the general procedure for Intermediate H1. LCMS: MS m/z=617.6 [M+1], $t_R$=0.90 min, 617.6 [M+1], $t_R$=0.92 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 µL/min. Mixture of isomers: $^1$H NMR (400 MHz, Methanol-d4) δ 7.88 (d, J=7.3 Hz, 1H), 7.32 (q, J=7.9 Hz, 2H), 7.25-7.13 (m, 3H), 6.97-6.87 (m, 2H), 4.81 (dd, J=5.3, 4.2 Hz, 1H), 4.49-4.27 (m, 3H), 4.20 (dt, J=19.1, 5.5 Hz, 1H), 4.15-4.01 (m, 2H), 3.85 (dddd, J=18.6, 9.3, 7.1, 2.4 Hz, 1H), 1.49 (q, J=7.9 Hz, 2H), 1.33-1.19 (m, 5H), 0.92-0.77 (m, 9H). $^{31}$P NMR (162 MHz, Methanol-d4) δ 3.71 (s).

Example 74: [(2R,3R,4R,5R)-5-(4-aminopyrrolo[2,1-f][1,2,4]triazin-7-yl)-5-cyano-2-[[[[(1S)-2-(3,3-dimethylpentoxy)-1-methyl-2-oxo-ethyl]amino]-phenoxy-phosphoryl]oxymethyl]-4-(2-methylpropanoyloxy)tetrahydrofuran-3-yl] 2-methylpropanoate

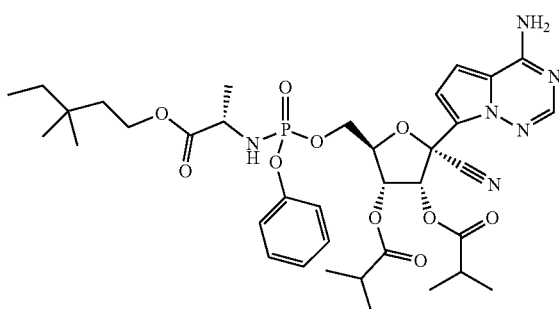

This compound was prepared from Intermediate S4 (36 mg, 0.23 mmol) following the procedure for Example 14. LCMS: MS m/z=757.8 [M+1], $t_R$=1.16 min, 757.8 [M+1], $t_R$=1.17 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 µL/min. Mixture of isomers: $^1$H NMR (400 MHz, Methanol-d4) δ 7.87 (d, J=2.0 Hz, 1H), 7.31 (ddd, J=16.4, 8.7, 7.1 Hz, 2H), 7.22-7.13 (m, 3H), 6.91 (d, J=0.8 Hz, 1H), 6.88-6.80 (m, 1H), 6.30 (d, J=5.9 Hz, 0.5H), 6.20 (d, J=5.8 Hz, 0.5H), 5.58 (ddd, J=6.5, 5.8, 3.7 Hz, 1H), 4.63 (dtd, J=11.5, 3.7, 2.0 Hz, 1H), 4.50-4.36 (m, 2H), 4.18-4.05 (m, 2H), 3.84 (ddd, J=26.5, 9.5, 7.1 Hz, 1H), 2.73-2.58 (m, 2H), 1.51 (dt, J=10.3, 7.6 Hz, 2H), 1.37-1.18 (m, 17H), 0.85 (dd, J=16.4, 6.4 Hz, 9H). $^{31}$P NMR (162 MHz, Methanol-d4) δ 3.65 (s), 3.50 (s).

Example 75: (3-methoxy-3-methyl-butyl) (2S)-2-[[[(2R,3S,4R,5R)-5-(4-aminopyrrolo[2,1-f][1,2,4]triazin-7-yl)-5-cyano-3,4-dihydroxy-tetrahydrofuran-2-yl]methoxy-phenoxy-phosphoryl]amino]propanoate

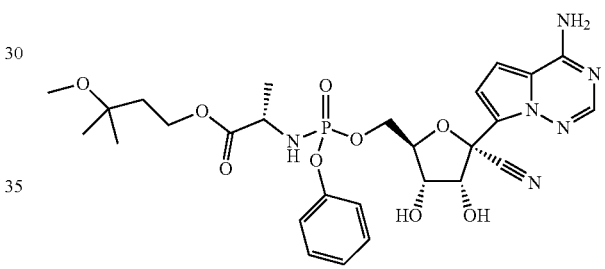

This compound was prepared from 3-methoxy-3-methyl-butyl ((perfluorophenoxy)(phenoxy)phosphoryl)-L-alaninate (150 mg, 0.29 mmol) following the procedure for Example 13. 3-methoxy-3-methylbutyl ((perfluorophenoxy)(phenoxy)phosphoryl)-L-alaninate was prepared from 3-methoxy-3-methylbutyl L-alaninate following the procedure for Intermediate H2. 3-methoxy-3-methylbutyl L-alaninate was prepared from 3-methoxy-3-methylbutan-1-ol following the general procedure for Intermediate H1. LCMS: MS m/z=619.6 [M+1], $t_R$=0.77 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 µL/min. Mixture of isomers: $^1$H NMR (400 MHz, Methanol-d4) δ 7.88 (d, J=7.3 Hz, 1H), 7.33 (dt, J=9.1, 7.0 Hz, 2H), 7.24-7.15 (m, 3H), 6.96-6.88 (m, 2H), 4.81 (dd, J=5.4, 3.5 Hz, 1H), 4.46-4.37 (m, 2H), 4.35-4.29 (m, 1H), 4.27-4.04 (m, 4H), 3.90-3.81 (m, 1H), 3.17 (d, J=2.5 Hz, 3H), 1.79 (q, J=7.0 Hz, 2H), 1.27 (ddd, J=20.6, 7.1, 1.1 Hz, 3H), 1.19-1.12 (m, 6H). $^{31}$P NMR (162 MHz, Methanol-d4) δ 3.69 (s).

Example 76: [(2R,3R,4R,5R)-5-(4-aminopyrrolo[2,1-f][1,2,4]triazin-7-yl)-5-cyano-2-[[[[(1S)-2-(3-methoxy-3-methyl-butoxy)-1-methyl-2-oxo-ethyl]amino]-phenoxy-phosphoryl]oxymethyl]-4-(2-methylpropanoyloxy)tetrahydrofuran-3-yl] 2-methylpropanoate

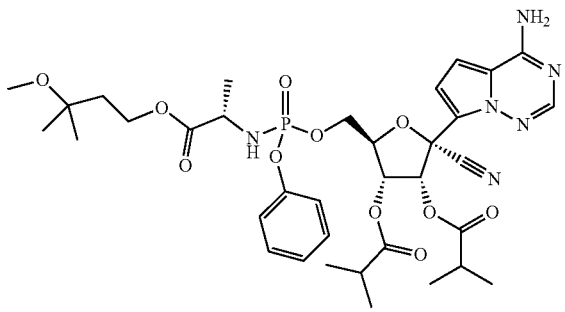 [SMILES: COC(C)(C)CCOC(=O)[C@H](C)NP(=O)(OC[C@H]1O[C@@](C#N)(c2ccc3c(N)ncnn23)[C@H](OC(=O)C(C)C)[C@@H]1OC(=O)C(C)C)Oc1ccccc1]

This compound was prepared from Example 75 (29 mg, 0.05 mmol) following the procedure for Example 14. LCMS: MS m/z=759.8 [M+1], $t_R$=1.03 min, 759.8 [M+1], $t_R$=1.05 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min. Mixture of isomers: $^1$H NMR (400 MHz, Methanol-d4) δ 7.87 (d, J=1.8 Hz, 1H), 7.30 (dq, J=14.1, 7.3, 6.6 Hz, 2H), 7.22-7.07 (m, 3H), 6.91 (s, 1H), 6.88-6.79 (m, 1H), 6.20 (d, J=5.8 Hz, 0.5H), 5.58 (td, J=5.9, 3.7 Hz, 0.5H), 4.73-4.57 (m, 2H), 4.50-4.36 (m, 2H), 4.21-4.08 (m, 2H), 3.92-3.75 (m, 1H), 3.18 (d, J=5.5 Hz, 3H), 2.66 (dddd, J=20.4, 15.0, 7.5, 5.1 Hz, 2H), 1.79 (dt, J=10.6, 7.3 Hz, 2H), 1.44-0.98 (m, 20H). $^{31}$P NMR (162 MHz, Methanol-d$_4$) δ 3.54 (s).

Example 77: [(2R,3R,4R,5R)-5-(4-aminopyrrolo[2,1-f][1,2,4]triazin-7-yl)-2-[[(4-tert-butylphenoxy)-[[(1S)-2-(cyclooctoxy)-1-methyl-2-oxo-ethyl]amino]phosphoryl]oxymethyl]-5-cyano-4-(2-methylpropanoyloxy)tetrahydrofuran-3-yl] 2-methylpropanoate

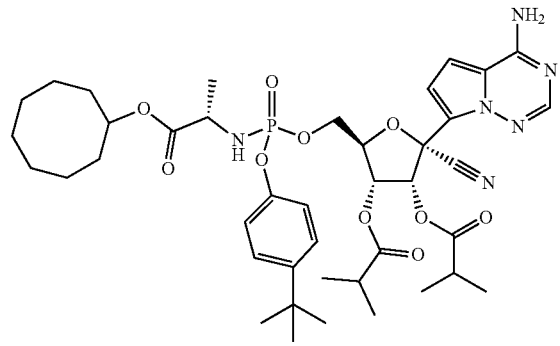 [SMILES: CC(C)C(=O)O[C@H]1[C@@H](OC(=O)C(C)C)[C@](C#N)(c2ccc3c(N)ncnn23)O[C@@H]1COP(=O)(N[C@@H](C)C(=O)OC1CCCCCCC1)Oc1ccc(C(C)(C)C)cc1]

This compound was prepared from Example 73 (32 mg, 0.20 mmol) following the procedure for Example 14. Individual isomers of Compound 77 were separated by preparatory HPLC (Gemini 5 um NX-C18 110A LC column 100×30 mm, 95% to 0% water acetonitrile gradient).

First eluting isomer Compound 77a (LCMS: MS m/z=825.9 [M+1], $t_R$=1.27 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min. $^1$H NMR (400 MHz, Methanol-d4) δ 7.87 (s, 1H), 7.40-7.29 (m, 2H), 7.14-7.04 (m, 2H), 6.96-6.86 (m, 2H), 6.27 (d, J=5.9 Hz, 1H), 5.56 (dd, J=5.9, 3.7 Hz, 1H), 4.87 (q, J=5.2, 4.7 Hz, 2H), 4.69-4.61 (m, 1H), 4.43 (qdd, J=7.9, 5.7, 2.6 Hz, 2H), 3.76 (dq, J=9.2, 7.1 Hz, 1H), 2.66 (dp, J=21.2, 7.0 Hz, 2H), 2.24 (s, 1H), 1.84-1.46 (m, 14H), 1.42 (s, 3H), 1.39-1.09 (m, 23H). $^{31}$P NMR (162 MHz, Methanol-d$_4$) δ 3.77 (s).

Second eluting isomer Compound 77b LCMS: MS m/z=825.9 [M+1], $t_R$=1.28 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min. $^1$H NMR (400 MHz, Methanol-d$_4$) δ 7.88 (s, 1H), 7.31-7.25 (m, 2H), 7.09-7.03 (m, 2H), 6.92-6.83 (m, 2H), 6.16 (d, J=5.9 Hz, 1H), 5.56 (dd, J=5.9, 3.8 Hz, 1H), 4.61 (dd, J=3.8, 1.9 Hz, 1H), 4.47-4.34 (m, 2H), 3.84 (dq, J=9.8, 7.1 Hz, 1H), 2.67 (dp, J=23.2, 7.0 Hz, 2H), 2.06 (s, 1H), 1.79-1.47 (m, 14H), 1.42 (s, 1H), 1.32-1.23 (m, 17H), 1.20 (d, J=7.0 Hz, 6H). $^{31}$P NMR (162 MHz, Methanol-d$_4$) δ 3.73 (s).

Example 78: 2-ethylbutyl (2S)-2-[[[(2R,3R,4R,5R)-3,4-diacetoxy-5-(4-aminopyrrolo[2,1-f][1,2,4]triazin-7-yl)-5-cyano-tetrahydrofuran-2-yl]methoxy-(1-naphthyloxy)phosphoryl]amino]propanoate

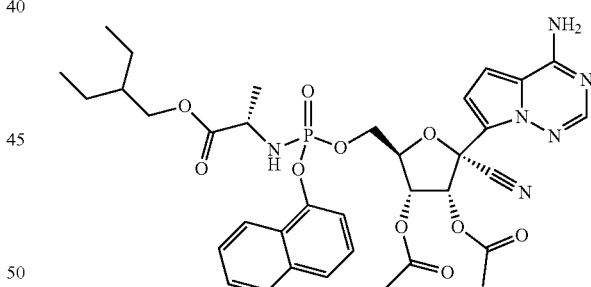

This compound was prepared from Intermediate S2 (12 mg, 0.12 mmol) following the procedure for Example 14. Individual isomers of Compound 78 were separated by preparatory HPLC (Gemini 5um NX-C18 110A LC column 100×30 mm, 95% to 0% water acetonitrile gradient).

First eluting isomer Compound 78a: LCMS: MS m/z=737.7 [M+1], $t_R$=1.02 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% $^1$H NMR (400 MHz, Methanol-d4) δ 8.17-8.08 (m, 1H), 7.93-7.86 (m, 1H), 7.79 (s, 1H), 7.70 (d, J=8.1 Hz, 1H), 7.53 (tt, J=7.4, 5.4 Hz, 2H), 7.48-7.42 (m, 1H), 7.38 (t, J=7.9 Hz, 1H), 6.92-6.83 (m, 2H), 6.32 (d, J=6.1 Hz, 1H), 5.60 (dd, J=6.0, 4.3 Hz, 1H), 4.67 (d, J=4.1 Hz, 1H), 4.53 (ddd, J=11.5, 6.2, 3.2 Hz, 1H), 4.46 (dt, J=11.6, 4.5 Hz, 1H), 3.96 (dd, J=10.9, 5.9 Hz, 1H), 3.93-3.83 (m, 2H), 2.15 (d, J=11.9 Hz, 6H), 1.42 (dt, J=12.3, 6.2 Hz, 1H), 1.33-1.23 (m, 4H), 1.18 (dd, J=7.2, 1.3 Hz, 3H), 0.82 (td, J=7.5, 2.5 Hz, 6H). $^{31}$P NMR (162 MHz, Methanol-d4) δ 3.98 (s).

Second eluting isomer Compound 78b: LCMS: MS m/z=737.7 [M+1], $t_R$=1.04 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min. $^1$H NMR (400 MHz, Methanol-d4) δ 8.09 (dd, J=8.2, 1.1 Hz, 1H), 7.88 (d, J=8.1 Hz, 1H), 7.82 (s, 1H), 7.68 (d, J=8.2 Hz, 1H), 7.55-7.38 (m, 3H), 7.32 (t, J=7.9 Hz, 1H), 6.80-6.71 (m, 2H), 6.20 (d, J=5.9 Hz, 1H), 5.58 (dd, J=5.9, 4.2 Hz, 1H), 4.69-4.62 (m, 1H), 4.47 (qdd, J=11.5, 5.9, 3.6 Hz, 2H), 4.07-3.91 (m, 3H), 2.15 (d, J=9.1 Hz, 6H), 1.47 (d, J=6.2 Hz, 1H), 1.37-1.25 (m, 7H), 0.86 (t, J=7.4 Hz, 6H). $^{31}$P NMR (162 MHz, Methanol-d4) δ 3.94 (s).

Example 79: 2-ethylbutyl (2S)-2-[[[(2R,3R,4R,5R)-5-(4-aminopyrrolo[2,1-f][1,2,4]triazin-7-yl)-5-cyano-3,4-di(propanoyloxy)tetrahydrofuran-2-yl]methoxy-(1-naphthyloxy)phosphoryl]amino]propanoate

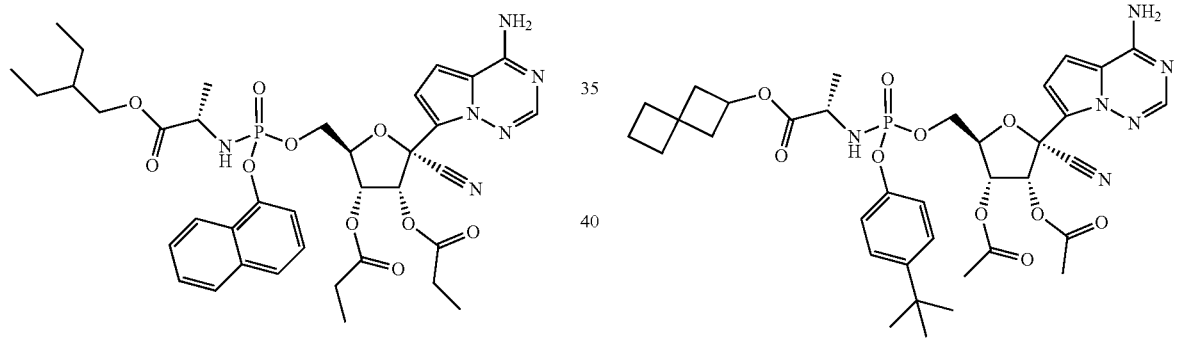

This compound was prepared from Intermediate S2 (12 mg, 0.09 mmol) following the procedure for Example 14. Individual isomers of Compound 79 were separated by preparatory HPLC (Gemini 5 um NX-C18 110A LC column 100×30 mm, 95% to 0% water acetonitrile gradient).

First eluting isomer Compound 79a (LCMS: MS m/z=765.8 [M+1], $t_R$=1.11 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min. $^1$H NMR (400 MHz, Methanol-d4) δ 8.19-8.08 (m, 1H), 7.94-7.86 (m, 1H), 7.80 (s, 1H), 7.73-7.66 (m, 1H), 7.58-7.48 (m, 2H), 7.46 (dt, J=7.7, 1.3 Hz, 1H), 7.38 (t, J=7.9 Hz, 1H), 6.88 (q, J=4.7 Hz, 2H), 6.33 (d, J=6.0 Hz, 1H), 5.62 (dd, J=6.0, 4.1 Hz, 1H), 4.67 (dd, J=4.0, 2.2 Hz, 1H), 4.57-4.41 (m, 2H), 3.96 (dd, J=10.9, 5.9 Hz, 1H), 3.93-3.83 (m, 2H), 2.54-2.31 (m, 4H), 1.42 (dt, J=12.4, 6.2 Hz, 1H), 1.34-1.23 (m, 4H), 1.23-1.10 (m, 9H), 0.83 (td, J=7.4, 2.5 Hz, 6H). $^{31}$P NMR (162 MHz, Methanol-d4) δ 4.00 (s).

Second eluting isomer Compound 79b: LCMS: MS m/z=765.8 [M+1], $t_R$=1.13 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min. $^1$H NMR (400 MHz, Methanol-d4) δ 8.10 (d, J=8.5 Hz, 1H), 7.88 (d, J=8.3 Hz, 1H), 7.82 (s, 1H), 7.68 (d, J=8.2 Hz, 1H), 7.56-7.39 (m, 3H), 7.32 (t, J=7.9 Hz, 1H), 6.79-6.68 (m, 2H), 6.21 (d, J=5.9 Hz, 1H), 5.61 (dd, J=5.9, 3.9 Hz, 1H), 4.65 (d, J=3.6 Hz, 1H), 4.53-4.41 (m, 2H), 4.06-3.91 (m, 3H), 2.52-2.38 (m, 4H), 1.47 (dt, J=12.5, 6.2 Hz, 1H), 1.40-1.24 (m, 7H), 1.18 (dt, J=12.8, 7.5 Hz, 6H), 0.87 (t, J=7.5 Hz, 6H). $^{31}$P NMR (162 MHz, Methanol-$d_4$) δ 3.93 (s).

Example 80: Spiro[3.3]heptan-2-yl (2S)-2-[[[(4-tert-butylphenoxy)-[[(2R,3R,4R,5R)-3,4-diacetoxy-5-(4-aminopyrrolo[2,1-f][1,2,4]triazin-7-yl)-5-cyano-tetrahydrofuran-2-yl]methoxy]phosphoryl]amino]propanoate

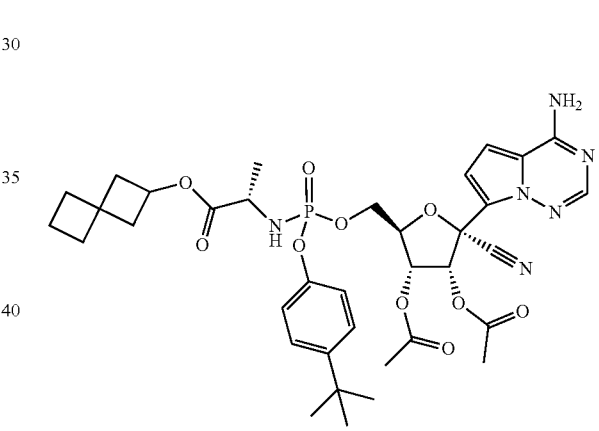

This compound was prepared from Example 65 (12 mg, 0.12 mmol) following the procedure for Example 14. LCMS: MS m/z=753.8 [M+1], $t_R$=1.12 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min. Mixture of isomers: $^1$H NMR (400 MHz, Methanol-d4) δ 7.88 (s, 1H), 7.33-7.25 (m, 2H), 7.11-7.02 (m, 2H), 6.90 (s, 2H), 6.19 (d, J=6.0 Hz, 1H), 5.54 (dd, J=6.0, 4.3 Hz, 1H), 4.82 (p, J=7.3 Hz, 1H), 4.62 (dd, J=4.2, 1.8 Hz, 1H), 4.47-4.31 (m, 2H), 3.88-3.79 (m, 1H), 2.45-2.35 (m, 2H), 2.16 (d, J=14.0 Hz, 6H), 2.07-1.92 (m, 6H), 1.90-1.80 (m, 2H), 1.38-1.22 (m, 12H). $^{31}$P NMR (162 MHz, Methanol-$d_4$) δ 3.72 (s).

Example 81: Spiro[3.3]heptan-2-yl (2S)-2-[[[(2R, 3R,4R,5R)-5-(4-aminopyrrolo[2,1-f][1,2,4]triazin-7-yl)-5-cyano-3,4-di(propanoyloxy) tetrahydrofuran-2-yl]methoxy-(4-tert-butylphenoxy)phosphoryl]amino] propanoate

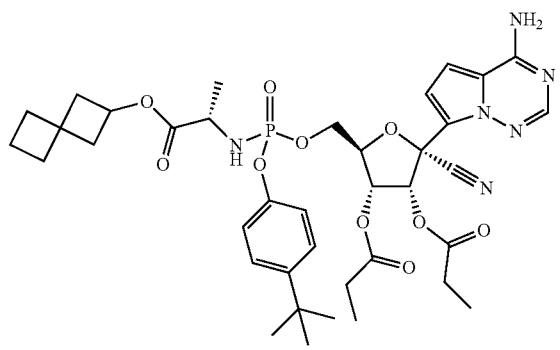 [SMILES: CCC(=O)O[C@H]1[C@@H](OC(=O)CC)[C@](C#N)(c2ccc3c(N)ncnn23)O[C@@H]1COP(=O)(N[C@@H](C)C(=O)OC1CC2(CCC2)C1)Oc1ccc(C(C)(C)C)cc1]

This compound was prepared from Example 65 (25 mg, 0.37 mmol) following the procedure for Example 14. Individual isomers of Compound 81 were separated by preparatory HPLC (Gemini 5 um NX-C18 110A LC column 100×30 mm, 95% to 0% water acetonitrile gradient).

First eluting isomer Compound 81a: LCMS: MS m/z=781.8 [M+1], $t_R$=1.17 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 µL/min. $^1$H NMR (400 MHz, Methanol-d4) δ 7.87 (s, 1H), 7.34 (d, J=8.7 Hz, 2H), 7.09 (dd, J=8.8, 1.3 Hz, 2H), 6.91 (q, J=4.6 Hz, 2H), 6.29 (d, J=5.9 Hz, 1H), 5.57 (dd, J=5.9, 4.1 Hz, 1H), 4.77 (p, J=7.3 Hz, 1H), 4.65 (ddd, J=5.7, 4.1, 2.3 Hz, 1H), 4.48-4.36 (m, 2H), 3.75 (ddd, J=10.5, 8.1, 4.6 Hz, 1H), 2.52-2.35 (m, 6H), 2.07-1.90 (m, 6H), 1.90-1.79 (m, 2H), 1.33-1.13 (m, 18H). $^{31}$P NMR (162 MHz, Methanol-d$_4$) δ 3.70 (s).

Second eluting isomer Compound 81b: LCMS: MS m/z=781.8 [M+1], $t_R$=1.18 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 µL/min. $^1$H NMR (400 MHz, Methanol-d$_4$) δ 7.88 (s, 1H), 7.32-7.24 (m, 2H), 7.11-7.02 (m, 2H), 6.93-6.85 (m, 2H), 6.19 (d, J=5.9 Hz, 1H), 5.57 (dd, J=5.9, 4.1 Hz, 1H), 4.83 (p, J=7.4 Hz, 2H), 4.62 (dd, J=4.0, 1.9 Hz, 1H), 4.39 (dddd, J=21.4, 11.5, 6.0, 3.7 Hz, 2H), 3.89-3.78 (m, 1H), 2.54-2.35 (m, 6H), 2.08-1.92 (m, 6H), 1.91-1.80 (m, 2H), 1.33-1.24 (m, 11H), 1.18 (dt, J=18.7, 7.6 Hz, 6H). $^{31}$P NMR (162 MHz, Methanol-d$_4$) δ 3.69 (s).

Intermediate S5: Spiro[3.3]heptan-2-yl ((naphthalen-1-yloxy)(perfluorophenoxy) phosphoryl)-L-alaninate

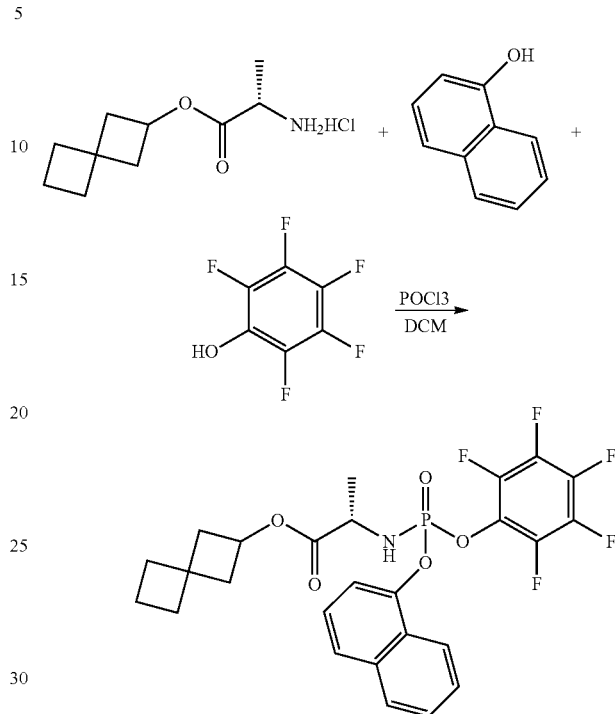

Intermediate S5 was synthesized as explained in Intermediate E2, except that 1-naphthol was used instead of 4-tert-butyl-phenol. LCMS: MS m/z=556.1 [M+1], $^1$H NMR (400 MHz, Chloroform-d) δ 8.14-8.09 (m, 1H), 7.90-7.85 (m, 1H), 7.72 (d, J=8.3 Hz, 1H), 7.64-7.51 (m, 3H), 7.43 (td, J=8.0, 1.4 Hz, 1H), 4.87 (dp, J=32.4, 7.3 Hz, 1H), 4.32-3.90 (m, 2H), 2.52-2.32 (m, 2H), 2.03-1.88 (m, 5H), 1.88-1.77 (m, 2H), 1.44 (dd, J=7.0, 3.0 Hz, 3H). $^{31}$P NMR (162 MHz, Chloroform-d) 6-1.14. $^{19}$F NMR (376 MHz, Chloroform-d) 6-153.60 (ddt, J=38.4, 22.7, 4.8 Hz, 2F), −159.84 (dtd, J=47.2, 21.8, 3.6 Hz, 1F), −162.53 (dtd, J=26.8, 22.5, 4.5 Hz, 2F).

Example 82: spiro[3.3]heptan-2-yl (2S)-2-[[[(3aR, 4R,6R,6aR)-4-(4-aminopyrrolo[2,1-f][1,2,4]triazin-7-yl)-4-cyano-2,2-dimethyl-6,6a-dihydro-3aH-furo [3,4-d][1,3]dioxol-6-yl]methoxy-(1-naphthyloxy) phosphoryl]amino]propanoate

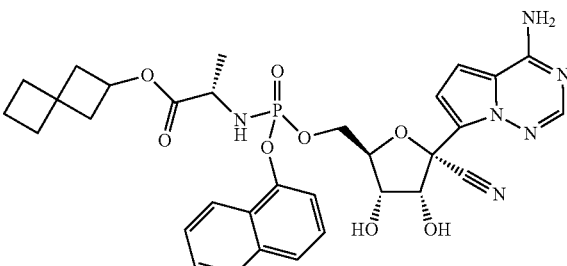

This compound was prepared from spiro[3.3]heptan-2-yl ((naphthalen-1-yloxy)(perfluorophenoxy)phosphoryl)-L-alaninate, Intermediate S5 (240 mg, 0.43 mmol) following the procedure for Example 13. Spiro[3.3]heptan-2-yl ((naphthalen-1-yloxy)(perfluorophenoxy)phosphoryl)-L-alaninate was prepared from spiro[3.3]heptan-2-yl L-alaninate following the procedure for Intermediate H2. Spiro[3.3]heptan-2-yl L-alaninate was prepared from spiro[3.3]heptan-2-ol and naphthalen-1-ol following the general procedure for Intermediate H1. Individual isomers of Compound 82 were separated by preparatory HPLC (Gemini 5 um NX-C18 110A LC column 100×30 mm, 95% to 0% water acetonitrile gradient).

First eluting isomer Compound 82a: LCMS: MS m/z=703.7 [M+1], $t_R$=0.92 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min. $^1$H NMR (400 MHz, Methanol-d4) δ 8.08 (d, J=8.4 Hz, 1H), 7.89 (d, J=8.1 Hz, 1H), 7.82 (s, 1H), 7.70 (d, J=8.1 Hz, 1H), 7.54 (ddd, J=8.2, 6.8, 1.3 Hz, 1H), 7.50-7.42 (m, 2H), 7.38 (t, J=7.9 Hz, 1H), 6.91-6.84 (m, 2H), 4.71-4.65 (m, 2H), 4.48 (ddd, J=11.0, 5.8, 2.5 Hz, 1H), 4.39 (ddd, J=15.0, 9.5, 4.4 Hz, 2H), 4.20 (t, J=5.4 Hz, 1H), 3.90-3.79 (m, 1H), 2.39-2.27 (m, 2H), 2.00 (t, J=7.4 Hz, 2H), 1.95-1.76 (m, 6H), 1.21 (dd, J=7.2, 1.3 Hz, 3H). $^{31}$P NMR (162 MHz, Methanol-d4) δ 4.03 (s).

Second eluting isomer Compound 82b: LCMS: MS m/z=703.7 [M+1], $t_R$=0.94 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min. $^1$H NMR (400 MHz, Methanol-d4) δ 8.14 (dd, J=8.2, 1.6 Hz, 1H), 7.91-7.84 (m, 2H), 7.69 (d, J=8.2 Hz, 1H), 7.57-7.48 (m, 2H), 7.46 (dt, J=7.7, 1.3 Hz, 1H), 7.36 (t, J=7.9 Hz, 1H), 6.90-6.80 (m, 2H), 4.80-4.70 (m, 2H), 4.48 (ddd, J=11.0, 6.1, 2.8 Hz, 1H), 4.38 (ddt, J=21.1, 10.5, 5.1 Hz, 2H), 4.21 (t, J=5.5 Hz, 1H), 3.92 (dq, J=9.9, 7.1 Hz, 1H), 2.40-2.30 (m, 2H), 2.00 (t, J=7.4 Hz, 2H), 1.95-1.76 (m, 6H), 1.25 (dd, J=7.2, 1.1 Hz, 3H). $^{31}$P NMR (162 MHz, Methanol-d4) δ 4.07 (s).

Example 83: spiro[3.3]heptan-2-yl (2S)-2-[[[(2R,3R,4R,5R)-3,4-diacetoxy-5-(4-aminopyrrolo[2,1-f][1,2,4]triazin-7-yl)-5-cyano-tetrahydrofuran-2-yl]methoxy-(1-naphthyloxy)phosphoryl]amino]propanoate

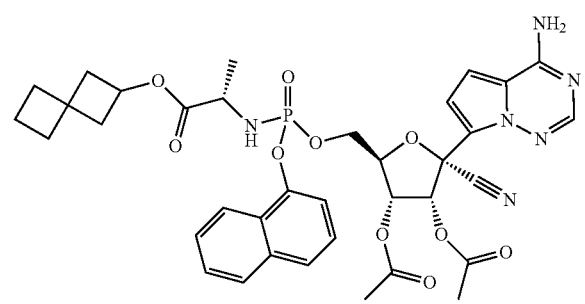 [SMILES: CC(=O)O[C@H]1[C@@H](OC(C)=O)[C@](C#N)(c2ccc3c(N)ncnn23)O[C@@H]1COP(=O)(N[C@@H](C)C(=O)OC1CC2(CCC2)C1)Oc1cccc2ccccc12]

This compound was prepared from Compound 82 (13 mg, 0.12 mmol) following the procedure for Example 14. Individual isomers of Compound 83 were separated by preparatory HPLC (Gemini 5um NX-C18 110A LC column 100×30 mm, 95% to 0% water acetonitrile gradient).

First eluting isomer Compound 83a: LCMS: MS m/z=747.7 [M+1], $t_R$=1.04 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min. $^1$H NMR (400 MHz, Methanol-d4) δ 8.14-8.09 (m, 1H), 7.90 (dd, J=7.0, 2.2 Hz, 1H), 7.79 (s, 1H), 7.74-7.67 (m, 1H), 7.54 (ddd, J=7.8, 5.6, 1.6 Hz, 2H), 7.46 (dt, J=7.6, 1.4 Hz, 1H), 7.38 (t, J=7.9 Hz, 1H), 6.92-6.84 (m, 2H), 6.32 (d, J=6.0 Hz, 1H), 5.60 (dd, J=6.0, 4.2 Hz, 1H), 4.69-4.63 (m, 2H), 4.55-4.42 (m, 2H), 3.85-3.75 (m, 1H), 2.37-2.25 (m, 2H), 2.15 (d, J=13.5 Hz, 6H), 2.02-1.95 (m, 2H), 1.93-1.77 (m, 6H), 1.14 (dd, J=7.1, 1.3 Hz, 3H). $^{31}$P NMR (162 MHz, Methanol-$d_4$) δ 3.92 (s).

Second eluting isomer Compound 83b: LCMS: MS m/z=747.7 [M+1], $t_R$=1.05 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% $^1$H NMR (400 MHz, Methanol-d4) δ 8.09 (d, J=8.2 Hz, 1H), 7.88 (d, J=7.9 Hz, 1H), 7.82 (s, 1H), 7.69 (d, J=8.3 Hz, 1H), 7.57-7.40 (m, 3H), 7.32 (t, J=7.9 Hz, 1H), 6.77 (q, J=4.7 Hz, 2H), 6.21 (d, J=5.9 Hz, 1H), 5.58 (dd, J=5.9, 4.2 Hz, 1H), 4.79 (d, J=7.3 Hz, 1H), 4.66 (s, 1H), 4.53-4.39 (m, 2H), 3.96-3.86 (m, 1H), 2.37 (ddd, J=8.9, 7.1, 3.9 Hz, 2H), 2.16 (d, J=9.8 Hz, 5H), 2.05-1.97 (m, 3H), 1.97-1.81 (m, 6H), 1.24 (dd, J=7.2, 1.1 Hz, 3H). $^{31}$P NMR (162 MHz, Methanol-$d_4$) δ 3.96 (s).

Example 84: [4-(trifluoromethyl)cyclohexyl] (2S)-2-[[[(2R,3S,4R,5R)-5-(4-aminopyrrolo[2,1-f][1,2,4]triazin-7-yl)-5-cyano-3,4-dihydroxy-tetrahydrofuran-2-yl]methoxy-(4-tert-butylphenoxy)phosphoryl]amino]propanoate

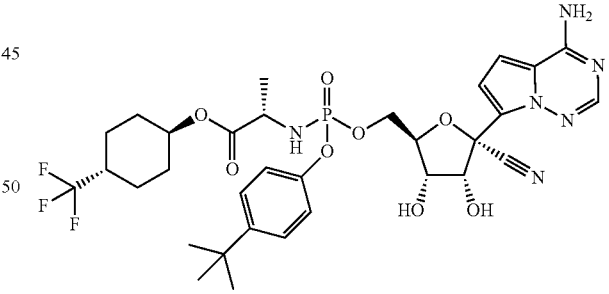

This compound was prepared from (1r,4S)-4-(trifluoromethyl)cyclohexyl ((4-(tert-butyl)phenoxy)(perfluorophenoxy)phosphoryl)-L-alaninate (205 mg, 0.33 mmol) following the procedure for Example 13. (1r,4S)-4-(trifluoromethyl)cyclohexyl ((4-(tert-butyl)phenoxy)(perfluorophenoxy)phosphoryl)-L-alaninate was prepared from (1r,4S)-4-(trifluoromethyl)cyclohexyl L-alaninate following the procedure for Intermediate H2. (1r,4S)-4-(trifluoromethyl)cyclohexyl L-alaninate was prepared from (1r,4r)-4-(trifluoromethyl)cyclohexan-1-ol following the general procedure for Intermediate H1. Individual isomers of Compound 84 were separated by preparatory HPLC (Gemini Sum NX-C18 110A LC column 100×30 mm, 95% to 0% water acetonitrile gradient).

First eluting isomer Compound 84a: LCMS: MS m/z=725.7 [M+1], $t_R$=0.97 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min. $^1$H NMR (400 MHz, Methanol-d4) δ 8.00 (s, 1H), 7.88 (s, 1H), 7.20 (s, 1H), 7.06 (dd, J=8.7, 1.3 Hz, 2H), 6.95 (s, 2H), 4.66-4.59 (m, 1H), 4.34-4.20 (m, 4H), 3.84-3.71 (m, 2H), 2.52 (ddd, J=10.0, 7.1, 3.1 Hz, 1H), 1.23 (dd, J=7.1, 1.2 Hz, 3H), 0.98-0.86 (m, 12H). $^{31}$P NMR (162 MHz, Methanol-d4) δ 3.82 (s). $^{19}$F NMR (376 MHz, Methanol-$d_4$) δ −75.45 (d, J=8.4 Hz).

Second eluting isomer Compound 84b: LCMS: MS m/z=725.7 [M+1], $t_R$=1.00 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min. $^1$H NMR (400 MHz, Methanol-d4) δ 7.89 (s, 1H), 7.37-7.29 (m, 2H), 7.15-7.08 (m, 2H), 6.99-6.89 (m, 2H), 4.82 (d, J=5.4 Hz, 2H), 4.66-4.59 (m, 1H), 4.44-4.35 (m, 2H), 4.34-4.27 (m, 2H), 4.17 (t, J=5.7 Hz, 1H), 3.84 (dd, J=9.6, 7.1 Hz, 1H), 1.98 (d, J=25.3 Hz, 3H), 1.30 (d, J=7.5 Hz, 12H). $^{31}$P NMR (162 MHz, Methanol-$d_4$) δ 3.80 (s). $^{19}$F NMR (376 MHz, Methanol-d4) δ −75.46 (d, J=8.5 Hz).

Example 85: [(2R,3R,4R,5R)-5-(4-aminopyrrolo[2,1-f][1,2,4]triazin-7-yl)-2-[[(4-tert-butylphenoxy)-[[(1S)-1-methyl-2-oxo-2-[4-(trifluoromethyl)cyclohexoxy]ethyl]amino]phosphoryl]oxymethyl]-5-cyano-4-(2-methylpropanoyloxy)tetrahydrofuran-3-yl] 2-methylpropanoate

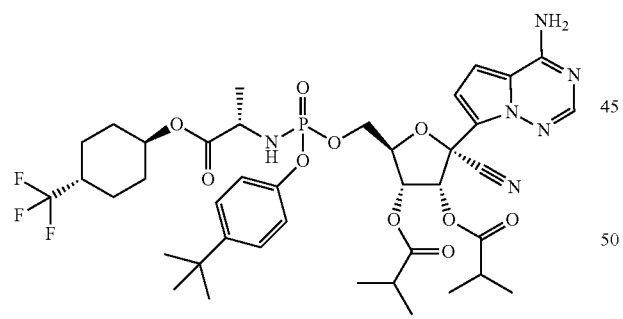

This compound was prepared from Compound 84 (11 mg, 0.07 mmol) following the procedure for Example 14. Individual isomers of Compound 85 were separated by preparatory HPLC (Gemini Sum NX-C18 110A LC column 100×30 mm, 95% to 0% water acetonitrile gradient).

First eluting isomer Compound 85a: LCMS: MS m/z=865.8 [M+1], $t_R$=1.20 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min. $^1$H NMR (400 MHz, Methanol-d4) δ 7.88 (s, 1H), 7.37-7.31 (m, 2H), 7.13-7.05 (m, 2H), 6.94-6.86 (m, 2H), 6.29 (d, J=6.0 Hz, 1H), 5.58 (dd, J=5.9, 3.7 Hz, 1H), 4.68-4.58 (m, 2H), 4.42 (tt, J=6.3, 3.0 Hz, 2H), 3.81-3.70 (m, 1H), 2.66 (dp, J=25.9, 7.0 Hz, 2H), 2.14 (d, J=8.0 Hz, 1H), 2.05-1.90 (m, 4H), 1.48-1.35 (m, 4H), 1.32-1.23 (m, 15H), 1.19 (dd, J=7.0, 2.2 Hz, 9H). 31P NMR (162 MHz, Methanol-d4) δ 3.68 (s). 19F NMR (376 MHz, Methanol-d4) δ −75.46 (d, J=8.3 Hz).

Second eluting isomer Compound 85b: LCMS: MS m/z=865.8 [M+1], $t_R$=1.21 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min. $^1$H NMR (400 MHz, Methanol-d4) δ 7.88 (s, 1H), 7.29 (d, J=8.7 Hz, 2H), 7.10-7.02 (m, 2H), 6.93-6.82 (m, 2H), 6.14 (d, J=5.9 Hz, 1H), 5.57 (dd, J=5.9, 3.7 Hz, 1H), 4.69-4.59 (m, 2H), 4.41 (dt, J=6.6, 3.7 Hz, 2H), 3.90-3.79 (m, 1H), 2.67 (dp, J=27.5, 7.0 Hz, 2H), 2.18-1.92 (m, 5H), 1.47-1.18 (m, 29H). $^{31}$P NMR (162 MHz, Methanol-$d_4$) δ 3.61 (s). $^{19}$F NMR (376 MHz, Methanol-d4) δ −75.46 (d, J=8.4 Hz).

Example 86: [(2R,3R,4R,5R)-5-(4-aminopyrrolo[2,1-f][1,2,4]triazin-7-yl)-5-cyano-2-[[[[(1S)-1-methyl-2-oxo-2-spiro[3.3]heptan-2-yloxy-ethyl]amino]-(1-naphthyloxy)phosphoryl]oxymethyl]-4-(2-methylpropanoyloxy)tetrahydrofuran-3-yl] 2-methylpropanoate

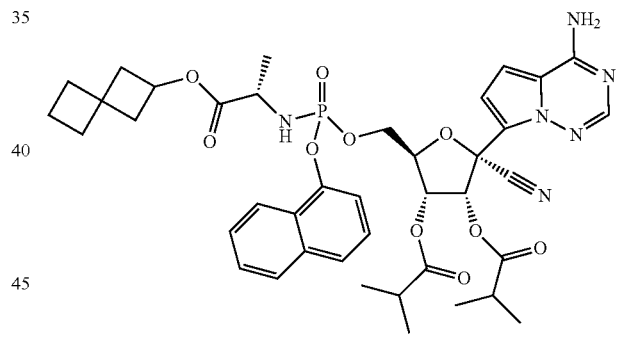

This compound was prepared from Compound 82 (13 mg, 0.08 mmol) following the procedure for Example 14. Individual isomers of Compound 86 were separated by preparatory HPLC (Gemini 5 um NX-C18 110A LC column 100×30 mm, 95% to 0% water acetonitrile gradient).

First eluting isomer Compound 86a: LCMS: MS m/z=803.8 [M+1], $t_R$=1.17 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min. $^1$H NMR (400 MHz, Methanol-d4) δ 8.13 (d, J=7.9 Hz, 1H), 7.90 (d, J=8.0 Hz, 1H), 7.80 (s, 1H), 7.71 (d, J=8.2 Hz, 1H), 7.59-7.49 (m, 2H), 7.46 (d, J=7.7 Hz, 1H), 7.38 (t, J=7.9 Hz, 1H), 6.86 (s, 2H), 6.30 (d, J=6.0 Hz, 1H), 5.62 (dd, J=6.0, 3.7 Hz, 1H), 4.87 (s, 2H), 4.66 (q, J=7.3 Hz, 3H), 4.55-4.42 (m, 2H), 3.81 (p, J=7.2 Hz, 1H), 2.64 (dq, J=23.3, 7.0 Hz, 2H), 2.38-2.25 (m, 2H), 1.99

(t, J=7.3 Hz, 2H), 1.94-1.78 (m, 5H), 1.29-1.11 (m, 12H). $^{31}$P NMR (162 MHz, Methanol-d4) δ 3.93 (s).

Second eluting isomer Compound 86b: LCMS: MS m/z=803.8 [M+1], $t_R$=1.19 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min. $^1$H NMR (400 MHz, Methanol-d4) δ 8.09 (d, J=8.3 Hz, 1H), 7.92-7.85 (m, 1H), 7.82 (s, 1H), 7.68 (d, J=8.2 Hz, 1H), 7.56-7.38 (m, 3H), 7.32 (t, J=7.9 Hz, 1H), 6.76-6.69 (m, 2H), 6.18 (d, J=5.9 Hz, 1H), 5.60 (dd, J=5.8, 3.5 Hz, 1H), 4.83-4.78 (m, 1H), 4.70-4.61 (m, 2H), 4.54-4.39 (m, 2H), 3.96-3.86 (m, 1H), 2.66 (dp, J=19.5, 7.0 Hz, 2H), 2.42-2.32 (m, 2H), 2.06-1.79 (m, 8H), 1.33-1.15 (m, 14H). $^{31}$P NMR (162 MHz, Methanol-d$_4$) δ 3.91 (s).

Example 87: spiro[3.3]heptan-2-yl (2S)-2-[[[(2R,3R,4R,5R)-5-(4-aminopyrrolo[2,1-f][1,2,4]triazin-7-yl)-5-cyano-3,4-di(propanoyloxy) tetrahydrofuran-2-yl]methoxy-(1-naphthyloxy)phosphoryl]amino] propanoate

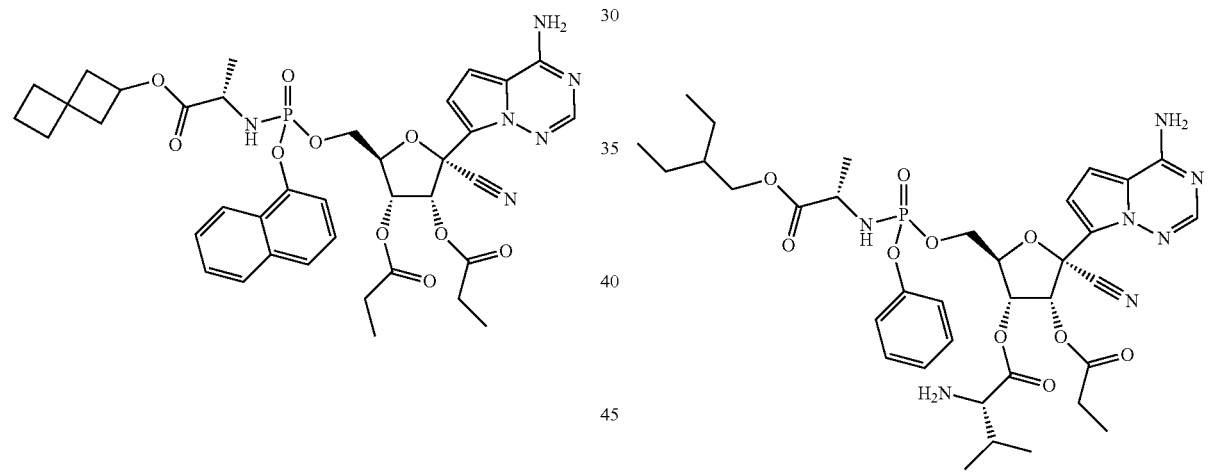

This compound was prepared from Compound 82 (13 mg, 0.10 mmol) following the procedure for Example 14. Individual isomers of Compound 87 were separated by preparatory HPLC (Gemini Sum NX-C18 110A LC column 100×30 mm, 95% to 0% water acetonitrile gradient).

First eluting isomer Compound 87a: LCMS: MS m/z=775.8 [M+1], $t_R$=1.11 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min. $^1$H NMR (400 MHz, Methanol-d$_4$) δ 8.16-8.09 (m, 1H), 7.93-7.86 (m, 1H), 7.79 (s, 1H), 7.71 (d, J=8.2 Hz, 1H), 7.54 (ddd, J=7.6, 5.5, 1.7 Hz, 2H), 7.46 (d, J=7.6 Hz, 1H), 7.38 (t, J=8.0 Hz, 1H), 6.88 (q, J=4.7 Hz, 2H), 6.33 (d, J=6.0 Hz, 1H), 5.63 (dd, J=5.9, 4.0 Hz, 1H), 4.69-4.62 (m, 2H), 4.56-4.41 (m, 2H), 3.85-3.74 (m, 1H), 2.51-2.38 (m, 4H), 2.38-2.24 (m, 2H), 1.99 (t, J=7.1 Hz, 2H), 1.85 (ddd, J=25.8, 13.6, 7.4 Hz, 6H), 1.33-1.10 (m, 9H). $^{31}$P NMR (162 MHz, Methanol-d$_4$) δ 3.93 (s).

Second eluting isomer Compound 87b: LCMS: MS m/z=775.8 [M+1], $t_R$=1.13 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min. $^1$H NMR (400 MHz, Methanol-d$_4$) δ 8.09 (d, J=8.2 Hz, 1H), 7.88 (d, J=8.0 Hz, 1H), 7.82 (s, 1H), 7.69 (d, J=8.2 Hz, 1H), 7.57-7.38 (m, 3H), 7.32 (t, J=7.9 Hz, 1H), 6.81-6.71 (m, 2H), 6.22 (d, J=5.9 Hz, 1H), 5.61 (dd, J=5.9, 3.9 Hz, 1H), 4.80 (q, J=7.3 Hz, 2H), 4.68-4.64 (m, 1H), 4.53-4.39 (m, 2H), 3.90 (dt, J=9.9, 7.1 Hz, 1H), 2.52-2.32 (m, 6H), 2.03 (t, J=7.3 Hz, 2H), 1.98-1.78 (m, 6H), 1.26-1.12 (m, 8H). $^{31}$P NMR (162 MHz, Methanol-d$_4$) δ 3.94 (s).

Example 88: [(2R,3R,4R,5R)-5-(4-aminopyrrolo[2,1-f][1,2,4]triazin-7-yl)-5-cyano-2-[[[[(1S)-2-(2-ethylbutoxy)-1-methyl-2-oxo-ethyl]amino]-phenoxy-phosphoryl]oxymethyl]-4-propanoyloxy-tetrahydrofuran-3-yl] (2R)-2-amino-3-methyl-butanoate To an oven-dried 2-dram vial was added 2-ethylbutyl ((S)-(((2R,3S,4R,5R)-5-(4-aminopyrrolo[2,1-f][1,2,4]triazin-7-yl)-5-cyano-3,4-dihydroxytetrahydrofuran-2-yl) methoxy)(phenoxy)phosphoryl)-L-alaninate (prepared according to WO2016069825) followed by DMF (0.1M), 1.2 eqiuv. L-valine, 1.1 equiv DIC, and 2 equiv. diisopropyl ethylamine at room temperature. The mixture was stirred for 1 hour, and 2.0 equiv. propionic anhydride was added. The mixture was stirred for an additional 15 min. The mixture was purified by reverse-phase preparative HPLC.

LCMS: MS m/z=758.8 [M+1], $t_R$=1.00 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min. Mixture of isomers: $^1$H NMR (400 MHz, Methanol-d$_4$) δ 7.88 (s, 1H), 7.29 (dd, J=8.7, 7.1 Hz, 2H), 7.21-7.12 (m, 3H), 6.86 (q, J=4.7 Hz, 2H), 6.24 (d, J=5.8 Hz, 1H), 5.62 (dd, J=5.8, 3.4 Hz, 1H), 4.91-4.86 (m, 1H), 4.65 (dd, J=3.7, 1.9 Hz, 1H), 4.49-4.37 (m, 2H), 4.07 (dd, J=10.9, 5.8 Hz, 1H), 4.00-3.93 (m, 1H), 3.93-3.84 (m, 1H), 3.40 (d, J=5.1 Hz, 1H), 2.47 (q, J=7.4 Hz, 2H), 2.16 (td, J=7.0, 5.3 Hz, 1H), 1.49 (dq, J=12.1, 6.1 Hz, 1H), 1.42-1.26 (m, 7H), 1.15 (t, J=7.5 Hz, 3H), 1.02 (dd, J=15.8, 6.9 Hz, 5H), 0.89 (t, J=7.5 Hz, 6H). $^{31}$P NMR (162 MHz, Methanol-d$_4$) δ 3.55 (s).

Example 89: tetrahydropyran-4-yl (2S)-2-[[[(3aR,4R,6R,6aR)-4-(4-aminopyrrolo[2,1-f][1,2,4]triazin-7-yl)-4-cyano-2,2-dimethyl-6,6a-dihydro-3aH-furo[3,4-d][1,3]dioxol-6-yl]methoxy-(4-tert-butylphenoxy)phosphoryl]amino]propanoate

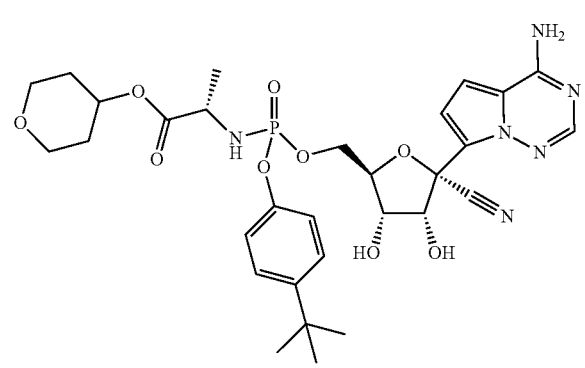 [SMILES: C[C@H](NP(=O)(OC[C@H]1O[C@@](C#N)(c2ccc3c(N)ncnn23)[C@H](O)[C@@H]1O)Oc1ccc(C(C)(C)C)cc1)C(=O)OC1CCOCC1]

This compound was prepared from tetrahydro-2H-pyran-4-yl ((4-(tert-butyl)phenoxy)(perfluorophenoxy)phosphoryl)-L-alaninate (100 mg, 0.18 mmol) following the procedure for Example 13. Tetrahydro-2H-pyran-4-yl ((4-(tert-butyl)phenoxy)(perfluorophenoxy)phosphoryl)-L-alaninate was prepared from tetrahydro-2H-pyran-4-yl L-alaninate following the procedure for Intermediate H2. Tetrahydro-2H-pyran-4-yl L-alaninate was prepared from tetrahydro-2H-pyran-4-ol following the general procedure for Intermediate H1. LCMS: MS m/z=699.7 [M+1], t$_R$=0.82 min, 699.7 [M+1], t$_R$=0.84 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min. Mixture of isomers: $^1$H NMR (400 MHz, Methanol-d$_4$) δ 7.88 (d, J=6.5 Hz, 1H), 7.36-7.27 (m, 2H), 7.16-7.09 (m, 1H), 7.09-7.03 (m, 1H), 6.99-6.90 (m, 2H), 4.81 (t, J=5.6 Hz, 1H), 4.50-4.23 (m, 4H), 4.18 (td, J=5.6, 1.6 Hz, 1H), 3.93-3.71 (m, 4H), 3.51 (dddd, J=14.6, 11.9, 9.2, 3.2 Hz, 2H), 1.91-1.83 (m, 2H), 1.61 (ddp, J=12.9, 8.6, 4.4 Hz, 2H), 1.33-1.24 (m, 12H). $^{31}$P NMR (162 MHz, Methanol-d$_4$) δ 3.82 (s).

Example 90: [(2R,3R,4R,5R)-5-(4-aminopyrrolo[2,1-f][1,2,4]triazin-7-yl)-2-[[(4-tert-butylphenoxy)-[[(1S)-1-methyl-2-oxo-2-tetrahydropyran-4-yloxy-ethyl]amino]phosphoryl]oxymethyl]-5-cyano-4-(2-methylpropanoyloxy)tetrahydrofuran-3-yl] 2-methylpropanoate

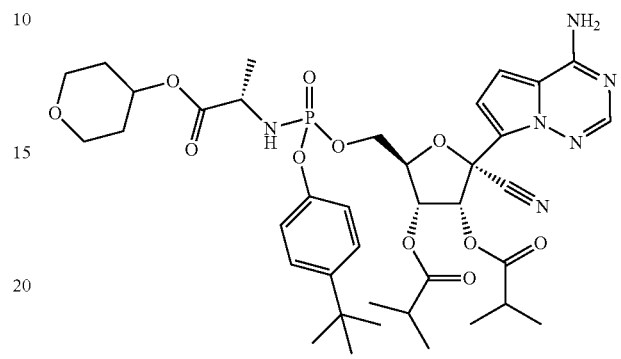

This compound was prepared from Compound 89 (12 mg, 0.08 mmol) following the procedure for Example 14. LCMS: MS m/z=799.8 [M+1], t$_R$=1.08 min, 799.8 [M+1], t$_R$1.10 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min. Mixture of isomers: $^1$H NMR (400 MHz, Methanol-d$_4$) δ 7.88 (d, J=1.5 Hz, 1H), 7.38-7.25 (m, 2H), 7.14-7.04 (m, 2H), 6.89 (ddd, J=15.7, 10.3, 4.7 Hz, 2H), 6.28 (d, J=5.9 Hz, 0.5H), 6.15 (d, J=5.9 Hz, 0.5H), 5.57 (dd, J=5.9, 3.7 Hz, 1H), 4.68-4.59 (m, 1H), 4.41 (tdd, J=11.7, 8.0, 4.5 Hz, 2H), 3.95-3.78 (m, 3H), 3.53 (dq, J=8.6, 2.8 Hz, 2H), 2.76-2.56 (m, 2H), 1.93-1.84 (m, 2H), 1.61 (dtq, J=13.3, 8.9, 5.1, 4.3 Hz, 2H), 1.30-1.22 (m, 11H). $^{31}$P NMR (162 MHz, Methanol-d$_4$) δ 3.67 (s).

Example 91: [(2R,3R,4R,5R)-5-(4-aminopyrrolo[2,1-f][1,2,4]triazin-7-yl)-2-[[(3-tert-butylphenoxy)-[[(1S)-2-(2-ethylbutoxy)-1-methyl-2-oxo-ethyl]amino]phosphoryl]oxymethyl]-5-cyano-4-(2-methylpropanoyloxy) tetrahydrofuran-3-yl] 2-methylpropanoate

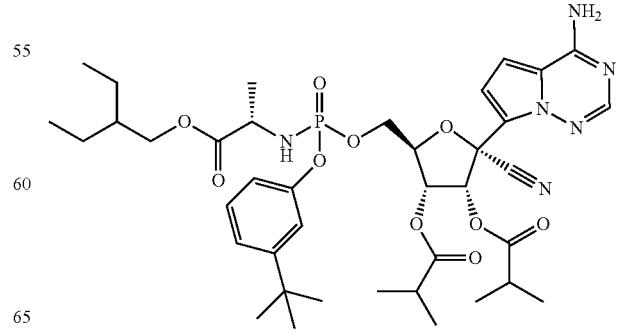

This compound was prepared from Example 68 (10 mg, 0.02 mmol) following the procedure for Example 14. LCMS: MS m/z=799.9 [M+1], $t_R$=1.23 min, 799.9 [M+1], $t_R$=1.25 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min. Mixture of isomers: $^1$H NMR (400 MHz, Methanol-$d_4$) δ 7.88 (d, J=2.1 Hz, 1H), 7.28-7.18 (m, 3H), 7.05-6.96 (m, 1H), 6.91 (s, 1H), 6.86 (q, J=4.7 Hz, 1H), 6.27 (dd, J=24.7, 5.9 Hz, 1H), 5.58 (ddd, J=9.3, 5.9, 3.9 Hz, 1H), 4.64 (ddd, J=16.6, 3.9, 1.9 Hz, 1H), 4.52-4.36 (m, 2H), 4.10-3.80 (m, 3H), 2.74-2.58 (m, 2H), 1.55-1.15 (m, 29H), 0.93-0.83 (m, 6H). $^{31}$P NMR (162 MHz, Methanol-$d_4$) δ 3.75 (s), 3.56 (s).

Example 92: 2-ethylbutyl (((((2R,3S,4R,5R)-5-(4-aminopyrrolo[2,1-f][1,2,4]triazin-7-yl)-5-cyano-3,4-dihydroxytetrahydrofuran-2-yl)methoxy)(4-morpholinophenoxy)phosphoryl)-L-alaninate

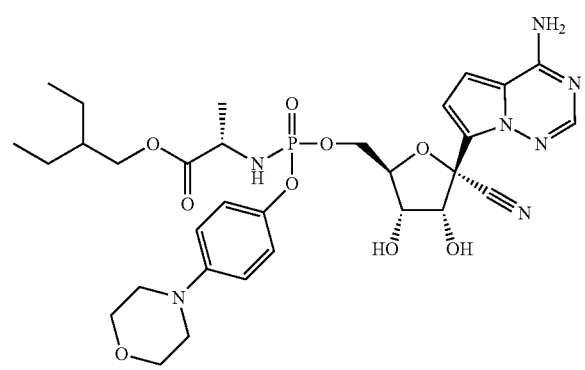 [SMILES: CCC(CC)COC(=O)[C@H](C)NP(=O)(OC[C@H]1O[C@@](C#N)(c2ccc3c(N)ncnn23)[C@H](O)[C@@H]1O)Oc1ccc(N2CCOCC2)cc1]

Example 92 was synthesized as explained in example 212, using 4-morpholinophenol instead of the pyridine-2-ol. The product was obtained as mixture of isomers. LCMS: MS m/z=688.3 [M+1], Mixture of isomers: $^1$H NMR (400 MHz, Methanol-d4) δ 7.90 (d, J=5.4 Hz, 1H), 7.13-7.05 (m, 1H), 7.05-7.00 (m, 1H), 6.99-6.89 (m, 3H), 6.89-6.80 (m, 2H), 4.77 (dd, J=5.5, 3.5 Hz, 1H), 4.50-4.23 (m, 3H), 4.18 (t, J=5.5 Hz, 1H), 4.12-3.92 (m, 2H), 3.88-3.78 (m, 5H), 3.06 (q, J=5.3 Hz, 4H), 1.48 (ddt, J=15.9, 12.4, 6.2 Hz, 1H), 1.42-1.21 (m, 8H), 0.88 (td, J=7.5, 4.6 Hz, 6H); 31P NMR (162 MHz, Methanol-d4) δ 4.11.

Intermediate K6: 3,3-dimethylcyclobutyl (tert-butoxycarbonyl)-L-alaninate

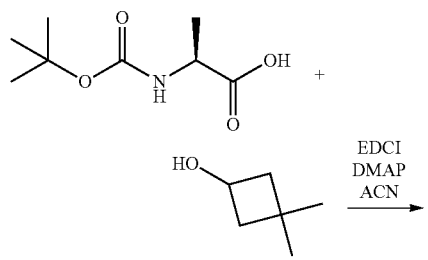

-continued

To a mixture of 3,3-dimethylcyclobutanol (1.00 g, 9.98 mmol), Boc-L-alanine (3.04 g, 15.0 mmol), and DMAP (2.44 g, 20.0 mmol) in acetonitrile (15 mL) was added EDCI (3.10 g, 20.0 mmol). Then the mixture was stirred at rt for 3 h, quenched with water, and concentrated in vacuo. The residue was dissolved in EtOAc, washed with brine, and the aqueous layer extracted with EtOAc. The combined organic layer was dried with sodium sulfate, concentrated in vacuo, and purified by silica gel chromatography (0 to 20% EtOAc in DCM) to give K6. $^1$H NMR (400 MHz, Acetonitrile-d3) δ 5.60 (s, 1H), 4.99 (m, 1H), 4.08 (dd, J=8.5, 6.4 Hz, 1H), 2.27-2.19 (m, 2H), 1.85 (m, 2H), 1.43 (s, 9H), 1.31 (d, J=7.3 Hz, 3H), 1.16 (d, J=2.6 Hz, 6H).

Intermediate K7: 3,3-dimethylcyclobutyl L-alaninate hydrochloride

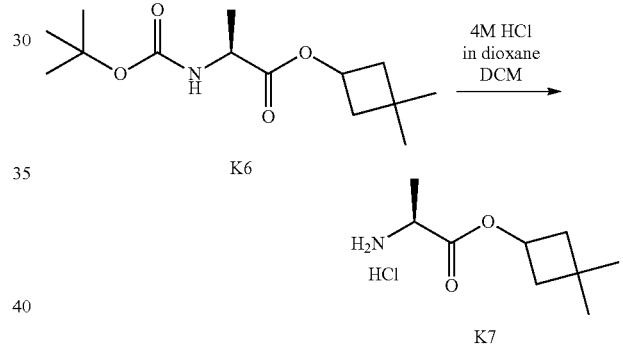

To a mixture of K6 (2.40 g, 8.84 mmol) in DCM (15 mL) was added 4M HCL in dioxane (12 mL) slowly at rt. The resulting mixture was stirred at rt for 3 h, concentrated in vacuo, co-evaporated with DCM several times, and dried under high vacuum for 15 h to give K7. $^1$H NMR (400 MHz, Chloroform-d) δ 8.79 (s, 3H), 5.12 (m, 1H), 4.15 (s, 1H), 2.25 (m, 2H), 195 (ddd, J=19.5, 12.5, 7.1 Hz, 2H), 1.73 (d, J=7.2 Hz, 3H), 1.18 (s, 3H), 1.15 (s, 3H).

Intermediate K8: -3,3-dimethylcyclobutyl ((4-(tert-butyl)phenoxy) (perfluorophenoxy)phosphoryl)-L-alaninate

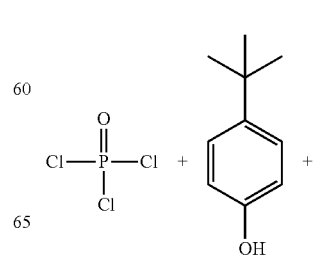

Intermediate K9: 3,3-dimethylcyclobutyl ((((3aR, 4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methoxy)(4-(tert-butyl)phenoxy) phosphoryl)-L-alaninate

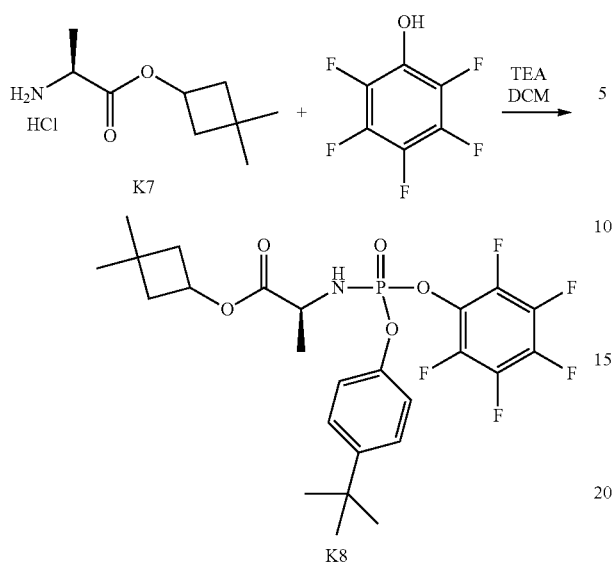

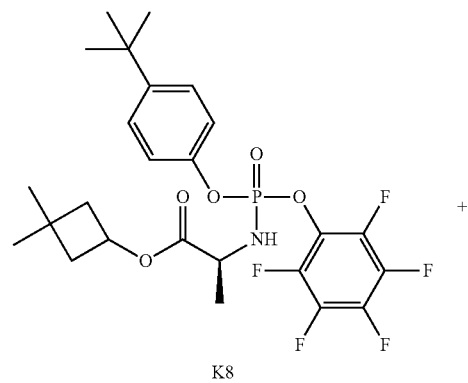

To a solution of POCl$_3$ (0.790 mL, 8.48 mmol) in DCM (40 mL) at −78° C. was added tBuPhOH (1.27 g, 8.48 mmol) in one portion. Then TEA (1.18 mL, 8.48 mmol) was added dropwise. The reaction mixture was placed under ice bath and stirred for 1 hr. The reaction mixture was cooled to −78° C. and K7 (1.76 g, 8.48 mmol) was added in one portion. Then TEA (2.36 mL, 16.96 mmol) was added over 5 min. The reaction mixture was stirred for 15 min and then placed under ice bath. Pentafluorophenol (1.56 g, 8.48 mmol) was added to the reaction mixture and then TEA (1.18 mL, 8.48 mmol) added over 2 min. The reaction mixture was exposed to rt and stirred for 20 min, diluted with DCM, washed with water, dried over sodium sulfate, filtered, and concentrated in vacuo. The obtained residue was purified by silica gel chromatography (0-40% EtOAc in Hex) to give K8 (2.70 g, 58%) as a white solid. $^1$H NMR (400 MHz, Acetonitrile-d3) δ 7.52-7.41 (m, 2H), 7.27-7.02 (m, 2H), 4.97 (dt, J=10.9, 7.2 Hz, 1H), 4.82-4.54 (m, 1H), 4.17-3.94 (m, 1H), 2.22 (m, 3H), 1.89-1.78 (m, 2H), 1.38 (ddd, J=7.1, 2.0, 1.0 Hz, 4H), 1.33 (d, J=0.9 Hz, 9H), 1.15 (d, J=1.3 Hz, 6H). $^{19}$F NMR (376 MHz, Acetonitrile-d3) δ-155.28--155.69 (m), −162.73 (m), −165.29 (m). $^{31}$P NMR (162 MHz, Acetonitrile-d3) δ-0.29, −0.42. LCMS: MS m/z=549.85 [M+1]; $t_R$=2.10 min; LC system: Thermo Accela 1250 UHPLC; MS system: Thermo LCQ Fleet; Column: Phenomenex Kinetex 2.6p XB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 µl/min.

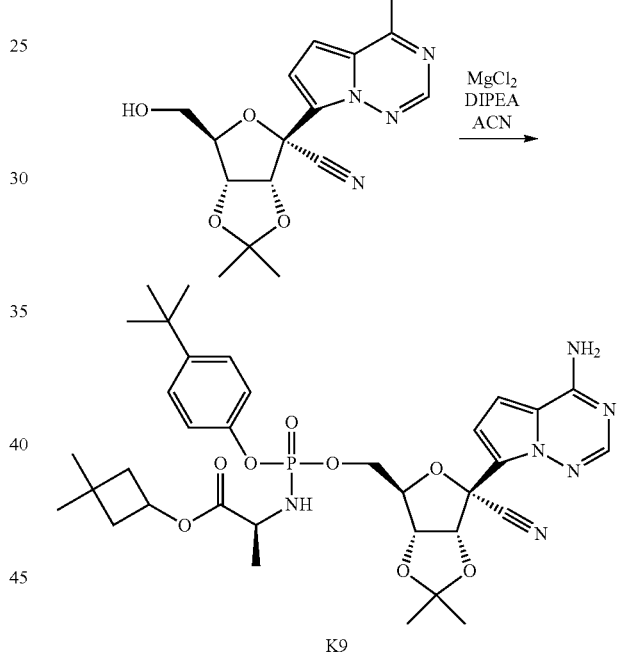

To a solution of (3aR,4R,6R,6aR)-4-(4-aminopyrrolo[2,1-f][1,2,4]triazin-7-yl)-6-(hydroxymethyl)-2,2-dimethyltetrahydrofuro[3,4-d][1,3]dioxole-4-carbonitrile (1.60 g, 4.83 mmol) in DCM, K8 (2.74 g, 4.98 mmol), and MgCl$_2$ (0.460 g, 4.83 mmol) in ACN (5 mL) were added and stirred for 15 min at 50° C. and then DIPEA (2.10 mL, 12.10 mmol) was added. The reaction mixture was allowed to cool to rt, diluted with ethyl acetate, washed saturated sodium bicarbonate solution, dried over anhydrous sodium sulfate, and concentrated in vacuo. The residue was purified by silica gel chromatography (0-20% MeOH in DCM) to K9. Mixture of isomers: $^1$H NMR (400 MHz, Acetonitrile-d3) δ 7.94 (s, 1H), 7.35-7.22 (m, 2H), 7.09-7.00 (m, 1H), 6.97-6.91 (m, 1.6H), 6.89 (d, J=4.6 Hz, 0.4H), 6.82 (m, 1H), 6.37 (s, 2H), 5.27 (m, 1H), 4.98-4.88 (m, 1.6H), 4.89-4.83 (m, 0.4H), 4.65-4.55 (m, 1H), 4.28-4.18 (m, 1.6H), 4.15-4.04 (m, 1.4H), 3.89-3.73 (m, 1H), 2.27-2.13 (m, 2H), 1.87-1.75 (m, 2H), 1.71 (s, 1.8H), 1.70 (s, 1.2H), 1.41 (s, 1.8H), 1.37 (s, 1.2H), 1.32-1.20 (m, 12H), 1.14 (s, 6H). $^{31}$P NMR (162 MHz, Acetonitrile-d3) δ 2.96, 2.85. LCMS: MS m/z=697.22 [M+1]; tR=1.90, 1.93 min; LC system: Thermo Accela 1250 UHPLC; MS system: Thermo LCQ Fleet; Column: Phenomenex Kinetex 2.6p XB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μl/min.

Example 93: 3,3-dimethylcyclobutyl (((((2R,3S,4R, 5R)-5-(4-aminopyrrolo[2,1-f][1,2,4]triazin-7-yl)-5-cyano-3,4-dihydroxytetrahydrofuran-2-yl)methoxy) (4-(tert-butyl)phenoxy)phosphoryl)-L-alaninate

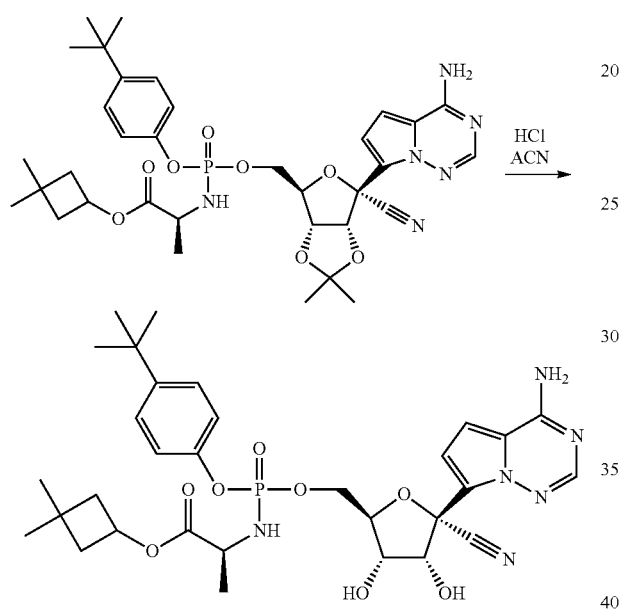

Intermediate K9 (1.3 g, 1.87 mmol) was dissolved in ACN (10 mL) and conc. HCl (2 mL) was added at rt. Then the reaction mixture was stirred at rt for 30 min, diluted with saturated sodium bicarbonate solution (10 mL) and ethyl acetate (10 mL). The organic layer was dried over anhydrous sodium sulfate and concentrated in vacuo. The resulting residue was purified by silica gel chromatography (0-30% MeOH in DCM) to give Example 93. Mixture of isomers: $^1$H NMR (400 MHz, Acetonitrile-d3) δ 7.95 (s, 1H), 7.34-7.25 (m, 2H), 7.07-7.00 (m, 2H), 6.88 (d, J=4.6 Hz, 1H), 6.83 (d, J=4.6 Hz, 1H), 6.45 (s, 2H), 4.92 (m, 1H), 4.80 (d, J=5.2 Hz, 1H), 4.64 (t, J=4.9 Hz, 1H), 4.40 (m, 1H), 4.35-4.11 (m, 4H), 3.86 (d, J=4.8 Hz, 1H), 3.79 (m, 1H), 2.22 (m, 2H), 1.80 (m, 2H), 1.29 (s, 9H), 1.22 (dd, J=7.1, 1.0 Hz, 3H), 1.13 (s, 6H). $^{31}$P NMR (162 MHz, Acetonitrile-d3) δ 3.14. LCMS: MS m/z=657.15 [M+1]; $t_R$=1.68 min; LC system: Thermo Accela 1250 UHPLC; MS system: Thermo LCQ Fleet; Column: Phenomenex Kinetex 2.6p XB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μl/min. HPLC: $t_R$=5.60 min; HPLC system: 1290 Infinity II; Column: Phenomenex 2.6μ C18 100A, 100×4.6 mm; Solvents: Acetonitrile with 0.1% TFA, Water with 0.1% TFA; Gradient: 0 min-8.5 min 2-98% ACN at 1.5 mL/min.

Example 94: (2R,3R,4R,5R)-2-(4-aminopyrrolo[2,1-f][1,2,4]triazin-7-yl)-5-((((4-(tert-butyl)phenoxy) (((S)-1-(3,3-dimethylcyclobutoxy)-1-oxopropan-2-yl)amino)phosphoryl)oxy)methyl)-2-cyanotetrahydrofuran-3,4-diyl bis(2-methylpropanoate)

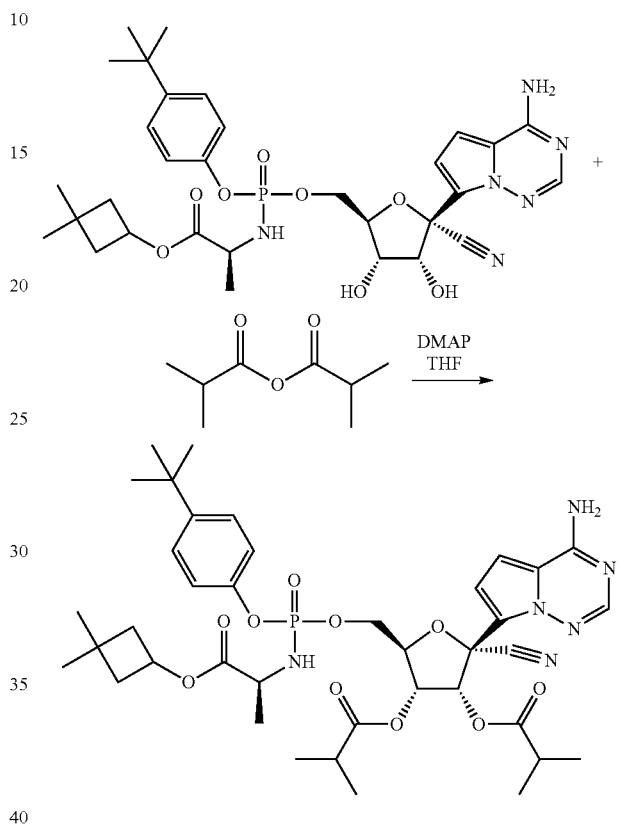

To a solution of Example 93 (50 mg, 0.0761 mmol) and isobutyric anhydride (0.0631 mL, 0.381 mmol) was added DMAP (1.38 mg, 0.0114 mmol) at rt. After 20 min, the reaction mixture was purified by prep HPLC (0 to 100% ACN for 5 min, then 100% ACN for 8 min) to give Example 94. Mixture of isomers: $^1$H NMR (400 MHz, Acetonitrile-d3) δ 7.95 (s, 0.6H), 7.93 (s, 0.4H), 7.39-7.26 (m, 2H), 7.06 (m, 2H), 6.86 (m, 1H), 6.80 (m, 1H), 6.44 (s, 2H), 6.15 (d, J=6.0 Hz, 0.4H), 6.09 (d, J=5.9 Hz, 0.6H), 5.52 (m, 1H), 4.93 (m, 1H), 4.62 (m, 1H), 4.43-4.27 (m, 2H), 4.19 (m, 1H), 3.94-3.68 (m, 1H), 2.65 (m, 2H), 2.26-2.09 (m, 2H), 1.80 (m, 2H), 1.32-1.25 (m, 12H), 1.23 (m, 6H), 1.17 (m, 6H), 1.13 (m, 6H). $^{31}$P NMR (162 MHz, Acetonitrile-d3) δ 3.16, 2.95. LCMS: MS m/z=797.41 [M+1]; $t_R$=2.11 min; LC system: Thermo Accela 1250 UHPLC; MS system: Thermo LCQ Fleet; Column: Phenomenex Kinetex 2.6μ XB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μl/min. HPLC: $t_R$=7.23 min (42%), 7.28 min (58%); HPLC system: 1290 Infinity II; Column: Phenomenex 2.6μ C18 100A, 100×4.6 mm; Solvents: Acetonitrile with 0.1% TFA, Water with 0.1% TFA; Gradient: 0 min-8.5 min 2-98% ACN at 1.5 mL/min.

Example 95: (2R,3R,4R,5R)-2-(4-aminopyrrolo[2,1-f][1,2,4]triazin-7-yl)-5-((((4-(tert-butyl)phenoxy)(((S)-1-(3,3-dimethylcyclobutoxy)-1-oxopropan-2-yl)amino)phosphoryl)oxy)methyl)-2-cyanotetrahydrofuran-3,4-diyl dipropionate Example 96: (2R,3R,4R,5R)-2-(4-aminopyrrolo[2,1-f][1,2,4]triazin-7-yl)-5-((((4-(tert-butyl)phenoxy)(((S)-1-(3,3-dimethylcyclobutoxy)-1-oxopropan-2-yl)amino)phosphoryl)oxy)methyl)-2-cyanotetrahydrofuran-3,4-diyl diacetate

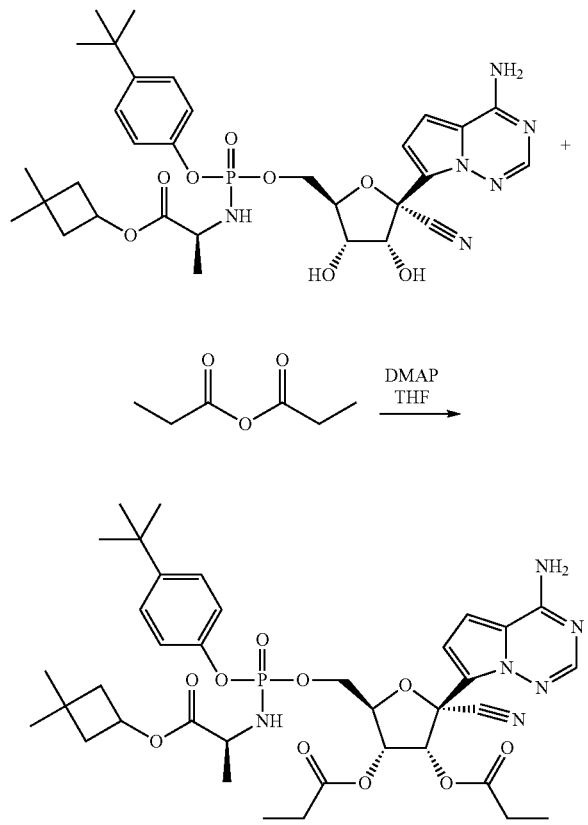

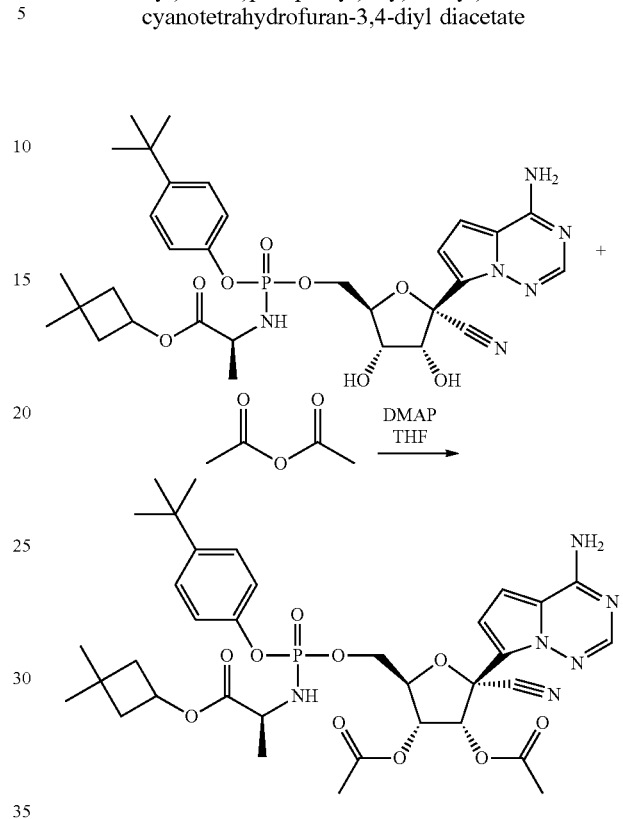

To a solution of Example 93 (50 mg, 0.0761 mmol) and propionic anhydride (0.0486 mL, 0.381 mmol) was added DMAP (1.41 mg, 0.0114 mmol) at rt. After 20 min, the reaction mixture was purified by prep HPLC (0 to 100% ACN in water for 5 min, 100% ACN for 8 min) to give Example 95. Mixture of isomers: $^1$H NMR (400 MHz, Acetonitrile-d3) δ 7.94 (s, 0.6H), 7.93 (s, 0.4H), 7.38-7.29 (m, 2H), 7.06 (m, 2H), 6.88 (m, 1H), 6.80 (m, 1H), 6.42 (s, 2H), 6.17 (d, J=6.1 Hz, 0.4H), 6.11 (d, J=6.0 Hz, 0.6H), 5.53 (m, 1H), 4.92 (m, 1H), 4.62 (m, 1H), 4.44-4.26 (m, 2H), 4.20 (dd, J=11.6, 9.9 Hz, 0.6H), 4.12 (dd, J=11.9, 10.1 Hz, 0.4H), 3.92-3.80 (m, 0.6H), 3.79-3.69 (m, 0.4H), 2.52-2.36 (m, 4H), 2.25-2.08 (m, 2H), 1.80 (m, 2H), 1.33-1.25 (m, 12H), 1.21-1.09 (m, 12H). $^{31}$P NMR (162 MHz, Acetonitrile-d3) δ 3.16, 2.95. LCMS: MS m/z=769.29 [M+1]; $t_R$=2.01 min; LC system: Thermo Accela 1250 UHPLC; MS system: Thermo LCQ Fleet; Column: Phenomenex Kinetex 2.6μ XB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μl/min. HPLC: $t_R$=6.81 min (40%), 6.86 min (60%); HPLC system: 1290 Infinity II; Column: Phenomenex 2.6μ C18 100A, 100×4.6 mm; Solvents: Acetonitrile with 0.1% TFA, Water with 0.1% TFA; Gradient: 0 min-8.5 min 2-98% ACN at 1.5 mL/min.

To a solution of Example 93 (50 mg, 0.0761 mmol) and acetic anhydride (0.0360 mL, 0.381 mmol) was added DMAP (1.41 mg, 0.0114 mmol) at rt. After 20 min, the reaction mixture was purified by prep HPLC (0 to 100% ACN in water for 5 min, 100% ACN for 8 min) to give example 96. Mixture of stereoisomers: $^1$H NMR (400 MHz, Acetonitrile-d3) δ 7.94 (s, 0.6H), 7.93 (s, 0.4H), 7.33 (m 2H), 7.06 (m, 2H), 6.89 (m, 1H), 6.80 (m, 1H), 6.44 (s, 2H), 6.16 (d, J=6.1 Hz, 0.4H), 6.10 (d, J=6.0 Hz, 0.6H), 5.58-5.42 (m, 1H), 4.92 (dt, J=13.3, 7.1 Hz, 1H), 4.67-4.58 (m, 1H), 4.41-4.27 (m, 2H), 4.17 (m, 1H), 3.93-3.70 (m, 1H), 2.18-2.15 (m, 2H), 2.14 (m, 3H), 2.12 (m, 3H), 1.80 (m, 2H), 1.32-1.26 (m, 10.8H), 1.19-1.08 (m, 7.2H). $^{31}$P NMR (162 MHz, Acetonitrile-d3) δ 3.18, 2.95. LCMS: MS m/z=741.27 [M+1]; $t_R$=1.90 min; LC system: Thermo Accela 1250 UHPLC; MS system: Thermo LCQ Fleet; Column: Phenomenex Kinetex 2.6μ XB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μl/min. HPLC: $t_R$=6.37 min (40%), 6.42 min (60%); HPLC system: 1290 Infinity II; Column: Phenomenex 2.6μ C18 100A, 100×4.6 mm; Solvents: Acetonitrile with 0.1% TFA, Water with 0.1% TFA; Gradient: 0 min-8.5 min 2-98% ACN at 1.5 mL/min.

Individual isomers of example 96 were separated by preparatory HPLC (Gemini 5 um NX-C18 110A LC column 100×30 mm, 95% to 0% water acetonitrile gradient).

Peak 1 Example 96a (faster eluting isomer) data: LCMS: MS m/z=741.2 [M+1], $t_R$=1.09 min; $^1$H NMR (400 MHz, Methanol-d4) δ 7.86 (s, 1H), 7.38-7.29 (m, 2H), 7.14-7.06

(m, 2H), 6.92 (s, 2H), 6.28 (d, J=6.0 Hz, 1H), 5.55 (dd, J=6.0, 4.2 Hz, 1H), 4.91 (t, J=7.2 Hz, 1H), 4.65 (dt, J=3.7, 1.8 Hz, 1H), 4.42 (ddd, J=14.7, 5.7, 3.5 Hz, 2H), 3.79 (dd, J=9.2, 7.1 Hz, 1H), 2.23-2.08 (m, 8H), 1.81 (dt, J=13.6, 7.4 Hz, 2H), 1.31 (s, 9H), 1.20 (dd, J=7.1, 1.2 Hz, 3H), 1.12 (d, J=4.1 Hz, 6H). $^{31}$P NMR (162 MHz, Methanol-d4) δ 3.67.

Peak 2 Example 96b (slower eluting isomer) data: LCMS: MS m/z=629.2 [M+1], $t_R$=1.11 min; $^1$H NMR (400 MHz, Methanol-d4) δ 7.88 (s, 1H), 7.33-7.26 (m, 2H), 7.13-7.03 (m, 2H), 6.90 (s, 2H), 6.19 (d, J=6.0 Hz, 1H), 5.55 (dd, J=6.0, 4.3 Hz, 1H), 5.03-4.92 (m, 1H), 4.62 (dd, J=3.8, 1.7 Hz, 1H), 4.39 (ddd, J=15.6, 6.1, 3.9 Hz, 2H), 3.86 (dd, J=9.7, 7.1 Hz, 1H), 2.24-2.11 (m, 8H), 1.89-1.76 (m, 2H), 1.37-1.26 (m, 12H), 1.13 (d, J=4.5 Hz, 6H). $^{31}$P NMR (162 MHz, Methanol-d4) δ 3.72.

Intermediate R1: Spiro[3.4]octan-2-yl L-alaninate hydrochloride

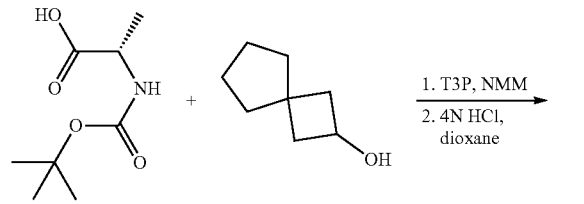

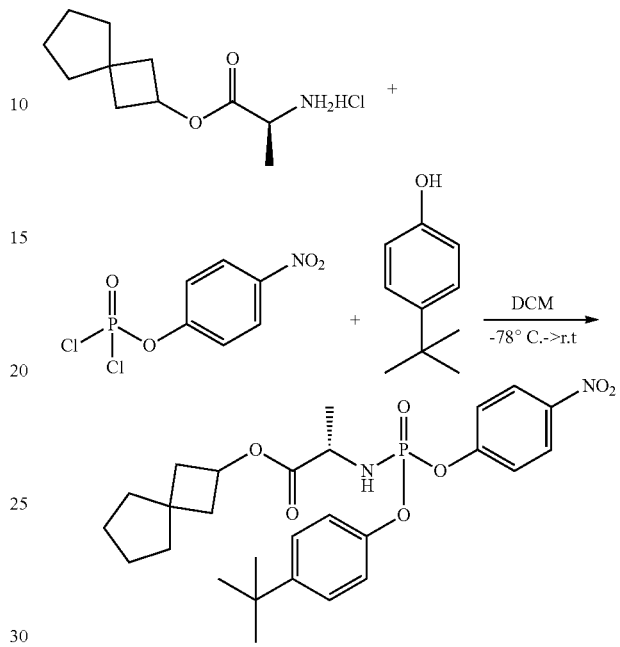

To a stirred solution of acid (825 mg, 4.4 mmol) and alcohol (500 mg, 4 mmol)) in 50 ml of dry dichloromethane were added under argon n-methyl morpholine (1200 mg, 12 mmol), DMAP (100 mg, 0.08 mmol) and tri-propyl phosphonic acid cyclic anhydride (50% in ethyl acetate) (3030 mg, 4.8 mmol) at 0° C. The reaction mixture was then stirred at room temperature for 2 hours. The reaction mixture was washed with water, 2×10% solution of citric acid, 2× with sat. solution of NaHCO₃ and once with brine. Dried over Na2SO4, filtered and concentrated down under reduced pressure. The residue was purified by flash chromatography using hexanes/ethyl acetate as eluents reaching up to 30% ethyl acetate/hexanes. $^1$H NMR (400 MHz, Chloroform-d) δ 5.00 (p, J=7.3 Hz, 2H), 4.25 (q, J=7.3 Hz, 1H), 2.29 (ddt, J=12.0, 7.4, 2.1 Hz, 2H), 1.97 (dddd, J=14.7, 12.4, 6.2, 2.5 Hz, 2H), 1.67-1.49 (m, 8H), 1.44 (s, 9H), 1.37 (d, J=7.2 Hz, 3H). LCMS: MS m/z=298.2 [M+1].

The ester was dissolved 4N HCl/Dioxane and stirred at room temperature for 2 h. Solvents were distilled off and the residue was treated with ether, filtered the precipitate, washed with ether and dried under vacuum to get the Intermediate R1. MS m/z=198.2 [M+1].

Intermediate R2: Spiro[3.4]octan-2-yl ((4-(tert-butyl)phenoxy)(4-nitrophenoxy)phosphoryl)-L-alaninate To a solution of 4-Nitrophenyl dichlorophosphate (1 eq) in DCM (5 mL) the amine hydrochloride (1 eq) was added the reaction mixture was cooled to 0° C. To the cooled solution TEA (1 eq) was added and stirred at 0° C. for 1 h. To the reaction mixture at 0° C., phenol was added followed by TEA (1 eq) and stirred at 0-r.t for 2 h. Reaction mixture was diluted with ether and solids removed by filtration. Filtrate concentrated and product isolated by flash silica gel column chromatography using hexanes/ethyl acetate as eluents reaching up to 30% ethyl acetate/hexanes. $^1$H NMR (400 MHz, Chloroform-d) δ 8.27-8.19 (m, 2H), 7.44-7.31 (m, 4H), 7.14 (ddt, J=8.7, 7.3, 1.7 Hz, 2H), 4.96 (pd, J=7.3, 1.8 Hz, 1H), 4.20-4.02 (m, 1H), 3.82 (t, J=10.3 Hz, 1H), 2.27 (ddq, J=10.6, 4.9, 1.8 Hz, 2H), 1.91 (ddt, J=9.4, 7.3, 4.7 Hz, 2H), 1.71-1.48 (m, 8H), 1.41 (dd, J=7.0, 2.3 Hz, 3H), 1.30 (d, J=0.8 Hz, 9H). $^{31}$P NMR (162 MHz, methanol-d₄) δ 2.89; LCMS: MS m/z=531.2 [M+1].

Intermediate R3: Spiro[3.4]octan-2-yl ((((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methoxy)(4-(tert-butyl)phenoxy)phosphoryl)-L-alaninate

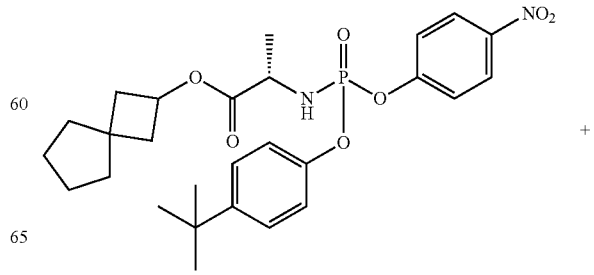

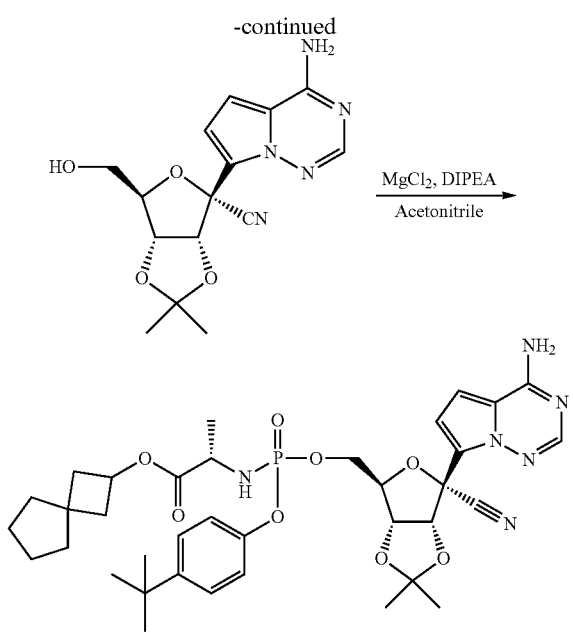

Intermediate R3 was made in a similar manner as intermediate A2 except that intermediate R² (290 mg, 0.55 mmol) was used instead of intermediate A1. Intermediate R3 was isolated after column chromatography eluting with ethyl acetate/hexane (0-100%). LCMS: MS m/z=723.4 [M+1].

Example 97: Spiro[3.4]octan-2-yl ((((2R,3S,4R,5R)-5-(4-aminopyrrolo[2,1-f][1,2,4]triazin-7-yl)-5-cyano-3,4-dihydroxytetrahydrofuran-2-yl)methoxy)(4-(tert-butyl)phenoxy)phosphoryl)-L-alaninate

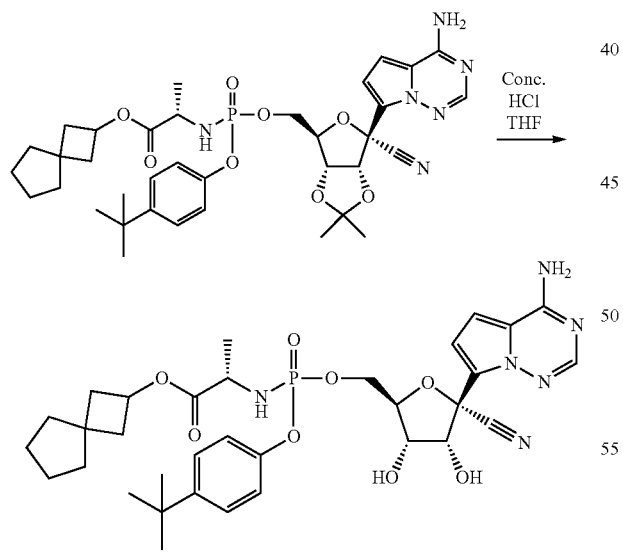

To a solution of spiro[3.4]octan-2-yl ((((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methoxy)(4-(tert-butyl)phenoxy)phosphoryl)-L-alaninate (300 mg, 0.42 mmol) in THF (5 mL) concentrated hydrochloric acid (0.400 mL, 4.2 mmol) was added and stirred at room temperature for 2 h. After 2 h, the reaction was diluted with ethyl acetate and neutralized with a saturated aqueous solution of sodium bicarbonate. The layers were separated, and the organics were washed with water, saturated aqueous sodium chloride, dried over sodium sulfate, filtered and concentrated. The product was purified by flash chromatography to afford the title compound as 1:1 mixture of diastereomers. The material was further purified by preparatory HPLC (Gemini 5 um NX-C18 110A LC column 100×30 mm, 95% to 0% water acetonitrile gradient) to separate the individual isomers.

First eluent Example 97a: $^1$H NMR (400 MHz, Methanol-d4) δ 7.87 (s, 1H), 7.35-7.27 (m, 2H), 7.11-7.01 (m, 2H), 6.99-6.88 (m, 2H), 4.80 (d, J=5.4 Hz, 1H), 4.53-4.26 (m, 3H), 4.18 (t, J=5.5 Hz, 1H), 3.93-3.74 (m, 1H), 2.32-2.18 (m, 2H), 1.94 (ddd, J=12.2, 8.9, 5.5 Hz, 2H), 1.68-1.49 (m, 8H), 1.29 (s, 9H), 1.25 (dd, J=7.2, 1.2 Hz, 3H). $^{31}$P NMR (162 MHz, methanol-d$_4$) δ 3.85; LCMS: MS m/z=683.3 [M+1].

Second eluent Example 97b: $^1$H NMR (400 MHz, Methanol-d4) δ 7.89 (s, 1H), 7.38-7.28 (m, 2H), 7.17-7.07 (m, 2H), 7.01-6.88 (m, 2H), 4.81 (d, J=5.4 Hz, 1H), 4.49-4.35 (m, 2H), 4.29 (ddd, J=10.4, 5.9, 4.2 Hz, 1H), 4.18 (t, J=5.6 Hz, 1H), 3.85 (dq, J=9.8, 7.1 Hz, 1H), 2.33-2.16 (m, 2H), 1.91 (ddd, J=12.1, 7.1, 4.3 Hz, 2H), 1.66-1.49 (m, 8H), 1.37-1.25 (m, 12H); $^{31}$P NMR (162 MHz, methanol-d$_4$) δ 3.80; LCMS: MS m/z=683.3 [M+1].

Example 98: (2R,3R,4R,5R)-2-(4-aminopyrrolo[2,1-f][1,2,4]triazin-7-yl)-5-(((((4-(tert-butyl)phenoxy)(((S)-1-oxo-1-(spiro[3.4]octan-2-yloxy)propan-2-yl)amino)phosphoryl)oxy)methyl)-2-cyanotetrahydrofuran-3,4-diyl diacetate

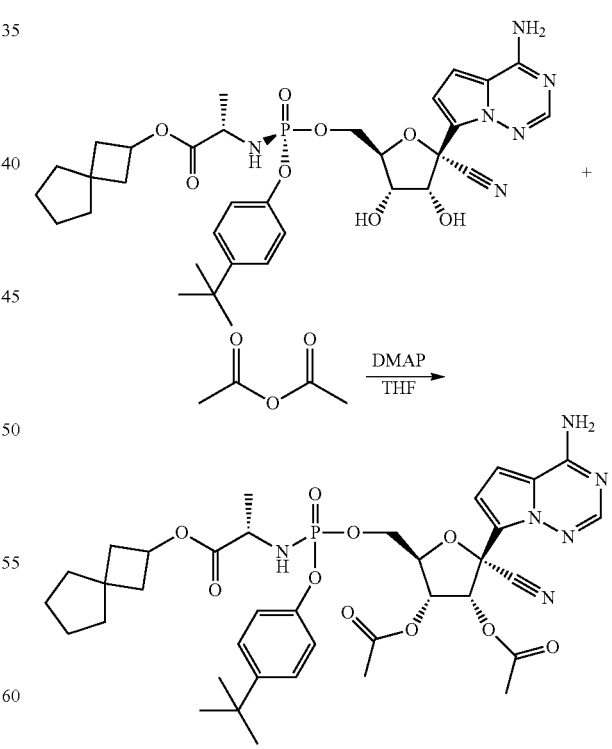

To a mixture of spiro[3.4]octan-2-yl ((((2R,3S,4R,5R)-5-(4-aminopyrrolo[2,1-f][1,2,4]triazin-7-yl)-5-cyano-3,4-dihydroxytetrahydrofuran-2-yl)methoxy)(4-(tert-butyl)phenoxy)phosphoryl)-L-alaninate (15 mg, 0.022 mmol) and 4-(dimethylamino)pyridine (2.7 mg, 0.022 mmol) in tetrahydrofuran (1 mL) was added acetic anhydride (7 mg, 0.044 mmol) at RT. After 30 min, the reaction mixture was quenched with few drops off water. The material was purified by preparatory HPLC (Gemini 5 um NX-C18 110A LC column 100×30 mm, 95% to 0% water acetonitrile gradient) to afford the product as individual isomers.

First eluent Example 98a: $^1$H NMR (400 MHz, Methanol-d4) δ 7.86 (s, 1H), 7.39-7.28 (m, 2H), 7.15-7.04 (m, 2H), 6.92 (s, 2H), 6.28 (d, J=5.9 Hz, 1H), 5.55 (dd, J=6.0, 4.2 Hz, 1H), 4.74-4.58 (m, 1H), 4.42 (qdd, J=11.6, 5.8, 3.6 Hz, 2H), 3.78 (dq, J=9.3, 7.1 Hz, 1H), 2.30-2.19 (m, 2H), 2.15 (d, J=12.5 Hz, 6H), 1.92 (ddt, J=10.5, 6.2, 3.4 Hz, 2H), 1.65-1.50 (m, 8H), 1.31 (s, 9H), 1.19 (dd, J=7.2, 1.2 Hz, 3H); $^{31}$P NMR (162 MHz, methanol-d$_4$) δ 3.72; LCMS: MS m/z=767.4 [M+1].

Second eluent Example 98b: $^1$H NMR (400 MHz, Methanol-d4) δ 7.88 (s, 1H), 7.35-7.26 (m, 2H), 7.14-7.03 (m, 2H), 6.90 (s, 2H), 6.19 (d, J=5.9 Hz, 1H), 5.62-5.47 (m, 1H), 5.01-4.89 (m, 1H), 4.62 (qd, J=4.1, 1.7 Hz, 1H), 4.52-4.27 (m, 3H), 3.86 (dq, J=9.7, 7.0 Hz, 1H), 2.35-2.21 (m, 2H), 2.15 (d, J=14.1 Hz, 6H), 2.03-1.88 (m, 3H), 1.67-1.47 (m, 8H), 1.36-1.24 (m, 12H). $^{31}$P NMR (162 MHz, methanol-d$_4$) δ 3.68; LCMS: MS m/z=767.4 [M+1].

Example 99: (2R,3R,4R,5R)-2-(4-aminopyrrolo[2,1-f][1,2,4]triazin-7-yl)-5-(((((4-(tert-butyl)phenoxy)(((S)-1-oxo-1-(spiro[3.4]octan-2-yloxy)propan-2-yl)amino)phosphoryl)oxy)methyl)-2-cyanotetrahydrofuran-3,4-diyl dipropionate noxy)phosphoryl)-L-alaninate (15 mg, 0.022 mmol) and 4-(dimethylamino)pyridine (2.7 mg, 0.022 mmol) in tetrahydrofuran (1 mL) was added propionic anhydride (7 mg, 0.044 mmol) at RT. After 30 min, the reaction mixture was quenched with few drops off water. The mixture was purified by preparatory HPLC (Gemini 5 um NX-C18 110A LC column 100×30 mm, 95% to 0% water acetonitrile gradient) to afford the as individual isomers.

First eluent Example 99a: $^1$H NMR (400 MHz, Methanol-d4) δ 7.86 (s, 1H), 7.41-7.28 (m, 2H), 7.16-7.06 (m, 2H), 6.97-6.88 (m, 2H), 6.29 (d, J=6.0 Hz, 1H), 5.57 (dd, J=6.0, 4.1 Hz, 1H), 4.65 (qd, J=3.6, 2.0 Hz, 1H), 4.42 (qdd, J=11.5, 5.8, 3.6 Hz, 2H), 3.79 (dq, J=9.2, 7.1 Hz, 1H), 2.55-2.35 (m, 4H), 2.31-2.17 (m, 2H), 1.92 (tt, J=10.9, 3.7 Hz, 2H), 1.68-1.44 (m, 9H), 1.31 (s, 10H), 1.25-1.10 (m, 10H). $^{31}$P NMR (162 MHz, methanol-d$_4$) δ 3.73; LCMS: MS m/z=795.4 [M+1].

Second eluent Example 99b: $^1$H NMR (400 MHz, Methanol-d4) δ 7.87 (s, 1H), 7.35-7.25 (m, 2H), 7.13-7.02 (m, 2H), 6.97-6.85 (m, 2H), 6.19 (d, J=5.9 Hz, 1H), 5.57 (dd, J=5.9, 4.1 Hz, 1H), 4.94 (q, J=7.3 Hz, 1H), 4.62 (qd, J=4.0, 1.7 Hz, 1H), 4.39 (qdd, J=11.5, 6.1, 3.8 Hz, 2H), 3.86 (dq, J=9.8, 7.1 Hz, 1H), 2.59-2.35 (m, 4H), 2.33-2.18 (m, 2H), 1.94 (dddd, J=12.3, 6.1, 4.5, 1.8 Hz, 2H), 1.70-1.46 (m, 8H), 1.36-1.25 (m, 12H), 1.18 (dt, J=18.9, 7.5 Hz, 6H). $^{31}$P NMR (162 MHz, methanol-d$_4$) δ 3.70; LCMS: MS m/z=795.4 [M+1].

Example 100: (2R,3R,4R,5R)-2-(4-aminopyrrolo[2,1-f][1,2,4]triazin-7-yl)-5-((((4-(tert-butyl)phenoxy)(((S)-1-oxo-1-(spiro[3.4]octan-2-yloxy)propan-2-yl)amino)phosphoryl)oxy)methyl)-2-cyanotetrahydrofuran-3,4-diyl bis(2-methylpropanoate)

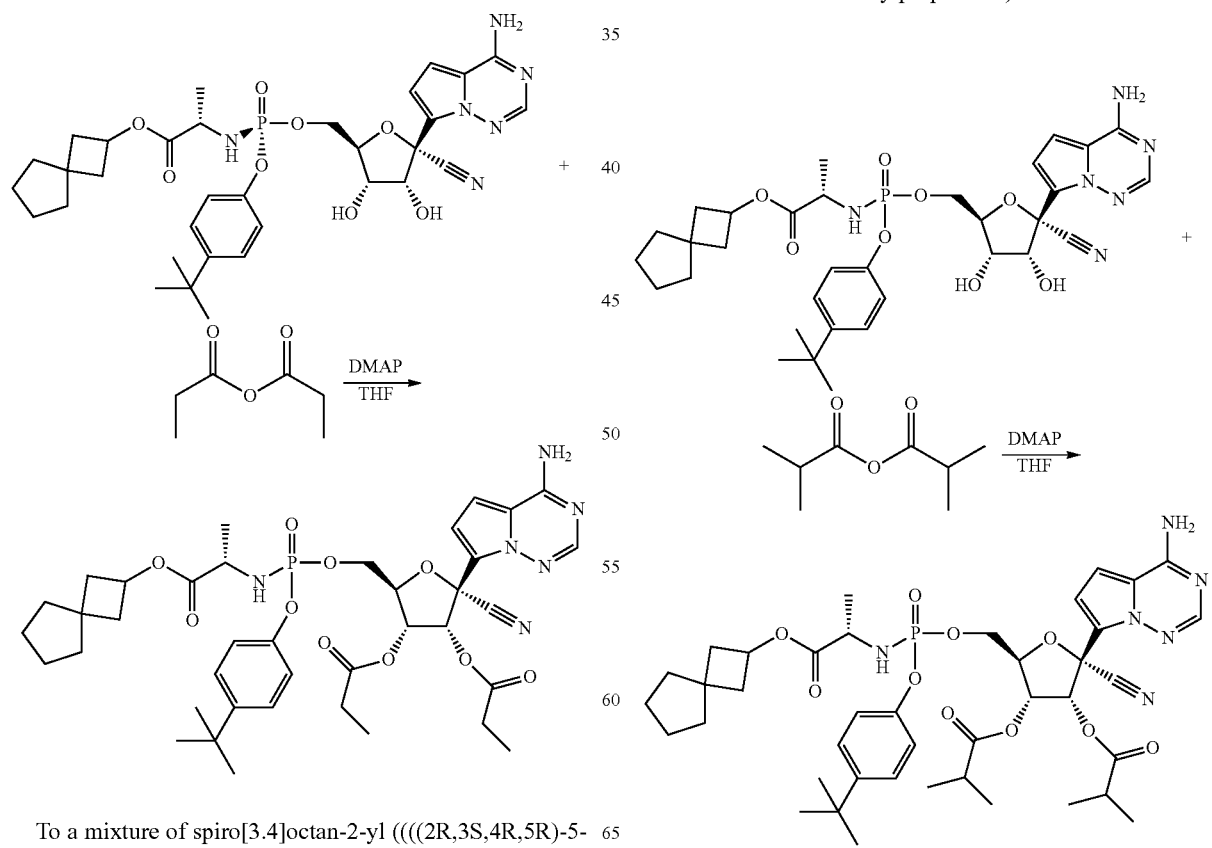

To a mixture of spiro[3.4]octan-2-yl (((((2R,3S,4R,5R)-5-(4-aminopyrrolo[2,1-f][1,2,4]triazin-7-yl)-5-cyano-3,4-dihydroxytetrahydrofuran-2-yl)methoxy)(4-(tert-butyl)phe- To a mixture of spiro[3.4]octan-2-yl ((((2R,3S,4R,5R)-5-(4-aminopyrrolo[2,1-f][1,2,4]triazin-7-yl)-5-cyano-3,4-dihydroxytetrahydrofuran-2-yl)methoxy)(4-(tert-butyl)phenoxy)phosphoryl)-L-alaninate (15 mg, 0.022 mmol) and 4-(dimethylamino)pyridine (2.7 mg, 0.022 mmol) in tetrahydrofuran (1 mL) was added isobutyric anhydride (7 mg, 0.044 mmol) at RT. After 30 min, the reaction mixture was quenched with few drops off water. The mixture was purified by preparatory HPLC (Gemini 5 um NX-C18 110A LC column 100×30 mm, 95% to 0% water acetonitrile gradient) to afford the product as individual isomers.

First eluent Example 100a: $^1$H NMR (400 MHz, Methanol-d4) δ 7.87 (s, 1H), 7.38-7.24 (m, 2H), 7.14-7.04 (m, 2H), 6.95-6.84 (m, 2H), 6.28 (d, J=5.9 Hz, 1H), 5.56 (dd, J=5.9, 3.8 Hz, 1H), 4.68-4.57 (m, 1H), 4.50-4.35 (m, 2H), 3.79 (dq, J=9.2, 7.1 Hz, 1H), 2.66 (dp, J=22.8, 7.0 Hz, 2H), 2.30-2.17 (m, 2H), 1.98-1.87 (m, 2H), 1.64-1.50 (m, 8H), 1.33-1.11 (m, 24H); $^{31}$P NMR (162 MHz, methanol-d$_4$) δ 3.73; LCMS: MS m/z=823.4 [M+1].

Second eluent Example 100b: $^1$H NMR (400 MHz, Methanol-d4) δ 7.87 (d, J=2.6 Hz, 1H), 7.37-7.24 (m, 2H), 7.08 (ddd, J=8.9, 7.8, 1.3 Hz, 2H), 6.99-6.82 (m, 2H), 6.16 (d, J=5.9 Hz, 1H), 5.56 (dd, J=5.9, 3.8 Hz, 1H), 4.95 (q, J=7.3 Hz, 1H), 4.61 (dd, J=3.9, 1.8 Hz, 1H), 4.51-4.30 (m, 2H), 3.87 (dt, J=9.8, 7.1 Hz, 1H), 2.66 (ddt, J=24.3, 14.0, 7.0 Hz, 2H), 2.35-2.17 (m, 2H), 2.07-1.88 (m, 2H), 1.70-1.48 (m, 8H), 1.33-1.23 (m, 18H), 1.19 (d, J=7.0 Hz, 6H). $^{31}$P NMR (162 MHz, methanol-d$_4$) δ 3.73; LCMS: MS m/z=823.4 [M+1].

Intermediate R4: Cyclopropylmethyl L-alaninate hydrochloride

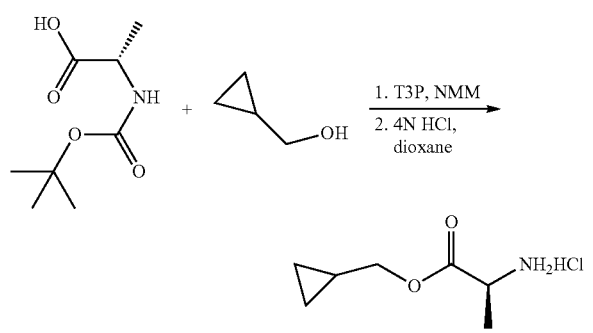

To a stirred solution of acid (825 mg, 4.4 mmol) and alcohol (500 mg, 4 mmol)) in 50 ml of dry dichloromethane were added under argon n-methyl morpholine (1200 mg, 12 mmol), DMAP (100 mg, 0.08 mmol) and tri-propyl phosphonic acid cyclic anhydride (50% in ethyl acetate) (3030 mg, 4.8 mmol) at 0° C. The reaction mixture was then stirred at room temperature for 2 hours. The reaction mixture was washed with water, 2×10% solution of citric acid, 2× with sat. solution of NaHCO$_3$ and once with brine. Dried over Na2SO4, filtered and concentrated down under reduced pressure. The residue was purified by flash chromatography using hexanes/ethyl acetate as eluents reaching up to 30% ethyl acetate/hexanes. $^1$H NMR (400 MHz, Chloroform-d) δ 5.00 (p, J=7.3 Hz, 2H), 4.25 (q, J=7.3 Hz, 1H), 2.29 (ddt, J=12.0, 7.4, 2.1 Hz, 2H), 1.97 (dddd, J=14.7, 12.4, 6.2, 2.5 Hz, 2H), 1.67-1.49 (m, 8H), 1.44 (s, 9H), 1.37 (d, J=7.2 Hz, 3H). LCMS: MS m/z=298.2 [M+1].

The ester was dissolved 4N HCl/Dioxane and stirred at room temperature for 2 h. Solvents were distilled off and the residue was treated with ether, filtered the precipitate, washed with ether and dried under vacuum to get the Intermediate R1. MS m/z=198.2 [M+1].

Intermediate R5: Cyclopropylmethyl ((4-(tert-butyl)phenoxy)(4-nitrophenoxy)phosphoryl)-L-alaninate

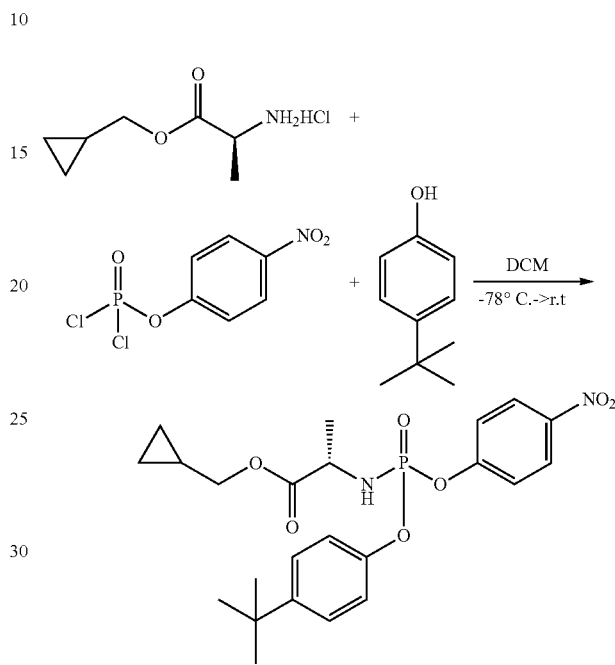

To a solution of 4-Nitrophenyl dichlorophosphate (1 eq) in DCM (5 mL) the amine hydrochloride (1 eq) was added the reaction mixture was cooled to 0° C. To the cooled solution TEA (1 eq) was added and stirred at 0° C. for 1 h. To the reaction mixture at 0° C., phenol was added followed by TEA (1 eq) and stirred at 0-r.t for 2 h. Reaction mixture was diluted with ether and solids removed by filtration. Filtrate concentrated and product isolated by flash silica gel column chromatography using hexanes/ethyl acetate as eluents reaching up to 30% ethyl acetate/hexanes. LCMS: MS m/z=477.2[M+1].

Intermediate R6: Cyclopropylmethyl ((((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methoxy)(4-(tert-butyl)phenoxy)phosphoryl)-L-alaninate

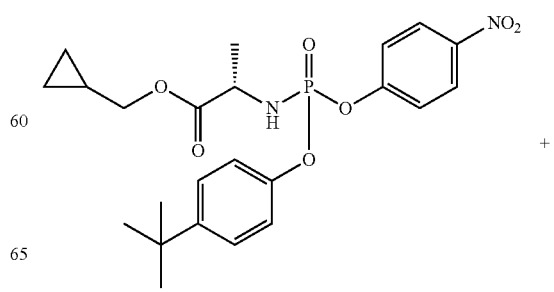

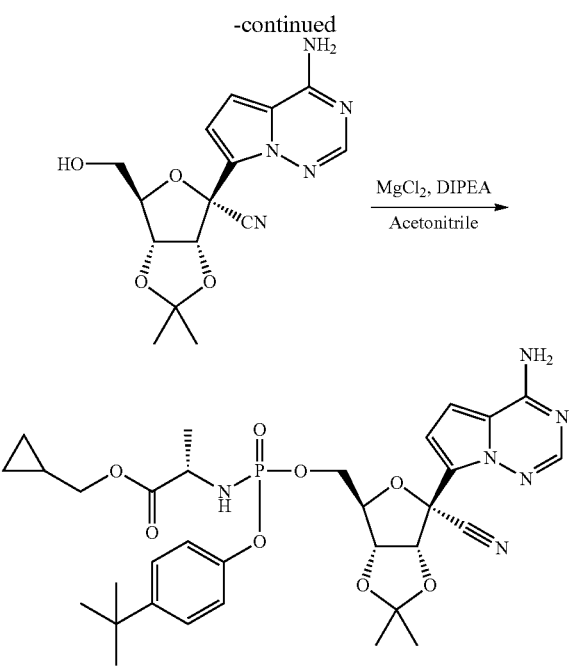

Intermediate R6 was made in a similar manner as intermediate A2 except that intermediate R5 (180 mg, 0.4 mmol) was used instead of intermediate A1. Intermediate R6 was isolated after column chromatography eluting with ethyl acetate/hexane (0-100%). LCMS: MS m/z=669.3 [M+1].

Example 101: Cyclopropyl methyl (((((2R,3S,4R,5R)-5-(4-aminopyrrolo[2,1-f][1,2,4]triazin-7-yl)-5-cyano-3,4-dihydroxytetrahydrofuran-2-yl)methoxy)(4-(tert-butyl)phenoxy)phosphoryl)-L-alaninate mmol) in THF (5 mL) concentrated hydrochloric acid (11.7 M, 0.400 mL, 4.2 mmol) was added and stirred at room temperature for 2 h. After 2 h, the reaction was diluted with ethyl acetate and neutralized with a saturated aqueous solution of sodium bicarbonate. The layers were separated, and the organics were washed with water, saturated aqueous sodium chloride, dried over sodium sulfate, filtered and concentrated. The product was purified by flash chromatography to afford the title compound as 1:1 mixture of diastereomers. A small amount of the compound was further purified by preparatory HPLC (Gemini Sum NX-C18 110A LC column 100×30 mm, 95% to 0% water acetonitrile gradient) to afford the product as individual isomers.

First eluent Example 101a: $^1$H NMR (400 MHz, Methanol-d4) δ 7.87 (s, 1H), 7.34-7.24 (m, 2H), 7.10-7.00 (m, 2H), 6.93 (d, J=1.1 Hz, 2H), 4.80 (d, J=5.5 Hz, 1H), 4.53-4.25 (m, 3H), 4.19 (t, J=5.5 Hz, 1H), 4.00-3.78 (m, 3H), 1.34-1.25 (m, 13H), 1.20-1.03 (m, 1H), 0.62-0.47 (m, 2H), 0.27 (dt, J=6.1, 4.5 Hz, 2H); $^{31}$P NMR (162 MHz, methanol-d$_4$) δ 3.91; LCMS: MS m/z=629.20 [M+1].

Second eluent Example 101b: $^1$H NMR (400 MHz, Methanol-d4) δ 7.89 (s, 1H), 7.35-7.29 (m, 2H), 7.14-7.08 (m, 2H), 6.96 (d, J=4.6 Hz, 1H), 6.91 (d, J=4.6 Hz, 1H), 4.86-4.78 (m, 1H), 4.48-4.35 (m, 2H), 4.35-4.24 (m, 1H), 4.20 (t, J=5.5 Hz, 1H), 3.97-3.80 (m, 4H), 1.30 (s, 12H), 1.19-0.99 (m, 1H), 0.60-0.47 (m, 2H), 0.25 (dt, J=5.7, 4.4 Hz, 2H). $^{31}$P NMR (162 MHz, methanol-d$_4$) δ 3.81; LCMS: MS m/z=629.20 [M+1].

Example 102: (2R,3R,4R,5R)-2-(4-aminopyrrolo[2,1-f][1,2,4]triazin-7-yl)-5-(((((4-(tert-butyl)phenoxy)(((S)-1-(cyclopropylmethoxy)-1-oxopropan-2-yl)amino)phosphoryl)oxy)methyl)-2-cyanotetrahydrofuran-3,4-diyl diacetate

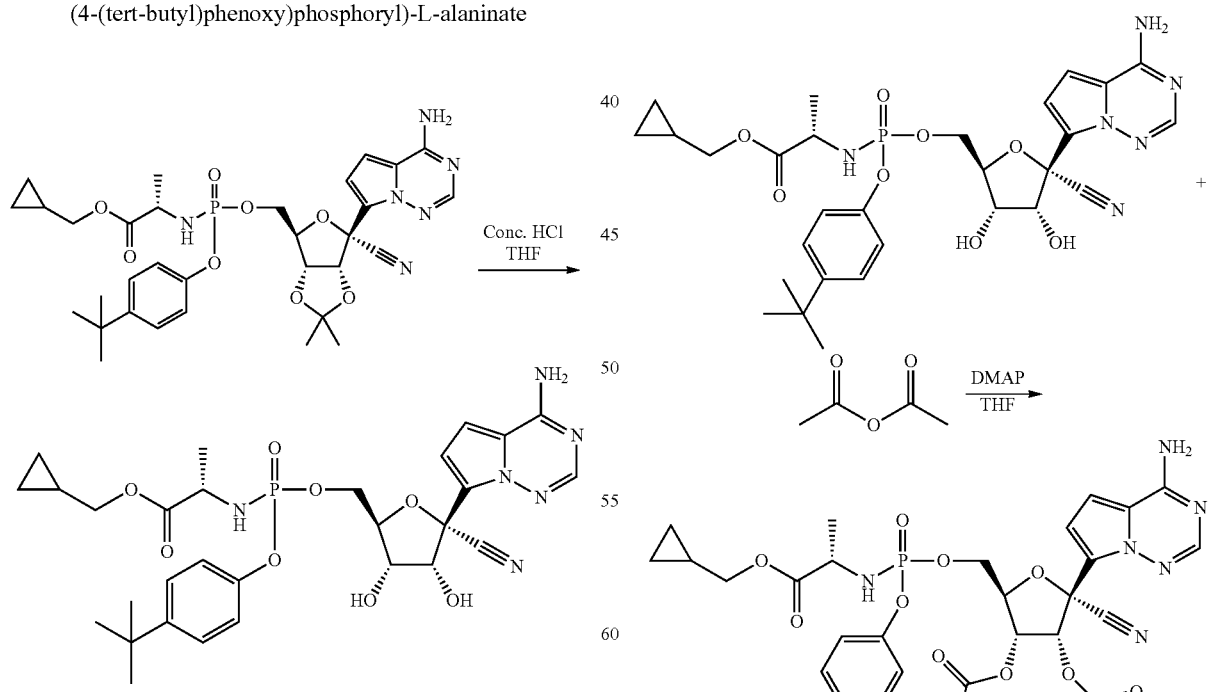

To a solution of cyclopropylmethyl (((((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methoxy)(4-(tert-butyl)phenoxy)phosphoryl)-L-alaninate (200 mg, 0.3

To a mixture of cyclopropylmethyl ((((2R,3S,4R,5R)-5-(4-aminopyrrolo[2,1-f][1,2,4]triazin-7-yl)-5-cyano-3,4-dihydroxytetrahydrofuran-2-yl)methoxy)(4-(tert-butyl)phenoxy)phosphoryl)-L-alaninate (15 mg, 0.022 mmol) and 4-(dimethylamino)pyridine (2.7 mg, 0.022 mmol) in tetrahydrofuran (1 mL) was added acetic anhydride (7 mg, 0.044 mmol) at RT. After 30 min, the reaction mixture was quenched with few drops off water. The crude residue was purified by preparatory HPLC (Gemini Sum NX-C18 110A LC column 100×30 mm, 95% to 0% water acetonitrile gradient) to afford the product as singe isomers.

First eluent Example 102a: $^1$H NMR (400 MHz, Methanol-d4) δ 7.86 (s, 1H), 7.41-7.27 (m, 2H), 7.09 (dd, J=8.8, 1.4 Hz, 2H), 6.91 (s, 2H), 6.28 (d, J=6.0 Hz, 1H), 5.55 (dd, J=6.0, 4.3 Hz, 1H), 4.64 (dt, J=5.7, 2.8 Hz, 1H), 4.50-4.33 (m, 2H), 4.00-3.71 (m, 4H), 2.15 (d, J=11.4 Hz, 7H), 1.30 (s, 11H), 1.20 (dd, J=7.2, 1.2 Hz, 3H), 1.15-0.99 (m, 1H), 0.58-0.45 (m, 2H), 0.25 (dt, J=6.0, 4.4 Hz, 2H); $^{31}$P NMR (162 MHz, methanol-d4) δ 3.73; LCMS: MS m/z=713.30 [M+1].

Second eluent Example 102b: $^1$H NMR (400 MHz, Methanol-d4) δ 7.87 (d, J=6.6 Hz, 1H), 7.40-7.23 (m, 2H), 7.08 (td, J=9.4, 8.8, 1.3 Hz, 2H), 6.91 (d, J=7.2 Hz, 2H), 6.24 (dd, J=36.7, 6.0 Hz, 1H), 5.55 (ddd, J=6.1, 4.3, 2.0 Hz, 1H), 4.70-4.57 (m, 1H), 4.40 (ddtd, J=17.5, 11.5, 6.1, 3.7 Hz, 2H), 3.99-3.75 (m, 3H), 2.15 (d, J=14.2 Hz, 6H), 1.30 (d, J=7.0 Hz, 12H), 1.10 (ddd, J=7.8, 4.4, 3.0 Hz, 1H), 0.53 (dtd, J=6.8, 5.5, 3.4 Hz, 2H), 0.26 (ddd, J=6.1, 5.0, 2.7 Hz, 2H). $^{31}$P NMR (162 MHz, methanol-d$_4$) δ 3.70; LCMS: MS m/z=713.30 [M+1].

Example 103: (2R,3R,4R,5R)-2-(4-aminopyrrolo[2,1-f][1,2,4]triazin-7-yl)-5-((((4-(tert-butyl)phenoxy)(((S)-1-(cyclopropylmethoxy)-1-oxopropan-2-yl)amino)phosphoryl)oxy)methyl)-2-cyanotetrahydrofuran-3,4-diyl dipropionate

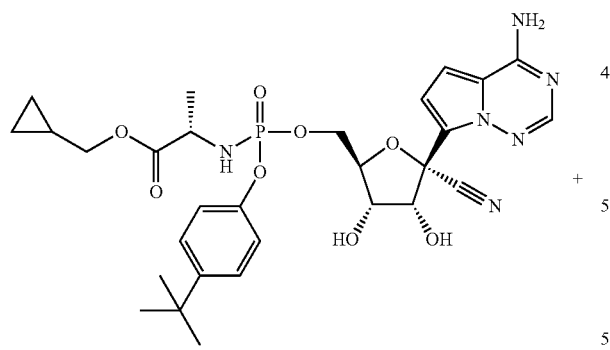

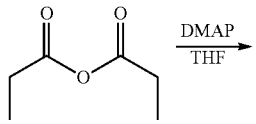

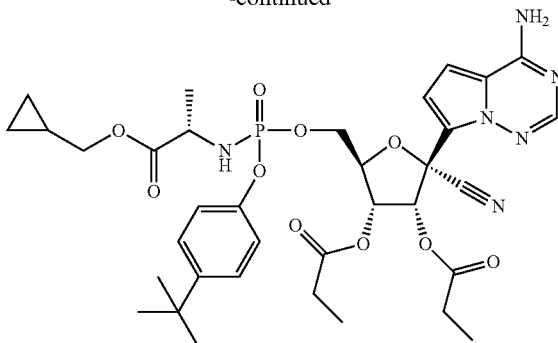

To a mixture of cyclopropylmethyl ((((2R,3S,4R,5R)-5-(4-aminopyrrolo[2,1-f][1,2,4]triazin-7-yl)-5-cyano-3,4-dihydroxytetrahydrofuran-2-yl)methoxy)(4-(tert-butyl)phenoxy)phosphoryl)-L-alaninate (15 mg, 0.022 mmol) and 4-(dimethylamino)pyridine (2.7 mg, 0.022 mmol) in tetrahydrofuran (1 mL) was added propionic anhydride (7 mg, 0.044 mmol) at RT. After 30 min, the reaction mixture was quenched with few drops off water. The crude residue was purified by preparatory HPLC (Gemini Sum NX-C18 110A LC column 100×30 mm, 95% to 0% water acetonitrile gradient) to afford the product as individual isomers.

First eluent Example 103a: $^1$H NMR (400 MHz, Methanol-d4) δ 7.87 (d, J=3.9 Hz, 1H), 7.35-7.23 (m, 2H), 7.14-7.02 (m, 2H), 6.97-6.85 (m, 2H), 6.19 (d, J=6.0 Hz, 1H), 5.57 (dd, J=5.9, 4.1 Hz, 1H), 4.62 (qd, J=3.9, 1.7 Hz, 1H), 4.40 (dddd, J=17.4, 11.5, 6.1, 3.8 Hz, 2H), 4.03-3.76 (m, 3H), 2.55-2.35 (m, 4H), 1.34-1.26 (m, 12H), 1.18 (dt, J=18.3, 7.5 Hz, 6H), 1.12-1.06 (m, OH), 0.57-0.50 (m, 2H), 0.26 (t, J=5.3 Hz, 2H); $^{31}$P NMR (162 MHz, methanol-d$_4$) δ 3.75; LCMS: MS m/z=755.20 [M+1].

Second eluent Example 103b: $^1$H NMR (400 MHz, Methanol-d4) δ 7.87 (d, J=3.9 Hz, 1H), 7.35-7.23 (m, 2H), 7.14-7.02 (m, 2H), 6.97-6.85 (m, 2H), 6.19 (d, J=6.0 Hz, 1H), 5.57 (dd, J=5.9, 4.1 Hz, 1H), 4.62 (qd, J=3.9, 1.7 Hz, 1H), 4.40 (dddd, J=17.4, 11.5, 6.1, 3.8 Hz, 2H), 4.03-3.76 (m, 3H), 2.55-2.35 (m, 4H), 1.34-1.26 (m, 12H), 1.18 (dt, J=18.3, 7.5 Hz, 6H), 1.12-1.06 (m, OH), 0.57-0.50 (m, 2H), 0.26 (t, J=5.3 Hz, 2H). $^{31}$P NMR (162 MHz, methanol-d$_4$) δ 3.68; LCMS: MS m/z=755.20 [M+1].

Example 104: (2R,3R,4R,5R)-2-(4-aminopyrrolo[2,1-f][1,2,4]triazin-7-yl)-5-((((4-(tert-butyl)phenoxy)(((S)-1-(cyclopropylmethoxy)-1-oxopropan-2-yl)amino)phosphoryl)oxy)methyl)-2-cyanotetrahydrofuran-3,4-diyl bis(2-methylpropanoate)

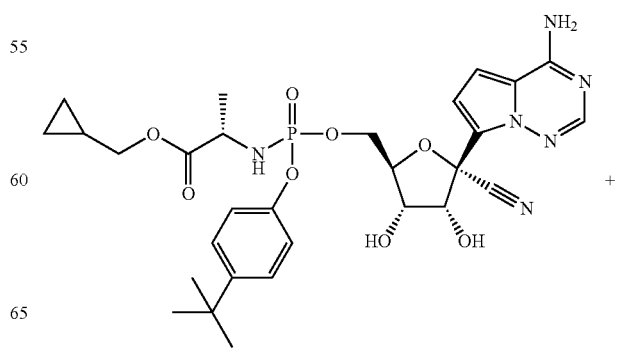

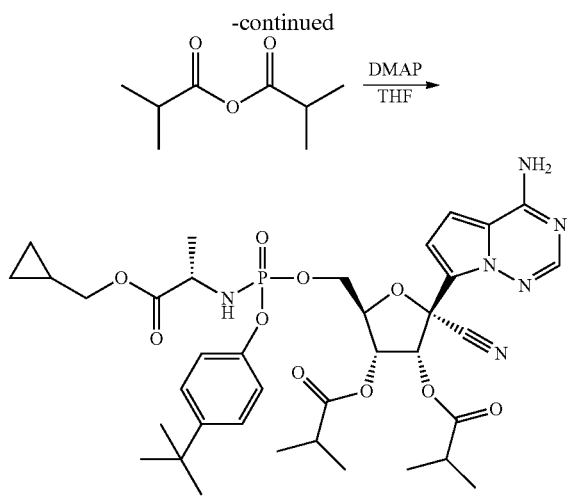 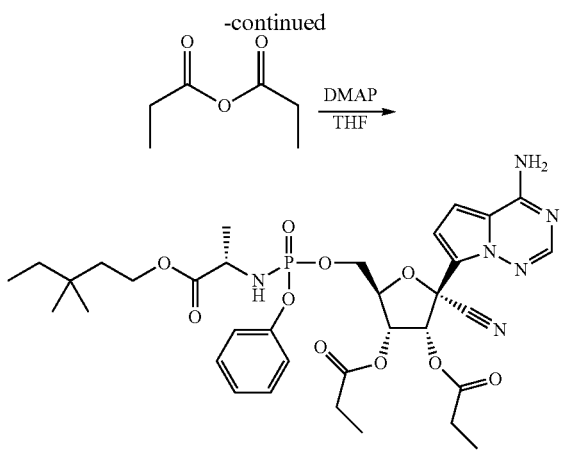

To a mixture of cyclopropylmethyl ((((2R,3S,4R,5R)-5-(4-aminopyrrolo[2,1-f][1,2,4]triazin-7-yl)-5-cyano-3,4-dihydroxytetrahydrofuran-2-yl)methoxy)(4-(tert-butyl)phenoxy)phosphoryl)-L-alaninate (15 mg, 0.022 mmol) and 4-(dimethylamino)pyridine (2.7 mg, 0.022 mmol) in tetrahydrofuran (1 mL) was added isobutyric anhydride (7 mg, 0.044 mmol) at RT. After 30 min, the reaction mixture was quenched with few drops off water. The crude residue was purified by preparatory HPLC (Gemini 5 um NX-C18 110A LC column 100×30 mm, 95% to 0% water acetonitrile gradient) to afford the product as separate isomers.

First eluent Example 104a: $^1$H NMR (400 MHz, Methanol-d4) δ 7.87 (s, 1H), 7.38-7.29 (m, 2H), 7.14-7.04 (m, 2H), 6.96-6.83 (m, 2H), 6.28 (d, J=5.9 Hz, 1H), 5.56 (dd, J=6.0, 3.8 Hz, 1H), 4.68-4.56 (m, 1H), 4.43 (qdd, J=11.5, 5.6, 3.5 Hz, 2H), 4.01-3.73 (m, 4H), 2.65 (dp, J=21.1, 7.0 Hz, 2H), 1.30 (s, 9H), 1.29-1.17 (m, 19H), 1.10 (ddd, J=7.7, 4.7, 3.0 Hz, 1H), 0.60-0.45 (m, 2H), 0.26 (dt, J=5.9, 4.4 Hz, 2H). $^{31}$P NMR (162 MHz, methanol-d$_4$) δ 3.68; LCMS: MS m/z=769.3 [M+1].

Second eluent Example 104b: $^1$H NMR (400 MHz, Methanol-d4) δ 7.87 (d, J=2.4 Hz, 1H), 7.40-7.21 (m, 2H), 7.09 (td, J=9.2, 1.3 Hz, 2H), 6.96-6.80 (m, 2H), 6.22 (dd, J=46.0, 6.0 Hz, 1H), 5.56 (dt, J=5.9, 3.6 Hz, 1H), 4.62 (dqd, J=7.5, 3.9, 2.1 Hz, 1H), 4.40 (qdd, J=11.4, 6.0, 3.8 Hz, 2H), 4.02-3.79 (m, 3H), 2.82-2.53 (m, 2H), 1.34-1.21 (m, 19H), 1.19 (d, J=7.0 Hz, 7H), 1.10 (td, J=7.8, 3.8 Hz, 1H), 0.63-0.46 (m, 2H), 0.38-0.19 (m, 2H). $^{31}$P NMR (162 MHz, methanol-d$_4$) δ 3.67; LCMS: MS m/z=769.3 [M+1].

Example 105: (2R,3R,4R,5R)-2-(4-aminopyrrolo[2,1-f][1,2,4]triazin-7-yl)-2-cyano-5-(((((S)-1-((3,3-dimethylpentyl)oxy)-1-oxopropan-2-yl)amino)(phenoxy)phosphoryl)oxy)methyl)tetrahydrofuran-3,4-diyl dipropionate To a mixture of 3,3-dimethylpentyl ((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)-L-alaninate, Intermediate S4 (15 mg, 0.022 mmol) and 4-(dimethylamino)pyridine (2.7 mg, 0.022 mmol) in tetrahydrofuran (1 mL) was added isobutyric anhydride (7 mg, 0.044 mmol) at RT. After 30 min, the reaction mixture was quenched with few drops off water. The crude residue was purified by preparatory HPLC (Gemini 5 um NX-C18 110A LC column 100×30 mm, 95% to 0% water acetonitrile gradient) to afford the product as individual isomers.

First eluent Example 105a: $^1$H NMR (400 MHz, Methanol-d4) δ 7.87 (s, 1H), 7.38-7.29 (m, 2H), 7.14-7.04 (m, 2H), 6.96-6.83 (m, 2H), 6.28 (d, J=5.9 Hz, 1H), 5.56 (dd, J=6.0, 3.8 Hz, 1H), 4.68-4.56 (m, 1H), 4.43 (qdd, J=11.5, 5.6, 3.5 Hz, 2H), 4.01-3.73 (m, 4H), 2.65 (dp, J=21.1, 7.0 Hz, 2H), 1.30 (s, 9H), 1.29-1.17 (m, 19H), 1.10 (ddd, J=7.7, 4.7, 3.0 Hz, 1H), 0.60-0.45 (m, 2H), 0.26 (dt, J=5.9, 4.4 Hz, 2H). $^{31}$P NMR (162 MHz, methanol-d$_4$) δ 3.66; LCMS: MS m/z=729.30 [M+1].

Second eluent Example 105b: $^1$H NMR (400 MHz, Methanol-d4) δ 7.86 (s, 1H), 7.28 (dd, J=8.8, 7.1 Hz, 2H), 7.23-7.09 (m, 3H), 6.91-6.79 (m, 2H), 6.22 (d, J=5.9 Hz, 1H), 5.58 (dd, J=5.8, 4.0 Hz, 1H), 4.69-4.57 (m, 1H), 4.53-4.31 (m, 2H), 4.12 (qt, J=10.8, 7.5 Hz, 2H), 3.87 (dq, J=9.9, 7.2 Hz, 1H), 2.55-2.33 (m, 5H), 1.51 (t, J=7.6 Hz, 2H), 1.37-1.09 (m, 13H), 0.93-0.78 (m, 10H); $^{31}$P NMR (162 MHz, methanol-d$_4$) δ 3.53; LCMS: MS m/z=729.30 [M+1].

Example 106: (2R,3R,4R,5R)-2-(4-aminopyrrolo[2,1-f][1,2,4]triazin-7-yl)-2-cyano-5-(((((S)-1-((3,3-dimethylpentyl)oxy)-1-oxopropan-2-yl)amino)(phenoxy)phosphoryl)oxy)methyl)tetrahydrofuran-3,4-diyl diacetate

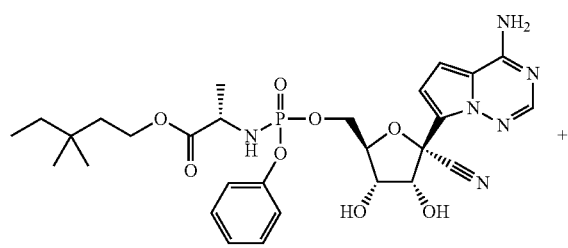 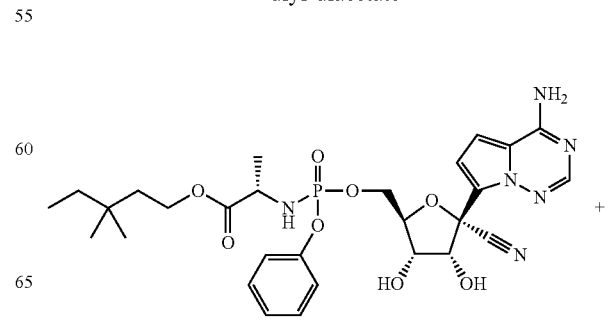

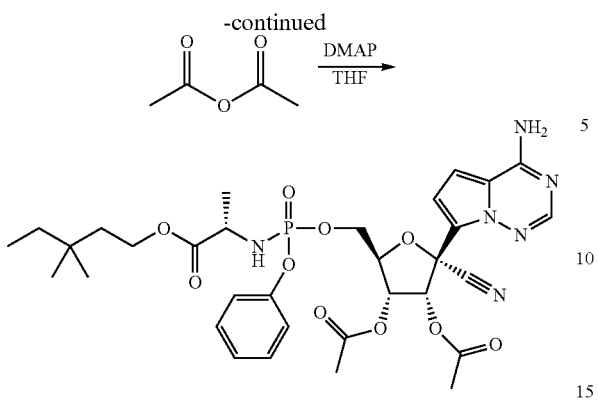

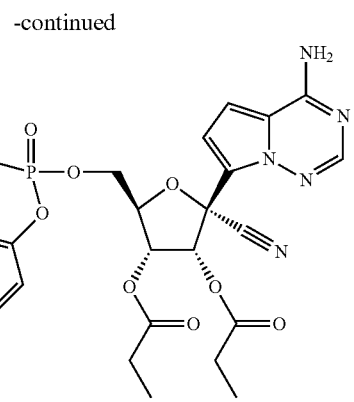

To a mixture of 3,3-dimethylpentyl (((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)-L-alaninate, Intermediate S4 (15 mg, 0.022 mmol) and 4-(dimethylamino)pyridine (2.7 mg, 0.022 mmol) in tetrahydrofuran (1 mL) was added acetic anhydride (7 mg, 0.044 mmol) at RT. After 30 min, the reaction mixture was quenched with few drops off water. The crude residue was purified by preparatory HPLC (Gemini 5 um NX-C18 110A LC column 100×30 mm, 95% to 0% water acetonitrile gradient) to afford the product as individual isomers.

First eluent Example 106a: $^1$H NMR (400 MHz, Methanol-d4) δ 7.86 (s, 1H), 7.39-7.27 (m, 2H), 7.24-7.14 (m, 3H), 6.97-6.87 (m, 2H), 6.30 (d, J=6.0 Hz, 1H), 5.57 (dd, J=6.0, 4.3 Hz, 1H), 4.65 (qd, J=3.5, 1.9 Hz, 1H), 4.54-4.32 (m, 2H), 4.16-4.01 (m, 2H), 3.80 (dq, J=9.2, 7.1 Hz, 1H), 2.15 (d, J=12.2 Hz, 6H), 1.55-1.43 (m, 2H), 1.24 (q, J=7.5 Hz, 2H), 1.19 (dd, J=7.2, 1.2 Hz, 3H), 0.86 (s, 6H), 0.82 (t, J=7.5 Hz, 3H); $^{31}$P NMR (162 MHz, methanol-d$_4$) δ 3.64; LCMS: MS m/z=701.30 [M+1].

Second eluent Example 106b: $^1$H NMR (400 MHz, Methanol-d4) δ 7.87 (s, 1H), 7.37-7.22 (m, 2H), 7.24-7.10 (m, 3H), 6.86 (s, 2H), 6.20 (d, J=5.9 Hz, 1H), 5.55 (dd, J=5.9, 4.3 Hz, 1H), 4.63 (qd, J=4.0, 1.7 Hz, 1H), 4.40 (qdd, J=11.5, 6.0, 3.9 Hz, 2H), 4.21-4.01 (m, 2H), 3.87 (dq, J=10.1, 7.1 Hz, 1H), 2.24-2.08 (m, 6H), 1.51 (t, J=7.6 Hz, 2H), 1.34-1.18 (m, 6H), 0.88 (s, 6H), 0.87-0.80 (m, 4H). $^{31}$P NMR (162 MHz, methanol-d$_4$) δ 3.54; LCMS: MS m/z=701.30 [M+1].

Example 107: (2R,3R,4R,5R)-2-(4-aminopyrrolo[2,1-f][1,2,4]triazin-7-yl)-2-cyano-5-((((((S)-1-cyclobutoxy-1-oxopropan-2-yl)amino)(phenoxy)phosphoryl)oxy)methyl)tetrahydrofuran-3,4-diyl dipropionate

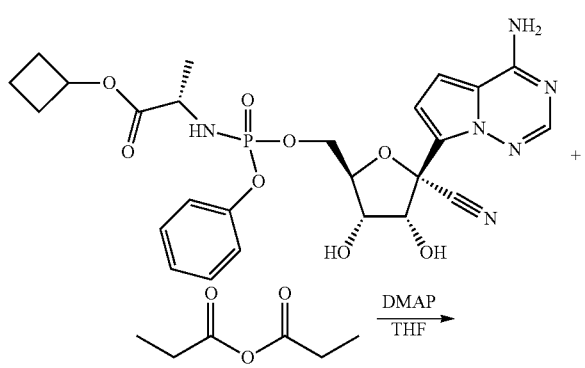

To a mixture of cyclobutyl (((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)-L-alaninate (15 mg, 0.022 mmol) and 4-(dimethylamino)pyridine (2.7 mg, 0.022 mmol) in tetrahydrofuran (1 mL) was added proprionoic anhydride (7 mg, 0.044 mmol) at RT. After 30 min, the reaction mixture was quenched with few drops off water. The crude residue was purified by preparatory HPLC (Gemini Sum NX-C18 110A LC column 100×30 mm, 95% to 0% water acetonitrile gradient) to afford the product as a mixture of isomers. Mixture of stereoisomers: $^1$H NMR (400 MHz, Methanol-d$_4$) δ 7.87 (s, 0.5H), 7.87 (s, 0.5H), 7.37-7.26 (m, 2H), 7.23-7.14 (m, 3H), 6.92 (s, 1H), 6.89-6.83 (m, 1H), 6.32 (d, J=5.9 Hz, 0.5H), 6.23 (d, J=5.9 Hz, 0.5H), 5.62-5.57 (m, 1H), 4.92-4.86 (m, 1H), 4.69-4.59 (m, 1H), 4.51-4.33 (m, 2H), 3.91-3.72 (m, 1H), 2.55-2.39 (m, 4H), 2.35-2.24 (m, 2H), 2.10-1.97 (m, 2H), 1.85-1.73 (m, 1H), 1.71-1.59 (m, 1H), 1.23-1.13 (m, 9H). $^{31}$P NMR (162 MHz, Methanol-d$_4$) δ 3.76-3.48 (m). LCMS: MS m/z=685.7, 685.7 [M+1], t$_R$=0.97, 0.98 min.

Example 108: (2R,3R,4R,5R)-2-(4-aminopyrrolo[2,1-f][1,2,4]triazin-7-yl)-5-((((4-(tert-butyl)phenoxy)(((S)-1-ethoxy-1-oxopropan-2-yl)amino)phosphoryl)oxy)methyl)-2-cyanotetrahydrofuran-3,4-diyl dipropionate

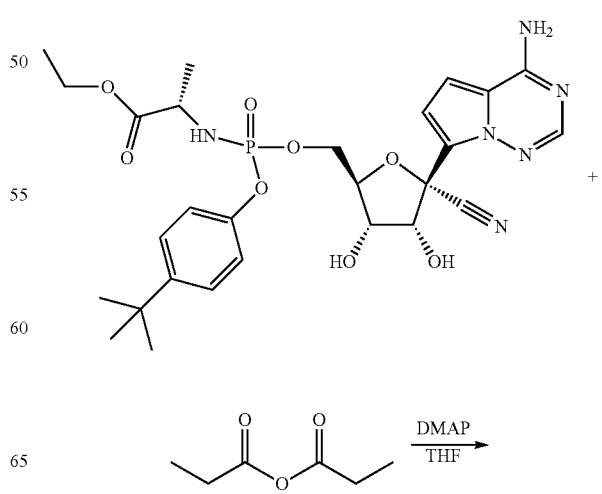

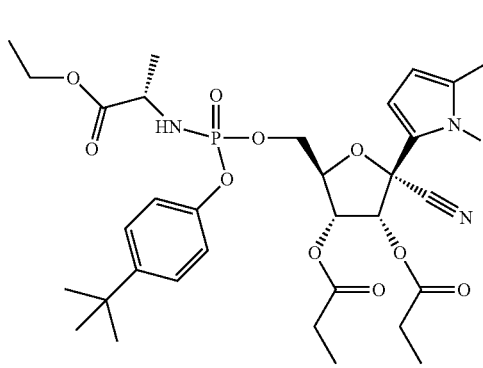
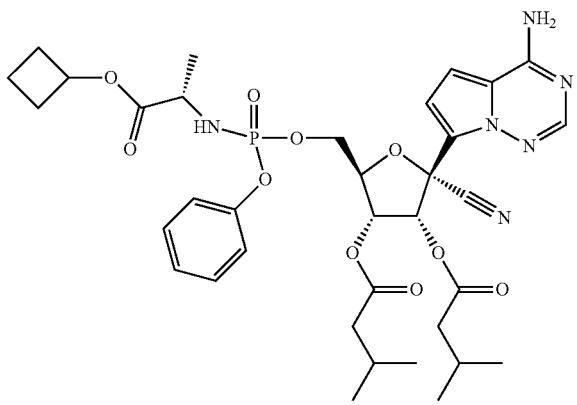

Example 108 was made in a similar fashion as Example 107 except that ethyl ((((2R,3S,4R,5R)-5-(4-aminopyrrolo[2,1-f][1,2,4]triazin-7-yl)-5-cyano-3,4-dihydroxytetrahydrofuran-2-yl)methoxy)(4-(tert-butyl)phenoxy)phosphoryl)-L-alaninate was used instead of cyclobutyl ((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)-L-alaninate. Mixture of stereoisomers: $^1$H NMR ((400 MHz, Methanol-d4) δ 7.88 (s, 0.5H), 7.87 (s, 0.5H), 7.38-7.32 (m, 1H), 7.31-7.26 (m, 1H), 7.12-7.05 (m, 2H), 6.95-6.88 (m, 2H), 6.29 (d, J=6.0 Hz, 0.5H), 6.19 (d, J=5.9 Hz, 0.5H), 5.61-5.56 (m, 1H), 4.68-4.60 (m, 1H), 4.49-4.34 (m, 2H), 4.17-4.04 (m, 2H), 3.92-3.83 (m, 0.5H), 3.81-3.72 (m, 0.5H), 2.52-2.38 (m, 4H), 1.34-1.12 (m, 21H). 31P NMR (162 MHz, Methanol-d4) δ 3.86-3.58 (m). LCMS: MS m/z=715.8, 715.8 [M+1], tR=1.04, 1.05 min.

Example 109: (2R,3R,4R,5R)-2-(4-aminopyrrolo[2,1-f][1,2,4]triazin-7-yl)-2-cyano-5-((((((S)-1-cyclobutoxy-1-oxopropan-2-yl)amino)(phenoxy)phosphoryl)oxy)methyl)tetrahydrofuran-3,4-diyl bis(3-methylbutanoate)

Example 109 was made in a similar fashion as Example 107 except that 3-methyl butanoic anhydride was used instead of proprionoic anhydride. Mixture of stereoisomers: $^1$H NMR (400 MHz, Methanol-d4) δ 7.88 (s, 0.5H), 7.87 (s, 0.5H), 7.36-7.26 (m, 2H), 7.22-7.15 (m, 3H), 6.93-6.90 (m, 1H), 6.88-6.84 (m, 1H), 6.37 (d, J=5.9 Hz, 0.5H), 6.28 (d, J=5.9 Hz, 0.5H), 5.62-5.56 (m, 1H), 4.92-4.88 (m, 1H), 4.66-4.58 (m, 1H), 4.51-4.34 (m, 2H), 3.90-3.74 (m, 1H), 2.36-1.97 (m, 10H), 1.84-1.73 (m, 1H), 1.70-1.58 (m, 1H), 1.31-1.27 (m, 1.5H), 1.21-1.17 (m, 1.5H), 1.05-0.99 (m, 6H), 0.97-0.92 (m, 6H). 31P NMR (162 MHz, Methanol-d4) δ 3.74-3.45 (m). LCMS: MS m/z=741.8, 741.8 [M+1], tR=1.11, 1.12 min.

Example 110: (2R,3R,4R,5R)-2-(4-aminopyrrolo[2,1-f][1,2,4]triazin-7-yl)-5-((((4-(tert-butyl)phenoxy)(((S)-1-(2-ethylbutoxy)-1-oxopropan-2-yl)amino)phosphoryl)oxy)methyl)-2-cyanotetrahydrofuran-3,4-diyl dipropionate

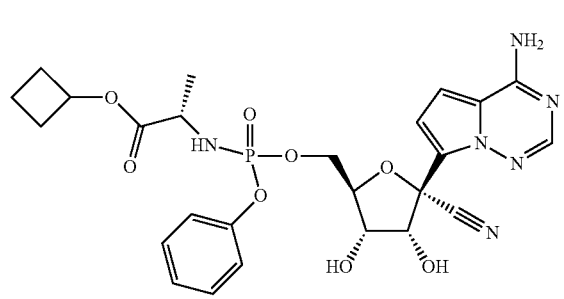
+
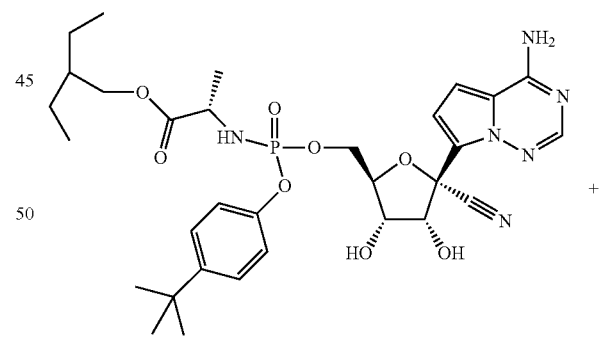
+

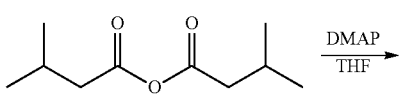 $\xrightarrow{\text{DMAP}}_{\text{THF}}$

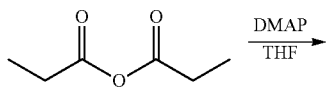 $\xrightarrow{\text{DMAP}}_{\text{THF}}$

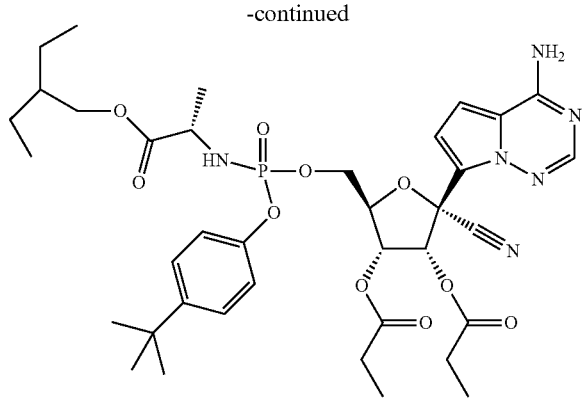

Example 110 was made in a similar fashion as Example 107 except that 2-ethylbutyl ((((2R,3S,4R,5R)-5-(4-aminopyrrolo[2,1-f][1,2,4]triazin-7-yl)-5-cyano-3,4-dihydroxytetrahydrofuran-2-yl)methoxy)(4-(tert-butyl)phenoxy)phosphoryl)-L-alaninate was used instead of cyclobutyl ((((2R, 3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)-L-alaninate. Mixture of stereoisomers: $^1$H NMR (400 MHz, Methanol-d4) δ 7.88 (s, 0.5H), 7.87 (s, 0.5H), 7.36-7.33 (m, 1H), 7.31-7.27 (m, 1H), 7.12-7.05 (m, 2H), 6.94-6.87 (m, 2H), 6.29 (d, J=5.9 Hz, 0.5H), 6.18 (d, J=5.9 Hz, 0.5H), 5.61-5.55 (m, 1H), 4.67-4.59 (m, 1H), 4.48-4.33 (m, 2H), 4.11-3.78 (m, 3H), 2.52-2.39 (m, 4H), 1.55-1.44 (m, 1H), 1.41-1.27 (m, 15H), 1.23-1.13 (m, 7H), 0.93-0.86 (m, 6H). 31P NMR (162 MHz, Methanol-d4) δ 3.81-3.55 (m). LCMS: MS m/z=771.7, 771.7 [M+1], tR=1.18, 1.20 min.

Intermediate D1a: 2-methoxy-2-methylpropyl (tert-butoxycarbonyl)-L-alaninate hydrochloride

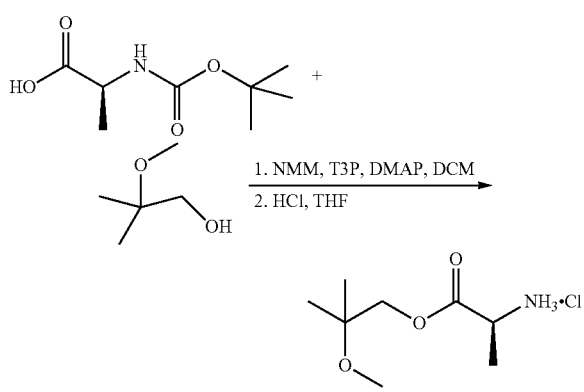

To a solution of (tert-butoxycarbonyl)-L-alanine (2.54 g, 24.0 mmol) and 2-methyl, 2-methoxy-1-propanol (2.24 g, 22 mmol) in DCM (50 mL) at 0° C. under an atmosphere of argon was added NMM (7.19 mL, 65.4 mmol). After 10 minutes, DMAP (53 mg, 0.44 mmol) and T3P (15.6 mL, 26 mmol, 50% in EtOAc) was added. The reaction was allowed to warm to RT and stirred for 2 hours. The reaction was washed with water (30 mL), a 10% aq solution of citric acid (2×30 mL), a saturated solution of aq NaHCO₃ then brine. The organics were loaded on to 40 g of silica gel and washed with a 3:1 mixture of dichloromethane:ethylacetate. The residue was taken up in a 4:1 mixture of THF:conc HCl. After 30 minutes, the reaction was concentrated to afford intermediate D1. $^1$H NMR (400 MHz, DMSO-d₆) δ 8.66 (s, 3H), 4.17-4.07 (m, 2H), 4.00 (d, J=11.3 Hz, 1H), 3.12 (s, 3H), 1.44 (d, J=7.2 Hz, 3H), 1.16-1.10 (m, 6H).

Intermediate D2: 2-methoxy-2-methylpropyl ((4-(tert-butyl)phenoxy) (perfluorophenoxy)phosphoryl)-L-alaninate

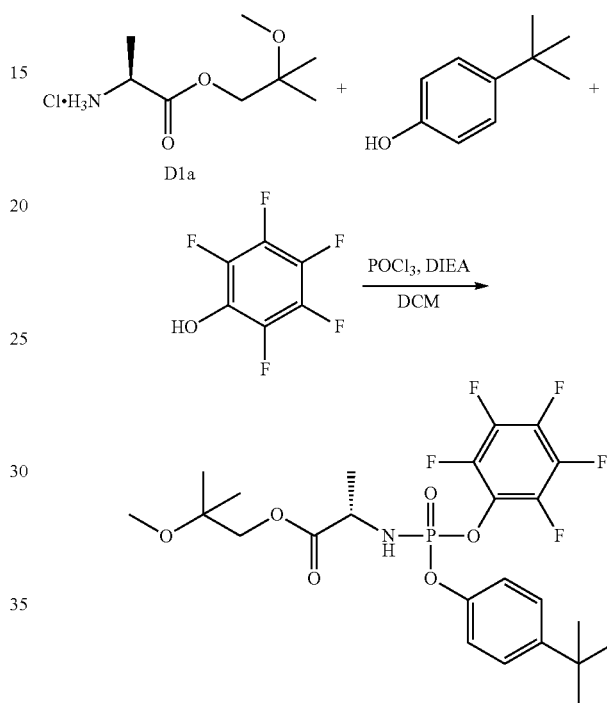

To a solution of phosphorus(V) oxychloride (5.00 g, 32.6 mmol) in dichloromethane (80 mL) under an atmosphere of argon was added 4-tert-butylphenol (4.90 g, 32.6 mmol) at −78° C. N,N-diisopropylethylamine (5.68 mL, 32.6 mmol) was added slowly over 5 minutes. After 15 minutes, the reaction was allowed to warm to 0° C. After 15 minutes, the reaction was cooled to −78° C. D1a (6.84 g, 32.6 mmol) was added. N,N-diisopropylethylamine (11.4 mL, 65.2 mmol) was added slowly over 5 minutes. After 30 minutes, 2,3,4, 5,6-pentafluorophenol (6.0 g, 32.6 mmol) was added. N,N-diisopropylethylamine (5.68 mL, 32.6 mmol) was added slowly over 5 minutes. After 15 minutes, the reaction was allowed to warm to room temperature. After 30 minutes, the reaction was acidified with acetic acid (5 mL). The reaction was washed with water (50 mL). The organics were dried over sodium sulfate, filtered and concentrated. The product was purified by silica gel chromatography (0-20% ethyl acetate in hexanes) to afford intermediate D2. $^1$H NMR (400 MHz, DMSO-d6) δ 7.44-7.38 (m, 2H), 7.20-7.11 (m, 2H), 6.97-6.87 (m, 1H), 4.06-3.87 (m, 3H), 3.09 (s, 3H), 1.36-1.29 (m, 3H), 1.30-1.24 (m, 9H), 1.09 (s, 6H). $^{19}$F NMR (376 MHz, DMSO-d₆) δ −153.99--154.53 (m, 2F), −160.66--161.08 (m, 1F), −163.49--163.83 (m, 2F). $^{31}$P NMR (162 MHz, DMSO-d₆) δ 0.85-0.45 (m). LCMS: MS m/z=554.7 [M+1], tR=1.21 min.

Example 111: 2-methoxy-2-methylpropyl ((((2R,3S, 4R,5R)-5-(4-aminopyrrolo[2,1-f][1,2,4]triazin-7-yl)-5-cyano-3,4-dihydroxytetrahydrofuran-2-yl)methoxy)(4-(tert-butyl)phenoxy)phosphoryl)-L-alaninate

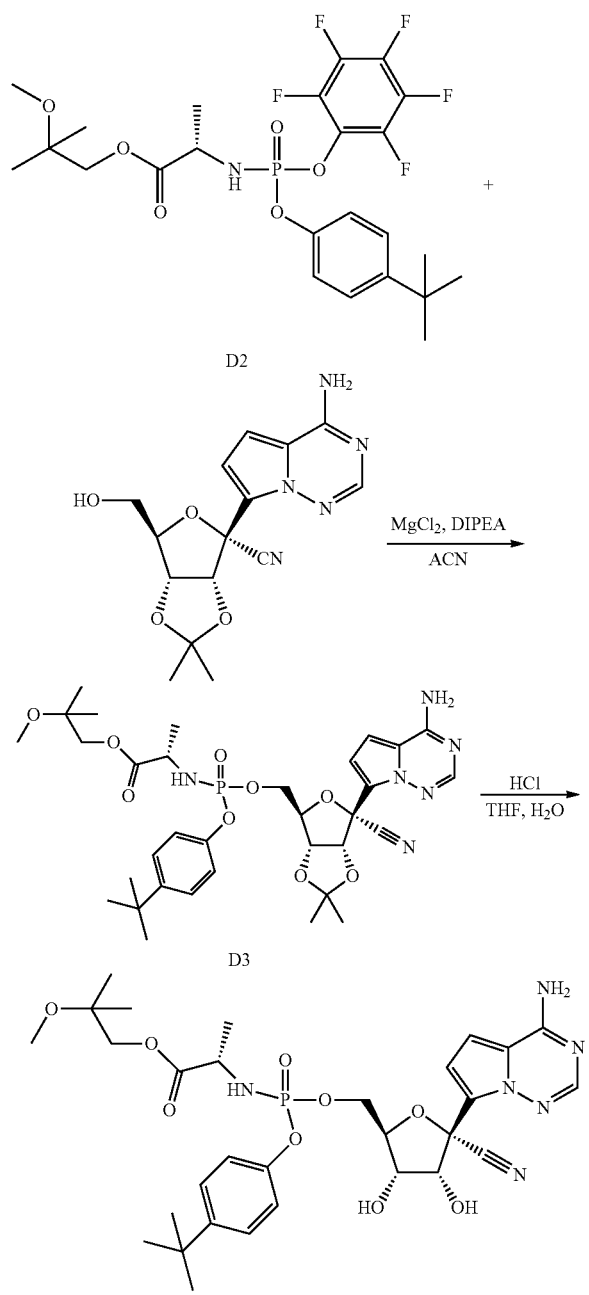

To a suspension of D2, 0.366 g, 0.664 mmol), (3aR,4R, 6R,6aR)-4-(4-aminopyrrolo[2,1-f][1,2,4]triazin-7-yl)-6-(hydroxymethyl)-2,2-dimethyltetrahydrofuro[3,4-d][1,3]dioxole-4-carbonitrile (Prepared according to WO2017049060, 0.200 g, 0.604 mmol) and magnesium chloride (0.058 g, 0.604 mmol) in acetonitrile (6 mL) under an atmosphere of argon was added N,N-diisopropylethylamine (0.263 mL, 1.51 mmol) at 0° C. After 10 min, the reaction was heated to 50° C. After 2 h, the reaction was cooled to room temperature, diluted with ethyl acetate and the organics were washed with water, dried over sodium sulfate, filtered and concentrated to afford intermediate D3 (LCMS: MS m/z=701.8 and 701.8 [M+1], $t_R$=1.01 and 1.03 min; LC system: Agilent 1260 Infinity II HPLC; MS system: G6124B Single Quad; Column: Kinetix 2.6u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 µL/min). Intermediate D3 was taken up in tetrahydrofuran (2 mL) and concentrated hydrochloric acid (11.7 M, 0.400 mL, 4.66 mmol) was added. After 2 h, the reaction was diluted with ethyl acetate and neutralized with a saturated aqueous solution of sodium bicarbonate. The layers were separated, and the organics were washed with water, saturated aqueous sodium chloride, dried over sodium sulfate, filtered and concentrated. The product was purified by HPLC chromatography (0-100% acetonitrile in water) to afford the title compound. Mixture of stereoisomers: $^1$H NMR (400 MHz, Methanol-d4) δ 7.89 (s, 0.5H), 7.87 (s, 0.5H), 7.35-7.28 (m, 2H), 7.13-7.09 (m, 1H), 7.08-7.04 (m, 1H), 6.98-6.91 (m, 2H), 4.82-4.78 (m, 1H), 4.48-4.27 (m, 3H), 4.21-4.14 (m, 1H), 4.07-4.03 (m, 1H), 4.01-3.89 (m, 2H), 3.22-3.19 (m, 3H), 1.35-1.26 (m, 12H), 1.19-1.15 (m, 6H). 31P NMR (162 MHz, Methanol-d4) δ 3.81-3.59 (m). LCMS: MS m/z=661.9, 661.9 [M+1], tR=0.87, 0.88 min.

Intermediate D4: 2-(2-ethoxyethoxy)ethyl L-alaninate hydrochloride

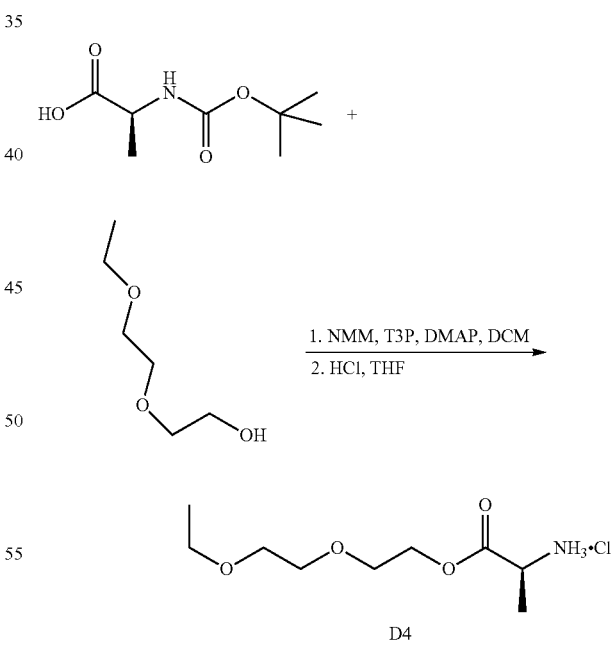

Intermediate D4 was made in a similar fashion as intermediate D1 except that 2-(2-ethoxyethoxy)ethyl alcohol was used instead of 2-methyl, 2-methoxy-propanol. $^1$H NMR (400 MHz, DMSO-d$_6$) δ 8.66 (s, 3H), 4.36-4.28 (m, 1H), 4.27-4.20 (m, 1H), 4.10-4.00 (m, 1H), 3.65 (t, J=4.7 Hz, 2H), 3.56-3.52 (m, 2H), 3.49-3.39 (m, 4H), 1.43 (d, J=7.2 Hz, 3H), 1.10 (t, J=7.0 Hz, 3H).

Intermediate D5: 2-(2-ethoxyethoxy)ethyl ((4-(tert-butyl)phenoxy)(perfluorophenoxy)phosphoryl)-L-alaninate

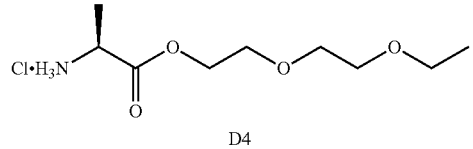

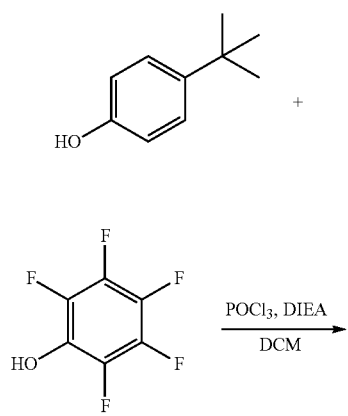

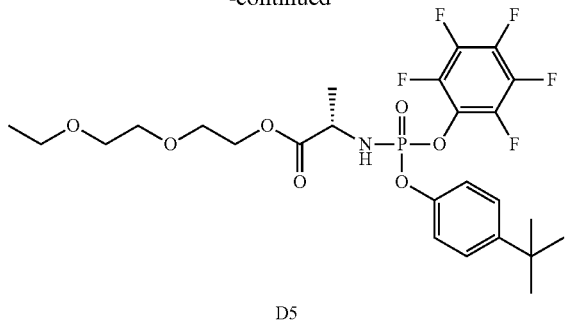

Intermediate D5 was made in a similar fashion as intermediate D2 except that intermediate D4 was used instead of intermediate D1. $^1$H NMR (400 MHz, DMSO-d$_6$) δ 7.45-7.40 (m, 2H), 7.21-7.10 (m, 2H), 6.96-6.86 (m, 1H), 4.22-4.08 (m, 2H), 4.05-3.93 (m, 1H), 3.60-3.56 (m, 2H), 3.52-3.48 (m, 2H), 3.46-3.36 (m, 4H), 1.32-1.29 (m, 3H), 1.28-1.25 (m, 9H), 1.08 (t, J=7.0 Hz, 3H). $^{31}$P NMR (162 MHz, DMSO-d$_6$) δ 2.72--4.57 (m). $^{19}$F NMR (376 MHz, DMSO-d$_6$) δ -154.10--154.35 (m, 2F), -160.70--161.09 (m, 1F), -163.50--163.90 (m, 2F). LCMS: MS m/z=584.4 [M+1], tR=1.19 min.

Example 112: 2-(2-ethoxyethoxy)ethyl (((((2R,3S,4R,5R)-5-(4-aminopyrrolo[2,1-f][1,2,4]triazin-7-yl)-5-cyano-3,4-dihydroxytetrahydrofuran-2-yl)methoxy)(4-(tert-butyl)phenoxy)phosphoryl)-L-alaninate

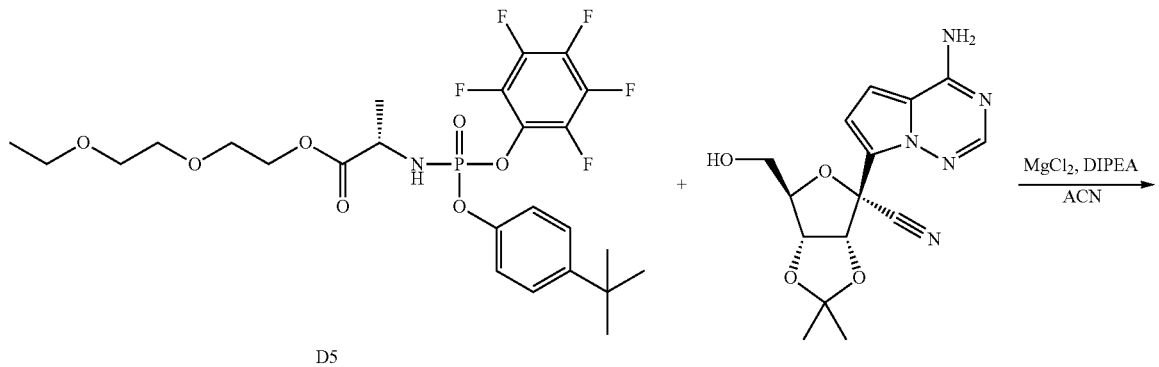

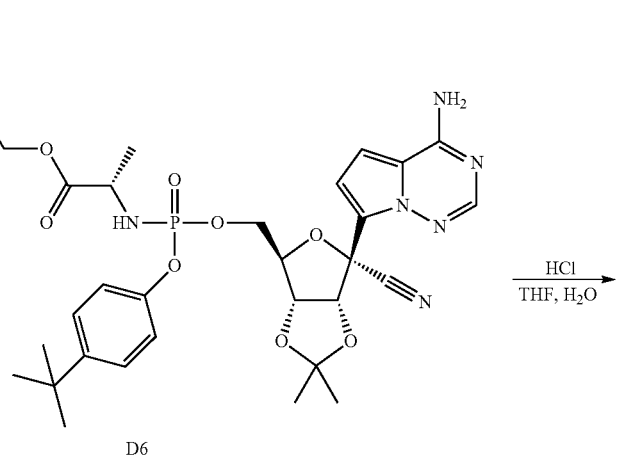

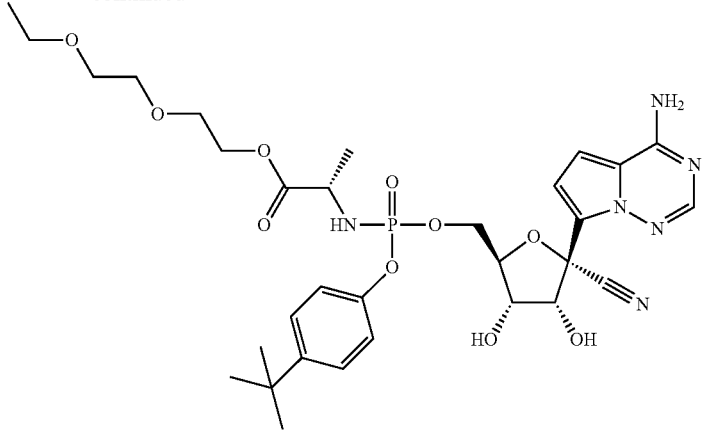

Compound 112 was made in a similar fashion as compound 111 except that intermediate D5 was used instead of intermediate D2. Intermediate D6: 2-(2-ethoxyethoxy)ethyl ((((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methoxy)(4-(tert-butyl)phenoxy)phosphoryl)-L-alaninate. LCMS: MS m/z=731.4.8, 731.4 [M+1], tR=0.98, 1.00 min. Compound 112: Mixture of stereoisomers: $^1$H NMR (400 MHz, Methanol-d4) δ 7.89 (s, 0.5H), 7.88 (s, 0.5H), 7.35-7.29 (m, 2H), 7.14-7.05 (m, 2H), 6.99-6.90 (m, 2H), 4.84-4.78 (m, 1H), 4.66 (s, 1H), 4.47-4.15 (m, 5H), 3.92-3.81 (m, 1H), 3.71-3.47 (m, 8H), 1.33-1.22 (m, 12H), 1.20-1.15 (m, 3H). 31P NMR (162 MHz, Methanol-d4) δ 3.97-3.59 (m). LCMS: MS m/z=691.8, 691.8 [M+1], tR=0.85, 0.86 min.

Intermediate D7: 2,2-dimethylbutyl L-alaninate hydrochloride

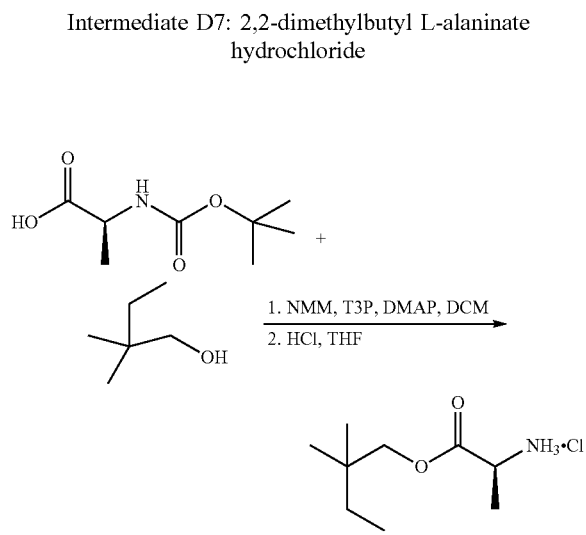

Intermediate D7 was made in a similar fashion as intermediate D1 except that 2,2-dimethylbutanol was used instead of 2-methyl, 2-methoxy-1-propanol. $^1$H NMR (400 MHz, DMSO-d$_6$) δ 8.51 (s, 3H), 4.12 (q, J=7.2 Hz, 1H), 3.96 (d, J=10.6 Hz, 1H), 3.83 (d, J=10.6 Hz, 1H), 1.44 (d, J=7.2 Hz, 3H), 1.29 (q, J=7.5 Hz, 2H), 0.88 (s, 6H), 0.81 (t, J=7.5 Hz, 3H).

Intermediate D8: 2,2-dimethylbutyl ((perfluorophenoxy)(phenoxy)phosphoryl)-L-alaninate Intermediate D7 (18.3 g, 59.93 mmol) was dissolved in dichloromethane (100 mL) and phenyl dichlorophosphate (9.81 mL, 65.92 mmol) then triethylamine (18.28 mL, 131.84 mmol) were sequentially added at 0° C. The resulting mixture was stirred at room temperature for 2 hours. The reaction mixture was cooled down to 0° C. and pentafluorophenol (11.03 g, 59.93 mmol) then triethylamine (10.80 mL, 78.05 mmol) were then sequentially added and the resulting mixture was then allowed to warm to room temperature. After 3 hours, the reaction mixture was cooled down to 0° C. and solids were filtered off, the filtrate was washed with saturated ammonium chloride water solution (100 mL), water (100 mL) and brine (50 mL). The organics were dried over sodium sulfate and filtered through a 3 cm layer of silica gel which was washed with 1:1 ethyl acetate and dichloromethane mixture (100 mL). Combined organics were concentrated down under reduced pressure. The product was purified by silica gel chromatography (0-20% EtOAc in Hex) to afford the title compound Intermediate D8. $^1$H NMR (400 MHz, DMSO-d$_6$) δ 7.45-7.40 (m, 2H), 7.28-7.20 (m, 3H), 6.98-6.90 (m, 1H), 4.08-3.98 (m, 1H), 3.84-3.72 (m, 2H), 1.35-1.29 (m, 3H), 1.28-1.21 (m, 2H), 0.83 (s, 6H), 0.76 (t, J=7.5 Hz, 3H). $^{31}$P NMR (162 MHz, DMSO-d$_6$) δ 0.65-0.34 (m). $^{19}$F NMR (376 MHz, DMSO-d$_6$) δ −154.02−−154.46 (m, 2F), −160.59−−160.88 (m, 1F), −163.39−−163.85 (m, 2F). LCMS: MS m/z=496.6 [M+1], tR=1.22 min.

Intermediate D9: 2,2-dimethylbutyl ((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)-L-alaninate Intermediate D9 was made in a similar fashion as compound 130 except that intermediate D8 was used instead of intermediate D2. Intermediate D9: LCMS: MS m/z=643.4, 643.4 [M+1], tR=1.00, 1.02 min. Mixture of stereoisomers: $^1$H NMR (400 MHz, Methanol-d4) δ 7.88 (s, 0.5H), 7.87 (s, 0.5H), 7.35-7.27 (m, 2H), 7.23-7.14 (m, 3H), 6.95-6.89 (m, 2H), 4.82-4.79 (m, 1H), 4.48-4.27 (m, 3H), 4.23-4.16 (m, 1H), 3.98-3.84 (m, 2H), 3.81-3.70 (m, 1H), 1.36-1.25 (m, 5H), 0.91-0.78 (m, 9H). 31P NMR (162 MHz, Methanol-d4) δ 3.90-3.57 (m). LCMS: MS m/z=603.9, 603.9 [M+1], tR=0.85, 0.87 min.

Example 113: (2R,3R,4R,5R)-2-(4-aminopyrrolo[2,1-f][1,2,4]triazin-7-yl)-5-((((4-(tert-butyl)phenoxy)(((S)-1-methoxy-1-oxopropan-2-yl)amino)phosphoryl)oxy)methyl)-2-cyanotetrahydrofuran-3,4-diyl dipropionate

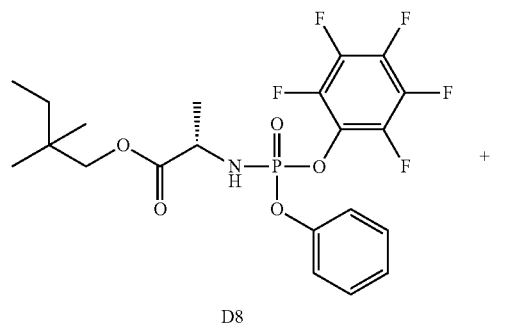

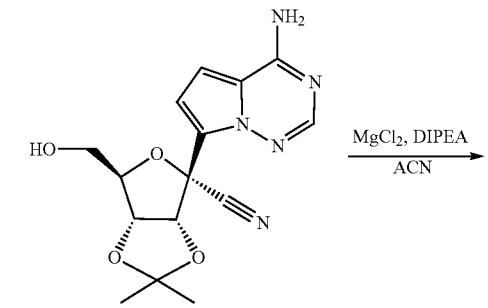

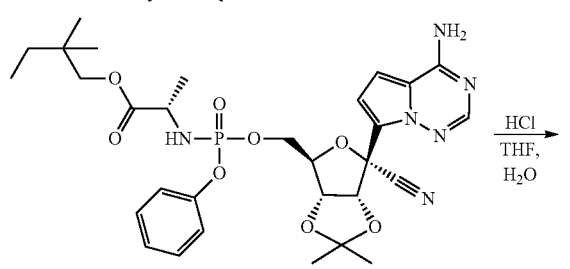

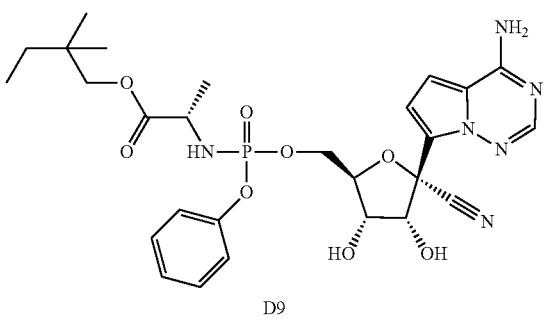

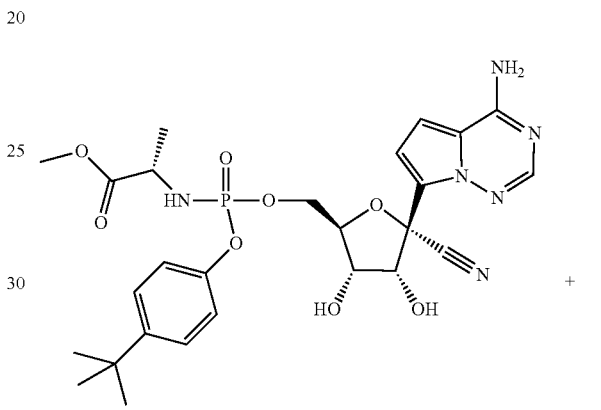

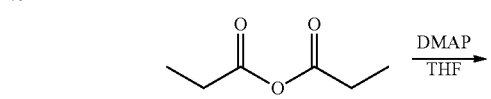

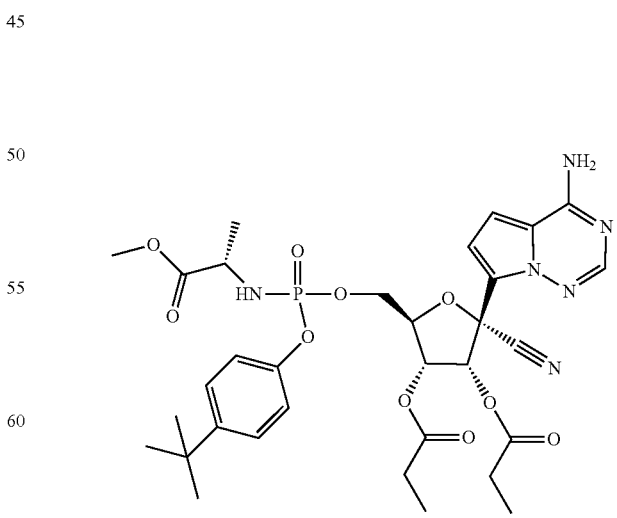

Compound 113 was made in a similar fashion as compound 107 except that Compound 15 was used instead of

305 cyclobutyl ((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)-L-alaninate. Mixture of stereoisomers: ¹H NMR (400 MHz, Methanol-d4) δ 7.88 (s, 0.5H), 7.86 (s, 0.5H), 7.38-7.33 (m, 1H), 7.31-7.27 (m, 1H), 7.13-7.05 (m, 2H), 6.95-6.87 (m, 2H), 6.30 (d, J=6.0 Hz, 0.5H), 6.19 (d, J=5.9 Hz, 0.5H), 5.62-5.57 (m, 1H), 4.69-4.62 (m, 1H), 4.49-4.32 (m, 2H), 3.93-3.84 (m, 0.5H), 3.82-3.72 (m, 0.5H), 3.68-3.63 (m, 3H), 2.54-2.39 (m, 4H), 1.35-1.10 (m, 18H). 31P NMR (162 MHz, Methanol-d4) δ 3.78-3.56 (m). LCMS: MS m/z=701.8, 701.8 [M+1], tR=1.02, 1.03 min.

Example 114: (2R,3R,4R,5R)-2-(4-aminopyrrolo[2,1-f][1,2,4]triazin-7-yl)-2-cyano-5-((((((S)-1-(2,2-dimethylbutoxy)-1-oxopropan-2-yl)amino)(phenoxy)phosphoryl)oxy)methyl)tetrahydrofuran-3,4-diyl bis(2-methylpropanoate)

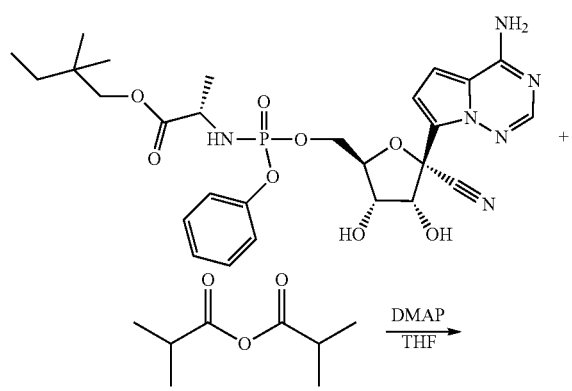

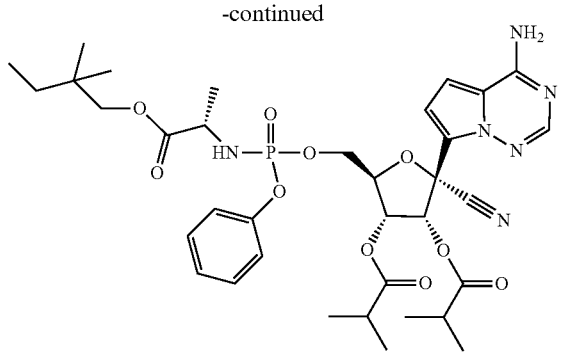

Example 114 was made in a similar manner as Example 107 except that Intermediate D9 was used instead of cyclobutyl ((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)-L-alaninate and 2-methylproprionic anhydride was used instead of proprionic anhydride. Mixture of stereoisomers: ¹H NMR (400 MHz, Methanol-d4) δ 7.87 (s, 1H), 7.36-7.25 (m, 2H), 7.21-7.13 (m, 3H), 6.92-6.89 (m, 1H), 6.86 (d, J=4.6 Hz, 0.5H), 6.83 (d, J=4.7 Hz, 0.5H), 6.29 (d, J=5.9 Hz, 0.5H), 6.20 (d, J=5.9 Hz, 0.5H), 5.60-5.54 (m, 1H), 4.67-4.58 (m, 1H), 4.51-4.37 (m, 2H), 3.99-3.83 (m, 2H), 3.80-3.74 (m, 1H), 2.74-2.59 (m, 2H), 1.35-1.15 (m, 17H), 0.89-0.80 (m, 9H). 31P NMR (162 MHz, Methanol-d4) δ 3.79-3.38 (m). LCMS: MS m/z=743.7, 743.7 [M+1], tR=1.12 min.

Example 115: (2R,3R,4R,5R)-2-(4-aminopyrrolo[2,1-f][1,2,4]triazin-7-yl)-5-((((4-(tert-butyl)phenoxy)(((S)-1-(2-(2-ethoxyethoxy)ethoxy)-1-oxopropan-2-yl)amino)phosphoryl)oxy)methyl)-2-cyanotetrahydrofuran-3,4-diyl bis(2-methylpropanoate)

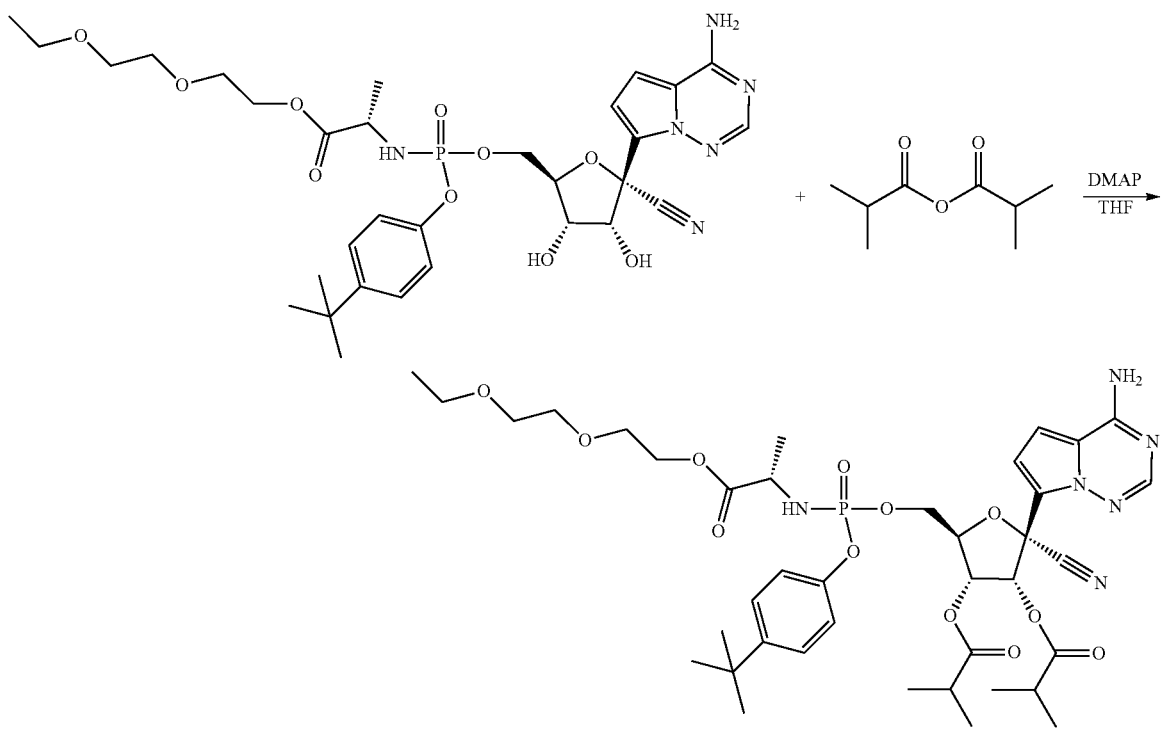

Example 115 was made in a similar fashion as example 112 except that example 131 was used instead of example 132. Mixture of stereoisomers: $^1$H NMR (400 MHz, Methanol-d4) δ 7.89-7.86 (m, 1H), 7.37-7.33 (m, 1H), 7.31-7.27 (m, 1H), 7.12-7.05 (m, 2H), 6.94-6.86 (m, 2H), 6.28 (d, J=5.9 Hz, 0.5H), 6.16 (d, J=6.0 Hz, 0.5H), 5.60-5.53 (m, 1H), 4.67-4.58 (m, 1H), 4.47-4.36 (m, 2H), 4.27-4.17 (m, 2H), 3.96-3.85 (m, 0.5H), 3.82-3.73 (m, 0.5H), 3.71-3.47 (m, 8H), 2.78-2.53 (m, 2H), 1.33-1.14 (m, 27H). $^{31}$P NMR (162 MHz, Methanol-d4) δ 3.76-3.46 (m). LCMS: MS m/z=831.8 [M+1], tR=1.12 min.

Example 116: (2R,3R,4R,5R)-2-(4-aminopyrrolo[2,1-f][1,2,4]triazin-7-yl)-5-((((4-(tert-butyl)phenoxy)(((S)-1-(2-methoxy-2-methylpropoxy)-1-oxopropan-2-yl)amino)phosphoryl)oxy)methyl)-2-cyanotetrahydrofuran-3,4-diyl bis(2-methylpropanoate)

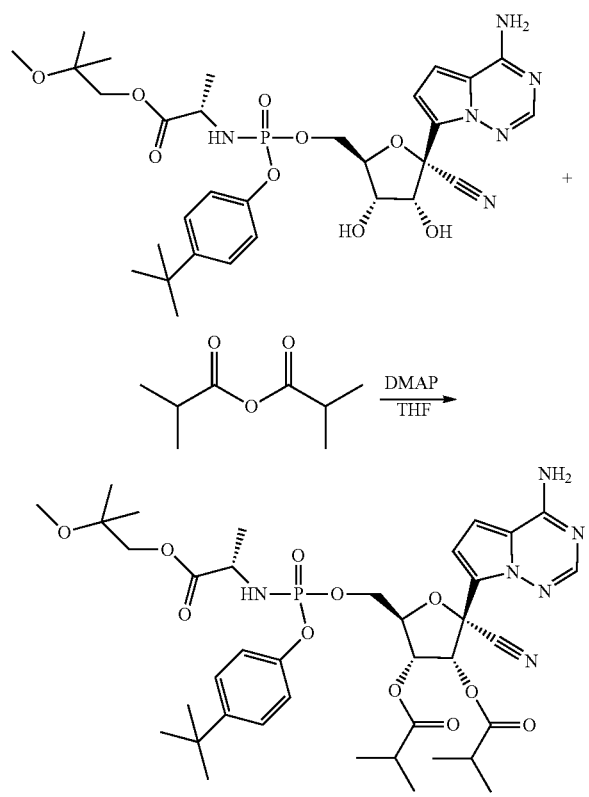

Example 116 was made in a similar fashion as example 114 except that example 111 was used instead of Intermediate D9. Mixture of stereoisomers: $^1$H NMR (400 MHz, Methanol-d4) δ 7.88 (s, 0.5H), 7.88 (s, 0.5H), 7.36-7.32 (m, 1H), 7.30-7.26 (m, 1H), 7.12-7.05 (m, 2H), 6.93-6.85 (m, 2H), 6.27 (d, J=5.9 Hz, 0.5H), 6.14 (d, J=5.9 Hz, 0.5H), 5.58-5.54 (m, 1H), 4.67-4.60 (m, 1H), 4.49-4.36 (m, 2H), 4.10-4.03 (m, 1H), 4.00-3.84 (m, 2H), 3.22-3.20 (m, 3H), 2.73-2.59 (m, 2H), 1.35-1.22 (m, 18H), 1.21-1.16 (m, 12H). 31P NMR (162 MHz, Methanol-d4) δ 3.79-3.48 (m). LCMS: MS m/z=801.8 [M+1], tR=1.13 min.

Example 117: (2R,3R,4R,5R)-2-(4-aminopyrrolo[2,1-f][1,2,4]triazin-7-yl)-2-cyano-5-((((((S)-1-(cyclobutylmethoxy)-1-oxopropan-2-yl)amino)(phenoxy)phosphoryl)oxy)methyl)tetrahydrofuran-3,4-diyl bis(2-methylpropanoate)

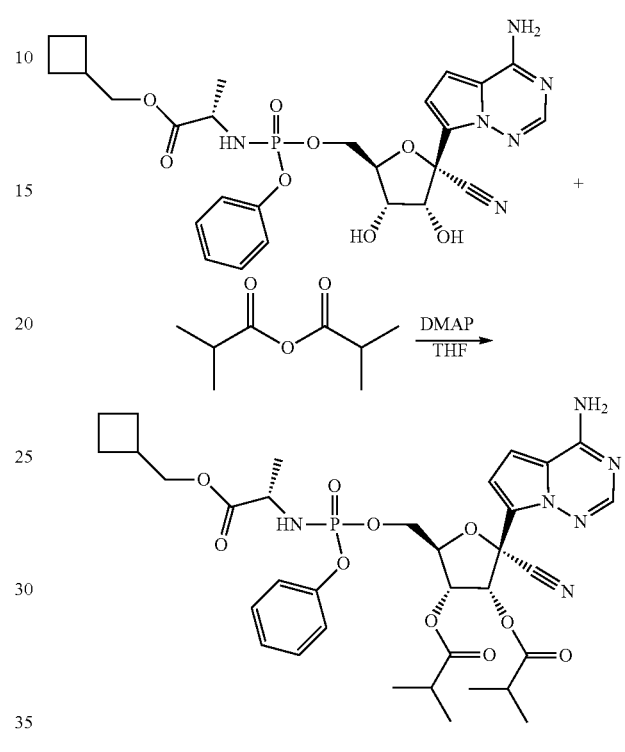

Example 117 was made in a similar fashion as example 114 except that example cyclobutylmethyl ((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)-L-alaninate was used instead of Intermediate D9. Mixture of stereoisomers: $^1$H NMR (400 MHz, Methanol-d4) δ 7.89-7.86 (m, 1H), 7.37-7.26 (m, 2H), 7.22-7.13 (m, 3H), 6.93-6.89 (m, 1H), 6.87 (d, J=4.7 Hz, 0.5H), 6.83 (d, J=4.6 Hz, 0.5H), 6.30 (d, J=5.9 Hz, 0.5H), 6.20 (d, J=5.8 Hz, 0.5H), 5.61-5.56 (m, 1H), 4.69-4.60 (m, 1H), 4.51-4.34 (m, 2H), 4.12-3.97 (m, 2H), 3.93-3.77 (m, 1H), 2.74-2.55 (m, 2H), 2.10-1.71 (m, 4H), 1.34-1.14 (m, 18H). 31P NMR (162 MHz, Methanol-d4) δ 3.82-3.40 (m). LCMS: MS m/z=727.8, 727.8 [M+1], tR=1.08, 1.10 min.

Intermediate D10: isobutyl ((4-(tert-butyl)phenoxy)(perfluorophenoxy)phosphoryl)-L-alaninate

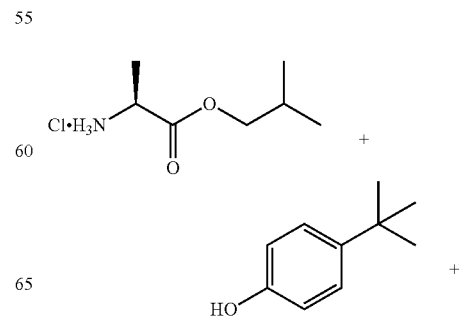

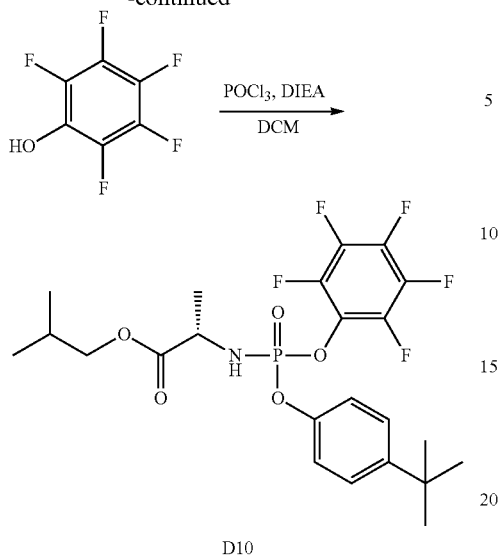

D10

Intermediate D10 was made in a similar fashion as intermediate D2 except that isobutyl (2S)-2-aminopropanoate hydrochloride was used instead of intermediate D1. $^1$H NMR (400 MHz, DMSO-d$_6$) δ 7.46-7.34 (m, 2H), 7.21-7.10 (m, 2H), 6.93-6.80 (m, 1H), 4.05-3.94 (m, 1H), 3.88-3.74 (m, 2H), 1.89-1.77 (m, 1H), 1.35-1.20 (m, 12H), 0.93-0.79 (m, 6H). $^{19}$F NMR (377 MHz, DMSO-d$_6$) δ −153.98-−154.44 (m, 2F), −160.71-−161.09 (m, 1F), −163.46-−163.83 (m, 2F). $^{31}$P NMR (162 MHz, DMSO-d$_6$) δ 1.11-0.33 (m). LCMS: MS m/z=524.3 [M+1], tR=1.08, 1.23 min.

Example 118: isobutyl ((((2R,3S,4R,5R)-5-(4-aminopyrrolo[2,1-f][1,2,4]triazin-7-yl)-5-cyano-3,4-dihydroxytetrahydrofuran-2-yl)methoxy)(4-(tert-butyl)phenoxy)phosphoryl)-L-alaninate

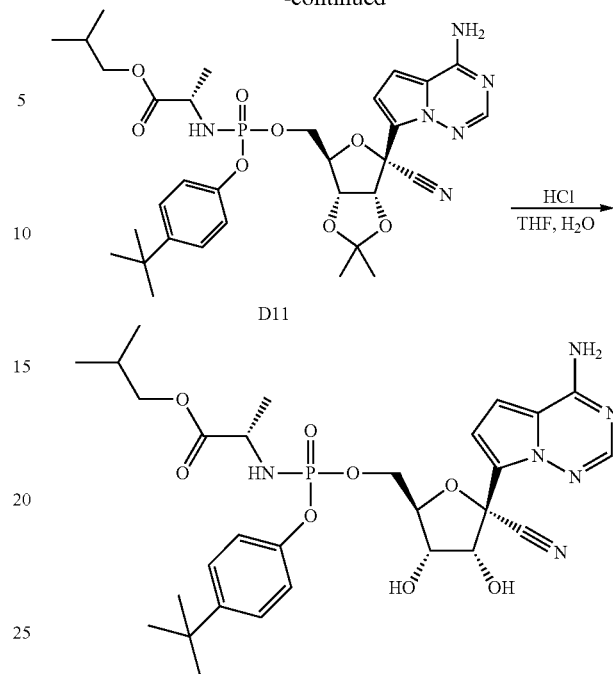

D11

Example 118 (1:1 mixture of isomers at phosphorus) was made in a similar fashion as example 111 except that intermediate D10 was used instead of intermediate D2. Intermediate D11: LCMS: MS m/z=671.3, 671.3 [M+1], tR=1.06, 1.09 min. Compound 118: Mixture of stereoisomers: $^1$H NMR (400 MHz, Methanol-d4) δ 7.89 (s, 0.5H), 7.87 (s, 0.5H), 7.35-7.29 (m, 2H), 7.13-7.09 (m, 1H), 7.08-7.04 (m, 1H), 6.98-6.91 (m, 2H), 4.82-4.79 (m, 1H), 4.49-4.36 (m, 2H), 4.35-4.26 (m, 1H), 4.20-4.17 (m, 1H), 3.94-3.78 (m, 3H), 1.94-1.84 (m, 1H), 1.33-1.26 (m, 12H), 0.94-0.89 (m, 6H). 31P NMR (162 MHz, Methanol-d4) δ 3.95-3.73 (m). LCMS: MS m/z=631.9, 631.9 [M+1], tR=0.92, 0.94 min.

Intermediate D12: hexyl ((4-(tert-butyl)phenoxy)(perfluorophenoxy)phosphoryl)-L-phenylalaninate

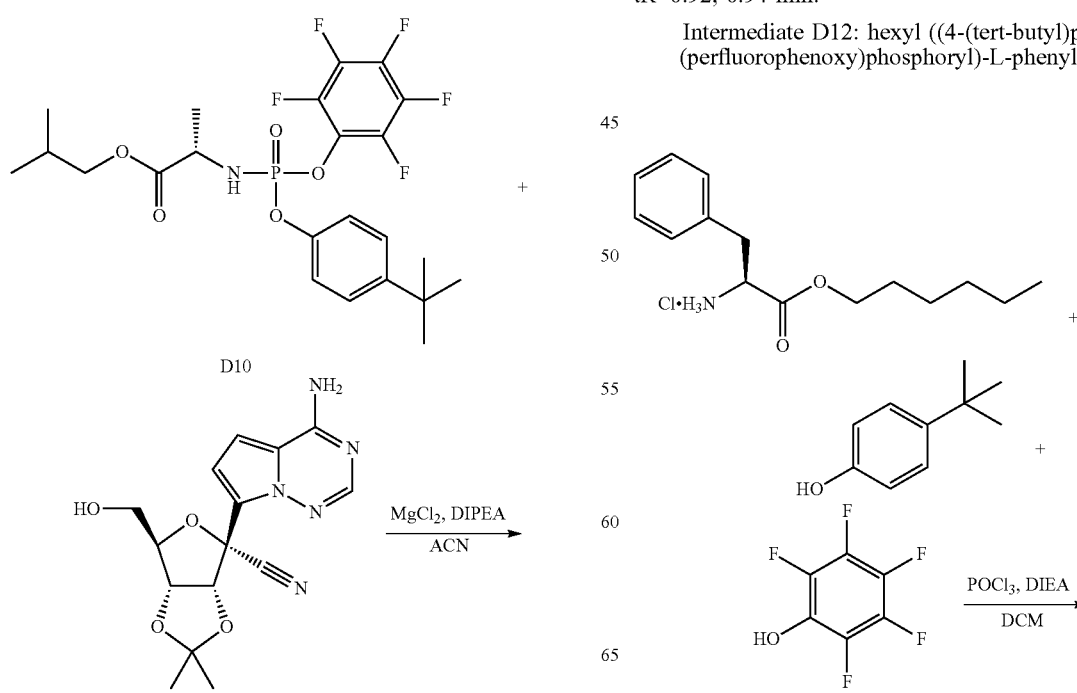

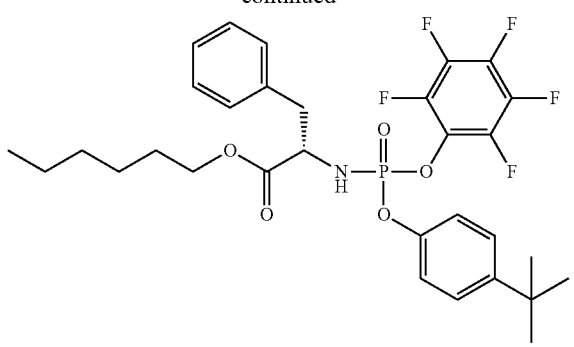

D12

Intermediate D12 was made in a similar fashion as intermediate D2 except that hexyl L-phenylalaninate hydrochloride was used instead of intermediate D1. $^1$H NMR (400 MHz, DMSO-$d_6$) δ 7.38-7.30 (m, 2H), 7.30-7.10 (m, 5H), 7.09-6.94 (m, 3H), 4.11-4.02 (m, 1H), 3.99-3.89 (m, 2H), 3.09-2.79 (m, 2H), 1.51-1.01 (m, 17H), 0.89-0.77 (m, 3H). $^{31}$P NMR (162 MHz, DMSO-$d_6$) δ 0.83-0.02 (m). $^{19}$F NMR (376 MHz, DMSO-$d_6$) δ −153.86−−154.36 (m, 2F), −160.58−−161.08 (m, 1F), −163.24−−163.94 (m, 2F). LCMS: MS m/z=628.2 [M+1], tR=1.40 min.

Example 119: hexyl ((((2R,3S,4R,5R)-5-(4-aminopyrrolo[2,1-f][1,2,4]triazin-7-yl)-5-cyano-3,4-dihydroxytetrahydrofuran-2-yl)methoxy)(4-(tert-butyl)phenoxy)phosphoryl)-L-phenylalaninate

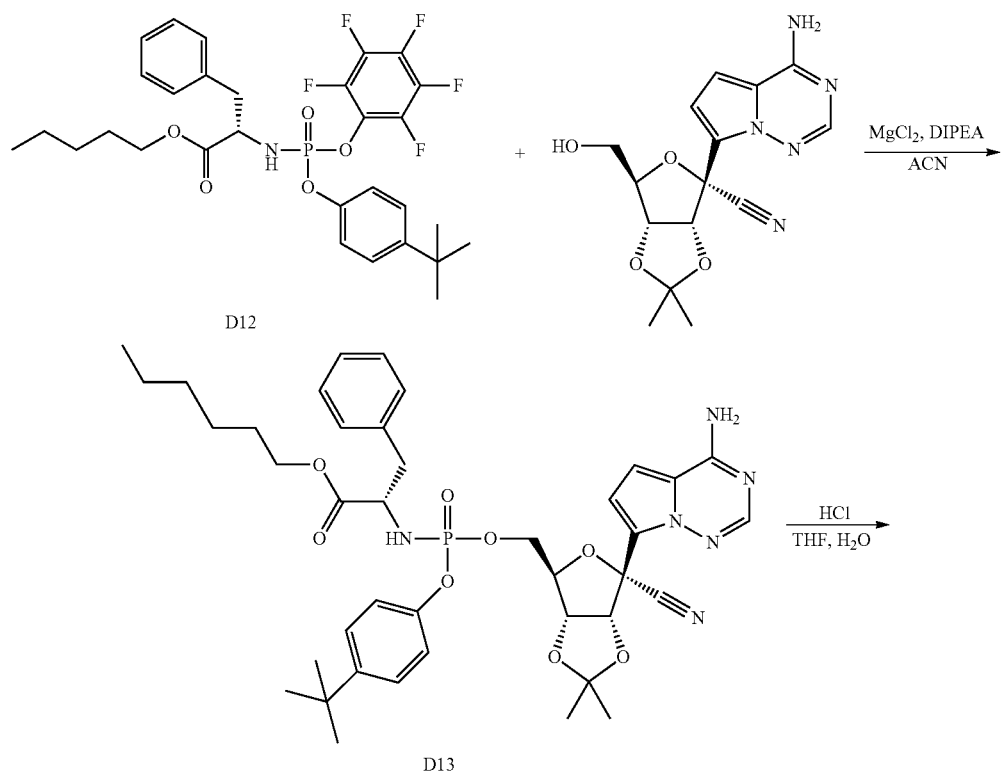

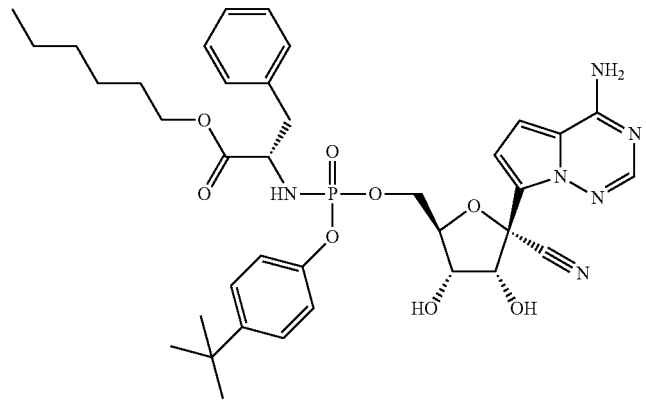

Example 119 was made in a similar fashion as example 111 except that intermediate D12 was used instead of intermediate D2. Intermediate D13: LCMS: MS m/z=775.2, 775.2 [M+1], tR=1.22, 1.24 min. Example 119; Mixture of stereoisomers: $^1$H NMR (400 MHz, Methanol-d4) δ 7.88 (s, 0.5H), 7.87 (s, 0.5H), 7.29-7.14 (m, 7H), 7.01-6.91 (m, 4H), 4.77 (d, J=5.5 Hz, 0.5H), 4.74 (d, J=5.4 Hz, 0.5H), 4.31-4.24 (m, 1H), 4.18-3.90 (m, 6H), 3.05-2.96 (m, 1H), 2.88-2.80 (m, 1H), 1.56-1.44 (m, 2H), 1.35-1.19 (m, 15H), 0.92-0.83 (m, 3H). 31P NMR (162 MHz, Methanol-d4) δ 3.81-3.61 (m, 0.5P), 3.46-3.26 (m, 0.5P). LCMS: MS m/z=735.8, 735.8 [M+1], tR=1.10, 1.11 min.

Intermediate D14: hexyl ((4-(tert-butyl)phenoxy)(perfluorophenoxy)phosphoryl)-L-alaninate Intermediate D14 was made in a similar fashion as intermediate D2 except that hexyl L-alaninate hydrochloride was used instead of intermediate D1. $^1$H NMR (400 MHz, DMSO-d$_6$) δ 7.45-7.39 (m, 2H), 7.20-7.10 (m, 2H), 6.93-6.80 (m, 1H), 4.07-3.92 (m, 3H), 1.57-1.47 (m, 2H), 1.35-1.19 (m, 18H), 0.89-0.78 (m, 3H). $^{19}$F NMR (376 MHz, DMSO-d$_6$) δ -154.05--154.46 (m, 2F), -160.63--161.18 (m, 1F), -163.37--163.90 (m, 2F). $^{31}$P NMR (162 MHz, DMSO-d$_6$) δ 0.79-0.40 (m). LCMS: MS m/z=552.2 [M+1], tR=1.36 min.

Example 120: hexyl ((((2R,3S,4R,5R)-5-(4-aminopyrrolo[2,1-f][1,2,4]triazin-7-yl)-5-cyano-3,4-dihydroxytetrahydrofuran-2-yl)methoxy)(4-(tert-butyl)phenoxy)phosphoryl)-L-alaninate

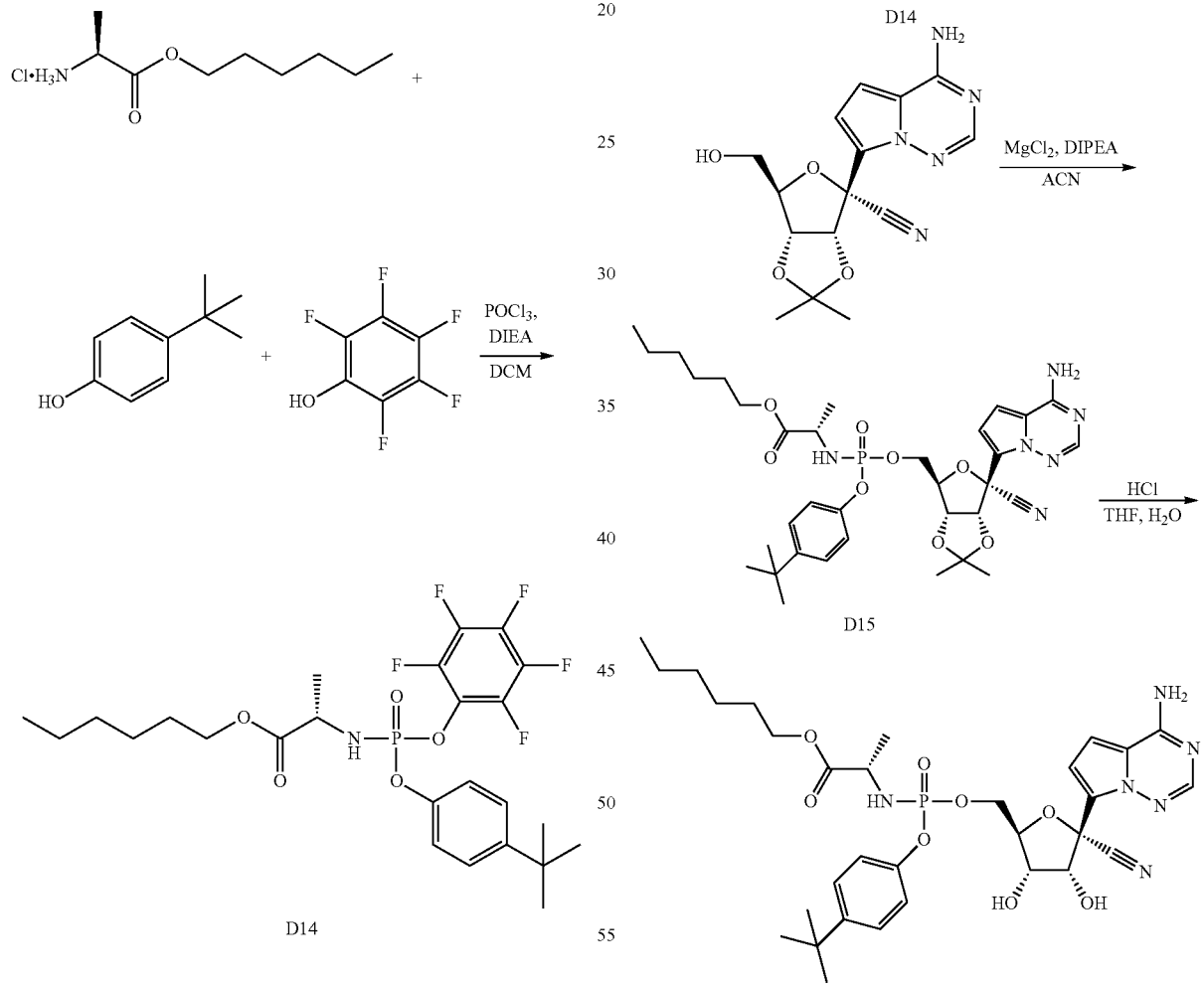

Example 120 was made in a similar fashion as example 111 except that intermediate D14 was used instead of intermediate D2. Intermediate D15: LCMS: MS m/z=699.3, 699.3 [M+1], tR=1.14, 1.17 min. Compound 120: Mixture of stereoisomers: $^1$H NMR (400 MHz, Methanol-d4) δ 7.89 (s, 0.5H), 7.88 (s, 0.5H), 7.36-7.28 (m, 2H), 7.14-7.09 (m, 1H), 7.08-7.04 (m, 1H), 6.99-6.91 (m, 2H), 4.83-4.77 (m, 1H), 4.48-4.36 (m, 2H), 4.35-4.24 (m, 1H), 4.20-4.15 (m, 1H), 4.13-3.97 (m, 2H), 3.94-3.79 (m, 1H), 1.65-1.53 (m, 2H), 1.39-1.22 (m, 18H), 0.92-0.86 (m, 3H). 31P NMR (162 MHz, Methanol-d4) δ 4.00-3.73 (m). LCMS: MS m/z=659.8, 659.8 [M+1], tR=1.01, 1.03 min.

Intermediate D16: 2,2-dimethylbutyl ((4-(tert-butyl)phenoxy) (perfluorophenoxy)phosphoryl)-L-alaninate

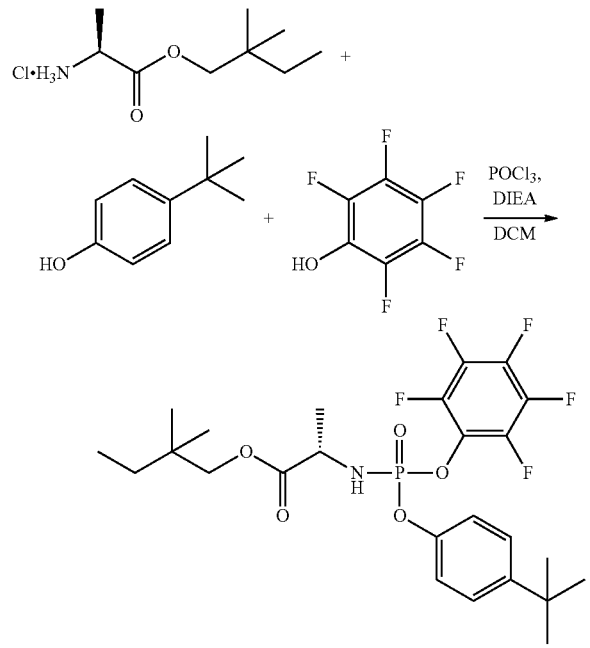

D16

Intermediate D16 was made in a similar fashion as intermediate D2 except that 2,2-dimethylbutyl L-alaninate hydrochloride was used instead of intermediate D1. ¹H NMR (400 MHz, DMSO-d₆) δ 7.44-7.39 (m, 2H), 7.19-7.11 (m, 2H), 6.92-6.83 (m, 1H), 4.06-3.97 (m, 1H), 3.82-3.72 (m, 2H), 1.34-1.31 (m, 3H), 1.29-1.22 (m, 11H), 0.84-0.81 (m, 6H), 0.77 (t, J=7.5 Hz, 3H). ¹⁹F NMR (377 MHz, DMSO-d₆) δ −153.96−−154.42 (m, 2F), −160.68−−161.08 (m, 1F), −163.52−−163.90 (m, 2F). LCMS: MS m/z=552.3 [M+1], tR=1.34.

Example 121: 2,2-dimethylbutyl ((((2R,3S,4R,5R)-5-(4-aminopyrrolo[2,1-f][1,2,4]triazin-7-yl)-5-cyano-3,4-dihydroxytetrahydrofuran-2-yl)methoxy)(4-(tert-butyl)phenoxy)phosphoryl)-L-alaninate

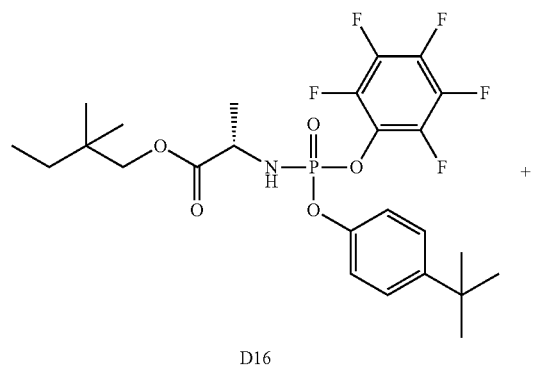

D16

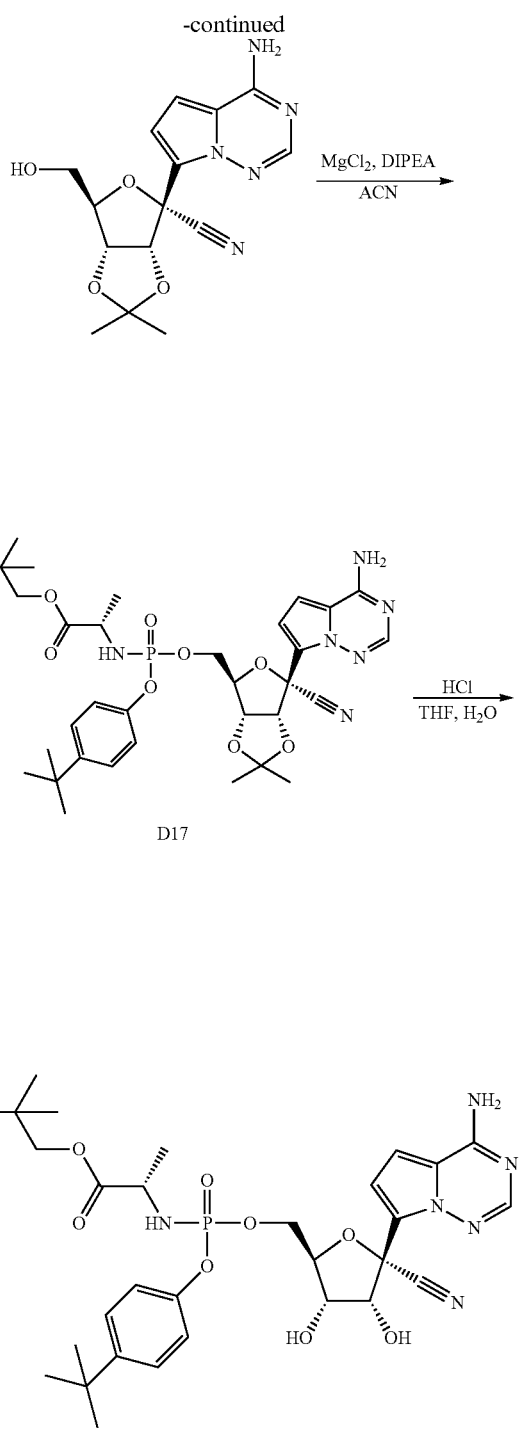

D17

Example 121 was made in a similar fashion as example 111 except that intermediate D16 was used instead of intermediate D2. Intermediate D17: LCMS: MS m/z=699.3, 699.3 [M+1], tR=1.13, 1.15 min. Compound 121, Mixture of stereoisomers: ¹H NMR (400 MHz, Methanol-d4) δ 7.90 (s, 0.5H), 7.88 (s, 0.5H), 7.35-7.27 (m, 2H), 7.14-7.09 (m, 1H), 7.08-7.04 (m, 1H), 6.98-6.93 (m, 2H), 4.82-4.78 (m, 1H), 4.48-4.27 (m, 3H), 4.20-4.15 (m, 1H), 3.97-3.83 (m, 2H), 3.81-3.72 (m, 1H), 1.37-1.25 (m, 14H), 0.91-0.80 (m, 9H). 31P NMR (162 MHz, Methanol-d4) δ 3.99-3.71 (m). LCMS: MS m/z=659.8, 659.8 [M+1], tR=0.99, 1.00 min.

317

Example 122: (2R,3R,4R,5R)-2-(4-aminopyrrolo[2,1-f][1,2,4]triazin-7-yl)-5-((((4-(tert-butyl)phenoxy)(((S)-1-isobutoxy-1-oxopropan-2-yl)amino)phosphoryl)oxy)methyl)-2-cyanotetrahydrofuran-3,4-diyl bis(2-methylpropanoate)

318

Example 123: (2R,3R,4R,5R)-2-(4-aminopyrrolo[2,1-f][1,2,4]triazin-7-yl)-5-((((4-(tert-butyl)phenoxy)(((S)-1-(hexyloxy)-1-oxo-3-phenylpropan-2-yl)amino)phosphoryl)oxy)methyl)-2-cyanotetrahydrofuran-3,4-diyl bis(2-methylpropanoate)

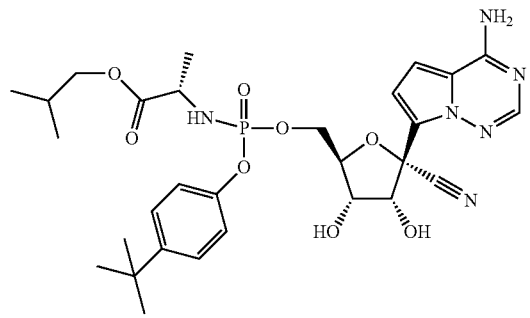

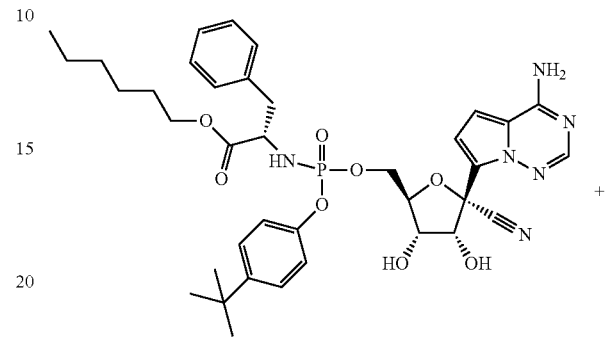

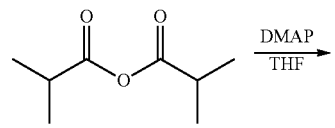

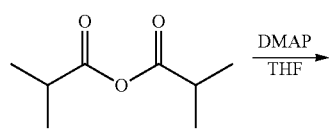

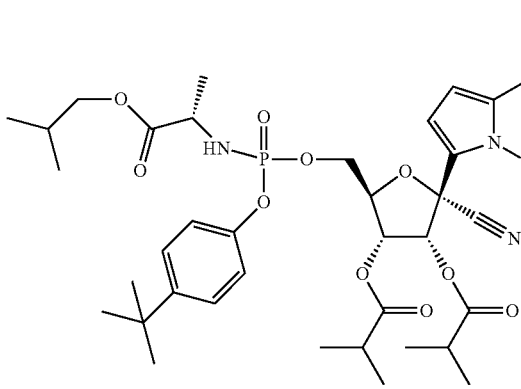

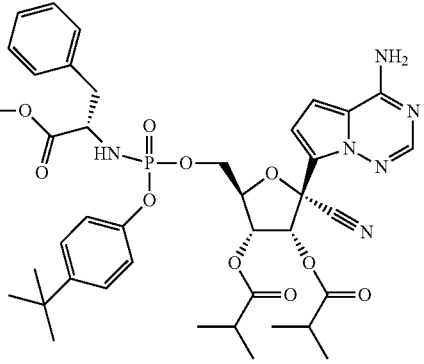

Example 122 was made in a similar fashion as example 114 except that example 118 was used instead of Intermediate D9. Mixture of stereoisomers: $^1$H NMR (400 MHz, Methanol-d4) δ 7.88 (s, 0.5H), 7.87 (s, 0.5H), 7.36-7.32 (m, 1H), 7.31-7.26 (m, 1H), 7.13-7.05 (m, 2H), 6.94-6.85 (m, 2H), 6.28 (d, J=5.9 Hz, 0.5H), 6.16 (d, J=5.9 Hz, 0.5H), 5.59-5.54 (m, 1H), 4.68-4.59 (m, 1H), 4.49-4.35 (m, 2H), 3.96-3.78 (m, 3H), 2.75-2.58 (m, 2H), 1.97-1.84 (m, 1H), 1.34-1.18 (m, 24H), 0.95-0.90 (m, 6H). 31P NMR (162 MHz, Methanol-d4) δ 3.81-3.56 (m). LCMS: MS m/z=771.8, 771.8 [M+1], tR=1.18, 1.20 min.

Example 123 was made in a similar fashion as example 114 except that example 119 was used instead of Intermediate D9. Mixture of stereoisomers: $^1$H NMR (400 MHz, Methanol-d4) δ 7.88 (s, 0.5H), 7.86 (s, 0.5H), 7.29-7.17 (m, 6H), 7.11-7.06 (m, 1H), 7.02-6.82 (m, 4H), 6.30 (d, J=6.0 Hz, 0.5H), 6.13 (d, J=5.9 Hz, 0.5H), 5.49-5.45 (m, 0.5H), 5.45-5.41 (m, 0.5H), 4.52-4.46 (m, 1H), 4.29-3.94 (m, 5H), 3.08-3.01 (m, 0.5H), 3.00-2.93 (m, 0.5H), 2.88-2.77 (m, 1H), 2.76-2.56 (m, 2H), 1.57-1.48 (m, 2H), 1.32-1.15 (m, 27H), 0.93-0.85 (m, 3H). 31P NMR (162 MHz, Methanol-d4) δ 3.84-3.46 (m, 0.5P), 3.39-2.94 (m, 0.5P). LCMS: MS m/z=875.5 [M+1], tR=1.32 min.

Example 124: ethyl ((((2R,3R,4R,5R)-5-(4-aminopyrrolo[2,1-f][1,2,4]triazin-7-yl)-5-cyano-3,4-bis((ethoxycarbonyl)oxy)tetrahydrofuran-2-yl)methoxy)(4-(tert-butyl)phenoxy)phosphoryl)-L-alaninate

Example 125: (2R,3R,4R,5R)-2-(4-aminopyrrolo[2,1-f][1,2,4]triazin-7-yl)-5-((((4-(tert-butyl)phenoxy)(((S)-1-(hexyloxy)-1-oxopropan-2-yl)amino)phosphoryl)oxy)methyl)-2-cyanotetrahydrofuran-3,4-diyl bis(2-methylpropanoate)

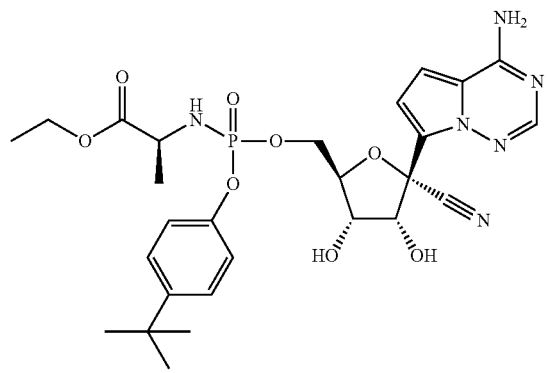

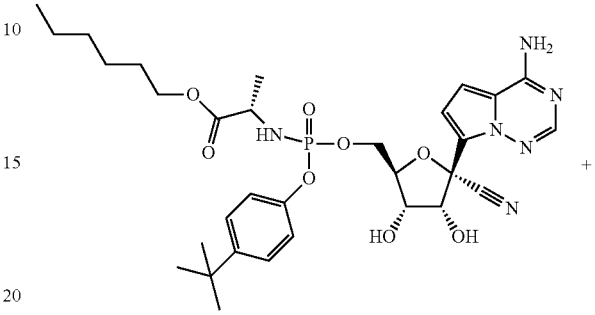

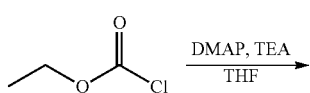

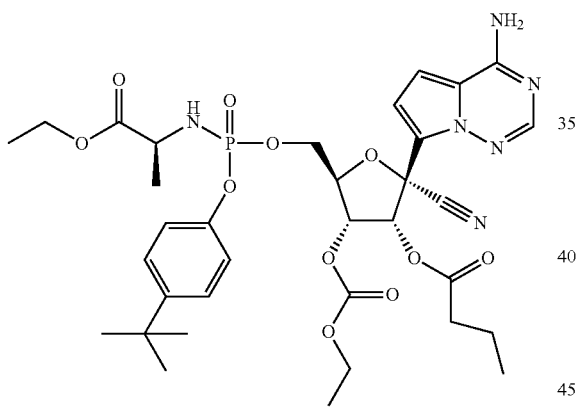

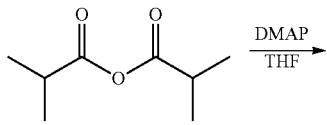

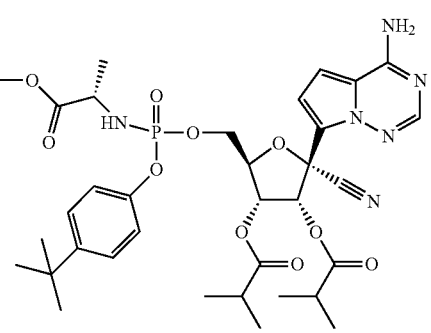

To a solution of ethyl (((((2R,3S,4R,5R)-5-(4-aminopyrrolo[2,1-f][1,2,4]triazin-7-yl)-5-cyano-3,4-dihydroxytetrahydrofuran-2-yl)methoxy)(4-(tert-butyl)phenoxy)phosphoryl)-L-alaninate (20 mg, 0.03 mmol) in THF (2 mL) was added TEA (9 µL, 0.06 mmol) and DMAP (0.5 mg, 0.005 mmol). After 5 minutes, ethyl carbonochloridate (0.07 mL, 0.07 mmol) was added as a solution in THF (0.5 mL). After 30 minutes, the reaction was quenched with water (0.5 mL) and concentrated. The product was purified by HPLC chromatograph (5-99% ACN in water) to afford example 124. Mixture of stereoisomers: $^1$H NMR (400 MHz, Methanol-d4) δ 7.88 (s, 0.5H), 7.87 (s, 0.5H), 7.38-7.33 (m, 1H), 7.32-7.27 (m, 1H), 7.12-7.06 (m, 2H), 6.97-6.90 (m, 2H), 6.20 (d, J=6.0 Hz, 0.5H), 6.11 (d, J=6.0 Hz, 0.5H), 5.50-5.45 (m, 1H), 4.69-4.63 (m, 1H), 4.52-4.34 (m, 2H), 4.31-4.04 (m, 6H), 3.94-3.83 (m, 0.5H), 3.82-3.73 (m, 0.5H), 1.40-1.17 (m, 21H). 31P NMR (162 MHz, Methanol-d4) δ 3.88-3.61 (m). LCMS: MS m/z=747.8, 747.8 [M+1], tR=1.04, 1.05 min.

Example 125 was made in a similar fashion as example 114 except that example 120 was used instead of Intermediate D9. Mixture of stereoisomers: $^1$H NMR (400 MHz, Methanol-d4) δ 7.89-7.86 (m, 1H), 7.37-7.32 (m, 1H), 7.31-7.26 (m, 1H), 7.13-7.05 (m, 2H), 6.95-6.84 (m, 2H), 6.28 (d, J=5.9 Hz, 0.5H), 6.16 (d, J=5.9 Hz, 0.5H), 5.59-5.53 (m, 1H), 4.68-4.59 (m, 1H), 4.49-4.33 (m, 2H), 4.14-4.00 (m, 2H), 3.94-3.84 (m, 0.5H), 3.84-3.75 (m, 0.5H), 2.76-2.59 (m, 2H), 1.66-1.54 (m, 2H), 1.41-1.14 (m, 30H), 0.94-0.86 (m, 3H). 31P NMR (162 MHz, Methanol-d4) δ 3.82-3.57 (m). LCMS: MS m/z=799.6, 799.6 [M+1], tR=1.26, 1.27 min.

Example 126: (2R,3R,4R,5R)-2-(4-aminopyrrolo[2,1-f][1,2,4]triazin-7-yl)-5-(((((4-(tert-butyl)phenoxy)(((S)-1-(2,2-dimethylbutoxy)-1-oxopropan-2-yl)amino)phosphoryl)oxy)methyl)-2-cyanotetrahydrofuran-3,4-diyl bis(2-methylpropanoate)

Example 127: 2-ethylbutyl ((S)-(((2R,3R,4R,5R)-5-(4-aminopyrrolo[2,1-f][1,2,4]triazin-7-yl)-5-cyano-3,4-bis((ethoxycarbonyl)oxy)tetrahydrofuran-2-yl)methoxy)(phenoxy)phosphoryl)-L-alaninate

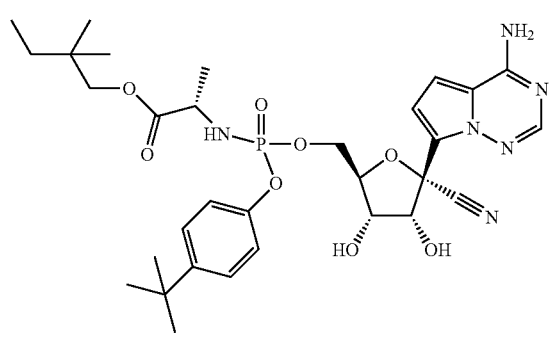

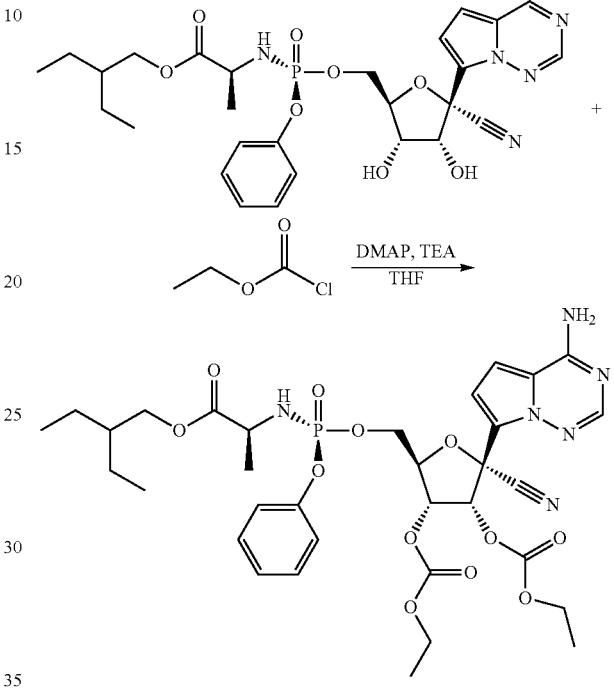

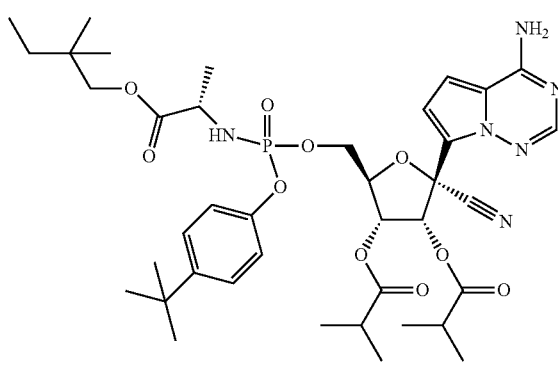

Example 126 was made in a similar fashion as example 114 except that example 121 was used instead of Intermediate D9. Mixture of stereoisomers: $^1$H NMR (400 MHz, Methanol-d4) δ 7.88 (s, 0.5H), 7.87 (s, 0.5H), 7.36-7.32 (m, 1H), 7.31-7.26 (m, 1H), 7.14-7.04 (m, 2H), 6.94-6.84 (m, 2H), 6.27 (d, J=5.9 Hz, 0.5H), 6.15 (d, J=5.9 Hz, 0.5H), 5.59-5.53 (m, 1H), 4.68-4.58 (m, 1H), 4.49-4.35 (m, 2H), 3.98-3.83 (m, 2H), 3.81-3.73 (m, 1H), 2.75-2.59 (m, 2H), 1.36-1.17 (m, 26H), 0.91-0.81 (m, 9H). 31P NMR (162 MHz, Methanol-d4) δ 3.82-3.58 (m). LCMS: MS m/z=799.8, 799.8 [M+1], tR=1.25, 1.26 min.

Example 127 was made in a similar fashion as example 124 except that 2-ethylbutyl ((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)-L-alaninate was used instead of ethyl ((((2R,3S,4R,5R)-5-(4-aminopyrrolo[2,1-f][1,2,4]triazin-7-yl)-5-cyano-3,4-dihydroxytetrahydrofuran-2-yl)methoxy)(4-(tert-butyl)phenoxy)phosphoryl)-L-alaninate. Individual isomers: $^1$H NMR (400 MHz, Methanol-d4) δ 7.87 (s, 1H), 7.34-7.26 (m, 2H), 7.22-7.13 (m, 3H), 6.93-6.87 (m, 2H), 6.13 (d, J=5.9 Hz, 1H), 5.49-5.45 (m, 1H), 4.67-4.57 (m, 1H), 4.49-4.35 (m, 2H), 4.31-4.14 (m, 4H), 4.09-4.02 (m, 1H), 4.01-3.86 (m, 2H), 1.54-1.45 (m, 1H), 1.40-1.26 (m, 13H), 0.89 (t, J=7.4 Hz, 6H). 31P NMR (162 MHz, Methanol-d4) δ 3.73-3.36 (m). LCMS: MS m/z=747.7 [M+1], tR=1.06 min.

Intermediate D18: 2-methoxy-2-methylpropyl ((naphthalen-1-yloxy)(perfluorophenoxy)phosphoryl)-L-alaninate

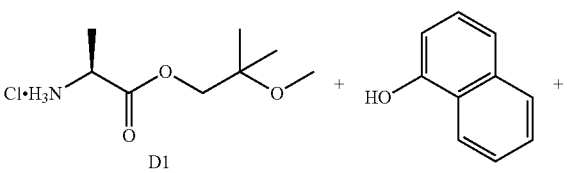

-continued

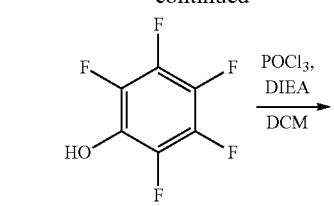

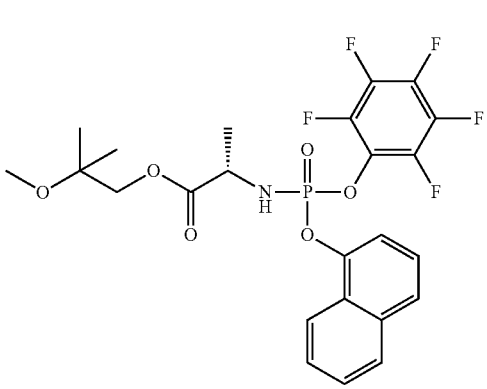

D18

Intermediate D18 was made in a similar fashion as intermediate D2 except that naphthalen-1-ol was used instead of intermediate 4-tert-butylphenol. $^1$H NMR (400 MHz, DMSO-d$_6$) δ 8.16-8.08 (m, 1H), 8.02-7.98 (m, 1H), 7.85-7.81 (m, 1H), 7.67-7.49 (m, 4H), 7.18-7.07 (m, 1H), 4.19-3.84 (m, 3H), 3.07 (d, J=5.9 Hz, 3H), 1.39-1.33 (m, 3H), 1.11-1.06 (m, 6H). $^{19}$F NMR (376 MHz, DMSO-d$_6$) δ −153.84−−154.48 (m, 2F), −160.47−−160.91 (m, 1F), −163.31−−163.75 (m, 2F). $^{31}$P NMR (162 MHz, DMSO-d$_6$) δ 1.25-0.97 (m, 0.5P), 0.83-0.55 (m, 0.5P).

Example 128: 2-methoxy-2-methylpropyl (((((2R,3S, 4R,5R)-5-(4-aminopyrrolo[2,1-f][1,2,4]triazin-7-yl)-5-cyano-3,4-dihydroxytetrahydrofuran-2-yl) methoxy)(naphthalen-1-yloxy)phosphoryl)-L-alaninate

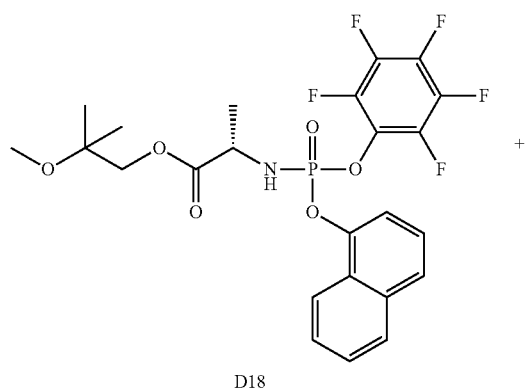

D18

-continued

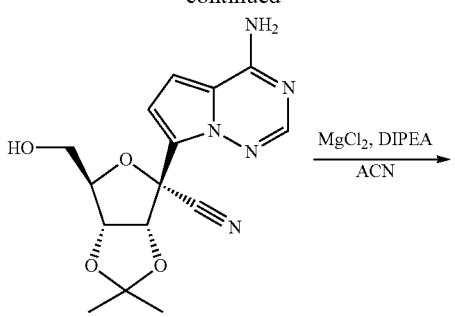

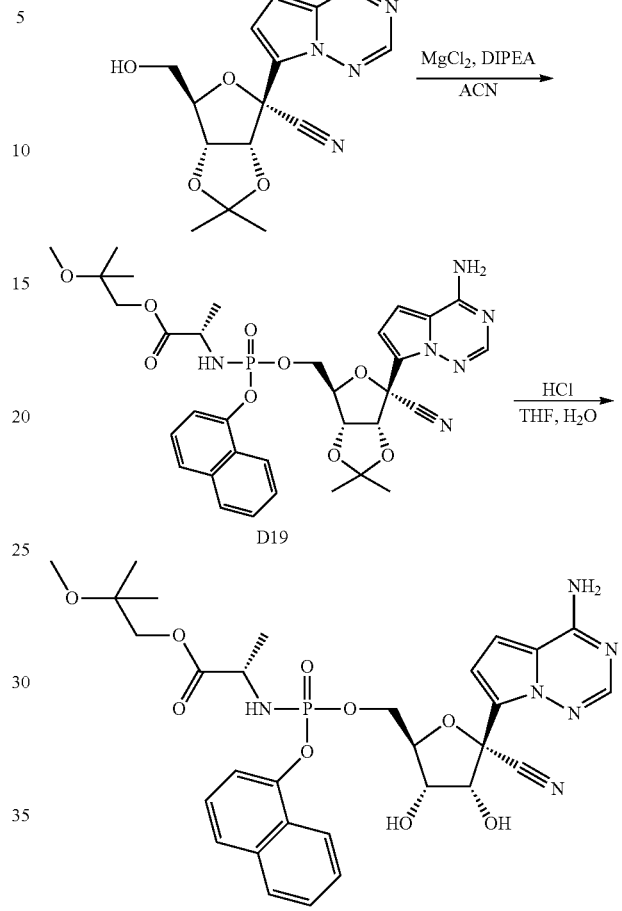

Example 128 was made in a similar fashion as example 111 except that intermediate D18 was used instead of intermediate D2. Intermediate D19: LCMS: MS m/z=695.3 [M+1], tR=1.24 min. Example 128, Mixture of stereoisomers: $^1$H NMR (400 MHz, Methanol-d4) δ 8.16-8.08 (m, 1H), 7.91-7.81 (m, 2H), 7.72-7.66 (m, 1H), 7.56-7.42 (m, 3H), 7.39-7.32 (m, 1H), 6.89-6.80 (m, 2H), 4.71 (d, J=5.4 Hz, 0.5H), 4.68 (d, J=5.6 Hz, 0.5H), 4.60 (s, 1H), 4.55-4.34 (m, 2H), 4.24-4.17 (m, 1H), 4.06-3.88 (m, 3H), 3.18 (s, 3H), 1.33-1.30 (m, 1.5H), 1.29-1.25 (m, 1.5H), 1.16-1.12 (m, 6H). 31P NMR (162 MHz, Methanol-d4) δ 4.20-4.05 (m). LCMS: MS m/z=694.8, 694.8 [M+1], tR=0.92, 0.94 min.

Intermediate D20: 2-ethylbutyl ((perfluorophenoxy) ((5,6,7,8-tetrahydronaphthalen-2-yl)oxy)phosphoryl)-L-alaninate

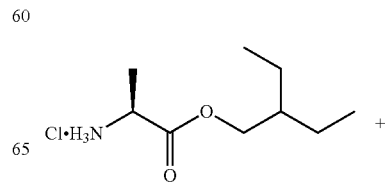

325

-continued

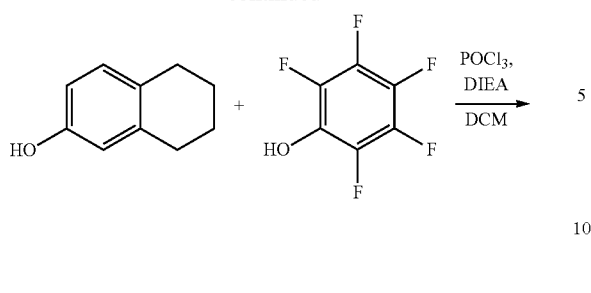

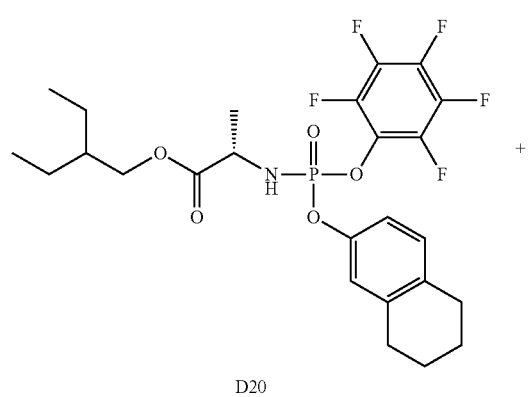

D20

Intermediate D20 was made in a similar fashion as intermediate D2 except that 5,6,7,8-tetrahydronaphthalen-2-ol was used instead of intermediate 4-tert-butylphenol and 2-ethylbutyl L-alaninate hydrochloride was used instead of D1. $^{1}$H NMR (400 MHz, Methanol-d4) δ 8.01-7.87 (m, 2H), 7.80-7.60 (m, 2H), 4.86-4.73 (m, 3H), 3.56-3.51 (m, 2H), 3.47-3.38 (m, 1H), 2.58-2.46 (m, 4H), 2.31-2.20 (m, 1H), 2.17-2.05 (m, 7H), 1.68-1.58 (m, 6H). $^{19}$F NMR (376 MHz, Methanol-d$_4$) δ −152.85−−153.56 (m, 2F), −159.72−−160.49 (m, 1F), −162.40−−163.07 (m, 2F). $^{31}$P NMR (162 MHz, Methanol-d4) δ 1.25-0.84 (m).

Example 129: 2-ethylbutyl ((((2R,3S,4R,5R)-5-(4-aminopyrrolo[2,1-f][1,2,4]triazin-7-yl)-5-cyano-3,4-dihydroxytetrahydrofuran-2-yl)methoxy)((5,6,7,8-tetrahydronaphthalen-2-yl)oxy)phosphoryl)-L-alaninate

326

-continued

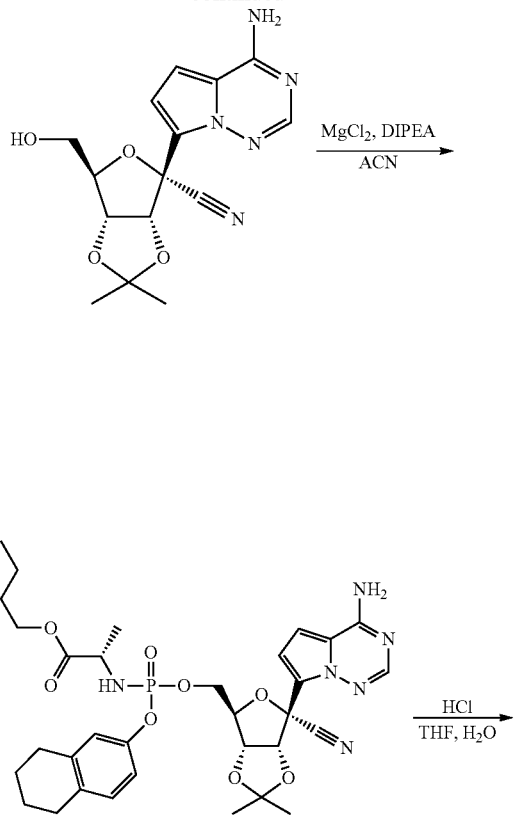

D21

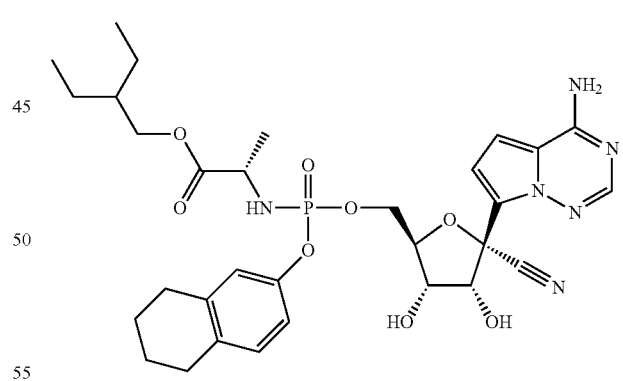

Example 129 was made in a similar fashion as example 111 except that intermediate D20 was used instead of intermediate D2. Mixture of stereoisomers: $^{1}$H NMR (400 MHz, Methanol-d4) δ 7.89-7.85 (m, 1H), 6.96-6.77 (m, 5H), 4.81-4.75 (m, 1H), 4.45-4.35 (m, 2H), 4.35-4.25 (m, 1H), 4.23-4.18 (m, 1H), 4.06-3.82 (m, 3H), 2.74-2.61 (m, 4H), 1.80-1.70 (m, 4H), 1.51-1.39 (m, 1H), 1.37-1.25 (m, 7H), 0.92-0.83 (m, 6H). 31P NMR (162 MHz, Methanol-d4) δ 3.95-3.64 (m). LCMS: MS m/z=696.8, 696.8 [M+1], tR=1.12, 1.14 min.

Example 130: (2R,3R,4R,5R)-2-(4-aminopyrrolo[2,1-f][1,2,4]triazin-7-yl)-5-((((4-(tert-butyl)phenoxy)(((S)-1-(2-methoxy-2-methylpropoxy)-1-oxopropan-2-yl)amino)phosphoryl)oxy)methyl)-2-cyanotetrahydrofuran-3,4-diyl dipropionate Example 131: (2R,3R,4R,5R)-2-(4-aminopyrrolo[2,1-f][1,2,4]triazin-7-yl)-5-((((4-(tert-butyl)phenoxy)(((S)-1-(2-methoxy-2-methylpropoxy)-1-oxopropan-2-yl)amino)phosphoryl)oxy)methyl)-2-cyanotetrahydrofuran-3,4-diyl diacetate

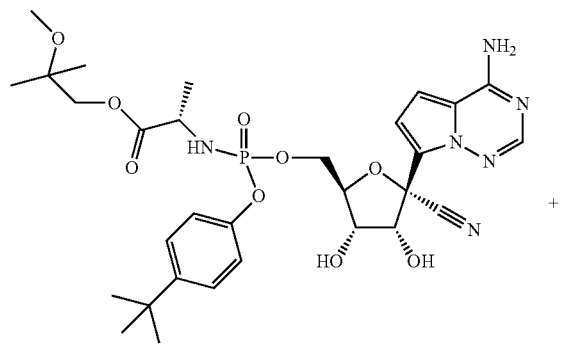

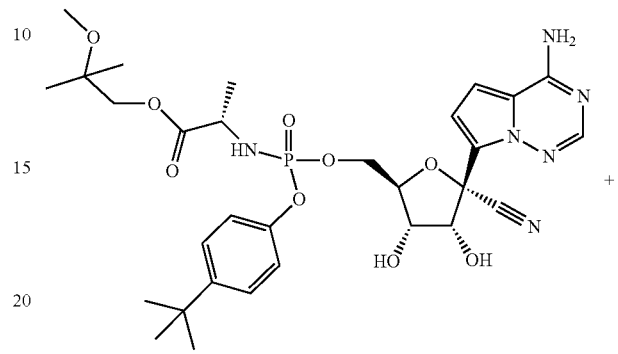

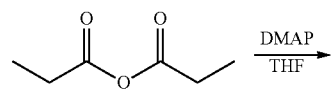

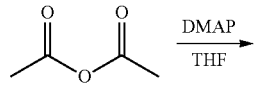

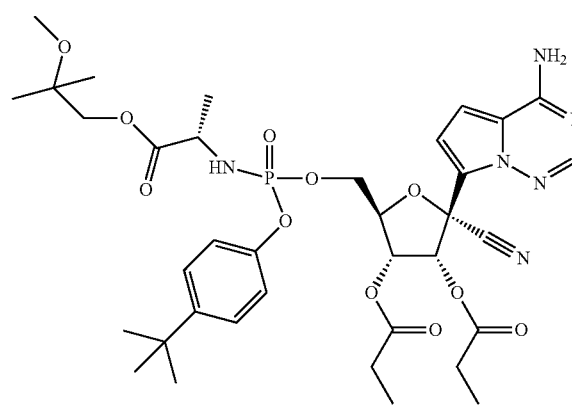

Example 130 was made in a similar fashion as Example 107 except that example 111 was used instead of cyclobutyl (((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)-L-alaninate. Mixture of stereoisomers: $^1$H NMR (400 MHz, Methanol-d4) δ 7.91-7.83 (m, 1H), 7.38-7.22 (m, 2H), 7.16-7.02 (m, 2H), 7.01-6.86 (m, 2H), 6.28 (d, J=6.0 Hz, 0.5H), 6.18 (d, J=5.9 Hz, 0.5H), 5.64-5.49 (m, 1H), 4.70-4.53 (m, 1H), 4.48-4.27 (m, 2H), 4.22-4.02 (m, 1H), 4.00-3.84 (m, 2H), 3.24-3.17 (m, 3H), 2.54-2.38 (m, 2H), 2.41-2.28 (m, 2H), 1.37-1.07 (m, 24H). 31P NMR (162 MHz, Methanol-d4) δ 3.80-3.49 (m). LCMS: MS m/z=772.8, 772.8 [M+1], tR=1.07, 1.09 min.

Example 131 was made in a similar fashion as example 130 except that acetic anhydride was used instead of propionic anhydride. Mixture of stereoisomers: $^1$H NMR (400 MHz, Methanol-d4) δ 7.92-7.86 (m, 1H), 7.40-7.24 (m, 2H), 7.14-7.04 (m, 2H), 6.95-6.86 (m, 2H), 6.27 (d, J=6.0 Hz, 0.5H), 6.17 (d, J=6.0 Hz, 0.5H), 5.60-5.51 (m, 1H), 4.68-4.60 (m, 1H), 4.48-4.36 (m, 2H), 4.09-4.03 (m, 1H), 3.99-3.84 (m, 2H), 3.21-3.20 (m, 3H), 2.14 (s, 3H), 2.04 (s, 3H), 1.33-1.28 (m, 12H), 1.20-1.14 (m, 6H). 31P NMR (162 MHz, Methanol-d4) δ 3.81-3.57 (m). LCMS: MS m/z=800.8 [M+1], tR=1.13 min.

Example 132: (2R,3R,4R,5R)-2-(4-aminopyrrolo[2,1-f][1,2,4]triazin-7-yl)-2-cyano-5-(((((S)-1-(2-ethylbutoxy)-1-oxopropan-2-yl)amino)((5,6,7,8-tetrahydronaphthalen-2-yl)oxy)phosphoryl)oxy)methyl)tetrahydrofuran-3,4-diyl bis(2-methylpropanoate)

Example 133: (2R,3R,4R,5R)-2-(4-aminopyrrolo[2,1-f][1,2,4]triazin-7-yl)-2-cyano-5-(((((S)-1-(2-methoxy-2-methylpropoxy)-1-oxopropan-2-yl)amino)(naphthalen-1-yloxy)phosphoryl)oxy)methyl)tetrahydrofuran-3,4-diyl bis(2-methylpropanoate)

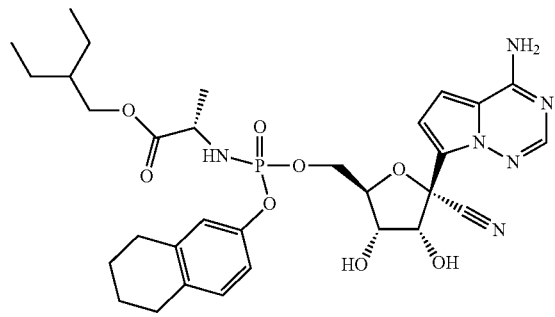

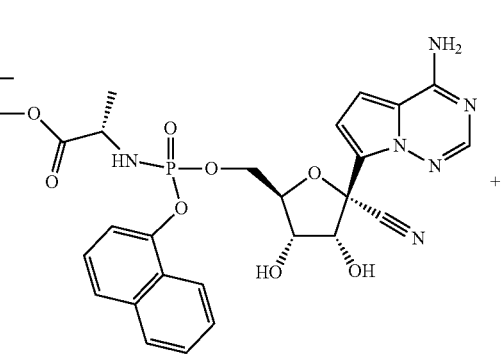

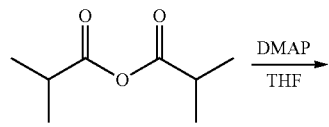

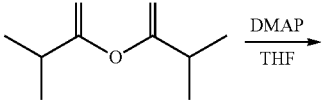

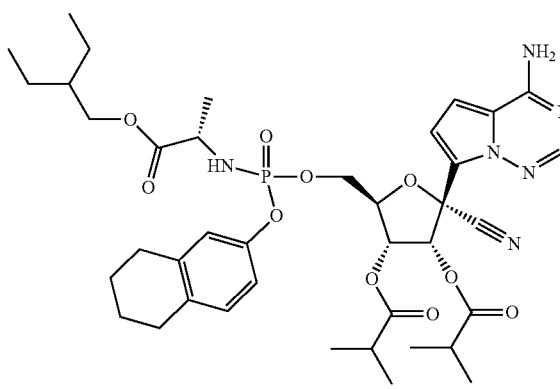

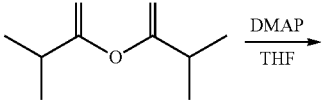

Example 132 was made in a similar fashion as example 114 except that example 129 was used instead of Intermediate D9. Mixture of stereoisomers: ¹H NMR (400 MHz, Methanol-d4) δ 7.89-7.84 (m, 1H), 6.98-6.79 (m, 5H), 6.25 (d, J=5.9 Hz, 0.5H), 6.15 (d, J=5.9 Hz, 0.5H), 5.58-5.51 (m, 1H), 4.67-4.62 (m, 0.5H), 4.62-4.58 (m, 0.5H), 4.48-4.34 (m, 2H), 4.13-3.95 (m, 2H), 3.95-3.87 (m, 0.5H), 3.86-3.77 (m, 0.5H), 2.75-2.56 (m, 6H), 1.83-1.70 (m, 4H), 1.55-1.44 (m, 1H), 1.41-1.30 (m, 6H), 1.29-1.15 (m, 13H), 0.93-0.85 (m, 6H). 31P NMR (162 MHz, Methanol-d4) δ 3.77-3.49 (m). LCMS: MS m/z=796.80, 796.8 [M+1], tR=1.24, 1.25 min.

Example 133 was made in a similar fashion as example 114 except that example 128 was used instead of Intermediate D9. Mixture of stereoisomers: ¹H NMR (400 MHz, Methanol-d4) δ 8.15-8.07 (m, 1H), 7.91-7.85 (m, 1H), 7.82 (s, 0.5H), 7.80 (s, 0.5H), 7.73-7.65 (m, 1H), 7.57-7.28 (m, 4H), 6.86 (s, 1H), 6.76-6.71 (m, 1H), 6.30 (d, J=5.9 Hz, 0.5H), 6.17 (d, J=5.9 Hz, 0.5H), 5.63-5.56 (m, 1H), 4.69-4.63 (m, 1H), 4.57-4.45 (m, 2H), 4.08-3.84 (m, 3H), 3.20-3.14 (m, 3H), 2.75-2.57 (m, 2H), 1.33-1.11 (m, 21H). 31P NMR (162 MHz, Methanol-d4) δ 4.11-3.89 (m, 0.5P), 3.87-3.67 (m, 0.5P).

Example 134: (2R,3R,4R,5R)-2-(4-aminopyrrolo[2,1-f][1,2,4]triazin-7-yl)-2-cyano-5-(((((S)-1-(cyclobutylmethoxy)-1-oxopropan-2-yl)amino)(phenoxy)phosphoryl)oxy)methyl)tetrahydrofuran-3,4-diyl dipropionate

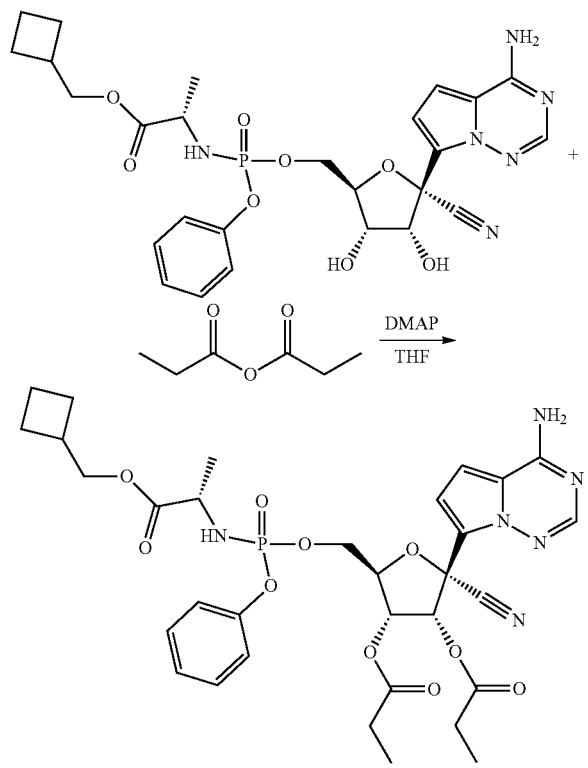

Example 134 was made in a similar fashion as example 107 except that cyclobutylmethyl (((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)-L-alaninate was used instead of cyclobutyl (((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)-L-alaninate. Mixture of stereoisomers: ¹H NMR (400 MHz, Methanol-d4) δ 7.90-7.83 (m, 1H), 7.36-7.25 (m, 2H), 7.24-7.10 (m, 3H), 6.97-6.82 (m, 2H), 6.32 (d, J=6.0 Hz, 0.5H), 6.22 (d, J=6.0 Hz, 0.5H), 5.63-5.55 (m, 1H), 4.64-4.59 (m, 1H), 4.49-4.35 (m, 2H), 4.12-3.96 (m, 3H), 2.66-2.56 (m, 1H), 2.55-2.40 (m, 4H), 2.03 (s, 2H), 1.96-1.85 (m, 2H), 1.81-1.72 (m, 2H), 1.39-1.28 (m, 3H), 1.23-1.11 (m, 6H). 31P NMR (162 MHz, Methanol-d4) δ 3.90-3.73 (m).

Intermediate D22: 2-ethylbutyl ((perfluorophenoxy)((5,6,7,8-tetrahydronaphthalen-2-yl)oxy)phosphoryl)-L-alaninate

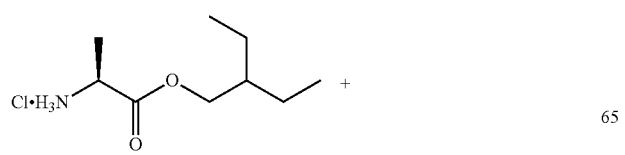

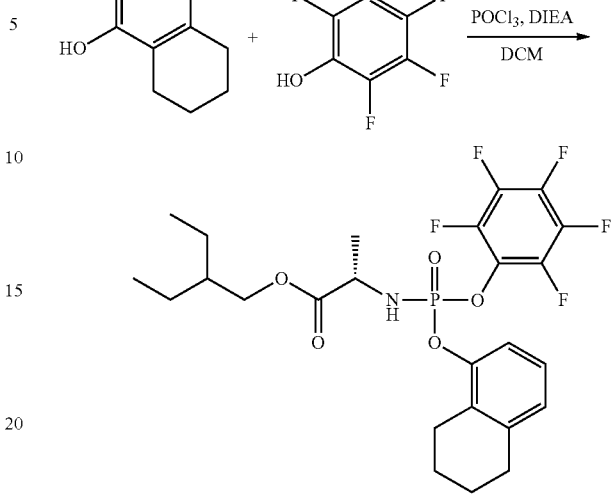

Intermediate D22 was made in a similar fashion as intermediate D20 except that 5,6,7,8-tetrahydronaphthalen-1-ol was used instead of 5,6,7,8-tetrahydronaphthalen-2-ol.

Example 135 and Example 136: 2-ethylbutyl ((S)-((((2R,3S,4R,5R)-5-(4-aminopyrrolo[2,1-f][1,2,4]triazin-7-yl)-5-cyano-3,4-dihydroxytetrahydrofuran-2-yl)methoxy)((5,6,7,8-tetrahydronaphthalen-1-yl)oxy)phosphoryl)-L-alaninate

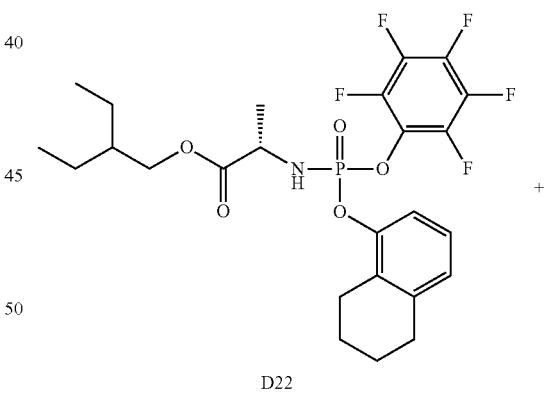

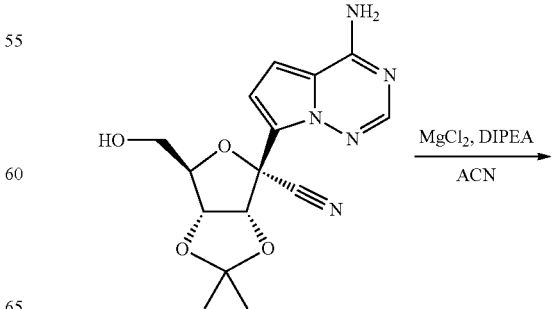

333
-continued

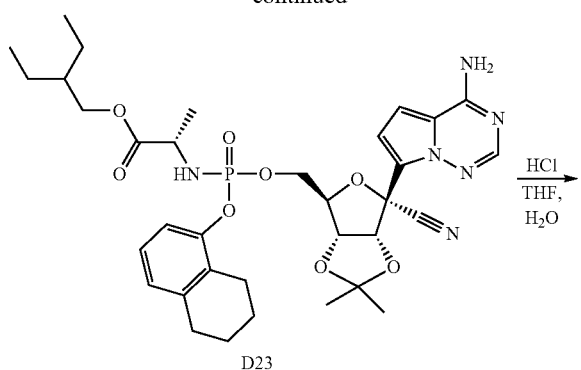

D23

Example 137: (2R,3R,4R,5R)-2-(4-aminopyrrolo[2,1-f][1,2,4]triazin-7-yl)-5-((((4-(tert-butyl)phenoxy)(((S)-1-isobutoxy-1-oxopropan-2-yl)amino)phosphoryl)oxy)methyl)-2-cyanotetrahydrofuran-3,4-diyl diacetate

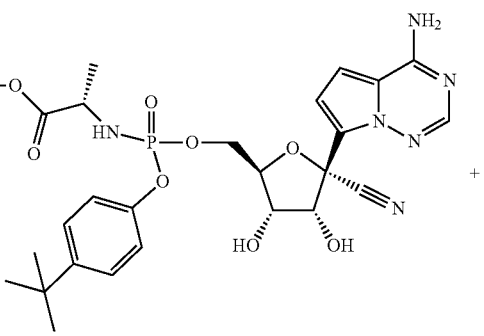

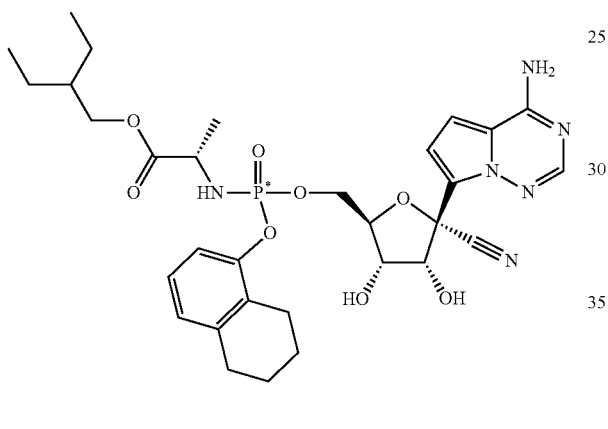

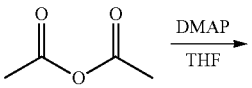

Example 135 and 136 was made in a similar fashion as example 111 except that intermediate D22 was used instead of intermediate D2. Intermediate D23: LCMS: MS m/z=698.3, 698.3, tR=1.12, 1.14 min.

Individual isomers were separated by preparatory HPLC (Gemini 5 um NX-C18 110A LC column 100×30 mm, 95% to 0% water acetonitrile gradient).

Example 135, first eluting peak: 1H NMR (400 MHz, Methanol-d4) δ 7.85 (s, 1H), 7.08-7.03 (m, 1H), 7.00-6.94 (m, 1H), 6.92-6.84 (m, 3H), 4.76 (d, J=5.6 Hz, 1H), 4.46-4.37 (m, 2H), 4.36-4.27 (m, 1H), 4.25-4.19 (m, 1H), 4.08-3.95 (m, 2H), 3.93-3.80 (m, 1H), 2.80-2.58 (m, 4H), 1.84-1.68 (m, 4H), 1.55-1.45 (m, 1H), 1.40-1.31 (m, 4H), 1.30-1.25 (m, 3H), 0.93-0.86 (m, 6H). 31P NMR (162 MHz, Methanol-d4) δ 3.81-3.59 (m). LCMS: MS m/z=657.2, tR=0.96 min.

Example 136, second eluting peak: 1H NMR (400 MHz, Methanol-d4) δ 7.88 (s, 1H), 7.10-7.04 (m, 1H), 6.98-6.93 (m, 1H), 6.91-6.84 (m, 3H), 4.74 (d, J=5.4 Hz, 1H), 4.42-4.34 (m, 2H), 4.33-4.25 (m, 1H), 4.19 (t, J=5.5 Hz, 1H), 4.08-4.01 (m, 1H), 4.00-3.89 (m, 2H), 2.79-2.68 (m, 4H), 1.83-1.71 (m, 4H), 1.52-1.42 (m, 1H), 1.39-1.29 (m, 7H), 0.88 (t, J=7.5 Hz, 6H). 31P NMR (162 MHz, Methanol-d4) δ 3.77-3.55 (m). LCMS: MS m/z=657.2, tR=0.98 min.

Example 137 was made in a similar fashion as Example 107 except that example 118 was used instead of cyclobutyl ((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)-L-alaninate and acetic anhydride was used instead of 3-methyl butanoic anhydride. Mixture of stereoisomers: 1H NMR (400 MHz, Methanol-d4) δ 7.88 (s, 0.5H), 7.86 (s, 0.5H), 7.36-7.32 (m, 1H), 7.31-7.26 (m, 1H), 7.11-7.05 (m, 2H), 6.94-6.89 (m, 2H), 6.28 (d, J=6.0 Hz, 0.5H), 6.19 (d, J=6.0 Hz, 0.5H), 5.58-5.52 (m, 1H), 4.66-4.58 (m, 1H), 4.49-4.32 (m, 2H), 3.95-3.77 (m, 3H), 2.18-2.16 (m, 3H), 2.14 (s, 3H), 1.95-1.83 (m, 1H), 1.33-1.28 (m, 10.5H), 1.23-1.19 (m, 1.5H), 0.91 (t, J=6.5 Hz, 6H). 31P NMR (162 MHz, Methanol-d4) δ 3.85-3.58 (m). LCMS: MS m/z=715.2, 715.2 [M+1], tR=1.04, 1.06 min.

Example 138: (2R,3R,4R,5R)-2-(4-aminopyrrolo[2,1-f][1,2,4]triazin-7-yl)-5-((((4-(tert-butyl)phenoxy)(((S)-1-isobutoxy-1-oxopropan-2-yl)amino)phosphoryl)oxy)methyl)-2-cyanotetrahydrofuran-3,4-diyl dipropionate Example 139: (2R,3R,4R,5R)-2-(4-aminopyrrolo[2,1-f][1,2,4]triazin-7-yl)-5-((((4-(tert-butyl)phenoxy)(((S)-1-isobutoxy-1-oxopropan-2-yl)amino)phosphoryl)oxy)methyl)-2-cyanotetrahydrofuran-3,4-diyl bis(3-methylbutanoate)

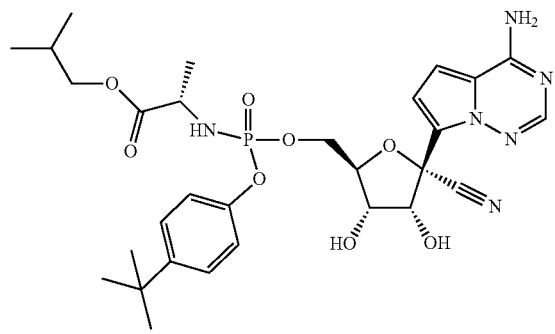

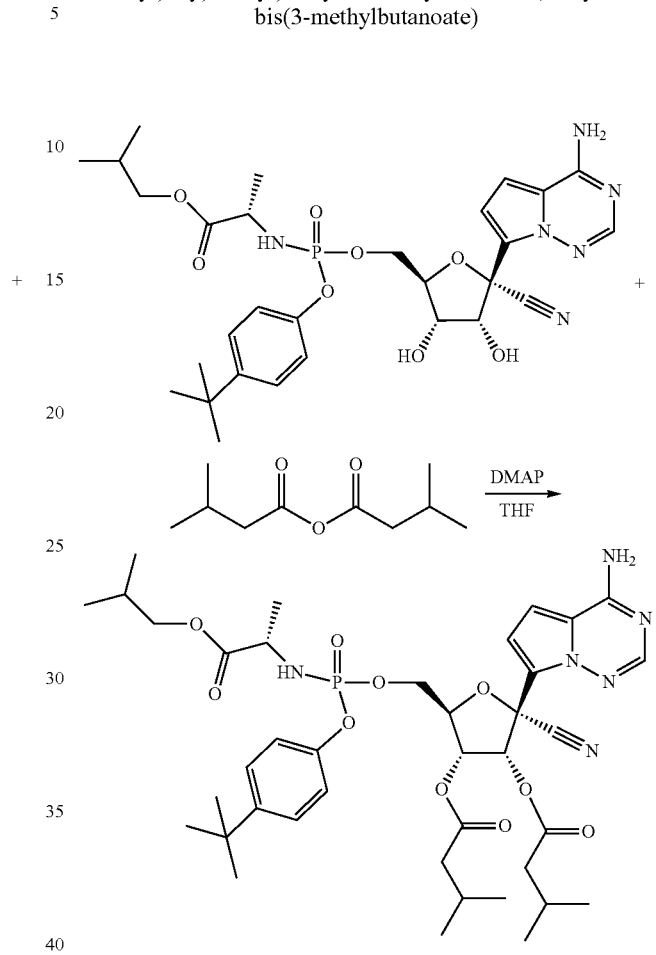

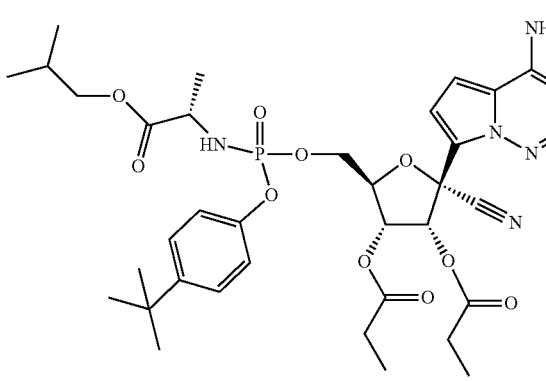

Example 138 was made in a similar fashion as example 137 except that proprionic anhydride was used instead of acetic anhydride. Mixture of stereoisomers: ¹H NMR (400 MHz, Methanol-d4) δ 7.87 (s, 0.5H), 7.86 (s, 0.5H), 7.37-7.32 (m, 1H), 7.31-7.26 (m, 1H), 7.13-7.04 (m, 2H), 6.94-6.87 (m, 2H), 6.29 (d, J=6.0 Hz, 0.5H), 6.19 (d, J=6.0 Hz, 0.5H), 5.61-5.53 (m, 1H), 4.71-4.57 (m, 1H), 4.48-4.33 (m, 2H), 3.96-3.76 (m, 3H), 2.52-2.40 (m, 4H), 1.96-1.85 (m, 1H), 1.34-1.11 (m, 18H), 0.91 (t, J=6.7 Hz, 6H). 31P NMR (162 MHz, Methanol-d4) δ 3.81-3.58 (m). LCMS: MS m/z=743.2, 743.2 [M+1], tR=1.12, 1.13 min.

Example 139 was made in a similar fashion as example 137 except that 3-methyl butanoic anhydride was used instead of acetic anhydride. Mixture of stereoisomers: ¹H NMR (400 MHz, Methanol-d4) δ 7.88 (s, 0.5H), 7.86 (s, 0.5H), 7.37-7.32 (m, 1H), 7.31-7.27 (m, 1H), 7.13-7.06 (m, 2H), 6.93-6.87 (m, 2H), 6.36 (d, J=6.0 Hz, 0.5H), 6.25 (d, J=6.0 Hz, 0.5H), 5.60-5.54 (m, 1H), 4.66-4.57 (m, 1H), 4.51-4.34 (m, 2H), 3.95-3.78 (m, 3H), 2.36-2.27 (m, 4H), 2.22-2.04 (m, 2H), 1.97-1.85 (m, 1H), 1.34-1.27 (m, 10.5H), 1.24-1.20 (m, 1.5H), 1.05-1.00 (m, 6H), 0.97-0.89 (m, 12H). 31P NMR (162 MHz, Methanol-d4) δ 3.79-3.54 (m). LCMS: MS m/z=799.4, 799.4 [M+1], tR=1.14, 1.16 min.

Intermediate D24: 2-ethylbutyl ((4-(cyclohexyloxy)phenoxy)(perfluorophenoxy)phosphoryl)-L-alaninate

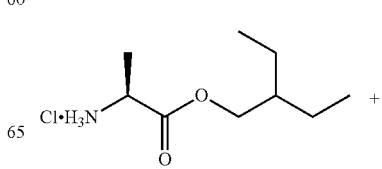

337
-continued

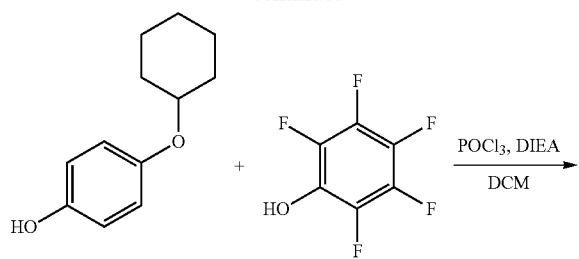

338
-continued

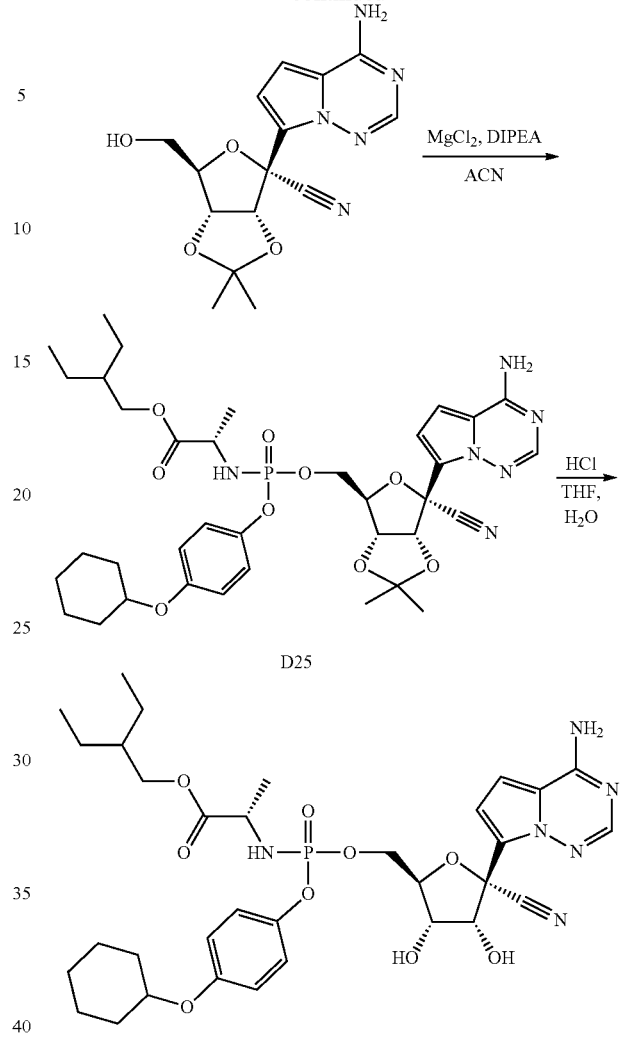

Intermediate D24 was made in a similar fashion as intermediate D20 except that 4-(cyclohexyloxy)phenol was used instead of 5,6,7,8-tetrahydronaphthalen-2-ol. $^1$H NMR (400 MHz, DMSO-$d_6$) δ 7.16-7.09 (m, 2H), 6.97-6.92 (m, 2H), 6.88-6.79 (m, 1H), 4.33-4.24 (m, 1H), 4.11-3.90 (m, 3H), 1.94-1.88 (m, 2H), 1.74-1.66 (m, 2H), 1.58-1.22 (m, 14H), 0.88-0.78 (m, 6H). $^{19}$F NMR (376 MHz, DMSO-$d_6$) δ −154.09−−154.51 (m, 2F), −160.59−−161.06 (m, 1F), −163.44−−163.95 (m, 2F). $^{31}$P NMR (162 MHz, DMSO-$d_6$) δ 1.17-0.78 (m). LCMS: MS m/z=594.2 [M+1], tR=1.37 min.

Example 140: 2-ethylbutyl ((((2R,3S,4R,5R)-5-(4-aminopyrrolo[2,1-f][1,2,4]triazin-7-yl)-5-cyano-3,4-dihydroxytetrahydrofuran-2-yl)methoxy)(4-(cyclohexyloxy)phenoxy)phosphoryl)-L-alaninate

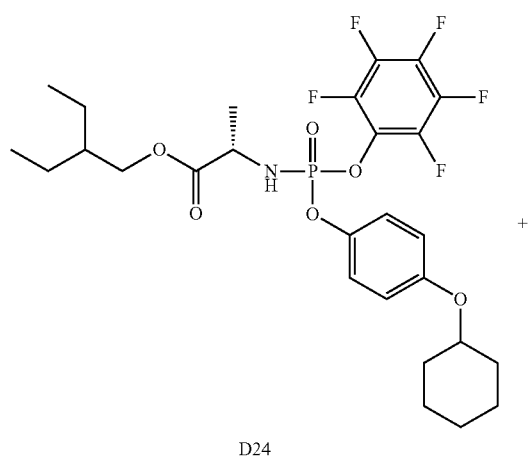

Example 140 was made in a similar fashion as example 111 except that intermediate D24 was used instead of intermediate D2. Mixture of stereoisomers: $^1$H NMR (400 MHz, Methanol-d4) δ 7.89 (s, 0.5H), 7.88 (s, 0.5H), 7.13-7.06 (m, 1H), 7.06-7.01 (m, 1H), 6.97-6.90 (m, 2H), 6.85-6.76 (m, 2H), 4.81-4.76 (m, 1H), 4.47-4.35 (m, 2H), 4.34-4.14 (m, 2H), 4.09-3.82 (m, 3H), 3.37-3.35 (m, 1H), 2.01-1.90 (m, 2H), 1.84-1.74 (m, 2H), 1.65-1.55 (m, 1H), 1.55-1.22 (m, 13H), 0.96-0.84 (m, 6H). 31P NMR (162 MHz, Methanol-d4) δ 4.23-3.99 (m). LCMS: MS m/z=701.3, 701.3 [M+1], tR=1.03, 1.05 min.

Intermediate D26: 2-methoxyethyl L-alaninate hydrochloride

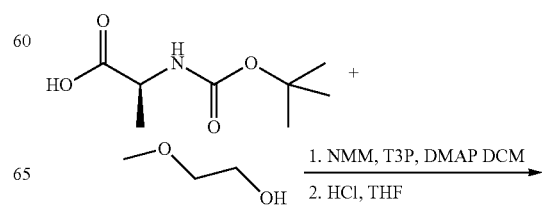

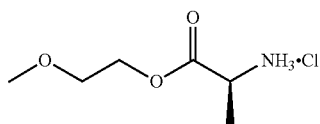

Example D26 was made in a similar fashion as intermediate D1 except that 2-methoxyethanol was used instead of 2-methyl, 2-methoxy-1-propanol. $^1$H NMR (400 MHz, DMSO-$d_6$) δ 8.46 (s, 3H), 4.35-4.26 (m, 2H), 4.17-4.07 (m, 1H), 3.38 (s, 2H), 3.27 (s, 3H), 1.41 (d, J=7.1 Hz, 3H).

Intermediate D27: 2-methoxyethyl ((4-(tert-butyl)phenoxy)(perfluorophenoxy)phosphoryl)-L-alaninate

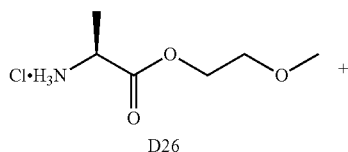

Intermediate D27 was made in a similar fashion as intermediate D2 except that intermediate D26 was used instead of intermediate D1. LCMS: MS m/z=526.1 [M+1], tR=1.16 min.

Example 141: 2-methoxyethyl ((((2R,3S,4R,5R)-5-(4-aminopyrrolo[2,1-f][1,2,4]triazin-7-yl)-5-cyano-3,4-dihydroxytetrahydrofuran-2-yl)methoxy)(4-(tert-butyl)phenoxy)phosphoryl)-L-alaninate

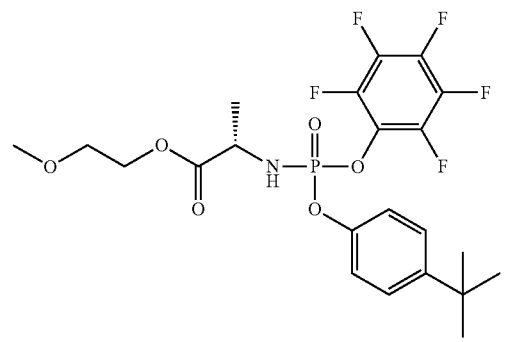

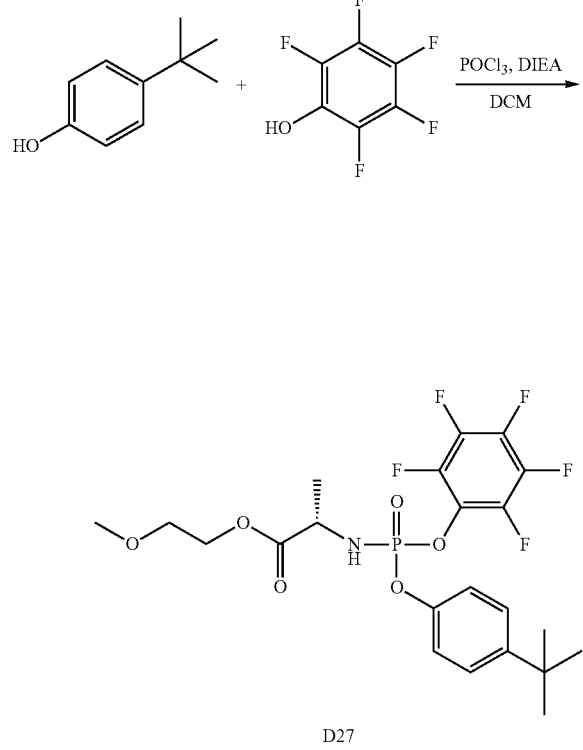

Example 141 was made in a similar fashion as example 130 except that intermediate D27 was used instead of intermediate D2. Intermediate D28: LCMS: MS m/z=673.2, 673.2 [M+1], tR=0.94, 0.97 min. Compound 141, Mixture of stereoisomers: $^1$H NMR (400 MHz, Methanol-d4) δ 7.89 (s, 0.5H), 7.87 (s, 0.5H), 7.35-7.26 (m, 2H), 7.12-7.04 (m, 2H), 6.97-6.90 (m, 2H), 4.83-4.58 (m, 1H), 4.48-4.37 (m, 2H), 4.35-4.27 (m, 1H), 4.25-4.15 (m, 3H), 3.96-3.83 (m, 1H), 3.62-3.55 (m, 2H), 3.38-3.34 (m, 3H), 1.33-1.25 (m, 12H). 31P NMR (162 MHz, Methanol-d4) δ 4.00-3.79 (m, 0.5P), 3.78-3.64 (m, 0.5P). LCMS: MS m/z=633.2, 633.2 [M+1], tR=0.81, 0.82 min.

Intermediate D29: cyclohexyl ((4-(tert-butyl)phenoxy)(perfluorophenoxy)phosphoryl)-L-alaninate

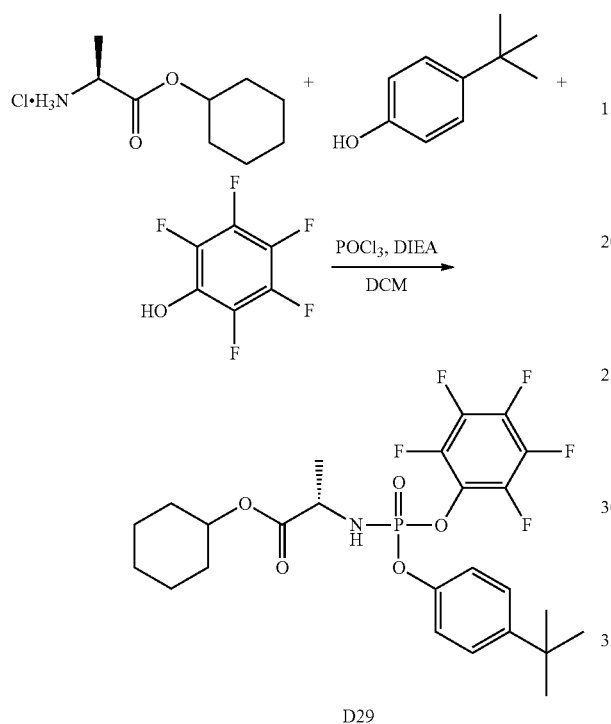

Intermediate D29 was made in a similar fashion as intermediate D2 except that intermediate cyclohexyl L-alaninate hydrochloride was used instead of intermediate D1. LCMS: MS m/z=550.2 [M+1], tR=1.33 min.

Example 142: cyclohexyl ((((2R,3S,4R,5R)-5-(4-aminopyrrolo[2,1-f][1,2,4]triazin-7-yl)-5-cyano-3,4-dihydroxytetrahydrofuran-2-yl)methoxy)(4-(tert-butyl)phenoxy)phosphoryl)-L-alaninate

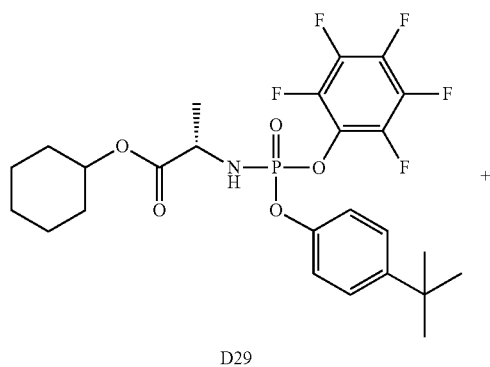

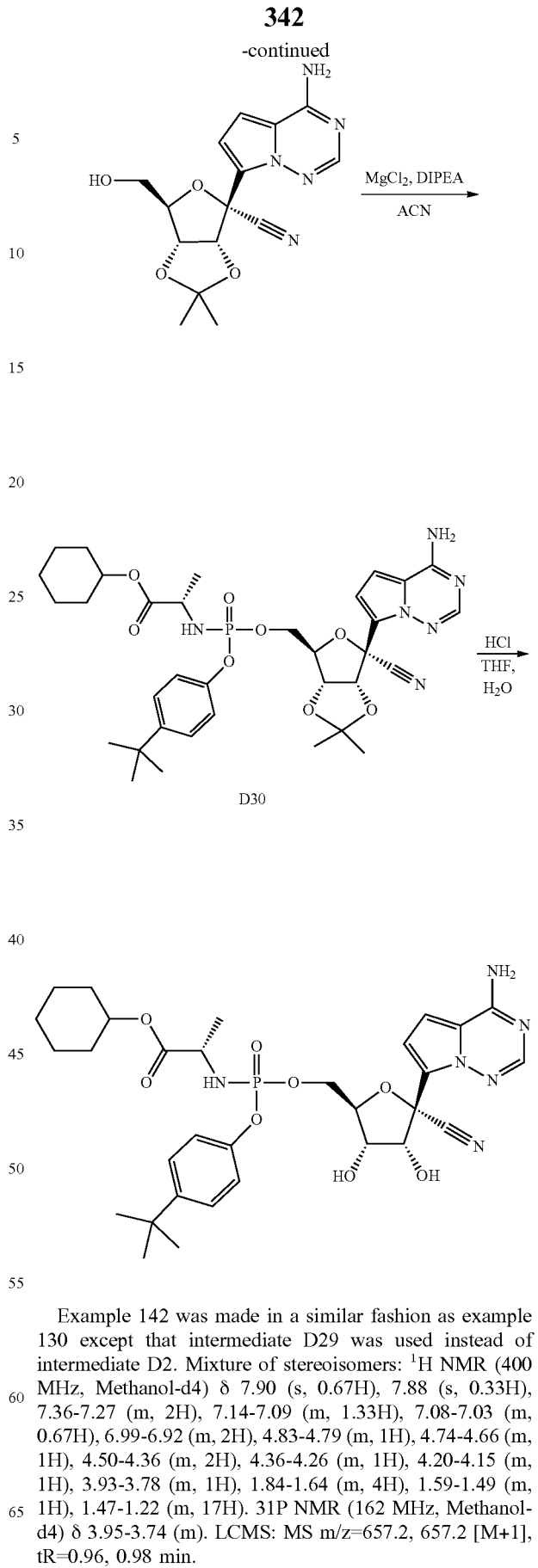

Example 142 was made in a similar fashion as example 130 except that intermediate D29 was used instead of intermediate D2. Mixture of stereoisomers: $^1$H NMR (400 MHz, Methanol-d4) δ 7.90 (s, 0.67H), 7.88 (s, 0.33H), 7.36-7.27 (m, 2H), 7.14-7.09 (m, 1.33H), 7.08-7.03 (m, 0.67H), 6.99-6.92 (m, 2H), 4.83-4.79 (m, 1H), 4.74-4.66 (m, 1H), 4.50-4.36 (m, 2H), 4.36-4.26 (m, 1H), 4.20-4.15 (m, 1H), 3.93-3.78 (m, 1H), 1.84-1.64 (m, 4H), 1.59-1.49 (m, 1H), 1.47-1.22 (m, 17H). 31P NMR (162 MHz, Methanol-d4) δ 3.95-3.74 (m). LCMS: MS m/z=657.2, 657.2 [M+1], tR=0.96, 0.98 min.

Example 143: (2R,3R,4R,5R)-2-(4-aminopyrrolo[2,1-f][1,2,4]triazin-7-yl)-2-cyano-5-((((S)-(((S)-1-(2-ethylbutoxy)-1-oxopropan-2-yl)amino)((5,6,7,8-tetrahydronaphthalen-1-yl)oxy)phosphoryl)oxy)methyl)tetrahydrofuran-3,4-diyl diacetate Example 144: (2R,3R,4R,5R)-2-(4-aminopyrrolo[2,1-f][1,2,4]triazin-7-yl)-2-cyano-5-((((S)-(((S)-1-(2-ethylbutoxy)-1-oxopropan-2-yl)amino)((5,6,7,8-tetrahydronaphthalen-1-yl)oxy)phosphoryl)oxy)methyl)tetrahydrofuran-3,4-diyl bis(2-methylpropanoate)

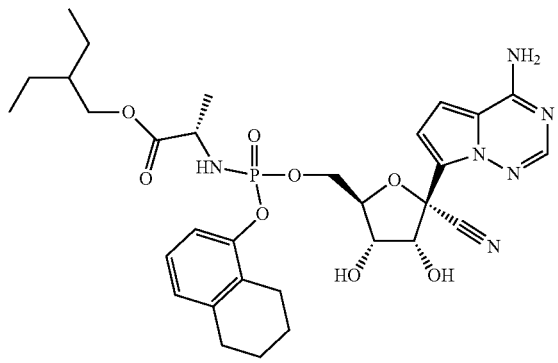

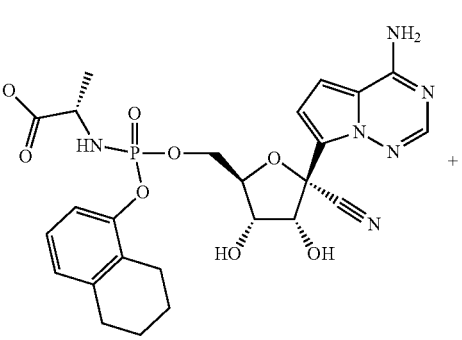

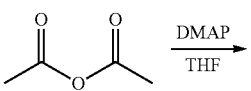

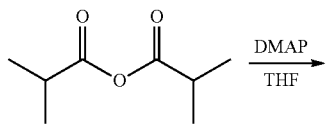

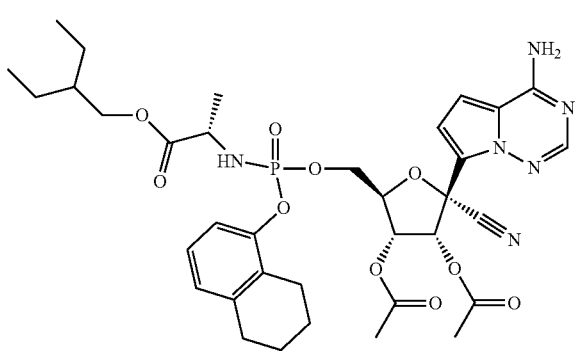

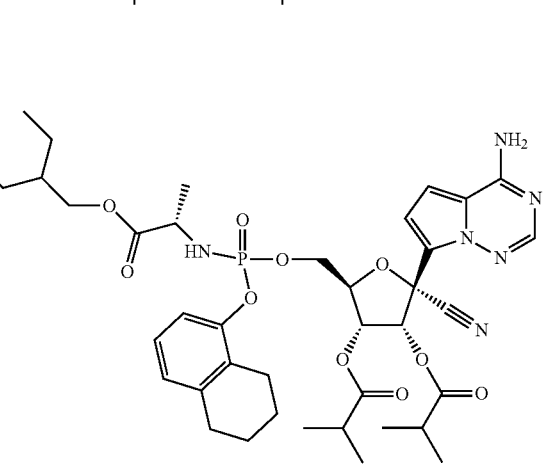

Example 143 was made in a similar fashion as Example 107 except that example 135 was used instead of cyclobutyl ((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)-L-alaninate and acetic anhydride was used instead of 3-methyl butanoic anhydride. Mixture of stereoisomers: $^1$H NMR (400 MHz, Methanol-d4) δ 7.84 (s, 1H), 7.11-7.06 (m, 1H), 7.02-6.96 (m, 1H), 6.93-6.85 (m, 3H), 6.28 (d, J=6.0 Hz, 1H), 5.58-5.53 (m, 1H), 4.67-4.62 (m, 1H), 4.49-4.42 (m, 1H), 4.40-4.33 (m, 1H), 4.06-4.00 (m, 1H), 3.99-3.93 (m, 1H), 3.90-3.78 (m, 1H), 2.79-2.72 (m, 2H), 2.71-2.65 (m, 2H), 2.16 (s, 3H), 2.13 (s, 3H), 1.84-1.72 (m, 4H), 1.53-1.43 (m, 1H), 1.38-1.29 (m, 4H), 1.23-1.19 (m, 3H), 0.91-0.83 (m, 6H). 31P NMR (162 MHz, Methanol-d4) δ 3.75-3.51 (m). LCMS: MS m/z=771.3 [M+1], tR=1.10 min.

Example 144 was made in a similar fashion as Example 107 except that example 135 was used instead of cyclobutyl ((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)-L-alaninate and 2-methylpropanoic anhydride was used instead of 3-methyl butanoic anhydride. Mixture of stereoisomers: $^1$H NMR (400 MHz, Methanol-d4) δ 7.85 (s, 1H), 7.11-7.06 (m, 1H), 7.01-6.96 (m, 1H), 6.92-6.86 (m, 3H), 6.27 (d, J=6.0 Hz, 1H), 5.59-5.56 (m, 1H), 4.66-4.62 (m, 1H), 4.49-4.42 (m, 1H), 4.41-4.34 (m, 1H), 4.05-4.00 (m, 1H), 3.99-3.94 (m, 1H), 3.89-3.80 (m, 1H), 2.79-2.73 (m, 2H), 2.72-2.57 (m, 4H), 1.81-1.72 (m, 4H), 1.53-1.44 (m, 1H), 1.40-1.30 (m, 4H), 1.28-1.17 (m, 15H), 0.91-0.85 (m, 6H). 31P NMR (162 MHz, Methanol-d4) δ 3.72-3.49 (m). LCMS: MS m/z=797.3 [M+1], tR=1.23 min.

Example 145: (2R,3R,4R,5R)-2-(4-aminopyrrolo[2,1-f][1,2,4]triazin-7-yl)-2-cyano-5-((((((S)-1-(cyclobutylmethoxy)-1-oxopropan-2-yl)amino)(phenoxy)phosphoryl)oxy)methyl)tetrahydrofuran-3,4-diyl diacetate Example 146: (2R,3R,4R,5R)-2-(4-aminopyrrolo[2,1-f][1,2,4]triazin-7-yl)-2-cyano-5-(((((R)-(((S)-1-(2-ethylbutoxy)-1-oxopropan-2-yl)amino)((5,6,7,8-tetrahydronaphthalen-1-yl)oxy)phosphoryl)oxy)methyl)tetrahydrofuran-3,4-diyl bis(2-methylpropanoate)

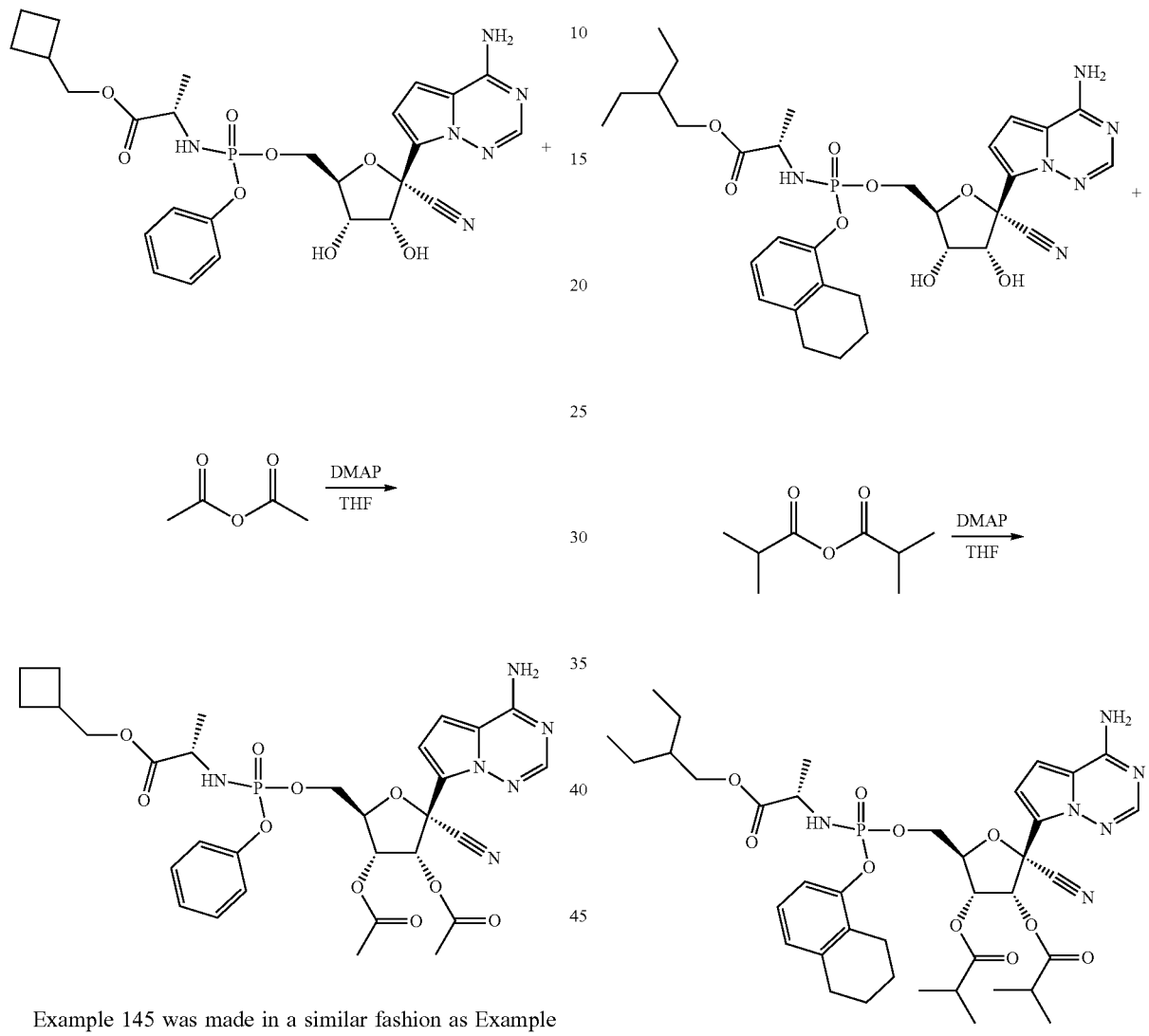

Example 145 was made in a similar fashion as Example 107 except that cyclobutylmethyl (((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)-L-alaninate was used instead of cyclobutyl (((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)-L-alaninate and acetic anhydride was used instead of 3-methyl butanoic anhydride. Mixture of stereoisomers: $^1$H NMR (400 MHz, Methanol-d4) δ 7.87 (s, 0.33H), 7.86 (s, 0.67H), 7.36-7.25 (m, 2H), 7.22-7.14 (m, 3H), 6.95-6.90 (m, 1.33H), 6.88-6.84 (m, 0.67H), 6.30 (d, J=6.0 Hz, 0.67H), 6.21 (d, J=5.9 Hz, 0.33H), 5.59-5.53 (m, 1H), 4.68-4.59 (m, 1H), 4.50-4.33 (m, 2H), 4.10-4.03 (m, 1H), 4.02-3.96 (m, 1H), 3.94-3.75 (m, 1H), 2.66-2.53 (m, 1H), 2.19-2.12 (m, 6H), 2.08-1.68 (m, 6H), 1.33-1.27 (m, 1H), 1.23-1.17 (m, 2H). 31P NMR (162 MHz, Methanol-d4) δ 3.78-3.40 (m).

Example 146 was made in a similar fashion as Example 107 except that example 135 was used instead of cyclobutyl (((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)-L-alaninate and 2-methylpropanoic anhydride was used instead of 3-methyl butanoic anhydride. Mixture of stereoisomers: $^1$H NMR (400 MHz, Methanol-d4) δ 7.86 (s, 1H), 7.07-7.02 (m, 1H), 6.96-6.90 (m, 1H), 6.89-6.84 (m, 2H), 6.82-6.78 (m, 1H), 6.15 (d, J=5.9 Hz, 1H), 5.57-5.52 (m, 1H), 4.60-4.55 (m, 1H), 4.43-4.36 (m, 2H), 4.10-4.05 (m, 1H), 4.02-3.96 (m, 1H), 3.96-3.87 (m, 1H), 2.78-2.59 (m, 6H), 1.76-1.69 (m, 4H), 1.55-1.46 (m, 1H), 1.41-1.30 (m, 7H), 1.29-1.23 (m, 6H), 1.21-1.16 (m, 6H), 0.89 (t, J=7.5 Hz, 6H). 31P NMR (162 MHz, Methanol-d4) δ 3.61-3.41 (m). LCMS: MS m/z=797.3 [M+1], tR=1.25 min.

347

Example 147: (2R,3R,4R,5R)-2-(4-aminopyrrolo[2,1-f][1,2,4]triazin-7-yl)-2-cyano-5-((((R)-(((S)-1-(2-ethylbutoxy)-1-oxopropan-2-yl)amino)((5,6,7,8-tetrahydronaphthalen-1-yl)oxy)phosphoryl)oxy)methyl)tetrahydrofuran-3,4-diyl diacetate

348

Example 148: (2R,3R,4R,5R)-2-(4-aminopyrrolo[2,1-f][1,2,4]triazin-7-yl)-5-((((4-(tert-butyl)phenoxy)(((S)-1-(cyclohexyloxy)-1-oxopropan-2-yl)amino)phosphoryl)oxy)methyl)-2-cyanotetrahydrofuran-3,4-diyl diacetate

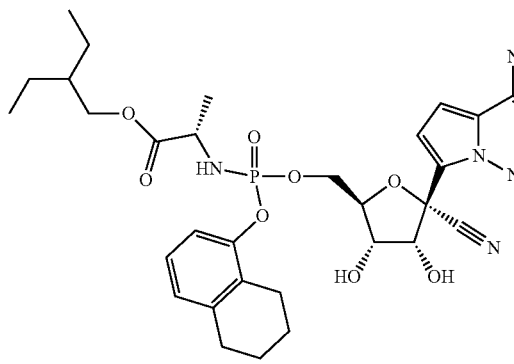

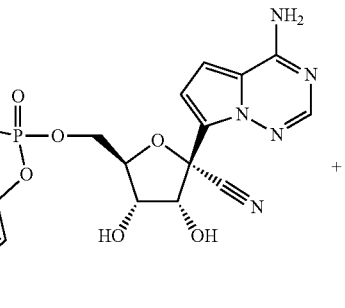

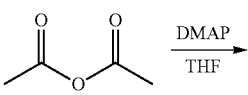

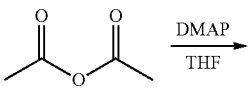

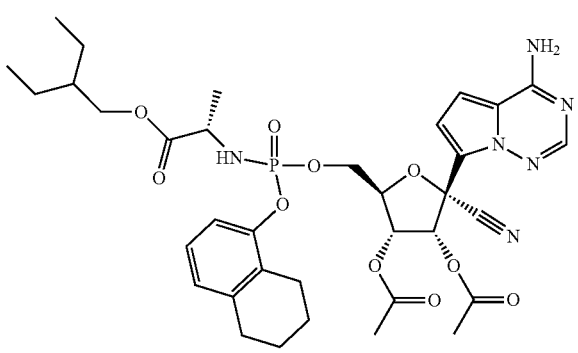

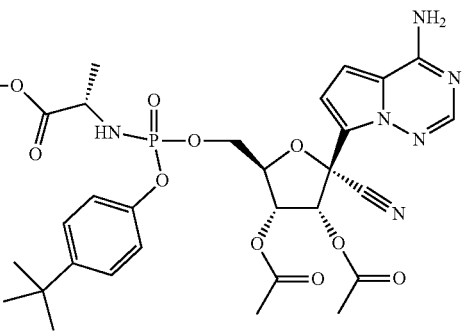

Example 147 was made in a similar fashion as Example 107 except that example 136 was used instead of cyclobutyl (((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)-L-alaninate and acetic anhydride was used instead of 3-methyl butanoic anhydride. Mixture of stereoisomers: $^1$H NMR (400 MHz, Methanol-d4) δ 7.86 (s, 1H), 7.07-7.02 (m, 1H), 6.96-6.90 (m, 1H), 6.88-6.83 (m, 3H), 6.17 (d, J=6.0 Hz, 1H), 5.55-5.50 (m, 1H), 4.62-4.56 (m, 1H), 4.43-4.31 (m, 2H), 4.10-4.02 (m, 1H), 4.01-3.95 (m, 1H), 3.94-3.88 (m, 1H), 2.78-2.72 (m, 2H), 2.68-2.61 (m, 2H), 2.17 (s, 3H), 2.13 (s, 3H), 1.77-1.69 (m, 4H), 1.50 (p, J=6.1 Hz, 1H), 1.40-1.28 (m, 7H), 0.89 (t, J=7.5 Hz, 6H). 31P NMR (162 MHz, Methanol-d4) δ 3.64-3.41 (m). LCMS: MS m/z=741.2 [M+1], tR=1.10 min.

Example 148 was made in a similar fashion as Example 107 except that example 142 was used instead of cyclobutyl (((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)-L-alaninate and acetic anhydride was used instead of 3-methyl butanoic anhydride. Mixture of stereoisomers: $^1$H NMR (400 MHz, Methanol-d4) δ 7.88 (s, 0.67H), 7.86 (s, 0.33H), 7.37-7.32 (m, 0.67H), 7.31-7.26 (m, 1.33H), 7.14-7.04 (m, 2H), 6.95-6.87 (m, 2H), 6.27 (d, J=6.0 Hz, 0.33H), 6.19 (d, J=5.9 Hz, 0.66H), 5.58-5.50 (m, 1H), 4.75-4.59 (m, 2H), 4.50-4.33 (m, 2H), 3.92-3.82 (m, 0.67H), 3.82-3.73 (m, 0.33H), 2.19-2.11 (m, 6H), 1.84-1.67 (m, 4H), 1.59-1.50 (m, 1H), 1.47-1.18 (m, 17H). 31P NMR (162 MHz, Methanol-d4) δ 3.88-3.56 (m). LCMS: MS m/z=741.2, 741.2 [M+1], tR=1.09, 1.10 min.

Example 149: (2R,3R,4R,5R)-2-(4-aminopyrrolo[2,1-f][1,2,4]triazin-7-yl)-5-((((4-(tert-butyl)phenoxy)(((S)-1-(cyclohexyloxy)-1-oxopropan-2-yl)amino)phosphoryl)oxy)methyl)-2-cyanotetrahydrofuran-3,4-diyl bis(2-methylpropanoate)

Example 150: (2R,3R,4R,5R)-2-(4-aminopyrrolo[2,1-f][1,2,4]triazin-7-yl)-5-((((4-(tert-butyl)phenoxy)(((S)-1-(2-methoxyethoxy)-1-oxopropan-2-yl)amino)phosphoryl)oxy)methyl)-2-cyanotetrahydrofuran-3,4-diyl diacetate

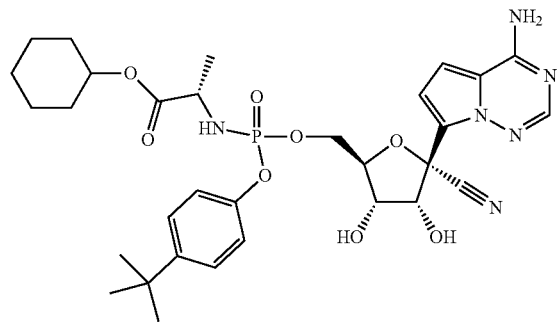

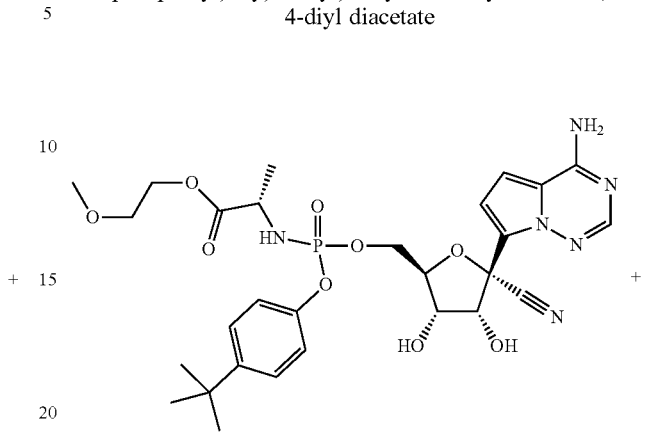

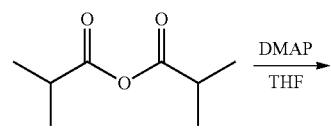

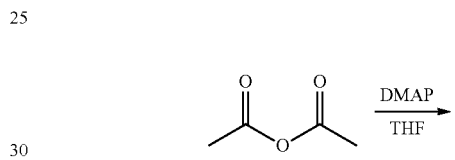

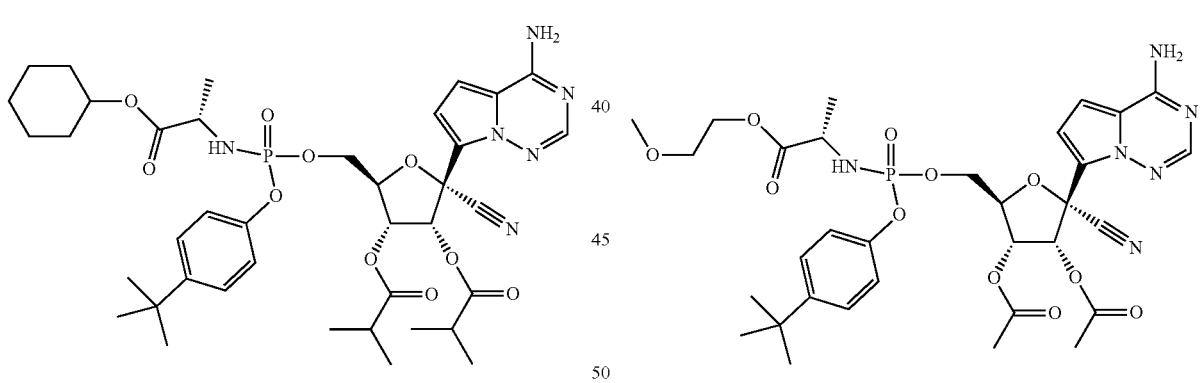

Example 149 was made in a similar fashion as Example 107 except that example 142 was used instead of cyclobutyl (((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)-L-alaninate and 2-methylpropanoic anhydride was used instead of 3-methyl butanoic anhydride. Mixture of stereoisomers: $^1$H NMR (400 MHz, Methanol-d4) δ 7.91-7.85 (m, 1H), 7.38-7.31 (m, 0.66H), 7.31-7.26 (m, 1.33H), 7.13-7.05 (m, 2H), 6.94-6.85 (m, 2H), 6.27 (d, J=5.9 Hz, 0.33H), 6.17 (d, J=5.9 Hz, 0.66H), 5.60-5.53 (m, 1H), 4.79-4.56 (m, 2H), 4.50-4.34 (m, 2H), 3.92-3.83 (m, 0.66H), 3.83-3.74 (m, 0.33H), 2.74-2.59 (m, 2H), 1.86-1.68 (m, 4H), 1.59-1.13 (m, 30H). 31P NMR (162 MHz, Methanol-d4) δ 3.87-3.63 (m). LCMS: MS m/z=797.3, 797.3 [M+1], tR=1.22, 1.24 min.

Example 150 was made in a similar fashion as Example 107 except that example 141 was used instead of cyclobutyl (((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)-L-alaninate and acetic anhydride was used instead of 3-methyl butanoic anhydride. Mixture of stereoisomers: $^1$H NMR (400 MHz, Methanol-d4) δ 7.88 (s, 0.5H), 7.87 (s, 0.5H), 7.36-7.32 (m, 1H), 7.30-7.26 (m, 1H), 7.12-7.05 (m, 2H), 6.94-6.89 (m, 2H), 6.28 (d, J=6.0 Hz, 0.5H), 6.19 (d, J=6.0 Hz, 0.5H), 5.57-5.52 (m, 1H), 4.67-4.60 (m, 1H), 4.49-4.34 (m, 2H), 4.27-4.15 (m, 2H), 3.95-3.87 (m, 0.5H), 3.87-3.79 (m, 0.5H), 3.60-3.54 (m, 2H), 3.38-3.34 (m, 3H), 2.19-2.16 (m, 3H), 2.14 (s, 3H), 1.33-1.18 (m, 12H). 31P NMR (162 MHz, Methanol-d4) δ 3.80-3.47 (m). LCMS: MS m/z=717.2 [M+1], tR=0.94 min.

Example 151: (2R,3R,4R,5R)-2-(4-aminopyrrolo[2,1-f][1,2,4]triazin-7-yl)-5-(((((4-(tert-butyl)phenoxy)(((S)-1-(2-methoxyethoxy)-1-oxopropan-2-yl)amino)phosphoryl)oxy)methyl)-2-cyanotetrahydrofuran-3,4-diyl bis(2-methylpropanoate)

Example 152: (2R,3R,4R,5R)-2-(4-aminopyrrolo[2,1-f][1,2,4]triazin-7-yl)-2-cyano-5-(((((4-(cyclohexyloxy)phenoxy)(((S)-1-(2-ethylbutoxy)-1-oxopropan-2-yl)amino)phosphoryl)oxy)methyl)tetrahydrofuran-3,4-diyl diacetate

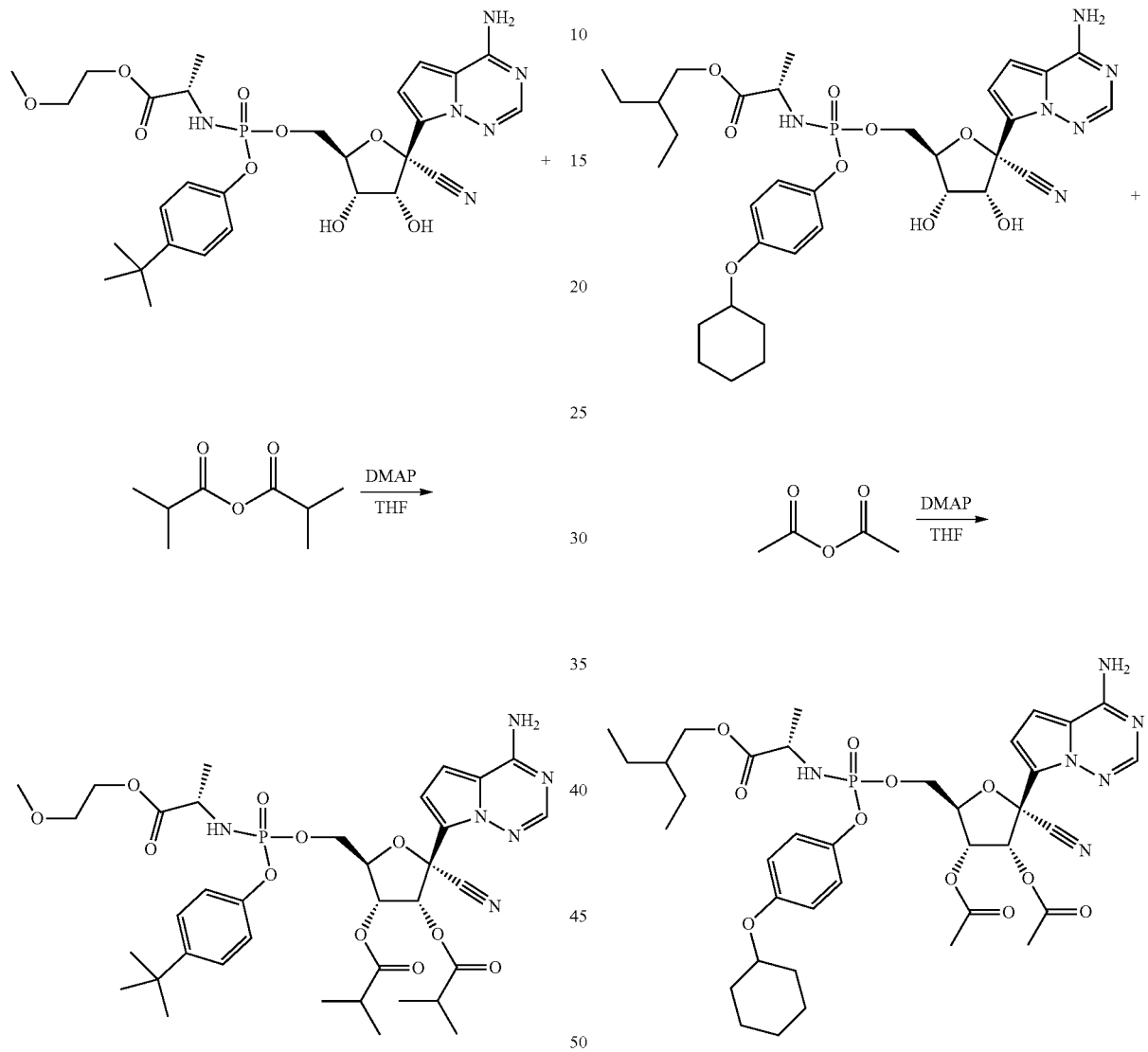

Example 151 was made in a similar fashion as Example 107 except that example 141 was used instead of cyclobutyl (((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)-L-alaninate and 2-methylproprionic anhydride was used instead of 3-methyl butanoic anhydride. Mixture of stereoisomers: $^1$H NMR (400 MHz, Methanol-d4) δ 7.89-7.87 (m, 1H), 7.36-7.33 (m, 1H), 7.31-7.26 (m, 1H), 7.13-7.05 (m, 2H), 6.93-6.85 (m, 2H), 6.28 (d, J=5.9 Hz, 0.5H), 6.16 (d, J=5.9 Hz, 0.5H), 5.59-5.53 (m, 1H), 4.66-4.60 (m, 1H), 4.49-4.35 (m, 2H), 4.25-4.17 (m, 2H), 3.97-3.87 (m, 0.5H), 3.87-3.78 (m, 0.5H), 3.61-3.54 (m, 2H), 3.36-3.34 (m, 3H), 2.74-2.59 (m, 2H), 1.34-1.16 (m, 24H). 31P NMR (162 MHz, Methanol-d4) δ 3.82-3.50 (m). LCMS: MS m/z=773.2, 773.2 [M+1], tR=1.09, 1.10 min.

Example 152 was made in a similar fashion as Example 107 except that example 140 was used instead of cyclobutyl (((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)-L-alaninate and acetic anhydride was used instead of 3-methyl butanoic anhydride. Mixture of stereoisomers: $^1$H NMR (400 MHz, Methanol-d4) δ 7.88 (s, 0.5H), 7.87 (s, 0.5H), 7.11-7.02 (m, 2H), 6.93-6.75 (m, 4H), 6.28 (d, J=6.0 Hz, 0.5H), 6.18 (d, J=5.9 Hz, 0.5H), 5.56-5.51 (m, 1H), 4.66-4.58 (m, 1H), 4.49-4.32 (m, 2H), 4.28-4.17 (m, 1H), 4.09-3.95 (m, 2H), 3.94-3.77 (m, 1H), 2.19-2.11 (m, 6H), 2.01-1.89 (m, 2H), 1.85-1.75 (m, 2H), 1.65-1.55 (m, 1H), 1.54-1.17 (m, 13H), 0.93-0.85 (m, 6H). 31P NMR (162 MHz, Methanol-d4) δ 4.11-3.86 (m). LCMS: MS m/z=785.2, 785.3 [M+1], tR=1.14, 1.16 min.

Example 153: (2R,3R,4R,5R)-2-(4-aminopyrrolo[2,1-f][1,2,4]triazin-7-yl)-2-cyano-5-((((4-(cyclohexyloxy)phenoxy)(((S)-1-(2-ethylbutoxy)-1-oxopropan-2-yl)amino)phosphoryl)oxy)methyl)tetrahydrofuran-3,4-diyl bis(2-methylpropanoate)

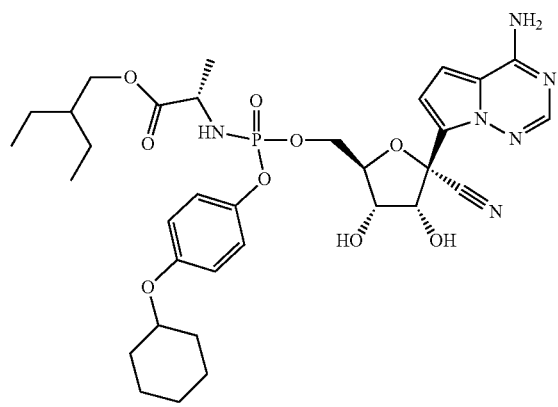

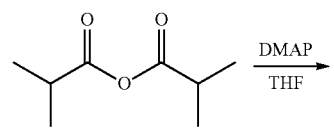

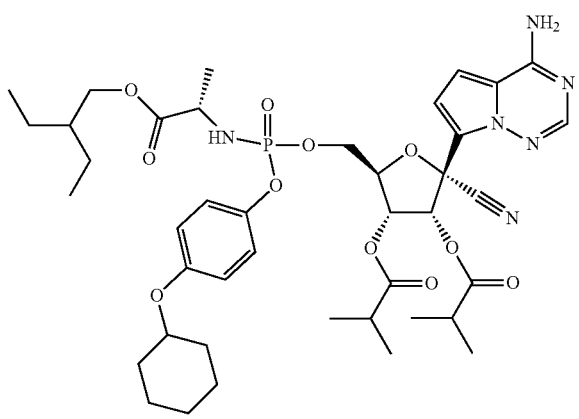

Example 153 was made in a similar fashion as Example 107 except that example 140 was used instead of cyclobutyl ((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)-L-alaninate and 2-methylproprionic anhydride was used instead of 3-methyl butanoic anhydride. Mixture of stereoisomers: $^1$H NMR (400 MHz, Methanol-d4) δ 7.88 (s, 1H), 7.11-7.02 (m, 2H), 6.94-6.81 (m, 3H), 6.80-6.75 (m, 1H), 6.28 (d, J=6.0 Hz, 0.5H), 6.15 (d, J=6.0 Hz, 0.5H), 5.58-5.53 (m, 1H), 4.65-4.57 (m, 1H), 4.48-4.33 (m, 2H), 4.28-4.17 (m, 1H), 4.10-3.96 (m, 2H), 3.95-3.78 (m, 1H), 2.74-2.59 (m, 2H), 2.00-1.91 (m, 2H), 1.84-1.75 (m, 2H), 1.64-1.56 (m, 1H), 1.54-1.29 (m, 12H), 1.29-1.15 (m, 13H), 0.93-0.84 (m, 6H). 31P NMR (162 MHz, Methanol-d4) δ 4.09-3.81 (m). LCMS: MS m/z=841.3, 841.3 [M+1], tR=1.27, 1.29 min.

Intermediate D31: 3,3-dimethylpentyl L-alaninate hydrochloride

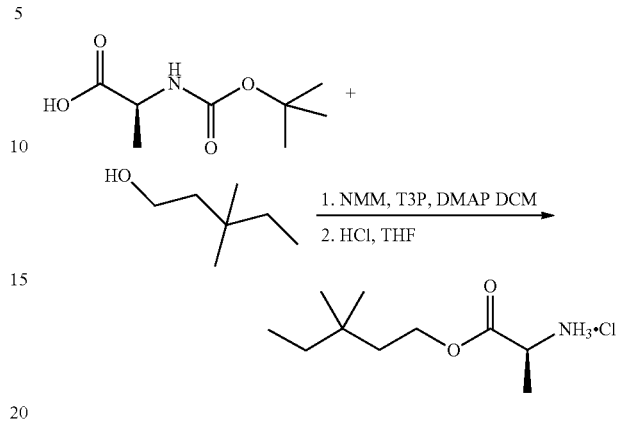

Example D31 was made in a similar fashion as intermediate D1 except that 3,3-dimethylpentanol was used instead of 2-methyl, 2-methoxy-1-propanol. $^1$H NMR (400 MHz, DMSO-d$_6$) δ 8.59-8.50 (m, 3H), 4.25-4.13 (m, 2H), 4.09-4.01 (m, 1H), 1.53 (t, J=7.5 Hz, 2H), 1.41 (d, J=7.2 Hz, 3H), 1.24 (q, J=7.5 Hz, 2H), 0.87 (s, 6H), 0.81 (t, J=7.5 Hz, 3H).

Intermediate D32: 3,3-dimethylpentyl ((4-(tert-butyl)phenoxy) (perfluorophenoxy)phosphoryl)-L-alaninate

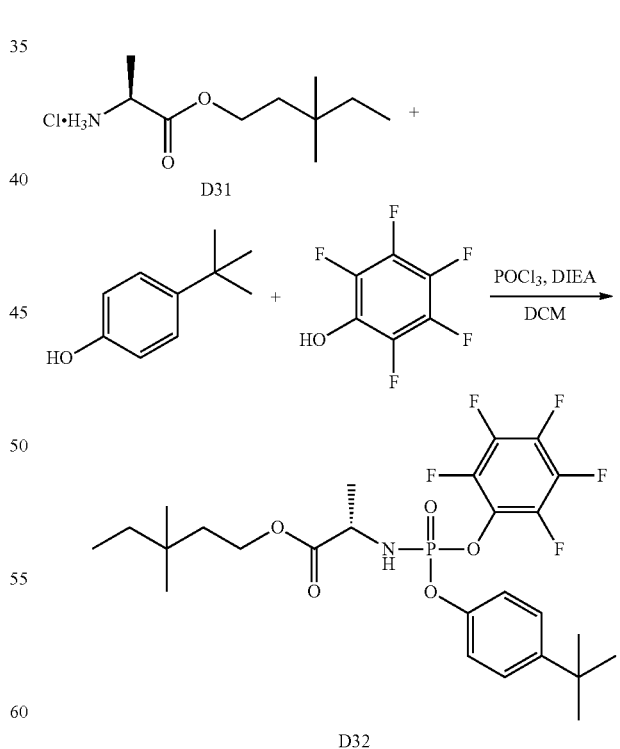

Intermediate D32 was made in a similar fashion as intermediate D2 except that intermediate D31 was used instead of intermediate D1. LCMS: MS m/z=566.1 [M+1], tR=1.38 min.

Example 154: 3,3-dimethylpentyl ((((2R,3S,4R,5R)-5-(4-aminopyrrolo[2,1-f][1,2,4]triazin-7-yl)-5-cyano-3,4-dihydroxytetrahydrofuran-2-yl)methoxy)(4-(tert-butyl)phenoxy)phosphoryl)-L-alaninate

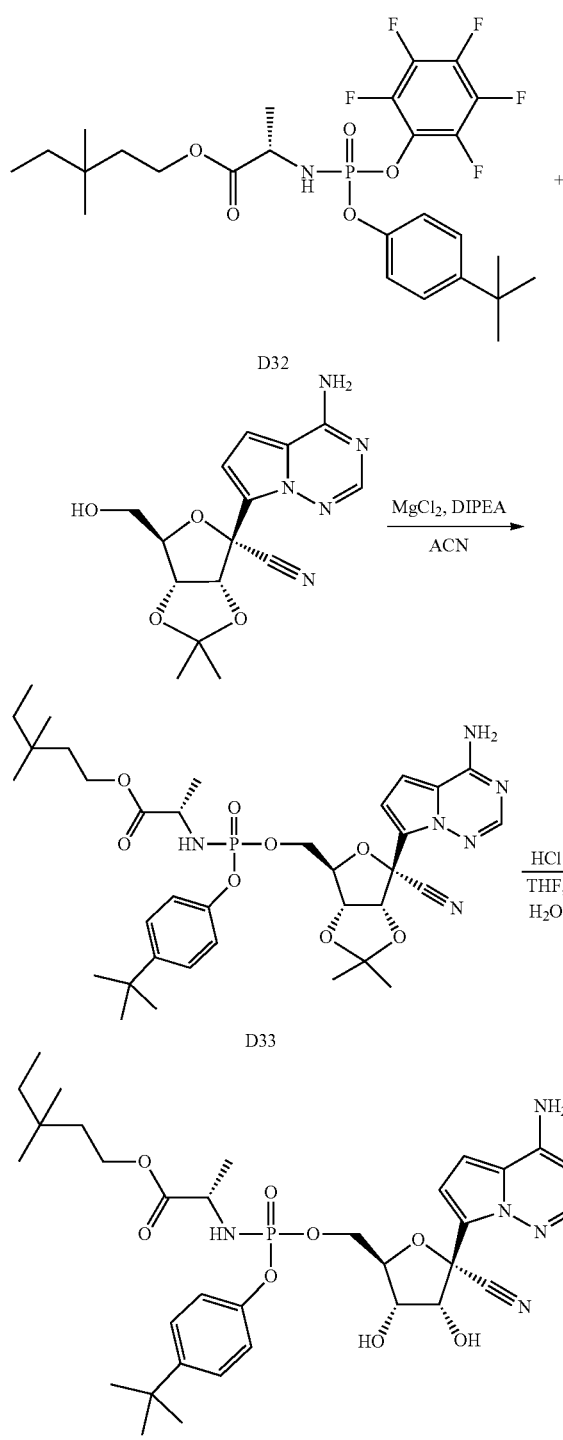

Example 154 was made in a similar fashion as example 111 except that intermediate D33 was used instead of intermediate D2.

Intermediate D33: LCMS: MS m/z=713.3, 713.3 [M+1], tR=1.16, 1.18 min.

Compound 154, Mixture of stereoisomers: ¹H NMR (400 MHz, Methanol-d4) δ 7.89 (s, 0.5H), 7.87 (s, 0.5H), 7.36-7.28 (m, 2H), 7.14-7.10 (m, 1H), 7.08-7.04 (m, 1H), 6.97-6.91 (m, 2H), 4.83-4.79 (m, 1H), 4.48-4.37 (m, 2H), 4.36-4.26 (m, 1H), 4.22-4.15 (m, 1H), 4.14-4.04 (m, 2H), 3.96-3.80 (m, 1H), 1.58-1.47 (m, 2H), 1.35-1.21 (m, 14H), 0.91-0.77 (m, 9H). 31P NMR (162 MHz, Methanol-d4) δ 3.96-3.68 (m). LCMS: MS m/z=673.2, 673.2 [M+1], tR=1.02, 1.06 min.

Intermediate D34: 2-methoxypropyl L-alaninate hydrochloride

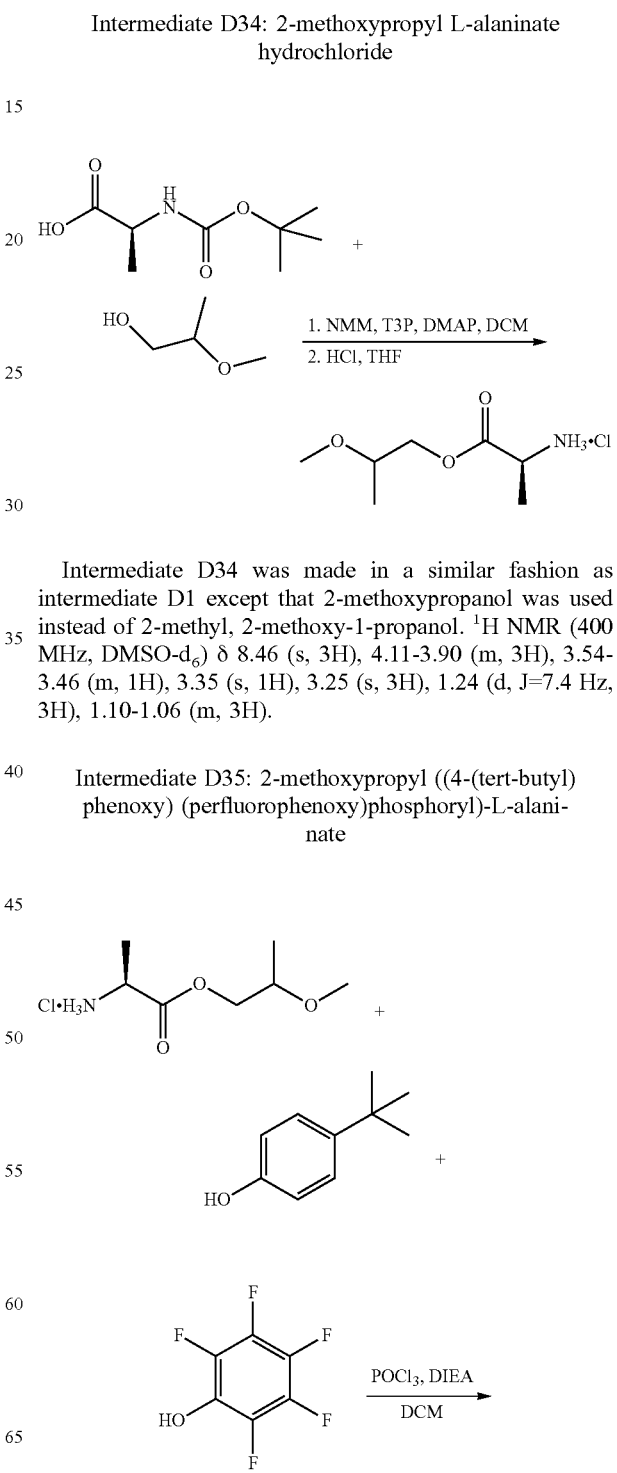

Intermediate D34 was made in a similar fashion as intermediate D1 except that 2-methoxypropanol was used instead of 2-methyl, 2-methoxy-1-propanol. ¹H NMR (400 MHz, DMSO-d₆) δ 8.46 (s, 3H), 4.11-3.90 (m, 3H), 3.54-3.46 (m, 1H), 3.35 (s, 1H), 3.25 (s, 3H), 1.24 (d, J=7.4 Hz, 3H), 1.10-1.06 (m, 3H).

Intermediate D35: 2-methoxypropyl ((4-(tert-butyl)phenoxy)(perfluorophenoxy)phosphoryl)-L-alaninate

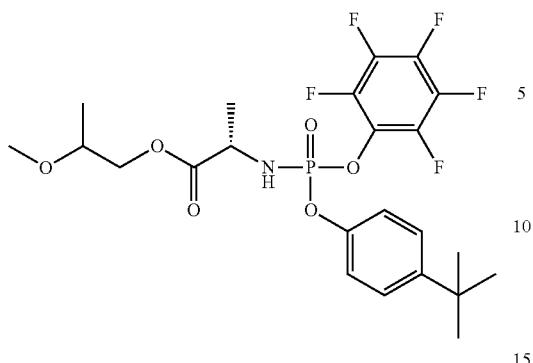

Intermediate D35 was made in a similar fashion as intermediate D2 except that intermediate D34 was used instead of intermediate D1. LCMS: MS m/z=540.1 [M+1], tR=1.19 min.

Example 155: 2-methoxypropyl ((((2R,3S,4R,5R)-5-(4-aminopyrrolo[2,1-f][1,2,4]triazin-7-yl)-5-cyano-3,4-dihydroxytetrahydrofuran-2-yl)methoxy)(4-(tert-butyl)phenoxy)phosphoryl)-L-alaninate

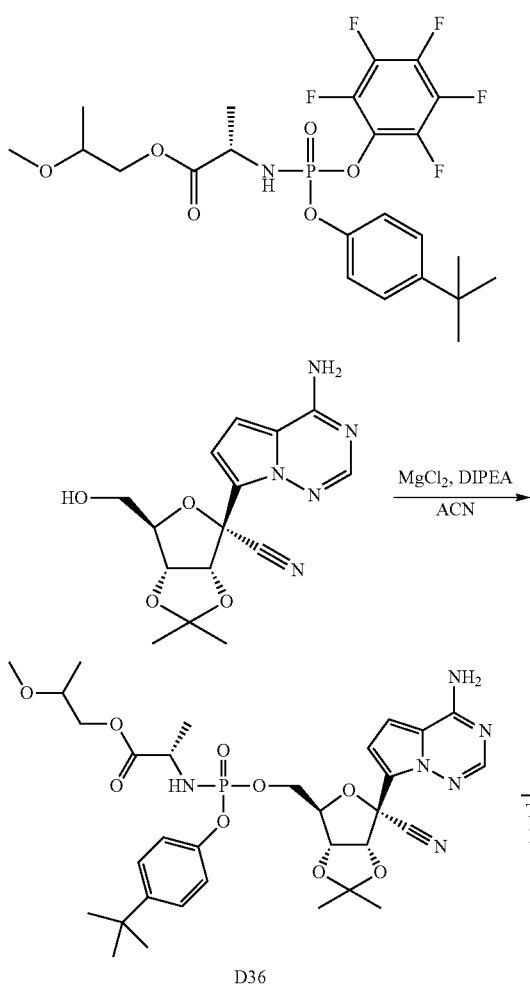

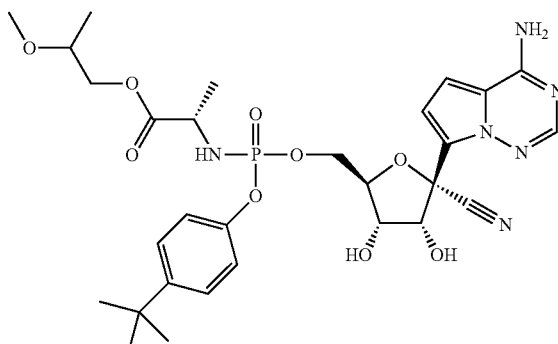

Example 155 was made in a similar fashion as example 111 except that intermediate D35 was used instead of intermediate D2.

Intermediate D36: LCMS: MS m/z=687.2, 687.2 [M+1], tR=0.98, 1.00 min.

Compound 176, Mixture of stereoisomers: $^1$H NMR (400 MHz, Methanol-d4) δ 7.89 (s, 0.5H), 7.87 (s, 0.5H), 7.34-7.28 (m, 2H), 7.12-7.08 (m, 1H), 7.08-7.04 (m, 1H), 6.98-6.90 (m, 2H), 4.84-4.79 (m, 1H), 4.48-4.27 (m, 3H), 4.22-4.16 (m, 1H), 4.13-3.86 (m, 3H), 3.60-3.51 (m, 1H), 3.35-3.32 (m, 3H), 1.34-1.26 (m, 12H), 1.16-1.09 (m, 3H). 31P NMR (162 MHz, Methanol-d4) δ 4.01-3.61 (m). LCMS: MS m/z=647.2, 647.2 [M+1], tR=0.84, 0.86 min.

Intermediate D37: cyclohexylmethyl L-alaninate hydrochloride

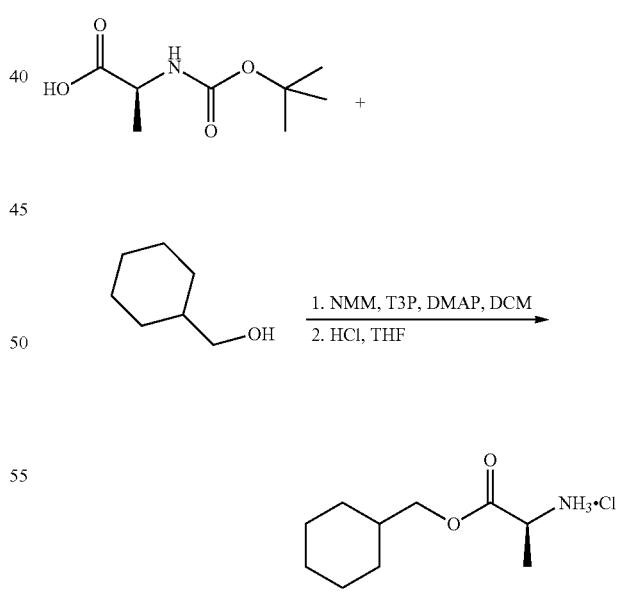

Intermediate D37 was made in a similar fashion as intermediate D1 except that cyclohexylmethanol was used instead of 2-methyl, 2-methoxy-1-propanol. $^1$H NMR (400 MHz, DMSO-d$_6$) δ 8.58 (s, 3H), 4.05-3.94 (m, 1H), 3.94-3.85 (m, 1H), 3.82-3.76 (m, 1H), 1.71-1.53 (m, 5H), 1.28-1.10 (m, 5H), 1.01-0.89 (m, 2H).

Intermediate D38: cyclohexylmethyl ((4-(tert-butyl)phenoxy) (perfluorophenoxy)phosphoryl)-L-alaninate

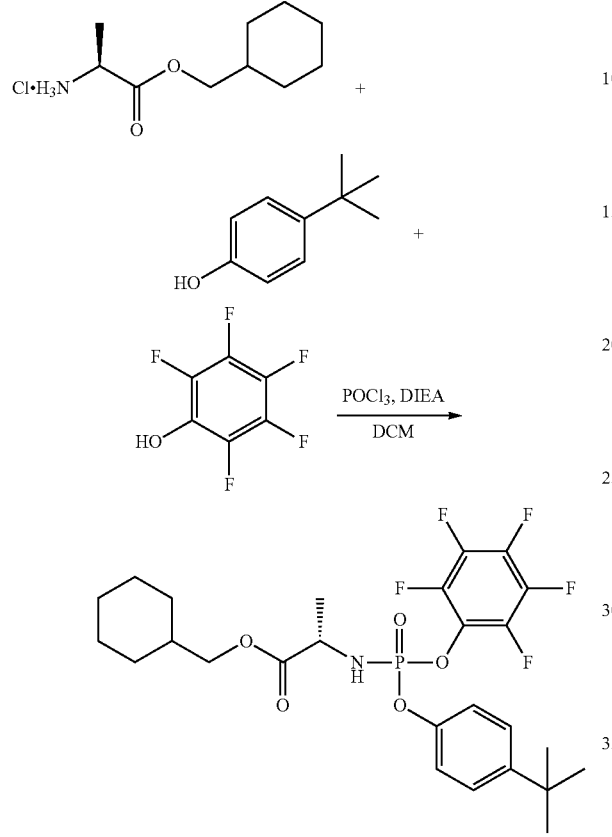

Intermediate D38 was made in a similar fashion as intermediate D2 except that intermediate D37 was used instead of intermediate D1. LCMS: MS m/z=564.1 [M+1], tR=1.36 min.

Example 156: cyclohexylmethyl (((((2R,3S,4R,5R)-5-(4-aminopyrrolo[2,1-f][1,2,4]triazin-7-yl)-5-cyano-3,4-dihydroxytetrahydrofuran-2-yl)methoxy)(4-(tert-butyl)phenoxy)phosphoryl)-L-alaninate

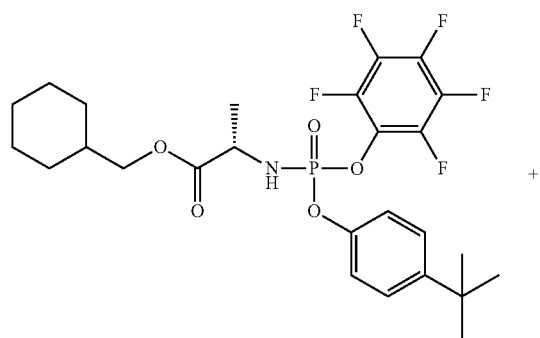

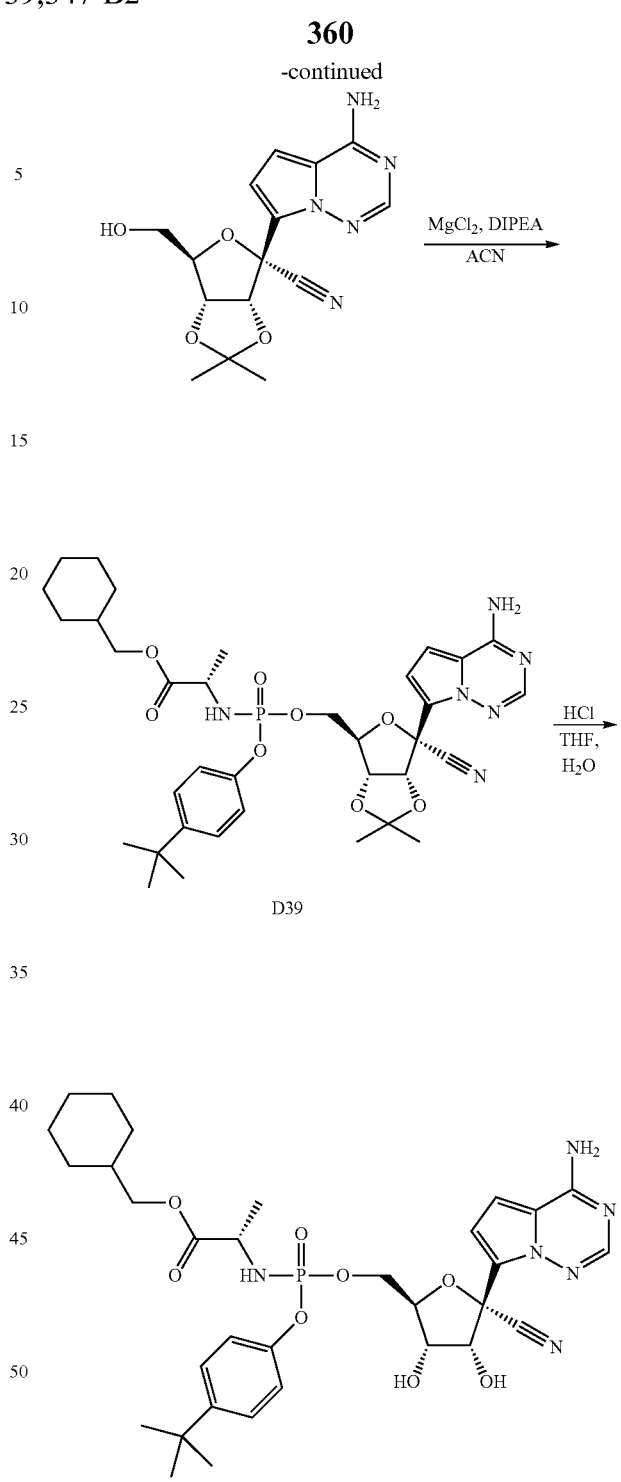

Example 156 was made in a similar fashion as example 111 except that intermediate D38 was used instead of intermediate D2. Intermediate D39: LCMS: MS m/z=711.3, 711.3 [M+1], tR=1.14, 1.17 min. Compound 177, Mixture of stereoisomers: $^1$H NMR (400 MHz, Methanol-d4) δ 7.89 (s, 0.5H), 7.88 (s, 0.5H), 7.36-7.28 (m, 2H), 7.13-7.09 (m, 1H), 7.08-7.04 (m, 1H), 6.99-6.90 (m, 2H), 4.83-4.79 (m, 1H), 4.49-4.26 (m, 3H), 4.23-4.16 (m, 1H), 3.95-3.79 (m, 3H), 1.80-1.52 (m, 6H), 1.38-1.14 (m, 15H), 1.05-0.86 (m, 2H). 31P NMR (162 MHz, Methanol-d4) δ 4.04-3.57 (m). LCMS: MS m/z=671.3, 671.3 [M+1], tR=1.01, 1.04 min.

Example 157: (2R,3R,4R,5R)-2-(4-aminopyrrolo[2,1-f][1,2,4]triazin-7-yl)-5-((((4-(tert-butyl)phenoxy)(((S)-1-ethoxy-1-oxopropan-2-yl)amino)phosphoryl)oxy)methyl)-2-cyanotetrahydrofuran-3,4-diyl diacetate

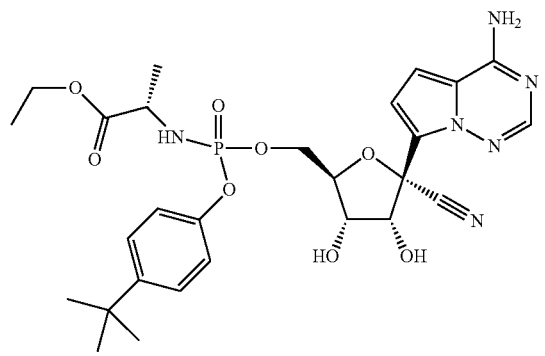

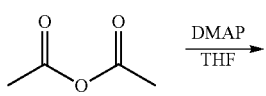

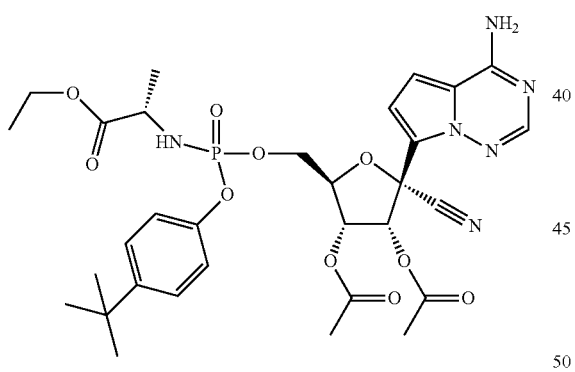

Example 158: (2R,3R,4R,5R)-2-(4-aminopyrrolo[2,1-f][1,2,4]triazin-7-yl)-5-((((4-(tert-butyl)phenoxy)(((S)-1-ethoxy-1-oxopropan-2-yl)amino)phosphoryl)oxy)methyl)-2-cyanotetrahydrofuran-3,4-diyl bis(3-methylbutanoate)

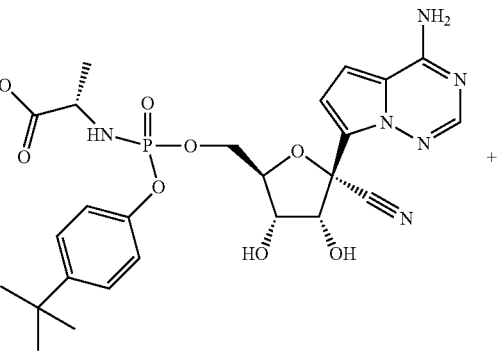

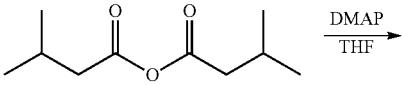

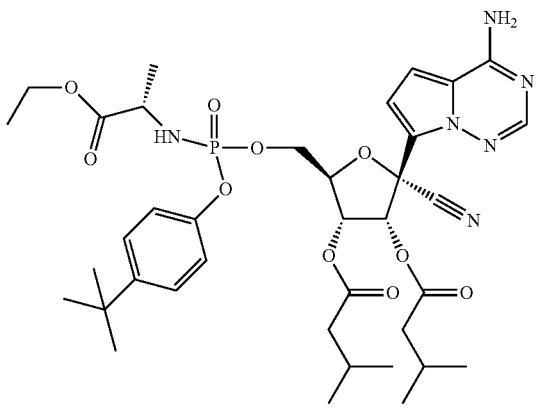

Example 157 was made in a similar fashion as Example 107 except that Example 17 was used instead of cyclobutyl (((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)-L-alaninate and acetic anhydride was used instead of 3-methyl butanoic anhydride. Mixture of stereoisomers: $^1$H NMR (400 MHz, Methanol-d4) δ 7.88 (s, 0.5H), 7.86 (s, 0.5H), 7.36-7.32 (m, 1H), 7.30-7.26 (m, 1H), 7.12-7.04 (m, 2H), 6.93-6.88 (m, 2H), 6.28 (d, J=6.0 Hz, 0.5H), 6.19 (d, J=6.0 Hz, 0.5H), 5.58-5.53 (m, 1H), 4.67-4.59 (m, 1H), 4.49-4.33 (m, 2H), 4.17-4.04 (m, 2H), 3.92-3.82 (m, 0.5H), 3.81-3.72 (m, 0.5H), 2.19-2.16 (m, 3H), 2.14 (s, 3H), 1.33-1.16 (m, 15H). 31P NMR (162 MHz, Methanol-d4) δ 3.85-3.60 (m). LCMS: MS m/z=687.2, 687.2 [M+1], tR=0.96, 0.98 min.

Example 158 was made in a similar fashion as Example 107 except that Example 17 was used instead of cyclobutyl (((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)-L-alaninate. Mixture of stereoisomers: $^1$H NMR (400 MHz, Methanol-d4) δ 7.88 (s, 0.5H), 7.86 (s, 0.5H), 7.37-7.32 (m, 1H), 7.31-7.27 (m, 1H), 7.13-7.06 (m, 2H), 6.93-6.88 (m, 2H), 6.36 (d, J=6.0 Hz, 0.5H), 6.26 (d, J=6.0 Hz, 0.5H), 5.60-5.56 (m, 1H), 4.65-4.58 (m, 1H), 4.50-4.34 (m, 2H), 4.17-4.05 (m, 2H), 3.92-3.83 (m, 0.5H), 3.82-3.73 (m, 0.5H), 2.36-2.26 (m, 4H), 2.22-2.03 (m, 2H), 1.32-1.17 (m, 15H), 1.05-1.00 (m, 6H), 0.98-0.92 (m, 6H). 31P NMR (162 MHz, Methanol-d4) δ 3.81-3.45 (m). LCMS: MS m/z=771.3 [M+1], tR=1.19 min.

Example 159: (2R,3R,4R,5R)-2-(4-aminopyrrolo[2,1-f][1,2,4]triazin-7-yl)-5-((((4-(tert-butyl)phenoxy)(((S)-1-((3,3-dimethylpentyl)oxy)-1-oxopropan-2-yl)amino)phosphoryl)oxy)methyl)-2-cyanotetrahydrofuran-3,4-diyl diacetate Example 160: (2R,3R,4R,5R)-2-(4-aminopyrrolo[2,1-f][1,2,4]triazin-7-yl)-5-((((4-(tert-butyl)phenoxy)(((S)-1-((3,3-dimethylpentyl)oxy)-1-oxopropan-2-yl)amino)phosphoryl)oxy)methyl)-2-cyanotetrahydrofuran-3,4-diyl bis(2-methylpropanoate)

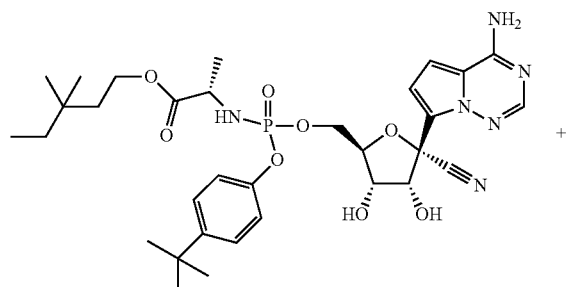
+

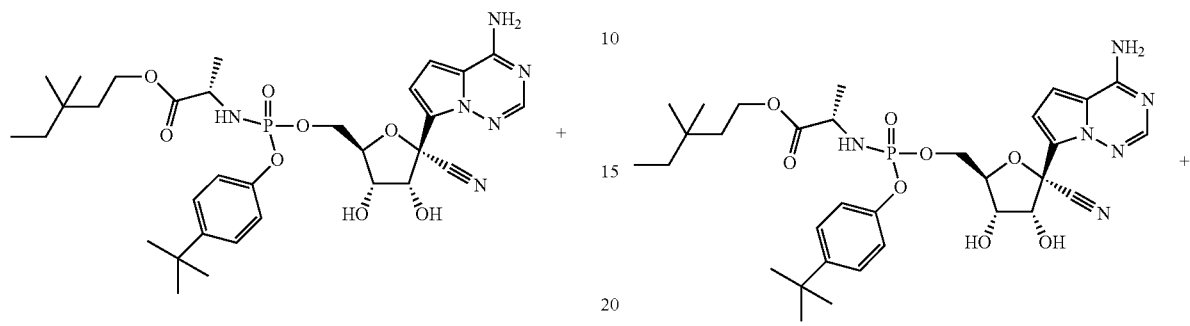
+

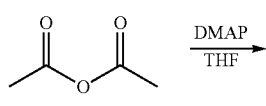

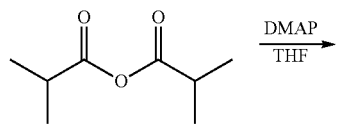

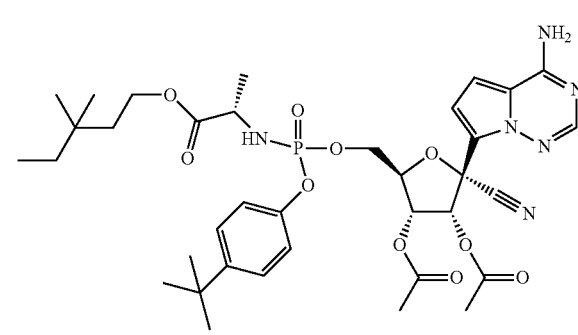

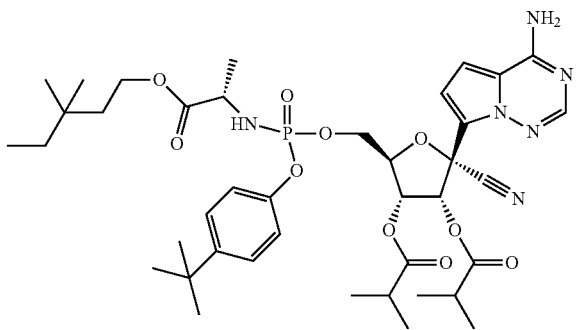

Example 159 was made in a similar fashion as Example 107 except that example 154 was used instead of cyclobutyl (((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)-L-alaninate and acetic anhydride was used instead of 3-methyl butanoic anhydride. Mixture of stereoisomers: $^1$H NMR (400 MHz, Methanol-d4) δ 7.88 (s, 0.5H), 7.86 (s, 0.5H), 7.36-7.32 (m, 1H), 7.31-7.27 (m, 1H), 7.12-7.05 (m, 2H), 6.92 (s, 1H), 6.90 (s, 1H), 6.28 (d, J=6.0 Hz, 0.5H), 6.18 (d, J=5.9 Hz, 0.5H), 5.58-5.52 (m, 1H), 4.67-4.60 (m, 1H), 4.50-4.33 (m, 2H), 4.19-4.06 (m, 2H), 3.93-3.75 (m, 1H), 2.18-2.16 (m, 3H), 2.15-2.12 (m, 3H), 1.56-1.47 (m, 2H), 1.32-1.19 (m, 14H), 0.91-0.80 (m, 9H). 31P NMR (162 MHz, Methanol-d4) δ 3.87-3.53 (m). LCMS: MS m/z=757.3, 757.3 [M+1], tR=1.14, 1.18 min.

Example 160 was made in a similar fashion as Example 107 except that example 154 was used instead of cyclobutyl (((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)-L-alaninate and 2-methylproprionic anhydride was used instead of 3-methyl butanoic anhydride. Mixture of stereoisomers: $^1$H NMR (400 MHz, Methanol-d4) δ 7.88 (s, 0.5H), 7.87 (s, 0.5H), 7.37-7.32 (m, 1H), 7.31-7.27 (m, 1H), 7.12-7.05 (m, 2H), 6.95-6.85 (m, 2H), 6.28 (d, J=5.9 Hz, 0.5H), 6.16 (d, J=5.9 Hz, 0.5H), 5.58-5.54 (m, 1H), 4.67-4.59 (m, 1H), 4.50-4.34 (m, 2H), 4.21-4.06 (m, 2H), 3.93-3.77 (m, 1H), 2.74-2.59 (m, 2H), 1.58-1.48 (m, 2H), 1.33-1.16 (m, 26H), 0.91-0.79 (m, 9H). 31P NMR (162 MHz, Methanol-d4) δ 3.84-3.50 (m). LCMS: MS m/z=813.4, 813.4 [M+1], tR=1.27, 1.28 min.

Example 161: (2R,3R,4R,5R)-2-(4-aminopyrrolo[2,1-f][1,2,4]triazin-7-yl)-5-((((4-(tert-butyl)phenoxy)(((2S)-1-(2-methoxypropoxy)-1-oxopropan-2-yl)amino)phosphoryl)oxy)methyl)-2-cyanotetrahydrofuran-3,4-diyl diacetate

Example 162: (2R,3R,4R,5R)-2-(4-aminopyrrolo[2,1-f][1,2,4]triazin-7-yl)-5-((((4-(tert-butyl)phenoxy)(((2S)-1-(2-methoxypropoxy)-1-oxopropan-2-yl)amino)phosphoryl)oxy)methyl)-2-cyanotetrahydrofuran-3,4-diyl bis(2-methylpropanoate)

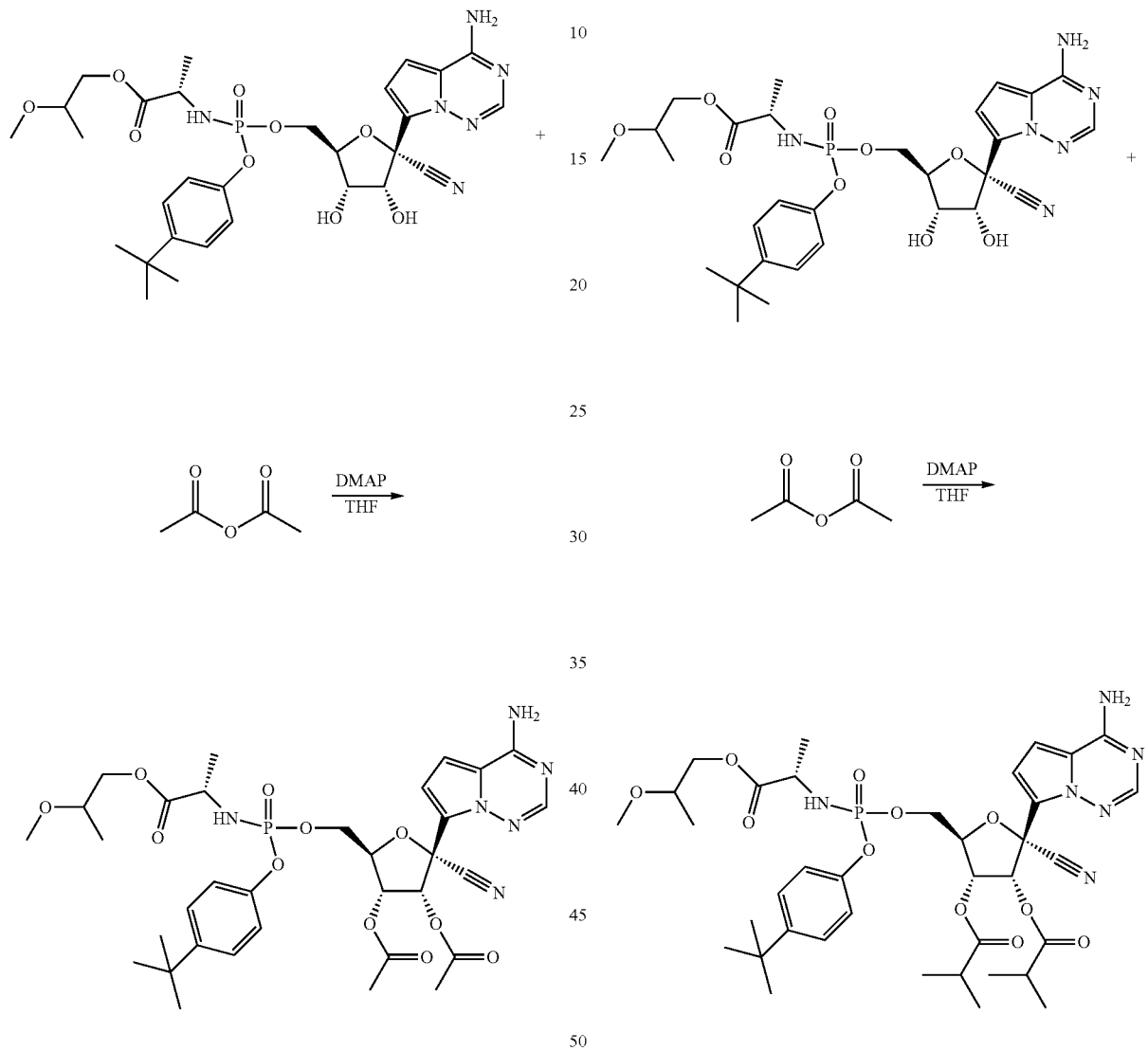

Example 161 was made in a similar fashion as Example 107 except that example 155 was used instead of cyclobutyl (((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)-L-alaninate and acetic anhydride was used instead of 3-methyl butanoic anhydride. Mixture of stereoisomers: $^1$H NMR (400 MHz, Methanol-d4) δ 7.88 (s, 0.5H), 7.86 (s, 0.5H), 7.36-7.32 (m, 1H), 7.30-7.26 (m, 1H), 7.12-7.03 (m, 2H), 6.93-6.89 (m, 2H), 6.30-6.26 (m, 0.5H), 6.20-6.16 (m, 0.5H), 5.57-5.53 (m, 1H), 4.67-4.61 (m, 1H), 4.50-4.33 (m, 2H), 4.16-3.96 (m, 2H), 3.95-3.80 (m, 1H), 3.60-3.52 (m, 1H), 3.36-3.34 (m, 3H), 2.19-2.16 (m, 3H), 2.15-2.12 (m, 3H), 1.34-1.27 (m, 10.5H), 1.25-1.19 (m, 1.5H), 1.17-1.10 (m, 3H). 31P NMR (162 MHz, Methanol-d4) δ 3.77-3.45 (m). LCMS: MS m/z=731.2, 731.2 [M+1], tR=0.96, 0.99 min.

Example 162 was made in a similar fashion as Example 107 except that example 155 was used instead of cyclobutyl (((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)-L-alaninate and 2-methylproprionic anhydride was used instead of 3-methyl butanoic anhydride. Mixture of stereoisomers: $^1$H NMR (400 MHz, Methanol-d4) δ 7.88 (s, 0.5H), 7.87 (d, J=0.7 Hz, 0.5H), 7.36-7.32 (m, 1H), 7.30-7.26 (m, 1H), 7.12-7.05 (m, 2H), 6.93-6.86 (m, 2H), 6.29-6.27 (m, 0.5H), 6.17-6.15 (m, 0.5H), 5.59-5.54 (m, 1H), 4.67-4.59 (m, 1H), 4.49-4.35 (m, 2H), 4.16-3.97 (m, 2H), 3.96-3.80 (m, 1H), 3.62-3.52 (m, 1H), 3.38-3.34 (m, 3H), 2.75-2.58 (m, 2H), 1.34-1.17 (m, 24H), 1.16-1.11 (m, 3H). 31P NMR (162 MHz, Methanol-d4) δ 3.84-3.41 (m). LCMS: MS m/z=787.3, 787.3 [M+1], tR=1.11, 1.13 min.

Example 163: (2R,3R,4R,5R)-2-(4-aminopyrrolo[2,1-f][1,2,4]triazin-7-yl)-5-((((4-(tert-butyl)phenoxy)(((S)-1-(cyclohexylmethoxy)-1-oxopropan-2-yl)amino)phosphoryl)oxy)methyl)-2-cyanotetrahydrofuran-3,4-diyl diacetate

Example 164: (2R,3R,4R,5R)-2-(4-aminopyrrolo[2,1-f][1,2,4]triazin-7-yl)-5-((((4-(tert-butyl)phenoxy)(((S)-1-(cyclohexylmethoxy)-1-oxopropan-2-yl)amino)phosphoryl)oxy)methyl)-2-cyanotetrahydrofuran-3,4-diyl bis(2-methylpropanoate)

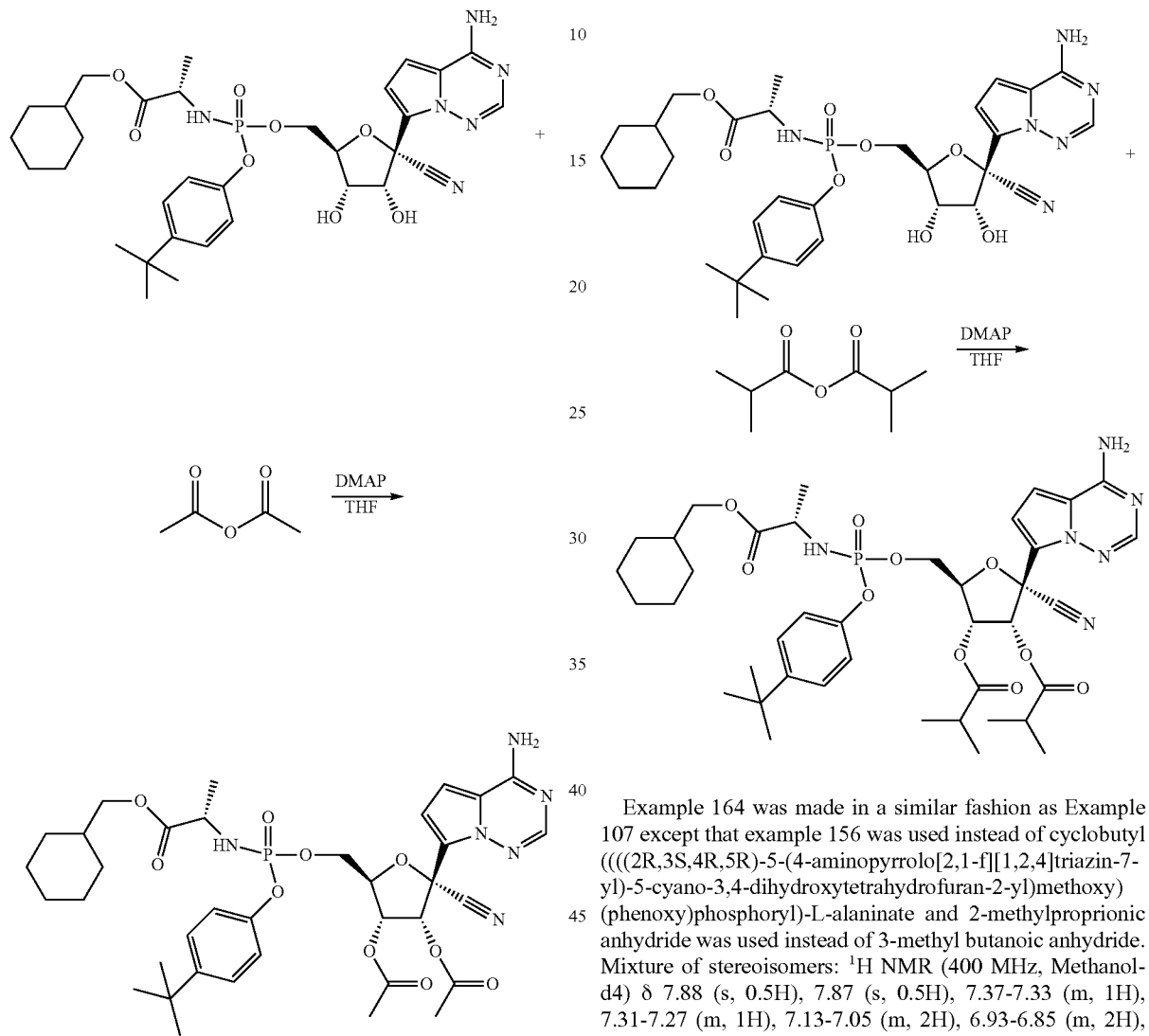

Example 163 was made in a similar fashion as Example 107 except that example 156 was used instead of cyclobutyl (((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)-L-alaninate and acetic anhydride was used instead of 3-methyl butanoic anhydride. Mixture of stereoisomers: $^1$H NMR (400 MHz, Methanol-d4) δ 7.88 (s, 0.5H), 7.86 (s, 0.5H), 7.37-7.32 (m, 1H), 7.32-7.27 (m, 1H), 7.14-7.04 (m, 2H), 6.94-6.88 (m, 2H), 6.29 (d, J=6.0 Hz, 0.5H), 6.19 (d, J=6.0 Hz, 0.5H), 5.59-5.51 (m, 1H), 4.68-4.58 (m, 1H), 4.48-4.33 (m, 2H), 3.96-3.76 (m, 3H), 2.20-2.10 (m, 6H), 1.78-1.54 (m, 6H), 1.37-1.12 (m, 15H), 1.04-0.89 (m, 2H). 31P NMR (162 MHz, Methanol-d4) δ 3.94-3.46 (m). LCMS: MS m/z=755.3, 755.2 [M+1], tR=1.13, 1.14 min.

Example 164 was made in a similar fashion as Example 107 except that example 156 was used instead of cyclobutyl (((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)-L-alaninate and 2-methylproprionic anhydride was used instead of 3-methyl butanoic anhydride. Mixture of stereoisomers: $^1$H NMR (400 MHz, Methanol-d4) δ 7.88 (s, 0.5H), 7.87 (s, 0.5H), 7.37-7.33 (m, 1H), 7.31-7.27 (m, 1H), 7.13-7.05 (m, 2H), 6.93-6.85 (m, 2H), 6.29 (d, J=5.9 Hz, 0.5H), 6.16 (d, J=5.9 Hz, 0.5H), 5.58-5.54 (m, 1H), 4.67-4.58 (m, 1H), 4.48-4.33 (m, 2H), 3.95-3.78 (m, 3H), 2.74-2.58 (m, 2H), 1.77-1.57 (m, 6H), 1.34-1.15 (m, 27H), 1.05-0.89 (m, 2H). 31P NMR (162 MHz, Methanol-d4) δ 3.81-3.51 (m). LCMS: MS m/z=811.3, 811.3 [M+1], tR=1.26, 1.27 min.

Intermediate D40: cyclobutyl (3S)-3-(((4-(tert-butyl)phenoxy)(perfluorophenoxy)phosphoryl)amino)butanoate

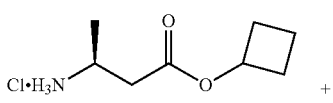

369

-continued

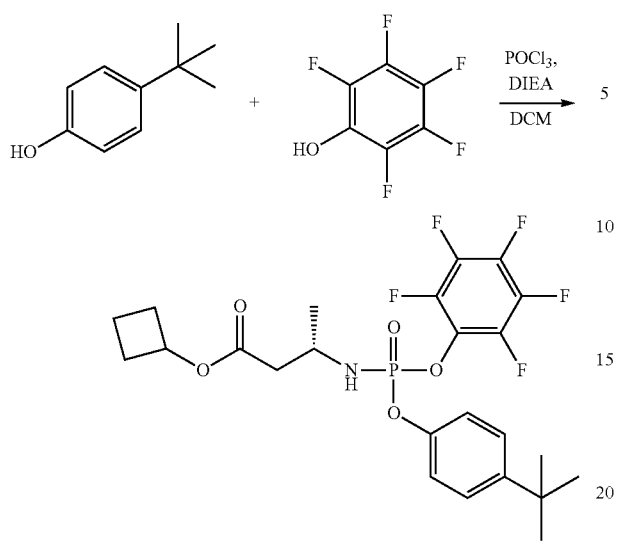

Intermediate D40 was made in a similar fashion as intermediate D2 except that cyclobutyl (S)-3-aminobutanoate was used instead of intermediate D1. LCMS: MS m/z=536.1 [M+1], tR=1.26 min.

Example 165: cyclobutyl (3S)-3-(((((2R,3S,4R,5R)-5-(4-aminopyrrolo[2,1-f][1,2,4]triazin-7-yl)-5-cyano-3,4-dihydroxytetrahydrofuran-2-yl)methoxy)(4-(tert-butyl)phenoxy)phosphoryl)amino)butanoate

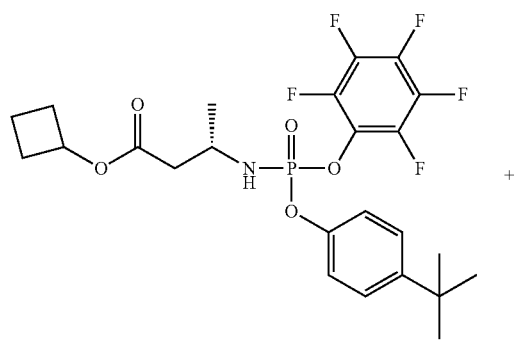

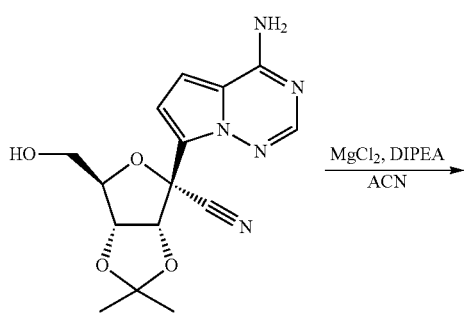

370

-continued

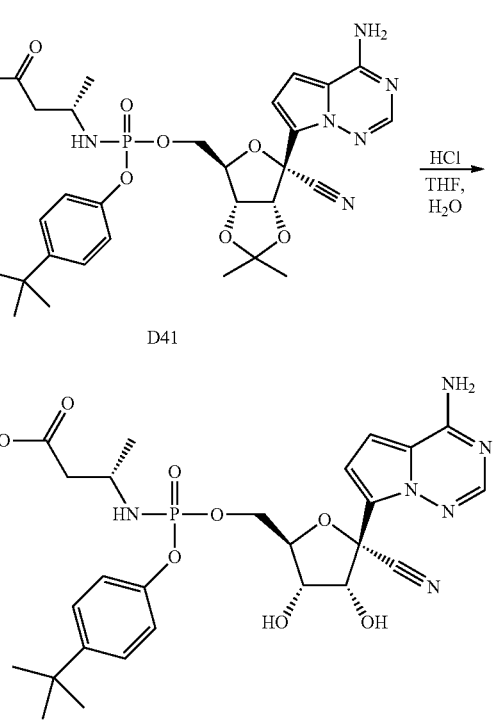

Example 165 was made in a similar fashion as example 111 except that intermediate D40 was used instead of intermediate D2. Intermediate D41: LCMS: MS m/z=683.2, 683.2 [M+1], tR=1.04, 1.07 min. Compound 165, Mixture of stereoisomers: ¹H NMR (400 MHz, Methanol-d4) δ 7.89 (s, 0.5H), 7.87 (s, 0.5H), 7.36-7.24 (m, 2H), 7.13-7.04 (m, 2H), 6.99-6.89 (m, 2H), 4.98-4.88 (m, 1H), 4.83 (d, J=5.5 Hz, 0.5H), 4.78 (d, J=5.4 Hz, 0.5H), 4.42-4.33 (m, 2H), 4.33-4.25 (m, 1H), 4.24-4.20 (m, 0.5H), 4.15-4.11 (m, 0.5H), 3.73-3.62 (m, 1H), 2.48-2.23 (m, 4H), 2.12-1.96 (m, 2H), 1.84-1.71 (m, 1H), 1.69-1.55 (m, 1H), 1.30 (s, 4.5H), 1.28 (s, 4.5H), 1.15 (d, J=6.6 Hz, 1.5H), 1.11 (d, J=6.6 Hz, 1.5H). 31P NMR (162 MHz, Methanol-d4) δ 4.58-4.22 (m). LCMS: MS m/z=643.2, 643.2 [M+1], tR=0.90, 0.93 min.

Example 166: (2R,3R,4R,5R)-2-(4-aminopyrrolo[2,1-f][1,2,4]triazin-7-yl)-5-(((((4-(tert-butyl)phenoxy)(((S)-4-cyclobutoxy-4-oxobutan-2-yl)amino)phosphoryl)oxy)methyl)-2-cyanotetrahydrofuran-3,4-diyl diacetate

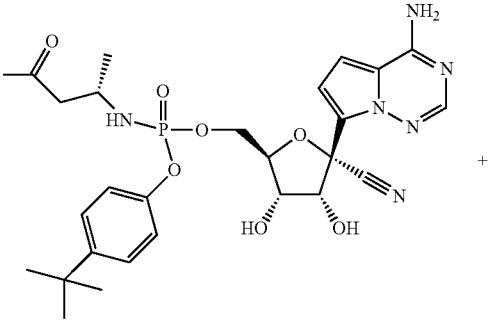

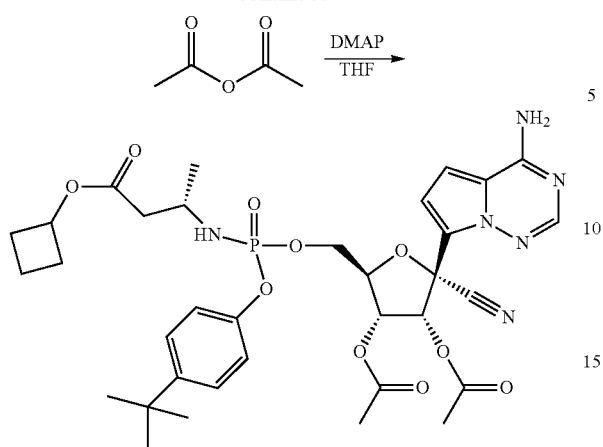

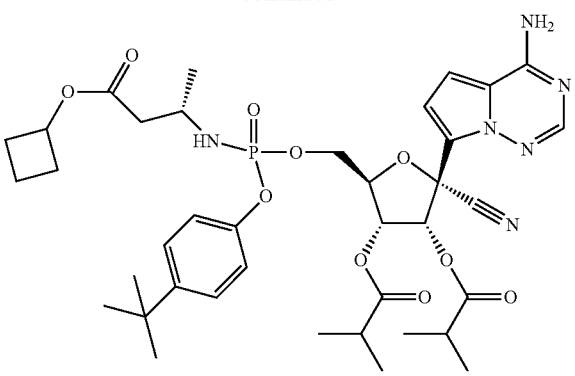

Example 166 was made in a similar fashion as Example 167 except that example 165 was used instead of cyclobutyl (((((2R,3S,4R,5R)-5-(4-aminopyrrolo[2,1-f][1,2,4]triazin-7-yl)-5-cyano-3,4-dihydroxytetrahydrofuran-2-yl)methoxy) (phenoxy)phosphoryl)-L-alaninate and acetic anhydride was used instead of 3-methyl butanoic anhydride. Mixture of stereoisomers: $^1$H NMR (400 MHz, Methanol-d4) δ 7.88 (s, 0.5H), 7.86 (s, 0.5H), 7.36-7.31 (m, 1H), 7.29-7.25 (m, 1H), 7.13-7.08 (m, 1H), 7.07-7.01 (m, 1H), 6.94-6.88 (m, 2H), 6.27 (d, J=6.0 Hz, 0.5H), 6.20 (d, J=6.0 Hz, 0.5H), 5.60 (dd, J=6.0, 4.3 Hz, 0.5H), 5.52 (dd, J=6.0, 4.3 Hz, 0.5H), 4.96-4.89 (m, 1H), 4.67-4.61 (m, 1H), 4.44-4.31 (m, 2H), 3.72-3.57 (m, 1H), 2.49-2.23 (m, 4H), 2.19-2.11 (m, 6H), 2.09-1.97 (m, 2H), 1.83-1.72 (m, 1H), 1.70-1.55 (m, 1H), 1.33-1.27 (m, 9H), 1.15 (d, J=6.6 Hz, 1.5H), 1.06 (d, J=6.6 Hz, 1.5H). 31P NMR (162 MHz, Methanol-d4) δ 4.40-4.14 (m). LCMS: MS m/z=727.2 [M+1], tR=1.04 min.

Example 167: (2R,3R,4R,5R)-2-(4-aminopyrrolo[2,1-f][1,2,4]triazin-7-yl)-5-((((4-(tert-butyl)phenoxy)(((S)-4-cyclobutoxy-4-oxobutan-2-yl)amino)phosphoryl)oxy)methyl)-2-cyanotetrahydrofuran-3,4-diyl bis(2-methylpropanoate)

Example 167 was made in a similar fashion as Example 107 except that example 165 was used instead of cyclobutyl ((((2R,3S,4R,5R)-5-(4-aminopyrrolo[2,1-f][1,2,4]triazin-7-yl)-5-cyano-3,4-dihydroxytetrahydrofuran-2-yl)methoxy) (phenoxy)phosphoryl)-L-alaninate and 2-methylproprionic anhydride was used instead of 3-methyl butanoic anhydride. Mixture of stereoisomers: $^1$H NMR (400 MHz, Methanol-d4) δ 7.88 (s, 0.5H), 7.87 (s, 0.5H), 7.37-7.32 (m, 1H), 7.30-7.24 (m, 1H), 7.14-7.10 (m, 1H), 7.07-7.02 (m, 1H), 6.93-6.86 (m, 2H), 6.27 (d, J=6.0 Hz, 0.5H), 6.18 (d, J=5.9 Hz, 0.5H), 5.62 (dd, J=5.9, 3.8 Hz, 0.5H), 5.52 (dd, J=5.9, 3.8 Hz, 0.5H), 4.96-4.87 (m, 1H), 4.65-4.57 (m, 1H), 4.43-4.32 (m, 2H), 3.73-3.58 (m, 1H), 2.75-2.59 (m, 2H), 2.50-2.23 (m, 4H), 2.11-1.97 (m, 2H), 1.84-1.72 (m, 1H), 1.68-1.56 (m, 1H), 1.38-1.03 (m, 24H). 31P NMR (162 MHz, Methanol-d4) δ 4.36-4.12 (m). LCMS: MS m/z=783.3 [M+1], tR=1.18 min.

Example 168: (2R,3R,4R,5R)-2-(4-aminopyrrolo[2,1-f][1,2,4]triazin-7-yl)-2-cyano-5-(((((S)-(((S)-1-(2-methoxy-2-methylpropoxy)-1-oxopropan-2-yl)amino)(phenoxy)phosphoryl)oxy)methyl) tetrahydrofuran-3,4-diyl bis(3-methylbutanoate)

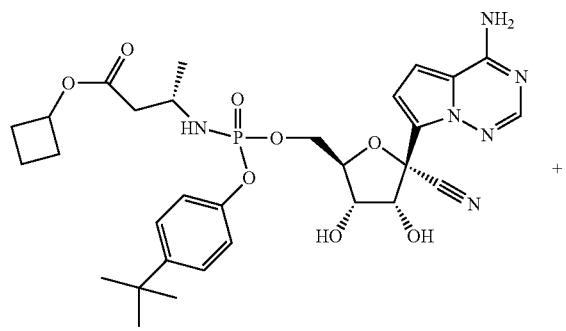

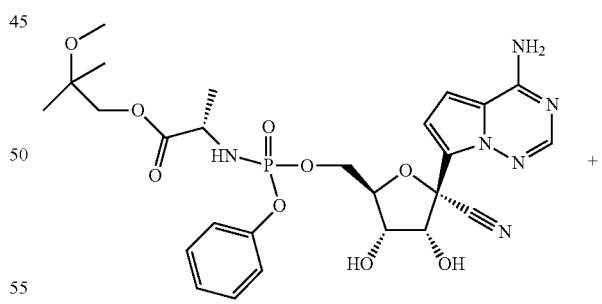

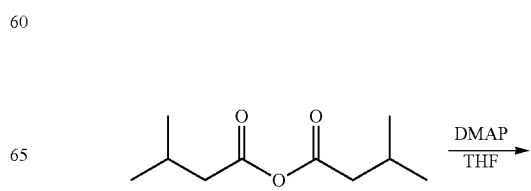

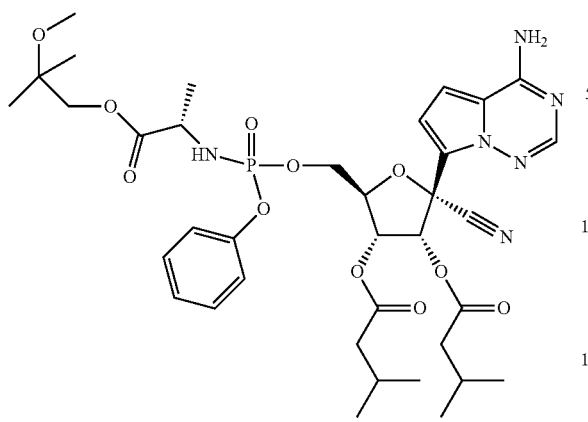
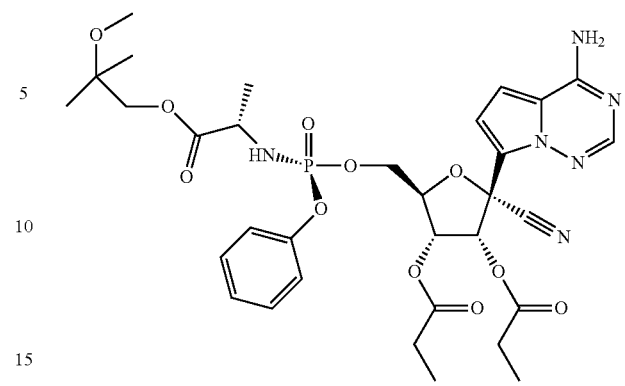

Example 168 was made in a similar fashion as Example 109 except that 2-methoxy-2-methylpropyl ((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)-L-alaninate (Example 24) was used instead of cyclobutyl ((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)-L-alaninate. Mixture of stereoisomers: ¹H NMR (400 MHz, Methanol-d4) δ 7.88 (s, 1H), 7.32-7.26 (m, 2H), 7.20-7.13 (m, 3H), 6.88-6.84 (m, 2H), 6.26 (d, J=5.9 Hz, 1H), 5.60-5.56 (m, 1H), 4.64-4.59 (m, 1H), 4.46-4.36 (m, 2H), 4.09-4.05 (m, 1H), 3.99-3.90 (m, 2H), 3.21 (s, 3H), 2.37-2.02 (m, 6H), 1.35-1.31 (m, 3H), 1.19-1.16 (m, 6H), 1.05-1.01 (m, 6H), 0.97-0.93 (m, 6H). 31P NMR (162 MHz, Methanol-d4) δ 3.58-3.28 (m). LCMS: MS m/z=773.8 [M+1], tR=1.08 min.

Example 169: (2R,3R,4R,5R)-2-(4-aminopyrrolo[2,1-f][1,2,4]triazin-7-yl)-2-cyano-5-((((S)-(((S)-1-(2-methoxy-2-methylpropoxy)-1-oxopropan-2-yl)amino)(phenoxy)phosphoryl)oxy)methyl)tetrahydrofuran-3,4-diyl dipropionate Example 169 was made in a similar fashion as Example 107 except that 2-methoxy-2-methylpropyl ((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)-L-alaninate (Example 24) was used instead of cyclobutyl ((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)-L-alaninate. Mixture of stereoisomers: ¹H NMR (400 MHz, Methanol-d4) δ 7.89 (s, 0.5H), 7.87 (s, 0.5H), 7.35-7.25 (m, 2H), 7.23-7.12 (m, 3H), 6.95-6.88 (m, 1H), 6.88-6.83 (m, 1H), 6.21 (d, J=5.9 Hz, 1H), 5.61-5.55 (m, 1H), 4.70-4.61 (m, 1H), 4.46-4.35 (m, 2H), 4.10-4.03 (m, 1H), 3.99-3.91 (m, 2H), 3.24-3.17 (m, 3H), 2.54-2.32 (m, 4H), 1.35-1.29 (m, 3H), 1.24-1.10 (m, 12H). 31P NMR (162 MHz, Methanol-d4) δ 3.70-3.32 (m). LCMS: MS m/z=717.8 [M+1], tR=0.94 min.

Intermediate T34: 2-ethylbutyl (((4-(tert-butyl)naphthalen-1-yl)oxy)(perfluorophenoxy)phosphoryl)-L-alaninate

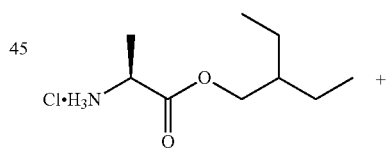

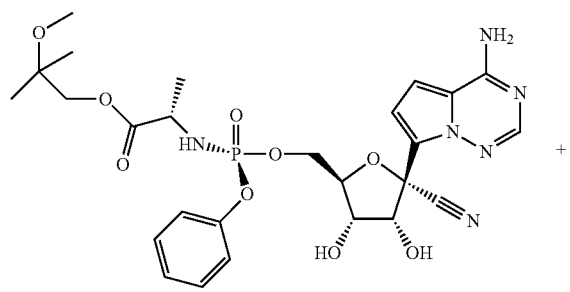

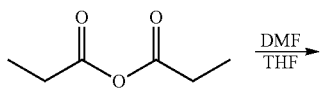

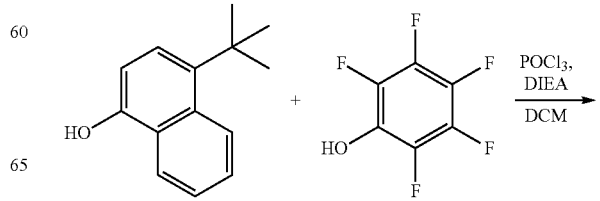

-continued

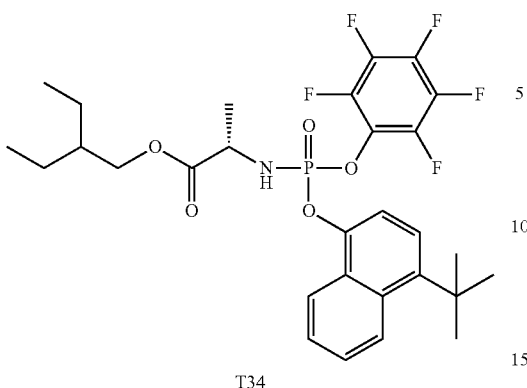

T34

Intermediate T34 was made in a similar manner as intermediate A1 except that 4-(tert-butyl)naphthalen-1-ol (653 mg, 3.26 mmol) was used instead of 4-tert-butylphenol. $^1$H NMR (400 MHz, Chloroform-d) δ 8.06 (t, J=2.4 Hz, 1H), 7.83 (dd, J=8.7, 1.6 Hz, 1H), 7.73-7.50 (m, 3H), 7.38 (td, J=7.9, 2.2 Hz, 1H), 4.29 (dt, J=15.9, 8.1 Hz, 1H), 4.20-3.99 (m, 2H), 1.59-1.23 (m, 17H), 0.95-0.81 (m, 6H). $^{19}$F NMR (376 MHz, Chloroform-d) δ −153.54 (tt, J=18.6, 3.7 Hz), −159.77 (d, J=3.8 Hz), −162.18−−162.78 (m).

Example 170: 2-ethylbutyl (((((2R,3S,4R,5R)-5-(4-aminopyrrolo[2,1-f][1,2,4]triazin-7-yl)-5-cyano-3,4-dihydroxytetrahydrofuran-2-yl)methoxy)((4-(tert-butyl)naphthalen-1-yl)oxy)phosphoryl)-L-alaninate

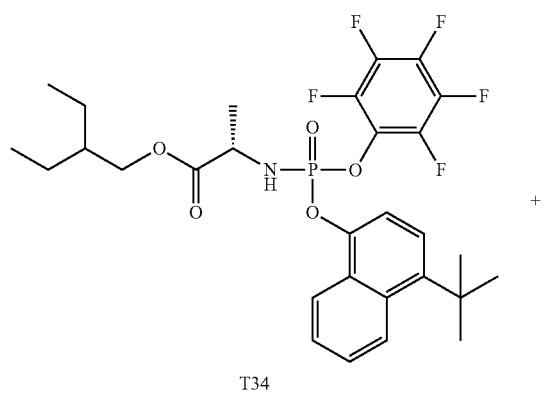

T34

+

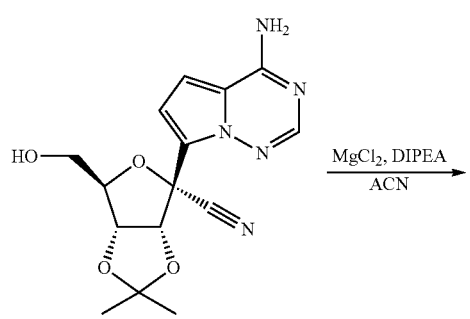

→ MgCl$_2$, DIPEA / ACN

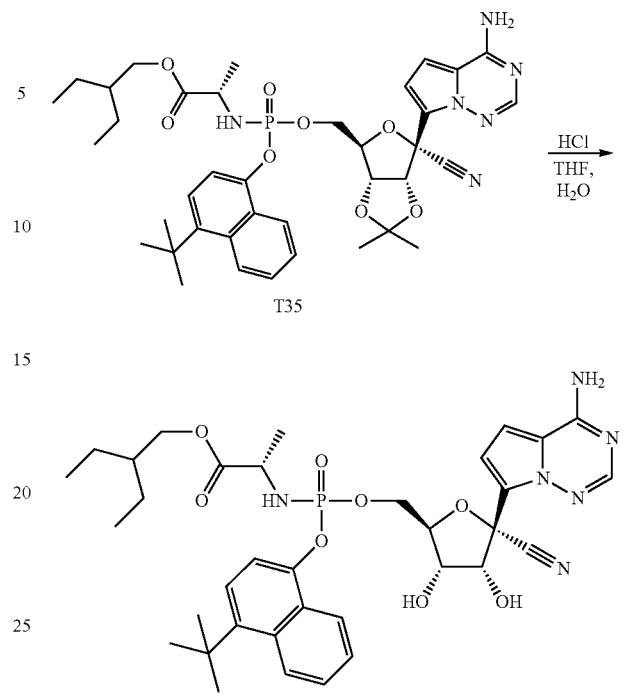

T35

→ HCl, THF, H$_2$O

Intermediate T35 was made in a similar manner as intermediate A2 except that intermediate T34 (1.4 g, 2.33 mmol) was used instead of intermediate A1. LCMS: MS m/z=749.2 and 749.2 [M+1], $t_R$=1.20 min and 1.22 min.

Example 170 was made in a similar manner as Example 13 except that intermediate T35 (600 mg, 0.801 mmol) was used instead of intermediate A2. Mixture of stereoisomers: LCMS: MS m/z=709.2 and 709.2 [M+1], $t_R$=1.07 min and 1.08 min; $^1$H NMR (400 MHz, Methanol-d4) δ 8.08 (d, J=1.9 Hz, 1H), 7.82 (dd, J=13.7, 4.9 Hz, 2H), 7.71-7.60 (m, 2H), 7.39 (dt, J=7.7, 1.3 Hz, 1H), 7.29 (t, J=7.9 Hz, 1H), 6.93-6.78 (m, 2H), 4.77 (d, J=5.5 Hz, 1H), 4.56-4.35 (m, 3H), 4.26 (t, J=5.5 Hz, 1H), 4.07-3.87 (m, 3H), 1.46-1.23 (m, 17H), 0.82 (td, J=7.4, 2.0 Hz, 6H). $^{31}$P NMR (162 MHz, Methanol-d4) δ 4.20.

Individual isomers of Example 170 were separated by preparatory HPLC (Gemini 5 um NX-C18 110A LC column 100×30 mm, 95% to 0% water acetonitrile gradient).

Peak 1 Example 170a (faster eluting isomer) data: LCMS: MS m/z=709.4 [M+1], $t_R$=1.07 min; $^1$H NMR (400 MHz, Methanol-d4) δ 8.08 (d, J=1.9 Hz, 1H), 7.89-7.75 (m, 2H), 7.71-7.60 (m, 2H), 7.39 (dt, J=7.7, 1.3 Hz, 1H), 7.29 (t, J=7.9 Hz, 1H), 6.92-6.78 (m, 2H), 4.77 (d, J=5.5 Hz, 1H), 4.59-4.48 (m, 1H), 4.42 (dt, J=10.9, 5.9 Hz, 2H), 4.26 (t, J=5.5 Hz, 1H), 4.03-3.86 (m, 3H), 1.47-1.22 (m, 17H), 0.83 (tt, J=7.5, 2.8 Hz, 6H). $^{31}$P NMR (162 MHz, Methanol-d4) δ 4.20.

Peak 2 Example 170b (slower eluting isomer) data: LCMS: MS m/z=709.2 [M+1], $t_R$=1.08 min; $^1$H NMR (400 MHz, Methanol-d4) δ 8.14-8.04 (m, 1H), 7.87-7.79 (m, 2H), 7.65 (ddd, J=13.4, 8.5, 1.5 Hz, 2H), 7.43 (dt, J=7.7, 1.3 Hz, 1H), 7.30 (t, J=7.9 Hz, 1H), 6.90-6.73 (m, 2H), 4.68 (d, J=5.4 Hz, 1H), 4.53-4.31 (m, 3H), 4.19 (t, J=5.5 Hz, 1H), 4.07-3.87 (m, 3H), 1.47-1.21 (m, 17H), 0.84 (td, J=7.5, 1.5 Hz, 6H). $^{31}$P NMR (162 MHz, Methanol-d4) δ 4.05.

Example 171: (2R,3R,4R,5R)-2-(4-aminopyrrolo[2,1-f][1,2,4]triazin-7-yl)-5-(((((4-(tert-butyl)naphthalen-1-yl)oxy)(((S)-1-(2-ethylbutoxy)-1-oxopropan-2-yl)amino)phosphoryl)oxy)methyl)-2-cyanotetrahydrofuran-3,4-diyl diacetate Example 172: (2R,3R,4R,5R)-2-(4-aminopyrrolo[2,1-f][1,2,4]triazin-7-yl)-5-(((((4-(tert-butyl)naphthalen-1-yl)oxy)(((S)-1-(2-ethylbutoxy)-1-oxopropan-2-yl)amino)phosphoryl)oxy)methyl)-2-cyanotetrahydrofuran-3,4-diyl dipropionate

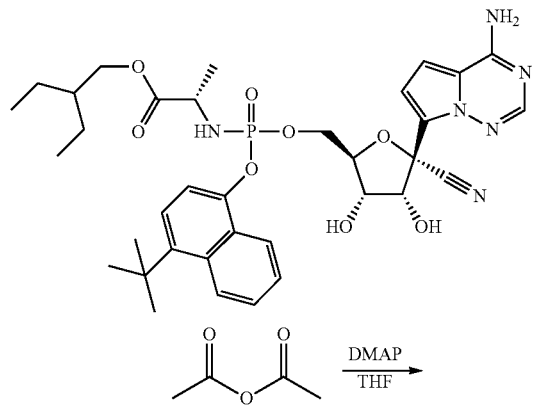

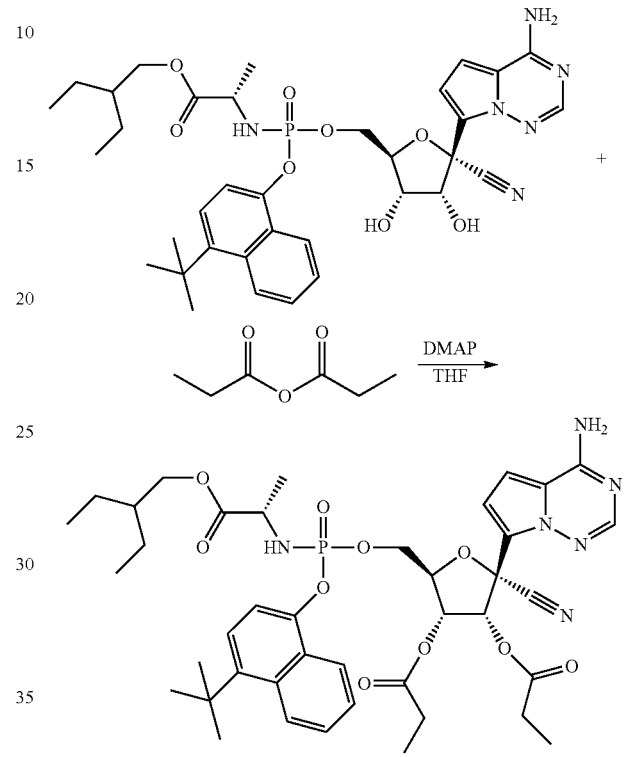

Example 171 was made in a similar manner as Example 33 except that example 170 (86 mg, 0.121 mmol) was used instead of 31.

Individual isomers of Example 171 were separated by preparatory HPLC (Gemini 5 um NX-C18 110A LC column 100×30 mm, 95% to 0% water acetonitrile gradient).

Peak 1 Example 171a (faster eluting isomer) data: LCMS: MS m/z=793.2 [M+1], $t_R$=1.18 min; $^1$H NMR (400 MHz, Methanol-d4) δ 8.09 (d, J=1.9 Hz, 1H), 7.82 (d, J=8.7 Hz, 1H), 7.76 (s, 1H), 7.69-7.59 (m, 2H), 7.43 (dt, J=7.6, 1.3 Hz, 1H), 7.31 (t, J=7.9 Hz, 1H), 6.94-6.83 (m, 2H), 6.33 (d, J=6.0 Hz, 1H), 5.63 (dd, J=6.0, 4.4 Hz, 1H), 4.69 (dd, J=4.0, 1.7 Hz, 1H), 4.60-4.43 (m, 2H), 4.03-3.83 (m, 3H), 2.15 (d, J=12.0 Hz, 6H), 1.44-1.20 (m, 17H), 0.81 (td, J=7.5, 2.0 Hz, 6H). $^{31}$P NMR (162 MHz, Methanol-d4) δ 4.09.

Peak 2 Example 171b (slower eluting isomer) data: LCMS: MS m/z=793.2 [M+1], $t_R$=1.19 min; $^1$H NMR (400 MHz, Methanol-d4) δ 8.09 (d, J=1.9 Hz, 1H), 7.84 (d, J=8.8 Hz, 2H), 7.65 (ddd, J=15.4, 8.6, 1.5 Hz, 2H), 7.40 (dt, J=7.7, 1.2 Hz, 1H), 7.26 (t, J=7.9 Hz, 1H), 6.86-6.76 (m, 2H), 6.20 (d, J=5.9 Hz, 1H), 5.55 (dd, J=5.9, 4.5 Hz, 1H), 4.68-4.58 (m, 1H), 4.47 (ddd, J=11.3, 5.9, 3.9 Hz, 2H), 4.05-3.87 (m, 3H), 2.13 (d, J=3.7 Hz, 6H), 1.43-1.24 (m, 17H), 0.84 (qd, J=7.5, 1.5 Hz, 6H). $^{31}$P NMR (162 MHz, Methanol-d4) δ 3.99.

Example 172 (43 mg, 43%) was made in a similar manner as Example 32 except that Example 170 (86 mg, 0.121 mmol) was used instead of 31.

Individual isomers of Example 172 were separated by preparatory HPLC (Gemini 5 um NX-C18 110A LC column 100×30 mm, 95% to 0% water acetonitrile gradient).

Peak 1 Example 172a faster eluting isomer) data: LCMS: MS m/z=821.4 [M+1], $t_R$=1.25 min; $^1$H NMR (400 MHz, Methanol-d4) δ 8.09 (d, J=1.9 Hz, 1H), 7.87-7.73 (m, 2H), 7.69-7.59 (m, 2H), 7.43 (dt, J=7.7, 1.2 Hz, 1H), 7.30 (t, J=7.9 Hz, 1H), 6.94-6.83 (m, 2H), 6.34 (d, J=6.0 Hz, 1H), 5.65 (dd, J=6.0, 4.1 Hz, 1H), 4.69 (dt, J=4.1, 2.1 Hz, 1H), 4.62-4.44 (m, 2H), 4.03-3.84 (m, 3H), 2.53-2.37 (m, 4H), 1.43-1.12 (m, 23H), 0.81 (td, J=7.4, 2.0 Hz, 7H). $^{31}$P NMR (162 MHz, Methanol-d4) δ 4.09.

Peak 2 Example 172b (slower eluting isomer) data: LCMS: MS m/z=821.3 [M+1], $t_R$=1.26 min; $^1$H NMR (400 MHz, Methanol-d4) δ 8.09 (d, J=1.9 Hz, 1H), 7.84 (t, J=4.4 Hz, 2H), 7.70-7.61 (m, 2H), 7.40 (dt, J=7.8, 1.3 Hz, 1H), 7.26 (t, J=7.9 Hz, 1H), 6.82 (s, 2H), 6.19 (d, J=5.8 Hz, 1H), 5.58 (dd, J=5.8, 4.3 Hz, 1H), 4.68-4.59 (m, 1H), 4.47 (ddd, J=10.8, 5.7, 2.4 Hz, 2H), 4.07-3.87 (m, 3H), 2.53-2.33 (m, 4H), 1.58-0.98 (m, 23H), 0.97-0.58 (m, 6H). $^{31}$P NMR (162 MHz, Methanol-d4) δ 3.98.

Example 173 (2R,3R,4R,5R)-2-(4-aminopyrrolo[2,1-f][1,2,4]triazin-7-yl)-5-(((((4-(tert-butyl)naphthalen-1-yl)oxy)(((S)-1-(2-ethylbutoxy)-1-oxopropan-2-yl)amino)phosphoryl)oxy)methyl)-2-cyanotetrahydrofuran-3,4-diyl bis(2-methylpropanoate)

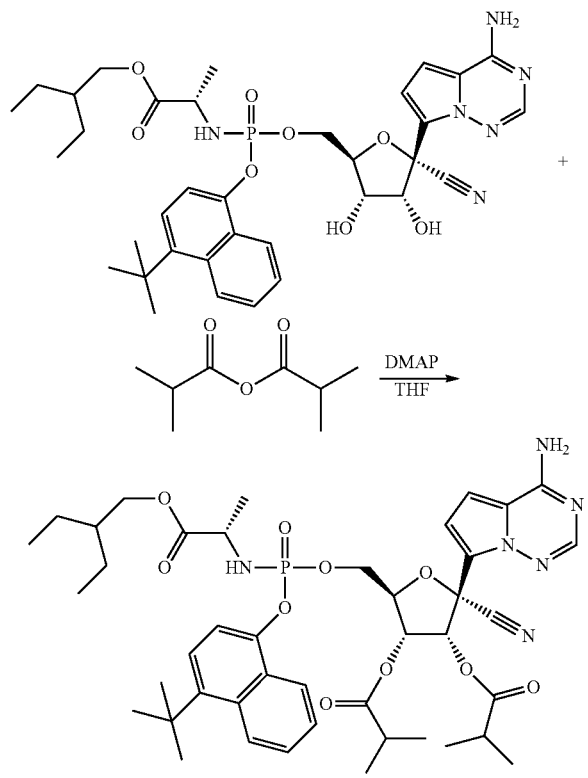

Example 173 was made in a similar manner as Example 14 except that Example 170 (86 mg, 0.121 mmol) was used instead of A3. Mixture of stereoisomers: LCMS: MS m/z=849.8 and 849.8 [M+1], $t_R$=1.30 min and 1.32 min; $^1$H NMR (400 MHz, Methanol-d4) δ 8.09 (d, J=1.9 Hz, 1H), 7.88-7.76 (m, 2H), 7.72-7.61 (m, 2H), 7.42 (t, J=8.5 Hz, 1H), 7.28 (dt, J=16.2, 7.9 Hz, 1H), 6.92-6.75 (m, 2H), 6.26 (dd, J=57.3, 5.9 Hz, 1H), 5.61 (ddd, J=29.7, 5.9, 3.8 Hz, 1H), 4.73-4.39 (m, 3H), 4.08-3.87 (m, 3H), 2.73-2.56 (m, 2H), 1.50-1.01 (m, 29H), 0.92-0.70 (m, 6H). $^{31}$P NMR (162 MHz, Methanol-d4) δ 4.01.

Individual isomers of Example 173 were separated by preparatory HPLC (Gemini Sum NX-C18 110A LC column 100×30 mm, 95% to 0% water acetonitrile gradient).

Peak 1 Example 173a (faster eluting isomer) data: LCMS: MS m/z=849.5 [M+1], $t_R$=1.30 min; $^1$H NMR (400 MHz, Methanol-d4) δ 8.09 (d, J=1.9 Hz, 1H), 7.88-7.75 (m, 2H), 7.72-7.59 (m, 2H), 7.43 (dt, J=7.7, 1.3 Hz, 1H), 7.30 (t, J=7.9 Hz, 1H), 6.93-6.81 (m, 2H), 6.33 (d, J=5.9 Hz, 1H), 5.65 (dd, J=6.0, 3.8 Hz, 1H), 4.69 (dt, J=4.0, 2.0 Hz, 1H), 4.60-4.45 (m, 2H), 3.99-3.84 (m, 3H), 2.64 (dq, J=21.1, 7.0 Hz, 2H), 1.43-1.15 (m, 29H), 0.81 (td, J=7.5, 2.0 Hz, 6H). $^{31}$P NMR (162 MHz, Methanol-d4) δ 4.07.

Peak 2 Example 173b (slower eluting isomer) data: LCMS: MS m/z=849.3 [M+1], $t_R$=1.32 min; $^1$H NMR (400 MHz, Methanol-d4) δ 8.09 (d, J=1.9 Hz, 1H), 7.84 (d, J=9.4 Hz, 2H), 7.72-7.60 (m, 2H), 7.40 (dt, J=7.7, 1.2 Hz, 1H), 7.26 (t, J=7.9 Hz, 1H), 6.79 (d, J=0.7 Hz, 2H), 6.19 (d, J=5.9 Hz, 1H), 5.57 (dd, J=5.9, 3.9 Hz, 1H), 4.62 (dd, J=3.9, 1.9 Hz, 1H), 4.48 (td, J=6.0, 3.9 Hz, 2H), 4.08-3.86 (m, 3H), 2.64 (dt, J=13.8, 6.9 Hz, 2H), 1.56-1.07 (m, 27H), 0.92-0.69 (m, 6H). $^{31}$P NMR (162 MHz, Methanol-d4) δ 3.96.

Intermediate T36: cyclooctyl L-alaninate hydrogenchloride

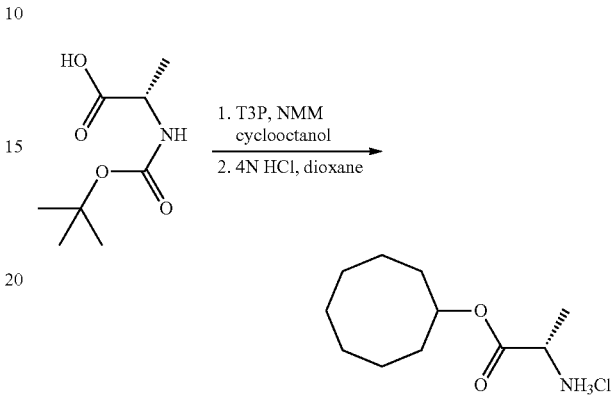

Intermediate T36 was made in a similar manner as T3 except that cyclooctanol (2.0 g, 15.6 mmol) was used instead of Rac-(1r,3s)-3-butylcyclobutan-1-ol, cis.

Intermediate T37: cyclooctyl ((4-chlorophenoxy)(perfluorophenoxy)phosphoryl)-L-alaninate

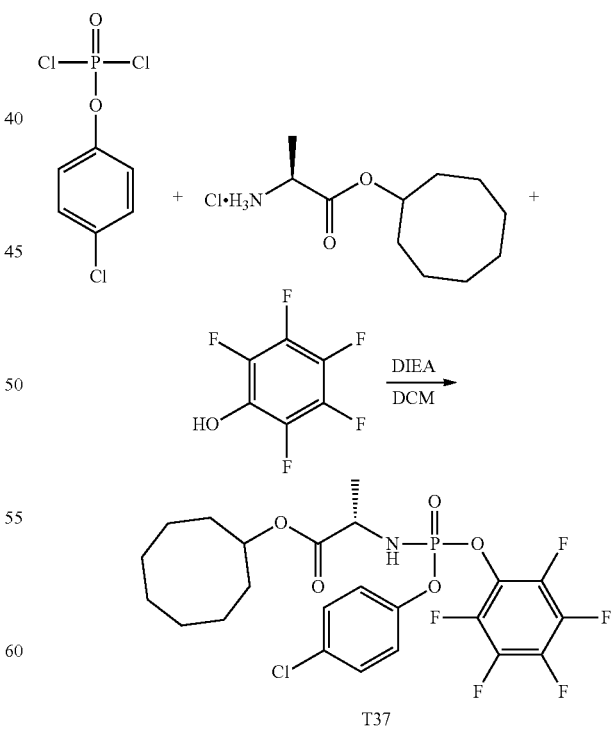

To a solution of 1-chloro-4-dichlorophosphoryl-benzene (1.7 g, 7.41 mmol) in dichloromethane (19 mL) at −78° C. was added T36 (1.75 g, 7.41 mmol) followed by N-ethyl- N-isopropyl-propan-2-amine (2 equiv, 2.6 mL) dropwise over 5 min time. The reaction was allowed to warm to 0° C. for 1 hr. 2,3,4,5,6-pentafluorophenol (456 mg, 3.14 mmol) was then added followed by 1 equivalent (1.3 mL) of N-ethyl-N-isopropyl-propan-2-amine dropwise. After 30 minutes, the reaction was allowed to warm to 0° C. then room temperature. The reaction mixture was acidified with acetic acid (1.5 mL) and washed with water. The organic extract was dried over sodium sulfate, filtered and concentrated in vacuo. The residue was purified by silica gel chromatography (0-20-40-80% ethyl acetate in hexanes) to afford T37 (3.0 g, 62%). $^1$H NMR (400 MHz, Chloroform-d) δ 7.36-6.97 (m, 4H), 5.06-4.83 (m, 1H), 4.24-4.01 (m, 1H), 1.88-1.25 (m, 17H). $^{19}$F NMR (376 MHz, Chloroform-d) δ −153.29−−154.02 (m), −159.72 (td, J=21.9, 3.7 Hz), −162.06−−163.08 (m).

Example 174: Cyclooctyl ((((2R,3S,4R,5R)-5-(4-aminopyrrolo[2,1-f][1,2,4]triazin-7-yl)-5-cyano-3,4-dihydroxytetrahydrofuran-2-yl)methoxy)(4-chlorophenoxy)phosphoryl)-L-alaninate

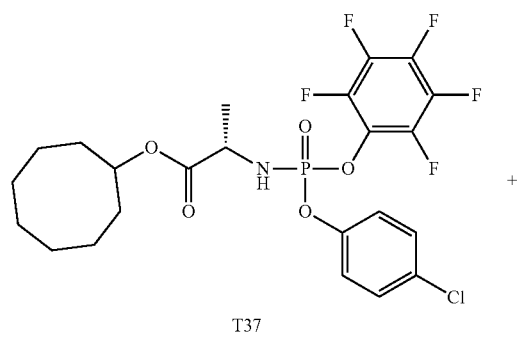

T37

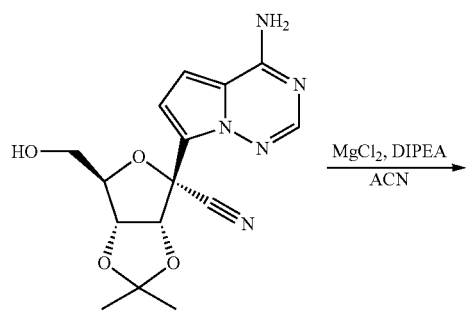

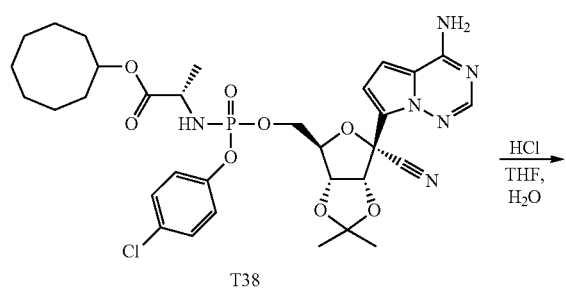

T38

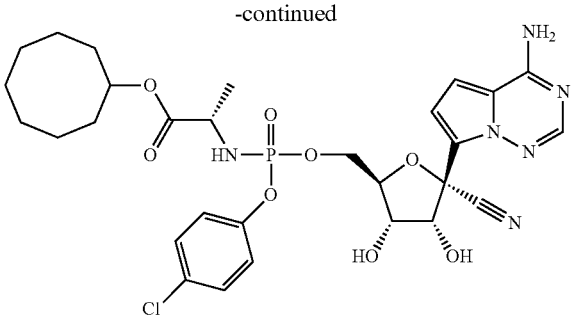

Intermediate T38 was made in a similar manner as intermediate T2 except that intermediate T37 (2.0 g, 3.60 mmol) was used instead of intermediate T1. LCMS: MS m/z=703.2 and 703.2 [M+1], $t_R$=1.10 min and 1.12 min.

Example 174 was made in a similar manner as Example 31 except that T38 (2.5 g, 3.56 mmol) was used instead of T2.

Individual isomers of Example 174 were separated by preparatory HPLC (Gemini 5 um NX-C18 110A LC column 100×30 mm, 95% to 0% water acetonitrile gradient).

Peak 1 Example 174a (faster eluting isomer) data: LCMS: MS m/z=663.2 [M+1], $t_R$=0.95 min; $^1$H NMR (400 MHz, Methanol-d4) δ 7.87 (s, 1H), 7.33-7.26 (m, 2H), 7.19-7.12 (m, 2H), 7.00-6.87 (m, 2H), 4.83 (d, J=5.4 Hz, 1H), 4.50-4.29 (m, 4H), 4.23 (t, J=5.5 Hz, 1H), 3.80 (dd, J=9.2, 7.1 Hz, 1H), 1.90-1.40 (m, 14H), 1.25 (dd, J=7.2, 1.2 Hz, 3H). $^{31}$P NMR (162 MHz, Methanol-d4) δ 3.76.

Peak 2 Example 174b (slower eluting isomer) data: LCMS: MS m/z=663.1 [M+1], $t_R$=0.96 min; $^1$H NMR (400 MHz, Methanol-d4) δ 7.88 (s, 1H), 7.35-7.24 (m, 2H), 7.24-7.14 (m, 2H), 6.96-6.85 (m, 2H), 4.81 (d, J=5.4 Hz, 2H), 4.47-4.28 (m, 3H), 4.19 (t, J=5.6 Hz, 1H), 3.84 (dd, J=9.7, 7.0 Hz, 1H), 1.75-1.40 (m, 14H), 1.29 (dd, J=7.1, 1.0 Hz, 3H). $^{31}$P NMR (162 MHz, Methanol-d4) δ 3.84.

Example 175: 2-ethylbutyl ((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(pyridin-2-yloxy)phosphoryl)-L-alaninate

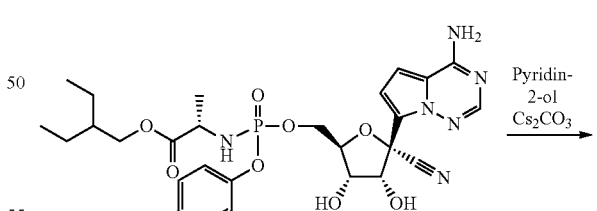

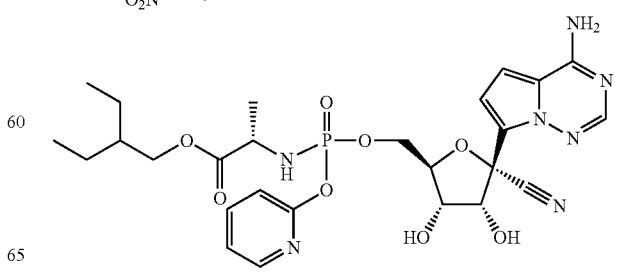

Example 175 was synthesized by treating 2-ethylbutyl ((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(4-nitrophenoxy)phosphoryl)-L-alaninate with pyridine-2-ol with cesium carbonate in the acetonitrile. The starting material is prepared as explained in example 105 starting with 2-ethylbutyl (bis(4-nitrophenoxy)phosphoryl)-L-alaninate.

Individual isomers of Compound 175 were separated by preparatory HPLC (Gemini Sum NX-C18 110A LC column 100×30 mm, 95% to 0% water acetonitrile gradient).

Peak 1: Example 175a, LCMS: MS m/z=644.3 [M+1], $^1$H NMR (400 MHz, Methanol-d4) δ 8.23-8.16 (m, 1H), 7.87 (d, J=1.5 Hz, 1H), 7.79 (ddtt, J=7.2, 5.1, 2.1, 1.0 Hz, 1H), 7.19 (dt, J=7.0, 4.9 Hz, 1H), 7.03-6.97 (m, 1H), 6.93-6.84 (m, 2H), 5.38 (dd, J=20.6, 6.5 Hz, 1H), 5.08 (ddd, J=11.0, 6.6, 3.2 Hz, 1H), 4.63 (d, J=4.4 Hz, 1H), 4.49-4.31 (m, 2H), 4.01 (ddt, J=19.4, 8.6, 5.5 Hz, 2H), 3.95-3.81 (m, 1H), 1.43 (d, J=3.1 Hz, 3H), 1.39-1.24 (m, 7H), 0.95-0.81 (m, 6H); $^{31}$P NMR (162 MHz, Methanol-d4) δ 2.96.

Peak 2: Example 175b, LCMS: MS m/z=644.3 [M+1], $^1$H NMR (400 MHz, Methanol-d4) δ 8.18-8.10 (m, 2H), 7.84 (s, 1H), 7.34 (dd, J=9.2, 1.1 Hz, 1H), 7.32-7.25 (m, 1H), 6.96-6.85 (m, 2H), 5.39 (dd, J=22.1, 6.7 Hz, 1H), 5.04 (dd, J=6.7, 3.5 Hz, 1H), 4.60 (dtd, J=21.4, 4.4, 3.9, 1.1 Hz, 1H), 4.41 (ddd, J=7.0, 4.3, 2.8 Hz, 2H), 4.05 (ddd, J=10.7, 5.7, 4.8 Hz, 1H), 4.01-3.86 (m, 2H), 1.72 (d, J=1.5 Hz, 3H), 1.53-1.44 (m, 1H), 1.42 (d, J=2.8 Hz, 3H), 1.39-1.28 (m, 8H), 0.88 (td, J=7.5, 1.0 Hz, 6H); $^{31}$P NMR (162 MHz, Methanol-d4) δ 3.23 (dd, J=16.8, 8.9 Hz).

Example 176: spiro[3.3]heptan-2-yl ((((2R,3S,4R, 5R)-5-(3-(((((benzyloxy)(hydroxy)phosphoryl)oxy)methyl)-4-imino-3,4-dihydropyrrolo[2,1-f][1,2,4]triazin-7-yl)-5-cyano-3,4-dihydroxytetrahydrofuran-2-yl)methoxy)(naphthalen-1-yloxy)phosphoryl)-L-alaninate Example 176 was synthesized as explained in Intermediate M1, but starting with Compound 82b. Individual isomer: LCMS: MS m/z=863.2 [M+1], $^1$H NMR (400 MHz, Methanol-d4) δ 8.16 (s, 1H), 8.14-8.09 (m, 1H), 7.94-7.87 (m, 1H), 7.74-7.69 (m, 1H), 7.54 (tt, J=6.9, 5.3 Hz, 2H), 7.46 (dt, J=7.6, 1.3 Hz, 1H), 7.39 (t, J=7.9 Hz, 1H), 7.28-7.22 (m, 2H), 7.22-7.10 (m, 4H), 6.98 (d, J=4.8 Hz, 1H), 5.64 (d, J=12.9 Hz, 2H), 4.90 (d, J=8.1 Hz, 3H), 4.77 (p, J=7.3 Hz, 1H), 4.60 (d, J=5.2 Hz, 1H), 4.52 (ddd, J=11.5, 6.5, 2.4 Hz, 1H), 4.47-4.31 (m, 2H), 4.16 (dd, J=6.6, 5.2 Hz, 1H), 3.95 (dq, J=9.7, 7.1 Hz, 1H), 2.37 (ddt, J=12.1, 7.3, 2.6 Hz, 2H), 2.05-1.98 (m, 2H), 1.97-1.86 (m, 4H), 1.86-1.76 (m, 2H), 1.32 (dd, J=7.1, 1.1 Hz, 4H); $^{31}$P NMR (162 MHz, Methanol-d4) δ 4.18 (d, J=8.8 Hz), −0.40 (td, J=12.9, 6.7 Hz).

Example 177: spiro[3.3]heptan-2-yl ((((2R,3S,4R, 5R)-5-cyano-3,4-dihydroxy-5-(4-imino-3-((phosphonooxy)methyl)-3,4-dihydropyrrolo[2,1-f][1,2,4]triazin-7-yl)tetrahydrofuran-2-yl)methoxy)(naphthalen-1-yloxy)phosphoryl)-L-alaninate

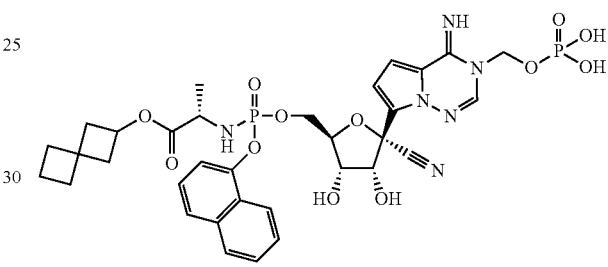

Example 177 was synthesized as explained in Example 28 but starting from Compound 176. Individual isomer: LCMS: MS m/z=773.1 [M+1], $^1$H NMR (400 MHz, Methanol-d4) δ 8.23 (s, 1H), 8.14-8.07 (m, 1H), 7.91 (dd, J=7.4, 1.9 Hz, 1H), 7.71 (d, J=8.0 Hz, 1H), 7.61-7.49 (m, 2H), 7.48-7.35 (m, 2H), 7.24 (d, J=4.8 Hz, 1H), 6.98 (d, J=4.8 Hz, 1H), 5.69 (d, J=11.4 Hz, 2H), 4.77 (p, J=7.3 Hz, 1H), 4.65 (d, J=5.2 Hz, 1H), 4.50 (ddd, J=11.4, 6.5, 2.4 Hz, 1H), 4.45-4.30 (m, 2H), 4.17 (dd, J=6.3, 5.2 Hz, 1H), 3.95 (dq, J=9.9, 7.1 Hz, 1H),

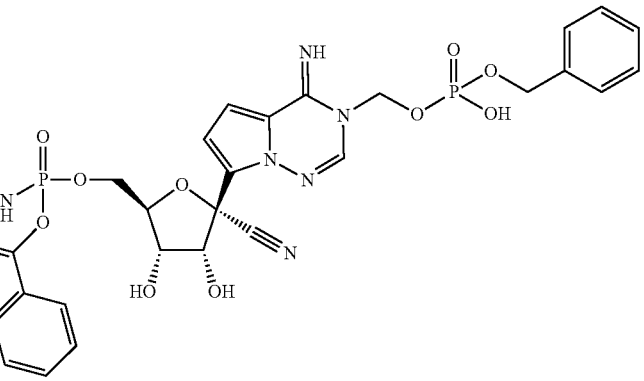

2.37 (ddt, J=12.1, 7.5, 2.6 Hz, 2H), 2.07-1.97 (m, 2H), 1.97-1.87 (m, 4H), 1.87-1.77 (m, 2H), 1.32 (dd, J=7.1, 1.1 Hz, 3H); $^{31}$P NMR (162 MHz, Methanol-d4) δ 4.17, 1.05 (t, J=11.4 Hz).

Example 178: (2R,3R,4R,5R)-2-cyano-2-(4-imino-3-((phosphonooxy)methyl)-3,4-dihydropyrrolo[2,1-f][1,2,4]triazin-7-yl)-5-(((((naphthalen-1-yloxy)(((S)-1-oxo-1-(spiro[3.3]heptan-2-yloxy)propan-2-yl) amino)phosphoryl)oxy)methyl)tetrahydrofuran-3,4-diyl bis(2-methylpropanoate)

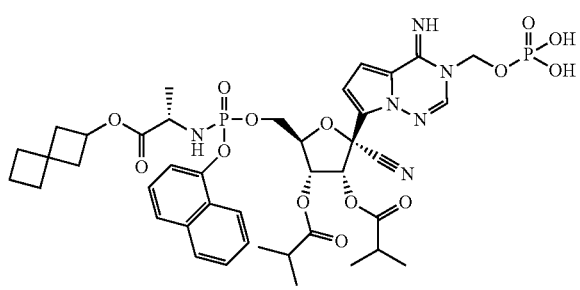 [SMILES: CC(C)C(=O)O[C@H]1[C@@H](OC(=O)C(C)C)[C@](C#N)(c2ccc3c(=N)n(COP(=O)(O)O)cnn23)O[C@@H]1COP(=O)(N[C@@H](C)C(=O)OC1CC2(CCC2)C1)Oc1cccc2ccccc12]

Example 178 was synthesized following the procedures explained in example 176 and 177 starting from example 86a. Individual isomer: LCMS: MS m/z=913.2 [M+1], $^{1}$H NMR (400 MHz, Methanol-d4) δ 8.18 (s, 1H), 8.06-8.00 (m, 1H), 7.88 (d, J=8.2 Hz, 1H), 7.68 (d, J=8.1 Hz, 1H), 7.53 (ddd, J=8.2, 6.8, 1.3 Hz, 1H), 7.49-7.40 (m, 2H), 7.38 (d, J=8.0 Hz, 1H), 7.35-7.28 (m, 1H), 7.02 (d, J=4.8 Hz, 1H), 6.08 (d, J=5.7 Hz, 1H), 5.67-5.53 (m, 3H), 4.78-4.63 (m, 2H), 4.60-4.46 (m, 2H), 3.91 (dq, J=9.4, 7.1 Hz, 1H), 2.65 (dp, J=24.0, 7.0 Hz, 2H), 2.32 (ddt, J=12.1, 7.8, 2.5 Hz, 2H), 2.07-1.95 (m, 2H), 1.91 (dd, J=8.2, 5.6 Hz, 2H), 1.87-1.73 (m, 4H), 1.34-1.21 (m, 9H), 1.18 (d, J=7.0 Hz, 6H); $^{31}$P NMR (162 MHz, Methanol-d4) δ 3.55 (q, J=6.5 Hz), 1.04 (t, J=11.0 Hz).

Example 179: 2-ethylbutyl ((4-(tert-butyl)phenoxy) (((2R,3S,4R,5R)-5-cyano-3,4-dihydroxy-5-(4-imino-3-((phosphonooxy)methyl)-3,4-dihydropyrrolo[2,1-f][1,2,4]triazin-7-yl)tetrahydrofuran-2-yl)methoxy) phosphoryl)-L-alaninate

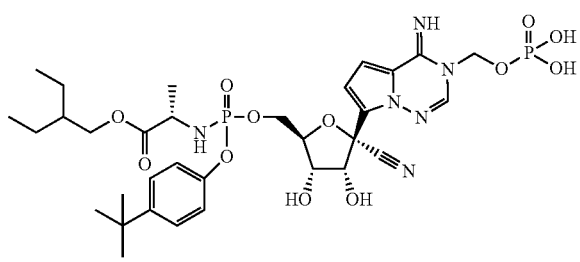 [SMILES: CCC(CC)COC(=O)[C@H](C)NP(=O)(OC[C@H]1O[C@@](C#N)(c2ccc3c(=N)n(COP(=O)(O)O)cnn23)[C@H](O)[C@@H]1O)Oc1ccc(C(C)(C)C)cc1]

Example 179 was synthesized following the procedures explained in example 176 and 177 starting from example 13b. Individual isomer: LCMS: MS m/z=769.2 [M+1], $^{1}$H NMR (400 MHz, Methanol-d4) δ 8.33 (s, 1H), 7.48 (d, J=4.8 Hz, 1H), 7.44-7.34 (m, 2H), 7.21-7.10 (m, 3H), 5.79 (d, J=11.6 Hz, 2H), 4.70 (d, J=5.2 Hz, 1H), 4.51-4.36 (m, 2H), 4.30 (ddd, J=12.1, 5.8, 3.0 Hz, 1H), 4.11 (dd, J=6.7, 5.1 Hz, 1H), 4.06 (dd, J=10.9, 5.8 Hz, 1H), 4.01-3.87 (m, 2H), 2.70 (dd, J=10.6, 0.8 Hz, 0H), 1.52 (td, J=12.8, 6.5 Hz, 1H), 1.41-1.33 (m, 7H), 1.32 (s, 9H), 0.89 (t, J=7.5 Hz, 6H). $^{31}$P NMR (162 MHz, Methanol-d4) δ 3.95 (q, J=6.5 Hz), 0.93 (t, J=11.5 Hz).

Example 180. RSV Antiviral Assay

The HEp-2 cell line was purchased from ATCC (Manassas, VA Cat #CCL-23) and maintained in Dulbecco's Minimum Essential Medium (DMEM) with GlutaMAX™ (Gibco, Carlsbad, CA Cat #10569-010) supplemented with 10% heat inactivated fetal bovine serum (FBS) (Hyclone, Logan, UT, Cat #SH30396.03), 100 units/mL penicillin and 100 units/mL streptomycin (Gibco, Carlsbad, CA Cat #15140-122). Cells were passaged 2-3 times per week to maintain sub-confluent densities and were used for experiments at passage 5-20. Respiratory syncytial virus (RSV) strain A2 direct pelleted virus (2-8×10$^7$ TCID$_{50}$/ml) was purchased from ViraPur (San Diego, CA). Antiviral potency against RSV was determined in HEp-2 cells in the following manner.

HEp-2 cells were suspended in DMEM+GlutaMAX (supplemented with 10% FBS and 1% Penicillin/Streptomycin) and seeded into 96 well plates (3×10$^3$/well). After a 4-hour incubation at 37° C.+5% CO2, three-fold serial dilutions of compounds were added to each well using an HP D300e digital dispenser. The cells were then infected with RSV A2 virus diluted in DMEM+GlutaMAX at an MOI=4 and incubated for 4 days at 37° C. and 5% CO2. The final volume in each well was 200 μL. Uninfected and untreated wells were included as controls for 100% cell viability. Following the incubation, 100 μL of culture supernatant was removed from each well and replaced with 100 μL of CellTiter-Glo reagent (Promega, Madison, WI, Cat #G7573). The plates were then rocked for 2 minutes followed by a 10-minute incubation at 25° C. Virus-induced cytopathic effect was then assessed by measuring luminescence signal using and Envision plate reader. Values were normalized to the uninfected and infected DMSO controls (as 0% and 100% infection, respectively) and data was fit using non-linear regression analysis using XLfit4. The EC$_{50}$ value for each compound was then determined as the concentration reducing the RSV-induced cytopathic effect by 50%. The values (nM) of exemplary compounds are shown in Table 1 and Table 2 below.

Example 181. SARS-CoV-2 Antiviral Assay 1.2×10$^4$ A549-hACE2 cells in 50 μl phenol red-free DMEM medium supplemented with 2% FBS were seeded in each well of a white opaque 96-well plate (Corning, Cat #3916). On the next day, 2-fold serial dilutions of compounds were prepared in DMSO. The compounds were further diluted as 100 folds in the 2% FBS culture medium. Cell culture fluids were removed and incubated with 50 μl diluted compound solutions and 50 μl of SARS-CoV2-Nano viruses (MOI 0.025). At 48 h post-infection, 50 μl Nano luciferase substrates (Promega, Cat #N1150) were added to each well. Luciferase signals were measured using a Synergy™ Neo2 Multi-Mode microplate reader (BioTek). The relative luciferase signals were calculated by normalizing the luciferase signals of the compound-treated groups to that of the DMSO-treated groups (expressed in percentages). The relative luciferase signals (Y axis) to the log 10 values of compound concentration (X axis) were plotted in the software GraphPad Prism 8. The EC$_{50}$ (compound concentration for reducing 50% of luciferase signals) were calculated using a nonlinear regression model (four parameters). The values (nM) of exemplary compounds are shown in Table 1 and Table 2 below.

Example 182. $CC_{50}$ Assay

The cytopathology of compounds in HEp-2 cells is determined in the following manner. HEp-2 cells are suspended in DMEM+GlutaMAX (supplemented with 10% FBS and 1% Penicillin/Streptomycin) and seeded into 96 well plates ($3\times10^3$/well). After a 4-hour incubation at 37° C.+5% CO2, three-fold serial dilutions of compounds are added to each well using an HP D300e digital dispenser. The cells are then incubated for 4 days at 37° C. and 5% CO2. The final volume in each well is 200 µL. Untreated wells are included as controls for 100% cell viability, while compounds treated with 5 uM puromycin are included as controls for 0% viability. Following the incubation, 100 µL of culture supernatant is removed from each well and replaced with 100 µL of CellTiter-Glo reagent (Promega, Madison, WI, Cat #G7573). The plates are then rocked for 2 minutes followed by a 10-minute incubation at 25° C. Compound-induced cytopathic effect is then assessed by measuring luminescence signal using and Envision plate reader. Values are normalized to the untreated DMSO and puromycin-treated controls (as 100% and 0% viability, respectively) and data is fit using non-linear regression analysis using XLfit4. The $CC_{50}$ value for each compound is then determined as the concentration reducing cell viability by 50%. The results (nM) are presented in Tables 1 and 2 below.

Example 183: Hep-2 RSV2 384-Well Assay (EC50-HEP2-384)

The HEp-2 cell line was purchased from ATCC (Manassas, VA, Cat #CCL-23) and maintained in Dulbecco's Minimum Essential Medium (DMEM) (Corning, New York, NY, Cat #15-018CM) supplemented with 10% fetal bovine serum (FBS) (Hyclone, Logan, UT, Cat #SH30071-03) and 1× Penicillin-Streptomycin-L-Glutamine (Corning, New York, NY, Cat #30-009-CI). Cells were passaged 2 times per week to maintain sub-confluent densities and were used for experiments at passage 5-20. Respiratory syncytial virus (RSV) strain A2 direct pelleted virus ($\geq 1\times 107$ TCID50/ml) was purchased from Microbiologics (Saint Cloud, MN). Antiviral potency against RSV was determined in HEp-2 cells in the following manner.

Compounds are prepared in 384-well polypropylene plates (Greiner, Monroe, NC, Cat #784201) with 8 compounds per plate in grouped replicates of 4 at 10 serially diluted concentrations (1:3). The serial-diluted compounds were then transferred to Echo qualified 384-well polypropylene microplate 2.0 (Labcyte, San Jose, CA, Cat #PP-0200-BC) using Biomek FX pipette station. 100 nL of compound per well was spotted into 384-well tissue culture plate (Greiner, Monroe, NC, Cat #781091) using Labcyte Echo Acoustic Transfer Instrument.

HEp-2 cells were suspended in DMEM (supplemented with 10% FBS and 1× Penicillin-Streptomycin-L-Glutamine) at 50,000 cells per mL (1,000 cells per well in 20 uL) and then infected with RSV A2 virus diluted in DMEM (supplemented with 10% FBS and 1× Penicillin-Streptomycin-L-Glutamine) at an MOI=4. Immediately after addition of virus, the RSV infected Hep-2 cell suspension is added to each 384-well compound plate at 20 uL per well using a Biotek MultiFlo dispenser. The assay plates were incubated for 4 days at 37° C. and 5% CO2. At the end of incubation, CellTiter-Glo reagent (Promega, Madison, WI, Cat #G7573) was prepared following CTG kit protocol. The assay plate and the reagent were equilibrated to room temperature for 30 minutes. CellTiter Glo reagent was added to each plate by Biomek FX at 16 uL per well with 3 times pipetting and mixing to induce cell lysis. The plates were spun down at 1,000 rpm for 1 minute. Virus-induced cytopathic effect was assessed by measuring luminescence signal using an Envision plate reader. EV0984 was used as positive control and DMSO was used as negative control. Values were normalized to the positive and negative controls (as 0% and 100% infection, respectively) and data was fitted using non-linear regression analysis by Gilead's dose response tool. The EC50 value for each compound was then determined as the concentration reducing the RSV-induced cytopathic effect by 50%.

Example 184: Hep-2 RSV-Luc5 384-Well Assay (EC50_RSVFLUC_Hep2-384)

HEp-2 cell line was purchased from ATCC (Manassas, VA Cat #CCL-23) and maintained in Dulbecco's Minimum Essential Medium (DMEM) (Corning, New York, NY, Cat #15-018CM) supplemented with 10% fetal bovine serum (FBS) (Hyclone, Logan, UT, Cat #SH30071-03) and 1× Penicillin-Streptomycin-L-Glutamine (Corning, New York, NY, Cat #30-009-CI). Cells were passaged 2 times per week to maintain sub-confluent densities and were used for experiments at passage 5-20. Respiratory syncytial virus recombinant with luciferase (RSV-Luc5) direct pelleted virus ($\geq 1\times 107$ TCID50/ml) was purchased from Microbiologics (Saint Cloud, MN). Viral replication was determined in HEp-2 cells in the following manner.

Compounds are prepared in 384-well polypropylene plates (Greiner, Monroe, NC, Cat #784201) with 8 compounds per plate in grouped replicates of 4 at 10 serially diluted concentrations (1:3).

HEp-2 cells were suspended in DMEM (supplemented with 10% FBS and 1× Penicillin-Streptomycin-L-Glutamine) and 60 uL of 4,000 cells per well were seeded into 384-well plates (Greiner, Monroe, NC, Cat #781080) using Biotek MultiFlo dispenser. After overnight incubation at 37° C. and 5% CO2, 0.4 uL of three-fold serial dilutions of compound was added to each well using a Biomek FX pipette station. RSV-Luc5 viruses were diluted in DMEM (supplemented with 10% FBS and 1× Penicillin-Streptomycin-L-Glutamine) at an MOI=0.5. Virus suspension was added to each 384-well compound plate at 20 uL per well using a Biotek MultiFlo dispenser. The assay plates were incubated for 3 days at 37° C. and 5% CO2. At the end of incubation, One-Glo reagent (Promega, Madison, WI, Cat #E6120) was prepared. The assay plate and the reagent were equilibrated to room temperature for 30 minutes. 50 uL per well of medium was removed from assay plate and 40 uL per well of One-Glo reagent was added to each plate by Biomek FX. The plates were sat at room temp for 15 minutes. Viral replication was then assessed by measuring luminescence signal using and Envision plate reader. Remdesivir was used as positive control and DMSO was used as negative control. Values were normalized to the positive and negative controls (as 0% and 100% replication, respectively) and data was fitted using non-linear regression analysis by Gilead's dose response tool. The EC50 value for each compound was then determined as the concentration reducing the viral replication by 50%.

Example 185: NHBE RSV-Fluc 96-Well Assay (EC50 RSVFluc NHBE 96)

Cell Culture

Normal human bronchial epithelial (NHBE) cells, donor 32027, were purchased from Lonza (Walkersville, MD Cat #CC-2540) and maintained in bronchial epithelial cell growth medium (BEGM) (Lonza, Walkersville, MD, Cat #CC-3170) with all provided supplements in the BulletKit at 37° C. with 5% CO2. NHBE cells were passaged 2-3 times per week to maintain sub-confluent densities and were used for experiments at passages 2-4.

Virus

Recombinant respiratory syncytial virus expressing the firefly luciferase protein (RSV-Fluc), was purchased by ViraTree (RTP, NC, #R145) and propagated by Virapur (San Diego, CA).

Antiviral Assay

NHBE cells ($5.0 \times 10^3$ cells/well) were seeded in white wall/clear bottom 96-well plates (Corning) with culture medium to a final volume of 100 µL and incubated for 24 hours at 37° C. with 5% CO2. On the following day, three-fold serial dilutions (starting at 0.23 nM and ending at 500 nM) of compounds dissolved in DMSO were added to the wells using the HP D300e digital dispenser with normalization to the highest concentration of DMSO in all wells (>0.1% final volume). The cells were then infected with RSV-Fluc diluted with BEGM media at MOI of 0.1 for a final volume of 200 µL media/well. Uninfected and untreated wells were included as controls. Following incubation with compound and virus for three days at 37° C. with 5% CO2, 100 µL of culture supernatant was removed from each well and replaced with 100 µL of ONE-Glo luciferase reagent (Promega, Madison, WI, Cat #E6110). The plates were gently mixed by rocking for 10 minutes at room temperature and luminescence signal was measured using an Envision plate reader (PerkinElmer). Values were normalized to the uninfected and infected DMSO controls (0% and 100% infection, respectively). Data was fit using non-linear regression analysis using XLfit4. Compound $EC_{50}$ values were then determined as the concentration reducing the firefly luciferase signal by 50%. The compiled data was generated based on least two independent experimental replicates, each containing technical duplicates for each concentration.

TABLE 1

Antiviral activity of exemplary compounds

| Example No. | $EC_{50}$-RSV-HEP-2-96 (nM) | SARS-CoV-2 $EC_{50}$ (nM) | RSV $CC_{50}$ (nM) | EC50 RSV HEP2 384 (nM) | EC50 RSVFluc-Hep2 384 (nM) |
|---|---|---|---|---|---|
| 1 | 121.7 | — | 5486 | | |
| 2 | 84.4 | — | 8408 | | |
| 3 | 44.119 | 113.2 | 5823 | | 18.3 |
| 4 | 93.9 | | 5583 | | |
| 5 | 109 | — | 9542 | | |
| 6 | 192.6 | — | 26391 | | |
| 7 | 77.9 | 241.4 | 12558 | | |
| 8 | 156.5 | | >40000 | | |
| 9 | 227.8 | | >50000 | | |
| 10 | 52.93 | | 10336 | | |
| 11 | 67.2 | 76.8 | 12825 | | |
| 12 | 165.7 | — | 30885 | | |
| 13 | 34.5 | 88.9 | 3797 | 58.8 | 20.1 |
| 13a | | | | 91.2 | 52.1 |
| 13b | | | | 33.4 | 26.7 |
| 14 | 29 | | 2730 | | |
| 15 | 184.8 | — | 22931 | | |
| 16 | 9.3 | 83.8 | 2838 | | |
| 17 | 164 | | 20789 | | |
| 18 | 7.7494 | | 2615 | 83.4 | |
| 18a | | | | 65.4 | |
| 18b | | | | 75.0 | |
| 19 | 687.3 | — | 26513 | | |
| 20 | 444.1 | — | 5178 | | |
| 21 | 19.8 | 122.7 | 3110 | 58.8 | 29.4 |
| 21a | | | | 92.0 | |
| 21b | | | | 34.7 | |
| 22 | >4715 | — | >50000 | | |
| 23 | 75.9 | — | 5643 | | |
| 24 | 1474.6 | — | >50000 | | |
| 25 | 11.1 | 121.7 | 4778 | | |
| 26a | 1156.4 | — | >45000 | | |
| 26b | 603.4 | — | 2404 | | |
| 27 | 958.2 | — | 5855 | | |
| 28 | 31 | — | 7451 | | 21.5 |
| 29 | 10.7 | 65.1 | 2652 | 62.2 | 36.9 |
| 30 | 7.3 | — | 2313 | 39.7 | 27.1 |

TABLE 2

Antiviral activity of further exemplary compounds

| Compound | $EC_{50}$-RSV-HEP-2-96 (nM) | SARS-CoV-2 $EC_{50}$ (nM) | RSV $CC_{50}$ (nM) |
|---|---|---|---|
| 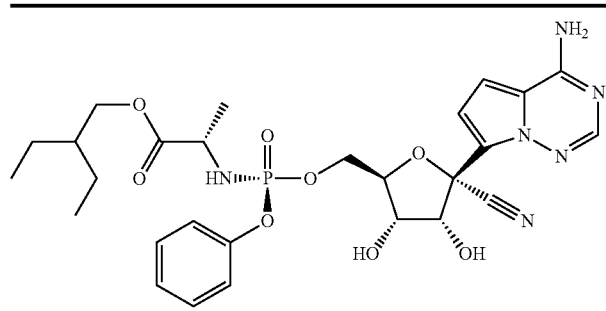 | 14.9 | 110 | 6077 |

TABLE 2-continued

Antiviral activity of further exemplary compounds

| Compound | EC₅₀-RSV-HEP-2-96 (nM) | SARS-CoV-2 EC₅₀ (nM) | RSV CC₅₀ (nM) |
|---|---|---|---|
| 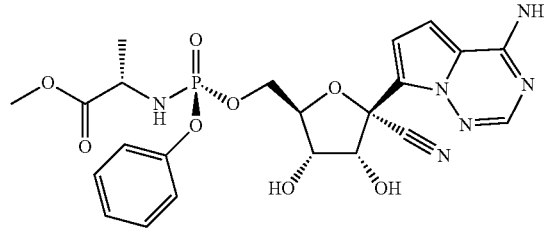 | 143.9 | — | 48533 |
| 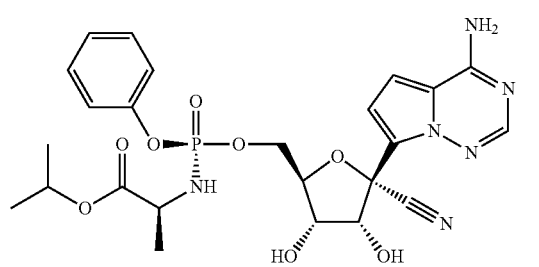 [SMILES: CC(C)OC(=O)[C@H](C)N[P@](=O)(OC[C@H]1O[C@@](C#N)(c2ccc3c(N)ncnn23)[C@H](O)[C@@H]1O)Oc1ccccc1] | 363.9 | — | >9600 |
| 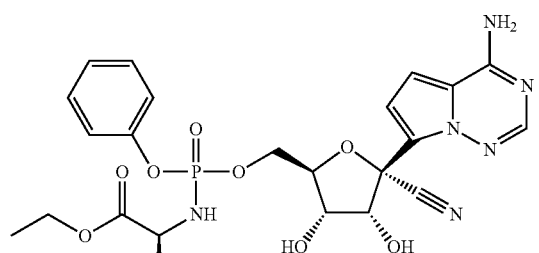 | 295.9 | — | >70000 |
| 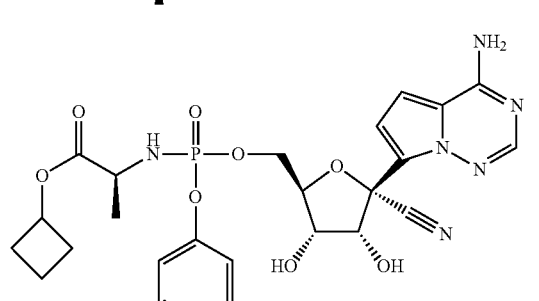 | 75.1 | — | 34179 |

TABLE 3

Antiviral activity of further exemplary compounds in HEP-2- Cells

| Example | EC₅₀ RSV HEP2 96 (nM) | EC₅₀ RSV HEP2 384 (nM) | EC₅₀ RSVFluc-Hep2 384 (nM) |
|---|---|---|---|
| Example 31 |  | 53.23 |  |
| Example 31a |  | 29.24 |  |
| Example 31b |  | 41.06 |  |
| Example 32a |  | 25.39 |  |
| Example 32b |  | 30.00 |  |
| Example 33a |  | 22.72 |  |
| Example 33b |  | 27.16 |  |
| Example 34 |  | 1498.40 |  |
| Example 35 |  | 185.18 |  |
| Example 36 |  | 101.75 |  |
| Example 37 |  | 187.42 |  |
| Example 38 |  | 137.92 |  |
| Example 39 |  | 1602.40 |  |
| Example 40 |  | 226.18 |  |
| Example 41 |  | 141.84 |  |
| Example 42a |  | 68.30 |  |
| Example 42b |  | 68.83 |  |
| Example 43 |  | 62.83 |  |

TABLE 3-continued

Antiviral activity of further exemplary compounds in HEP-2- Cells

| Example | $EC_{50}$ RSV HEP2 96 (nM) | $EC_{50}$ RSV HEP2 384 (nM) | $EC_{50}$ RSVFluc-Hep2 384 (nM) |
|---|---|---|---|
| Example 44 | | 56.02 | 18.32 |
| Example 44a | | | 21.67 |
| Example 44b | | | 22.90 |
| Example 45 | | 31.09 | 19.02 |
| Example 45a | | 60.37 | 22.72 |
| Example 45b | | 23.88 | 6.87 |
| Example 46 | | 52.33 | 19.26 |
| Example 46a | | | 30.22 |
| Example 46b | | | 30.03 |
| Example 47a | | 41.64 | |
| Example 47b | | 68.26 | |
| Example 48a | | 34.05 | |
| Example 48b | | 55.43 | |
| Example 50a | 21.28 | | |
| Example 50b | 8.52 | | |
| Example 51a | 66.07 | | |
| Example 51b | 86.80 | | |
| Example 52a | 20.46 | | |
| Example 52b | 25.44 | | |
| Example 53a | 38.11 | | |
| Example 53b | 21.23 | | |
| Example 54a | 13.05 | | |
| Example 54b | 20.92 | | |
| Intermediate P7a-1 | 224.36 | | |
| Intermediate P7a-2 | 65.09 | | |
| Example 55a | 7.09 | | |
| Example 55b | 7.44 | | |
| Intermediate P8a | 20.28 | | |
| Example 56a | 35.52 | | |
| Example 56b | 74.73 | | |
| Example 57 | | 186.29 | |
| Example 58 | | 71.54 | |
| Example 59 | 25.29 | | |
| Example 60 | 64.05 | | |
| Example 61 | 36.73 | 72.41 | |
| Example 62 | 70.63 | | |
| Example 63a | 104.24 | | |
| Example 63b | 98.56 | | |
| Example 64 | 57.88 | | |
| Example 65 | 335.73 | | |
| Example 66 | 61.87 | | |
| Intermediate S1 | 93.30 | | |
| Example 67 | 17.98 | | |
| Example 68a | 60.81 | | |
| Example 68b | 34.44 | | |
| Intermediate S2 | 84.85 | | |
| Intermediate S3-a | 28.25 | | |
| Intermediate S3-b | 18.78 | 67.95 | |
| Example 69a | 22.08 | | |
| Example 69b | 36.86 | | |
| Example 70 | 48.98 | | |
| Example 71 | 1788.50 | | |
| Example 72 | 555.65 | | |
| Example 73 | 551.89 | | |
| Intermediate S4 | 14.91 | | |
| Example 74 | 131.39 | | |
| Example 75 | 288.64 | | |
| Example 76 | 29.21 | | |
| Example 77a | 194.33 | | |
| Example 77b | 197.56 | | |
| Example 78a | 65.24 | | |
| Example 78b | 20.97 | 75.64 | 33.80 |
| Example 79a | 61.24 | | |
| Example 79b | 21.65 | | 45.61 |
| Example 80 | 16.89 | | |
| Example 81a | 16.12 | | 37.66 |
| Example 81b | 20.63 | | |
| Example 82a | 62.81 | 168.45 | 61.83 |
| Example 82b | 16.53 | 41.36 | 16.22 |
| Example 83a | 21.85 | | 32.76 |
| Example 83b | 7.32 | 27.88 | 20.40 |
| Example 84a | 184.95 | | |
| Example 84b | 186.15 | | |
| Example 85a | 62.73 | | |
| Example 85b | 80.54 | | |
| Example 86a | 21.60 | | 88.16 |
| Example 86b | 20.92 | | 28.30 |
| Example 87a | 31.12 | | |
| Example 87b | 8.30 | 44.85 | |
| Example 88 | 21.38 | | |
| Example 89 | 387.62 | | |
| Example 90 | 20.37 | 123.67 | |
| Example 91 | 194.20 | | |
| Example 92 | | 2490.50 | |
| Example 93 | | 67.59 | |
| Example 94 | | 84.55 | |
| Example 95 | | 61.75 | |
| Example 96 | | 39.87 | 30.25 |
| Example 96a | | 26.54 | 21.18 |
| Example 96b | | 27.94 | 22.47 |
| Example 97a | | 102.96 | |
| Example 97b | | 105.82 | |
| Example 98a | | 62.12 | |
| Example 98b | | 52.20 | |
| Example 99a | | 81.73 | |
| Example 99b | | 66.90 | |
| Example 100a | | 110.76 | |
| Example 100b | | 95.47 | |
| Example 101a | | 41.10 | |
| Example 101b | | 79.23 | |
| Example 102a | | 31.98 | 8.68 |
| Example 102b | | 42.97 | 25.96 |
| Example 103a | | | |
| Example 103b | | 42.02 | |
| Example 104a | | 39.04 | |
| Example 104b | | 57.81 | 22.79 |
| Example 105a | | 54.62 | |
| Example 105b | | 60.67 | |
| Example 106a | | 46.82 | |
| Example 106b | | 34.20 | |
| Example 107 | 20.07 | | |
| Example 108 | 27.73 | | |
| Example 109 | 43.48 | | |
| Example 110 | 57.61 | | |
| Example 111 | 846.22 | | |
| Example 112 | 560.08 | | |
| Intermediate D9 | 65.39 | | |
| Example 113 | 22.06 | | |
| Example 114 | 61.02 | | |
| Example 115 | 62.59 | | |
| Example 116 | 11.25 | | |
| Example 117 | 11.01 | | |
| Example 118 | 23.52 | | |
| Example 119 | 559.43 | | |
| Example 120 | 73.88 | | |
| Example 121 | 23.50 | | |
| Example 122 | 16.43 | | |
| Example 123 | 63.68 | | |
| Example 124 | 67.14 | | |
| Example 125 | 21.14 | | |
| Example 126 | 17.04 | 116.35 | |
| Example 127 | 34.12 | | |
| Example 128 | | 524.78 | |
| Example 129 | | 361.82 | |
| Example 130 | | 52.81 | |
| Example 131 | | 56.20 | |
| Example 132 | | 125.62 | |
| Example 133 | | 33.65 | |
| Example 134 | | 93.82 | |
| Example 135 | | 1260.10 | |
| Example 136 | | 376.58 | |
| Example 137 | | 31.48 | 22.11 |
| Example 138 | | 36.62 | |
| Example 139 | | 194.21 | |
| Example 140 | | 301.61 | |
| Example 141 | | 305.03 | |
| Example 142 | | 73.51 | |
| Example 143 | | 737.36 | |

TABLE 3-continued

Antiviral activity of further exemplary compounds in HEP-2- Cells

| Example | EC$_{50}$ RSV HEP2 96 (nM) | EC$_{50}$ RSV HEP2 384 (nM) | EC$_{50}$ RSVFluc-Hep2 384 (nM) |
|---|---|---|---|
| Example 144 | | 780.17 | |
| Example 145 | | 34.97 | |
| Example 146 | | 459.06 | |
| Example 147 | | 334.36 | |
| Example 148 | | 59.30 | |
| Example 149 | | 99.37 | |
| Example 150 | | 78.23 | |
| Example 151 | | 55.58 | |
| Example 152 | | 210.69 | |
| Example 153 | | 270.37 | |
| Example 154 | | 104.95 | |
| Example 155 | | 682.67 | |
| Example 156 | | 195.34 | |
| Example 157 | | 79.55 | |
| Example 158 | | 272.19 | |
| Example 159 | | 79.33 | |
| Example 160 | | 218.62 | |
| Example 161 | | 112.97 | |
| Example 162 | | 72.45 | |
| Example 163 | | 68.04 | |
| Example 164 | | 107.27 | |
| Example 165 | | 5000.00 | |
| Example 166 | | 5000.00 | |
| Example 167 | | 5000.00 | |
| Example 168 | 110.64 | | |
| Example 169 | 62.88 | | |
| Example 170 | | | 1009.60 |
| Example 170a | | | 1418.70 |
| Example 170b | | | 843.40 |
| Example 171a | | | 712.47 |
| Example 171b | | | 537.13 |
| Example 172a | | | 749.62 |
| Example 172b | | | 610.07 |
| Example 173 | | | 797.51 |
| Example 173a | | | 821.80 |
| Example 173b | | | 765.36 |
| Example 174a | | | 7.09 |
| Example 174b | | | 62.84 |
| Example 175a | | 5000.00 | |
| Example 175b | | 5000.00 | |
| Example 176 | | | 153.25 |
| Example 177 | | | 16.98 |
| Example 178 | | | 84.98 |
| Example 179 | | | 16.78 |

TABLE 4

Antiviral activity of exemplary compounds in SARS CoV-2 Cells and NHBE cells

| Example | EC50 SARS CoV2 (nM) | EC$_{50}$ RSVFluc NHBE 96 (nM) |
|---|---|---|
| Example 1 | 338.29 | 6.56 |
| Example 2 | 102.24 | 4.53 |
| Example 3 | 129.32 | 5.55 |
| Example 7 | 372.22 | |
| Example 11 | 208.03 | |
| Example 12 | 139.22 | |
| Example 13 | 319.48 | 2.92 |
| Example 13a | 180.72 | 5.92 |
| Example 13b | 174.26 | 6.86 |
| Example 14 | 186.22 | 3.72 |
| Example 15 | 776.55 | |
| Example 16 | 199.03 | |
| Example 17 | 850.40 | |
| Example 18 | 209.94 | 6.69 |
| Example 18a | 312.41 | 22.23 |
| Example 18b | 332.42 | 15.07 |
| Example 21 | 234.15 | 5.36 |
| Example 21a | 125.10 | 37.37 |
| Example 21b | 190.67 | 33.11 |
| Example 25 | 349.95 | |
| Example 28 | 1616.90 | 35.05 |
| Example 29 | 123.24 | 3.93 |
| Example 30 | 201.89 | 4.49 |
| Example 31 | 249.62 | |
| Example 31a | 92.29 | 6.33 |
| Example 32a | 157.14 | 16.73 |
| Example 32b | 59.70 | 10.70 |
| Example 33a | 133.75 | 9.06 |
| Example 33b | 231.31 | 12.23 |
| Example 37 | 282.44 | |
| Example 42a | 120.87 | 9.56 |
| Example 42b | 51.32 | 8.00 |
| Example 43 | 167.81 | |
| Example 44 | 104.05 | 9.47 |
| Example 44a | 101.81 | 9.13 |
| Example 44b | 129.94 | 12.45 |
| Example 45 | 105.46 | 5.29 |
| Example 45a | 72.76 | 7.29 |
| Example 45b | 56.93 | 10.30 |
| Example 46 | 237.16 | 7.79 |
| Example 46a | 249.41 | 5.59 |
| Example 46b | 399.74 | 6.63 |
| Example 50a | 38.79 | 27.48 |
| Example 50b | 239.35 | 5.36 |
| Example 52a | 64.53 | 20.76 |
| Example 53b | 102.58 | |
| Example 54a | 101.55 | |
| Example 54b | 163.70 | |
| Intermediate P7a-2 | 275.19 | |
| Example 55a | 104.08 | 19.86 |
| Example 55b | 108.34 | 6.12 |
| Example 59 | 159.54 | |
| Example 60 | 180.04 | |
| Example 66 | 207.48 | |
| Example 65 | 264.52 | 3.24 |
| Intermediate S1 | 713.80 | |
| Example 67 | 27.17 | 8.72 |
| Intermediate S2 | 207.08 | |
| Intermediate S2-b | 116.33 | 2.96 |
| Example 70 | 319.43 | |
| Intermediate S3 | 112.93 | 5.51 |
| Example 78a | 116.74 | |
| Example 78b | 20.03 | 5.67 |
| Example 79a | 125.88 | |
| Example 79b | 27.84 | 6.33 |
| Example 80 | 310.17 | 16.46 |
| Example 81a | 236.88 | 8.39 |
| Example 81b | 226.69 | 14.79 |
| Example 82a | 151.06 | |
| Example 82b | 71.30 | 4.84 |
| Example 83a | 49.04 | 6.98 |
| Example 83b | 32.80 | 7.12 |
| Example 86a | 109.37 | 7.93 |
| Example 86b | 23.60 | 9.46 |
| Example 87a | 60.19 | |
| Example 87b | 16.34 | 7.36 |
| Example 93 | 123.38 | 4.43 |
| Example 94 | 369.64 | |
| Example 95 | 263.98 | |
| Example 96 | 95.88 | 5.48 |
| Example 96a | 198.45 | 8.53 |
| Example 96b | 276.15 | 25.13 |
| Example 98a | 176.03 | |
| Example 101a | 148.06 | |
| Example 102a | 154.80 | 8.46 |
| Example 102b | 86.01 | |
| Example 103b | 363.22 | |
| Example 104a | 233.59 | 10.84 |
| Example 104b | 293.65 | |
| Example 105a | 132.69 | |
| Example 106a | 83.08 | |
| Example 106b | 97.78 | 12.18 |

TABLE 4-continued

Antiviral activity of exemplary compounds in SARS CoV-2 Cells and NHBE cells

| Example | EC50 SARS CoV2 (nM) | EC$_{50}$ RSVFluc NHBE 96 (nM) |
|---|---|---|
| Example 107 | 180.38 | |
| Example 108 | 82.92 | |
| Example 113 | 125.80 | |
| Example 116 | 55.97 | 24.98 |
| Example 117 | 191.52 | 22.06 |
| Example 118 | 328.77 | |
| Example 121 | 110.02 | |
| Example 122 | 167.41 | 8.73 |
| Example 126 | 77.42 | |
| Example 133 | 36.88 | 13.79 |
| Example 137 | 67.39 | 4.82 |
| Example 138 | 341.59 | |
| Example 145 | 101.43 | |
| Example 154 | 330.04 | |
| Example 156 | 363.01 | |
| Example 159 | 369.16 | |
| Example 163 | 377.72 | |
| Example 165 | 10000.00 | |
| Example 166 | 10000.00 | |
| Example 170a | 959.84 | |
| Example 170b | 923.18 | |
| Example 171a | 930.87 | |
| Example 171b | 415.35 | |
| Example 172b | 871.30 | |
| Example 173a | 10000.00 | |
| Example 175a | 3364.10 | |
| Example 175b | 10000.00 | |
| Example 177 | 410.27 | 15.96 |
| Example 178 | 1371.20 | 12.20 |
| Example 179 | 849.5 | 7.84 |

Although the foregoing invention has been described in some detail by way of illustrations and Examples for purpose of clarity of understanding, one of sill in the art will appreciate that certain changes and modifications may be practiced within the scope of the appended claims. In addition, each reference is individually incorporated by reference in its entirety to the same extent as if each reference is individually incorporated by reference. Where a conflict exists between the instant application and a reference provided herein, the instant application shall dominate.

What is claimed is:
1. A compound of Formula I:

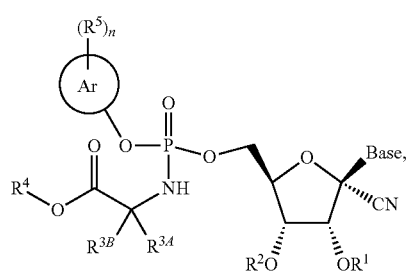

Formula I or a pharmaceutically acceptable salt thereof, wherein
each $R^1$ and $R^2$ is independently H, —(CO)$C_1$-$C_6$ alkyl or —(CO)O$C_1$-$C_6$ alkyl, wherein the —(C(O)$C_1$-$C_6$ alkyl or —(CO)O$C_1$-$C_6$ alkyl is optionally substituted with a NH$_2$ group; or
$R^1$ and $R^2$ are combined to form —CO—, —CO—CO—, or —C(O)—C($R^{1A}$)($R^{1B}$)—C(O)—;

wherein each $R^{1A}$ and $R^{1B}$ is independently H or $C_1$-$C_6$ alkyl;
$R^{3A}$ is H or $C_1$-$C_6$ alkyl; wherein the $C_1$-$C_6$ alkyl is optionally substituted with a —OH or phenyl;
$R^{3B}$ is H or $C_1$-$C_3$ alkyl; and
$R^4$ is (i) $C_1$-$C_8$ alkyl, (ii) (C$R^8R^9$C$R^{10}R^{11}$O)$_m$$R^{12}$, (iii) $C_3$-$C_{10}$ cycloalkyl, (iv) 4 to 6 membered heterocyclyl having 1 to 3 heteroatoms independently selected from N, O and S, or (v) 5 to 6 membered heteroaryl having 1 to 3 heteroatoms independently selected from N, O and S; wherein the $C_1$-$C_8$ alkyl, $C_3$-$C_{10}$ cycloalkyl, 4 to 6 membered heterocyclyl, or 5 to 6 membered heteroaryl is optionally substituted with one or two $R^{4A}$ groups; wherein
each $R^{4A}$ is independently $C_1$-$C_3$ alkyl, $C_1$-$C_3$ alkoxy, $C_1$-$C_3$ haloalkyl, $C_3$-$C_{10}$ cycloalkyl, $C_6$-$C_{10}$ aryl, or 4 to 6 membered heterocyclyl having 1 to 3 heteroatoms independently selected from N, O and S; wherein the $C_3$-$C_{10}$ cycloalkyl, $C_6$-$C_{10}$ aryl, or 4 to 6 membered heterocyclyl is optionally substituted with one or two substituents independently selected from the group consisting of $C_1$-$C_6$ alkyl, halo, $C_1$-$C_6$ haloalkyl, and $C_1$-$C_6$ alkoxy;
Base is

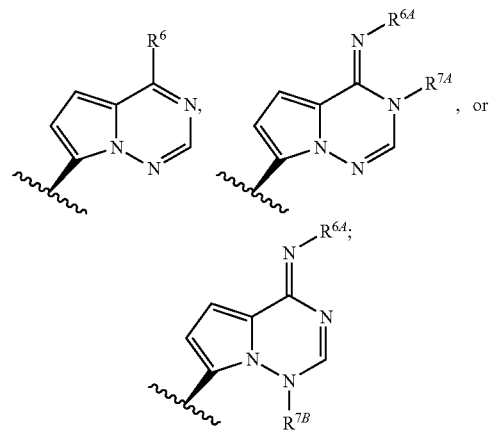

wherein
$R^6$ is —N(H)$R^{6A}$; and
each $R^{6A}$, $R^{7A}$ and $R^{7B}$ is independently H or —CH$_2$OP(O)(OH)$_2$;
Ar is $C_6$-$C_{10}$ aryl or 5 to 10 membered heteroaryl containing one, two, or three heteroatoms selected from the group consisting of O, N, and S;
n is 0, 1, 2, or 3;
each $R^5$ is independently halo, cyano, $C_1$-$C_6$ alkyl, $C_1$-$C_6$ haloalkyl, $C_3$-$C_6$ cycloalkyl, $C_1$-$C_6$ alkoxy, $C_3$-$C_6$ cycloalkoxy, —COO$R^{5A}$, —SO$_2R^{5A}$, 4 to 6 membered heterocycloalkyl containing one, two or three heteroatoms selected from N, O, and S, or 5 to 6 membered heteroaryl containing one, two or three heteroatoms selected from N, O, and S; wherein the $C_1$-$C_6$ alkyl, $C_1$-$C_6$ haloalkyl, $C_3$-$C_6$ cycloalkyl, $C_3$-$C_6$ cycloalkoxy, $C_1$-$C_6$ alkoxy, 4 to 6 membered heterocycloalkyl and 5 to 6 membered heteroaryl is optionally substituted with one or two $R^{5B}$ groups; or two R⁵ groups on adjacent carbon atoms are joined to form a C₅-C₆ cycloalkyl;
each $R^{5A}$ is independently C₁-C₆ alkyl;
each $R^{5B}$ is independently —OH, —OR⁵ᶜ, —COOR⁵ᶜ and —NHCOOR⁵ᴰ; wherein R⁵ᶜ is C₁-C₆ alkyl and R⁵ᴰ is C₁-C₃ alkyl optionally substituted with a phenyl group;
each R⁸, R⁹, R¹⁰, R¹¹ and R¹² is independently H or C₁-C₃ alkyl;
m is 1, 2, 3, 4, or 5;
provided that when R¹ and R² are both H then:
  (i) n is 1, 2, or 3; or
  (ii) R⁴ is C₁-C₈ alkyl substituted with one or two groups independently selected from C₁-C₃ alkoxy, C₁-C₃ haloalkyl, C₃-C₁₀ cycloalkyl, C₆-C₁₀ aryl, or 4 to 6 membered heterocyclyl having 1 to 3 heteroatoms independently selected from N, O and S;
    wherein the C₃-C₁₀ cycloalkyl, C₆-C₁₀ aryl, or 4 to 6 membered heterocyclyl is optionally substituted with one or two substituents independently selected from the group consisting of C₁-C₆ alkyl, halo, C₁-C₆ haloalkyl, and C₁-C₆ alkoxy; or
  (iii) R⁴ is (a) —(CR⁸R⁹CR¹⁰R¹¹O)ₘR¹², (b) monocyclic C₃-C₁₀ cycloalkyl substituted with substituted with one or two R⁴ᴬ groups, (c) bicyclic C₃-C₁₀ cycloalkyl, (d) 4 to 6 membered heterocyclyl having 1 to 3 heteroatoms independently selected from N, O and S, or (e) 5 to 6 membered heteroaryl having 1 to 3 heteroatoms independently selected from N, O and S;
    wherein the bicyclic C₃-C₁₀ cycloalkyl, 4 to 6 membered heterocyclyl, or 5 to 6 membered heteroaryl is optionally substituted with one or two R⁴ᴬ groups; or
  (iv) Base is

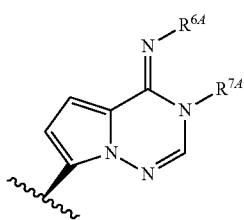

and at least one of R⁶ᴬ and R⁷ᴬ is —CH₂OP(O)(OH)₂; or Base is

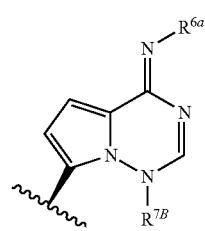

«and at least one of R⁶ᴬ and R⁷ᴮ is —CH₂OP(O)(OH)₂.

2. The compound of claim 1, or a pharmaceutically acceptable salt thereof, wherein the compound has a Formula Ia:

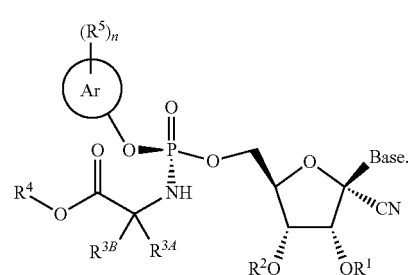

Formula Ia

3. The compound of claim 1, or a pharmaceutically acceptable salt thereof, wherein the compound has a Formula Ib:

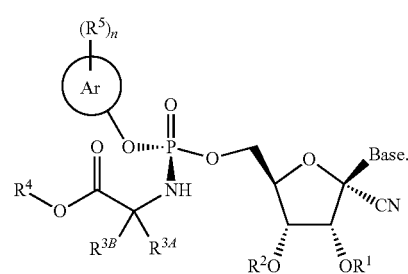

Formula Ib

4. The compound of claim 1, or a pharmaceutically acceptable salt thereof, wherein Base is

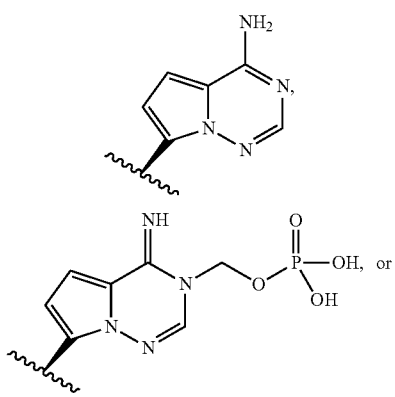

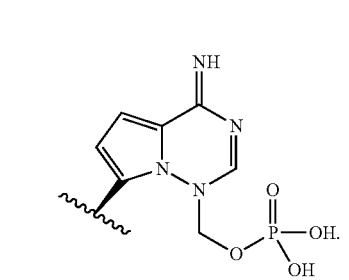

5. The compound of claim 1, or a pharmaceutically acceptable salt thereof, wherein the Base is

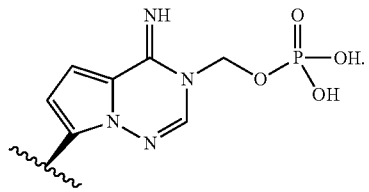

6. The compound of claim 1, or a pharmaceutically acceptable salt thereof, wherein n is 0, 1, or 2.

7. The compound of claim 1, or a pharmaceutically acceptable salt thereof, wherein

is 5 to 10 membered heteroaryl containing one, two, or three heteroatoms selected from the group consisting of O, N, and S.

8. The compound of claim 1, or a pharmaceutically acceptable salt thereof, wherein

is a $C_6$-$C_{10}$ aryl; n is 0, 1 or 2; and each $R^5$ is independently halo, cyano, $C_1$-$C_6$ alkyl, $C_3$-$C_6$ cycloalkyl, $C_1$-$C_6$ alkoxy, or —$SO_2R^{5A}$; or two $R^5$ groups on adjacent carbon atoms are joined to form a $C_5$-$C_6$ cycloalkyl.

9. The compound of claim 1, or a pharmaceutically acceptable salt thereof, wherein

is selected from the group consisting of:

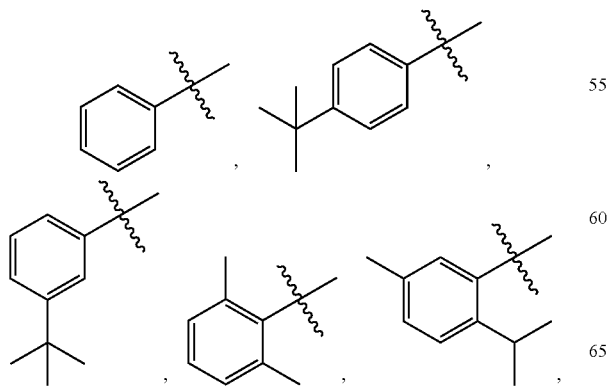

-continued

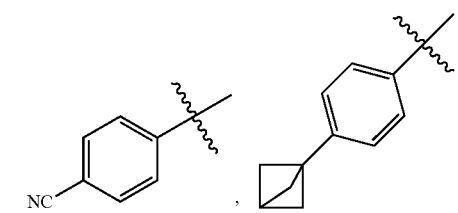

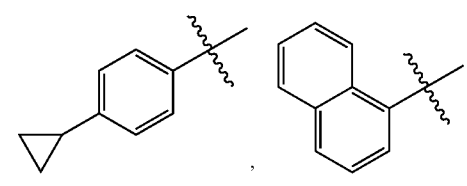

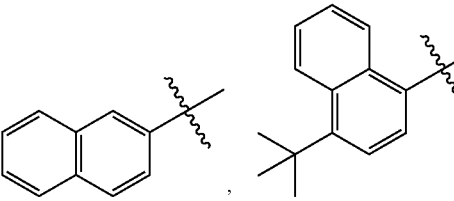

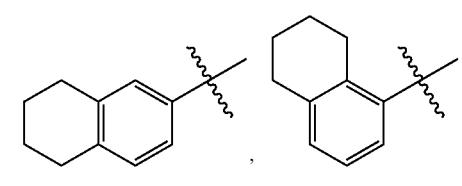

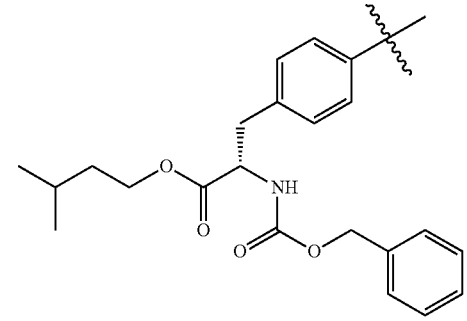

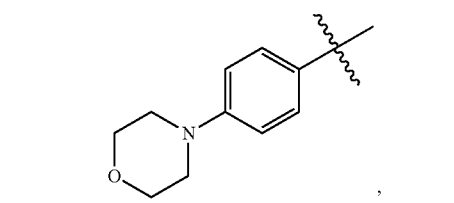

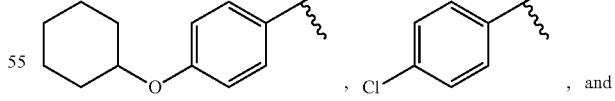, and

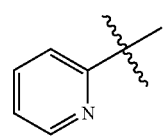.

10. The compound of claim 1, or a pharmaceutically acceptable salt thereof, wherein

is a phenyl or napthyl; n is 0, 1, or 2; and each $R^5$ is independently $C_1$-$C_6$ alkyl or $C_3$-$C_6$ cycloalkyl; or two $R^5$ groups on adjacent carbon atoms are joined to form a $C_5$-$C_6$ cycloalkyl.

11. The compound of claim 8, or a pharmaceutically acceptable salt thereof, wherein the compound has a Formula II:

Formula II

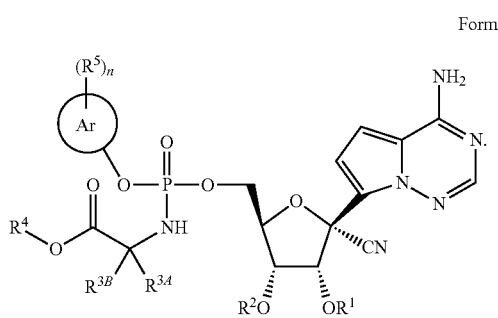

12. The compound of claim 11, or a pharmaceutically acceptable salt thereof, wherein the compound has a Formula IIa:

Formula IIa

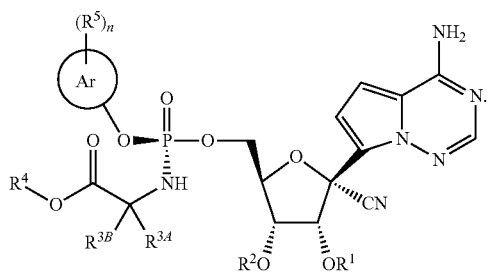

13. The compound of claim 11, or a pharmaceutically acceptable salt thereof, wherein the compound has a Formula IIb:

Formula IIb

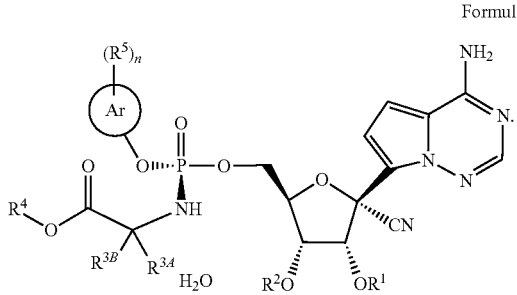

14. The compound of claim 11, or a pharmaceutically acceptable salt thereof, wherein $R^{3A}$ is $C_1$-$C_6$ alkyl optionally substituted with a —OH or phenyl.

15. The compound of claim 11, or a pharmaceutically acceptable salt thereof, wherein $R^{3A}$ is methyl.

16. The compound of claim 11, or a pharmaceutically acceptable salt thereof, wherein $R^{3B}$ is H.

17. The compound of claim 11, or a pharmaceutically acceptable salt thereof, wherein the compound has a Formula III:

Formula III

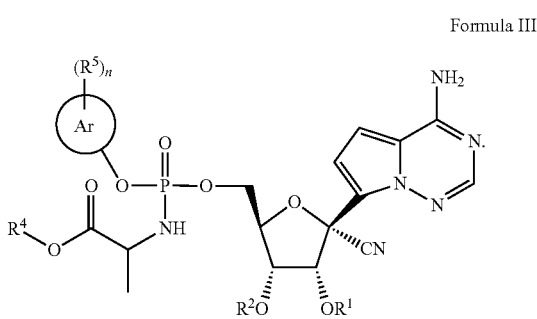

18. The compound of claim 17, or a pharmaceutically acceptable salt thereof, wherein the compound has a Formula IIIa:

Formula IIIa

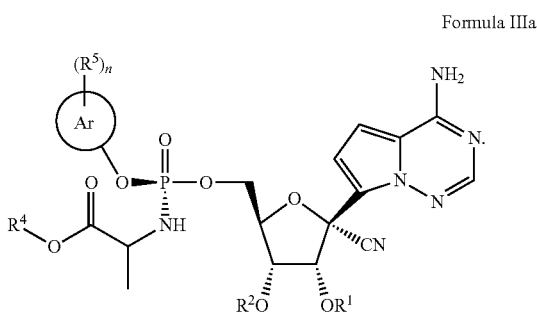

19. The compound of claim 17, or a pharmaceutically acceptable salt thereof, wherein the compound has a Formula IIIb:

Formula IIIb

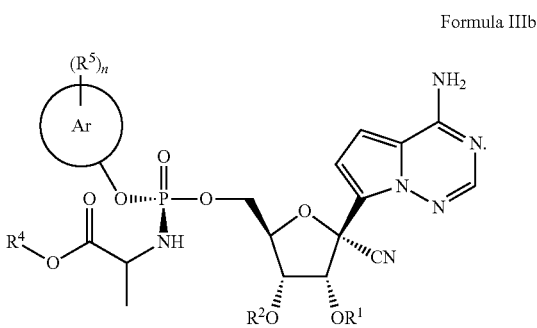

20. The compound of claim 17, or a pharmaceutically acceptable salt thereof, wherein the compound has a Formula IIIc:

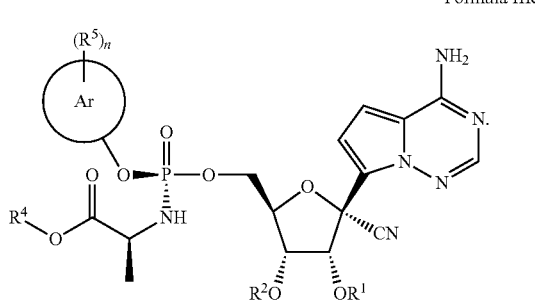

Formula IIIc

21. The compound of claim 20, or a pharmaceutically acceptable salt thereof, wherein
each $R^1$ and $R^2$ is independently —(CO)$C_1$-$C_6$ alkyl or —(CO)O$C_1$-$C_6$ alkyl; or
one of R and $R^2$ is H and the other is —(CO)$C_1$-$C_6$ alkyl or —(CO)O$C_1$-$C_6$ alkyl.

22. The compound of claim 20, or a pharmaceutically acceptable salt thereof, wherein $R^1$ and $R^2$ are independently selected from the group consisting of —COCH(CH$_3$)$_2$, —COCH$_3$, —COCH$_2$CH$_3$, —COCH$_2$CH(CH$_3$)$_2$ or —COCH(NH$_2$)CH(CH$_3$)$_2$.

23. The compound of claim 20, or a pharmaceutically acceptable salt thereof, wherein one of $R^1$ and $R^2$ is H and the other is —(CO)$C_1$-$C_6$ alkyl or —(CO)O$C_1$-$C_6$ alkyl.

24. The compound of claim 20, or a pharmaceutically acceptable salt thereof, wherein each $R^1$ and $R^2$ is independently —(CO)$C_1$-$C_6$ alkyl or —(CO)O$C_1$-$C_6$ alkyl.

25. The compound of claim 20, or a pharmaceutically acceptable salt thereof, wherein each $R^1$ and $R^2$ is independently —(CO)$C_1$-$C_6$ alkyl.

26. The compound of claim 20, or a pharmaceutically acceptable salt thereof, wherein $R^1$ is a —(CO)$C_1$-$C_3$ alkyl.

27. The compound of claim 20, or a pharmaceutically acceptable salt thereof, wherein $R^2$ is a —(CO)$C_1$-$C_3$ alkyl.

28. The compound of claim 20, or a pharmaceutically acceptable salt thereof, wherein $R^1$ and $R^2$ are each —(CO)CH$_3$, or $R^1$ and $R^2$ are each —(CO)CH$_2$CH$_3$ or $R^1$ and $R^2$ are each —(CO)CH(CH$_3$)$_2$.

29. The compound of claim 20, or a pharmaceutically acceptable salt thereof, wherein $R^1$ and $R^2$ are both H and n is 1, 2, or 3.

30. The compound of claim 20, or a pharmaceutically acceptable salt thereof, wherein $R^1$ and $R^2$ are both H and $R^4$ is —(CR$^8$R$^9$CR$^{10}$R$^{11}$O)$_m$R$^{12}$.

31. The compound of claim 1, or a pharmaceutically acceptable salt thereof, wherein $R^1$ and $R^2$ are both H and Base is

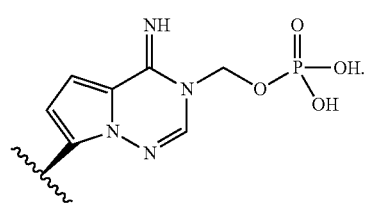

32. The compound of claim 20, wherein $R^1$ and $R^2$ are combined to form —C(O)—, —C(O)—C(O)—, or —C(O)—C(R$^{1A}$)(R$^{1B}$)—C(O)—, wherein each R$^{1A}$ and R$^{1B}$ is independently H or $C_1$-$C_6$ alkyl.

33. The compound of claim 20, or a pharmaceutically acceptable salt thereof, wherein $R^4$ is $C_1$-$C_8$ alkyl optionally substituted with one or two $R^{4A}$.

34. The compound of claim 20, or a pharmaceutically acceptable salt thereof, wherein $R^{4A}$ is $C_3$-$C_{10}$ cycloalkyl or 4 to 6 membered heterocyclyl having one O.

35. The compound of claim 20, or a pharmaceutically acceptable salt thereof, wherein $R^{4A}$ is cyclobutyl, cyclohexyl, cyclooctyl, oxetanyl or tetrahydropyranyl.

36. The compound of claim 20, or a pharmaceutically acceptable salt thereof, wherein $R^4$ is selected from the group consisting of hexyl, methyl, and ethyl.

37. The compound of claim 20, or a pharmaceutically acceptable salt thereof, wherein $R^4$ is 4 to 6 membered heterocyclyl having 1 to 3 heteroatoms independently selected from N, O and S.

38. The compound of claim 20, or a pharmaceutically acceptable salt thereof, wherein $R^4$ is —(CR$^8$R$^9$CR$^{10}$R$^{11}$O)$_m$R$^{12}$; wherein each $R^1$, $R^9$, $R^{10}$, $R^{11}$, and $R^{12}$ is independently H or $C_1$-$C_3$ alkyl and m is 1, 2, 3, 4, or 5.

39. The compound of claim 20, or a pharmaceutically acceptable salt thereof, wherein $R^4$ is selected from the group consisting of:

(i) methyl,
(ii) ethyl,
(iii) n-propyl,
(iv) isopropyl, (v)
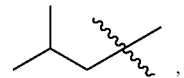, (vi)
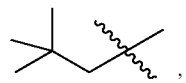, (vii)
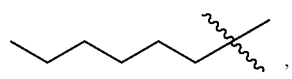, (viii)
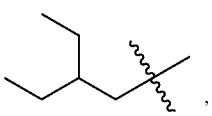, (ix) 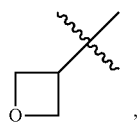,
(x) 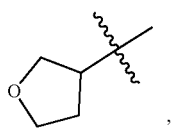,
(xi) 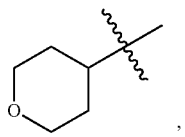,
(xii) cyclobutyl,
(xiii) cyclohexyl,
(xiv) cyclooctyl,
(xv) 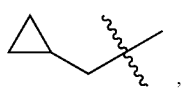,
(xvi) 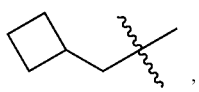,
(xvii) 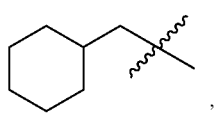,
(xviii) 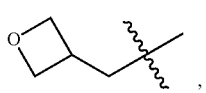,
(xix) 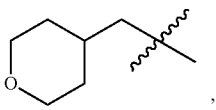,
(xx) 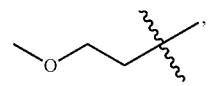,
(xxi) 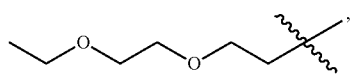,
(xxii) 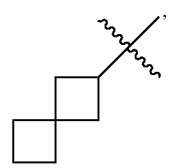,
(xxiii) 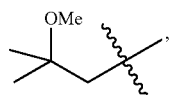,
(xxiv) 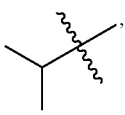,
(xxv) 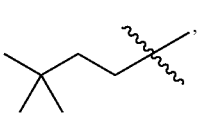, (xxvi) 

(xxvii) 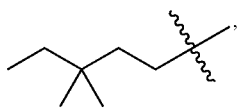

(xxviii) 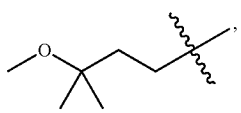

(xxix) 

(xxx) 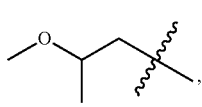

(xxxi) 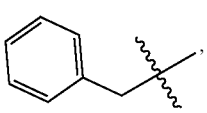

(xxxii) 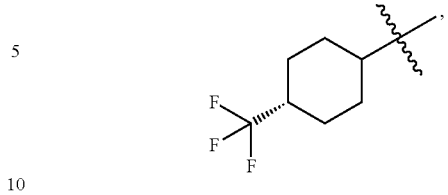

(xxxiii) 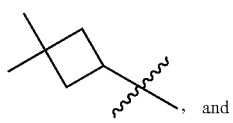, and (xxxiv) 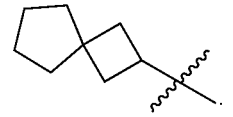.

40. The compound of claim 20, or a pharmaceutically acceptable salt thereof, wherein each $R^5$ is independently $C_1$-$C_6$ alkyl or $C_3$-$C_6$ cycloalkyl.

41. The compound of claim 20, or a pharmaceutically acceptable salt thereof, wherein $R^5$ is t-Bu, isopropyl, methyl, or cyclopropyl.

42. The compound of claim 11, or a pharmaceutically acceptable salt thereof, wherein:
each $R^1$ and $R^2$ is independently H, —(CO)$C_1$-$C_3$ alkyl;
$R^{3A}$ is H or methyl;
$R^{3B}$ is H or methyl;
$R^4$ is $C_3$-$C_8$ cycloalkyl;
Ar is $C_6$-$C_{10}$ aryl;
n is 0 or 1; and
$R^5$ is $C_1$-$C_6$ alkyl.

43. A pharmaceutical formulation comprising a pharmaceutically effective amount of a compound of claim 1, or a pharmaceutically acceptable salt thereof, and a pharmaceutically acceptable carrier or excipient.

44. A method of treating or preventing a viral infection in a human in need thereof, wherein the method comprises administering to the human the compound of claim 1 and wherein the viral infection is a coronavirus infection, pneumoviridae virus infection, picornaviridae virus infection, flaviviridae virus infection, filoviridae virus infection, orthomyxovirus infection, or paramyxoviridae virus infection.

45. The method of claim 44, wherein the method comprises administering to the human at least one additional therapeutic agent.

\* \* \* \* \*

UNITED STATES PATENT AND TRADEMARK OFFICE
CERTIFICATE OF CORRECTION

PATENT NO. : 11,939,347 B2  
APPLICATION NO. : 17/355813  
DATED : March 26, 2024  
INVENTOR(S) : Daniel H. Byun et al.

Page 1 of 2

It is certified that error appears in the above-identified patent and that said Letters Patent is hereby corrected as shown below:

In the Claims

Column 397, Line 63, Claim 1, delete "—(C(O)C$_1$-C$_6$" and insert -- —(CO)C$_1$-C$_6$ --.

Column 398, Line 6, Claim 1, delete "(CR$^8$" and insert -- -(CR$^8$ --.

Column 399, Line 5, Claim 1, delete "—COOR$^{5c}$" and insert -- —COOR$^{5C}$ --.

Column 399, Line 28-29, Claim 1, delete "substituted with substituted with" and insert -- substituted with --.

Column 399, Line 55-63, Claim 1, delete " 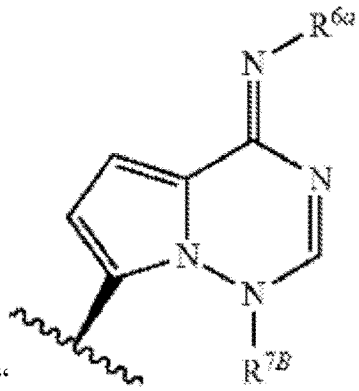 " and insert

Signed and Sealed this  
Twenty-seventh Day of August, 2024

Katherine Kelly Vidal  
*Director of the United States Patent and Trademark Office*

CERTIFICATE OF CORRECTION (continued)
U.S. Pat. No. 11,939,347 B2

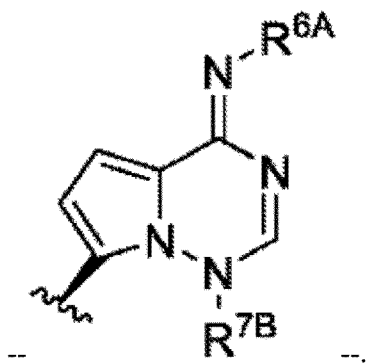

Column 399, Line 66, Claim 1, delete "<<and" and insert -- and --.

Column 401, Line 25, Claim 7, delete "0," and insert -- O, --.

Column 403, Line 9, Claim 10, delete "napthyl;" and insert -- naphthyl; --.

Column 405, Line 24, Claim 21, delete "R" and insert -- $R^1$ --.

Column 406, Line 25, Claim 38, delete "$R^1$," and insert -- $R^8$, --.